US012048722B2

(12) United States Patent
Toledo et al.

(10) Patent No.: US 12,048,722 B2
(45) **Date of Patent: *Jul. 30, 2024**

(54) METHODS AND COMPOSITIONS FOR TREATING MUSCULOSKELETAL DISEASES

(71) Applicant: Solarea Bio, Inc., Cambridge, MA (US)

(72) Inventors: Gerardo V. Toledo, Hopkinton, MA (US); Maria Juliana Soto-Giron, Cambridge, MA (US); Jinwoo Kim, Acton, MA (US); Julie E. Button, Lincoln, MA (US); Eric Michael Schott, West Roxbury, MA (US)

(73) Assignee: Solarea Bio, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/816,371

(22) Filed: Jul. 29, 2022

(65) Prior Publication Data

US 2023/0210917 A1 Jul. 6, 2023

Related U.S. Application Data

(60) Division of application No. 16/694,876, filed on Nov. 25, 2019, now Pat. No. 11,819,524, which is a continuation of application No. PCT/US2019/049823, filed on Sep. 5, 2019.

(Continued)

(51) Int. Cl.

*A61K 35/741* (2015.01)
*A23L 33/125* (2016.01)

(Continued)

(52) U.S. Cl.

CPC .......... *A61K 35/741* (2013.01); *A23L 33/125* (2016.08); *A23L 33/135* (2016.08);

(Continued)

(58) Field of Classification Search

None

See application file for complete search history.

(56) References Cited

U.S. PATENT DOCUMENTS 3,048,526 A 8/1962 Bloswell
3,108,046 A 10/1963 Harbit (Continued)

FOREIGN PATENT DOCUMENTS

AU 2008231930 A1 10/2008
BR PI0905590 A2 8/2011

(Continued)

OTHER PUBLICATIONS

Patnode, et al., "Interspecies Competition Impacts Targeted Manipulation of Human Gut Bacteria by Fiber-Derived Glycans", Cell, Sep. 19, 2019, vol. 159: pp. 59-73.

(Continued)

*Primary Examiner* — Erin M. Bowers
(74) *Attorney, Agent, or Firm* — Goodwin Procter LLP

(57) ABSTRACT

Described herein are methods and compositions for using microbial agents (probiotics) and agents that promote growth of certain microbes (prebiotics) for management (including prevention and treatment) of musculoskeletal disorders, including osteoporosis, osteopenia, Paget's disease, stunting, osteoarthritis, osteomyelitis, and delayed or non-union fractures.

20 Claims, 46 Drawing Sheets

Specification includes a Sequence Listing.

Related U.S. Application Data

(60) Provisional application No. 62/863,722, filed on Jun. 19, 2019, provisional application No. 62/728,019, filed on Sep. 6, 2018, provisional application No. 62/728,020, filed on Sep. 6, 2018, provisional application No. 62/728,018, filed on Sep. 6, 2018, provisional application No. 62/727,503, filed on Sep. 5, 2018.

(51) Int. Cl.

| | |
|---|---|
| ***A23L 33/135*** | (2016.01) |
| ***A23L 33/14*** | (2016.01) |
| ***A61K 31/702*** | (2006.01) |
| ***A61K 35/744*** | (2015.01) |
| ***A61K 36/062*** | (2006.01) |
| ***A61K 45/06*** | (2006.01) |
| ***A61P 19/08*** | (2006.01) |
| ***A61P 19/10*** | (2006.01) |

(52) U.S. Cl.

CPC ............ *A23L 33/14* (2016.08); *A61K 31/702* (2013.01); *A61K 35/744* (2013.01); *A61K 36/062* (2013.01); *A61K 45/06* (2013.01); *A61P 19/08* (2018.01); *A61P 19/10* (2018.01); *A23V 2002/00* (2013.01); *A23V 2400/173* (2023.08); *A23V 2400/321* (2023.08); *A23V 2400/427* (2023.08)

(56) References Cited

U.S. PATENT DOCUMENTS

| | | | |
|---|---|---|---|
| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 4,478,822 | A | 10/1984 | Haslam et al. |
| 4,532,126 | A | 7/1985 | Ebert et al. |
| 4,625,494 | A | 12/1986 | Iwatschenko |
| 4,671,953 | A | 6/1987 | Stanley et al. |
| 4,786,505 | A | 11/1988 | Lovgren et al. |
| 4,800,083 | A | 1/1989 | Hom et al. |
| 4,904,479 | A | 2/1990 | Illum |
| 4,919,939 | A | 4/1990 | Baker |
| 4,935,243 | A | 6/1990 | Borkan et al. |
| 4,950,484 | A | 8/1990 | Olthoff et al. |
| 5,013,726 | A | 5/1991 | Ivy et al. |
| 5,059,595 | A | 10/1991 | Grazie |
| 5,073,543 | A | 12/1991 | Marshall et al. |
| 5,120,548 | A | 6/1992 | McClelland et al. |
| 5,225,202 | A | 7/1993 | Hodges et al. |
| 5,354,556 | A | 10/1994 | Sparks et al. |
| 5,591,767 | A | 1/1997 | Mohr et al. |
| 5,610,184 | A | 3/1997 | Shahinian, Jr. |
| 5,639,476 | A | 6/1997 | Oshlack et al. |
| 5,674,533 | A | 10/1997 | Santus et al. |
| 5,733,556 | A | 3/1998 | Schrier et al. |
| 5,733,575 | A | 3/1998 | Mehra et al. |
| 5,837,284 | A | 11/1998 | Mehta |
| 5,871,776 | A | 2/1999 | Mehta |
| 5,902,632 | A | 5/1999 | Mehta |
| 6,139,875 | A | 10/2000 | Adams et al. |
| 6,258,380 | B1 | 7/2001 | Overholt |
| 6,420,473 | B1 | 7/2002 | Chittamuru et al. |
| 6,455,052 | B1 | 9/2002 | Marcussen et al. |
| 6,482,435 | B1 | 11/2002 | Stratton et al. |
| 6,544,510 | B2 | 4/2003 | Olshenitsk et al. |
| 6,569,457 | B2 | 5/2003 | Ullah et al. |
| 6,572,871 | B1 | 6/2003 | Church et al. |
| 6,750,331 | B1 | 6/2004 | Takaichi et al. |
| 7,214,370 | B2 | 5/2007 | Naidu et al. |
| 8,318,151 | B2 | 11/2012 | Darimont-Nicolau et al. |
| 8,460,726 | B2 | 6/2013 | Harel et al. |
| 8,802,158 | B2 | 8/2014 | Boileau et al. |
| 8,871,266 | B2 | 10/2014 | Sanguansri et al. |
| 8,877,178 | B2 | 11/2014 | Boileau et al. |
| 9,040,101 | B2 | 5/2015 | Heiman et al. |
| 9,095,604 | B2 | 8/2015 | Ikegami et al. |
| 9,173,910 | B2 | 11/2015 | Kaplan et al. |
| 9,301,983 | B2 | 4/2016 | Huang et al. |
| 9,371,510 | B2 | 6/2016 | Moore |
| 9,386,793 | B2 | 7/2016 | Blaser et al. |
| 9,487,764 | B2 | 11/2016 | Falb et al. |
| 9,549,955 | B2 | 1/2017 | Rittmann et al. |
| 9,636,367 | B2 | 5/2017 | Garcia-Rodenas et al. |
| 9,937,211 | B2 | 4/2018 | Kelly et al. |
| 10,064,895 | B2 | 9/2018 | Vincent |
| 2004/0213828 | A1 | 10/2004 | Smith |
| 2005/0147710 | A1 | 7/2005 | Teckoe et al. |
| 2010/0172874 | A1 | 7/2010 | Turnbaugh et al. |
| 2011/0111094 | A1 | 5/2011 | Lavermicocca et al. |
| 2011/0177567 | A1* | 7/2011 | Bakker .................... C12P 7/56 435/141 |
| 2011/0177976 | A1 | 7/2011 | Gordon et al. |
| 2012/0015075 | A1 | 1/2012 | Davis et al. |
| 2012/0040387 | A1 | 2/2012 | Matsuoka |
| 2014/0044858 | A1 | 2/2014 | Quevedo |
| 2014/0065209 | A1 | 3/2014 | Putaala et al. |
| 2014/0147425 | A1 | 5/2014 | Henn et al. |
| 2014/0179726 | A1 | 6/2014 | Bajaj et al. |
| 2014/0314719 | A1 | 10/2014 | Smith et al. |
| 2015/0126463 | A1 | 5/2015 | Hsiao et al. |
| 2015/0259728 | A1 | 9/2015 | Cutcliffe et al. |
| 2015/0366941 | A1 | 12/2015 | Menear et al. |
| 2016/0067289 | A1 | 3/2016 | Berggren et al. |
| 2016/0081309 | A1 | 3/2016 | Newton et al. |
| 2016/0143961 | A1 | 5/2016 | Berry et al. |
| 2016/0199424 | A1 | 7/2016 | Berry et al. |
| 2016/0206666 | A1 | 7/2016 | Falb et al. |
| 2016/0235792 | A1 | 8/2016 | Berry et al. |
| 2016/0263166 | A1 | 9/2016 | Elinav et al. |
| 2016/0271189 | A1 | 9/2016 | Cutcliffe et al. |
| 2016/0302464 | A1 | 10/2016 | Egli et al. |
| 2016/0354417 | A1 | 12/2016 | Smittle et al. |
| 2017/0165303 | A1 | 6/2017 | Olmstead |
| 2017/0326190 | A1 | 11/2017 | Ansell et al. |
| 2019/0321420 | A1 | 10/2019 | Chen et al. |
| 2020/0164002 | A1 | 5/2020 | Toledo et al. |
| 2022/0354907 | A1 | 11/2022 | Toledo et al. |

FOREIGN PATENT DOCUMENTS

| | | | |
|---|---|---|---|
| CA | 2334877 | A1 | 10/2000 |
| EP | 1495109 | A1 | 1/2005 |
| EP | 1794283 | A1 | 6/2007 |
| WO | WO-2004/080200 | A1 | 9/2004 |
| WO | WO-2010/099617 | A1 | 9/2010 |
| WO | WO-2012/098254 | A1 | 7/2012 |
| WO | WO-2012/170047 | A2 | 12/2012 |
| WO | WO-2013/067146 | A1 | 5/2013 |
| WO | WO-2013/176774 | A1 | 11/2013 |
| WO | WO-2014/068338 | A1 | 5/2014 |
| WO | WO-2014/145958 | A2 | 9/2014 |
| WO | WO-2015/172191 | A1 | 11/2015 |
| WO | WO-2015/177246 | A2 | 11/2015 |
| WO | WO-2015/200842 | A1 | 12/2015 |
| WO | WO-2016/065075 | A1 | 4/2016 |
| WO | WO-2016/086205 | A2 | 6/2016 |
| WO | WO-2016/086210 | A1 | 6/2016 |
| WO | WO-2016/124940 | A1 | 8/2016 |
| WO | WO-2016172658 | A2 | 10/2016 |
| WO | WO-2017/160711 | A1 | 9/2017 |
| WO | WO-2019/118984 | A2 | 6/2019 |
| WO | WO-2020/051379 | A1 | 3/2020 |
| WO | WO-2020/257722 | A2 | 12/2020 |

OTHER PUBLICATIONS

Brunkwall, L et. al., (2017) The gut microbiome as a target for prevention and treatment of hyperglycaemia in type 2 diabetes: from

(56) References Cited

OTHER PUBLICATIONS current human evidence to future possibilities. Diabetalogia 60: 943-951.
Lee, et al., "Gut microbiota-generated metabolites in animal health and disease", Nat Chem Biol, 2014, vol. 10: pp. 416-424.
Lee, et al., "Effect of Metformin on Metabolic Improvement and Gut Microbiota", Appl Environ Microbiol, 2014, vol. 80, No. 19: p. 59355943.
Perry, et al., "Acetate mediates a microbiome-brain-β-cell axis to promote metabolic syndrome", Nature, 2016, vol. 534: pp. 213-217.
Camacho, L. et al (2015) Metformin in breast cance—an evolving mystery. Breast Cancer Res 17(88): 1-4.
Madiraju, et al., "Metformin suppresses gluconeogenesis by inhibiting mitochondrial glycerophosphate dehydrogenase", Nature, 2014, vol. 510: pp. 542-546.
Magnusdottir, et al., "Generation of genome-scale metabolic reconstructions for 773 members of the human gut microbiota", Nature Biotechnology, Jan. 2017, vol. 35, No. 1: pp. 81-89.
Plovier, et al., "A purified membrane protein from *Akkermansia muciniphila* or the pasteurized bacterium improves metabolism in obese and diabetic mice", Nat. Med., 2017, vol. 23, No. 1: pp. 107-113.
Campbell, T.C. et al., "The China Study: The most comprehensive study of nutrition ever conducted and startling implications for diet, weight loss, and long term health," Benbella, 2006, 1-425.
Naylor, et al., "Response of bone turnover markers to three oral bisphosphonatetherapies in postmenopausal osteoporosis: the TRIO study", Osteoporos Int, 2016, vol. 27: pp. 21-31.
Ni, et al., "A Molecular-Level Landscape of Diet-Gut Microbiome Interactions: Toward Dietary Interventions Targeting Bacterial Genes", mBio, 2015, vol. 6, No. 6: e01263-15.
Postler, et al., "Understanding the Holobiont: How Microbial Metabolites Affect Human Health and Shape the Immune System", Cell, 2017, vol. 26: pp. 110-130.
Cockburn, OW et al., (2016) Polysaccharide Degradation by the Intestinal Microbiota and Its Influence on Human Health and Disease. J Mol Biol 428: 3230-3252.
Cani, et al., "Improvement of glucose tolerance and hepatic insulin sensitivity by oligofructose requires a functional glucagon-like peptide 1 receptor", Diabetes, 2006, vol. 55: pp. 1484-1490.
Cani, et al., "Selective increases of bifidobacteria in gut microflora improve high-fat-diet-induced diabetes in mice through a mechanism associated with endotoxaemia", Diabetologica, 2007, vol. 50: pp. 2374-2383.
Psichas, et al., "The short chain fatty acid propionate stimulates GLP-1 and PYY secretion via free fatty acid receptor 2 in rodents", Int J Obes, 2015, vol. 39: pp. 424-429.
Codella, R et al (2018) Exercise has the guts: how physical activity may positively modulate gut microbiota in chronic and immune-based diseases. Digest Liv Dis 50: 331-341.
Engelke, et al., "Clinical Use of Quantitative Computed Tomography and Peripheral Quantitative Computed Tomography in the Management of Osteoporosis in Adults: The 2007 ISCD Official Positions", Journal of Clinical Densitometry, 2008, vol. 11, No. 1: pp. 123-162.
Engelke, et al., "Regional distribution of spine and hip QCT BMD responses after one year of once-monthly ibandronate in postmenopausal osteoporosis", Bone, 2010, vol. 46: pp. 1626-1632.
Puertollano, et al., "Biological significance of short-chain fatty acid metabolism by the intestinal microbiome", Curr Opin Clin Nutr Metab Care, 2014, vol. 17, No. 2: pp. 139-144.
David, LA et al (2014) Diet rapidly and reproducibly alters the human gut microbiome. Nature 505: 559-563.
Hehemann, et al., "Transfer of carbohydrate-active enzymes from marine bacteria to Japanese gut microbiota", Nature, 2010, vol. 464: pp. 908-914.
Heineken, et al., "Systems-level characterization of a host-microbe metabolic symbiosis in the mammalian gut", Gut microbes, 2013, vol. 4, No. 1: pp. 28-40.
Pyra, et al., "Prebiotic Fiber Increases Hepatic Acetyl CoA Carboxylase Phosphorylation and Suppresses Glucose-Dependent Insulinotropic Polypeptide Secretion More Effectively When Used with Metformin in Obese Rats", J Nutr, 2012, vol. 142, No. 2: pp. 213-220.
De Vadder, F et al (2016) Microbiota-Produced Succinate Improves Glucose Homeostasis via Intestinal Gluconeogenesis. Cell Metab 24: 151-157.
Kishida, et al., "Effect of miglitol on the suppression of nonalcoholic steatohepatitis development and improvement of thegut environment in a rodent model", J Gastroenterol, 2017, vol. 52, No. 11: pp. 1180-1191.
Koh, et al., "From Dietary Fiber to Host Physiology: Short Chain Fatty Acids as Key Bacterial Metabolites", Cell, 2016, vol. 165: pp. 1332-1345.
Qin, et al., "A human gut microbial gene catalogue established by metagenomic sequencing", Nature, 2010, vol. 464: pp. 59-65.
Delzenne, NM (2015) Gut microorganisms as promising targets for the management of type 2 diabetes. Diabetalogia 58: 2206-2217.
Montandon, et al., "Effects of Antidiabetic Drugs on Gut Microbiota Composition", Genes, 2017, vol. 8, No. 250: pp. 1-12.
Moriwake, et al., "Delphinidin, One of the Major Anthocyanidins, Prevents Bone Loss through the Inhibition of Excessive Osteoclastogenesis in Osteoporosis Model Mice", PLoS One, May 2014, vol. 9, No. 5: pp. 1-11.
Quach, et al., "Characterizing how probiotic *Lactobacillus reuteri* 6475 and lactobacillic acid mediate suppression of osteoclast differentiation", Bone Reports, 2019, vol. 11, pp. 1-14.
Derrien, M et al., (2015) Fate, activity, and impact of ingested bacteria within the human gut microbiota. Trends in Microbiol 23(6): 354-366.
Cowardin, et al., "Mechanisms by which sialylated milk oligosaccharides impact bone biology in a gnotobiotic mouse model of infant undernutrition", PNAS, Jun. 11, 2019, vol. 116, No. 24: pp. 11988-11996.
Cox, et al., "SolexaQA: At-a-glance quality assessment of Illumina second-generation sequencing data", BMC Bioinformatics, 2010, vol. 11, No. 485: pp. 1-6.
Raisz, et al., "Short-Term Risedronate Treatment in Postmenopausal Women: Effects on Biochemical Markers of Bone Turnover", Osteoporosis International, 2000, vol. 11: pp. 615-620.
Devaraj, S et al (2013) The Human Gut Microbiome and Body Metabolism: Implications for Obesity and Diabetes. Clin Chem 59(4): 617-628.
Jahangir, et al., "Type 2 Diabetes Current and Future Medications: A Short Review", Int J Pharm Pharmacol, 2017, vol. 1, No. 1: p. 101.
Jain, et al., "High throughput ANI analysis of 90K prokaryotic genomes reveals clear species boundaries", Nature Communications, 2018, vol. 9, No. 5114: pp. 1-8.
Ramirez-Puebla, et al., "Gut and Root Microbiota Commonalities", App Environ Microbiol, 2013, vol. 79, No. 1: pp. 2-9.
Drew, L (2016) Reseeding the gut. Nature 540:s109-s112.
Bai, et al., "Response of gut microbiota and inflammatory status to bitter melon (*Momordica charantia* L.) in high fat diet induced obese rats", J Ethnopharmacol, 2016, vol. 194: pp. 717-726.
Bakker-Zierikzee, et al., "Effects of infant formula containing a mixture of galacto- and fructo-oligosaccharides or viable Bifidobacterium animalis on the intestinal microflora during the first 4 months of life", Br J Nutr, 2005, vol. 94: pp. 783-790.
Rastall, et al., "Recent developments in prebiotics to selectively impact beneficial microbes and promote intestinal health", Curr Opin Biotechnol, 2015, vol. 32, pp. 42-46.
Duncan, SH et al (2004) Contribution of acetate to butyrate formation by human faecal bacteria. Br J Nutr 91: 915-923.
Li, et al., "Sex steroid deficiency-associated bone loss is microbiota dependent and prevented by probiotics", The Journal of Clinical Investigation, Jun. 2016, vol. 126, No. 6: pp. 2049-2063.
Li, et al., "Microbial osteoporosis: The interplay between the gut microbiota and bones via host metabolism and immunity", MicrobiologyOpen, 2019: pp. 1-15.
Rastogi, et al., "Leaf microbiota in an agroecosystem: spatiotemporal variation in bacterial community composition on field-grown lettuce", ISME J, 2012, vol. 6: pp. 1812-1822.

(56) References Cited

OTHER PUBLICATIONS

Frost, G et al (2014) The short-chain fatty acid acetate reduces appetite via a central homeostatic mechanism. Nat Commun. 5(3611): 1-11.
Gehrig, et al., "Effects of microbiota-directed foods in gnotobiotic animals and undernourished children", Science, Jul. 12, 2019, vol. 365, No. 139: pp. 1-12.
Gehrig, et al., "Supplementary Material for: Effects of microbiota-directed foods in gnotobiotic animals and undernourished children", Science, Jul. 12, 2019, vol. 365, No. 139: pp. 1-42.
Ravussin, et al., "Responses of Gut Microbiota to Diet Composition and Weight Loss in Lean and Obese Mice", Obesity, 2012, vol. 20, No. 4: pp. 738-747.
Gibson, G et al., (1995) Dietary Modulation of the Human Colonic Microbiota: Introducing the Concept of Prebiotics. J Nutr 125(6):1401-1412.
Dar, et al., "*Bacillus clausii* inhibits bone loss by skewing Treg-Th17 cell equilibrium in postmenopausal osteoporotic mice model", Nutrition, 2018, vol. 54, pp. 118-128.
Das, et al., "Prevention of Diabetes—A Historical Note", IJHS, 2013, vol. 48, No. 4, pp. 625-642.
Davies, et al., "Effect of Oral Semaglutide Compared With Placebo and Subcutaneous Semaglutide on Glycemic Control in Patients With Type 2 Diabetes", JAMA, 2017, vol. 318, No. 15: pp. 1460-1470.
Gunnarsson, et al., "Potential of Jerusalem artichoke (*Helianthus tuberosus* L.) as a biorefinery crop." *Industrial Crops and Products* 56 (2014): 231-240.
Vorholt, et al., "Microbial life in the phyllosphere", Institute of Microbiology, Dec. 2012, vol. 10: pp. 828-840.
De La Cuesta-Zuluaga, et al., "Metformin Is Associated With Higher Relative Abundance of Mucin-Degrading Akkermansia muciniphila and Several Short-Chain Fatty Acid-Producig Microbiota in the Gut", Diabetes Care, 2017, vol. 40: pp. 54-62.
Di Francesco, et al., "A time to fast", Science, 2018, vol. 362: pp. 770-775.
Duong-Ly, et al., "T cell activation triggers reversible inosine-5'-monophosphate dehydrogenase assembly", Journal of Cell Science, 2018, vol. 131: pp. 1-8.
Wagner, et al., "The Pentose Phosphate Pathway in Regenerating Skeletal Muscle", Biochem. 1978, vol. 170: pp. 17-22.
Eastell, et al., "Use of bone turnover markers in postmenopausal osteoporosis", Lancet Diabetes Endocrinol 2017, vol. 5: pp. 908-923.
Elzinga, et al., "The Use of Defined Microbial Communities To Model Host-Microbe Interactions in the Human Gut", Microbiology and Molecular Biology Reviews, Jun. 2019, vol. 83, No. 2: pp. 1-40.
Yang et al., "The prospects of Jerusalem artichoke in functional food ingredients and bioenergy production," Biotechnology Reports 5: 77-88 (2015).
Wahlstrom, et al., "Intestinal Crosstalk between Bile Acids and Microbiota and Its Impact on Host Metabolism", Cell Metab, 2016, vol. 24: pp. 41-50.
Engelke, et al., "Clinical Use of Quantitative Computed Tomography (QCT) of the Hip in the Management of Osteoporosis in Adults: the 2015 ISCD Official Positions—Part I", Journal of Clinical Densitometry: Assessment & Management of Musculoskeletal Health, 2015, vol. 18, No. 3: pp. 338-358.
Ericsson, et al., "Variable Colonization after Reciprocal Fecal Microbiota Transfer between Mice with Low and High Richness Microbiota", Front Microbiol, 2017, vol. 8, No. 196: pp. 1-13.
Everard, et al., "Microbiome of prebiotic-treated mice reveals novel targets involved in host response during obesity", ISME, 2014, vol. 8: pp. 2116-2130.
Wallace, et al., "Use and Abuse of HOMA Modeling", Diabetes Care, 2004, vol. 27, No. 6: pp. 1487-1495.
Everard, et al., "Diabetes, obesity and gut microbiota", Best Pract Res Clin Gastroenterol, 2013, vol. 27: pp. 73-83.
Fairbanks, et al., "Importance of Ribonucleotide Availability to ProliferatingT-lymphocytes from Healthy Humans", The Journal of Biological Chemistry, 1995, vol. 270, No. 50; pp. 29682-29689.
Edgar, "Updating the 97% identity threshold for 16S ribosomal RNA OTUs." *Bioinformatics* 34, No. 14 (2018): 2371-2375.
Wang, et al., "Modulation of gut microbiota during probiotic-mediated attenuation of metabolic syndrome in high fat diet-fed mice", ISME J, 2015, vol. 9: pp. 1-15.
Fletcher, et al., "Shifts in the Gut Metabolome and Clostridium difficile Transcriptome throughout Colonization and Infection in a Mouse Model", mSphere, Mar. 2018, vol. 3, No. 2: pp. 1-18.
Forslund, et al., "Corrigendum: Disentangling type 2 diabetes and metformin treatment signatures in the human gut microbiota", Nature, 2015, vol. 528, No. 7581: pp. 262-266.
Gad, et al., "Anti-aging effects of L-arginine", Journal of Advanced Research, 2010, vol. 1: pp. 169-177.
Wassermann, et al., "Harnessing the microbiomes of *Brassica* vegetables for health issues", Sci Rep, 2017, vol. 7: p. 17649.
Gagnon, et al., "Bone Health After Bariatric Surgery", JBMR Plus, 2017, vol. 2: pp. 1-13.
Garidou, et al., "The Gut Microbiota Regulates Intestinal CD4 T Cells Expressing RORγt and Controls Metabolic Disease", Cell Metab, 2015, vol. 22: pp. 100-112.
Nguyen, et al., "A perspective on 16S rRNA operational taxonomic unit clustering using sequence similarity." *NPJ biofilms and microbiomes* 2, No. 1 (2016): 1-8.
Wasserman, et al., "An Apple a Day: Which Bacteria Do We Eat With Organic and Conventional Apples", Frontiers in Microbiology, Jul. 24, 2019, vol. 10, Article 1629: pp. 1-13.
Gentile, et al., "The gut microbiota at the intersection of diet and human health", Science, 2018, vol. 362: pp. 776-780.
Geva-Zatorsky, et al., "Mining the Human Gut for Immunomodulatory Organisms", Cell, Feb. 23, 2017, vol. 168: pp. 928-943.
Gonzalez-Garcia, et al., "Microbial propionic acid production", Fermentation, 2017, vol. 3, No. 21: pp. 1-20.
Weitkunat, et al., "Short-chain fatty acids and inulin, but not guar gum, prevent diet-induced obesity and insulin resistance through differential mechanisms in mice", Sci Rep, 2017, vol. 7, No. 6109: pp. 1-13.
Gosalbes, et al., "Metabolic adaptation in the human gut microbiota during pregnancy and the first year of life", EBioMedicine, 2019, vol. 39: pp. 497-509.
Graessler, et al., "Metagenomic sequencing of the human gut microbiome before and after bariatric surgery in obese patients with type 2 diabetes: correlation with inflammatory and metabolic parameters", Pharmacogenetics J, 2013, vol. 13: pp. 514-522.
PCT/US2019/049823—International Search Report and Written Opinion, Feb. 20, 2020, 12 pages.
Weitzmann, et al., "Estrogen deficiency and bone loss: an inflammatory tale", The Journal of Clinical Investigation, May 2006, vol. 116, No. 5: pp. 1186-1194.
Grey, et al., "Duration of Antiresorptive Effects of Low-Dose Zoledronate in Osteopenic Postmenopausal Women: A Randomized, Placebo-Controlled Trial", Journal of Bone and Mineral Research, Jan. 2014, vol. 29, No. 1: pp. 166-172.
Gu, et al., "Analyses of gut microbiota and plasma bile acids enable stratification of patients for antidiabetic treatment", Nature Commun, 2017, vol. 8: p. 1785.
Hacquard, et al., "Microbiota and Host Nutrition across Plant and Animal Kingdoms", Cell Host & Microbe, 2015, vol. 17: pp. 603-616.
Welch, et al., "The Effects of Flavonoids on Bone", Curr Osteoporos Rep., 2014, vol. 12: pp. 205-210.
Harley, et al., "Obesity and the gut microbiome: Striving for causality", Mol Metab, 2012, vol. 1: pp. 21-31.
Heaney, et al., "Dairy and Bone Health", Journal of the American College of Nutrition, 2009, vol. 28, No. 1: pp. 82S-90S.
GenBank KC111446.1. Hanseniaspora opuntiae strain JEY269 18S ribosomal RNA gene, partial sequence; internal transcribed spacer 1, 5.8S ribosomal RNA gene, and internal transcribed spacer 2, complete sequence; and 28S ribosomal RNA gene, partial sequence.

(56) References Cited

OTHER PUBLICATIONS

Jul. 24, 2013 [online]. [Retrieved Dec. 10, 2019]. Retrieved from the internet: <URL: https:/twww.ncbi.nlm.nih.gov/nuccore/KC111446.1/ >. Especially p. 1.
White, et al., "A Brief History of the Development of Diabetes Medications", Diabetes Spectr, 2015, vol. 27, No. 2: pp. 82-86.
Henao-Mejia, et al., "Inflammasome-mediated dysbiosis regulates progression of NAFLD and obesity", Nature, 2012, vol. 482, No. 7384: p. 179-185.
Hess, et al., "Dairy Foods: Current Evidence of their Effects on Bone, Cardiometabolic, Cognitive, and Digestive Health", Comprehensive Reviews in Food Science and Food Safety, 2016, vol. 15: pp. 251-268.
Holmes, et al., "Diet-Microbiome Interactions in Health Are Controlled by Intestinal Nitrogen Source Constraints", Cell Metab, 2017, vol. 25: pp. 140-151.
Whisner, et al., "Prebiotics, Bone and Mineral Metabolism", Calcif Tissue Int, 2018, vol. 102: pp. 443-479.
Hooper, et al., "Interactions Between the Microbiota and the Immune System", Science, 2012, vol. 336, No. 6086: pp. 1268-1273.
Hugenholtz, et al., "Mouse models for human intestinal microbiota research: a critical evaluation", Cellular and Molecular Life Sciences, 2018, vol. 75: pp. 149-160.
PCT/US2019/049823—Invitation to Pay Additional Fees, Dec. 10, 2019, 2 pages.
Winer, et al., "The Intestinal Immune System in Obesity and Insulin Resistance", Cell Metab, 2016, vol. 23: pp. 413-426.
Imaoka, et al., "Anti-inflammatory activity of probiotic Bifidobacterium: enhancement of IL-10 production in peripheral blood mononuclear cells from ulcerative colitis patients and inhibition of IL-8 secretion in HT-29 cells", World J Gastroenterol, 2008, vol. 14, No. 16: pp. 2511-2516.
Imlay, et al., "Diagnosing oxidative stress in bacteria: not as easy as you might think", Current Opinion in Microbiology, 2015, vol. 24: pp. 124-131.
Jackson, et al., "Culture dependent and independent analysis of bacterial communities associated with commercial salad leaf vegetables", BMC Microbiol, 2013, vol. 13, No. 274: pp. 1-12.
Winer, et al., "Immunologic impact of the intestine in metabolic disease", J Clin Invest, 2017, vol. 127, No. 1: pp. 33-42.
Jackson, et al., "Emerging Perspectives on the Natural Microbiome of Fresh Produce Vegetables", Agriculture, 2015, vol. 5: pp. 170-187.
Jafarnejad, et al., "Effects of a Multispecies Probiotic Supplement on Bone Health in Osteopenic Postmenopausal Women: A Randomized, Double-blind, Controlled Trial", Journal of the American College of Nutrition, 2017, vol. 36, No. 7: pp. 497-506.
PCT/US2020/038830—Invitation to Pay Additional Fees, Oct. 29, 2020, 24 pages.
Wolfert, et al., "Adaptive immune activation: glycosylation does matter", Nat Chem Biol, Dec. 2013, vol. 9, No. 12: pp. 776-784.
Jain, et al., "Nanopore sequencing and assembly of a human genome with ultra-long reads", Nature Biotechnology, 2018, vol. 36, No. 4: p. 338.
Jansson, et al., "Probiotic treatment using a mix of three *Lactobacillus* strains for lumbar spine bone loss in postmenopausal women: a randomised, double-blind, placebo-controlled, multicentre trial", Lancet Rheumatol, Nov. 2019, vol. 1: e154-62.
Jennings, et al., "Amino Acid Intakes Are Associated With Bone Mineral Density and Prevalence of Low Bone Mass in Women: Evidence From Discordant Monozygotic Twins", Journal of Bone and Mineral Research, Feb. 2016, vol. 31, No. 2: pp. 326-335.
Woo, et al., "Metformin Ameliorates Hepatic Steatosis and Inflammation without Altering Adipose Phenotype in Diet-Induced Obesity", PLoS One, 2014, vol. 9, No. 3: e91111.
Jia, et al., "CARD 2017: expansion and model-centric curation of the comprehensive antibiotic resistance database", Nucleic Acids Res, 2017, No. 45: p. D566-D573.
Kaluzna-Czaplinska, et al., "Is there a relationship between intestinal microbiota, dietary compounds, and obesity?", Trends Food Sci Technol, 2017, vol. 70: p. 105-113.
Abubucker, et al., "Metabolic Reconstruction for Metagenomic Data and Its Application to the Human Microbiome", PLoS Computational Biology, Jun. 2012, vol. 8, No. 6: pp. 1-17.
Wu, et al., "Metformin alters the gut microbiome of individuals with treatment-naïve type 2 diabetes, contributing to the therapeutic effects of the drug", Nat Med, 2017, vol. 23, No. 7: pp. 850-858.
Kasubuchi, et al., "Dietary Gut Microbial Metabolites, Short-chain Fatty Acids, and Host Metabolic Regulation", Nutrients, 2015, vol. 7: pp. 2839-2849.
Kau, et al., "Human nutrition, the gut microbiome and the immune system", Nature, 2011, vol. 474: pp. 327-336.
Kim, et al., "Immune regulation by microbiome metabolites", Immunology, 2018, vol. 154, pp. 220-229.
Wu, et al., "Supplement: Metformin alters the gut microbiome of individuals with treatment-naïve type 2 diabetes, contributing to the therapeutic effects of the drug", Nat Med, 2017, vol. 23, No. 7.
Kimura, et al., "The gut microbiota suppresses insulin-mediated fat accumulation via the short-chain fatty acid receptor GPR43", Nat Commun, 2013, vol. 4, No. 1829: pp. 1-12.
King, et al., "Regulation of de novo purine synthesis inhuman bone marrow mononuclear cells by hypoxanthine.", The Journal of Clinical Investigation, 1983;72(3):965-970.
Akamatsu, et al., "Conversion of antigen-specific effector/memory T cells Into Foxp3-expressing Treg cells by inhibition of CDK8/19", Science Immunology, Oct. 25, 2019, vol. 4: pp. 1-16.
Wu, et al., "Arginine metabolism and nutrition in growth, health and disease", Amino Acids, May 2009, vol. 31, No. 1: pp. 153-168.
König, et al., "Specific Collagen Peptides Improve Bone Mineral Density and Bone Markers in Postmenopausal Women—A Randomized Controlled Study", Nutrients, 2018, vol. 10. No. 97: pp. 1-11.
Kreznar, et al., "Host Genotype and Gut Microbiome Modulate Insulin Secretion and Diet-Induced Metabolic Phenotypes", Cell Rep, 2017, vol. 18: pp. 1739-1750.
Lambert, et al., "Combined bioavailable isoflavones and probiotics improve bone status and estrogen metabolism in postmenopausal osteopenic women: a randomized controlled trial", Am J Clin Nutr, 2017, vol. 106: pp. 909-920.
Xu, et al., "Intestinal microbiota: a potential target for the treatment of postmenopausal osteoporosis", Bone Research, 2017, vol. 5: pp. 1-18.
Lang, et al., "The microbes we eat: abundance and taxonomy of microbes consumed in a day's worth of meals for three diet types", PeerJ, 2014, 2:e659; doi 10.7717/peerj.659.
Langmead, at al., "Fast gapped-read alignment with Bowtie 2", Nat Methods, 2012, vol. 9, No. 4: pp. 357-359.
Ananthakrishnan, et al., "Gut Microbiome Function Predicts Response to Anti-integrin Biologic Therapy in Inflammatory Bowel Diseases", Cell Host & Microbe, May 10, 2017, vol. 21: pp. 603-610.
Yan, et al., "Gut microbiota induce IGF-1 and promote bone formation and growth", PNAS, Nov. 7, 2016: pp. 1-10.
Lee, et al., "Blueberry Supplementation Influences the Gut Microbiota, Inflammation, and Insulin Resistance in High-Fat-Diet-Fed Rats", J Nutr, 2018, vol. 148, No. 2: pp. 209-219.
Lewiecki, et al., "Once-Monthly Oral Ibandronate Improves Biomechanical Determinants of Bone Strength in Women with Postmenopausal Osteoporosis", J Clin Endocrinol Metab, Jan. 2009, vol. 94, No. 1: pp. 171-180.
Li, et al., "Metabolic Surgery Profoundly Influences Gut Microbial-Host Metabolic Crosstalk", Gut, 2011, vol. 60, No. 9: pp. 1214-1223.
Yang, et al., "Potent Anti-Inflammatory and Antiadipogenic Properties of Bamboo (*Sasa coreana* Nakai) Leaves Extract and Its Major Constituent Flavonoids", J Agric Food Chem, 2017, vol. 65: pp. 6665-6673.
Li, et al., "Butyrate reduces appetite and activates brown adipose tissue via the gut-brain neural circuit", Gut, 2017: pp. 1-11.
Li, et al., "Intermittent Fasting Promotes White Adipose Browning and Decreases Obesity by Shaping the Gut Microbiota", Cell Metab, 2017, vol. 26: pp. 672-685.

(56) References Cited

OTHER PUBLICATIONS

Arjmandi, et al., "Bone-Protective Effects of Dried Plum in Postmenopausal Women: Efficacy and Possible Mechanisms", Nutrients, 2019, vol. 9, No. 496: pp. 1-19.
Yassour, et al., "Natural history of the infant gut microbiome and impact of antibiotic treatment on bacterial strain diversity and stability", Sci Transl Med, 2016, vol. 8, No. 343: pp. 1-12.
Lin, et al., "Butyrate and propionate protect against diet-induced obesity and regulate gut hormones via free fatty acid receptor 3-independent mechanisms", PLoS One, 2012, vol. 7, No. 4: pp. 1-9.
Liu, et al., "VFDB 2019: a comparative pathogenomic platform with an interactive web interface", Nucleic Acids Res, 2019, vol. 47: D687-D692.
Lu, et al., "Short Chain Fatty Acids Prevent High-fat-diet-induced Obesity in Mice by Regulating G Protein-coupled Receptors and Gut Microbiota", Sci Rep, 2016, vol. 6, No. 37589: pp. 1-13.
Yousef, et al., "Metformin: A Unique Herbal Origin Medication", GJMR-B: Pharma, Drug Discovery, Toxicology, and Medicine, 2017, vol. 17, No. 3: pp. 31-37.
Lucas, et al., "Short-chain fatty acids regulate systemic bone mass and protect from pathological bone loss", Nature Communications, 2018, vol. 9, No. 55: pp. 1-10.
Lyu, et al., "Balancing Herbal Medicine and Functional Food for Prevention and Treatment of Cardiometabolic Diseases through Modulating Gut Microbiota", Front Microbiol, 2017, vol. 8, No. 2146: pp. 1-21.
Atarashi, et al., "Induction of Colonic Regulatory T Cells by Indigenous Clostridium Species", Science, Jan. 21, 2011, vol. 331: pp. 337-341.
Zaiss, et al., "Treg Cells Suppress Osteoclast Formation", Arthritis & Rheumatism, Dec. 2017, vol. 56, No. 12: pp. 4104-4112.
Maier, et al., Extensive impact of non-antibiotic drugs on human gut bacteria, Nature, 2018: pp. 1-6.
Martinez-Lopez, et al., "System-wide Benefits of Intermeal Fasting by Autophagy", Cell Metab, 2017, vol. 26: pp. 856-871.
McCabe, et al., "Prebiotic and Probiotic Regulation of Bone Health: Role of the Intestine and its Microbiome", Curr Osteoporosis Rep., Dec. 2015, vol. 13, No. 6: pp. 636-371.
Zaiss, et al., "Increased Bone Density and Resistance to Ovariectomy-Induced Bone Loss in FoxP3-Transgenic Mice Based on Impaired Osteoclast Differentiation", Arthritis & Rheumatism, Aug. 2010, vol. 62, No. 8: pp. 2328-2338.
Meng, et al., "Anti-inflammatory effects of *Bifidobacterium longum* subsp *infantis* secretions on fetal human enterocytes are mediated by TLR-4 receptors", Am J Physiol Gastrointest Liver Physiol, 2016, vol. 311:G744-G753.
Milani, et al., "Bifidobacteria exhibit social behavior through carbohydrate resource sharing in the gut", Sci Rep, 2015, vol. 5, No. 15782: pp. 1-14.
Backhed, et al., "The gut microbiota as an environmental factor that regulates fat storage", PNAS, 2004, vol. 101, No. 44: pp. 15718-15723.
Zhang, et al., "Human gut microbiota in obesity and after gastric bypass", PNAS, 2009, vol. 106, No. 7: pp. 2365-2370.
Morrison, et al., "Formation of short chain fatty acids by the gut microbiota and their impact on human metabolism", Gut Microbes, 2016, vol. 7, No. 3: pp. 189-200.
Moslehi-Jenabian, et al., "Beneficial Effects of Probiotic and Food Borne Yeasts on Human Health", Nutrients, 2010, vol. 2: pp. 449-473.
Munder, et al., "Arginase: an emerging key player in the mammalian immune system", British Journal of Pharmacology, 2009, vol. 158: pp. 638-651.
Zhang, et al., "Effect of probiotics on glucose metabolism in patients with type 2 diabetes mellitus: a meta-analysis of randomized controlled trials", Medicina, 2016, vol. 52: pp. 28-34.
Myneni, et al., "Regulation of bone remodeling by vitamin K2", Oral Diseases, 2017, vol. 23 pp. 1021-1028.
Napolitano, et al., "Novel Gut-Based Pharmacology of Metformin in Patients with Type 2 Diabetes Mellitus", PLoS One, 2014, vol. 9, No. 7: e100778.
Backhed, et al., "Mechanisms underlying the resistance to diet-induced obesity in germ-free mice", PNAS, 2007, vol. 104, No. 3: pp. 979-984.
Zhang, et al., "Structural Changes of Gut Microbiota during Berberine-Mediated Prevention of Obesity and Insulin Resistance in High-Fat Diet-Fed Rats", PLoS One, 2012, vol. 7, No. 8: e42529.
Nilsson, et al., "*Lactobacillus reuteri* reduces bone loss in older women with low bone mineral density: a randomized, placebo-controlled, double-blind, clinical trial", The Journal of Internal Medicine, 2018, vol. 284: pp. 307-317.
Ohlsson, et al., "Probiotics Protect Mice from Ovariectomy-Induced Cortical Bone Loss", Plos One, Mar. 2014, vol. 9, No. 3: pp. 1-8.
Olar, et al., "Prospects for new antimicrobials based on N,N-dimethylbiguanide complexes as effective agents on both planktonic and adhered strains", Eur J Med Chem, 2010, vol. 45: pp. 2868-2875.
Zhang, et al., "Modulation of gut microbiota by berberine and metformin during the treatment of high-fat diet-induced obesity in rats", Sci Rep, 2015, vol. 5, No. 14405: pp. 1-10.
Olson, et al., "Obesity and the tumor microenvironment", Science, 2017, vol. 358, No. 6367: pp. 1130-1131.
Rosenbaum, M (2015) The gut microbiota in human energy homeostasis and obesity. Trends Endocrinol Metab 26(9): 493-501.
Morishita, et al., "Production of menaquinones by lactic acid bacteria." Journal of dairy science 82, No. 9 (1999): 1897-1903.
Zhang, et al., "Effects of Acarbose on the Gut Microbiota of Prediabetic Patients: A Randomized, Double-blind, Controlled Crossover Trial", 2017, vol. 8: pp. 293-307.
Bernini, et al., "Beneficial effects of Bifidobacterium lactis on lipid profile and cytokines in patients with metabolic syndrome", Nutrition, 2016, vol. 32: pp. 716-719.
Bleau, et al., "Crosstalk between intestinal microbiota, adipose tissue and skeletal muscle as an early event in systemic low-grade inflammation and the development of obesity and diabetes", Diabetes Metab Res Rev, 2015, vol. 31, No. 6: pp. 545-561.
Bouxsein, et al., "Considerations for Development of Surrogate Endpoints for Antifracture Efficacy of New Treatments in Osteoporosis: A Perspective", Journal of Bone and Mineral Research, Mar. 3, 2008, vol. 23, No. 8: pp. 1155-1167.
Zhao, et al., "Gut bacteria selectively promoted by dietary fibers alleviate type 2 diabetes", Science, 2018, vol. 359: pp. 1151-1156.
Bron, et al., "Emerging molecular insights into the interaction between probiotics and the host intestinal mucosa", Nat Rev Microbiol, 2012, vol. 10: pp. 66-78.
Brown, et al., "Gut Microbiota Regulation of T Cells During Inflammation and Autoimmunity", Annual Review of Immunology, 2019, vol. 37: pp. 599-624.
Wagner, et al., "Pyruvate fermentation by Oenococcus oeni and Leuconostoc mesenteroides and role of pyruvate dehydrogenase in anaerobic fermentation." Applied and environmental microbiology 71, No. 9 (2005): 4966-4971.
Zheng, et al., "Prebiotic mannan-oligosaccharides augment the hypoglycemic effects of metformin in correlation with modulating gut microbiota", J Agric Food Chem, 2018, vol. 66, No. 23: pp. 5821-5831.
Carbonero, et al., "Microbial pathways in colonic sulfur metabolism and links with health and disease", Frontiers in Immunology, Nov. 28, 2012, vol. 3, Article 448: pp. 1-11.
Chanclud, et al., "Plant hormones: key players in gut microbiota and human diseases?", Trends Plant Sci, 2017, vol. 22, No. 9: 754-758.
Chen, et al., "Metabolism of Fructooligosaccharides in Lactobacillus plantarum ST-III via Differential Gene Transcription and Alteration of Cell Membrane Fluidity", Appl Environ Microbiol, 2015, vol. 81, No. 22: pp. 7697-7707.
Zhou, et al., "Age-dependent variations of cancellous bone in response to ovariectomy in C57BL/6J mice", Experimental and Therapeutic Medicine, 2018, vol. 15: pp. 3623-3632.
Chiang, et al., "Antiosteoporotic Effects of *Lactobacillus*-Fermented Soy Skim Milk on Bone Mineral Density and the

(56) References Cited

OTHER PUBLICATIONS

Microstructure of Femoral Bone in Ovariectomized Mice", Journal of Agricultural and Food Chemistry, 2011, vol. 59: pp. 7734-7742.
Correa, et al., "Regulation of immune cell function by short-chain fatty acids", Clinical & Translational Immunology, 2016, vol. 5, pp. 1-8.
Wikipedia, https://en.wikipedia.org/wiki/Pyruvate_dehydrogenase_complex, accessed Dec. 3, 2021.
Zmora, et al., "Personalized Gut Mucosal Colonization Resistance to Empiric Probiotics Is Associated with Unique Host and Microbiome Features", Cell, 2018, vol. 174: pp. 1388-1405.
Dalby, et al., "Dietary Uncoupling of Gut Microbiota and Energy Harvesting from Obesity and Glucose Tolerance in Mice", Cell Reports, 2017, vol. 21 pp. 1521-1533.
Voreades, et al., "Diet and the development of the human intestinal microbiome", Front Microbiol, 2014, vol. 5, No. 494: 1-9.
De Jesus Raposo, et al., "Emergent Sources of prebiotics: seaweed and microalgae", Mar. Drugs, 2016, vol. 14, No. 2: doi: 10.3390/md14020027.
Reichold, et al., "*Bifidobacterium adolescentis* protects from the development of nonalcoholic steatohepatitis in a mouse model", J Nutr Biochem, 2014, vol. 25: pp. 118-125.
Ding, et al., "The regulation of immune cells by Lactobacilli: a potential therapeutic target for anti-atherosclerosis therapy", Oncotarget, 2017, vol. 8, No. 35: pp. 59915-59928.
Rios-Covain, et al., "Enhanced butyrate formation by cross-feeding between *Faecalibacterium prausnitzii* and *Bifidobacterium adolescentis*", FEMS Microbiol Lett, 2015, vol. 362, No. 21: pp. 1-7.
Allgeier, RJ et al (1929) A colorimetric method for the determination of butyric acid. J Bacteriol 17(2): 79-87.
Rosario, et al., "Understanding the Representative Gut Microbiota Dysbiosis in Metformin-Treated Type 2 Diabetes Patients Using Genome-Scale Metabolic Modeling", Front Physiol, 2018, vol. 9: p. 775.
Everard, et al., "Cross-talk between Akkermansia muciniphila and intestinal epithelium controls diet-induced obesity", PNAS, 2013, vol. 11, No. 22: pp. 9066-9071.
Fang, et al., "Intestinal FXR agonism promotes adipose tissue browning and reduces obesity and insulin resistance", Nature, 2015, vol. 21, No. 2: pp. 159-167.
Rosenblatt, et al., "Is It Ethical to Conduct Placebo-Controlled Clinical Trials in the Development of New Agents for Osteoporosis? An Industry Perspective", Journal of Bone and Mineral Research, 2003, vol. 18, No. 6: pp. 1142-1145.
Franzosa, et al., "Species-level functional profiling of metagenomes and metatranscriptomes", Nature Methods, Nov. 2018, vol. 15, pp. 962-968.
Round, et al., "The gut microbiota shapes intestinal immune responses during health and disease", Nat Rev Immunol, 2009, vol. 9: pp. 313-324.
Aron-Wisnewsky, J et al (2012) The importance of the gut microbiota after bariatric surgery. Nature 9(10): 590-598.
Saltiel, et al., "Inflammatory mechanisms linking obesity and metabolic disease", J Clin Invest, 2017, vol. 127, No. 1: pp. 1-4.
Gilbert, et al., "Current understanding of the human microbiome", Nature Medicine, Apr. 2018, vol. 24, No. 4: pp. 392-400.
Samah, et al., "Probiotics for the management of type 2 diabetes mellitus: A systematic review and meta-analysis", Diabetes Res Clin Pract, 2016, vol. 118: pp. 172-182.
Greenspan, et al., "Early Changes in Biochemical Markers of Bone Turnover Predict the Long-Term Response to Alendronate Therapy in Representative Elderly Women: A Randomized Clinical Trial", Journal of Bone and Mineral Research, 1998, vol. 13, No. 9: pp. 1431-1438.
Samuel, et al., "Effects of the gut microbiota on host adiposity are modulated by the short-chain fatty-acid binding G protein-coupled receptor, Gpr41", PNAS, 2008, vol. 105, No. 43: pp. 16767-16772.
Guo, et al., "Secretions of Bifidobacterium infantis and Lactobacillus acidophilus Protect Intestinal Epithelial Barrier Function", JPGN, 2017, vol. 64, No. 3: pp. 404-412.
Sawin, et al., "Glycomacropeptide is a prebiotic that reduces *Desulfovibrio* bacteria, increases cecal short-chain fatty acids, and is anti-inflammatory in mice", Am J Physiol Gastrointest Liver Physiol, 2015, vol. 309: G590-G601.
Berg, G et al (2015) The Edible Plant Microbiome: Importance and Health Issues. In: Lugtenberg B. (eds) Principles of Plant-Microbe Interactions, Chapter 44,. Springer, Cham.
Schoch, C.L. et al., "Nuclear ribosomal internal transcribed spacer (ITS) region as a universal DNA barcode marker for *Fungi*," Proceedings of the National Academy of Sciences, 2012, vol. 109, No. 16, pp. 6241-6246.
Hildebrandt, et al., "High Fat Diet Determines the Composition of the Murine Gut Microbiome Independently of Obesity", Gastroenterology, 2009, vol. 137, No. 5: p. 1716.
Schroeder, et al., "Bifidobacteria or Fiber Protects against Diet-Induced Microbiota-Mediated Colonic Mucus Deterioration", Cell Host & Microbe, 2018, vol. 23: pp. 27-40.
Ilhan, et al., (2017) "Distinctive microbiomes and metabolites linked with weight loss after gastric bypass, but not gastric banding", ISME J 11(9): 2047-2058.
Scott, et al., "Manipulating the gut microbiota to maintain health and treat disease", Micro Ecol Health Dis, 2015, vol. 26, No. 25877: pp. 1-10.
Iwami, et al., "Effects of Short Chain Fatty Acid, Sodium Butyrate, on Osteoblastic Cells and Osteoclastic Cells", Int. J. Biochem., 1993, vol. 25, No. 11: pp. 1631-1635.
Serino, et al., "Metabolic adaptation to a high-fat diet is associated with a change in the gut microbiota", Gut, 2012, vol. 61: pp. 543-553.
Brahe, LK et al (2013) Is butyrate the link between diet, intestinal microbiota and obesity-related metabolic diseases? Obes Rev 14: 950-959.
Sheth, et al., "Spatial metagenomic characterization of microbial biogeography in the gut", Nature Biotechnology, Aug. 2019, vol. 37, pp. 877-883.
Jarvis, et al., "Microbiomes Associated With Foods From Plant and Animal Sources", Front Microbiol, 2018, vol. 9: p. 2540.
Shoaie, et al., "Quantifying Diet-Induced Metabolic Changes of the Human Gut Microbiome", Cell Metab, 2015, vol. 22: pp. 320-331.
Kaplan, et al., "Fermentation of Fructooligosaccharides by Lactic Acid Bacteria and Bifidobacterial", Appl Environ Microbiol, 2000, vol. 66, No. 6: pp. 2682-2684.
Singer, et al., "The initiation of metabolic inflammation in childhood obesity", J Clin Invest, 2017, vol. 127, No. 1: pp. 65-73.
Kim, et al., "Impact of L-Arginine Metabolism on Immune Response and Anticancer Immunotherapy", Frontiers in Oncology, Mar. 2018, vol. 8, No. 67: pp. 1-5.
Sjogren, et al., "The Gut Microbiota Regulates Bone Mass in Mice", Journal of Bone and Mineral Research, Jun. 2012, vol. 27, No. 6: pp. 1357-1367.
Abuajah, et al., "Functional components and medicinal properties of food: a review", J Food Sci Technol, 2015, vol. 52, No. 5: pp. 2522-2529.
Smith, et al., "Yeast Modulation of Human Dendritic Cell Cytokine Secretion: An In Vitro Study", PLoS One, 2014, vol. 9, No. 5: pp. 1-14.
Kuo, et al., "Bone biomarker for the clinical assessment of osteoporosis: recent developments and future perspectives", Biomarker Research, 2017, vol. 5, No. 18: pp. 1-9.
Strorelli, et al., "Metformin, Microbes, and Aging", Cell Metab, 2013, vol. 17: pp. 809-811.
Ahlborg, et al., "Bone Loss and Bone Size after Menopause", The New England Journal of Medicine, Jul. 24, 2003, vol. 349, No. 4: pp. 327-334.
Stull, et al., "Blueberries' Impact on Insulin Resistance and Glucose Intolerance", Antioxidants, 2016, vol. 5, No. 44: pp. 1-11.
Ley, et al., "Obesity alters gut microbial ecology", PNAS, 2005, vol. 102, No. 31: pp. 11070-11075.

(56) References Cited

OTHER PUBLICATIONS

Suez, et al., "Post-Antibiotic Gut Mucosal Microbiome Reconstitution Is Impaired by Probiotics and Improved by Autologous FMT", Cell, 2018, vol. 174: pp. 1406-1423.
Alcock, et al., "Is eating behavior manipulated by the gastrointestinal microbiota? Evolutionary pressures and potential mechanisms", Bioessays 2014, vol. 36: pp. 940-949.
Suzek, et al., "UniRef clusters: a comprehensive and scalable alternative for improving sequence similarity searches", Bioinformatics, 2015, vol. 31, No. 6: pp. 926-932.
Louis, et al., "Formation of propionate and butyrate by the human colonic microbiota", Environ Microbiol, 2017, vol. 19, No. 1: pp. 29-41.
Takimoto, et al., "Effect of *Bacillus subtilis* C-3102 on bone mineral density in healthy postmenopausal Japanese women: a randomized, placebo-controlled, double-blind clinical trial", Bioscience of Microbiota, Food and Health, 2018, vol. 37, No. 4: pp. 87-96.
Anastasilakis, et al., "Head-to-head comparison of risedronate vs. teriparatideon bone turnover markers in women with postmenopausal osteoporosis: a randomised trial", Int J Clin Pract, Jun. 2008, vol. 62, No. 6: pp. 919-924.
Terrapon, et al., "How do gut microbes break down dietary fiber?", Trends Biochem Sci, 2014, vol. 39, No. 4: pp. 156-158.
McCabe, et al., "Exercise prevents high fat diet induced bone loss, marrow adiposity and dysbiosis in male mice", Bone, 2018: https://doi.org/10.1016/j.bone.2018.03.024.
Tohidi, et al., "Omentin-1, visfatin and adiponectin levels in relation to bone mineral density in Iranian postmenopausal women", Bone, 2012, vol. 51: pp. 876-881.
Arumugam, et al., "Enterotypes of the human gut microbiome", Nature, 2011, vol. 473, No. 7346: pp. 174-180.
Truong, et al., "MetaPhlAn2 for enhanced metagenomic taxonomic profiling", Nature Methods, Oct. 2015, vol. 12, No. 10: pp. 902-904.
Muller, et al., "The Plant Microbiota: Systems-Level Insights and Perspectives", The Annual Review of Genetics, 2016, vol. 50: pp. 211-234.
Turnbaugh, et al., "A core gut microbiome in obese and lean twins", Nature, 2009, vol. 457, No. 7228: pp. 480-484.
Atarashi, et al., "Treg induction by a rationally selected mixture of Clostridia strains from the human microbiota", Nature, Aug. 8, 2013, vol. 500: pp. 232-236.
Turnbaugh, et al., "Diet-Induced Obesity is Linked to Marked but Reversible Alterations in the Mouse Distal Gut Microbiome", Cell Host Microbe, 2008, vol. 3: pp. 213-223.
Okeke, et al., "The Role of the Gut Microbiome in the Pathogenesis and Treatment of Obesity", GAHMJ, 2014, vol. 3, No. 3: pp. 44-57.
Turnbaugh, et al., "The Effect of Diet on the Human Gut Microbiome: A Metagenomic Analysis in Humanized Gnotobiotic Mice", Sci Transl Med, 2009: pp. 1-23.
Ozcan, et al., "A Human Gut Commensal Ferments Cranberry Carbohydrates To Produce Formate", Appl Environ Microbiol, 2017, vol. 83, No. 17, pp. 1-16.
U.S. Appl. No. 16/235,858—Notice of Allowance, Jan. 23, 2020.
Body, et al., "A Randomized Double-Blind Trial to Compare the Efficacy of Teriparatide [Recombinant Human Parathyroid Hormone (1-34)] with Alendronate in Postmenopausal Women with Osteoporosis", The Journal of Clinical Endocrinology & Metabolism, Oct. 2002, vol. 87, No. 10: pp. 4528-4535.
Van Der Beek, et al., "Streptococcal dTDP-L-rhamnose biosynthesis enzymes: functional characterization and lead compound identification", Molecular Microbiology, Jan. 1, 2019, vol. 111, No. 4: pp. 1-32.
Pacifici, et al., "T cells: Critical bone regulators in health and disease", Bone, 2010, vol. 47, pp. 461-471.
Van Wyk, et al., "Current perspectives on the families of glycoside hydrolases of *Mycobacterium tuberculosis*: their importance and prospects for assigning function to unknowns", Glycobiology, 2017, vol. 27, No. 2: pp. 112-122.
Chaudhury, et al., "Clinical Review of Antidiabetic Drugs: Implications for Type 2 Diabetes Mellitus Management", Front Endocrinol, 2017, vol. 8, No. 6: pp. 1-12.
Verma, et al. "Cell surface polysaccharides of *Bifidobacterium bifidum* induce the generation of Foxp3+ regulatory T cells", Sci Immunol. 3, Oct. 19, 2018: pp. 1-14.
Pacifici, et al., "Bone Remodeling and the Microbiome", Cold Spring Harb Perspect Med, 2018, vol. 8, pp. 1-20.
Vogt, et al., "L-Rhamnose increases serum propionate in humans1-3", Am J Clin Nutr, 2004, vol. 80: pp. 89-94.
Deehan, et al., "Precision Microbiome Modulation with Discrete Dietary Fiber Structures Directs Short-Chain Fatty Acid Production", Cell Host & Microbe, Mar. 11, 2020, vol. 27: pp. 1-16.
Rendina, et al., "Dried Plum's Unique Capacity to Reverse Bone Loss and Alter Bone Metabolism in Postmenopausal Osteoporosis Model", PLoS One, Mar. 2013, vol. 8, No. 3: pp. 1-10.
Palacios, et al., "The effect of a novel probiotic on metabolic biomarkers in adults with prediabetes and recently diagnosed type 2 diabetes mellitus: study protocol for a randomized controlled trial", Trials, 2017, vol. 18, No. 7: pp. 1-8.
Rosen, et al., "Treatment With Once-Weekly Alendronate 70 mg Compared With Once-Weekly Risedronate 35 mg in Women With Postmenopausal Osteoporosis: A Randomized Double-Blind Study", Journal of Bone and Mineral Research, 2005, vol. 20, No. 1: pp. 141-151.
Famouri, et al., "Effects of Probiotics on Nonalcoholic Fatty Liver Disease in Obese Children and Adolescents", JPGN, 2017, vol. 64, No. 3: pp. 413-417.
Rothschild, et al., "Environment dominates over host genetics in shaping human gut microbiota", Nature, 2018: pp. 1-6.
Pan, et al., "A single bacterium restores the microbiome dysbiosis to protect bones from destruction in a rat model of rheumatoid arthritis", Microbiome, 2019, vol. 7, No. 107: pp. 1-11.
Sam, et al., "The Fungal Mycobiome and Its Interaction with Gut Bacteria in the Host", Int J Mol Sci, 2017, vol. 18, No. 330: pp. 1-11.
Greenblatt, et al., "Bone Turnover Markers in the Diagnosis and Monitoring of Metabolic Bone Disease", Clinical Chemistry, 2017, vol. 63, No. 2: pp. 464-474.
Sarioglu, et al., "Comparison of the effects of alendronate and risedronate on bone mineral density and bone turnover markers in postmenopausal osteoporosis", Rheumatol Int, 2006, vol. 26: pp. 195-200.
Pandiyan, et al., "Microbiome Dependent Regulation of Treg and Th17 Cells in Mucosa", Frontiers in Immunology, Mar. 8, 2019, vol. 10, Article 426: pp. 1-17.
Schroeder, et al., "Signals from the gut microbiota to distant organs in physiology and disease", Nat Med, 2016, vol. 22, No. 10: pp. 1079-1089.
Ibanez, et al., "Gut microbiome and bone", Joint Bone Spine, 2019, vol. 86: pp. 43-47.
Seeman, et al., "Age- and Menopause-Related Bone Loss Compromise Cortical and Trabecular Microstructure", J Gerontol A Biol Sci Med Sci, Oct. 2013, vol. 10: pp. 1218-1225.
Parekh, et al., "The role and influence of gut microbiota in pathogenesis and management of obesity and metabolic syndrome", Front Endocrinol, 2014, vol. 5, No. 47: pp. 1-7.
Shin, et al., "An increase in the *Akkermansia* spp population induced by metformin treatment improves glucose homeostasis in diet-induced obese mice", Gut, 2014, vol. 63: pp. 727-735.
Kapitza, et al., "Effects of semaglutide on beta cell function and glycaemic control in participants with type 2 diabetes: a randomized, double-blind, placebo-controlled trial", Diabetalogia, 2017, vol. 60: pp. 1390-1399.
Singh, et al., "Dysregulated Microbial Fermentation of Soluble Fiber Induces Cholestatic Liver Cancer", Cell, 2018, vol. 175: pp. 679-694.
Xu, et al., "Paenibacillus panacisoli enhances growth of Lactobacillus spp. by producing xylooligosaccharides in corn stover ensilages." Carbohydrate polymers 184 (2018): 435-444.
Sonnenburg, et al., "Diet-microbiota interactions as moderators of human metabolism", Nature, 2016, vol. 535: pp. 56-64.
Rosales-Bravo, et al., "Novel consortium of *Klebsiella variicola* and *Lactobacillus* species enhances the functional potential of

(56) References Cited

OTHER PUBLICATIONS fermented dairy products by increasing the availability of branched-chain amino acids and the amount of distinctive volatiles." Journal of applied microbiology 123, No. 5 (2017): 1237-1250.
Stull, et al., "Bioactives in Blueberries Improve Insulin Sensitivity in Obese, Insulin-Resistant Men and Women", J Nutr, 2010, vol. 140, No. 10: pp. 1764-1768.
PCT/US2020/038830—International Search Report and Written Opinion, Dec. 16, 2020, 23 pages.
Sweeney, et al., "Metabolic surgery: action via hormonal milieu changes, changes in bile acids or gut microbiota? A summary of the literature", Best Pract Res Clin Gastroenterol, 2014, vol. 28: pp. 727-740.
Biaggini, et al., "The pathogenic potential of Pseudomonas fluorescens MFN1032 on enterocytes can be modulated by serotonin, substance P and epinephrine." *Archives of microbiology* 197, No. 8 (2015): 983-990.
Tilg, et al., "The intestinal microbiota fuelling metabolic inflammation", Nature Reviews, Aug. 6, 2019: pp. 1-15.
Williams, et al., "Ethanol and volatile fatty acid production from lignocellulose by Clostridium cellulolyticum." *International Scholarly Research Notices* 2013, pp. 1-7.
Tuohy, et al., "Up-regulating the Human Intestinal Microbiome Using Whole Plant Foods, Polyphenols, and/or Fiber", J Agric Food Chem, 2012, vol. 60: pp. 8776-8782.
Li, et al., "Pro-and anti-inflammatory effects of short chain fatty acids on immune and endothelial cells." *European journal of pharmacology* 831 (2018): 52-59.
Turnbaugh, et al., "Supplementary Materials for : The Effect of Diet on the Human Gut Microbiome: A Metagenomic Analysis in Humanized Gnotobiotic Mice", Sci Transl Med, 2009: pp. 1-23.
Ozaki, et al., "The L-type amino acid transporter LAT1 inhibits osteoclastogenesis and maintains bone homeostasis through the mTORC1 pathway", Science Signaling, Jul. 9, 2019, vol. 12: pp. 1-14.
U.S. Appl. No. 16/235,858—Office Action, Aug. 6, 2019.
Bahr, et al., "Risperidone-induced weight gain is mediated through shifts in the gut microbiome and suppression of energy expenditure", EBioMedicine, 2015, vol. 2: pp. 1725-1734.
Vatanen, et al., "Variation in Microbiome LPS Immunogenicity Contributes to Autoimmunity in Humans", Cell, 2016, vol. 165: pp. 842-853.
Baker, et al., "Estrogen-gut microbiome axis: Physiological and clinical implications", Maturitas, 2017, vol. 103: pp. 45-53.
Reichardt, et al., "Phylogenetic distribution of three pathways for propionate production within the human gut microbiota", ISME J, 2014, vol. 8: pp. 1323-1335.
Basu, et al., "Blueberries decrease cardiovascular risk factors in obese men and women with metabolic syndrome", J Nutr, 2010, vol. 140, No. 9: pp. 1582-1587.
Rosenberg, et al., "Interaction between the Microbiome and Diet: The Hologenome Concept", J Nutr Food Sci, 2016, vol. 6, No. 5: p. 1000545.
Black, et al., "Postmenopausal Osteoporosis", The New England Journal of Medicine, Jan. 21, 2016, vol. 374, No. 3: pp. 254-262.
Samuel, et al., "A humanized gnotobiotic mouse model of host-archaeal-bacteria mutualism", PNAS, 2006, vol. 103, No. 26: pp. 10011-10016.
Boden, et al., "Obesity, Insulin Resistance and Free Fatty Acids", Curr Opin Endocrinol Diabetes Obes, 2011, vol. 18, No. 2: pp. 139-143.
Schwarzer, et al., "*Lactobacillus plantarum* strain maintains growth of infant mice during chronic undernutrition", Science, Feb. 19, 2016, vol. 351, No. 6275: pp. 854-857.
Bouxsein, et al., "Ovariectomy-Induced Bone Loss Varies Among Inbred Strains of Mice", Journal of Bone and Mineral Research, Mar. 7, 2005, vol. 20, No. 7: pp. 1085-1092.
Simpson, et al., "Review article: dietary fibre-microbiota interactions", Aliment Pharmacol Ther, 2015, vol. 42: pp. 158-179.
Britton, et al., "Probiotic *L. reuteri* Treatment Prevents Bone Loss in a Menopausal Ovariectomized Mouse Model", Journal of Cellular Physiology, 2014, vol. 229: pp. 1822-1830.
Stuible, et al., "Mechanism and Function of Monoclonal Antibodies Targeting Siglec-15 for Therapeutic Inhibition of Osteoclastic Bone Resorption*", The Journal of Biological Chemistry, vol. 289, No. 10: pp. 6498-6512.
Brown, et al., "Comparison of the Effect of Denosumab and Alendronate on BMD and Biochemical Markers of Bone Turnover in Postmenopausal Women With Low Bone Mass: A Randomized, Blinded, Phase 3 Trial*", Journal of Bone and Mineral Research, 2009, vol. 24: pp. 153-161.
Tan, et al., "The Role of Short-Chain Fatty Acids in Health and Disease", Advances in Immunology, 2014, vol. 121: pp. 91-119.
Calise, et el., "Immune Response-Dependent Assembly of IMP Dehydrogenase Filaments", Frontiers in Immunology, Nov. 29, 2018, vol. 9, Article 2789: pp. 1-15.
Turnbaugh, et al., "An obesity-associated gut microbiome with increased capacity for energy harvest", Nature, 2006, vol. 444: pp. 1027-1031.
Cani, et al., "Metabolic endotoxemia initiates obesity and insulin resistance", Diabetes, 2007, vol. 56: pp. 1761-1772.
Van Hul, et al., "Reduced obesity, diabetes and steatosis upon cinnamon and grape pomace are associated with changes in gut microbiota and markers of gut barrier", Am J Physiol Endocrinol Metab, 2017, vol. 314, No. 4: E3340E352.G.
Cani, et al., "Changes in gut microbiota control metabolic endotoxemia-induced inflammation in high-fat diet-induced obesity and diabetes in mice", Diabetes, 2008, vol. 57: pp. 1470-1481.
Rodriguez-R, et al., "The enveomics collection: a toolbox for specialized analyses of microbial genomes and metagenomes", PeerJ Preprints, 2016, vol. 4: e1900v1.
Chambers, et al., "Effects of targeted delivery of propionate to the human colon on appetite regulation, body weight maintenance and adiposity in overweight adults", Gut, 2015, vol. 64: pp. 1744-1754.
Schirmer, et al., "Linking the Human Gut Microbiome to Inflammatory Cytokine Production Capacity", Cell, 2016, vol. 167, No. 4: pp. 1125-1136.
Charbonneau, et al., "Sialylated Milk Oligosaccharides Promote Microbiota-Dependent Growth in Models of Infant Undernutrition", Cell, Feb. 25, 2016, vol. 164, pp. 859-871.
Slavin, et al., "Fiber and Prebiotics: Mechanisms and Health Benefits", Nutrients, 2013, vol. 5: pp. 1417-1435.
Chelliah, et al., "Evaluation of antimicrobial activity and probiotic properties of wild-strain *Pichia kudriavzevii* isolated from frozen *idli* batter", Yeast, 2016, vol. 33, pp. 385-401.
Tolhurst, et al., "Short-Chain Fatty Acids Stimulate Glucagon-Like Peptide-1 Secretion via the G-Protein-Coupled Receptor FFAR2", Diabetes, 2012, vol. 61: pp. 364-371.
Chen, et al., "Estrogen and Microbiota Crosstalk: Should We Pay Attention?", Trends in Endocrinology & Metabolism, Nov. 2016, vol. 27, No. 11, pp. 752-755.
Vital, et al., "A gene-targeted approach to investigate the intestinal butyrate-producing bacterial community", Microbiome, 2013, vol. 1, No. 8: pp. 1-14.
Collins, et al., "Beneficial effects of Lactobacillus reuteri 6475 on bone density in male mice is dependent on lymphocytes", Scientific Reports, 2019, vol. 9: pp. 1-17.
Sheikhi, et al., "Probiotic Yogurt Culture *Bifidobacterium animalis* Subsp *Lactis* BB-12 and *Lactobacillus acidophilus* LA-5 Modulate the Cytokine Secretion by Peripheral Blood Mononuclear Cells from Patients with Ulcerative Colitis", Drug Res, 2016, vol. 66: pp. 300-305.
Cosman, et al., "Clinician's Guide to Prevention and Treatment of Osteoporosis", 2014, vol. 25, pp. 2359-2381.
Tyagi, et al., "The Microbial Metabolite Butyrate Stimulates Bone Formation via T Regulatory Cell-Mediated Regulation of WNT10B Expression", Immunity, 2018, vol. 49: pp. 1116-1131.
Cowardin, et al., "Supplementary Information for: Mechanisms by which sialylated milk oligosaccharides impact bone biology in a gnotobiotic mouse model of infant undernutrition", PNAS, www.pnas.org/cgi/doi/10.1073/pnas.1821770116.

(56) References Cited

OTHER PUBLICATIONS

Sun, et al., "Gut mirobiota and intestinal FXR mediate the clinical benefits of metformin", Nat Med, 2018, vol. 24: pp. 1919-1929.
Coyle, et al., "Metformin as an adjuvant treatment for cancer: a systematic review and meta analysis", Ann Onc, 2016, vol. 27, pp. 2184-2195.
Saltiel, et al., "New therapeutic approaches for the treatment of obesity", Sci Transl Med, 2016, vol. 8, No. 323: p. 1-12.
Dane, et al., "Effect of risedronate on biochemical marker of bone resorption in postmenopausal women with osteoporosis or osteopenia", Gynecological Endocrinology, 2008, vol. 24, No. 4: pp. 207-213.
U.S. Appl. No. 16/694,876—Office Action, Dec. 8, 2021, 41 pages.
Gold, et al., "Longitudinal Analysis of the Association Between Vasomotor Symptoms and Race/Ethnicity Across the Menopausal Transition: Study of Women's Health Across the Nation", American Journal of Public Health, Jul. 2006, vol. 96, No. 7: pp. 1226-1235.
Lee, et al., "Effect of Enterotoxigenic *Escherichia coli* on Microbial Communities during Kimchi Fermentation", J. Microbiol. Biotechnol., Nov. 2021, vol. 31, No. 11: pp. 1552-1558.
Heinemann, et al., "The Menopause Rating Scale (MRS) scale: A methodological review", Health and Quality of Life Outcomes, Sep. 2004, vol. 2, No. 45: pp. 1-8.
Lim, et al., "The Effect of Lactobacillus acidophilus YT1(MENOLACTO) on Improving Menopausal Symptoms: A Randomized, Double-Blinded, Placebo-Controlled Clinical Trial", Journal of Clinical Medicine, Jul. 9, 2020, vol. 9, No. 7, Article 2173: pp. 1-16.
Liu, et al., "The relationship between menopausal syndrome and gut microbes", BMC Women's Health, Nov. 2022, vol. 22, Article 437: pp. 1-11.
Needleman, et al., "A General Method Applicable to the Search for Similarities in the Amino Acid Sequence of Two Proteins", J. Mol. Biol., Mar. 1970, vol. 48: pp. 443-453.
Herr, et al., "The Effects of Serotonin in Immune Cells", Frontiers in Cardiovascular Medicine, Jul. 2017, vol. 4, Article 48: pp. 1-11.
Ohlsson, et al., "Mild stimulatory effect of a probiotic mix on bone mass when treatment is initiated 1.5 weeks after ovariectomy in mice", Am J Physiol Endocrinol Metab., Feb. 1, 2021, vol. 320: pp. 591-E597.
Pearson, et al., "Improved tools for biological sequence comparison", Proc. Natl. Acad. Sci. USA, Apr. 1988, vol. 85: pp. 2444-2448.
Chiang, et al., "Effect of bioactive compounds in lactobacilli-fermented soy skim milk on femoral bone microstructure of aging mice", J Sci Food Agric, Jan. 2012, vol. 92, No. 2: pp. 328-335. Epub Aug. 4, 2011. doi: 10.1002/jsfa.4579.
Kellgren, et al., "Radiological Assessment of Osteo-Arthrosis", Ann. Rheum. Dis., Dec. 1957, vol. 16, No. 4: pp. 494-502.
Smith, et al., "Comparison of Biosequences", Advances in Applied Mathematics 2, 1981: pp. 482-489.
Solarea Bio, "Managing inflammatory diseases and aging with edible plant microbes", www.nature.com/biopharmdeal, Dec. 2022: pp. B2-B3.
"Solarea Bio Announces Licensing Agreement with ADM", Solarea Bio Press Release, Oct. 19, 2021, 10:17 ET: pp. 1-3.
Lambert, et al., "Combined Red Clover isoflavones and probiotics potently reduce menopausal vasomotor symptoms", Plos One, Jun. 7, 2017, vol. 12, No. 6: pp. 1-16.
"Solarea Bio Investigators Receive National Academy of Medicine Healthy Longevity 2022 Quickfire Challenge Award", Solarea Bio Press Release, Sep. 29, 2022, 09:17 ET: pp. 1-3.
"Solarea Bio Teams up with Hebrew SeniorLife Investigators on a Newly Awarded U.S. National Academy of Medicine Catalyst Grant", Solarea Bio Press Release, Nov. 4, 2021, 10:17 ET: pp. 1-4.
PCT/US2022/080362—International Search Report and Written Opinion, Mar. 21, 2023, 16 pages.
Lawenius, et al., "A probiotic mix partially protects against castration-induced bone loss in male mice", Journal of Endocrinology, Jun. 2022, vol. 254, No. 2: pp. 91-101.
U.S. Appl. No. 16/694,876—Office Action, Nov. 5, 2020, 34 pages.
U.S. Appl. No. 16/694,876—Office Action,m Jul. 20, 2022, 26 pages.
Anonymous, "Ther-Biotic Women's Formula—Probiotic Support for a Woman's special needs", Klaire Labs, Jan. 1, 2017: pp. 1-2, XP093030232, Retreived from the Internet: https://us.sfihealth.com/klairelabs/cache/file/837992BD-4CAF-4EA6-A3BA47C3C99BEAE8.pdf.
Altschul, et al., "Basic Local Alignment Search Tool", J Mol Biol., Oct. 5, 1990, vol. 215, No. 3: pp. 403-410.
Milajerdi, et al., "The effect of probiotics on inflammatory biomarkers: a meta-analysis of randomized clinical trials", European Journal of Nutrition, Mar. 11, 2020, vol. 59, No. 2: pp. 633-649.
Bellamy, et al., "Validation study of WOMAC: a health status instrument for measuring clinically important patient relevant outcomes to antirheumatic drug therapy in patients with osteoarthritis of the hip or knee", J Rheumatol, Dec. 1988, vol. 15, No. 12: pp. 1833-1840.
Gu, et al., "Analysis of bacterial diversity and biogenic amines content during the fermentation processing of stinky tofu", Food Res Int., Sep. 2018, vol. 111: pp. 689-698. Epub May 29, 2018. doi: 10.1016/j.foodres.2018.05.065.
Choi, et al., "Difference in the Gut Microbiome between Ovariectomy-Induced Obesity and Diet-Induced Obesity", J. Microbiol. Biotechnol, Dec. 28, 2017, vol. 27, No. 12: pp. 2228-2236.
Solarea Bio, Inc., "Food Trial Evaluating the Efficacy of SBD111 Versus Placebo for the Clinical Dietary Management of the Metabolic Processes of Osteopenia", NIH U.S. National Library of Medicine, Last updated Jan. 28, 2022: pp. 1-6. <https://beta.clinicaltrials.gov/study/NCT05009875>.
Damani, et al., "The Role of Prunes in Modulating Inflammatory Pathways to Improve Bone Health in Postmenopausal Women", Adv Nutr, Oct. 2, 2022, vol. 13, No. 5: pp. 1476-1492.
"Bone Density Study in Post-Menopausal Women", RDC Clinical, New Study Announcement, Dec. 3, 2021[online], [Retrieved Jun. 9, 2022]. Retrieved from the internet: https://www.rdcclinical.com.au/trials/bone-density-study/. 8 Pages.
Flores, et al., "Fecal microbial determinants of fecal and systemic estrogens and estrogen metabolites: a cross-sectional study", Journal of Translational Medicine, Dec. 21, 2012, vol. 10, No. 253: pp. 1-11.
Altman, et al., "Development of Criteria for the Classification and Reporting of Osteoarthritis," Arthritis and Rheumatism, Aug. 1986, vol. 29, No. 8: pp. 1039-1049.
Asgari, et al., "Nucleotide-pair encoding of 16S rRNA sequences for host phenotype and biomarker detection", bioRxiv, Jul. 19, 2018, pp. 1-25. https://doi.org/10.1101/334722.
Szydlowska, et al., "Effects of probiotics supplementation on the hormone and body mass index in perimenopausal and postmenopausal women using the standardized diet. A 5-week double-blind, placebo-controlled, and randomized clinical study", Randonmized Controlled Trial, Eur Rev Med Pharmacol Sci., May 2021, vol. 25, No. 10: pp. 3859-3867. doi: 10.26355/eurrev_202105_25953.
Cristofori, et al., "Anti-Inflammatory and Immunomodulatory Effects of Probiotics in Gut Inflammation: A Door to the Body", Frontiers of Immunology, Feb. 26, 2021, vol. 12, Article 578386: pp. 1-21.
"Solarea peer-review publication reveals green olives and other fruits and vegetables have vast microbial diversity with the potential to deliver probiotic functionality", Solarea Bio Press Release, Solarea Bio Press Release, Dec. 15, 2021, 10:17 ET: pp. 1-3.
Lawenius, et al., "Development of a synbiotic that protects against ovariectomy-induced trabecular bone loss", Am J Physiol Endocrinol Metab., Apr. 1, 2022, vol. 322, No. 4: pp. E344-E354.
Shajib, et al., "Diverse Effects of Gut-Derived Serotonin in Intestinal Inflammation", ACS Chemical Neuroscience, May 2017, vol. 8: pp. 920-931.
Easson, et al., "Food safety assessment and toxicity study of the synbiotic consortium SBD111", Food and Chemical Toxicology, Oct. 2022, vol. 168, Article 113329: pp. 1-14.
Santos-Marcos, et al., "Influence of gender and menopausal status on gut microbiota", Maturitas, Oct. 2018, vol. 116: pp. 43-53.
Bischoff, et al., "Role of serotonin in intestinal inflammation: knockout of serotonin reuptake transporter exacerbates 2,4,6-

(56) References Cited

OTHER PUBLICATIONS trinitrobenzene sulfonic acid colitis in mice", Am J Physiol Gastrointest Liver Physiol, Mar. 2009, vol. 296, No. 3: pp. G685-G695.
Jhun, et al., "Lactobacillus sakei suppresses collagen-induced arthritis and modulates the differentiation of T helper 17 cells and regulatory B cells", Journal of Translational Medicine, Month 2020, vol. 18(1):317: pp. 1-11.
Park, et al., "Probiotic Lactobacillus fermentum strain JDFM216 stimulates the longevity and immune response of Caenorhabditis elegans through a nuclear hormone receptor", Scientific Reports, 2018, pp. 1-10.
Poupet, et al., "Caenorhabditis elegans, a Host to Investigate the Probiotic Properties of Beneficial Microorganisms", Frontiers in Nutrition | www.frontiersin.org,Aug. 2020 | vol. 7 | Article 135, published: Aug. 21, 2020, doi: 10.3389/fnut.2020.00135: pp. 1-22.
Pryor, Rand Cabriero, F (2015) Repurposing metformin: an old drug with new tricks in its binding pockets. Biochem J 471: 307-322.
Gouda et al.., Endophytes: A Treasure House of Bioactive Compounds of Medicinal Importance, Frontiers in Microbiology, Mini Review, Sep. 29, 2016, vol. 7, article 1538, total pp. 1-8. (Front. Microbiol. 7:1538. doi: 10. 3389/fmicb.2016.01538). (Year: 2016).
Quinn, et al., "Global chemical effects of the microbiome include new bile-acid conjugations", https://doi.org/10.1038/s41586-020-2047-9, Published online: Feb. 26, 2020, Nature | vol. 579 | Mar. 5, 2020: pp. 123-129—Total pp. 22.
Vijay-Kumar et al (2010) Metabolic syndrome and altered gut microbiota in mice lacking toll-like receptor 5. Science 328(5975): 228-231.
White, J (2014) A Brief History of the Development of Diabetes Medications. Diabetes Spectr 27(2): 82-86.
Paul, et al., "Probiotics and Amelioration of Rheumatoid Arthritis: Significant Roles of Lactobacillus casei and Lactobacillus acidophilus", Microorganisms, 2021, pp. 1-17.
Raftis, et al., "An immunomodulatory member of the gut microbiota reduces clinical signs and inflammatory joint damage in an animal model of rheumatoid arthritis": 4D Pharma PLC, pp. 1.
Aletaha et. al. "2010 Rheumatoid arthritis classification criteria: An American College of Rheumatology/European League Against Rheumatism collaborative initiative." Arthritis & Rheumatism, 62: 2569-2581. https://doi.org/10.1002/art.27584.
Alipour, B. et.al.Effects of Lactobacillus casei supplementation on disease activity and inflammatory cytokines in rheumatoid arthritis patients: a randomized double-blind clinical trial. (2014) Int J Rheum Dis, 17: 519-527. https://doi.org/10.1111/1756-185X.12333.
Bürkle, et al., "Mark-Age Biomarkers of Ageing", Mechanisms of Ageing and Development 151 (2015), pp. 2-12.
Rahman, et al., "NemaLife chip: a micropillar-based microfluid culture device optimized for aging studies in crawling C. elegans", www.nature.com/scientificreports, (2020) 10:16190 | https://doi.org/10.1038/s41598-020-73002-6: pp. 1-19.
Caffaratti, et al., "What We Know So Far about the Metabolite-Mediated Microbiota-Intestinal Immunity Dialogue and How to Hear the Sound of This Crosstalk", Metabolites 2021, 11, 406. https://doi.org/10.3390/metabo11060406 https://www.mdpi.com/journal/metabolites: pp. 1-37.
Cario, "Barrier-protective function of intestinal epithelial Toll-like receptor 2", nature publishing group, vol. 1 Supplement 1 | Nov. 2008 | www.nature.com/mi, doi:10.1038/mi.2008.47: pp. S62-S66.
Paynich, et al., "Exopolysaccharide from Bacillus subtilis Induces Anti-Inflammatory M2 Macrophages That Prevent T Cell-Mediated Disease", The Journal of Immunology, 2017, pp. 1-10.
Rao, et al., "Human Peripheral Blood Mononuclear Cells Exhibit Heterogeneous CD52 Expression Levels and Show Differential Sensitivity to Alemtuzumab Mediated Cytolysis", PLoS One | Heterogeneous CD52 Expression on Human PBMCs, www.plosone.org, Jun. 2012 | vol. 7 | Issue 6 | e39416: pp. 1-12.
Choi, et al., "Diet mimicking fasting promotes regeneration and reduces autoimmunity and multiple sclerosis symptoms", Published in final edited form as: Cell Rep. Jun. 7, 2016; 15(10): 2136-2146. doi:10.1016/j.celrep.2016.05.009: pp. 1-18.
Chriswell, et al., "Microbiota mediated mucosal inflammation in arthritis", Published in final edited form as: Best Pract Res Clin Rheumatol. Dec. 2019 ; 33(6): 101492. doi:10.1016/j.berh.2020.101492; pp. 1-17.
Crimmins, et al., "Quest for a summary measure of biological age: the health and retirement study", GeroScience (2021) 43:395-408, https://doi.org/10.1007/s11357-021-00325-1: pp. 395-408.
Reinhoud, et al., "Analysis of Glutamate, GABA, Noradrenaline, Dopamine, Serotonin, and Metabolites Using Microbore UHPLC with Electrochemical Detection", ACS Chemical Neuroscience, pubs.acs.org/chemneuro, 2013 American Chemical Society, dx.doi.org/10.1021/cn400044s | ACS Chem. Neurosci. 2013, 4: pp. 888?894.
Cunha, et al., "Nisin Influence on the Antimicrobial Resistance Ability of Canine Oral Enterococci", Antibiotics 2020, 9, 890; doi:10.3390/antibiotics9120890 www.mdpi.com/journal/antibiotics: pp. 1-14.
Cuollo, et al., "The Senescence-Associated Secretory Phenotype (SASP) in the Challenging Future of Cancer Therapy and Age-Related Diseases", Biology 2020, 9, 485; doi: 10.3390/biology9120485 www.mdpi.com/journal/biology: pp. 1-16.
Peng, et al., "IDBA-UD: a de novo assembler for single-cell and metagenomic sequencing data with highly uneven depth", Bioinformatics, 2012, vol. 28, No. 11, 1420-1428.
Riskedal, et al., "Development and Performance of a Diagnostic Precision Biomarker for Seronegative Rheumatoid Arthritis Based on DNA Methylation in Blood", Meeting: ACR Convergence 2022, Date: Saturday, Nov. 12, 2022: pp. 1-4.
Fan, et al., "Protective effects of Bifidobacterium adolescentis on collagen-induced arthritis in rats depend on timing of administration", Food Funct., 2020, 11, 4499-4511 | DOI:10.1039/d0fo00077a | Published on Apr. 29, 2020. Downloaded by Harvard University on Dec. 7, 2021 9:17:48 PM: pp. 4499-4511.
Feres, et al., "The subgingival periodontal microbiota of the aging mouth", Periodontology 2000, vol. 72, 2016, 30-53 | Printed in Singapore. All rights reserved | © 2016 John Wiley & Sons A/S. Published by John Wiley & Sons Ltd.: pp. 30-53.
Fiorucci, et al., "Bile Acids Activated Receptors Regulate innate immunity", Frontiers in Immunology | www.frontiersin.org | Aug. 13, 2018 | vol. 9 | Article 1853 | doi: 10.3389/fimmu.2018.01853: pp. 1-17.
Robida-Stubbs, et al., "TOR Signaling and Rapamycin Influence Longevity by Regulating SKN-1/Nrf and DAF-16/FoxO", Cell Metabolism 15, 713-724, May 2, 2012 $^{ul;12ul;0}$ 2012 Elsevier Inc.: pp. 713-724.
Flanagan, et al., "Annual Review of Nutrition Calorie Restriction and Aging in Humans", Annu. Rev. Nutr. 2020.40:105-133. Downloaded from www.annualreviews.org | Access provided by CASA Institution Identity on Feb. 20, 2023 | https://doi.org/10.1146/annurev-nutr-122319-034601: pp. 105-135.
Yoneno, Kazuaki et al, "TGR5 signalling inhibits the production of pro-inflammatory cytokines by in vitro differentiated inflammatory and intestinal macrophages in Crohn's disease", Immunology, 2013, 139, pp. 19-29.
Pérez-Chaparro, "Newly Identified Pathogens Associated with Periodontitis: A Systematic Review", Journal of Dental Research, Jul. 29, 2014, pp. 846-858.
Rogier, et al., "Alteration of the intestinal microbiome characterizes preclinical inflammatory arthritis in mice and its modulation attenuates established arthritis", Published online: Nov. 15, 2017, www.nature.com/scientificreports | Scientific Reports 7:15613 | DOI:10.1038/s41598-017-15802-x: pp. 1-12.
Yu, Haitao, et al., "Protective Ability of Biogenic Antimicrobial Peptide Microcin J25 Against Enterotoxigenic *Escherichia coli*-Induced Intestinal Epithelial Dysfunction and Inflammatory Reponses IPEC-J2 Cells", Frontiers in Cellular and Infection Microbiology, Jul. 2018, vol. 8, Article 242.
Almutairi et al., "The global prevalence of rheumatoid arthritis: a meta-analysis based on a systematic review", Rheumatology International, 2020, https://doi.org/10.1007/s00296-020-04731-0: pp. 1-15.

(56) References Cited

OTHER PUBLICATIONS

Zaiss, Mario M., et al., "The gut-joint axis in rheumatoid arthritis", Nature Reviews | Rheumatology, vol. 17, Apr. 2021, pp. 224-237.
Romanin, et al., "Probiotic yeast Kluyveromyces marxianus CIDCA 8154 shows anti-inflammatory and anti-oxidative stress properties in in vivo models", Beneficial Microbes, 2016; 7(1): 83-93, ISSN 1876-2833 print, ISSN 1876-2891 online, DOI 10.3920/BM2015.0066, http://www.wageningenacademic.com/doi/pdf/10.3920/BM2015.0066—Friday, Sep. 22, 2017 8:40:22 AM—Göteborgs Universitet IP Address:130.241.16.16: pp. 83-93.
Zamani, Batol, et al., "Synbiotic supplementation and the effects on clinical and metabolic responses in patients with rheumatoid arthritis: a randomised, double-blind, placebo-controlled trial", British Journal of Nutrition, 2017, 117, pp. 1095-1102.
Alpert, et al., "A clinically meaningful metric of immune age derived from high-dimensional longitudinal monitoring", Nature Medcine, Mar. 2019, vol. 25, pp. 487-495.
Peters, et al., "The transcriptional landscape of age in human peripheral blood", Nature Communications, 2015, pp. 1-14.
Santano, et al., "Comparative Evaluation of the Antimicrobial and Mucus Induction Properties of Selected Bacillus Strains against Enterotoxigenic *Escherichia coli*", Antibiotics 2020, 9, 849; doi:10.3390/antibiotics9120849 www.mdpi.com/journal/antibiotics: pp. 1-10.
Zhang, Yuanyuan, et al., "Anti-inflammatory Activity and Mechanism of Surfactin in Lipopolysaccharide-Activated Macrophages", Inflammation, vol. 38, No. 2, Apr. 2015, pp. 756-764.
Zhou, Bin and Zhang, Defeng, "Antibacterial effects of bacteriocins isolated from Lactobacillus rhamnosus (ATCC 53103) in a rabbit model of knee implant infection", Experimental and Therapeutic Medicine, 15, 2018, pp. 2985-2989.
Zhao, Ruixiang, et al., "Purification and characterization of bacteriocin produced by Lactobacillus rhamnosus zrx01", Food Bioscience, 38, 2020, 100754.
Zhang, Xuan, et al., "The oral and gut microbiomes are perturbed in rheumatoid arthritis and partly normalized after treatment", Nature Medicine, vol. 21, No. 8, Aug. 2015, pp. 895-907.
Wilson, Timothy M., et al., "Microbial Influences of Mucosal Immunity in Rheumatoid Arthritis", Curr Rheumatol Rep., 22(11), 83, doi:10.1007/s11926-020-00960-1.
Piatek, et al., "In-Vitro Growth Inhibition of Bacterial Pathogens by Probiotics and a Synbiotic: Product Composition Matters", Int. J. Environ. Res. Public Health, 2020, pp. 1-10.
Roshchina, "Chapter 2 Evolutionary Considerations of Neurotransmitters in Microbial, Plant, and Animal Cells", M. Lyte and P.P.E. Freestone (eds.), Microbial Endocrinology, Interkingdom Signaling in Infectious Disease and Health, DOI 10.1007/978-1-4419-5576-0_2: pp. 17-52.
Xu, Huihui, et al., "Interactions between Gut Microbiota and Immunomodulatory Cells in Rheumatoid Arthritis", Hindawi, Mediators of Inflammation, vol. 2020, Article ID 1430605, 14 Pages, https://doi.org/10.1155/2020/1430605.
Yamashita, Maya, et al., "Preventive Effect of Lactobacillus helveticus SBT2171 on Collagen-Induced Arthritis in Mice", Frontiers in Microbiology, Jun. 2017, vol. 8, Article 1159.
Yamazaki, Munchiro, et al., "Dopamine inhibition of superoxide anion production by polymorphonuclear leukocytes", J. Allergy Clin. Immunol., May 1989, pp. 967-972.
Roselli, et al., "Caenorhabditis Elegans and Probiotics Interactions from a Prolongevity Perspective", International Journal o f Molecular Sciences, Int. J. Mol. Sci. 2019, 20, 5020; doi: 10.3390/ijms20205020, www.mdpi.com/journal/ijms: pp. 1-14.
Yan, Yiqing, et al., "Dopamine Controls Systemic Inflammation through Inhibition of NLRP3 Inflammasome", Cell, 160, Jan. 15, 2015, pp. 62-73.
Artacho, et al., "The Pretreatment Gut Microbiome Is Associated With Lack of Response to Methotrexate in New-Onset Rheumatoid Arthritis", American College of Rheumatology, vol. 73, No. 6, Jun. 2021, pp. 931-942.
Parks, et al., "CheckM: assessing the quality of microbial genomes recovered from isolates, single cells, and metagenomes", Genome Research, 2015, pp. 1043-1055.
Rühmann, et al., "Methods to identify the unexplored diversity of microbial exopolysaccharides", Frontiers in Microbiology | www.frontiersin.org, Jun. 2015 | vol. 6 | Article 565, published: Jun. 9, 2015, doi: 10.3389/fmicb.2015.00565: pp. 1-8.
Atkinson, et al., "Establishment and characterization of a sustained delayed-type hypersensitivity model with arthritic manifestations in C57BL/6J mice", Arthritis Research & Therapy (2012) 14:R134, pp. 1-16.
Weyand, et al., "The immunology of rheumatoid arthritis", Nature Immunology, Jan. 2021, vol. 22, No. 1: pp. 10-18.
Watanabe, et al., "Impact of senescence-associated secretory phenotype and its potential as a therapeutic target for senescence-associated diseases", Cancer Science, Apr. 2017, vol. 108, No. 4: pp. 563-569.
Rutledge, et a;., "Measuring biological age using omics data", Nature Reviews | Genetics vol. 23 | Dec. 2022: pp. 715-727.
Bae, et al., "Akkermansia muciniphila phospholipid induces homeostatic immune responses", Nature, Jul. 27, 2022, pp. 1-21.
Bagga, et al., "Differential effects of prostaglandin derived from w-6 and w-3 polyunsaturated fatty acids on COX-2 expression and IL-6 secretion", PNAS, Feb. 18, 2003, vol. 100, pp. 1751-1756.
Schiavi, et al., "The Surface-Associated Exopolysaccharide of Bifidobacterium longum 35624 Plays an Essential Role in Dampening Host Proinflammatory Responses and Repressing Local TH17 Responses", Appl Environ Microbiol, Nov. 2016, vol. 82, No. 24: pp. 7185-7196.
Saccon, et al., "Senolytic Combination of Dasatinib and Quercetin Alleviates Intestinal Senescence and Inflammation and Modulates the Gut Microbiome in Aged Mice", Journals of Gerontology: Biological Sciences, cite as: J Gerontol A Biol Sci Med Sci, 2021, vol. 76, No. 11, 1895-1905, doi:10.1093/gerona/glab002, Advance Access publication Jan. 6, 2021: pp. 1895-1905.
Gao, et al., "Impact of the Gut Microbiota on Intestinal Immunity Mediated by Tryptophan Metabolism", Frontiers in Cellular and Infection Microbiology, Feb. 2018, vol. 8, Article 13: pp. 1-22.
Franceschi, et al., "Inflammaging: a new immune-metabolic viewpoint for age-related diseases", Nat Rev Endocrinol., Oct. 2018, vol. 14, No. 10: pp. 576-590.
Salminen, et al., "Activation of innate immunity system during aging: NF-kB signaling is the molecular culprit of inflamm-aging", Ageing Research Reviews 7 (2008), doi:10.1016/j.arr.2007.09.002: pp. 83-105.
Bansal, et al., "The bacterial signal indole increases epithelial-cell tight-junction resistance and attenuates indicators of inflammation", PNAS, Jan. 5, 2010, vol. 107, pp. 1-6.
Gatej, et al., "Probiotic Lactobacillus rhamnosus GG prevents alveolar bone loss in a mouse model of experimental periodontitis", J Clin Periodontol., Nov. 2017, vol. 45, No. 2: pp. 1-21. doi: 10.1111/jcpe.12838.
Scher, et al., "Expansion of intestinal Prevotella copri correlates with enhanced susceptibility to arthritis", Elife, Nov. 2013, vol. 2:e01202 (20 pages).
Sanchez, et al., "Efficacy of Probiotics in Rheumatoid Arthritis and Spondyloarthritis: A Systematic Review and Meta-Analysis of Randomized Controlled Trials", Published: Jan. 14, 2022, Nutrients 2022, 14, 354. https://doi.org/10.3390/nu14020354, https://www.mdpi.com/journal/nutrients: pp. 1-19.
Guttman-Yassky, et al., "Contrasting pathogenesis of atopic dermatitis and psoriasis—Part I: Clinical and pathologic concepts", J Allergy Clin Immunol., Epub Mar. 2011, vol. 127, No. 5: pp. 1110-1118.
Bharath, et al., "Metformin Enhances Autophagy and Normalizes Mitochondrial Function to Alleviate Aging-Associated Inflammation", Cell Metabolism, 2020, 32, 44-55. https://doi.org/10.1016/j.cmet.2020.04.015.
Brand, et al., "Collagen-induced arthritis", Nature Protocols, 2007, vol. 2 No. 5., 1269-1275. doi:10.1038/nprot.2007.173.
Sandrini, et al., "Microbial endocrinology: host-bacteria communication within the gut microbiome", Journal of Endocrinology,

(56) References Cited

OTHER PUBLICATIONS (2015) 225, R21-R34, http://joe.endocrinology-journals.org, DOI: 10.1530/JOE-14-0615: pp. R21-R34.

Gusmao-Silva, et al., "Hsp65-Producing Lactococcocus lactis Prevents Antigen-Induced Arthritis in Mice", Frontiers in Immunology, Sep. 2020, vol. 11, Article: 562905: pp. 1-15.

Braun, et al., "Ankylosing spondylitis", Lancet 2007; 369: 1379-90.

Schott, et al., "Targeting the gut microbiome to treat the osteoarthritis of obesity", JCI Insight, Apr. 2018, vol. 3, No. 8: e95997 (18 pages).

Saraiva, et al., "The regulation of IL-10 production by immune cells", doi: 10.1038/nri2711, Published online Feb. 15, 2010, Mar. 2010 | vol. 10, www.nature.com/reviews/immunol: pp. 170-181.

Ge, et al., "Helicobacter pylori-infected C57BL/6 mice with different gastrointestinal microbiota have contrasting gastric pathology, microbial and host immune responses", Science Reports, May 2018, vol. 8, No. 1, Article: 8014: pp. 1-15.

Ghosh, et al., "The gut microbiome as a modulator of healthy ageing", Nature Reviews Gastroenterology & Hepatology, Epub: Apr. 2022, vol. 19, No. 9: pp. 565-584.

Glowacki, et al., "Prevention of inflammation-mediated bone loss in murine and canine periodontal disease via recruitment of regulatory lymphyocytes", Nov. 2013, Nov. 2013, vol. 110, No. 46: pp. 18525-18530 (7 pages). Epub Oct. 2013.

Saul, et al., "A new gene set identifies senescent cells and predicts senescence-associated pathways across tissues", Published online: Aug. 16, 2022, Nature Communications | (2022)13:4827, https://doi.org/10.1038/s41467-022-32552-1: pp. 1-15.

Han, et al., "Probiotic Gastrointestinal Transit and Colonization After Oral Administration: A Long Journey", Frontiers in Cellular and Infection Microbiology, Mar. 2021, vol. 11, Article 609722: pp. 1-12.

Higgins, et al., "Toll-Like Receptor 4-Mediated Innate IL-10 Activates Antigen-Specific Regulatory T Cells and Confers Resistance to Bordetella pertussis by Inhibiting Inflammatory Pathology", The Journal of Immunology, Sep. 2003, vol. 171, No. 6: pp. 3119-3127.

Scortichini, et al., "Development and validation of a GC-FID method for the analysis of short chain fatty acids in rat and human faeces and in fermentation fluids", J Chromatogr B Analyt Technol Biomed Life Sci., Apr. 2020, vol. 1143, Article 121972: pp. 1-9. Epub Jan. 13, 2020.

Sayed, et a;.,"An inflammatory aging clock (iAge) based on deep learning tracks multimorbidity, immunosenescence, frailty and cardiovascular aging", https://doi.org/10.1038/s43587-021-00082-y, Nature Aging | vol. 1 | Jul. 2021 | 598-615 | www.nature.com/nataging: pp. 598-615, Total pp. 31.

Heinken, et al., "Systematic assessment of secondary bile acid metabolism in gut microbes reveals distinct metabolic capabilities in inflammatory bowel disease", Microbiome, May 2019, vol. 7, No. 1: pp. 1-18.

An, et al., "GABA-producing Lactobacillus plantarum inhibits metastatic properties and induces apoptosis of 5-FU-resistant colorectal cancer cells via GABAB receptor signaling§", Journal of Microbiology (2021) vol. 59, No. 2, pp. 202-216.

Holmdahl, et al., "The molecular pathogenesis of collagen-induced arthritis in mice—a model for rheumatoid arthritis", Ageing Research Reviews, Feb. 2002, vol. 1, No. 1: pp. 135-147.

Oliviero, et al., "Benefits of Probiotics in Rheumatic Diseases", Frontiers in Nutrition, Sep. 2020, vol. 7, Article 157, pp. 1-6.

Huang, et al., "Bacteriocins: Potential for Human Health", Oxidative Medicine and Cellular Longevity, Apr. 2021, vol. 2021, Article 5518825: pp. 1-17.

Hug, et al., "Toll-Like Receptors: Regulators of the Immune Response in the Human Gut", Nutrients, Feb. 2018, vol. 10(2):203: pp. 1-16.

Schorpion, et al., "Can Probiotic Supplements Improve Outcomes in Rheumatoid Arthritis?", Curr Rheumatol Rep, Nov. 2017, vol. 19, No. 11, Article 73: pp. 7.

Ozogul, et al., "The Function of Lactic Acid Bacteria on Biogenic Amines Production by Food-Borne Pathogens in Arginine Decarboxylase Broth", Food Sci. Technol. Res., 18 (6), 795-804, 2012.

Hunter, et al., "Prevalence of rheumatoid arthritis in the United States adult population in healthcare claims databases, 2004-2014", Rheumatology International, Sep. 2017, vol. 37, No. 9: pp. 1551-1557. Epub Apr. 2017.

Millar, et al., "A Proinflammatory Diet is Associated with Increased Odds of Frailty after 12-year Follow-up in a Cohort of Adults," Am. J. Clin. Nutr. 2022, 115:334-343.

Jang, et al., "IL-6 and IL-10 Induction from Dendritic Cells in Response to Mycobacterium tuberculosis Is Predominantly Dependent on TLR2-Mediated Recognition", The Journal of Immunology, Sep. 2004, vol. 173, No. 5: pp. 3392-3397.

Pahor, et al., "Effect of Losartan and Fish Oil on Plasma IL-6 and Mobility in Older Persons. The ENRGISE Pilot Randomized Clinical Trial.", J Gerontol A Biol Sci Med Sci, 2019, vol. 74, No. 10, 1612-1619.

Jin, et al., "Isolation and characterization of high exopolysaccharide-producing Weissella confuse VP30 from young children's feces", Microbial Cell Factories, Jun. 2019, vol. 18(1):110: pp. 1-13.

Jubair, et al., "Modulation of inflammatory arthritis by gut microbiota through mucosal inflammation and autoantibody generation", Arthritis Rheumatol, Aug. 2018, vol. 70, No. 8: pp. 1220-1233 (21 pages). Author manuscript. Epub Jul. 2018.

Segata, et al., "Metagenomic microbial community profiling using unique clade-specific marker genes", Nature Methods, Jun. 2012, vol. 9, No. 8: pp. 811-814.

Paine, et al., "Dysregulation of bile acids, lipids, and nucleotides in psoriatic arthritis revealed by unbiased profiling of serum metabolites", American College of Rheumatology , Jul. 11, 2022. https://doi: 10.1002/art.42288.

Justice, et al., "Frameworks for Proof-of-Concept Clinical Trials of Interventions That Target Fundamental Aging Processes", J Gerontol A Biol Sci Med Sci, Nov. 2016, vol. 71, No. 11: pp. 1415-1423. Epub Aug. 2016.

Kindt, et al., "The G Protein-Coupled Bile Acid Receptor TGR5 (Gpbar1) Modulates Endothelin-1 Signaling in Liver", Cells, Nov. 2019, vol. 8(11):1467: pp. 1-21.

Jin, et al., "Localization and Function of GABA Transporters GAT-1 and GAT-3 in the Basal Ganglia", Frontiers in Systems Neuroscience, Jul. 2011, vol. 5, Article 63: pp. 1-10.

Pan, et al., "Key proteins and pathways that regulate lifespan", J. Biol. Chem. (2017) 292(16) 6452-6460.

Kang, et al., "Modulation of Inflammatory Cytokines by Omega-3 Fatty Acids", Subcell Biochem., 2008, vol. 49: pp. 133-143.

Kinane, et al., "Periodontal diseases", Nature Reviews Disease Primers, Jun. 2017, vol. 3, Article 17038: pp. 1-14.

Sethi, et al., "Design, synthesis and computational studies involving Indole-Coumarin hybrids as galectin-1 inhibitors", Chemical Papers, Month 2021, vol. 75: pp. 2791-2805. Epub Feb. 2, 2021.

Pan, et al., "Predominant gut Lactobacillus murinus strain mediates anti-inflammaging effects in calorie-restricted mice", Microbiome, vol. 6, Iss 1, pp. 1-17 (2018).

Kolmogorov, et al., "Assembly of long, error-prone reads using repeat graphs", Nature Biotechnology, May 2019, vol. 37, No. 5: pp. 540-546. Epub Apr. 2019.

Komura, et al., "Caenorhabditis elegans as an alternative model host for legionella pneumophila, and protective effects of Bifidobacterium infantis", Applied and Environmental Microbiology, Jun. 2010, vol. 76, No. 12: pp. 4105-4108. Epub Apr. 2010.

Kobayashi, et al., "Oral administration of Lactobacillus gasseri SBT2055 is effective in preventing Porphyromonas gingivalis-accelerated periodontal disease", Scientific Reports, Apr. 2017, vol. 7, No. 1, Article 545: pp. 1-10.

Park, et al., "Short communication: Development of a direct in vivo screening model to identify potential probiotic bacteria using Caenorhabditis elegans", Journal of Dairy Science, 2014, vol. 97, No. 11, pp. 6828-6834.

Kumar, et al., " A Potential Probiotic Lactobacillus plantarum JBC5 Improves Longevity and Healthy Aging by Modulating Antioxidative, Innate Immunity and Serotonin-Signaling Pathways in Caenorhabditis elegans", Antioxidants (Basel), Jan. 2022, vol. 11, No. 2, Article 268: pp. 1-25.

(56) References Cited

OTHER PUBLICATIONS

Kumari, et al., "Mechanisms of Cellular Senescence: Cell Cycle Arrest and Senescence Associated Secretory Phenotype", Frontiers in Cell and Developmental Biology, Mar. 2021, vol. 9, Article 645593: pp. 1-24.
Shahbizi, et al., "Anti-Inflammatory and Immunomodulatory Properties of Fermented Plant Foods", Nutrients, Apr. 2021, vol. 13, No. 5, Article 1516: pp. 1-20.
Wang, et al., "FXR: a metabolic regulator and cell protector", Cell Research, Nov. 2008, vol. 18, No. 11: pp. 1087-1095.
Wan, et al., "Serotonin: A Potent Immune Cell Modulator in Autoimmune Diseases", Frontiers in Immunology, Feb. 2020, vol. 11, Article 186: pp. 1-12.
Agus et al. "Gut Microbiota Regulation of Tryptophan Metabolism in Health and Disease," Cell Host & Microbe, vol. 23, Issue 6, 2018, pp. 716-724, ISSN 1931-3128, https://doi.org/10.1016/j.chom.2018.05.003.
Walsham, et al., "Lactobacillus reuteri Inhibition of Enteropathogenic *Escherichia coli* Adherence to Human Intestinal Epithelium", Frontiers in Microbiology, Mar. 2016, vol. 7, Article 244: pp. 1-10.
Allen. P. et al. "Immunomodulatory Roles of Polysaccharide Capsules in the Intestine Frontiers in Immunology" vol. 11 (2020) https://www.frontiersin.org/articles/10.3389/fimmu.2020.00690, DOI=10.3389/fimmu.2020.00690.
Villageliu, et al., "Dopamine production in Enterococcus faecium: A microbial endocrinology-based mechanism for the selection of probiotics based on neurochemical-producing potential", PLoS One, Nov. 2018, vol. 13, No. 11: e0207038 (10 pages).
Skelly, et al., "Mining the microbiota for microbial and metabolite-based immunotherapies", Nat Rev Immunol, May 2019, vol. 19, No. 5: pp. 305-323 (19 pages).
Vivekananda, et al., "Effect of the probiotic *Lactobacilli reuteri* (Prodentis) in the management of periodontal disease: a preliminary randomized clinical trial", Journal of Oral Microbiology, Nov. 2010, vol. 2, Article 5344: pp. 1-10.
Costa, et al., "Microbial Extracellular Polymeric Substances: Ecological Function and Impact on Soil Aggregation", Frontiers in Microbiology | www.frontiersin.org | Jul. 23, 2018 | vol. 9 | Article 1636 | doi: 10.3389/fmicb.2018.01636: pp. 1-14.
Langan, et al., "Microbiota-Derived Metabolites, Indole-3 aldehyde and Indole-3-acetic Acid, Differentially Modulate Innate Cytokines and Stromal Remodeling Processes Associated with Autoimmune Arthritis," Int. J. of Molecular Sciences 2021, 22:1-17.
Diebel, et al., "Determination of Biological Age: Geriatric Assessment vs Biological Biomarkers", Current Oncology Reports (2021) 23: 104 | https://doi.org/10.1007/s11912-021-01097-9: pp. 1-8.
The Tabula Muris Consortium, et al., "A single-cell transcriptomic atlas characterizes ageing tissues in the mouse", Nature, Jul. 2020, vol. 583, No. 7817: pp. 590-595. Epub Jul. 2020.
Ferro, et al., "Probiotic Supplementation for Rheumatoid Arthritis: A Promising Adjuvant Therapy in the Gut Microbiome Era", Frontiers in Pharmacology | www.frontiersin.org | Jul. 23, 2021 | vol. 12 | Article 711788 | doi: 10.3389/fphar.2021.711788: pp. 1-17.
Ternes, et al., "The gut microbial metabolite formate exacerbates colorectal cancer progression", Nature Metabolism, Apr. 2022, vol. 4, No. 4: pp. 458-475. Epub Apr. 2022.
Skirbekk, et al., "How to Measure Population Aging? The Answer Is Less than Obvious: A Review", Gerontology, 2019, vol. 65, No. 2: pp. 136-144. Epub Dec. 13, 2018.
Sutphin, et al., "Caenorhabditis elegans orthologs of human genes differentially expressed with age are enriched for determinants of longevity", Aging Cell, Aug. 2017, vol. 16, No. 4: pp. 672-682. Epub Apr. 2017.
Yusufu, Ibrahim, et al., "A Tryptophan-Deficient Diet Induces Gut Microbiota Dysbiosis and Increases Systemic Inflammation in Aged Mice", Int. J. Mol. Sci., 2021, 22, 5005, <https://doi.org/10.3390/ijms22095005>.
Thevaranjan, et al., "Age-Associated Microbial Dysbiosis Promotes Intestinal Permeability, Systemic Inflammation, and Macrophage Dysfunction", Cell Host & Microbe, Apr. 2017, vol. 21, No. 4: pp. 455-466 (19 pages).
Zhang, Yiqiang, et al., "Rapamycin Extends Life and Health in C57BL/6 Mice", J Gerontol A Biol Sci Med Sci, Feb. 2014, 69(2), pp. 119-130.
Nakagawa, et al., "Effects and mechanisms of prolongevity induced by Lactobacillus gasseri SBT2055 in Caenorhabditis elegans", Aging Cell (2016) 15, pp. 227-236.
Amdekar, et al., "Lactobacillus casei reduces the Inflammatory Joint Damage Associated with Collagen-Induced Arthritis (CIA) by Reducing the Pro-Inflammatory Cytokines", J Clin Immunol (2011) 31:147-154.
Lee, et al., "Heliobacter pylori Eradication Prevents Progression of Gastric Cancer in Hypergastrinemic INS-GAS Mice," Cancer Research 2008, 68:(9):3540-3548.
U.S. Appl. No. 16/826,078—Office Action, Oct. 5, 2022, 54 pages.
Lee, et al., "Elucidating the Mechanism of Weissella-dependent Lifespan Extension in Caenorhabditis elegans," Scientific Reports, 2015, 5:17128, pp. 1-13.
Yamashita, Maya, et al., "Lactobacillus helveticus SBT2171 Attenuates Experimental Autoimmune Encephalomyelitis in Mice", Frontiers in Microbiology, Jan. 2018, vol. 8, Article 2596.
Vanzanten, et al., "Gastric transitional zones, areas where Helicobacter treatment fails: results of a treatment trial using the Sydney strain mouse model", Antimicrobial Agents and Chemotherapy, Jul. 2003, vol. 47, No. 7: pp. 2249-2255.
Wilson, et al., "Microbial Influences of Mucosal Immunity in Rheumatoid Arthritis", Current Rheumatology Reports, Oct. 2020, vol. 22, No. 11: pp. 1-8.
Tsai, et al., "Gerobiotics: probiotics targeting fundamental aging processes", Bioscience of Microbiota, Food and Health, 2021, vol. 40, No. 1: pp. 1-11. Epub Oct. 2020.
Atkinson, et al., "Pharmacological Value of Murine Delayed-type Hypersensitivity Arthritis: A Robust Mouse Model of Rheumatoid Arthritis in C57BL/6 Mice", Basic & Clinical Pharmacology & Toxicology, 2017, 120, 108-114.
Vaghef-Mehrabany, et al., "Probiotic supplementation improves inflammatory status in patients with rheumatoid arthritis", Nutrition, Apr. 2014, vol. 30, No. 4: pp. 430-435. Epub Dec. 2013.
PCT/US2022/053684—Invitation to Pay Additional Fees, Jul. 7, 2023, 6 pages.
Liu, et al.., "Lactobacillus salivarius Isolated from Patients with Rheumatoid Arthritis Suppresses Collagen-Induced Arthritis and Increases Treg Frequency in Mice," J. of Interferon & Cytokine Research, 2016 36(12):1-7.
Fransen, et al., "Aged Gut Microbiota Contributes to Systemical Inflammaging after Transfer to Germ-Free Mice", Frontiers in Immunology, Nov. 2017, vol. 8, Article 1385: pp. 1-12.
Visser, et al., "Optimal dosage and route of administration of methotrexate in rheumatoid arthritis: a systematic review of the literature", Ann Rheum Dis., Jul. 2009, vol. 68, No. 7: pp. 1094-1099. Epub Nov. 2009.
Belsky, et al., "Change in the Rate of Biological Aging in Response to Caloric Restriction: Calerie Biobank Analysis", J Gerontol A Biol Sci Med Sci, 2018, vol. 73, No. 1, 4-10 doi:10.1093/gerona/glx096.
Nguyen, et al., "TLR2 and endosomal TLR-mediated secretion of IL-10 and immune suppression in response to phagosome-confined Listeria monocytogenes", PLOS Pathogens, Jul. 7, 2020, pp. 1-20.
Grootaert, et al., "Adherence and viability of intestinal bacteria to differentiated Caco-2 cells quantified by flow cytometry", Journal of Microbiological Methods, Epub: Apr. 2011, vol. 86, No. 1: pp. 33-41.
Ni, et al., "TGR5-HNF4a axis contributes to bile acid-induced gastric intestinal metaplasia markers expression", Cell Death Discovery, pp. 1-20 (2020).
PCT/US2018/066088—International Search Report and Written Opinion, Jun. 11, 2019, 20 pages.
Lopez-Otin, et al., "Hallmarks of Health," Cell 2021, 184:33-63.

(56) References Cited

OTHER PUBLICATIONS

Giri, et al., "Role of Bacillus licheniformis VS16-Derived Biosurfactant in Mediating Immune Responses in Carp Rohu and its Application to the Food Industry", Frontiers in Microbiology, Mar. 2017, vol. 8, Article 514: pp. 1-13.

Macfarlane et al., "Synbiotic Consumption Changes the Metabolism and Composition of the Gut Microbiota in Older People and Modifies Inflammatory Processes: a Randomized, Double-blind, Placebo-Controlled Crossover Study," Aliment Pharmacol. Ther. 2013, 38:804-816.

Hang, et al., "Bile acid metabolites control Th17 and Treg cell differentiation", Nature, Dec. 2019, vol. 576 (7785): pp. 143-148 (34 pages). Epub Nov. 2019. Author Manuscript.

Maeda et al., "Host-microbiota Interactions in Rheumatoid Arthritis," Experimental & Molecular Medicine 51:150 pp. 1-6.

Aghaloo, et al. "Periodontal Diseas and Bisphosphonates Induce Osteonecrosis of the Jaws in the Rat", Journal of Bone and Mineral Research, vol. 26, No. 8, Aug. 2011, pp. 1871-1882 DOI: 10.1002/jbmr.379.

Marietta, et al., "Human Gut-derived Prevotella histicola Suppresses Inflammatory Arthritis in Humanized Mice," Arthritis Rheumatol 2016, 68(12):2878-2888.

Musso, et al., "Obesity, diabetes, and gut microbiota: the hygiene hypothesis expanded?", Diabetes Care, Oct. 2010, vol. 33, No. 10: pp. 2277-2284. doi: 10.2337/dc10-0556.

McIntyre, et al., "Inhibition of the Neuromuscular Acetylcholine Receptor with Atracurium Activates FOXO/DAF-16-induced longevity," Aging Cell 2021 13381 pp. 1-16.

Boden, G (2011) Obesity, Insulin Resistance and Free Fatty Acids. Curr Opin Endocrinol Diabetes Obes 18(2): 139-143.

Mohammed, et al., "The Therapeutic Effect of Probiotics on Rheumatoid Arthritis: a Systemic Review and Meta-analysis of Randomized Control Trials," Clin. Rheumatol. 36:2697-2707 (2017).

Jia, et al., "Common methods of biological age estimation", Clinical Interventions in Aging, May 2017, vol. 12: pp. 759-772 (15 pages).

Morikawa, et al., "A Study on the Structure-function Relationship of Lipopeptide Biosurfactants," Biochimica et Biophysica Acta 2000, pp. 211-218.

Justice, et al., "A framework for selection of blood-based biomarkers for geroscience-guided clinical trials: report from the TAME Biomarkers Workgroup", GeroScience, Dec. 2018, vol. 40, No. 5-6: pp. 419-436 (18 pages). Epub Aug. 2018.

Sonowal, et al., "Indoles from commensal bacteria extend healthspan", Proc Natl Acad Sci USA, Sep. 2017, vol. 114, No. 36: pp. E7506-E7515. Epub Aug. 2017.

Anuj, et al., "Pseudomonas fluorescens strain VZW14 16S ribosomal RNA gene, partial sequence", GenBank: KX066864.1, Submitted Apr. 14, 2016; downloaded from the internet <https://www.ncbi.nlm.nih.gov/nuccore/KX066864> on Sep. 19, 2023, pp. 1-2.

Sun, et al., "Assessments of Probiotic Potentials of Lactiplantibacillus plantarum Strains Isolated From Chinese Traditional Fermented Food: Phenotypic and Genomic Analysis", Frontiers in Microbiology, May 2022, vol. 13, Article 895132: pp. 1-10.

Kushkevych, et al., "Sulfate-Reducing Bacteria of the Oral Cavity and Their Relation with Periodontitis—Recent Advances", Journal of Clinical Medicine, Jul. 2020, vol. 9, No. 8, Article 2347: pp. 1-20.

Pineda, et al., "A randomized, double-blinded, placebo-controlled pilot study of probiotics in active rheumatoid arthritis", Med Sci Monit, 2011; 17(6): CR347-354, Published: Jun. 1, 2011, http://www.medscimonit.com/fulltxt.php?ICID=881808: pp. 348-354.

Liu, et al., "Role of the Gut Microbiome in Modulating Arthritis Progression in Mice," Scientific Reports, 2016, vol. 6:30594 pp. 1-11.

Vyhlidalova, et al., "Gut Microbial Catabolites of Tryptophan Are Ligands and Agonists of the Aryl Hydrocarbon Receptor: A Detailed Characterization", International Journal of Molecular Sciences, Apr. 2020, vol. 21, No. 7, Article 2614: pp. 1-17.

Abdulla OA, Neamah W, Sultan M, Alghetaa HK, Singh N, Busbee PB, Nagarkatti M and Nagarkatti P (2021) The Ability of AhR Ligands to Attenuate Delayed Type Hypersensitivity Reaction Is Associated With Alterations in the Gut Microbiota. Front. Immunol. 12:684727. doi: 10.3389/fimmu.2021.684727.

Vavassori, et al., "The bile acid receptor FXR is a modulator of intestinal innate immunity", The Journal of Immunology, Nov. 2009, vol. 183, No. 10: pp. 6251-6261 (12 pages). Epub Oct. 2009.

Tu, et al., "Strain/species identification in metagenomes using genome-specific markers", Nucleic Acids Res, Apr. 2014, vol. 42, No. 8: pp. e67 (12 pages). doi: 10.1093/nar/gku138. Epub Feb. 12, 2014.

Verginer, et al., "Production of Volatile Metabolites by Grape-Associated Microorganisms", Journal Agricultural and Food Chemistry, Jul. 2010, vol. 58, No. 14: pp. 8344-8350.

Deshpande, et al., "Para-probiotics for Preterm Neonates—The Next Frontier", Nutrients 2018, 10, 871; doi: 10.3390/nu10070871 www.mdpi.com/journal/nutrients: pp. 1-9.

Théatre, et al., "The Surfactin-Like Lipopeptides From *Bacillus* spp.: Natural Biodiversity and Synthetic Biology for a Broader Application Range", Frontiers in Bioengineering and Biotechnology, Mar. 2021, vol. 9, Article 623701: pp. 1-20.

You, Xin-yu, et al., "Intestinal Mucosal Barrier Is Regulated by Intestinal Tract Neuro-Immune Interplay", Frontiers in Pharmacology, May 2021, vol. 12, Article 659716.

Nair, et al., "A simple practice guide for dose conversion between animals and human", Journal of Basic and Clinical Pharmacy, Mar.-May 2016, vol. 7, Issue. 2: pp. 27-31.

Zampieri, Raffaella Margherita, et al., "Anti-Inflammatory Activity of Exopolysaccharides from *Phormidium* sp. ETS05, the Most Abundant Cyanobacterium of the Therapeutic Euganean Thermal Muds, Using the Zebrafish Model", Biomolecules, Apr. 10, 2020, 10, 582.

Nayak, et al., "Methotrexate impacts conserved pathways in diverse human gut bacteria leading to decreased host immune activation", Cell Host & Microbe, Mar. 10, 2021, pp. 362-377.

Dufour, et al., "Molecular typing of industrial strains of *Pseudomonas* spp. isolated from milk and genetical and biochemical characterization of an extracellular protease produced by one of them", Int J Food Microbiol., Jul. 2008, vol. 125, No. 2: pp. 188-196. doi: 10.1016/j.ijfoodmicro.2008.04.004. Epub Apr. 16, 2008.

Liao, et al., "Mouse Models and Aging:Longevity and Progeria," Current Topics in Developmental Biology (2014), 109:249-285.

Wells, et al., "Associations between gut microbiota and genetic risk for rheumatoid arthritis in the absence of disease: a cross-sectional study", Lancet Rheumatology, Jul. 2020, vol. 2, No. 7: pp. e418-e427.

Neff, et al., "Rapamycin extends murine lifespan but has limited effects on aging",The Journal of Clinical Investigation, Aug. 2013, vol. 123, No. 8, pp. 3272-3291.

Bodkhe, et al., "The role of microbiome in rheumatoid arthritis treatment", Therapeutic Advances in Musculoskeletal Disease, Feb. 2019, vol. 11: pp. 1-16.

Negatu, et al., "Indole Propionic Acid, an Unusual Antibiotic Produced by the Gut Microbiota, With Anti-inflammatory and Antioxidant Properties", Frontiers in Microbiology, Oct. 2020, vol. 11, Article 575586, pp. 1-8.

Griffiths, et al., "Psoriasis and Atopic Dermatitis", Dermatol Ther (Heidelb), Epub: Feb. 2017, vol. 7 (Suppl 1): pp. S31-S41.

Liu, et al., "The Anti-Periodontitis Effects of Ethanol Extract Prepared Using *Lactobacillus paracasei* subsp. *paracasei* NTU 101," Nutrients 2018, 10:472 pp. 1-13.

Macfarlane, et al,, "Session: Short-chain Fatty Acids: Regulation of Short-chain Fatty Acid Production," Proceedings of the Nutrition Society 2003, 62:67-72.

Hofer, et al., "Caloric Restriction Mimetics in Nutrition and Clinical Trials", Frontiers in Nutrition, Sep. 2021, vol. 8, Article 717343: pp. 1-20.

Mandel, et al., "Bacillus Coagulans: a Viable Adjunct Therapy for Relieving Symptoms of Rheumatoid Arthritis According to a Randomized, Controlled Trial," BMC Complementary and Alternative Medicine 2010, 10:1-7.

Holden, et al., "Enteropathic arthritis", Rheumatic Disease Clinics of North America, Aug. 2003, vol. 29, No. 3: pp. 513-530.

(56) References Cited

OTHER PUBLICATIONS

Jenab, et al., "Bacterial Natural Compounds with Anti-Inflammatory and Immunomodulatory Properties (Mini Review)", Drug Design, Development and Therapy, Sep. 2020, vol. 14: pp. 3787-3801.
Klemera, et al., "A new approach to the concept and computation of biological age", Mechanisms of Ageing and Development, Mar. 2006, vol. 127, No. 3: pp. 240-248. Epub Nov. 2005.
Smollen, et al., "Rheumatoid arthritis", Nature Reviews Disease Primers, Feb. 2018, vol. 4, Article 18001: pp. 1-23.
Smolen, et al., "Clinical trials of new drugs for the treatment of rheumatoid arthritis: focus on early disease", Ann Rheum Dis., Jul. 2016, vol. 75, No. 7: pp. 1268-1271. Epub Apr. 2016.
Kulkarni, et al., "Benefits of Metformin in Attenuating the Hallmarks of Aging", Cell Metabolism, Jul. 2020, vol. 32, No. 1: pp. 15-30. Epub Apr. 2020.
Walter, et al., "Screening Concepts for the Isolation of Biosurfactant Producing Microorganisms", Part of the Advances in Experimental Medicine and Biology (AEMB) book series, 2010, vol. 672: pp. 1-13 (20 pages).
Chassaing, et al., "Intestinal Epithelial cell Toll-like Receptor 5 Regulates the Intestinal Microbiota to Prevent Low-grade Inflammation and Metabolic Syndrome in Mice", Published in final edited form as: Gastroenterology. Dec. 2014 ; 147(6): 1363-1377.e17. doi:10.1053/j.gastro.2014.08.033,; pp. 1-19.
Lavasani, et all., "A Novel Probiotic Mixture Exerts a Therapeutic Effect on Experimental Autoimmune Encephalomyelitis Mediated by IL-10 Producing Regulatory T Cells," PLoS One, 2010 5(2):1-11.
Forster, et al., "Identification of gut microbial species linked with disease variability in a widely used mouse model of colitis", https://doi.org/10.1038/s41564-022-01094-z | Nat ure Microbiology | vol. 7 | Apr. 2022 | www.nature.com/naturemicrobiology: pp. 590-599.
Lebeer, et al., "Functional Analysis of Lactobacillus rhamnosus GG Pili in Relation to Adhesition and Immunomodulatory Interactions with Intestinal Epithelial Cells," Applied and Environmental Microbiology, 2011, pp. 185-193.
Ley et al (2005) Obesity alters gut microbial ecology. PNAS 102(31): 11070-11075.
Vaghef-Mehrabany, et al., "Effects of Probiotic Supplementation on Oxidative Stress Indices in Women with Rheumatoid Arthritis: A Randomized Double-Blind Clinical Trial", Journal of the American College of Nutrition, May-Jun. 2016, vol. 35, No. 4: pp. 291-299 (10 pages). Epub Apr. 2015.
United Nations, et al., "World Population Prospects 2019: Highlights", Department of Economic and Social Affairs, Statistical Papers—United Nations (Ser. A), Population and Vital Statistics Report, Jun. 2019: pp. 1-2.
Newman, et al., "Strategies and Challenges in Clinical Trials Targeting Human Aging", Gerontol A Biol Sci Med Sci, 2016, vol. 71, No. 11, pp. 1424-1434.
Amalraj, et al., "A Novel Highly Bioavailable Curcumin Formulation Improves Symptoms and Diagnostic Indicators in Rheumatoid Arthritis Patients: A Randomized, Double-Blind, Placebo-Controlled, Two-Dose, Three-Arm, and Parallel-Group Study", J Med Food 20 (10) 2017, 1022-1030. DOI: 10.1089/jmf.2017.3930.
Maeda, et al., "Dysbiosis Contributes to Arthritis Development via Activation of Autoreactive TCells in the Intestine," Arthritis & Rheumatology 2016, 10.1002: 1-35.
Holers, et al., "Rheumatoid arthritis and the mucosal origins hypothesis: protection turns to destruction", Nature Reviews Rheumatology, Sep. 2018, vol. 14, No. 9: pp. 542-557 (16 pages).
Monteagudo-Mera, et al., "Adhesion Mechanisms Mediated by Probiotics and Prebiotics and their Potential Impact on Human Health," Applied Microbiology and Biotechnology 2019, 10.1007 pp. 1-10.
Lin, H et al (2016) Correlations of Fecal Metabonomic and Microbiomic Changes Induced by High-fat Diet in the Pre-Obesity State. Sci Rep 6(21618):1-14.
Pinoli, et al., "Dopaminergic Regulation of Innate Immunity: a Review", J Neuroimmune Pharmacol, DOI 10.1007/s11481-017-9749-2, Published online: Jun. 3, 2017: pp. 1-22.
Catrina, et al., "RA: from risk factors and pathogenesis to prevention, Gene, environment, microbiome and mucosal immune tolerance in rheumatoid arthritis", Rheumatology Advance Access published Dec. 23, 2014, doi: 10.1093/rheumatology/keu469, Downloaded from http://rheumatology.oxfordjournals.org/ at University of California, San Francisco on Mar. 11, 2015: pp. 1-12.
Le, et al., "Host Hepatic Metabolism is Modulated by Gut Microbiota-Derived Sphingolipids," Cell Host & Microbe, 2022 30:798-808.
Woo, Jae-Yeon, et al., "*Lactobacillus pentosus* var. *plantarum* C29 ameliorates memory impairment and inflammaging in a D-galactose-induced accelerated aging mouse model", Anaerobe, 27, 2014, pp. 22-26.
Liu, et al., "Deep Sequencing of the Oral Microbiome Reveals Signatures of Periodontal Disease," PLoS One 2012, 6:e7919, pp. 1-16.
Guo, et al., "*Clostridium* species as probiotics: potentials and challenges", Journal of Animal Science and Biotechnology, Feb. 2020, vol. 11, No. 24: pp. 1-10.
Marinelli, et al., "Identification of the Novel Role of Butyrate as AhR Ligand in Human Intestinal Epithelial Cells," Scientific Reports 2019, 10.1038 pp. 1-14.
Vijayakumar, et al., "A Microplate Growth Inhibition Assay for Screening Bacteriocins against Listeria monocytogenes to Differentiate Their Mode-of-Action", Biomolecules, Jun. 2015, vol. 5, No. 2: pp. 1178-1194.
Apweiler, et al., "Protein sequence databases", Current Opinion in Chemical Biology (2004) 8:76-80.
Liu, et al., "Targeted Small Molecule-Mediated Immunomodulation of GP130 Receptor Attenuates Rheumatoid Arthritis in Rats," Ostreoarthritis and Cartilage, 2019 27:S381-S382.
Ku, et al., "Anti-inflammatory effects of 27 selected terpenoid compounds tested through modulating Th1/Th2 cytokine secretion profiles using murine primary splenocytes", Food Chemistry, Nov. 2013, vol. 141, No. 2: pp. 1104-1113. Epub Apr. 2013.
Mulligan, et al., "Selection of Microbes Producing Biosurfactants in Media without Hydrocarbons", J. Ferment. Technol., vol. 62, No. 4, pp. 311-314, 1984.
Komura, et al., "Mechanism underlying prolongevity induced by bifidobacteria in Caenorhabditis elegans", Biogerontology, Feb. 2013, vol. 14, No. 1: pp. 73-87. Epub Jan. 2013.
Soto-Giron, et al., "The Edible Plant Microbiome represents a diverse genetic reservoir with functional potential in the human host", Scientific Reports, Dec. 2021, vol. 11, No. 1, Article 24017: pp. 1-14.
Olson, et al (2017) Obesity and the tumor microenvironment, Science 358(6367): 1130-1131.
Published as US 2020/0164002 A1, U.S. Appl. No. 16/694,876, filed Nov. 25, 2019, U.S. Pat. No. 11,819,524, Nov. 21, 2023, Issued.
Published as US 2023/0233625 A1, U.S. Appl. No. 18/053,262, filed Nov. 7, 2022, Allowed.
Published as US 2019/0269743 A1, U.S. Appl. No. 16/235,858, filed Dec. 28, 2018, U.S. Pat. No. 10,596,209, Mar. 24, 2020, Issued.
Published as US 2020/0376049 A1, U.S. Appl. No. 16/826,078, filed Mar. 20, 2020, U.S. Pat. No. 11,793,841, Oct. 24, 2023, Issued.
Published as US 2022/0354907 A1, U.S. Appl. No. 17/555,261, filed Dec. 17, 2021, Published.
Published as US 2023/0190834 A1, U.S. Appl. No. 17/816,932, filed Aug. 2, 2022, Published.
Published as US 2023/0256035 A1, U.S. Appl. No. 18/304,264, filed Apr. 20, 2023, Allowed.
U.S. Appl. No. 18/477,298, filed Sep. 28, 2023, Pending.
Published as US 2023/0346859 A1, U.S. Appl. No. 18/181,495, filed Mar. 9, 2023, Allowed.
U.S. Appl. No. 18/395,925, filed Dec. 26, 2023, Pending.

* cited by examiner

Red cabbage

Romaine lettuce

Celery sticks

Butterhead lettuce

Baby spinach

Green crisp gem lettuce

Red oak leaf lettuce

Green oak leaf lettuce

Cherry tomatoes

Crisp red gem lettuce

Broccoli juice

Broccoli head

| Name | Readcount (% of classified reads) |
| --- | --- |
| Neosartorya fischeri | 17656 (22.68%) |
| Aureimonas sp. Leaf427 | 7331 (9.42%) |
| Elizabethkingia anophelis | 6310 (8.1%) |
| Periglandula ipomoeae | 6185 (7.94%) |
| Bacillus sp. LL01 | 3385 (4.35%) |
| Candidatus Burkholderia verschuerenii | 2917 (3.75%) |
| Streptomyces olindensis | 2208 (2.84%) |
| Candidatus Burkholderia calva | 1880 (2.41%) |
| Penicillium paneum | 1444 (1.85%) |
| Pseudoalteromonas luteoviolacea | 1290 (1.66%) |

| Name | Estimated Abundance |
|---|---|
| Pseudomonas fluorescens | 53.94% |
| Pseudomonas sp. DSM 29167 | 10.99% |
| Propionibacterium acnes | 6.10% |
| Acinetobacter soli | 4.97% |
| Aureobasidium pullulans | 2.96% |
| Pseudomonas syringae | 2.76% |
| Pseudomonas sp. Leaf15 | 1.84% |
| Acinetobacter baumannii | 1.58% |
| Pantoea sp. SL1_M5 | 1.43% |
| Raoultella ornithinolytica | 1.32% |
| Sphingomonas sp. Ant20 | 1.27% |
| Comamonas testosteroni | 1.18% |
| Rahnella sp. WP5 | 1.18% |
| Enterobacter sp. 940_PEND | 1.06% |
| Pseudomonas sp. FH1 | 0.73% |
| Rothia dentocariosa | 0.54% |
| Pectobacterium carotovorum | 0.54% |
| Enhydrobacter aerosaccus | 0.54% |
| Bacillus sp. LL01 | 0.42% |
| Pseudomonas trivialis | 0.39% |

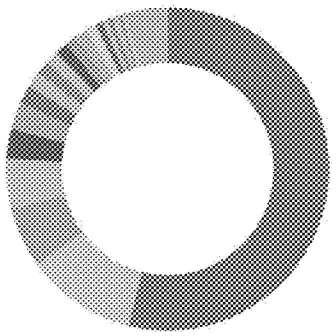

Blueberry

FIG 2B

Pickled green olives

| Name | | Estimated Abundance |
| --- | --- | --- |
| | Lactobacillus acetotolerans | 60.98% |
| | Lactobacillus buchneri | 12.34% |
| | Pediococcus ethanolidurans | 5.47% |
| | Lactobacillus parafarraginis | 4.32% |
| | Lactobacillus rapi | 2.91% |
| | Lactobacillus plantarum | 1.52% |
| | Lactobacillus kefiranofaciens | 1.40% |
| | Lactobacillus futsaii | 1.38% |
| | Lactobacillus brevis | 1.25% |
| | Lactobacillus panis | 1.16% |
| | (Remaining) | 7.26% |

Ginseng

Blackberries

Broccolini

- Ralstonia pickettii
- Pasteurella multocida
- Pantoea agglomerans
- Pseudomonas moraviensis
- Ralstonia mannitolilytica
- Pseudomonas sp. MYb193
- Ralstonia insidiosa
- Photobacterium damselae
- Clostridium botulinum
- Sphingobacteriaceae bacterium GW460-11-11-14-LB5
- Others

A.

Subject 2275

*B. thetaiotaomicron*

Subject 2275

*L. johnsonii*

SBD111 baseline vs 6 weeks

SBD111 vs OVX

METHODS AND COMPOSITIONS FOR TREATING MUSCULOSKELETAL DISEASES

CROSS REFERENCE TO RELATED APPLICATIONS

This application is a divisional of U.S. application Ser. No. 16/694,876 filed Nov. 25, 2019, which application is a continuation of International Application PCT/US2019/049823, filed Sep. 5, 2019, which claims the benefit of U.S. Provisional Application No. 62/727,503 filed Sep. 5, 2018; U.S. Provisional Application No. 62/728,018, filed Sep. 6, 2018; 62/728,019, filed Sep. 6, 2018; U.S. Provisional Application No. 62/728,020, filed Sep. 6, 2018, and U.S. Provisional Application No. 62/863,722, filed Jun. 19, 2019 each of which is hereby incorporated by reference in its entirety for all purposes.

SEQUENCE LISTING

The instant application contains a Sequence Listing which has been submitted electronically and is hereby incorporated herein by reference in its entirety. Said XML copy, created on Mar. 23, 2023, is named SBI-001D1_SL.xml, and is 439,687 bytes in size.

BACKGROUND

The disclosure relates to methods and compositions for treating or preventing musculoskeletal diseases, including osteoporosis, osteopenia, osteoarthritis, suboptimal fracture healing, and osteomyelitis.

Daily consumption of fresh fruits, vegetables, seeds and other plant-derived ingredients of salads and juices is recognized as part of a healthy diet and associated with weight loss, weight management and overall healthy life styles. This is demonstrated clinically and epidemiologically in the "China Study" (Campbell, T. C. and Campbell T. M. 2006. The China Study: startling implications for diet, weight loss and long-term health. Benbella books pp 419) where a lower incidence of inflammatory-related indications were observed in rural areas where diets are whole food plant-based. The benefit from these is thought to be derived from the vitamins, fiber, antioxidants and other molecules that are thought to benefit the microbial flora through the production of prebiotics. These can be in the form of fermentation products from the breakdown of complex carbohydrates and other plant-based polymers. There has been no clear mechanistic association between microbes in whole food plant-based diets and the benefits conferred by such a diet. The role of these microbes as probiotics, capable of contributing to gut colonization and thereby influencing a subject's microbiota composition in response to a plant-based diet, has been underappreciated.

Musculoskeletal disorders, including osteoporosis, osteopenia, Paget's disease, stunting, osteoarthritis, osteomyelitis, delayed or non-union fractures, are potentially disabling conditions whose current treatments are often accompanied by potentially serious negative side effects. Often therapies treat symptoms, while leaving underlying causes, such as chronic inflammation, unaddressed. Therefore, treatments with reduced side-effects and increased efficacy towards alleviating underlying causes represent a long-felt unmet need.

SUMMARY OF THE INVENTION

Provided for herein is a method of reducing bone loss, comprising administering to a subject in need thereof a pharmaceutical composition comprising an effective amount of at least two heterologous microbes selected from at least two groups selected from proteobacteria, lactic acid bacteria, and yeast, formulated for oral administration.

In some aspects, at least two of the heterologous microbes have at least 97% similarity to Seq ID Nos: 1-66 at the at 16S rRNA or fungal ITS sequence. In some aspects, at least two of the heterologous microbes have at least 98% similarity to Seq ID Nos: 1-66 at the at 16S rRNA or fungal ITS sequence. In some aspects, at least two of the heterologous microbes have at least 98.5% similarity to Seq ID Nos: 1-66 at the at 16S rRNA or fungal ITS sequence. In some aspects, at least two of the heterologous microbes have at least 99% similarity to Seq ID Nos: 1-66 at the at 16S rRNA or fungal ITS sequence. In some aspects, at least two of the heterologous microbes have 100% similarity to Seq ID Nos: 1-66 at the at 16S rRNA or fungal ITS sequence.

In some aspects, the pharmaceutical composition comprises an effective amount of at least three each heterologous microbes, selected from at least two groups selected from proteobacteria, lactic acid bacteria, and yeast, formulated for oral administration.

In some aspects, the pharmaceutical composition further comprises at least one additional microbe from table 4 or table 7. In some aspects, the pharmaceutical composition further comprises a cryoprotectant. In some aspects, the cryoprotectant extends room temperature survival of at least one microbe.

In some aspects, the pharmaceutical composition further comprises a prebiotic.

Also provided for herein is a method of reducing bone loss, comprising administering to a subject in need thereof a medical food composition comprising an effective amount of at least two heterologous microbes selected from at least two groups selected from proteobacteria, lactic acid bacteria, and yeast, formulated for oral administration. In some aspects, at least two of the heterologous microbes have at least 97% similarity to Seq ID Nos: 1-66 at the at 16S rRNA or fungal ITS sequence. In some aspects, the medical food composition comprises an effective amount of at least three of each heterologous microbes selected from at least two groups selected from proteobacteria, lactic acid bacteria, and yeast, formulated for oral administration. In some aspects, the medical food composition further comprises at least one additional microbe from table 4 or table 7. In some aspects, the medical food composition further comprises a cryoprotectant. In some aspects, the cryoprotectant extends room temperature survival of at least one microbe. In some aspects, the medical food composition further comprises a prebiotic.

Also provided for herein is a probiotic composition comprising an effective amount of at least two heterologous microbes selected from at least two groups selected from proteobacteria, lactic acid bacteria, and yeast, formulated for oral administration. In some aspects, at least two of the heterologous microbes have at least 97% similarity to Seq ID Nos: 1-66 at the at 16S rRNA or fungal ITS sequence. In some aspects, the probiotic composition comprises an effective amount of at least three of each heterologous microbes selected from at least two groups selected from proteobacteria, lactic acid bacteria, and yeast, formulated for oral administration. In some aspects, the probiotic composition further comprises at least one additional microbe from table 4 or table 7. In some aspects, the probiotic composition further comprises a cryoprotectant. In some aspects, the cryoprotectant extends room temperature survival of at least one microbe. In some aspects, the medical food composition further comprises a prebiotic.

Also provided for herein is a method of treating osteoarthritis, comprising administering to a subject in need thereof a pharmaceutical composition comprising an effective amount of at least two heterologous microbes selected from at least two groups selected from proteobacteria, lactic acid bacteria, and yeast, formulated for oral administration. In some aspects, at least two of the heterologous microbes have at least 97% similarity to Seq ID Nos: 1-66 at the at 16S rRNA or fungal ITS sequence. In some aspects, the pharmaceutical composition comprises an effective amount of at least three each heterologous microbes, selected from at least two groups selected from proteobacteria, lactic acid bacteria, and yeast, formulated for oral administration. In some aspects, the pharmaceutical composition further comprises at least one additional microbe from table 4 or table 7. In some aspects, the pharmaceutical composition further comprises a cryoprotectant.

Also provided for herein is a method of treating osteomyelitis, comprising administering to a subject in need thereof a pharmaceutical composition comprising an effective amount of at least two heterologous microbes selected from at least two groups selected from proteobacteria, lactic acid bacteria, and yeast, formulated for oral administration. In some aspects, at least two of the heterologous microbes have 97% similarity to Seq ID Nos: 1-66 at the at 16S rRNA or fungal ITS sequence. In some aspects, the pharmaceutical composition comprises an effective amount of at least three each heterologous microbes, selected from at least two groups selected from proteobacteria, lactic acid bacteria, and yeast, formulated for oral administration. In some aspects, the pharmaceutical composition further comprises at least one additional microbe from table 4 or table 7. In some aspects, the pharmaceutical composition further comprises a cryoprotectant.

Also provided for herein is a method of improving healing of non-union or delayed union fractures, comprising administering to a subject in need thereof a pharmaceutical composition comprising an effective amount of at least two heterologous microbes selected from at least two groups selected from proteobacteria, lactic acid bacteria, and yeast, formulated for oral administration. In some aspects, at least two of the heterologous microbes have at least 97% similarity to Seq ID Nos: 1-66 at the at 16S rRNA or fungal ITS sequence. In some aspects, the pharmaceutical composition comprises an effective amount of at least three each heterologous microbes, selected from at least two groups selected from proteobacteria, lactic acid bacteria, and yeast, formulated for oral administration. In some aspects, the pharmaceutical composition further comprises at least one additional microbe from table 4 or table 7. In some aspects, the pharmaceutical composition further comprises a cryoprotectant.

Also provided for herein is a pharmaceutical composition comprising an isolated population of bacterial cells comprising three or more strains present in whole food plant-based diets, wherein each strain is capable of modulating production of one or more short chain fatty acids, vitamin K2, and/or flavones such as apigenin, narigenin, hesperidin, nobiletin, tangeretin in the mammalian gut.

Also provided for herein is a synthetic combination comprising a purified bacterial population, wherein said population comprises at least three unique isolates selected from the group consisting of *Pseudomonas, Leuconostoc, Acinetobacter, Aeromonas, Curtobacterium, Escherichia, Lactobacillus, Serratia, Streptococcus*, and *Stenotrophomonas, Leuconostoc, Pediococous, Deboromyces, Pichia, Hanseniaspora*, where the purified bacterial population is capable of modulating production of one or more short chain fatty acids, flavones, and/or vitamin K2 in a mammalian gut.

Also provided for herein is a synthetic combination comprising a purified bacterial population, wherein said population comprises at least 3 isolates from Table 4 or Table 7 where the at least 3 isolates are capable of modulating production of one or more short chain fatty acids selected from the group consisting of acetate, butyrate, and propionate; or the enzymes acetolactate synthase I, N-acetylglutamate synthase, acetate kinase, Acetyl-CoA synthetase, acetyl-CoA hydrolase, Glucan 1,4-alpha-glucosidase, Bile acid symporter Acr3; and/or capable of modulating production of flavones and/or vitamin K2 and wherein the isolates are present in an amount effective to adhere to a mammalian mucosal lining, thereby modulating the bone health markers of a mammal treated with the synthetic combination, as compared to a reference mammal Also provided for herein is a synthetic population that mimics the composition seen in human stool from patients with desirable bone mineral density or other markers of normal bone health.

Also provided for herein is a synthetic microbial consortia comprising a purified bacterial population of lactic acid bacteria and gamma proteobacteria, wherein the synthetic consortia is capable of modulating production of one or more short chain fatty acids selected from the group consisting of acetate, butyrate, and propionate; and/or capable of modulating production of flavones and/or vitamin K2; and wherein the isolates are present in an amount effective to adhere to a mammalian mucosal lining, thereby modulating the bone health markers, such as bone density, of a mammal treated with the synthetic combination, as compared to a reference mammal.

Also provided for herein is a synthetic microbial consortia comprising a purified bacterial population isolated from a first plant-based sample selected from samples 1-21 in Table 3 artificially associated with a purified bacterial population isolated from a second plant-based sample from selected from samples 1-21 in Table 3, wherein the synthetic microbial consortia is capable of modulating the bone density of a mammal treated with the synthetic microbial consortia, as compared to a reference mammal.

Also provided for herein is a synthetic microbial composition that is not completely viable and can act by releasing metabolites that act in the GI tract of a patient reducing symptoms of osteoporosis or osteopenia.

BRIEF DESCRIPTION OF FIGURES

These and other features, aspects, and advantages of the present invention will become better understood with regard to the following description, and accompanying drawings, where:

FIGS. 1 A-L show plots depicting the diversity of microbial species detected in samples taken from 12 plants usually consumed raw by humans.

DETAILED DESCRIPTION

Figure 1A:
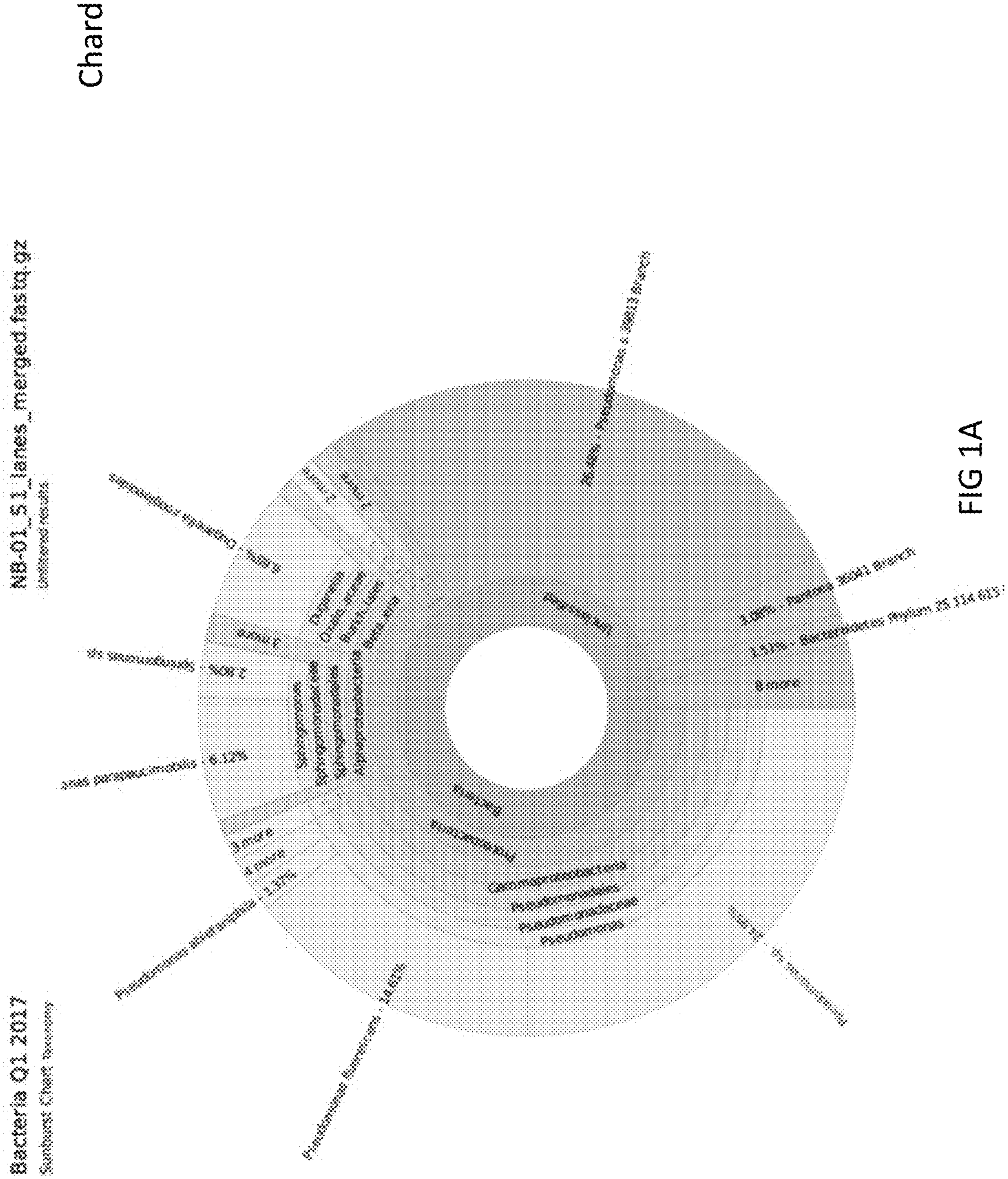
FIG. 1A shows bacterial diversity observed in a green chard.

Musculoskeletal disorders, including osteoporosis and osteopenia, represent a medical challenge presently without a satisfactory remedy. Approximately 10 million Americans over the age of 50 are currently living with osteoporosis or osteopenia culminating in 1.5 million fractures annually. The high incidence of disease leads to an annual economic burden of $17 billion that couples with significantly reduced quality of life. The current standards of care including anti-resorptive and anabolic therapies are limited due to their side effects and restrictive costs, leading to the current unmet need for a safe, effective, and low cost therapeutic that prevents bone loss.

Osteoarthritis (OA), another musculoskeletal disorder, is one of most prevalent diseases in the world, afflicting 31 million individuals in the US, and projected to impact 45 million by 2030. The United States reports the highest incidence of OA with 13% of US adult population affected, and more than 80% of persons over the age of 75 having some degree of disease. OA is a degenerative disease with multiple origins, characterized by progressive cartilage erosion, joint effusion, synovial hyperplasia, subchondral bone sclerosis, and osteophyte formation. Three main types of osteoarthritis are typically identified: aging-related, obesity-related, and post-traumatic. All of these varieties, however, share a root cause of deleterious inflammation.

Affected patients are left in a perpetual state of pain and discomfort, relying on non-steroidal anti-inflammatory drugs (NSAIDs) and opioid pain killers for relief, until end stage disease requires a total joint replacement to restore functionality to the ailing joint. A need for a therapy that modulates systemic inflammation to reduce or reverse the symptoms of osteoarthritis with naturally occurring products is needed for patients to avoid the side effects of current therapies.

Another musculoskeletal disorder involves fractures that do not properly heal. Fractures are a common orthopedic problem, with over 2 million occurring per year in the U.S. With treatment, most broken bones will heal over a 6 to 8-week period without clinically relevant delay. Delayed union and nonunion, the failure of a fractured bone to heal, occurs in approximately 5-10% of all fractures. Moreover, delayed and nonunion is associated with significant morbidity. (Amin et al. 2014)

Importantly, multiple clinical studies have demonstrated that obesity/type 2 diabetes (T2D) are risk factors for fracture nonunion. This is supported by previous studies demonstrating that mice fed a high-fat diet to induce obesity/T2D have impaired fracture healing. Despite this, little is known about the mechanism(s) that increase the risk of nonunion in obese patients, and there are no accepted therapeutic approaches to address the delay in healing that obese/T2D patients experience. (Zura et al. 2016) Thus, strategies to mitigate the deleterious effect of obesity/T2D on fracture are a critical unmet need.

One additional indication is osteomyelitis, which is inflammation of the bone or bone marrow. Although sometimes caused by infection, treatment of osteomyelitis could by aided by administration of probiotic compositions described herein. Modulation of the host immune system by intentionally dosed microbes could mitigate damage done by an overactive immune system or decrease recovery time by improving targeting of the immune system.

Advantages and Utility

Briefly, and as described in more detail below, described herein are methods and compositions for using microbial agents (probiotics) and agents that promote growth of certain microbes (prebiotics) for management (including prevention and treatment) of musculoskeletal disorders, including osteoporosis, osteopenia, Paget's disease, stunting, osteoarthritis, osteomyelitis, and delayed or non-union fractures.

Several features of the current approach should be noted. It is based on development of synergistic combinations of microbes as on those found in fruits and vegetables consumed as part of a plant-based diet. The combinations are based, in part, on analyses of biochemical pathways catalyzed by genes in these microbes and selection of microbial combinations that promote beneficial metabolic changes in a subject through the biochemical reactions they catalyze such as the production of short chain fatty acids (SCFA).

Advantages of this approach are numerous. They include reduction of the morbidity associated with musculoskeletal disorders, such as osteoporosis or osteopenia, without the use of traditional drugs and the side effects they can sometimes cause. The invention can also reduce chronic inflammation.

The invention is useful for providing health benefits associated with consumption of a plant-based diet, as the diet microbes and fibers are delivered in concentrated form. This can reduce the burden on a subject to ingest potentially unreasonable or inconvenient amounts of particular plants and/or plant-based products, such as fermented foods.

Definitions

Terms used in the claims and specification are defined as set forth below unless otherwise specified.

The term "ameliorating" refers to any therapeutically beneficial result in the treatment of a disease state, e.g., a metabolic disease state, including prophylaxis, lessening in the severity or progression, remission, or cure thereof.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

As used herein, the term "derived from" includes microbes immediately taken from an environmental sample and also microbes isolated from an environmental source and subsequently grown in pure culture. The term "derived from" also includes material isolated from the recited source, and materials obtained using the isolated materials (e.g., cultures of microorganisms made from microorganisms isolated from the recited source).

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

In some cases, alignment of an entire sequence is not necessary for identification or comparison purposes regarding a microbial entity. In such a case, a so-called diagnostic subsequence can be used. The term "diagnostic subsequence" refers to a portion of a known sequence which would be identified and used by one of skill in the art to identify or compare two or more microbial entities. One, non-limiting example is utilization of subsequences of 16S rRNA sequences found in Asgari et al (2018, bioRxiv).

The term "effective amount" is an amount that is effective to ameliorate a symptom of a disease. An effective amount can also be an amount effective for prophylaxis of a particular disease. More generally, an effective amount is an amount sufficient to produce a desired effect, e.g., an amount effective for alteration of the microbial content of a subject's microbiota.

The term "defined microbial assemblage" or "DMA" refers to a combination of two or more microbial strains (bacterial or fungal) wherein the two or more microbial strains are chosen because they are predicted to achieve a particular synergistic result when applied in concert. DMA compositions preferably further comprise prebiotics or other fiber sources predicted to heighten the desired effect of the microbial strains applied. A DMA is rationally designed to achieve a particular benefit, such as increase SCFA production in the gut lumen.

The term "SBD" refers to a DMA when it is used as a therapeutic intervention in a preclinical or clinical study.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition.

As used herein, the term "preventing" includes completely or substantially reducing the likelihood or occurrence or the severity of initial clinical or aesthetical symptoms of a condition.

As used herein, the term "about" includes variation of up to approximately +/−10% and that allows for functional equivalence in the product.

As used herein, the term "colony-forming unit" or "cfu" is an individual cell that is able to clone itself into an entire colony of identical cells.

As used herein all percentages are weight percent unless otherwise indicated.

As used herein, "viable organisms" are organisms that are capable of growth and multiplication. In some embodiments, viability can be assessed by numbers of colony-forming units that can be cultured. In some embodiments viability can be assessed by other means, such as quantitative polymerase chain reaction.

"Microbiota" refers to the community of microorganisms that occur (sustainably or transiently) in and on a plant or an animal subject, typically a mammal such as a human, including eukaryotes, archaea, bacteria, and viruses (including bacterial viruses i.e., phage).

"Microbiome" refers to the genetic content of the communities of microbes that live inside and on the human body, or inside or outside a plant, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

The term "subject" refers to any animal subject including humans, laboratory animals (e.g., primates, rats, mice), livestock (e.g., cows, sheep, goats, pigs, turkeys, and chickens), and household pets (e.g., dogs, cats, and rodents). The subject may be suffering from a dysbiosis, including, but not limited to, an infection due to a gastrointestinal pathogen or may be at risk of developing or transmitting to others an infection due to a gastrointestinal pathogen.

The "colonization" of a host organism includes the non-transitory residence of a bacterium or other microscopic organism. As used herein, "reducing colonization" of a host subject's gastrointestinal tract (or any other microbiotal niche) by a pathogenic bacterium includes a reduction in the residence time of the pathogen in the gastrointestinal tract as well as a reduction in the number (or concentration) of the pathogen in the gastrointestinal tract or adhered to the luminal surface of the gastrointestinal tract. Measuring reductions of adherent pathogens may be demonstrated, e.g., by a biopsy sample, or reductions may be measured indirectly, e.g., by measuring the pathogenic burden in the stool of a mammalian host.

A "combination" of two or more bacteria includes the physical co-existence of the two bacteria, either in the same material or product or in physically connected products, as well as the temporal co-administration or co-localization of the two bacteria.

As used herein "heterologous" designates organisms to be administered that are not naturally present in the same proportions as in the therapeutic composition as in subjects to be treated with the therapeutic composition. These can be organisms that are not normally present in individuals in need of the composition described herein, or organisms that are not present in sufficient proportion in said individuals. These organisms can comprise a synthetic composition of organisms derived from separate plant sources or can comprise a composition of organisms derived from the same plant source, or a combination thereof.

Compositions disclosed herein can be used to treat osteoporosis or osteopenia. Osteoporosis is a systemic skeletal disease characterized by decreasing bone mass and microarchitectural deterioration of bone tissue that leads to an increased risk for bone fragility and fracture. In patients without fragility fracture, osteoporosis is often diagnosed by low bone mineral density (BMD). The international reference standard for the description of osteoporosis in postmenopausal women and in men is a femoral neck or lumbar spine BMD of 2.5 standard deviations (SD) or more below the young female adult mean. Osteopenia is a less severe form of low BMD, defined by the international standard as between 1 and 2.5 SD below the young female average. As defined herein "osteoporosis or osteopenia" indicates a condition where the subject's bone mass per unit volume is reduced. Osteoporosis indicates bone mass reduction to a level below that required for the adequate mechanical support function of the bone. Osteopenia is a milder disease where bone mass per unit is reduced but not to the extent seen in osteoporosis. Patients with osteopenia may subsequently suffer from osteoporosis.

As used herein, "bone density" indicates "bone mineral density" (BMD).

In some embodiments, compositions disclosed herein can be used to treat osteoarthritis. As used herein, the term "osteoarthritis" (abbreviated as "OA"), refers to the disease also known as osteoarthrosis and degenerative joint disease, characterized by inflammation and damage to, or loss of cartilage in any joint or joints, and joint pain. Clinical standards for diagnosing osteoarthritis in subjects including mammalian subjects such as canines and humans are well known and include for example swelling or enlargement of joints, joint tenderness or pain, decreased range of motion in joints, visible joint deformities such as bony growths, and crepitus Symptoms can be identified by clinical observation and history, or imaging including MRI and X-ray. Criteria for diagnosing the presence or absence of OA and severity or degree of OA include but are not limited to the ACR Criteria for knee OA (R. Altman et al., Development of criteria for the classification and reporting of osteoarthritis: Classification of osteoarthritis of the knee: Diagnostic and Therapeutic Criteria Committee of the American Rheumatism Association. ARTHRITIS RHEUM. August 29(8): 1039-1049 (1986)), functional status criteria according to WOMAC (N. Bellamy et al., 1988, Validation study of WOMAC: a health status instrument for measuring clinically important patient relevant outcomes to antirheumatic drug therapy in patients with osteoarthritis of the hip or knee. J RHEUMATOL 15:1833-1840), and radiological standards for evaluating OA disease severity according to the Kellgren and Lawrence method for knee OA (Kellgren, J. H. and J. S. Lawrence, Radiological assessment of osteoarthrosis. ANN RHEUM DIS 16:494-502).

In some embodiments, compositions disclosed herein can be used to improve fracture healing. The term "fracture", as used herein, refers to a disruption in the integrity of a living bone involving injury to bone marrow, periosteum, and adjacent soft tissues. Many types of fractures exist such as, for example, pathological, stress, non-union, delayed-union, and greenstick fractures. A fracture includes open and closed fractures.

The term "fracture line" refers to the line across where disruption of the integrity of the living bone has occurred.

The term "non-union" fracture refers to the fractures which are not completely healed nine months after the initial fracture. These are commonly found in clavicle fractures that are not healed usually within three months, and are usually painful and require surgical fixation.

The term "delayed-union" refers to a fracture that has not healed at least about six months post injury.

In some embodiments, compositions disclosed herein can be used to prevent or treat osteomyelitis. As used herein, "osteomyelitis" is defined as inflammation of the bone or bone marrow. In some embodiments, osteomyelitis is caused by an infection.

Throughout this application, various embodiments of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

It is appreciated that certain features of the invention, which are, for clarity, described in the context of separate embodiments, can also be provided in combination in a single embodiment. Conversely, various features of the invention, which are, for brevity, described in the context of a single embodiment, can also be provided separately or in any suitable subcombination or as suitable in any other described embodiment of the invention. Certain features described in the context of various embodiments are not to be considered essential features of those embodiments, unless the embodiment is inoperative without those elements.

It must be noted that, as used in the specification and the appended claims, the singular forms "a," "an" and "the" include plural referents unless the context clearly dictates otherwise.

The following abbreviations are used in this specification and/or Figures: ac=acetic acid; but=butyric acid; ppa=propionic acid; etoh=ethanol; lac_L=lactic acid.

Methods of the Invention

The administration of the microbial composition can be accomplished orally or rectally, although administration is not limited to these methods. In some embodiments, the microbial composition is administered orally. In some embodiments, the microbial composition is delivered rectally. In some embodiments, the administration of the microbial composition occurs at regular intervals. In some embodiments, the administration occurs daily.

The microbial composition can be administered via typical pharmacological means, such as slurries, capsules, microcapsules, or solutions, although means of administration are not limited to these methods. In some embodiments, an enteric capsule or enteric microcapsule is used. In some embodiments the pharmaceutical composition involving the microbial composition described herein will be fresh or frozen prior to application. In some embodiments, said pharmaceutical composition will be lyophilized or otherwise treated to increase stability or otherwise obtain a benefit from said treatment.

Compositions of the Invention

In certain embodiments, compositions of the invention comprise probiotic compositions formulated for administration or consumption, with a prebiotic and any necessary or useful excipient. In other embodiments, compositions of the invention comprise probiotic compositions formulated for consumption without a prebiotic. Probiotic compositions of the invention are preferably isolated from foods normally consumed raw and isolated for cultivation. Preferably, microbes are isolated from different foods normally consumed raw, but multiple microbes from the same food source may be used.

It is known to those of skill in the art how to identify microbial strains. Bacterial strains are commonly identified by 16S rRNA gene sequence. Fungal species can be identified by sequence of the internal transcribed space (ITS) regions of rDNA.

One of skill in the art will recognize that the 16S rRNA gene and the ITS region comprise a small portion of the overall genome, and so sequence of the entire genome (whole genome sequence) may also be obtained and compared to known species.

Additionally, multi-locus sequence typing (MLST) is known to those of skill in the art. This method uses the sequences of 7 known bacterial genes, typically 7 housekeeping genes, to identify bacterial species based upon sequence identity of known species as recorded in the publicly available PubMLST database. Housekeeping genes are genes involved in basic cellular functions.

In certain embodiments, bacterial entities of the invention are identified by comparison of the 16S rRNA sequence to those of known bacterial species, as is well understood by those of skill in the art. In certain embodiments, fungal species of the invention are identified based upon comparison of the ITS sequence to those of known species (Schoch et al PNAS 2012). In certain embodiments, microbial strains of the invention are identified by whole genome sequencing and subsequent comparison of the whole genome sequence to a database of known microbial genome sequences. While microbes identified by whole genome sequence comparison, in some embodiments, are described and discussed in terms of their closest defined genetic match, as indicated by 16S rRNA gene sequence, it should be understood that these microbes are not identical to their closest genetic match and are novel microbial entities. This can be shown by examining the Average Nucleotide Identity (ANI) of microbial entities of interest as compared to the reference strain that most closely matches the genome of the microbial entity of interest. ANI is further discussed in example 6.

In other embodiments, microbial entities described herein are functionally equivalent to previously described strains with homology at the 16S rRNA or ITS region. In certain embodiments, functionally equivalent bacterial strains have at least 95% identity at the 16S rRNA region and functionally equivalent fungal strains have at least 95% identity at the ITS region. In certain embodiments, functionally equivalent bacterial strains have at least 96% identity at the 16S rRNA region and functionally equivalent fungal strains have at least 96% identity at the ITS region. In certain embodiments, functionally equivalent bacterial strains have at least 97% identity at the 16S rRNA region and functionally equivalent fungal strains have at least 97% identity at the ITS region. In certain embodiments, functionally equivalent bacterial strains have at least 98% identity at the 16S rRNA region and functionally equivalent fungal strains have at least 98% identity at the ITS region. In certain embodiments, functionally equivalent bacterial strains have at least 99% identity at the 16S rRNA region and functionally equivalent fungal strains have at least 99% identity at the ITS region. In certain embodiments, functionally equivalent bacterial strains have at least 99.5% identity at the 16S rRNA region and functionally equivalent fungal strains have at least 99.5% identity at the ITS region. In certain embodiments, functionally equivalent bacterial strains have 100% identity at the 16S rRNA region and functionally equivalent fungal strains have 100% identity at the ITS region.

16S rRNA sequences for strains tolerant of relevant stressors (described in table 7) are found in SEQ ID NOs 1-63. 16S rRNA is one way to classify bacteria into operational taxonomic units (OTUs). Bacterial strains with 97% sequence identity at the 16S rRNA locus are considered to belong to the same OTU. A similar calculation can be done with fungi using the ITS locus in place of the bacterial 16S rRNA sequence.

In some embodiments, the invention provides a probiotic composition for the treatment of osteoporosis, osteopenia, Paget's disease, or stunting comprising a mixture of Lactic acid bacteria, such as *Pediococcus* spp, *Leuconostoc* spp, *Lactobacillus* spp, *Lactobacillus crispatus, Lactobacillus plantarum, Lactobacillus reuteri*, combined with non-lactic acid bacteria isolated or identified from samples described in Table 3 or described in Table 4. In some embodiments, the invention provides a fermented probiotic composition for the treatment of bone diseases comprising a mixture of *Pediococcus pentosaceus* and/or *Leuconostoc mesenteroides* and at least one non-lactic acid bacterium, preferably a bacterium classified as a gamma proteobacterium or a filamentous fungus or yeast. Some embodiments comprise the probiotic being in a capsule or microcapsule adapted for enteric delivery.

The compositions disclosed herein are derived from edible plants and can comprise a mixture of microorganisms, comprising bacteria, fungi, archaea, and/or other indigenous or exogenous microorganisms, all of which work together to form a microbial ecosystem with a role for each of its members.

In some embodiments, species of interest are isolated from plant-based food sources normally consumed raw. These isolated compositions of microorganisms from individual plant sources can be combined to create a new mixture of organisms. Particular species from individual plant sources can be selected and mixed with other species cultured from other plant sources, which have been similarly isolated and grown. In some embodiments, species of interest are grown in pure cultures before being prepared for consumption or administration. In some embodiments, the organisms grown in pure culture are combined to form a synthetic combination of organisms.

In some embodiments, the microbial composition comprises proteobacteria or gamma proteobacteria. In some embodiments, at least one species from each of 4 groups is present, the four groups being: Lactic Acid bacteria, Bacilli, proteobacteria, and yeast. In some embodiments, at least one microbe from a group other than the four stated above is also present. In some embodiments, the microbial composition comprises several species of *Pseudomonas*. In some embodiments, species from another genus are also present. In some embodiments, a species from the genus *Duganella* is also present. In some embodiments of said microbial composition, the population comprises at least three unique isolates selected from the group consisting of *Pseudomonas, Acinetobacter, Aeromonas, Curtobacterium, Escherichia, Lactobacillus, Serratia, Streptococcus*, and *Stenotrophomonas*. In some embodiments, the bacteria are selected based upon their ability to degrade fibers, including plant fibers, and to modulate production of one or more branch chain fatty acids, short chain fatty acids, and/or flavones in a mammalian gut.

In some embodiments, microbial compositions comprise isolates that are capable of modulating production or activity of the enzymes involved in fatty acid metabolism, such as acetolactate synthase I, N-acetylglutamate synthase, acetate kinase, Acetyl-CoA synthetase, acetyl-CoA hydrolase, Glucan 1,4-alpha-glucosidase, or Bile acid symporter Acr3.

In some embodiments, the administered microbial compositions colonize the treated mammal's digestive tract. In some embodiments, these colonizing microbes comprise bacterial assemblages present in whole food plant-based diets. In some embodiments, these colonizing microbes comprise *Pseudomonas* with a diverse species denomination that is present and abundant in whole food plant-based diets. In some embodiments, these colonizing microbes reduce free fatty acids absorbed into the body of a host by absorbing the free fatty acids in the gastrointestinal tract of mammals. In some embodiments, these colonizing microbes comprise genes encoding metabolic functions related to desirable health outcomes such as increased bone mineral density, prevention of loss of bone mineral density, improved bone turnover markers, or improved low-grade inflammatory metabolic indicators, etc.

Some embodiments comprise bacteria that are not completely viable but act by releasing metabolites that act in the gastro-intestinal tract of a patient promoting bone health or other desirable outcome. Some embodiments comprise a prebiotic composition derived from metabolites present in whole food plant-based materials, identified and enriched as part of the formula for oral delivery.

Prebiotics

Prebiotics, in accordance with the teachings of this invention, comprise compositions that promote the growth of beneficial bacteria in the intestines. Prebiotic substances can be consumed by a relevant probiotic, or otherwise assist in keeping the relevant probiotic alive or stimulate its growth. When consumed in an effective amount, prebiotics also beneficially affect a subject's naturally-occurring gastrointestinal microflora and thereby impart health benefits apart from just nutrition. Prebiotic foods enter the colon and serve as substrate for the endogenous bacteria, thereby indirectly providing the host with energy, metabolic substrates, and essential micronutrients. The body's digestion and absorption of prebiotic foods is dependent upon bacterial metabolic activity, which salvages energy for the host from nutrients that escaped digestion and absorption in the small intestine.

Prebiotics help probiotics flourish in the gastrointestinal tract, and accordingly, their health benefits largely are indirect. Metabolites generated by colonic fermentation by intestinal microflora, such as short-chain fatty acids, can play important functional roles in the health of the host. Prebiotics can be useful agents for enhancing the ability of intestinal microflora to provide benefits to their host.

Prebiotics, in accordance with the embodiments of this invention, include, without limitation, mucopolysaccharides, oligosaccharides, polysaccharides, amino acids, vitamins, nutrient precursors, proteins, and combinations thereof.

According to particular embodiments, compositions comprise a prebiotic comprising a dietary fiber, including, without limitation, polysaccharides and oligosaccharides. These compounds have the ability to increase the number of probiotics, and augment their associated benefits. For example, an increase of beneficial Bifidobacteria likely changes the intestinal pH to support the increase of Bifidobacteria, thereby decreasing pathogenic organisms.

Non-limiting examples of oligosaccharides that are categorized as prebiotics in accordance with particular embodiments include fructooligosaccharides, inulins, isomalto-oligosaccharides, lactilol, lactosucrose, lactulose, pyrodextrins, soy oligosaccharides, transgalacto-oligosaccharides, cellulose, and xylo-oligosaccharides.

According to other particular embodiments, compositions comprise a prebiotic comprising an amino acid.

Prebiotics are found naturally in a variety of foods including, without limitation, cabbage, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans). Generally, according to particular embodiments, compositions comprise a prebiotic present in a sweetener composition or functional sweetened composition in an amount sufficient to promote health and wellness.

In particular embodiments, prebiotics also can be added to high-potency sweeteners or sweetened compositions. Non-limiting examples of prebiotics that can be used in this manner include fructooligosaccharides, xylooligosaccharides, galactooligosaccharides, and combinations thereof.

Many prebiotics have been discovered from dietary intake including, but not limited to: antimicrobial peptides, polyphenols, Okara (soybean pulp by product from the manufacturing of tofu), polydextrose, lactosucrose, malto-oligosaccharides, gluco-oligosaccharides (GOS), fructo-oligosaccharides (FOS), xantho-oligosaccharides, soluble dietary fiber in general. Types of soluble dietary fiber include, but are not limited to, psyllium, pectin, or inulin. Phytoestrogens (plant-derived isoflavone compounds that have estrogenic effects) have been found to have beneficial growth effects of intestinal microbiota through increasing microbial activity and microbial metabolism by increasing the blood testosterone levels, in humans and farm animals. Phytoestrogen compounds include but are not limited to: Oestradiol, Daidzein, Formononetin, Biochainin A, Genistein, and Equol.

Dosage for the compositions described herein are deemed to be "effective doses," indicating that the probiotic or prebiotic composition is administered in a sufficient quantity to alter the physiology of a subject in a desired manner. In some embodiments, the desired alterations include reducing osteoporosis or osteopenia and sequelae associated with these conditions. In some embodiments, the desired alterations occur in a post-menopausal subject. Vitamin K2 and osteoporosis:

Vitamin K is found in many fruits and vegetables including broccoli, grapes, lettuce, and olives and plays a role in a wide range of biological activities including calcium metabolism, cell proliferation, oxidative stress, and inflammation. Vitamin K2 (menaquinone) plays a vital role in bone synthesis and is produced by bacteria residing in the gastrointestinal tract. Vitamin K2 affects the proliferation and differentiation of osteoblasts, leading to increased osteoblast activity and bone matrix production. Specifically, Vitamin K2 stimulates the expression of osteoprotegerin (OPG) and inhibits the expression of receptor activator of nuclear factor kappa-B ligand (RANKL) on osteoblasts, leading to increased proliferation and activation. Vitamin K2 has also been shown to inhibit osteoclastic bone resorption, preventing the breakdown of bone.

In some embodiments, the compositions of the invention improve Vitamin K2 absorption. In some embodiments, the compositions of the invention produce Vitamin K2 in the gut of a subject. In some embodiments, the microbes of the invention are selected based upon their having genes involved in biosynthetic pathways for producing Vitamin K2.

In some embodiments, the composition comprises a cryoprotectant. In general, a cryoprotectant functions through work by dissolving in water, lowering the melting point or a composition containing cells, and preventing or limiting intracellular and extracellular crystals from forming in cells during a freezing process. A cryoprotectant can allow for preservation of strain viability for prolonged periods of time, including extending viability for years. In some embodiments, the cryoprotectant is a prebiotic. In some embodiments, the cryoprotectant includes glycerol, trehalose, or Dimethyl sulfoxide (DMSO). In some embodiments, the cryoprotectant is derived from a plant source. In some embodiments, viability, measured at room temperature, is increased for at least one microbe by addition of cryoprotectant to a composition comprising said microbe wherein the composition is stored frozen. In some embodiments, viability is increased by at least 10, 15, 25, 35, 45, 50, 55, 65, 75, 85, 95, or 100 percent. Typically, A cryoprotectant (e.g., glycerol, trehalose, or DMSO) concentration of about 5% to 15% is used and permits survival of a substantial fraction of isolated cells after freezing and thawing from cryogenic temperatures. One skilled in the art will recognize a cryoprotectant formulation can adjusted dependent on the cellular species to be preserved. For example, certain species (e.g., gamma proteobacteria) are sensitive to cryopreservation and lose considerable viability after few days in cryostorage. In some embodiments, biological materials (such as microbial strains including bacteria and fungi) are refrigerated at temperatures of −20° C. or at −80° C., e.g., with use of laboratory freezers. In some embodiments, biological materials are stored using the vapor phase of liquid nitrogen that brings the temperature to −170° C.

Methods of Use

Included within the scope of this disclosure are methods for treatment of musculoskeletal disorders including osteoporosis, osteopenia, Paget's disease, stunting, osteoarthritis, osteomyelitis, and delayed or non-union fractures.

These methods include treatment with a prebiotic composition (e.g., a composition comprising or consisting of FOS, GOS, or other appropriate polysaccharide), optionally in conjunction with a probiotic composition, one or more digestible saccharides (e.g. lactose, glucose, or galactose), a buffer, or a combination thereof. These methods optionally are used in combination with other treatments to reduce the musculoskeletal disorder. Any suitable treatment can be used. In some embodiments the additional treatment is administered before, during, or after treatment with a prebiotic composition, or any combination thereof. In an embodiment, when the musculoskeletal disorder or disorders are not completely or substantially completely eliminated by treatment with a prebiotic composition, the additional treatment is administered after prebiotic treatment is terminated. The additional treatment is used on an as-needed basis.

In an embodiment, a subject to be treated for one or more symptoms of a musculoskeletal disorder is a human. In an embodiment, the human subject is a preterm newborn, a full term newborn, an infant up to one year of age, a young child (e.g., 1 yr to 12 yrs), a teenager (e.g., 13-19 yrs), an adult (e.g., 20-64 yrs), a pregnant women, or an elderly adult (65 yrs and older).

In an embodiment, the condition to be treated is osteoporosis or osteopenia. In an embodiment, the condition to be treated is osteoporosis or osteopenia, and treating osteoporosis further involves administration of any one or combination of known anti-osteoporosis medications or treatments. These include, but are not limited to, bisphosphonates (alendronate, risedronate, ibandronate, zolendronate), biologics (denosumab, romosozumab), selective estrogen receptor mediators (Raloxifene), or anabolic agents (teriparatide, abaloparatide).

In an embodiment, the condition to be treated is osteoarthritis. In an embodiment, the condition to be treated is osteoarthritis, and treating the condition further involves administration of any one or combination of known anti-osteoarthritis medications or treatments. These include, but are not limited to, surgery, analgesics, non-steroidal anti-inflammatory drugs (aspirin, celecoxib, diclofenac, diflunisal, etodolac, ibuprofen, indomethacin, ketoprofen, ketorolac, nabumetone, naproxen, oxaprozin, piroxicam), menthol, weight loss regimens, physical exercise, acupuncture, narcotics (Codeine, Fentanyl, Hydrocodone, hydroporphone, meperidine, methadone, oxycodone), and physical therapy.

In an embodiment, the condition to be treated is a delayed or non-union fracture. In an embodiment, the condition to be treated is a delayed or non-union fracture, and treating the condition further involves administration of any one or combination of known treatments to improve delayed or non-union fractures. These include, but are not limited to surgical bone grafts or fixations and bone stimulation.

In an embodiment, the condition to be treated is osteomyelitis. The methods disclosed herein, optionally, are used in combination with other treatments to treat or prevent osteomyelitis. Typical treatments for osteomyelitis include, but are not limited to, intravenous or oral antibiotics (clindamycin, cefotetan, ticarcillin/clavulanate, ceftriaxone, metronidazole, piperacillin/tazobactam, fluoroquinolone, cefepime, ciprofloxacin, imipenem/cilastin, vancomycin, trimethoprim/sulfamethoxazole, minocycline, nafcillin, oxacillin, cefazolin, penicillin) and surgery. Any suitable treatment for osteomyelitis can be used. These include, but are not limited to, removal of diseased tissue and antibiotics, administered either orally or intravenously.

Timing and Dose of Probiotics and Prebiotics

In an embodiment, probiotic bacteria, such as a *Pediococcus* species or a *Leuconostoc* species, are given prior to beginning treatment with a prebiotic. In an embodiment, probiotic bacteria, such as a *Pediococcus* species or a *Leuconostoc* species, are given in conjunction with treatment with a prebiotic (e.g., comprising or consisting essentially of FOS, GOS, or other appropriate polysaccharide), for part or all of the treatment with the prebiotic. Thus, in an embodiment, some or all doses of a prebiotic (e.g., comprising or consisting essentially of FOS, GOS, or other appropriate polysaccharide) are accompanied by a dose of bacteria, e.g., live cultured bacteria, e.g., a *Pediococcus* species or a *Leuconostoc* species. In an embodiment, bacteria, e.g., a *Pediococcus* species or a *Leuconostoc* species, are given initially with a prebiotic (e.g., comprising or consisting essentially of FOS, GOS, or other appropriate polysaccharide), but then use of the bacteria is discontinued. For example, the initial one, two, three, four, five, six, seven, eight, nine, ten, or more than ten days of treatment with a prebiotic (e.g., comprising or consisting essentially of FOS, GOS, or other appropriate polysaccharide) further comprises doses of bacteria, with the use of bacteria discontinued after that time. In an embodiment, bacteria, (e.g., bacteria in yogurt), or bacteria by themselves, can be given for the first two days of treatment; then the administration of bacteria is discontinued. In another embodiment, probiotic bacteria, either alone or in combination with other substances or treatments are used after the treatment with a prebiotic (comprising or consisting essentially of FOS, GOS, or other appropriate polysaccharide) is terminated. The bacteria can be taken for any suitable period after the termination of treatment with prebiotic and can be taken daily or at regular or irregular intervals. Doses can be as described below.

Any suitable amount of probiotic per serving can be used that allows an effective microbiota in the GI as demonstrated by an increase in bone mineral density, improved bone architecture, protection from loss of bone mineral density, improved bone turnover markers, or improvement in other markers of osteoporosis or osteopenia. Markers of osteoporosis or osteopenia can include elevated levels of Inflammatory cytokines in the blood including: Tumor necrosis factor alpha (TNFα), Interleukin-17 (IL-17), Interleukin-4 (IL-4), Interferon gamma (IFNγ). Receptor activator of nuclear factor kappa-B ligand (RANKL). They can also include increased one resorption blood markers (breakdown) crosslinked C-telopeptide of type 1 collagen (CTX), or decreased Bone formation blood markers: osteocalcin, alkaline phosphatase, N-terminal propeptide of type 1 collagen.

Any suitable amount of probiotic per serving can be used that allows an effective microbiota in the GI as demonstrated by an increase in healthy bone healing, including decreased incidence of delayed or non-union fractures or increased normal fracture callus formation. Markers of fracture healing defects include delayed healing, non-union fracture healing, or changes in fracture callus architecture (including increased size or adiposity of the fracture callus).

Typically, probiotics are given as live cultured bacteria. The dose can be 0.001 mg to 1 mg, or 0.5 mg to 5 mg, or 1 mg to 1000 mg, or 2 mg to 200 mg, or 2 mg to 100 mg, or 2 mg to 50 mg, or 4 mg to 25 mg, or 5 mg to 20 mg, or 10 mg to 15 mg, or 50 mg to 200 mg, or 200 mg to 1000 mg, or 10, 11, 12, 12.5, 13, 14, or 15 mg per serving. In an embodiment, *L. acidophilus* is used in a dose of 12.5 mg per serving. The probiotic bacteria can also be 0.5% w/w to 20% w/w of the final composition. The dose of probiotics can be given in combination with one or more prebiotics. Another common way of specifying the amount of probiotics is as a colony forming unit (cfu). In an embodiment, one or more strains of probiotic bacteria are ingested in an amount of between 1×10^5 and 1×10^12 cfu's per serving. In an embodiment, one or more strains of probiotic bacteria are ingested in an amount of 1×10^5 to 1×10^9 cfu's, or 1×10^6 cfu's to 1×10^10 cfu's, or 1×10^6 cfu's to 1×10^9 cfu's, or 1×10^5 cfu's to 1×10^6 cfu's, or 1×10^5 cfu's to 1×10^12 cfu's, or 1×10^9 cfu's per serving. In another embodiment, one or more strains of probiotic bacteria are administered as part of a dairy product. In an embodiment, a typical serving size for a dairy product such as fluid milk is 240 g. In other embodiments, a serving size is 245 g, or 240 g to 245 g, or 227 to 300 g. In an embodiment the dairy product is yogurt. Yogurt can have a serving size of 4 oz, or 6 oz, or 8 oz, or 4 oz to 10 oz, or half cup, or 1 cup, or 113 g, or 170 g, or 227 g, or 245 g or 277 g, or 100 g to 350 g.

In an embodiment, probiotic bacteria are given as live cultured bacteria, e.g., in combination with a prebiotic (e.g., comprising or consisting essentially of FOS, GOS, or other appropriate polysaccharide) and, optionally, other substances. The dose can be 1 mg to 1000 mg, or 2 mg to 200 mg, or 2 mg to 100 mg, or 2 mg to 50 mg, or 4 mg to 25 mg, or 5 mg to 20 mg, or 10 mg to 15 mg, or 10, 11, 12, 12.5, 13, 14, or 15 mg of probiotic bacterial cell culture dry weight. In an embodiment, *L. acidophilus* is used in a dose of 12.5 mg. In an embodiment, as the administration of a prebiotic (e.g., comprising or consisting essentially of FOS, GOS, or other appropriate polysaccharide) dose to a subject increases, the dose of bacteria increases as well. For example, an initial dose of a prebiotic (e.g., comprising or consisting essentially of FOS, GOS, or other appropriate polysaccharides) can be 0.6 g to 1.0 g, e.g., 0.8 g, given in combination with 10-15 mg, e.g., 12.5 mg, of *L. acidophilus*. The dose of a prebiotic (e.g., comprising or consisting essentially of FOS, GOS, or other appropriate polysaccharide) can be increased incrementally by 0.6 g to 1.0 g, e.g., 0.8 g, and the accompanying dose of *L. acidophilus* can be increased by 10-15 mg, e.g., 12.5 mg, of *L. acidophilus*.

FOS, GOS, or Other Appropriate Polysaccharide Formulations

A. Formulations Introduction

In one aspect a prebiotic composition for the treatment of one or more musculoskeletal disorder is provided. In an embodiment a prebiotic composition comprises inulin, FOS, lactulose, GOS, raffinose, stachyose, or a combination thereof. In addition, other plant-derived polysaccharides such as xylan, pectin, isomalto-oligosaccharides, gentio-oligosaccharides, 4-O-methyl glucuronoxylan (GX), neutral arabinoxylan (AX), heteroxylan (HX) can be combined with the probiotics to enhance bacterial metabolic function. Some of these can be derived from plant material found in the plant host from which the probiotics were isolated from. Therefore, the probiotics are adapted to assimilate and digest the rich complexity and variety of polysaccharides present in the plant that play a role during digestion by the consumption of an animal.

In an embodiment a prebiotic composition comprises or consists of FOS, GOS, or other appropriate polysaccharide. In another embodiment a prebiotic composition comprises FOS, GOS, other, and one or more digestible saccharides. Digestible saccharides are saccharides that are digestible by humans and include, but are not limited to lactose, glucose, and galactose. In an embodiment a prebiotic composition comprises FOS, GOS, or other appropriate polysaccharide, and less than 20% weight/weight of one or more digestible saccharides (e.g. lactose, glucose, or galactose). In an embodiment a prebiotic composition comprises FOS, GOS, or other appropriate polysaccharide, and less than 10% of one or more digestible saccharides. In an embodiment a prebiotic composition comprises FOS, GOS, or other appropriate polysaccharide, and less than 5% of one or more digestible saccharides. In another embodiment a prebiotic composition contains less than 5% lactose. In another embodiment a prebiotic composition contains less than 4% lactose. In another embodiment a prebiotic composition contains less than 3% lactose. In another embodiment a prebiotic composition contains less than 2% lactose. In another embodiment a prebiotic composition contains less than 1% lactose. In another embodiment a prebiotic composition contains less than 0.5% lactose. In another embodiment a prebiotic composition contains less than 0.4% lactose. In another embodiment a prebiotic composition contains less than 0.3% lactose. In another embodiment a prebiotic composition contains less than 0.2% lactose. In another embodiment a prebiotic composition contains less than 0.1% lactose. In another embodiment a prebiotic composition contains less than 0.05% lactose. In another embodiment a prebiotic composition contains less than 0.01% lactose. In another embodiment a prebiotic composition contains less than 0.005% lactose. In an embodiment a prebiotic composition comprises FOS, GOS, or other appropriate polysaccharide, and essentially no lactose. In an embodiment a prebiotic composition does not contain any lactose. In another embodiment a prebiotic composition contains FOS, GOS, or other appropriate polysaccharide, and at least one probiotic bacteria strain. In another embodiment a prebiotic composition comprises FOS, GOS, or other appropriate polysaccharide, and optionally one or more of lactose, at least one probiotic bacteria strain, or a buffer. Additional ingredients include ingredients to improve handling, preservatives, antioxidants, flavorings and the like.

In an embodiment, a prebiotic composition comprises FOS, GOS, or other appropriate polysaccharide, or a probiotic. In other embodiment, a prebiotic composition is in the form of a powder, tablet, capsule, or liquid. In an embodiment, a prebiotic composition can be administered with a dairy product and is in the form of milk or other common dairy product such as a yogurt, shake, smoothie, cheese, and the like.

In embodiments where a prebiotic composition comprises less than 100% by weight of FOS, GOS, or other appropriate polysaccharide, the remaining ingredients can be any suitable ingredients intended for the consumption of the subject in need thereof, e.g., human, including, but not limited to, other prebiotics (e.g., FOS), a buffer, one or more digestible saccharides (e.g. lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings, and the like.

B. Buffer Components

One or more buffers, optionally with a calcium counter ion, can also be administered in methods and compositions described herein. Any buffer suitable for consumption by the subject being treated, e.g., human, are useful for the compositions herein. The buffer neutralizes stomach acidity, which can, e.g., allow live bacteria to reach the gut. Buffers include citrates, phosphates, and the like. One embodiment utilizes a buffer with a calcium counter ion, such as Calcium Phosphate Tribasic. The calcium can serve to restore the calcium that many lactose intolerant subjects are missing in their diet. Calcium phosphate can protect *Lactobacillus acidophilus* from bile. Calcium phosphate can help neutralize stomach acidity.

In an embodiment, a buffer such as calcium phosphate is given prior to beginning treatment with a prebiotic composition (such as a composition comprising or consisting essentially of FOS, GOS, or other appropriate polysaccharide), optionally in conjunction with administration of bacteria. As used herein FOS indications one or more fructo-oligosaccharides and GOS indicates one or more galacto-oligosaccharides. In an embodiment, a buffer such as calcium phosphate is given in conjunction with treatment with a prebiotic composition (e.g., a composition comprising or consisting essentially of FOS, GOS, or other appropriate polysaccharide), for part or all of the treatment with lactose. Thus, in an embodiment, some or all doses of a prebiotic composition are accompanied by a dose of a buffer such as calcium phosphate. In an embodiment, a buffer such as calcium phosphate is given initially with a prebiotic composition (such as a composition comprising or consisting essentially of FOS, GOS, or other appropriate polysaccharide), but then its use is discontinued. For example, the initial one, two, three, four, five, six, seven, eight, nine, ten, or more than ten days of treatment with a prebiotic composition can include doses of a buffer such as calcium phosphate, with the use of the buffer discontinued after that time. In an embodiment, a buffer such as calcium phosphate can be given for the first two days of treatment, and then the administration of buffer is discontinued. In an embodiment, a buffer such as calcium phosphate, either alone or in combination with other substances or treatments is used after the treatment with a prebiotic composition is terminated. A buffer such as calcium phosphate can be taken for any suitable period after the termination of treatment with lactose, and can be taken daily or at regular or irregular intervals. Doses can be as described below.

Numerous buffers suitable for human consumption are known in the art, and any suitable buffer can be used in the methods and compositions described herein. Calcium triphosphate is an exemplary buffer, and its counterion supplies a nutrient that is often lacking in lactose-intolerant subjects, i.e. calcium. In an embodiment a buffer can be used in a dose from 2 mg to 2000 mg, or 4 mg to 400 mg, or 4 mg to 200 mg, or 4 mg to 100 mg, or 8 mg to 50 mg, or 10 mg to 40 mg, or 20 mg to 30 mg, or 20, 21, 22, 23, 24, 25, 26, 27, 28, 29, or 30 mg. In another embodiment a prebiotic composition further comprises an amount of a buffer from 1-50 mg, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg. In an embodiment, buffer is used in a dose of 25 mg. In an embodiment, calcium phosphate is used in a dose of 25 mg. The dose can be given in combination with a prebiotic composition (e.g., a composition comprising or consisting essentially of FOS, GOS, or other appropriate polysaccharide). In an embodiment, as a prebiotic composition dose increases, the dose of buffer increases as well. For example, an initial dose of a prebiotic composition can be 0.6 g to 1.0 g, e.g., 0.8 g, given in combination with 20-30 mg, e.g., 25 mg, of buffer, e.g., calcium phosphate. The dose of a prebiotic composition can be increased incrementally by 0.6 g to 1.0 g, e.g., 0.8 g, and the accompanying dose of buffer, e.g., calcium phosphate, can be increased by 20-30 mg, e.g., 25 mg, of buffer, e.g., calcium phosphate.

C. Compositions Comprising GOS and at Least One Probiotic Bacteria Strain

In an embodiment, a prebiotic composition comprises FOS, GOS, or other appropriate polysaccharide, and at least one probiotic bacteria strain. The FOS, GOS, or other appropriate polysaccharide can comprise more than 1% of the weight of the composition while the at least one probiotic bacteria strain will typically comprise less than 10%, 5%, 4%, 3%, or 2% by weight of the compositions. For example, the FOS, GOS, or other appropriate polysaccharide can be present at 1-99.75% by weight and the at least one probiotic bacteria strain at 0.25-2% by weight, or the FOS, GOS, or other appropriate polysaccharide can be present at 89-96% by weight and the bacteria at 1.2-3.7% by weight. In an embodiment, FOS, GOS, or other appropriate polysaccharide are present at 92% by weight and at least one probiotic bacteria strain, (e.g., *L. mesenteroides, P. pentosaceus, Lactobacillus* or other members from Table 4), is present at 1.5% by weight. In an embodiment, FOS, GOS, or other appropriate polysaccharide are present at 2% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 93% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 94% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 95% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 96% by weight and at least one probiotic bacteria strain, (e.g *L. mesenteroides, P. pentosaceus*, or other members from Table 4), is present at 1.5% by weight. In another embodiment, FOS, GOS, or other appropriate polysaccharide are present at 97% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 98% by weight and at least one probiotic bacteria strain, (e.g., *L. mesenteroides, P. pentosaceus*, or other members from Table 4), is present at 1.5% by weight. In another embodiment, FOS, GOS, or other appropriate polysaccharide are present at 98.5% by weight and at least one probiotic bacteria strain, (e.g., *L. mesenteroides, P. pentosaceus*, or other members from Table 4), is present at 1.5% by weight. If the at least one probiotic bacteria strain and FOS, GOS, or other appropriate polysaccharide do not make up 100% by weight of the prebiotic composition, the remaining ingredients can be any suitable ingredients intended for consumption by the subject in need thereof, e.g., human, including, but not limited to, other prebiotics (e.g., FOS), one or more buffers, digestible saccharides (e.g. lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

D. Compositions Comprising FOS, GOS, or Other Appropriate Polysaccharide and a Buffer In another embodiment, a prebiotic composition comprises FOS, GOS, or other appropriate polysaccharide and a buffer (e.g., calcium phosphate tribasic). For example, FOS, GOS, or other appropriate polysaccharide can be present at 1-100% by weight and the buffer at 0.50-4% by weight, or FOS, GOS, or other appropriate polysaccharide can be present at 1-96% by weight and the buffer at 1 to 3.75% by weight. In an embodiment, FOS, GOS, or other appropriate polysaccharide are present at 1% by weight and buffer is present at 3% by weight. In an embodiment, FOS, GOS, or other appropriate polysaccharide are present at 5% by weight and buffer is present at 3% by weight. In an embodiment, FOS, GOS, or other appropriate polysaccharide are present at 10% by weight and buffer is present at 3% by weight. In an embodiment, FOS, GOS, or other appropriate polysaccharide are present at 15% by weight and buffer is present at 15% by weight. In an embodiment, FOS, GOS, or other appropriate polysaccharide are present at 20% by weight and buffer is present at 3% by weight. In an embodiment, FOS, GOS, or other appropriate polysaccharide are present at 25% by weight and buffer is present at 3% by weight. In an embodiment, FOS, GOS, or other appropriate polysaccharide are present at 30% by weight and buffer is present at 3% by weight. In an embodiment, FOS, GOS, or other appropriate polysaccharide are present at 35% by weight and buffer is present at 3% by weight. In an embodiment, FOS, GOS, or other appropriate polysaccharide are present at 40% by weight and buffer is present at 3% by weight. In an embodiment, FOS, GOS, or other appropriate polysaccharide are present at 50% by weight and buffer is present at 3% by weight. In an embodiment, FOS, GOS, or other appropriate polysaccharide are present at 60% by weight and buffer is present at 3% by weight. In an embodiment, FOS, GOS, or other appropriate polysaccharide are present at 70% by weight and buffer is present at 3% by weight. In another embodiment, FOS, GOS, or other appropriate polysaccharide are present at 90% by weight and buffer is present at 3% by weight. In another embodiment, FOS, GOS, or other appropriate polysaccharide are present at 92% by weight and buffer is present at 3% by weight. In another embodiment, FOS, GOS, or other appropriate polysaccharide are present at 93% by weight and buffer is present at 3% by weight. In another embodiment, FOS, GOS, or other appropriate polysaccharide are present at 94% by weight and buffer is present at 3% by weight. In another embodiment, FOS, GOS, or other appropriate polysaccharide are present at 95% by weight and buffer is present at 3% by weight. In another embodiment, FOS, GOS, or other appropriate polysaccharide are present at 96% by weight and buffer is present at 3% by weight. In another embodiment, FOS, GOS, or other appropriate polysaccharide are present at 97% by weight and buffer is present at 2% by weight. In another embodiment, FOS, GOS, or other appropriate polysaccharide are present at 98% by weight and buffer is present at 1% by weight. In another embodiment, FOS, GOS, or other appropriate polysaccharide are present at 99% by weight and buffer is present at 1% by weight. In another embodiment, FOS, GOS, or other appropriate polysaccharide are present at 100% by weight and buffer is present at less than 1% by weight. If the buffer and FOS, GOS, or other appropriate polysaccharide do not make up 100% by weight of the composition, the remaining ingredients can be any suitable ingredients intended for consumption by the subject (e.g., a human) including, but not limited to, probiotics (e.g., beneficial bacteria) or other prebiotics (e.g., FOS), but also including ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

E. Compositions Comprising a Digestible Saccharide, a Probiotic Bacteria, and FOS, GOS, or Other Appropriate Polysaccharide In an embodiment, a prebiotic composition comprises a digestible saccharide (e.g. lactose, glucose, or galactose), at least one probiotic bacterium (e.g., *L. mesenteroides, P. pentosaceus*, or other members from Table 4), and FOS, GOS, or other appropriate polysaccharide. In an embodiment, lactose can be present at 1-20% by weight, bacteria at 0.25-20.10% by weight, and FOS, GOS, or other appropriate polysaccharide at 1-98.75% by weight. In another embodiment lactose can be present at 5-20% by weight, bacteria at 0.91-1.95% by weight, and FOS, GOS, or other appropriate polysaccharide at 1 to 96% by weight. In another embodiment, lactose is present at 20% by weight, bacteria at 1.5% by weight, and FOS, GOS, or other appropriate polysaccharide are present at 1% by weight. In another embodiment, lactose is present at 20% by weight, bacteria at 1.5% by weight, and FOS, GOS, or other appropriate polysaccharide are present at 50% by weight. In another embodiment, lactose is present at 20% by weight, bacteria at 1.5% by weight, and FOS, GOS, or other appropriate polysaccharide are present at 60% by weight. In another embodiment, lactose is present at 20% by weight, bacteria at 1.5% by weight, and FOS, GOS, or other appropriate polysaccharide are present at 70% by weight. In another embodiment, lactose is present at 5% by weight, bacteria at 1.5% by weight, and FOS, GOS, or other appropriate polysaccharide are present at 90% by weight. In another embodiment, lactose is present at 5% by weight, bacteria at 1.5% by weight, and FOS, GOS, or other appropriate polysaccharide are present at 92% by weight. In another embodiment, lactose is present at 5% by weight, bacteria at 1.5% by weight, and FOS, GOS, or other appropriate polysaccharide are present at 93% by weight. In another embodiment, lactose is present at 5% by weight, bacteria at 1% by weight, and FOS, GOS, or other appropriate polysaccharide are present at 94% by weight. In another embodiment, lactose is present at 4.5% by weight, bacteria at 1.5% by weight, and FOS, GOS, or other appropriate polysaccharide are present at 94% by weight. In another embodiment, lactose is present at 4.5% by weight, bacteria at 0.5% by weight, and FOS, GOS, or other appropriate polysaccharide are present at 95% by weight. In another embodiment, lactose is present at 3.5% by weight, bacteria at 0.5% by weight, and FOS, GOS, or other appropriate polysaccharide are present at 96% by weight. In another embodiment, lactose is present at 2.5% by weight, bacteria at 0.5% by weight, and FOS, GOS, or other appropriate polysaccharides are present at 97% by weight. In another embodiment, lactose is present at 1.5% by weight, bacteria at 0.5% by weight, and FOS, GOS, or other appropriate polysaccharide are present at 98% by weight. In another embodiment, lactose is present at 0.5% by weight, bacteria at 0.5% by weight, and FOS, GOS, or other appropriate polysaccharide are present at 99% by weight. If the bacteria, FOS, GOS, or other appropriate polysaccharide and lactose do not make up 100% of the composition, the remaining ingredients can be any suitable ingredients intended for consumption by the subject, e.g., a human, including, but not limited to a buffer, digestible saccharides (e.g., lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

F. Compositions Comprising FOS, GOS, or Other Appropriate Polysaccharide, a Probiotic Bacteria, and Buffer In an embodiment, a prebiotic composition comprises FOS, GOS, or other appropriate polysaccharide, a probiotic bacteria strain, and buffer. In an embodiment, FOS, GOS, or other appropriate polysaccharide can be present at 1-100% by weight, a probiotic bacteria strain at 0.25-2% by weight, and the buffer at 0.50-4% by weight. In another embodiment, FOS, GOS, or other appropriate polysaccharide can be present at 1-95% by weight, a probiotic bacteria strain at 0.91-1.95% by weight, and the buffer at 1.2-30.75% by weight. In another embodiment, FOS, GOS, or other appropriate polysaccharide are present at 1% by weight, a probiotic bacteria strain at 1.5% by weight, and buffer is present at 3% by weight. In another embodiment, FOS, GOS, or other appropriate polysaccharide are present at 5% by weight, a probiotic bacteria strain at 1.5% by weight, and buffer is present at 3% by weight. In another embodiment, FOS, GOS, or other appropriate polysaccharide are present at 10% by weight, a probiotic bacteria strain at 1.5% by weight, and buffer is present at 3% by weight. In another embodiment, FOS, GOS, or other appropriate polysaccharide are present at 15% by weight, a probiotic bacteria strain at 1.5% by weight, and buffer is present at 3% by weight. In another embodiment, FOS, GOS, or other appropriate polysaccharide are present at 20% by weight, a probiotic bacteria strain at 1.5% by weight, and buffer is present at 3% by weight. In another embodiment, FOS, GOS, or other appropriate polysaccharide are present at 25% by weight, a probiotic bacteria strain at 1.5% by weight, and buffer is present at 3% by weight. In another embodiment, FOS, GOS, or other appropriate polysaccharide are present at 30% by weight, a probiotic bacteria strain at 1.5% by weight, and buffer is present at 3% by weight. In another embodiment, FOS, GOS, or other appropriate polysaccharide are present at 35% by weight, a probiotic bacteria strain at 1.5% by weight, and buffer is present at 3% by weight. In another embodiment, FOS, GOS, or other appropriate polysaccharide are present at 40% by weight, a probiotic bacteria strain at 1.5% by weight, and buffer is present at 3% by weight. In another embodiment, FOS, GOS, or other appropriate polysaccharide are present at 50% by weight, a probiotic bacteria strain at 1.5% by weight, and buffer is present at 3% by weight. In another embodiment, FOS, GOS, or other appropriate polysaccharide are present at 60% by weight, a probiotic bacteria strain at 1.5% by weight, and buffer is present at 3% by weight. In another embodiment, FOS, GOS, or other appropriate polysaccharide are present at 70% by weight, a probiotic bacteria strain at 1.5% by weight, and buffer is present at 3% by weight. In another embodiment, FOS, GOS, or other appropriate polysaccharide are present at 90% by weight, a probiotic bacteria strain at 1.5% by weight, and buffer is present at 3% by weight. In another embodiment, FOS, GOS, or other appropriate polysaccharide are present at 92% by weight, a probiotic bacteria strain at 1.5% by weight, and buffer is present at 3% by weight. In another embodiment, FOS, GOS, or other appropriate polysaccharide are present at 93% by weight, a probiotic bacteria strain at 1.5% by weight, and buffer is present at 3% by weight. In another embodiment, FOS, GOS, or other appropriate polysaccharide are present at 94% by weight, a probiotic bacteria strain at 1.5% by weight, and buffer is present at 3% by weight. In another embodiment, FOS, GOS, or other appropriate polysaccharide are present at 95% by weight, a probiotic bacteria strain at 1.5% by weight, and buffer is present at 3% by weight. In another embodiment, FOS, GOS, or other appropriate polysaccharide are present at 96% by weight, a probiotic bacteria strain at 1.5% by weight, and buffer is present at 2% by weight. In another embodiment, FOS, GOS, or other appropriate polysaccharide are present at 97% by weight, a probiotic bacteria strain at 1.5% by weight, and buffer is present at 1.5% by weight. In another embodiment, FOS, GOS, or other appropriate polysaccharide are present at 99% by weight, a probiotic bacteria strain at 0.5% by weight, and buffer is present at 0.5% by weight. In another embodiment, FOS, GOS, or other appropriate polysaccharide are present at 100% by weight, a probiotic bacteria strain at less than 0.5% by weight, and buffer is present at less than 0.5% by weight. If the probiotic bacteria strain, buffer, and FOS, GOS, or other appropriate polysaccharide do not make up 100% of the composition, the remaining ingredients can be any suitable ingredients intended for the consumption of a subject (e.g., human) including, but not limited to, other prebiotics (e.g., FOS), digestible saccharides (e.g., lactose, glucose or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

G. Compositions Comprising a Digestible Saccharide, FOS, GOS, or Other Appropriate Polysaccharide, and a Buffer In an embodiment, a prebiotic composition comprises a digestible saccharide (e.g. lactose, glucose, or galactose), FOS, GOS, or other appropriate polysaccharide, and a buffer. For example, lactose can be present at 1-20% by weight, FOS, GOS, or other appropriate polysaccharide at 1-100% by weight, and the buffer at 0.50-4% by weight, or the lactose can be present at 5-20% by weight, FOS, GOS, or other appropriate polysaccharide at 1-96% by weight, and the buffer at 1.2-30.75% by weight. In an embodiment, lactose is present at 20% by weight, FOS, GOS, or other appropriate polysaccharide at 1% by weight, and buffer is present at 3% by weight. In an embodiment, lactose is present at 5% by weight, FOS, GOS, or other appropriate polysaccharide at 1% by weight, and buffer is present at 3% by weight. In an embodiment, lactose is present at 20% by weight, FOS, GOS, or other appropriate polysaccharide at 10% by weight, and buffer is present at 3% by weight. In an embodiment, lactose is present at 20% by weight, FOS, GOS, or other appropriate polysaccharide at 15% by weight, and buffer is present at 3% by weight. In an embodiment, lactose is present at 20% by weight, FOS, GOS, or other appropriate polysaccharide at 20% by weight, and buffer is present at 3% by weight. In an embodiment, lactose is present at 20% by weight, FOS, GOS, or other appropriate polysaccharide at 25% by weight, and buffer is present at 3% by weight. In an embodiment, lactose is present at 20% by weight, FOS, GOS, or other appropriate polysaccharide at 30% by weight, and buffer is present at 3% by weight. In an embodiment, lactose is present at 20% by weight, FOS, GOS, or other appropriate polysaccharide at 35% by weight, and buffer is present at 3% by weight. In an embodiment, lactose is present at 20% by weight, FOS, GOS, or other appropriate polysaccharide at 40% by weight, and buffer is present at 3% by weight. In an embodiment, lactose is present at 20% by weight, FOS, GOS, or other appropriate polysaccharide at 50% by weight, and buffer is present at 3% by weight. In an embodiment, lactose is present at 20% by weight, FOS, GOS, or other appropriate polysaccharide at 60% by weight, and buffer is present at 3% by weight. In an embodiment, lactose is present at 20% by weight, FOS, GOS, or other appropriate polysaccharide at 70% by weight, and buffer is present at 3% by weight. In another embodiment, lactose is present at 5% by weight, FOS, GOS, or other appropriate polysaccharide at 90% by weight, and buffer is present at 3% by weight. In another embodiment, lactose is present at 5% by weight, FOS, GOS, or other appropriate polysaccharide at 92% by weight, and buffer is present at 3% by weight. In another embodiment, lactose is present at 4% by weight, FOS, GOS, or other appropriate polysaccharide at 93% by weight, and buffer is present at 3% by weight. In another embodiment, lactose is present at 3% by weight, FOS, GOS, or other appropriate polysaccharide at 94% by weight, and buffer is present at 3% by weight. In another embodiment, lactose is present at 2% by weight, FOS, GOS, or other appropriate polysaccharide at 95% by weight, and buffer is present at 3% by weight. In another embodiment, lactose is present at 1% by weight, FOS, GOS, or other appropriate polysaccharide at 96% by weight, and buffer is present at 3% by weight. If a suitable prebiotic, buffer and lactose do not make up 100% of the composition by weight, the remaining ingredients can be any suitable ingredients intended for consumption by a subject (e.g., human) including, but not limited to, bacteria, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

H. Compositions Comprising a Digestible Saccharide, Bacteria, GOS, and a Buffer

In an embodiment, a composition comprises a digestible saccharide (e.g. lactose, glucose, or galactose), bacteria, FOS, GOS, or other appropriate polysaccharide, and buffer. For example, lactose can be present at 1-20% by weight, bacteria at 0.25-2.10% by weight, FOS, GOS, or other appropriate polysaccharide at 1-100% by weight, and the buffer at 0.50-4% by weight, or the lactose can be present at 5-20% by weight, bacteria at 0.91-1.95% by weight, FOS, GOS, or other appropriate polysaccharide at 70-95% by weight, and the buffer at 1.2-30.75% by weight. In an embodiment, lactose is present at 20% by weight, bacteria at 1.47% by weight, FOS, GOS, or other appropriate polysaccharide at 1% by weight, and buffer is present at 3% by weight. In an embodiment, lactose is present at 20% by weight, bacteria at 1.47% by weight, FOS, GOS, or other appropriate polysaccharide at 10% by weight, and buffer is present at 3% by weight. In an embodiment, lactose is present at 20% by weight, bacteria at 1.47% by weight, FOS, GOS, or other appropriate polysaccharide at 15% by weight, and buffer is present at 3% by weight. In an embodiment, lactose is present at 20% by weight, bacteria at 1.47% by weight, FOS, GOS, or other appropriate polysaccharide at 20% by weight, and buffer is present at 3% by weight. In an embodiment, lactose is present at 20% by weight, bacteria at 1.47% by weight, FOS, GOS, or other appropriate polysaccharide at 25% by weight, and buffer is present at 3% by weight. In an embodiment, lactose is present at 20% by weight, bacteria at 1.47% by weight, FOS, GOS, or other appropriate polysaccharide at 30% by weight, and buffer is present at 3% by weight. In an embodiment, lactose is present at 20% by weight, bacteria at 1.47% by weight, FOS, GOS, or other appropriate polysaccharide at 35% by weight, and buffer is present at 3% by weight. In an embodiment, lactose is present at 20% by weight, bacteria at 1.47% by weight, FOS, GOS, or other appropriate polysaccharide at 40% by weight, and buffer is present at 3% by weight. In an embodiment, lactose is present at 20% by weight, bacteria at 1.47% by weight, FOS, GOS, or other appropriate polysaccharide at 50% by weight, and buffer is present at 3% by weight. In an embodiment, lactose is present at 20% by weight, bacteria at 1.47% by weight, FOS, GOS, or other appropriate polysaccharide at 60% by weight, and buffer is present at 3% by weight. In an embodiment, lactose is present at 20% by weight, bacteria at 1.47% by weight, FOS, GOS, or other appropriate polysaccharide at 70% by weight, and buffer is present at 3% by weight. In an embodiment, lactose is present at 5% by weight, bacteria at 1.47% by weight, FOS, GOS, or other appropriate polysaccharide at 90% by weight, and buffer is present at 3% by weight. In an embodiment, lactose is present at 3% by weight, bacteria at 1.47% by weight, FOS, GOS, or other appropriate polysaccharide at 92% by weight, and buffer is present at 3% by weight. In an embodiment, lactose is present at 2% by weight, bacteria at 1.47% by weight, FOS, GOS, or other appropriate polysaccharide at 93% by weight, and buffer is present at 3% by weight. In an embodiment, lactose is present at 1% by weight, bacteria at 1.47% by weight, FOS, GOS, or other appropriate polysaccharide at 94% by weight, and buffer is present at 3% by weight. In an embodiment, lactose is present at 0.5% by weight, bacteria at 1.47% by weight, FOS, GOS, or other appropriate polysaccharide at 95% by weight, and buffer is present at 3% by weight. If the bacteria, FOS, GOS, or other, buffer and lactose do not make up 100% of the composition by weight, the remaining ingredients can be any suitable ingredients intended for consumption by a subject, e.g., human, including, but not limited to, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

I. Additional Ingredients

Additional ingredients include ingredients to improve handling, preservatives, antioxidants, flavorings and the like. For example, in an embodiment, a prebiotic composition in powdered form can include flavorings such that when mixed in a liquid (e.g., water), the powder can flavor the liquid with various flavors such as grape, strawberry, lime, lemon, chocolate, and the like. In an embodiment, the compositions include microcrystalline cellulose or silicone dioxide. Preservatives can include, for example, benzoic acid, alcohols, for example, ethyl alcohol, and hydroxybenzoates. Antioxidants can include, for example, butylated hydroxyanisole (BHA), butylated hydroxytoluene (BHT), tocopherols (e.g., Vitamin E), and ascorbic acid (Vitamin C).

Timing and Dosage of Probiotic and Treatments Known to Combat Musculoskeletal Disorders In an embodiment, probiotic microbes, such as *L. mesenteroides* and *P. pentosaceus*, are given prior to beginning treatment with a drug typically prescribed for treatment of a musculoskeletal disorder.

Thus, in an embodiment, some or all doses of a treatment or drug are accompanied by a dose of microbes, e.g., live cultured bacteria or yeast, e.g., *L. mesenteroides, P. pentosaceus*. In an embodiment, microbes, e.g., *L. mesenteroides, P. pentosaceus*, are given initially with another treatment or drug, but then use of the microbes is discontinued. For example, the initial one, two, three, four, five, six, seven, eight, nine, ten, or more than ten days of treatment with a treatment or drug further comprises doses of microbes, with the use of microbes discontinued after that time. In an embodiment, microbes, (e.g., bacteria in yogurt), or microbes by themselves, can be given for the first two days of treatment; then the administration of microbes is discontinued. In another embodiment, probiotic microbes, either alone or in combination with other substances or treatments are used after the treatment with a drug or treatment for musculoskeletal disorders is terminated. The microbes can be taken for any suitable period after the termination of treatment with the drug and can be taken daily or at regular or irregular intervals. Doses can be as described below. Any suitable amount of probiotic per serving can be used that allows an effective microbiota in the GI as demonstrated by, for example, decreased symptoms of a given musculoskeletal disorder.

Examples of anti-osteoporosis combination partners are but are not limited to, bisphosphonates (alendronate, risedronate, ibandronate, zoledronate), biologics (denosumab, romosozumab), selective estrogen receptor mediators (Raloxifene), or anabolic agents (teriparatide, abaloparatide). In an embodiment, probiotic microbes, such as *L. mesenteroides, P. pentosaceus*, are given in conjunction with treatment, such as, but are not limited to, bisphosphonates (alendronate, risedronate, ibandronate, zoledronate), biologics (denosumab, romosozumab), selective estrogen receptor mediators (Raloxifene), or anabolic agents (teriparatide, abaloparatide).

Examples of anti-osteoarthritis combination partners are surgery, analgesics, non-steroidal anti-inflammatory drugs, menthol, weight loss regimens, physical exercise, acupuncture, narcotics, teriparatide, abaloparatide, and physical therapy.

Examples of treatments for osteomyelitis that may be used in combination with compositions disclosed herein, include, but are not limited to surgery and antibiotics. In some embodiments, antibiotics are given intravenously. In some embodiments, antibiotics are given orally. Typically, compositions disclosed herein are given after cessation of antibiotic therapy; however, in some cases, a suitable antibiotic or a suitable delivery route of antibiotic allows for concurrent use of compositions described herein and antibiotic therapy.

Examples of treatments for delayed or non-union fractures include bone stimulation and surgery, such as bone grafts or fixations.

Dosage Forms

A. General

Compositions described herein include any suitable form, including liquid or powder. Powdered compositions can be as pure powder, or can be in the form of capsules, tablets, or the like. Powder can be packaged in bulk (e.g., in a container containing sufficient prebiotic or other substances for a subject to follow for an entire course of treatment with increasing doses of prebiotic, or a portion of a course of treatment), or as individual packets (e.g., packets containing a single dose of prebiotic plus other components, or packets containing the dose of prebiotic and other components needed for a particular day of a prebiotic treatment regimen). If packaged in bulk, the powder can be in any suitable container, such as a packet, sachet, canister, ampoule, ramekin, or bottle. The container can also include one or more scoops or similar serving devices of a size or sizes appropriate to measure and serve one or more doses of prebiotic and, optionally, other ingredients included in the powder. Liquid compositions contain prebiotic and, optionally, other ingredients, in a suitable liquid, e.g., water or buffer. Liquid compositions can be provided in bulk (e.g., in a container containing sufficient prebiotic or other substances for one subject in need thereof to follow an entire course of treatment with increasing doses of prebiotic, or a portion of a course of treatment), or as individual containers, such as cans, bottles, soft packs, and the like (e.g., containers containing a single dose of prebiotic plus other components in suitable liquid, or containers containing the dose of prebiotic and other components needed for a particular day of a prebiotic treatment regimen). The container can also include one or more measuring cups or similar serving devices of a size or sizes appropriate to measure and serve one or more doses of prebiotic and, optionally, other ingredients included in the liquid.

In an embodiment, compositions described herein comprise one or more excipients. In an embodiment, the one or more excipients comprise one or more antiadherents, one or more binders, one or more coatings, one or more disintegrants, one or more fillers, one or more flavors, one or more colors, one or more lubricants, one or more glidants, one or more sorbents, one or more preservatives, one or more sweeteners, or a combination thereof. In an embodiment, the antiadherent is magnesium stearate. In an embodiment, the one or more binders are cellulose, microcrystalline cellulose, hydroxypropyl cellulose, xylitol, sorbitol, maltitol, gelatin, polyvinylpyrrolidone, polyethylene glycol, methyl cellulose, hydroxypropyl methylcellulose, or a combination thereof. In an embodiment, the one or more coatings are a hydroxypropyl methylcellulose film, shellac, corn protein zein, gelatin, methyl acrylate-methacrylic acid copolymers, cellulose acetate succinate, hydroxy propyl methyl cellulose phthalate, hydroxy propyl methyl cellulose acetate succinate, polyvinyl acetate phthalate, methyl methacrylate-methacrylic acid copolymers, sodium alginate, stearic acid, or a combination thereof. In an embodiment, the one or more disintegrants are crosslinked polyvinylpyrrolidone (crospovidone), crosslinked sodium carboxymethyl cellulose (croscarmellose sodium), sodium starch glycolate, or a combination thereof. In an embodiment, the one or more fillers are calcium carbonate, magnesium stearate, dibasic calcium phosphate, cellulose, vegetable oil, vegetable fat, or a combination thereof. In an embodiment, the one or more flavors are mint, cherry, anise, peach, apricot, licorice, raspberry, vanilla, or a combination thereof. In an embodiment, the one or more lubricants are talc, silica, vegetable stearin, magnesium stearate, stearic acid, or a combination thereof. In an embodiment, the one or more glidants are fumed silica, talc, magnesium carbonate, or a combination thereof. In an embodiment, the one or more sorbents are fatty acids, waxes, shellac, plastics, plant fibers, or a combination thereof. In an embodiment, the one or more preservatives are vitamin A, vitamin E, vitamin C, retinyl palmitate, selenium, cysteine, methionine, citric acid, sodium citrate, methyl paraben, propyl paraben, or a combination thereof. In an embodiment, the one or more sweeteners are stevia, aspartame, sucralose, neotame, acesulfame potassium, saccharin or a combination thereof.

B. Oral Dosage Forms and Components

In one aspect provided herein are methods and compositions formulated for oral delivery to a subject in need thereof. In an embodiment a composition is formulated to deliver a composition comprising a prebiotic to a subject in need thereof. In another embodiment, a pharmaceutical composition is formulated to deliver a composition comprising a prebiotic to a subject in need thereof. In another embodiment a composition is formulated to deliver a composition comprising prebiotic and a probiotic to a subject in need thereof.

1. Forms

In an embodiment, a composition is administered in solid, semi-solid, micro-emulsion, gel, or liquid form. Examples of such dosage forms include tablet forms disclosed in U.S. Pat. Nos. 3,048,526, 3,108,046, 4,786,505, 4,919,939, and 4,950,484; gel forms disclosed in U.S. Pat. Nos. 4,904,479, 6,482,435, 6,572,871, and 5,013,726; capsule forms disclosed in U.S. Pat. Nos. 4,800,083, 4,532,126, 4,935,243, and 6,258,380; or liquid forms disclosed in U.S. Pat. Nos. 4,625,494, 4,478,822, and 5,610,184; each of which is incorporated herein by reference in its entirety.

Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients including freeze-dried plant material serving both as prebiotic and as a filler. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut (e.g., colon, lower intestine) other than the stomach. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds (prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or Dragee coatings for identification or to characterize different combinations of active compound doses.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

Oral liquid preparations can be in the form of, for example, aqueous or oily suspensions, solutions, emulsions syrups or elixirs, or can be presented as a dry product for reconstitution with water or other suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; nonaqueous vehicles (which can include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

In an embodiment, a provided composition includes a softgel formulation. A softgel can contain a gelatin-based shell that surrounds a liquid fill. The shell can be made of gelatin, plasticiser (e.g., glycerin and/or sorbitol), modifier, water, color, antioxidant, or flavor. The shell can be made with starch or carrageenan. The outer layer can be enteric coated. In an embodiment, a softgel formulation can include a water or oil soluble fill solution, or suspension of a composition, for example, a prebiotic composition, covered by a layer of gelatin.

An enteric coating can control the location of where a prebiotic composition is absorbed in the digestive system. For example, an enteric coating can be designed such that a prebiotic composition does not dissolve in the stomach but rather travels to the small intestine, where it dissolves. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade name aquacoat CPD®, Sepifilm™ LP, Klucel, Aquacoat® ECD, and Metolose®); polyvinylacetate phthalate (trade name Sureteric®); and methacrylic acid (trade name Eudragit®).

In an embodiment, an enteric coated prebiotic composition is administered to a subject. In another embodiment, an enteric coated probiotic composition is administered to a subject. In another embodiment, an enteric coated probiotic and prebiotic composition is administered to a subject. In an embodiment, probiotic bacteria can be administered to a subject using an enteric coating. The stomach has an acidic environment that can kill probiotics. An enteric coating can protect probiotics as they pass through the stomach and small intestine.

Enteric coatings can be used to (1) prevent the gastric juice from reacting with or destroying the active substance, (2) prevent dilution of the active substance before it reaches the intestine, (3) ensure that the active substance is not released until after the preparation has passed the stomach, and (4) prevent live bacteria contained in the preparation from being killed because of the low pH-value in the stomach.

Enteric coatings can also be used for avoiding irritation of or damage to the mucous membrane of the stomach caused by substances contained in the oral preparation, and for counteracting or preventing formation or release of substances having an unpleasant odor or taste in the stomach. Finally, such coatings can be used for preventing nausea or vomiting on intake of oral preparations.

In an embodiment a prebiotic composition is provided as a tablet, capsule, or caplet with an enteric coating. In an embodiment the enteric coating is designed to hold the tablet, capsule, or caplet together when in the stomach. The enteric coating is designed to hold together in acid conditions of the stomach and break down in non-acid conditions and therefore release the drug in the intestines.

Softgel delivery systems can also incorporate phospholipids or polymers or natural gums to entrap a composition, for example, a prebiotic composition, in the gelatin layer with an outer coating to give desired delayed/control release effects, such as an enteric coating.

Formulations of softgel fills can be at pH 2.5-7.5.

A softgel formulation can be sealed tightly in an automatic manner. A softgel formulation can easily be swallowed, allow for product identification using colors and several shapes, allow uniformity, precision and accuracy between dosages, be safe against adulteration, provide good availability and rapid absorption, and offer protection against contamination, light and oxidation. Furthermore, softgel formulations can avoid unpleasant flavors due to content encapsulation.

A composition comprising a softgel formulation can be in any of number of different sizes, including, for example, round, oblong, oval, tube, droplet, or suppositories.

In an embodiment a composition is provided in a dosage form which comprises an effective amount of prebiotic and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. In an embodiment the dosage form is a tablet, caplet, capsule or lollipop. In another embodiment, the dosage form is a liquid, oral suspension, oral solution, or oral syrup. In yet another embodiment, the dosage form is a gel capsule, soft gelatin capsule, or hard gelatin capsule.

In an embodiment, the dosage form is a gelatin capsule having a size indicated in Table 1.

TABLE 1

Gel Cap Sizes Allowable For Human Consumption
Empty Gelatin Capsule Physical Specifications

| | Outer Diameter Size (mm) | Height or Locked Length (mm) | Actual Volume (ml) |
|---|---|---|---|
| 000 | 9.97 | 26.14 | 1.37 |
| 00 | 8.53 | 23.30 | 0.95 |
| 0 | 7.65 | 21.7 | 0.68 |
| 1 | 6.91 | 19.4 | 0.50 |
| 2 | 6.35 | 18.0 | 0.37 |
| 3 | 5.82 | 15.9 | 0.3 |
| 4 | 5.31 | 14.3 | 0.21 |
| 5 | 4.91 | 11.1 | 0.13 |

Note:
sizes and volumes are approximate.

In another embodiment a composition comprising a prebiotic is provided in effervescent dosage forms. The compositions can also comprise non-release controlling excipients.

In another embodiment, a composition comprising a prebiotic is provided in a dosage form that has at least one component that can facilitate release of the prebiotic. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semi-permeable membrane and as swellable substances.

In another embodiment the prebiotic mixture is a plant or plant extract, either in solid or liquid form.

In another embodiment a composition comprising a prebiotic is provided in an enteric coated dosage form. The composition can also comprise non-release controlling excipients.

In another embodiment a composition comprising a prebiotic is provided in a dosage form for oral administration to a subject in need thereof, which comprises one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In an embodiment a composition comprising a prebiotic is provided in the form of enteric-coated granules, for oral administration. The compositions can further comprise cellulose, disodium hydrogen phosphate, hydroxypropyl cellulose, hypromellose, lactose, mannitol, and sodium lauryl sulfate.

In another embodiment a composition comprising a prebiotic is provided in the form of enteric-coated pellets, for oral administration. The compositions can further comprise glyceryl monostearate 40-50, hydroxypropyl cellulose, hypromellose, magnesium stearate, methacrylic acid copolymer type C, polysorbate 80, sugar spheres, talc, and triethyl citrate.

In an embodiment a composition comprising a prebiotic is provided in the form of enteric-coated granules, for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In another embodiment a composition comprising a prebiotic can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The compositions provided herein can be in unit-dosage forms or multiple-dosage forms. Unit-dosage forms, as used herein, refer to physically discrete units suitable for administration to human or non-human animal subject in need thereof and packaged individually. Each unit-dose can contain a predetermined quantity of an active ingredient(s) sufficient to produce the desired therapeutic effect, in association with other pharmaceutical carriers or excipients. Examples of unit-dosage forms include, but are not limited to, ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents. For example a multiple dosage form can be provided which comprises a first dosage element comprising a composition comprising a prebiotic and a second dosage element comprising lactose or a probiotic, which can be in a modified release form.

In this example a pair of dosage elements can make a single unit dosage. In an embodiment a kit is provided comprising multiple unit dosages, wherein each unit comprises a first dosage element comprising a composition comprising a prebiotic and a second dosage element comprising probiotic, lactose or both, which can be in a modified release form. In another embodiment the kit further comprises a set of instructions.

In an embodiment, compositions can be formulated in various dosage forms for oral administration. The compositions can also be formulated as a modified release dosage form, including immediate-, delayed-, extended-, prolonged-, sustained-, pulsatile-, controlled-, extended, accelerated-, fast-, targeted-, programmed-release, and gastric retention dosage forms. These dosage forms can be prepared according to known methods and techniques (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126, which is herein incorporated by reference in its entirety).

In an embodiment, the compositions are in one or more dosage forms. For example, a composition can be administered in a solid or liquid form. Examples of solid dosage forms include but are not limited to discrete units in capsules or tablets, as a powder or granule, or present in a tablet conventionally formed by compression molding. Such compressed tablets can be prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, controlled or extended release of a composition comprising a prebiotic. Furthermore, dosage forms of the invention can comprise acceptable carriers or salts known in the art, such as those described in the Handbook of Pharmaceutical Excipients, American Pharmaceutical Association (1986), incorporated by reference herein in its entirety.

In an embodiment, an effective amount of a composition comprising a prebiotic is mixed with a pharmaceutical excipient to form a solid preformulation composition comprising a homogeneous mixture of compounds described herein. When referring to these compositions as "homogeneous," it is meant that the agents are dispersed evenly throughout the composition so that the composition can be subdivided into unit dosage forms such as tablets, caplets, or capsules. This solid preformulation composition can then be subdivided into unit dosage forms of the type described above comprising from, for example, 1 g to 20 mg of a prebiotic composition. A prebiotic composition can be formulated, in the case of caplets, capsules or tablets, to be swallowed whole, for example with water.

The compositions described herein can be in liquid form. The liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form comprises an effective amount of an active agent and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for oral administration. Examples of such vehicles and additives can be found in Remington's Pharmaceutical Sciences, 17th edition (1985).

2. Manufacturing

The dosage forms described herein can be manufactured using processes that are well known to those of skill in the art. For example, for the manufacture of tablets, an effective amount of a prebiotic can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers," can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc, and the like. Stabilizers can inhibit or retard drug decomposition reactions, including oxidative reactions. Surfactants can also include and can be anionic, cationic, amphoteric or nonionic. If desired, the tablets can also comprise nontoxic auxiliary substances such as pH buffering agents, preservatives, e.g., antioxidants, wetting or emulsifying agents, solubilizing agents, coating agents, flavoring agents, and the like.

In an embodiment, a softgel formulation is made with a gelatin mass for the outer shell, and a composition including one or more substances, for example prebiotics and/or probiotics, for the capsule fill can be prepared. To make the gelatin mass, gelatin powder can be mixed with water and glycerin, heated, and stirred under vacuum. Additives, for example, flavors or colors, can be added to molten gelatin using a turbine mixer and transferred to mobile vessels. The gelatin mass can be kept in a steam-jacketed storage vessel at a constant temperature.

The encapsulation process can begin when the molten gel is pumped to a machine and two thin ribbons of gel are formed on either side of machine. These ribbons can then pass over a series of rollers and over a set of die that determine the size and shapes of capsules. A fill composition, for example a prebiotic and/or probiotic fill composition, can be fed to a positive displacement pump, which can dose the fill and inject it between two gelatin ribbons prior to sealing them together through the application of heat and pressure. To remove excess water, the capsules can pass through a conveyer into tumble dryers where a portion of the water can be removed. The capsules can then be placed on, for example, trays, which can be stacked and transferred into drying rooms. In the drying rooms, dry air can be forced over capsules to remove any excess moisture.

3. Release Formulations

Immediate-release formulations of an effective amount of a prebiotic composition can comprise one or more combinations of excipients that allow for a rapid release of a pharmaceutically active agent (such as from 1 minute to 1 hour after administration). In an embodiment an excipient can be microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, Avicel PH200, and combinations of such excipients.

"Controlled-release" formulations (also referred to as sustained release (SR), extended-release (ER, XR, or XL), time-release or timed-release, controlled-release (CR), or continuous-release) refer to the release of a prebiotic composition from a dosage form at a particular desired point in time after the dosage form is administered to a subject. Controlled-release formulations can include one or more excipients, including but not limited to microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, or Avicel PH200. Generally, controlled-release includes sustained but otherwise complete release. A sudden and total release in the large intestine at a desired and appointed time or a release in the intestines such as through the use of an enteric coating are both considered controlled-release. Controlled-release can occur at a predetermined time or in a predetermined place within the digestive tract. It is not meant to include a passive, uncontrolled process as in swallowing a normal tablet. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,556; 5,871,776; 5,902,632; and 5,837,284 each of which is incorporated herein by reference in its entirety.

In an embodiment a controlled release dosage form begins its release and continues that release over an extended period of time. Release can occur beginning almost immediately or can be sustained. Release can be constant, can increase or decrease over time, can be pulsed, can be continuous or intermittent, and the like. Generally, however, the release of at least one pharmaceutically active agent from a controlled-release dosage form will exceed the amount of time of release of the drug taken as a normal, passive release tablet. Thus, for example, while all of at least one pharmaceutically active agent of an uncoated aspirin tablet should be released within, for example, four hours, a controlled-release dosage form could release a smaller amount of aspirin over a period of six hours, 12 hours, or even longer. Controlled-release in accordance with the compositions and methods described herein generally means that the release occurs for a period of six hours or more, such as 12 hours or more.

In another embodiment a controlled release dosage refers to the release of an agent, from a composition or dosage form in which the agent is released according to a desired profile over an extended period of time. In an embodiment, controlled-release results in dissolution of an agent within 20-720 minutes after entering the stomach. In another embodiment, controlled-release occurs when there is dissolution of an agent within 20-720 minutes after being swallowed. In another embodiment, controlled-release occurs when there is dissolution of an agent within 20-720 minutes after entering the intestine. In another embodiment, controlled-release results in substantially complete dissolution after at least 1 hour following administration. In another embodiment, controlled-release results in substantially complete dissolution after at least 1 hour following oral administration. For example, controlled-release compositions allow delivery of an agent to a subject in need thereof over an extended period of time according to a predetermined profile. Such release rates can provide therapeutically effective levels of agent for an extended period of time and thereby provide a longer period of pharmacologic or diagnostic response as compared with conventional rapid release dosage forms. Such longer periods of response provide for many inherent benefits that are not achieved with immediate-release dosages. When used in connection with the dissolution profiles discussed herein, the term "controlled-release" refers to wherein all or less than all of the total amount of a dosage form, made according to methods and compositions described herein, delivers an active agent over a period of time greater than 1 hour.

In one aspect, controlled-release refers to delayed release of an agent, from a composition or dosage form in which the agent is released according to a desired profile in which the release occurs after a period of time.

When present in a controlled-release oral dosage form, the compositions described herein can be administered at a substantially lower daily dosage level than immediate-release forms.

In an embodiment, the controlled-release layer is capable of releasing 30 to 40% of the one or more active agents (e.g., prebiotic and/or probiotic) contained therein in the stomach of a subject in need thereof in 5 to 10 minutes following oral administration. In another embodiment, the controlled-release layer is capable of releasing 90% of the one or more active agents (e.g., prebiotic and/or probiotic) is released in 40 minutes after oral administration.

In some embodiments, the controlled-release layer comprises one or more excipients, including but not limited to silicified microcrystalline cellulose (e.g., HD90), croscarmellose sodium (AC-Di-Sol), hydroxyl methyl propyl cellulose, magnesium stearate, or stearic acid. In an embodiment, a controlled release formulation weighs between 100 mg to 3 g.

Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action.

In another embodiment, an effective amount of the prebiotic is formulated in an immediate release form. In this embodiment the immediate-release form can be included in an amount that is effective to shorten the time to its maximum concentration in the blood. By way of example, certain immediate-release pharmaceutical preparations are taught in United States Patent Publication US 2005/0147710A1 entitled, "Powder Compaction and Enrobing," which is incorporated herein in its entirety by reference.

The dosage forms described herein can also take the form of pharmaceutical particles manufactured by a variety of methods, including but not limited to high-pressure homogenization, wet or dry ball milling, or small particle precipitation (nano spray). Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size.

In a further aspect the dosage form can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as a prebiotic). The acid sources can be any which are safe for human consumption and can generally include food acids, acid and hydrite antacids such as, for example: citric, tartaric, amalic, fiuneric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included. In an embodiment citric acid and sodium bicarbonate are used.

In another aspect the dosage form can be in a candy form (e.g., matrix), such as a lollipop or lozenge. In an embodiment an effective amount of a prebiotic is dispersed within a candy matrix. In an embodiment the candy matrix comprises one or more sugars (such as dextrose or sucrose). In another embodiment the candy matrix is a sugar-free matrix. The choice of a particular candy matrix is subject to wide variation. Conventional sweeteners such as sucrose can be utilized, or sugar alcohols suitable for use with diabetic patients, such as sorbitol or mannitol can be employed. Other sweeteners, such as the aspartame, can also be easily incorporated into a composition in accordance with compositions described herein. The candy base can be very soft and fast dissolving, or can be hard and slower dissolving. Various forms will have advantages in different situations.

A candy mass composition comprising an effective amount of the prebiotic can be orally administered to a subject in need thereof so that an effective amount of the prebiotic will be released into the subject's mouth as the candy mass dissolves and is swallowed. A subject in need thereof includes a human adult or child.

In an embodiment a candy mass is prepared that comprises one or more layers which can comprise different amounts or rates of dissolution of the prebiotic. In an embodiment a multilayer candy mass (such as a lollipop) comprises an outer layer with a concentration of the prebiotic differing from that of one or more inner layers. Such a drug delivery system has a variety of applications.

The choices of matrix and the concentration of the drug in the matrix can be important factors with respect to the rate of drug uptake. A matrix that dissolves quickly can deliver drug into the subject's mouth for absorption more quickly than a matrix that is slow to dissolve. Similarly, a candy matrix that contains the prebiotic in a high concentration can release more of the prebiotic in a given period of time than a candy having a low concentration. In an embodiment a candy matrix such as one disclosed in U.S. Pat. No. 4,671,953 or US Application Publication No. 2004/0213828 (which are herein incorporated by reference in their entirety) is used to deliver the prebiotic.

The dosage forms described herein can also take the form of pharmaceutical particles manufactured by a variety of methods, including but not limited to high-pressure homogenization, wet or dry ball milling, or small particle precipitation (e.g., nGimat's NanoSpray). Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In an embodiment the pharmaceutical particles have a final size of 3-1000 μM, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 μM. In another embodiment the pharmaceutical particles have a final size of 10-500 μM. In another embodiment the pharmaceutical particles have a final size of 50-600 μM. In another embodiment the pharmaceutical particles have a final size of 100-800 μM.

In an embodiment an oral dosage form (such as a powder, tablet, or capsule) is provided comprising a prebiotic composition comprising 0.7 g of FOS, GOS, or other FOS, GOS, or other appropriate polysaccharide, 0.2 g of lactose, 0.01 g of glucose, 0.01 g of galactose, 0.1-0.2 g of a binder, 0.1-0.2 g of a dispersant, 0.1-0.2 g of a solubilizer, wherein the FOS, GOS, or other FOS, GOS, or other appropriate polysaccharide are composed of 1-25% disaccharides, 1-25% trisaccharides, 1-25% tetrasaccharides, and 1-25% pentasaccharides. The oral dosage form can be in the form of a powder, capsule, or tablet. Suitable amounts of binders, dispersants, and solubilizers are known in the art for preparation of oral tablets or capsules.

In another embodiment an oral dosage form (such as a powder, tablet or capsule) is provided comprising a prebiotic composition comprising 1-99.9% by weight of FOS, GOS, or other FOS, GOS, or other appropriate polysaccharide 0.5-20% by weight of lactose, 0.1-2% by weight of glucose, 0.1-2% by weight of galactose, 0.05-2% by weight of a binder, 0.05-2% by weight of a dispersant, 0.05-2% by weight of a solubilizer, wherein the FOS, GOS, or other FOS, GOS, or other appropriate polysaccharide are composed of 1-25% by weight disaccharides, 1-25% by weight trisaccharides, 1-25% by weight tetrasaccharides, and 1-25% by weight pentasaccharides.

In another embodiment an oral dosage form (such as a powder, tablet, or capsule) is provided comprising a prebiotic composition comprising 1, 10, 20, 30, 40, 50, 60, 70, 80, 90, 95, 99.5, 100% by weight of FOS, GOS, or other FOS, GOS, or other appropriate polysaccharide 0, 5, 10, 15, or 20% by weight of lactose, 0.1, 0.5, 1, or 2% by weight of glucose, 0.1, 0.5, 1, or 2% by weight of galactose, 0.05, 0.1, 0.5, 1, or 2% by weight of a binder, 0.05, 0.1, 0.5, 1, or 2% by weight of a dispersant, 0.05, 0.1, 0.5, 1, or 2% by weight of a solubilizer, wherein the FOS, GOS, or other FOS, GOS, or other appropriate polysaccharide are composed of 1, 5, 10, 15, 20, or 25% by weight disaccharides, 1, 5, 10, 15, 20, or 25% by weight trisaccharides, 1, 5, 10, 15, 20, or 25% by weight tetrasaccharides, and 1, 5, 10, 15, 20, or 25% by weight pentasaccharides.

In another embodiment, an oral dosage form is provided comprising a prebiotic composition, wherein the oral dosage form is a syrup. The syrup can comprise 1%, 5%, 10%, 15%, 20%, 25%, 30%, 35%, 40%, 45%, 50%, 55%, 60%, 65%, 70%, 75%, 80%, or 85% solid. The syrup can comprise 15%, 20%, 25%, 30%, 35%, 40%, 45%, or 50% liquid, for example, water. The solid can comprise a prebiotic composition. The solid can be, for example, 1-96%, 10-96%, 20-96%, 30-96%, 40-96%, 50-96%, 60-96%, 70-96%, 80-96%, or 90-96% prebiotic composition. The solid can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96% prebiotic composition. In an embodiment a prebiotic composition comprises FOS, GOS, or other FOS, GOS, or other appropriate polysaccharide. In another embodiment a prebiotic composition comprises FOS, GOS, or other FOS, GOS, or other appropriate polysaccharide and another prebiotic. In another embodiment a prebiotic composition comprises FOS, GOS or other and inulin or GOS and FOS.

In an embodiment, the softgel capsule is 0.25 mL, 0.5 mL, 1.0 mL, 1.25 mL, 1.5 mL, 1.75 mL, or 2.0 mL. In another embodiment, a softgel capsule comprises 0.1 g to 2.0 g of prebiotic composition. In another embodiment, a softgel capsule comprises 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 g of a prebiotic composition. In an embodiment the prebiotic composition comprises FOS, GOS, or other FOS, GOS, or other appropriate polysaccharide. In another embodiment the prebiotic composition consists essentially of FOS, GOS, or other FOS, GOS, or other appropriate polysaccharide. In another embodiment, a softgel capsule comprises FOS, GOS, or other FOS, GOS, or other appropriate polysaccharide and inulin or FOS.

In another embodiment, the prebiotic composition is delivered in a gelatin capsule containing an amount of FOS, GOS, or other FOS, GOS, or other appropriate polysaccharide within the ranges listed in Table 2. In another embodiment, the number of pills taken per day is within the ranges listed in Table 2.

TABLE 2

Exemplary GOS Dosing Units
Exemplary GOS Composition
Dosages in Gel Caps

| Size | GOS/Pill (g) | # pills per day |
|---|---|---|
| 000 | 1-2 | 1-15 |
| 00 | 0.6-1.5 | 1-25 |
| 0 | 0.4-1.1 | 1-38 |
| 1 | 0.3-0.8 | 1-50 |
| 2 | 0.25-0.6 | 1-60 |
| 3 | 0.2-0.5 | 1-75 |
| 4 | 0.14-0.3 | 1-107 |

In another embodiment, a prebiotic composition is provided that does not contain a preservative. In another embodiment, a prebiotic composition is provided that does not contain an antioxidant. In another embodiment, a prebiotic composition is provided that does not contain a preservative or an antioxidant. In an embodiment a prebiotic composition comprising FOS, GOS, or other FOS, GOS, or other appropriate polysaccharide does not contain a preservative or an antioxidant.

In another embodiment, a prebiotic composition is formulated as a viscous fluid. In another embodiment, a prebiotic composition is formulated such that its water content is low enough that it does not support microbial growth. In an embodiment, this composition is an intermediate-moisture food, with a water activity between 0.6 and 0.85; in another embodiment this composition is a low-moisture food, with a water activity less than 0.6. Low-moisture foods limit microbial growth significantly and can be produced by one of ordinary skill in the art. For example, these products could be produced similarly to a liquid-centered cough drop. In another embodiment, a prebiotic composition is formulated as a viscous fluid without a preservative in a gel capsule. In another embodiment, a prebiotic composition comprising FOS, GOS, or other FOS, GOS, or other appropriate polysaccharide is a viscous fluid. In another embodiment, a prebiotic composition comprises a high percentage of FOS, GOS, or other FOS, GOS, or other appropriate polysaccharide that does not support microbial growth. In another embodiment, the prebiotic composition comprises FOS, GOS, or other FOS, GOS, or other appropriate polysaccharide and inulin or FOS.

In another embodiment, an oral dosage form is provided comprising a prebiotic composition, wherein the oral dosage form is a softgel. In an embodiment the softgel comprises a syrup. In an embodiment the syrup comprises a prebiotic composition. In an embodiment the prebiotic composition comprises FOS, GOS, or other FOS, GOS, or other appropriate polysaccharide. In another embodiment the prebiotic composition comprises more than 80% FOS, GOS, or other FOS, GOS, or other appropriate polysaccharide. In another embodiment the prebiotic composition comprises between 80-99.9% FOS, GOS, or other. In another embodiment the prebiotic composition comprises more than 80% FOS, GOS, or other FOS, GOS, or other appropriate polysaccharide. In another embodiment the prebiotic composition comprises 80, 81, 82, 83, 84, 85, 86, 87, 88, 89, 90, 91, 92, 93, 94, 95, 96, 97, 98, 99, or 99.9% FOS, GOS, or other FOS, GOS, or other appropriate polysaccharide.

In an embodiment a FOS, GOS, or other FOS, GOS, or other appropriate polysaccharide composition is formulated for delivery in a soft gel capsule. In an embodiment a FOS, GOS, or other FOS, GOS, or other appropriate polysaccharide composition formulated for delivery in a soft gel capsule is a high percentage FOS, GOS, or other FOS, GOS, or other appropriate polysaccharide composition, such as a 90-100% FOS, GOS, or other FOS, GOS, or other appropriate polysaccharide composition (e.g., 90, 91, 92, 93, 94, 95, 96, 97, 98, 99 or 100% FOS, GOS, or other FOS, GOS, or other appropriate polysaccharide composition by weight). In another embodiment a FOS, GOS, or other FOS, GOS, or other appropriate polysaccharide composition formulated for delivery in a soft gel capsule comprises 95% FOS, GOS, or other FOS, GOS, or other appropriate polysaccharide. In another embodiment a FOS, GOS, or other FOS, GOS, or other appropriate polysaccharide composition formulated for delivery in a soft gel capsule comprises 96% FOS, GOS, or other FOS, GOS, or other appropriate polysaccharide. In another embodiment, the FOS, GOS, or other FOS, GOS, or other appropriate polysaccharide composition is formulated such that its water content is low enough that it does not support microbial growth. In another embodiment, the FOS, GOS, or other FOS, GOS, or other appropriate polysaccharide composition is formulated as a viscous fluid without a preservative in a gel capsule. In another embodiment, the FOS, GOS, or other FOS, GOS, or other appropriate polysaccharide composition is formulated as a viscous fluid without an antioxidant in a gel capsule. In another embodiment the soft gel capsule comprises 0.1-2 g of a FOS, GOS, or other FOS, GOS, or other appropriate polysaccharide composition.

In another embodiment a prebiotic composition can be formulated as described, in U.S. Pat. No. 6,750,331, which is herein incorporated by reference in its entirety. A prebiotic composition can be formulated to comprise an oligosaccharide, a foaming component, a water-insoluble dietary fiber (e.g., cellulose or lignin), or a neutralizing component. In an embodiment a prebiotic composition can be in the form of a chewable tablet.

In an embodiment a foaming component can be at least one member selected from the group consisting of sodium hydrogencarbonate, sodium carbonate, and calcium carbonate. In an embodiment a neutralizing component can be at least one member selected from the group consisting of citric acid, L-tartaric acid, fumaric acid, L-ascorbic acid, DL-malic acid, acetic acid, lactic acid, and anhydrous citric acid. In an embodiment a water-insoluble dietary fiber can be at least one member selected from the group consisting of crystalline cellulose, wheat bran, oat bran, cone fiber, soy fiber, and beet fiber. The formulation can contain a sucrose fatty acid ester, powder sugar, fruit juice powder, and/or flavoring material.

Formulations of the provided invention can include additive components selected from various known additives. Such additives include, for example, saccharides (excluding oligosaccharides), sugar alcohols, sweeteners and like excipients, binders, disintegrators, lubricants, thickeners, surfactants, electrolytes, flavorings, coloring agents, pH modifiers, fluidity improvers, and the like. Specific examples of the additives include wheat starch, potato starch, corn starch, dextrin and like starches; sucrose, glucose, fructose, maltose, xylose, lactose and like saccharides (excluding oligosaccharides); sorbitol, mannitol, maltitol, xylitol and like sugar alcohols; calcium phosphate, calcium sulfate and like excipients; starch, saccharides, gelatin, gum arabic, dextrin, methyl cellulose, polyvinylpyrrolidone, polyvinyl alcohol, hydroxypropylcellulose, xanthan gum, pectin, gum tragacanth, casein, alginic acid and like binders and thickeners; leucine, isoleucine, L-valine, sugar esters, hardened oils, stearic acid, magnesium stearate, talc, macrogols and like lubricants; CMC, CMC-Na, CMC-Ca and like disintegrators; polysorbate, lecithin and like surfactants; aspartame, alitame and like dipeptides; silicon dioxide and like fluidity improvers; and stevia, saccharin, and like sweeteners. The amounts of these additives can be properly selected based on their relation to other components and properties of the preparation, production method, etc.

In an embodiment, a FOS, GOS, or other FOS, GOS, or other appropriate polysaccharide composition is a chewable oral dosage formulation. In an embodiment the chewable formulation can comprises between 1-99.9% FOS, GOS, or other FOS, GOS, or other appropriate polysaccharide. In an embodiment, a FOS, GOS, or other FOS, GOS, or other appropriate polysaccharide composition comprises 80% FOS, GOS, or other FOS, GOS, or other appropriate polysaccharide 5% L-ascorbic acid, 2% anhydrous citric acid, 3% sodium hydrogencarbonate, 3% calcium carbonate, 2% sucrose fatty acid, 3% fruit juice powder, and 2% potassium carbonate.

In another embodiment, a FOS, GOS, or other FOS, GOS, or other appropriate polysaccharide composition comprises 85% FOS, GOS, or other FOS, GOS, or other appropriate polysaccharide, 5% L-ascorbic acid, 3% sodium hydrogencarbonate, 2% sodium carbonate, 2% sucrose fatty acid ester, 2% fruit juice powder, and 1% potassium carbonate.

In another embodiment, a FOS, GOS, or other FOS, GOS, or other appropriate polysaccharide composition comprises 90% FOS, GOS, or other FOS, GOS, or other appropriate polysaccharide, 2% L-ascorbic acid, 1% anhydrous citric acid, 2% sodium hydrogencarbonate, 2% sodium carbonate, 2% sucrose fatty acid ester, and 1% potassium carbonate.

In another embodiment, a FOS, GOS, or other FOS, GOS, or other appropriate polysaccharide composition comprises 95% FOS, GOS, or other FOS, GOS, or other appropriate polysaccharide, 2% L-ascorbic acid, 1% sodium hydrogencarbonate, and 2% fruit juice powder. In another embodiment, a FOS, GOS, or other FOS, GOS, or other appropriate polysaccharide composition comprises 95% FOS, GOS, or other FOS, GOS, or other appropriate polysaccharide and 5% of L-ascorbic acid, anhydrous citric acid, sodium hydrogencarbonate, calcium carbonate, sucrose fatty acid, fruit juice powder, or potassium carbonate.

In another embodiment, a FOS, GOS, or other FOS, GOS, or other appropriate polysaccharide composition comprises 95% FOS, GOS, or other FOS, GOS, or other appropriate polysaccharide and 5% of L-ascorbic acid, anhydrous citric acid, sodium hydrogencarbonate, calcium carbonate, sucrose fatty acid, fruit juice powder, and potassium carbonate.

Combination Therapy

In some embodiments, the compositions of the present invention can be used in conjunction with traditional treatments for a musculoskeletal disorder, such as an anti-osteoporosis or osteopenia therapy. In some embodiments, the present invention is administered together with at least one other agent. In some embodiments, the present invention is administered before the at least one other agent. In other embodiments, the present invention is administered after cessation of another therapy. The therapy includes, but is not limited to, approved therapies for osteoporosis, osteopenia, Paget's disease, stunting, osteoarthritis, osteomyelitis, delayed or on-union fractures, or any combination of the foregoing.

Some therapies for osteoporosis or osteopenia that are known in the art include: estrogen, estrogen agonists, estrogen antagonists, and bisphosphonates. One of skill in the art would understand that the present invention may be used to supplement, increase efficacy of, or otherwise improve upon any of a number of known therapies for osteoporosis or osteopenia.

Medical Foods

An alternate embodiment of the present invention is a formulation as a medical food.

The consuming public has come to understand that foods possess more than basic nutrition (protein, carbohydrate, fat, etc). For example, 95% of consumers agree that "certain foods have health benefits that go beyond basic nutrition and may reduce the risk of disease or other health concerns." More than 50% of consumers believe that foods can replace the use of drugs. Replacing the use of drugs may have the benefit of reducing the incidence of adverse side effects suffered by patients following a pharmaceutical drug treatment regimen. In fact, medical foods are assumed to be generally safe, as people have historically consumed these foods safely in non-medical contexts.

The compositions of the invention may be administered under the supervision of a medical specialist, or may be self-administered. Medical foods could take the form of nutritional shakes or other liquids or meal replacements. Medical foods of the present invention could also take the form of a powder capable of being consumed upon addition to suitable food or liquid.

A medical food formulation of the present invention could confer benefits of a synthetic composition of microbes isolated from nutritionally beneficial plants, as well as the benefits of prebiotics, or other nutritionally beneficial inclusions, but not consumed to obtain nutrition from them but rather to provide a metabolic function different than a foodstuff. For example, medical foods of the invention may also include at least one vitamin, or vitamin precursor. Preferred vitamins possess antioxidant properties and include vitamins A, C and E, and/or their biochemical precursors. Another embodiment of the medical foods of the invention also includes at least one trace element, preferably selected from the group consisting of zinc, manganese and selenium. Medical foods of the invention also may include at least one additional antioxidant selected from the group consisting of carotenoids. N-acetylcysteine and L-glutamine. It is known to those of skill in the art how to construct medical foods containing these elements.

Medical foods of the present invention would include effective doses of microbes deemed useful for the indication and effective doses of any vitamin, prebiotic, or other beneficial additive not consumed to obtain nutrition but to add a therapeutic benefit mediated by the production of SCFA or other immuno-stimulant molecules when passing through the GI tract.

Typically, the dietary supplements and medical foods of the present invention are consumed at least once daily, and preferably administered two times per day, preferably once in the morning and once in the afternoon. A typical treatment regime for the dietary supplements or medical foods will continue for four to eight weeks. Depending on such factors as the medical condition being treated and the response of the patient, the treatment regime may be extended. A medical food of the present invention will typically be consumed in two servings per day as either a meal replacement or as a snack between meals.

Anyone perceived to be at risk from a musculoskeletal disorder, including, or already suffering from any of the foregoing, can potentially benefit from ingesting the compositions of the invention. According to the invention it is believed to be possible to effectively ameliorate symptoms and conditions associated with musculoskeletal disorders with natural compounds, which do not show any severe side effects. Furthermore, the present methods are expected to be well-tolerated, for example without causing any discomfort or nausea, and simple to apply.

Additional Embodiments

[Add Additional Embodiments Regarding Non-Osteoporosis Indications]

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1: Microbial Preparations and Metagenomic Analyses

A sample set of 15 vegetables typically eaten raw was selected to analyze the microbial communities by whole genome shotgun sequencing and comparison to microbial databases. The 15 fruits and vegetable samples are shown in Table 3 and represent ingredients in typical salads or eaten fresh. The materials were sourced at the point of distribution in supermarkets selling both conventional and organic farmed vegetables, either washed and ready to eat or without washing.

The samples were divided into 50 g portions, thoroughly rinsed with tap water and blended for 30 seconds on phosphate buffer pH 7.4 (PBS) in a household blender. The resulting slurry was strained by serial use of a coarse and then a fine household sieve followed by filtration through a 40 mm sieve. The cell suspension containing the plant microbiota, chloroplasts and plant cell debris was centrifuged at slow speed for removing plant material and the resulting supernatant centrifuged at high speed to pellet microbial cells. The pellet resuspended in a buffer containing a proprietary plant cell lysis buffer consisting of chelating agents such as EDTA or Versetene EDTA-based chelating agents to remove divalent ions and a suitable non-ionic detergent such as Tween-20, Tween 80, Triton X, and washed then with PBS. For sample #12 (broccoli) the cell pellet was washed and a fraction of the biomass separated and only the top part of the pellet collected. This was deemed “broccoli juice” for analyses. The resulting microbiota prep was inspected under fluorescence microscopy with DNA stains to visualize plant and microbial cells based on cell size and DNA structure (nuclei for plants) and selected for DNA isolation based on a minimum ratio of 9:1 microbe to plant cells. The DNA isolation was based on the method reported by Marmur (1961), or using commercial DNA extraction kits based on magnetic beads such as Thermo Charge Switch resulting in a quality suitable for DNA library prep and free of PCR inhibitors.

The DNA was used to construct a single read 150 base pair libraries and a total of 26 million reads sequenced per sample according to the standard methods done by CosmosID (www.cosmosid.com) for samples #1 to #12 or 300 base pair-end libraries and sequenced in an Illumina NextSeq instrument covering 4 Gigabases per sample for samples #13 to #15. The unassembled reads were then mapped to the CosmosID for first 12 samples or OneCodex for the last 3 samples databases containing 36,000 reference bacterial genomes covering representative members from diverse taxa. The mapped reads were tabulated and represented using a “sunburst” plot to display the relative abundance for each genome identified corresponding to that bacterial strain and normalized to the total of identified reads for each sample. In addition, phylogenetic trees were constructed based on the classification for each genome in the database with a curated review. There are genomes that have not been updated in the taxonomic classifier and therefore reported as unclassified here but it does not reflect a true lack of clear taxonomic position, it reflects only the need for manual curation and updating of those genomes in the taxonomic classifier tool. Lastly, samples 16 to 21 were analyzed using Kraken2 taxonomic sequence classification approach (Wood and Salzberg, 2014). The unassembled reads were filtered out by mapping the reads to each plant host genome sequences if available. Taxonomic labels were assigned to each sequencing read by Kraken2 according to the standard Kraken2 database that includes complete RefSeq genome sequences (O’Leary et al. 2016). Then, the abundance of species in each metagenomic sample was estimated using Bracken (Lu et al. 2017). The relative abundances were presented in pie chart at each taxonomic level.

In addition to the shotgun metagenomics survey, relevant microbes were isolated from fruits and vegetables listed in Table 3 using potato dextrose agar, nutrient agar or MRS agar and their genomes sequenced to cover 50× and analyzed their metabolic potential by using genome-wide models. For example, a yeast isolated from blueberries was sequenced and its genome showed identity to *Aureobasidium subglaciale* assembled in contigs with an N50 of 71 Kb and annotated to code for 10, 908 genes. Similarly, bacterial genomes from the same sample were sequenced and annotated for strains with high identity to *Pseudomonas* and *Rahnella*.

TABLE 3

Samples analyzed.

| Sample number | sample description |
|---|---|
| 1 | Chard |
| 2 | Red cabbage |
| 3 | Romaine romaine |

TABLE 3-continued

| Samples analyzed. | |
|---|---|
| Sample number | sample description |
| 4 | Celery |
| 5 | Butterhead lettuce |
| 6 | Baby spinach |
| 7 | Crisp green gem lettuce |
| 8 | Red oak leaf lettuce |
| 9 | Green oak leaf lettuce |
| 10 | Cherry tomato |
| 11 | Crisp red gem lettuce |
| 12 | Broccoli juice |
| 13 | Broccoli head |
| 14 | Blueberries |
| 15 | Pickled olives |
| 16 | Gingseng |
| 17 | Blackberries |
| 18 | Squash gourd |
| 19 | Broccolini |
| 20 | Fermented cabbage |
| 21 | Fermented pepper paste |

Results

For most samples, bacterial abundances of fresh material contain 10^4 to 10^8 microbes per gram of vegetable as estimated by direct microscopy counts or viable counts. Diverse cell morphologies were observed including rods, elongated rods, cocci and fungal hyphae. Microorganisms were purified from host cells, DNA was isolated and sequenced using a shotgun approach mapping reads to 35,000 bacterial genomes applying a k-mer method using Cosmos ID (https://www.cosmosid.com/). All samples were dominated by gamma proteobacteria, primarily Pseudomonadacea, presumably largely endophytes as some samples were triple washed before packaging. *Pseudomonas* cluster was the dominant genera for several samples with 10-90% of the bacterial relative abundance detected per sample and mapped to a total of 27 different genomes indicating it is a diverse group. A second relevant bacterial strain identified was *Duganella zoogloeoides* ATCC 25935 as it was present in almost all the samples ranging from 1-6% of the bacterial relative abundance detected per sample or can reach 29% of the bacterial relative abundance detected per sample in organic romaine. Red cabbage was identified to contain a relatively large proportion of lactic acid bacteria as it showed 22% *Lactobacillus crispatus*, a species commercialized as probiotic and recognized relevant in vaginal healthy microbial community. Another vegetable containing lactic acid bacteria was red oak leaf lettuce containing 1.5% of the bacterial relative abundance detected per sample *Lactobacillus reuteri*. Other bacterial species recognized as probiotics included *Bacillus, Bacteroidetes, Propionibacterium* and *Streptococcus*. A large proportion of the abundant taxa in most samples was associated with plant microbiota and members recognized to act as biocontrol agents against fungal diseases or growth promoting agents such as *Pseudomonas fluorescens*. The aggregated list of unique bacteria detected by the k-mer method is 287 (Table 4).

Blueberries contain a mixture of bacteria and fungi dominated by *Pseudomonas* and *Propionibacterium* but the yeast *Aureobasidium* was identified as a relevant member of the community. A lesser abundant bacterial species was *Rahnella*. Pickled olives are highly enriched in lactic acid bacteria after being pickled in brine allowing the endogenous probiotic populations to flourish by acidifying the environment and eliminating most of the acid-sensitive microbes including bacteria and fungi. This resulted in a large amount of *Lactobacillus* species and *Pediococcus* recognized as probiotics and related to osteoporosis treatment. Other fermented samples included fermented cabbage and chili pepper paste. Fermented cabbage contained *Pediococcus pentosaceus* as well as dominant gamma proteobacteria. Fermented chili pepper paste enriched for *Lactobacillus* with 31% of the bacterial population but also *Leuconostoc mesenteroides* and *Pediococcus pentosaceus* were enriched. One unexpected sample containing lactic acid bacteria was squash gourd showing 59% *Lactococcus* but also *Leuconostoc* was present at 3.5% of the bacterial population. In addition to the bacterial populations, some samples also contained yeast not shown in Kraken2 plots from which *Pichia* was isolated, such as fermented chili pepper paste.

The shotgun sequencing method allows for the analysis of the metagenome including genes coding for metabolic reactions involved in the assimilation of nutrient, fermentative processes to produce short chain fatty acids, flavonoids and other relevant molecules in human nutrition.

TABLE 4

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strains identified by k-mer based on entire genome | Strain number | Collection |
|---|---|---|
| *Acinetobacter baumannii* | — | |
| *Acinetobacter soli* | — | |
| *Acinetobacter* 41764 Branch | — | |
| *Acinetobacter* 41930 Branch | — | |
| *Acinetobacter* 41981 Branch | — | |
| *Acinetobacter* 41982 Branch | — | |
| *Acinetobacter baumannii* 348935 | — | |
| *Acinetobacter baumannii* 40298 Branch | — | |
| *Acinetobacter beijerinckii* 41969 Branch | — | |
| *Acinetobacter beijerinckii* CIP 110307 | CIP 110307 | WFCC |
| *Acinetobacter bohemicus* ANC 3994 | — | |
| *Acinetobacter guillouiae* 41985 Branch | — | |
| *Acinetobacter guillouiae* 41986 Branch | — | |
| *Acinetobacter gyllenbergii* 41690 Branch | — | |
| *Acinetobacter haemolyticus* TG19602 | — | |
| *Acinetobacter harbinensis* strain HITLi 7 | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strains identified by k-mer based on entire genome | Strain number | Collection |
|---|---|---|
| *Acinetobacter johnsonii* 41886 Branch | — | |
| *Acinetobacter johnsonii* ANC 3681 | — | |
| *Acinetobacter junii* 41994 Branch | — | |
| *Acinetobacter lwoffii* WJ10621 | — | |
| *Acinetobacter* sp 41945 Branch | — | |
| *Acinetobacter* sp 41674 Branch | — | |
| *Acinetobacter* sp 41698 Branch | — | |
| *Acinetobacter* sp ETR1 | — | |
| *Acinetobacter* sp NIPH 298 | — | |
| *Acinetobacter tandoii* 41859 Branch | — | |
| *Acinetobacter tjernbergiae* 41962 Branch | — | |
| *Acinetobacter towneri* 41848 Branch | — | |
| *Acinetobacter venetianus* VE C3 | — | |
| *Actinobacterium* LLX17 | — | |
| *Aeromonas bestiarum* strain CECT 4227 | CECT 4227 | CECT |
| *Aeromonas caviae* strain CECT 4221 | CECT 4221 | CECT |
| *Aeromonas hydrophila* 4AK4 | — | |
| *Aeromonas media* 37528 Branch | — | |
| *Aeromonas media* strain ARB 37524 Branch | — | |
| *Aeromonas salmonicida* subsp 37538 Branch | — | |
| *Aeromonas* sp ZOR0002 | — | |
| *Agrobacterium* 22298 Branch | — | |
| *Agrobacterium* 22301 Branch | — | |
| *Agrobacterium* 22313 Branch | — | |
| *Agrobacterium* 22314 Branch | — | |
| *Agrobacterium* sp ATCC 31749 | ATCC 31749 | ATCC |
| *Agrobacterium tumefaciens* 22306 Branch | | |
| *Agrobacterium tumefaciens* strain MEJ076 | — | |
| *Agrobacterium tumefaciens* strain S2 | — | |
| *Alkanindiges illinoisensis* DSM 15370 | DSM 15370 | WFCC |
| alpha proteobacterium L41A | — | |
| *Arthrobacter* 20515 Branch | — | |
| *Arthrobacter arilaitensis* Re117 | — | |
| *Arthrobacter chlorophenolicus* A6 | — | |
| *Arthrobacter nicotinovorans* 20547 Branch | — | |
| *Arthrobacter phenanthrenivorans* Sphe3 | — | |
| *Arthrobacter* sp 20511 Branch | — | |
| *Arthrobacter* sp PAO19 | — | |
| *Arthrobacter* sp W1 | — | |
| *Aureimonas* sp. Leaf427 | — | |
| *Aureobasidium pullulans* | — | |
| Bacillaceae Family 24 4101 12691 Branch | — | |
| *Bacillus* sp. LL01 | — | |
| *Bacillus* 12637 Branch | — | |
| *Bacillus aerophilus* strain C772 | — | |
| *Bacillus thuringiensis* serovar 12940 Branch | — | |
| *Brevundimonas nasdae* strain TPW30 | — | |
| *Brevundimonas* sp 23867 Branch | — | |
| *Brevundimonas* sp EAKA | — | |
| *Buchnera aphidicola* str 28655 Branch | — | |
| Burkholderiales Order 15 6136 Node 25777 | — | |
| *Buttiauxella agrestis* 35837 Branch | — | |
| *Candidatus Burkholderia verschuerenii* | — | |
| *Carnobacterium* 5833 Branch | — | |
| *Carnobacterium maltaromaticum* ATCC 35586 | ATCC 35586 | ATCC |
| *Chryseobacterium* 285 Branch | — | |
| *Chryseobacterium daeguense* DSM 19388 | DSM 19388 | WFCC |
| *Chryseobacterium formosense* | — | |
| *Chryseobacterium* sp YR005 | — | |
| *Clavibacter* 20772 Branch | — | |
| *Clostridium diolis* DSM 15410 | DSM 15410 | WFCC |
| *Comamonas* sp B 9 | — | |
| *Curtobacterium flaccumfaciens* 20762 Branch | — | |
| *Curtobacterium flaccumfaciens* UCD AKU | — | |
| *Curtobacterium* sp UNCCL17 | — | |
| *Deinococcus aquatilis* DSM 23025 | DSM 23025 | WFCC |
| *Debaromyces hansenii* | ATCC 36239 | ATCC |
| *Duganella zoogloeoides* | ATCC 25935 | |
| *Dyadobacter* 575 Branch | — | |
| *Elizabethkingia anophelis* | — | |
| *Empedobacter falsenii* strain 282 | — | |
| *Enterobacter* sp 638 | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strains identified by k-mer based on entire genome | Strain number | Collection |
|---|---|---|
| Enterobacteriaceae Family 9 3608 Node 35891 | — | |
| Enterobacteriaceae Family 9 593 Node 36513 | — | |
| *Epilithonimonas lactis* | — | |
| *Epilithonimonas tenax* DSM 16811 | DSM 16811 | WFCC |
| *Erwinia* 35491 Branch | — | |
| *Erwinia amylovora* 35816 Branch | — | |
| *Erwinia pyrifoliae* 35813 Branch | — | |
| *Erwinia tasmaniensis* Et1 99 | DSM 17950 | WFCC |
| *Escherichia coli* ISC11 | — | |
| *Exiguobacterium* 13246 Branch | — | |
| *Exiguobacterium* 13260 Branch | — | |
| *Exiguobacterium sibiricum* 255 15 | DSM 17290 | WFCC |
| *Exiguobacterium* sp 13263 Branch | — | |
| *Exiguobacterium undae* 13250 Branch | — | |
| *Exiguobacterium undae* DSM 14481 | DSM 14481 | WFCC |
| *Flavobacterium* 237 Branch | — | |
| *Flavobacterium aquatile* LMG 4008 | LMG 4008 | WFCC |
| *Flavobacterium chungangense* LMG 26729 | LMG 26729 | WFCC |
| *Flavobacterium daejeonense* DSM 17708 | DSM 17708 | WFCC |
| *Flavobacterium hibernum* strain DSM 12611 | DSM 12611 | WFCC |
| *Flavobacterium hydatis* | — | |
| *Flavobacterium johnsoniae* UW101 | ATCC 17061D-5 | ATCC |
| *Flavobacterium reichenbachii* | — | |
| *Flavobacterium soli* DSM 19725 | DSM 19725 | WFCC |
| *Flavobacterium* sp 238 Branch | — | |
| *Flavobacterium* sp EM1321 | — | |
| *Flavobacterium* sp MEB061 | — | |
| Hanseniaspora uvarum | ATCC 18859 | |
| *Hanseniaspora occidentalis* | ATCC 32053 | |
| *Herminiimonas arsenicoxydans* | — | |
| *Hymenobacter swuensis* DY53 | — | |
| *Janthinobacterium* 25694 Branch | — | |
| *Janthinobacterium agaricidamnosum* NBRC 102515 | DSM 9628 | WFCC |
| *Janthinobacterium lividum* strain RIT308 | — | |
| *Janthinobacterium* sp RA13 | — | |
| *Kocuria* 20614 Branch | — | |
| *Kocuria rhizophila* 20623 Branch | — | |
| *Lactobacillus acetotolerans* | — | |
| *Lactobacillus brevis* | — | |
| *Lactobacillus buchneri* | — | |
| *Lactobacillus futsaii* | — | |
| *Lactobacillus kefiranofaciens* | — | |
| *Lactobacillus panis* | — | |
| *Lactobacillus parafarraginis* | — | |
| *Lactobacillus plantarum* | — | |
| *Lactobacillus rapi* | — | |
| *Lactobacillus crispatus* 5565 Branch | — | |
| *Lactobacillus plantarum* WJL | — | |
| *Lactobacillus reuteri* 5515 Branch | — | |
| *Leuconostoc mesenteroides* | ATCC 8293 | |
| *Luteibacter* sp 9135 | — | |
| *Massilia timonae* CCUG 45783 | — | |
| *Methylobacterium extorquens* 23001 Branch | — | |
| *Methylobacterium* sp 22185 Branch | — | |
| *Methylobacterium* sp 285MFTsu5 1 | — | |
| *Methylobacterium* sp 88A | — | |
| *Methylotenera versatilis* 7 | — | |
| *Microbacterium laevaniformans* OR221 | — | |
| *Microbacterium oleivorans* | — | |
| *Microbacterium* sp MEJ108Y | — | |
| *Microbacterium* sp UCD TDU | — | |
| *Microbacterium testaceum* StLB037 | — | |
| *Micrococcus luteus* strain RIT304 | NCTC 2665 | NCTC |
| *Mycobacterium abscessus* 19573 Branch | — | |
| *Neosartorya fischeri* | — | |
| *Oxalobacteraceae bacterium* AB 14 | — | |
| *Paenibacillus* sp FSL 28088 Branch | — | |
| *Paenibacillus* sp FSL H7 689 | — | |
| *Pantoea* sp. SL1 M5 | — | |
| *Pantoea* 36041 Branch | — | |
| *Pantoea agglomerans* strain 4 | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strains identified by k-mer based on entire genome | Strain number | Collection |
|---|---|---|
| *Pantoea agglomerans* strain 4 | — | |
| *Pantoea agglomerans* strain LMAE 2 | — | |
| *Pantoea agglomerans* Tx10 | — | |
| *Pantoea* sp 36061 Branch | — | |
| *Pantoea* sp MBLJ3 | — | |
| *Pantoea* sp SL1 M5 | — | |
| *Paracoccus* sp PAMC 22219 | — | |
| *Patulibacter minatonensis* DSM 18081 | DSM 18081 | WFCC |
| *Pectobacterium carotovorum* subsp *carotovorum* strain 28625 Branch | — | |
| *Pediococcus ethanolidurans* | — | |
| *Pediococcus pentosaceus* | ATCC 33314 | |
| *Pedobacter* 611 Branch | — | |
| *Pedobacter agri* PB92 | — | |
| *Pedobacter borealis* DSM 19626 | DSM 19626 | WFCC |
| *Pedobacter kyungheensis* strain KACC 16221 | — | |
| *Pedobacter* sp R20 19 | — | |
| *Periglandula ipomoeae* | — | |
| *Planomicrobium glaciei* CHR43 | — | |
| *Propionibacterium acnes* | — | |
| *Propionibacterium* 20955 Branch | — | |
| *Propionibacterium acnes* 21065 Branch | — | |
| *Pseudomonas fluorescens* | — | |
| *Pseudomonas* sp. DSM 29167 | — | |
| *Pseudomonas* sp. Leaf15 | — | |
| *Pseudomonas syringae* | — | |
| *Pseudomonas* 39524 Branch | — | |
| *Pseudomonas* 39642 Branch | — | |
| *Pseudomonas* 39733 Branch | — | |
| *Pseudomonas* 39744 Branch | — | |
| *Pseudomonas* 39791 Branch | — | |
| *Pseudomonas* 39821 Branch | — | |
| *Pseudomonas* 39834 Branch | — | |
| *Pseudomonas* 39875 Branch | — | |
| *Pseudomonas* 39880 Branch | — | |
| *Pseudomonas* 39889 Branch | — | |
| *Pseudomonas* 39894 Branch | — | |
| *Pseudomonas* 39913 Branch | — | |
| *Pseudomonas* 39931 Branch | — | |
| *Pseudomonas* 39942 Branch | — | |
| *Pseudomonas* 39979 Branch | — | |
| *Pseudomonas* 39996 Branch | — | |
| *Pseudomonas* 40058 Branch | — | |
| *Pseudomonas* 40185 Branch | — | |
| *Pseudomonas abietaniphila* strain KF717 | — | |
| *Pseudomonas chlororaphis* strain EA105 | — | |
| *Pseudomonas cremoricolorata* DSM 17059 | DSM 17059 | WFCC |
| *Pseudomonas entomophila* L48 | — | |
| *Pseudomonas extremaustralis* 14 3 substr 14 3b | — | |
| *Pseudomonas fluorescens* BBc6R8 | — | |
| *Pseudomonas fluorescens* BS2 | ATCC 12633 | ATCC |
| *Pseudomonas fluorescens* EGD AQ6 | — | |
| *Pseudomonas fluorescens* strain AU 39831 Branch | — | |
| *Pseudomonas fluorescens* strain AU10973 | — | |
| *Pseudomonas fluorescens* strain AU14440 | — | |
| *Pseudomonas fragi* B25 | NCTC 10689 | NCTC |
| *Pseudomonas frederiksbergensis* strain SI8 | — | |
| *Pseudomonas fulva* strain MEJ086 | — | |
| *Pseudomonas fuscovaginae* 39768 Branch | — | |
| *Pseudomonas gingeri* NCPPB 3146 | NCPPB 3146 | NCPPB |
| *Pseudomonas lutea* | — | |
| *Pseudomonas luteola* XLDN4 9 | — | |
| *Pseudomonas mandelii* JR 1 | — | |
| *Pseudomonas moraviensis* R28 S | — | |
| *Pseudomonas mosselii* SJ10 | — | |
| *Pseudomonas plecoglossicida* NB 39639 Branch | — | |
| *Pseudomonas poae* RE*1 1 14 | — | |
| *Pseudomonas pseudoalcaligenes* AD6 | — | |
| *Pseudomonas psychrophila* HA 4 | — | |
| *Pseudomonas putida* DOT T1E | — | |
| *Pseudomonas putida* strain KF703 | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strains identified by k-mer based on entire genome | Strain number | Collection |
|---|---|---|
| *Pseudomonas putida* strain MC4 5222 | — | |
| *Pseudomonas rhizosphaerae* | — | |
| *Pseudomonas rhodesiae* strain FF9 | — | |
| *Pseudomonas* sp 39813 Branch | — | |
| *Pseudomonas simiae* strain 2 36 | — | |
| *Pseudomonas simiae* strain MEB105 | — | |
| *Pseudomonas* sp 11 12A | — | |
| *Pseudomonas* sp 2 922010 | — | |
| *Pseudomonas* sp CF149 | — | |
| *Pseudomonas* sp Eur1 9 41 | — | |
| *Pseudomonas* sp LAMO17WK12 I2 | — | |
| *Pseudomonas* sp PAMC 25886 | — | |
| *Pseudomonas* sp PTA1 | — | |
| *Pseudomonas* sp R62 | — | |
| *Pseudomonas* sp WCS374 | — | |
| *Pseudomonas synxantha* BG33R | — | |
| *Pseudomonas synxantha* BG33R | — | |
| *Pseudomonas syringae* 39550 Branch | — | |
| *Pseudomonas syringae* 39596 Branch | — | |
| *Pseudomonas syringae* 40123 Branch | — | |
| *Pseudomonas syringae* CC 39499 Branch | — | |
| *Pseudomonas syringae* pv panici str LMG 2367 | — | |
| *Pseudomonas syringae* strain mixed | — | |
| *Pseudomonas tolaasii* 39796 Branch | — | |
| *Pseudomonas tolaasii* PMS117 | — | |
| *Pseudomonas veronii* 1YdBTEX2 | — | |
| *Pseudomonas viridiflava* CC1582 | — | |
| *Pseudomonas viridiflava* strain LMCA8 | — | |
| *Pseudomonas viridiflava* TA043 | — | |
| *Pseudomonas viridiflava* UASWS0038 | — | |
| *Rahnella* 35969 Branch | — | |
| *Rahnella* 35970 Branch | — | |
| *Rahnella* 35971 Branch | — | |
| *Rahnella aquatilis* HX2 | — | |
| *Rahnella* sp WP5 | — | |
| *Raoultella ornithinolytica* | — | |
| Rhizobiales Order 22324 Branch | — | |
| *Rhizobium* sp YR528 | — | |
| *Rhodococcus fascians* A76 | — | |
| *Rhodococcus* sp BS 15 | — | |
| *Saccharomyces cerevisiae* | — | |
| *Sanguibacter keddieii* | DSM 10542 | WFCC |
| *Serratia fonticola* AU 35657 Branch | — | |
| *Serratia fonticola* AU AP2C | — | |
| *Serratia liquefaciens* ATCC 27592 | ATCC 27592 | ATCC |
| *Serratia* sp H 35589 Branch | — | |
| *Shewanella* 37294 Branch | — | |
| *Shewanella baltica* 37301 Branch | — | |
| *Shewanella baltica* 37315 Branch | — | |
| *Shewanella baltica* OS 37308 Branch | — | |
| *Shewanella baltica* OS 37312 Branch | — | |
| *Shewanella baltica* OS185 | — | |
| *Shewanella baltica* OS223 | — | |
| *Shewanella baltica* OS678 | — | |
| *Shewanella oneidensis* MR 1 | — | |
| *Shewanella putrefaciens* HRCR 6 | — | |
| *Shewanella* sp W3 18 1 | — | |
| *Sphingobacterium* sp ML3W | — | |
| *Sphingobium japonicum* BiD32 | — | |
| *Sphingobium xenophagum* 24443 Branch | — | |
| *Sphingomonas echinoides* ATCC 14820 | ATCC 14820 | ATCC |
| *Sphingomonas parapaucimobilis* NBRC 15100 | ATCC 51231 | ATCC |
| *Sphingomonas paucimobilis* NBRC 13935 | ATCC 29837 | ATCC |
| *Sphingomonas phyllosphaerae* 5 2 | — | |
| *Sphingomonas* sp 23777 Branch | — | |
| *Sphingomonas* sp STIS6 2 | — | |
| *Staphylococcus* 6317 Branch | — | |
| *Staphylococcus equorum* UMC CNS 924 | — | |
| *Staphylococcus* sp 6275 Branch | — | |
| *Staphylococcus* sp 6240 Branch | — | |
| Staphylococcus sp OJ82 | — | |
| *Staphylococcus xylosus* strain LSR 02N | — | |

TABLE 4-continued

Bacteria identified in a 15 sample survey identified by whole genome matching to reference genomes. The fruits and vegetables were selected based on their recognition as part of the whole food plant-based diet and some antidiabetic and obesogenic properties. There is general recognition of microbes in these vegetables relevant for plant health but not previously recognized for their use in human health.

| Strains identified by k-mer based on entire genome | Strain number | Collection |
|---|---|---|
| *Stenotrophomonas* 14028 Branch | — | |
| *Stenotrophomonas* 42816 Branch | — | |
| *Stenotrophomonas maltophilia* 42817 Branch | — | |
| *Stenotrophomonas maltophilia* PML168 | — | |
| *Stenotrophomonas maltophilia* strain ZBG7B | — | |
| *Stenotrophomonas rhizophila* | — | |
| *Stenotrophomonas* sp RIT309 | — | |
| *Streptococcus gallofyticus* subsp *gallofyticus* TX20005 | — | |
| *Streptococcus infantarius* subsp *infantarius* 2242 Branch | — | |
| *Streptococcus infantarius* subsp *infantarius* ATCC BAA 102 | ATCC BAA 102 | ATCC |
| *Streptococcus macedonicus* ACA DC 198 | ATCC BAA-249 | ATCC |
| *Streptomyces olindensis* | — | |
| *Variovorax paradoxus* 110B | — | |
| *Variovorax paradoxus* ZNC0006 | — | |
| *Variovorax* sp CF313 | — | |
| *Vibrio fluvialis* 44473 Branch | — | |
| *Xanthomonas campestris* 37936 Branch | — | |
| *Xanthomonas campestris* pv raphani 756C | — | |

FIG. 1 shows bacterial diversity observed in a set of 21 plant-derived samples as seen by a community reconstruction based on mapping the reads from a shotgun sequencing library into the full genomes of a database containing 36,000 genomes by the k-mer method (CosmosID, OneCodex or Kraken2). The display corresponds to a sunburst plot constructed with the relative abundance for each corresponding genome identified and their taxonomic classification or pie charts. The genomes identified as unclassified have not been curated in the database with taxonomic identifiers and therefore not assigned to a group. This does not represent novel taxa and it is an artifact of the database updating process.

More specifically, FIG. 1A shows bacterial diversity observed in a green chard. The dominant group is gamma proteobacteria with different *Pseudomonas* species. The members of the group "unclassified" are largely gamma proteobacteria not included in the hierarchical classification as an artifact of the database annotation.

Figure 1B:
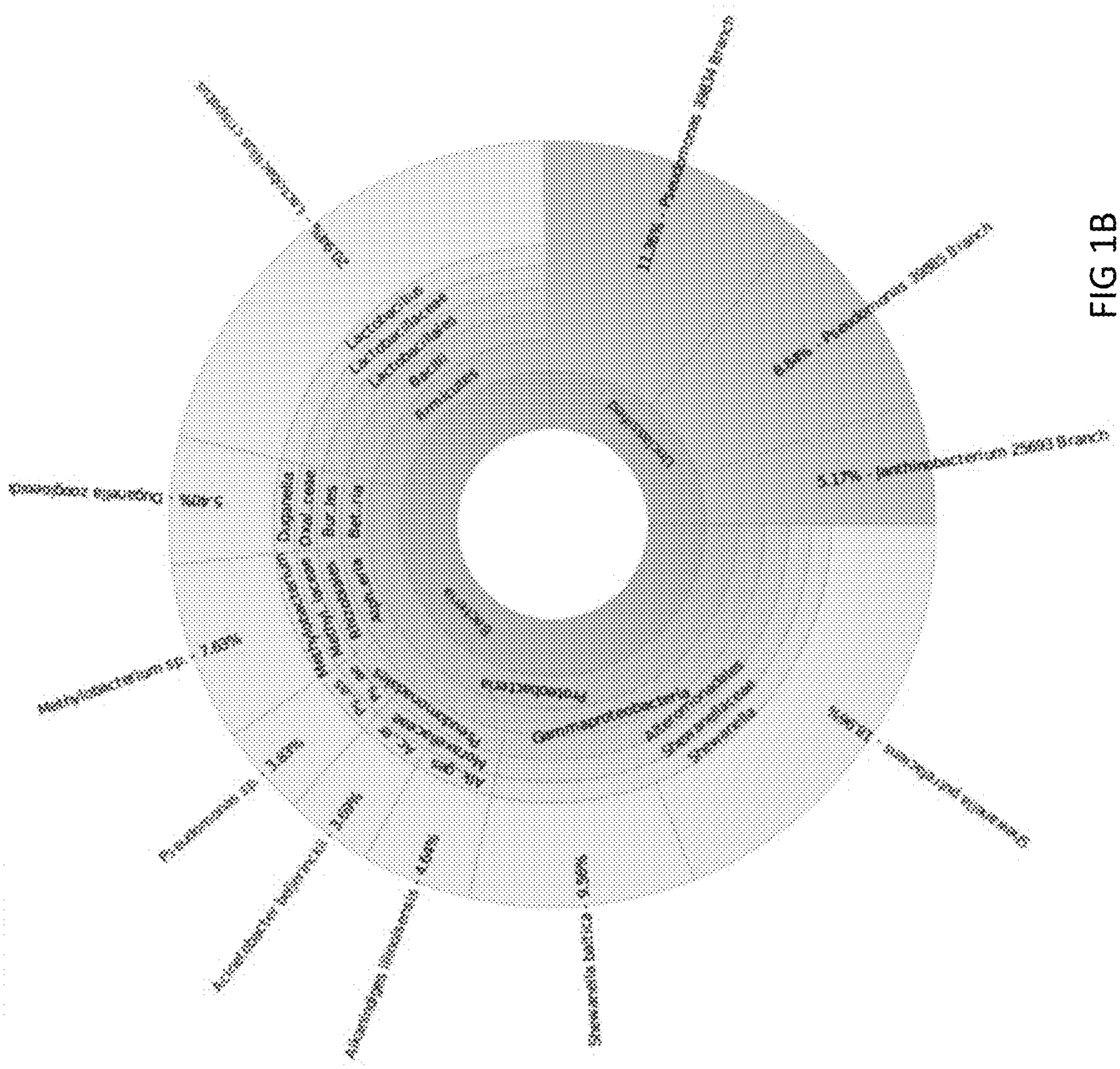
FIG. 1B shows bacterial diversity in red cabbage.

FIG. 1B shows bacterial diversity in red cabbage. There is a large abundance of *Lactobacillus* in the sample followed by a variety of *Pseudomonas* and *Shewanella.*

Figure 1C:
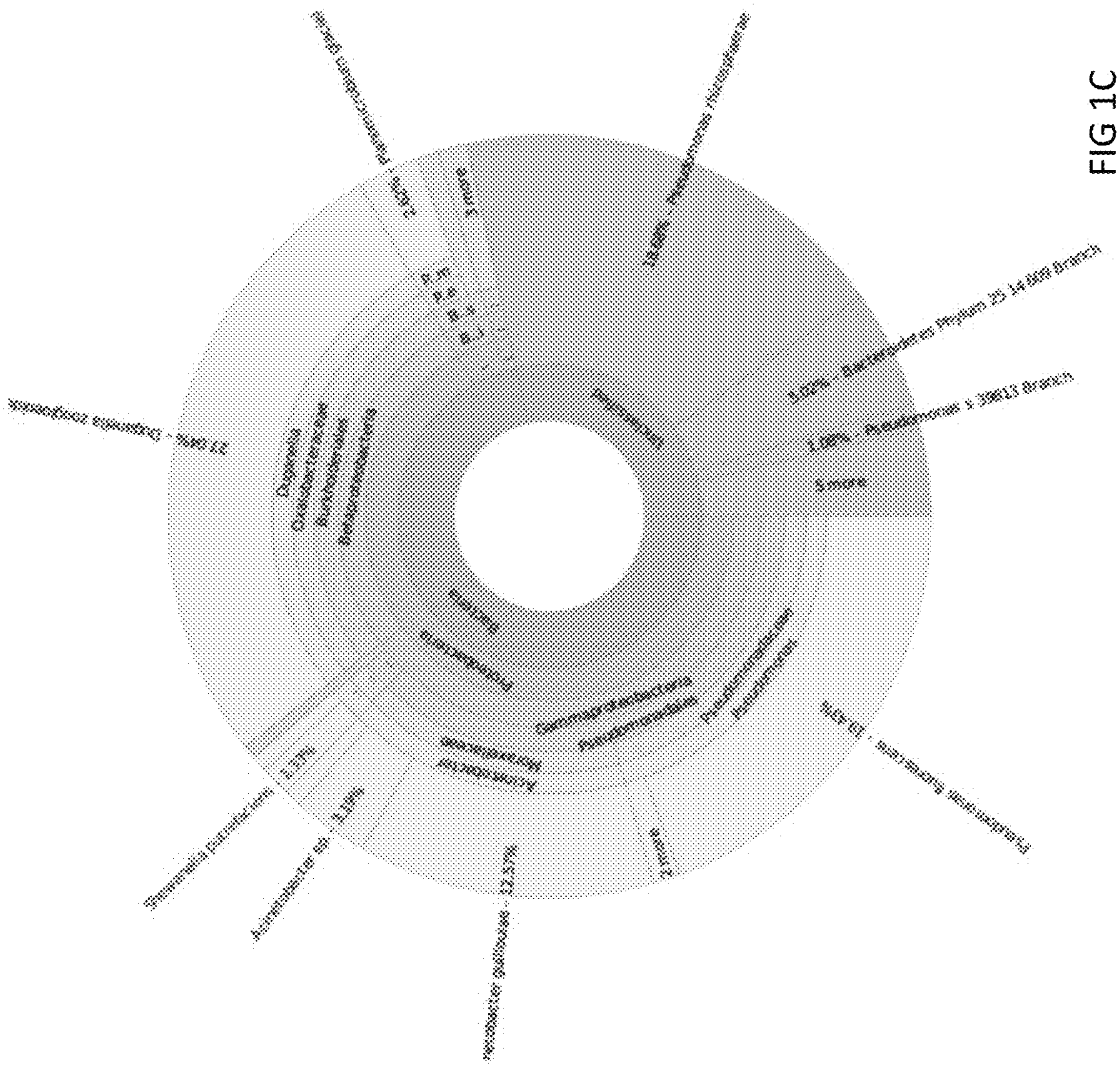
FIG. 1C shows bacterial diversity in romaine lettuce.

FIG. 1C shows bacterial diversity in romaine lettuce. *Pseudomonas* and *Duganella* are the dominant groups. A member of the Bacteroidetes was also identified.

Figure 1D:
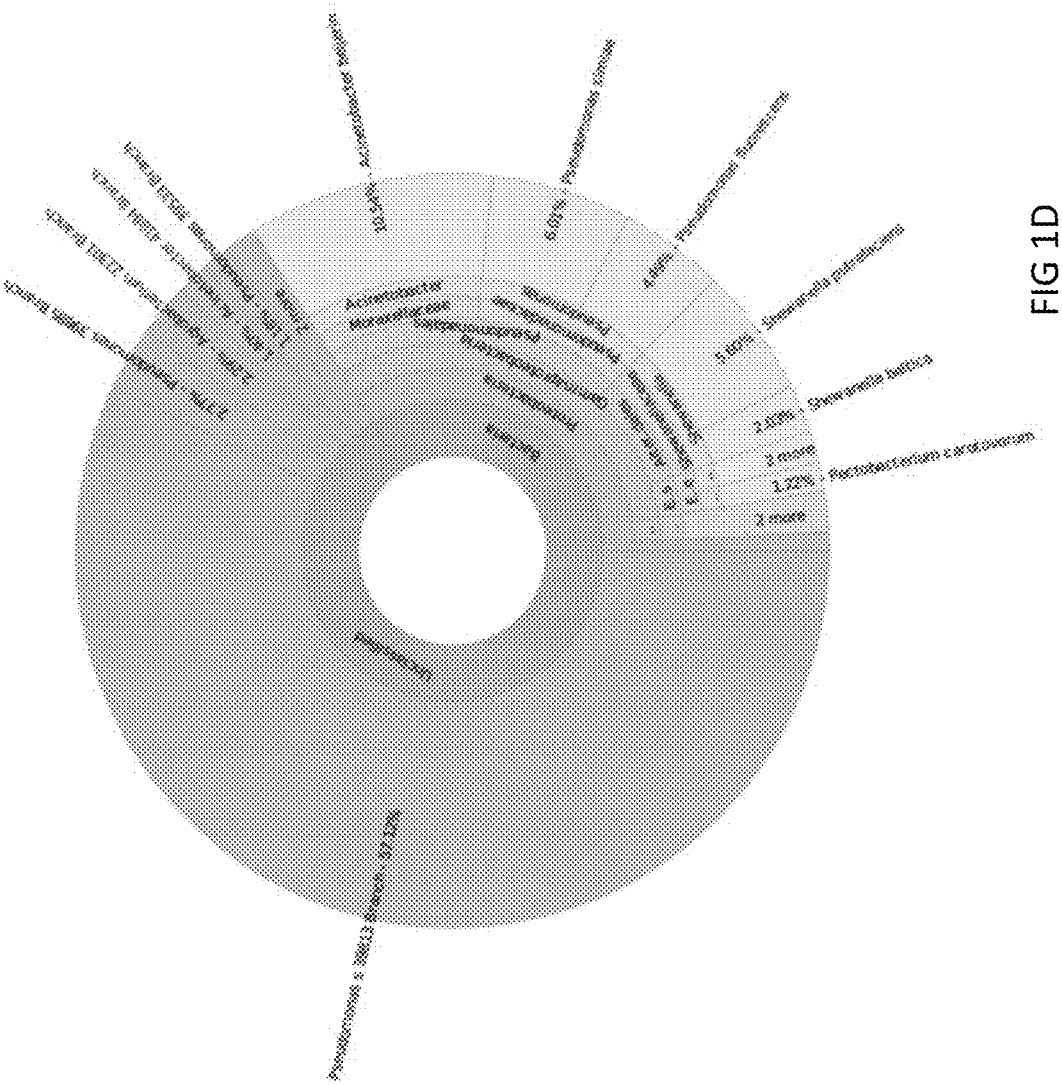
FIG. 1D shows bacterial diversity in celery sticks.

FIG. 1D shows bacterial diversity in celery sticks. This sample was dominated by a *Pseudomonas* species that was not annotated yet into the database and therefore appeared as "unclassified" same for *Agrobacterium* and *Acinetobacter.*

Figure 1E:
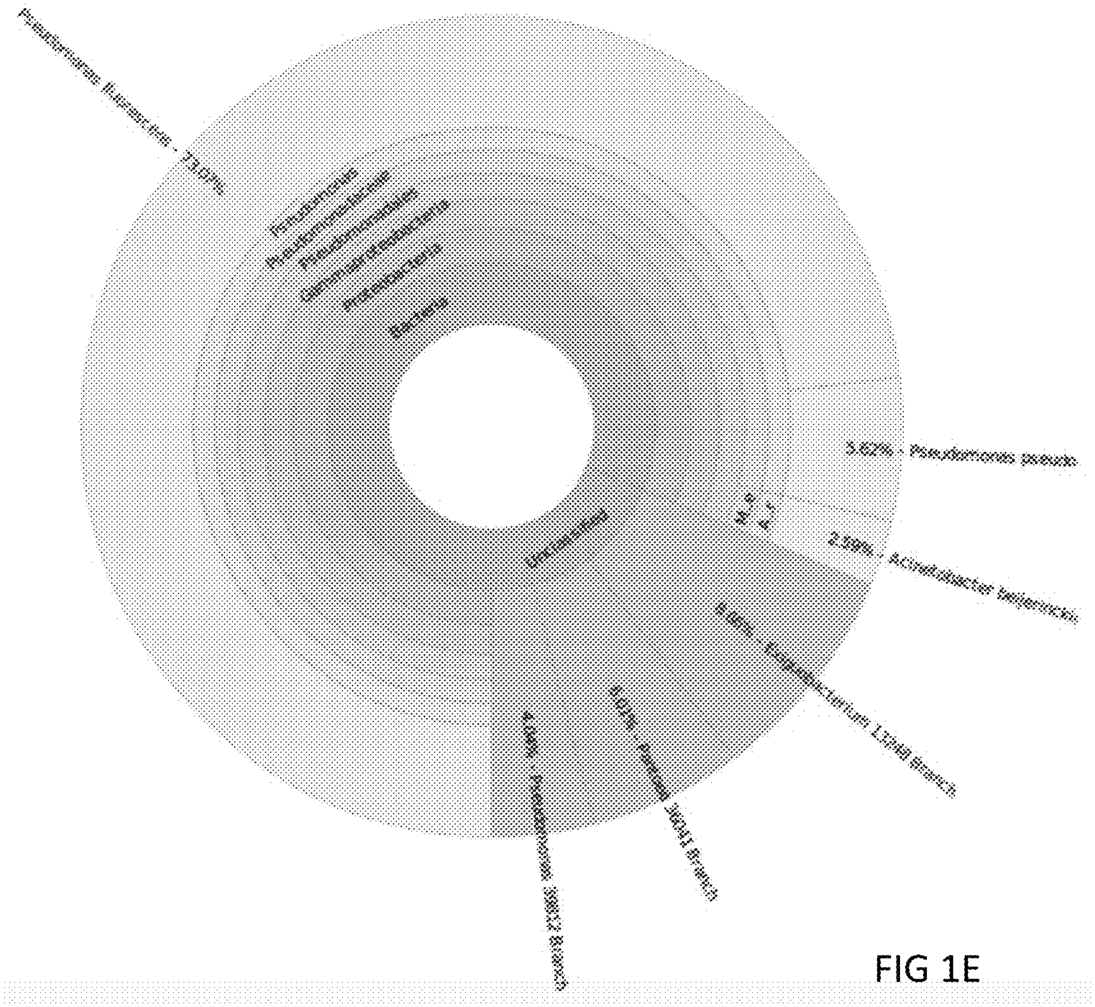
FIG. 1E shows bacterial diversity observed in butterhead lettuce grown hydroponically.

FIG. 1E shows bacterial diversity observed in butterhead lettuce grown hydroponically. The sample contains relatively low bacterial complexity dominated by *P. fluorescens* and other groups. Also, there is a 9% abundance of *Exiguobacterium.*

Figure 1F:
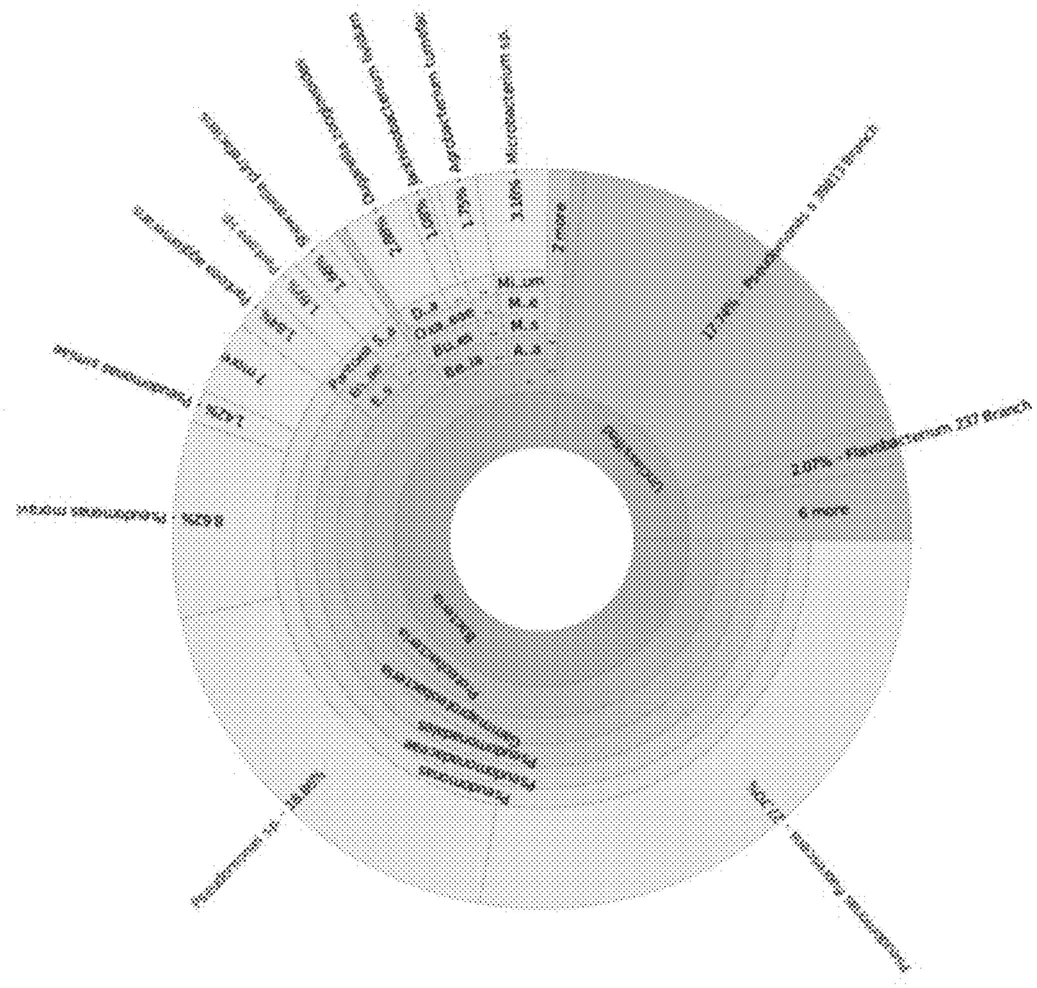
FIG. 1F shows bacterial diversity in organic baby spinach.

FIG. 1F shows bacterial diversity in organic baby spinach. The samples were triple-washed before distribution at the point of sale and therefore it is expected that must of the bacteria detected here are endophytes. Multiple *Pseudomonas* species observed in this sample including *P. fluorescens* and other shown as "unclassified."

Figure 1G:
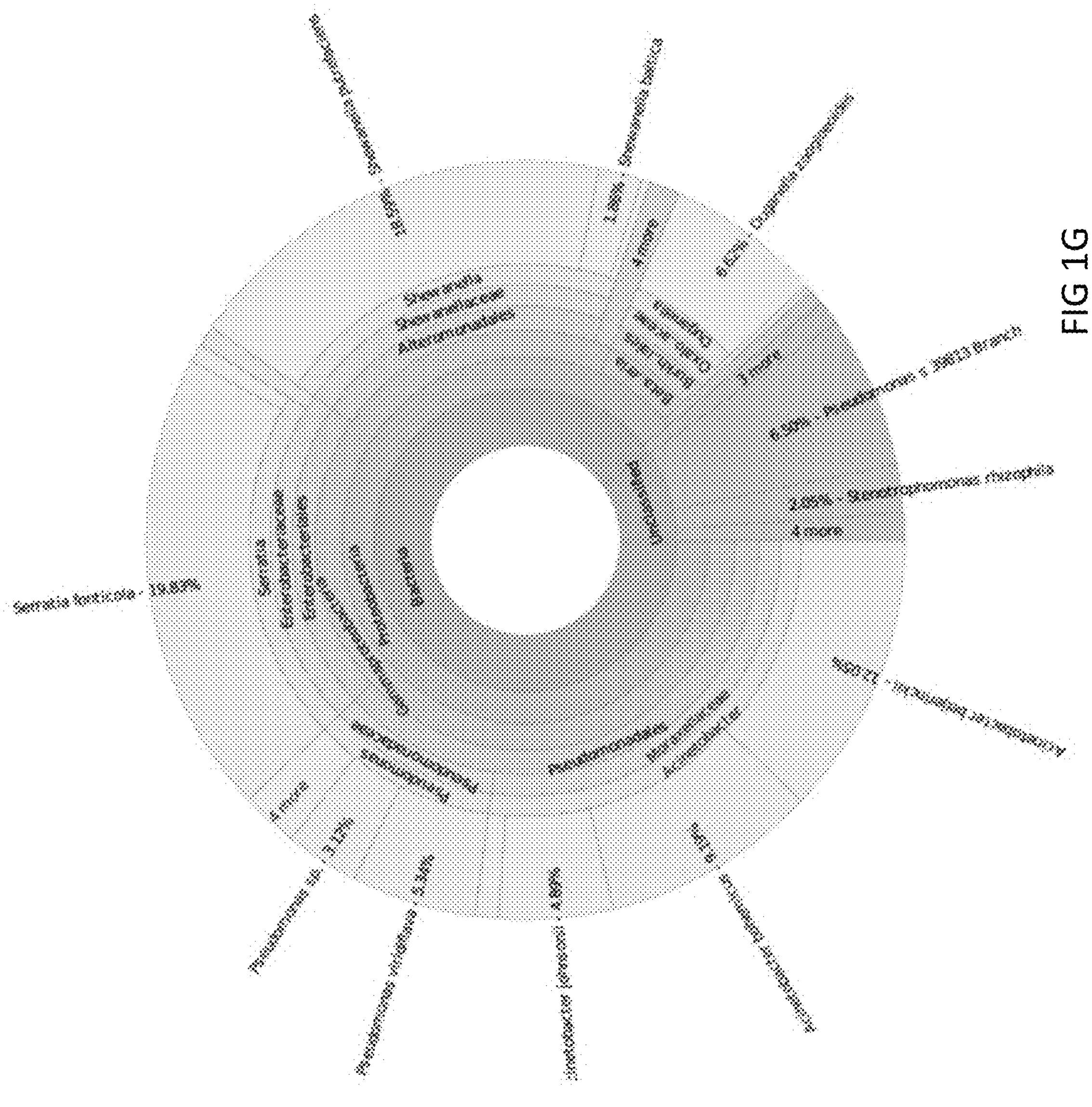
FIG. 1G shows bacterial diversity in green crisp gem lettuce

FIG. 1G shows bacterial diversity in green crisp gem lettuce. This variety of lettuce showed clear dominance of gamma proteobacteria and with *Pseudomonas, Shewanella, Serratia* as well as other groups such as *Duganella.*

Figure 1H:
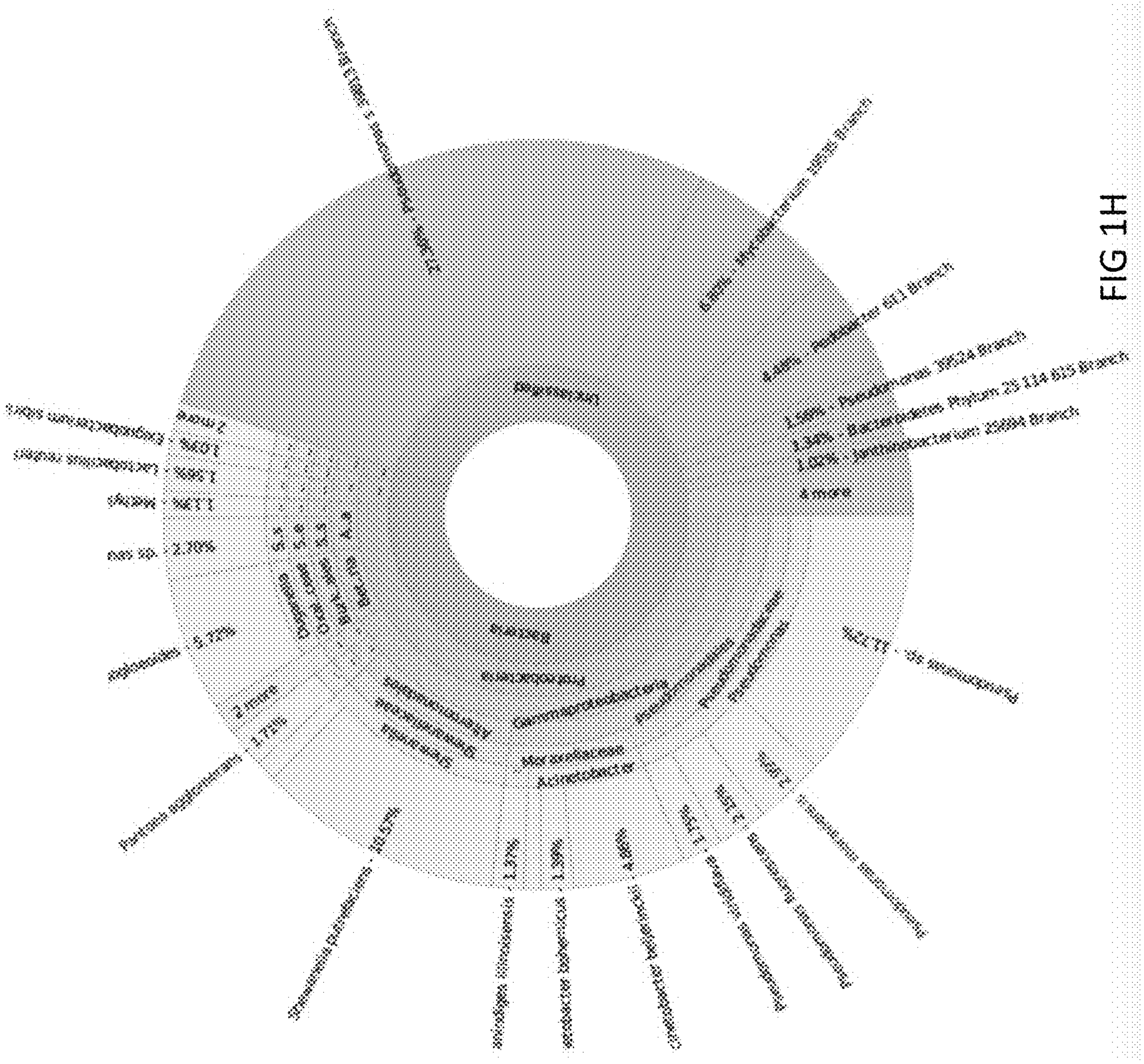
FIG. 1H shows bacterial diversity in red oak leaf lettuce.

FIG. 1H shows bacterial diversity in red oak leaf lettuce. There is a relative high diversity represented in this sample with members of *Lactobacillus, Microbacterium, Bacteroidetes, Exiguobacterium* and a variety of *Pseudomonas.*

Figure 1I:
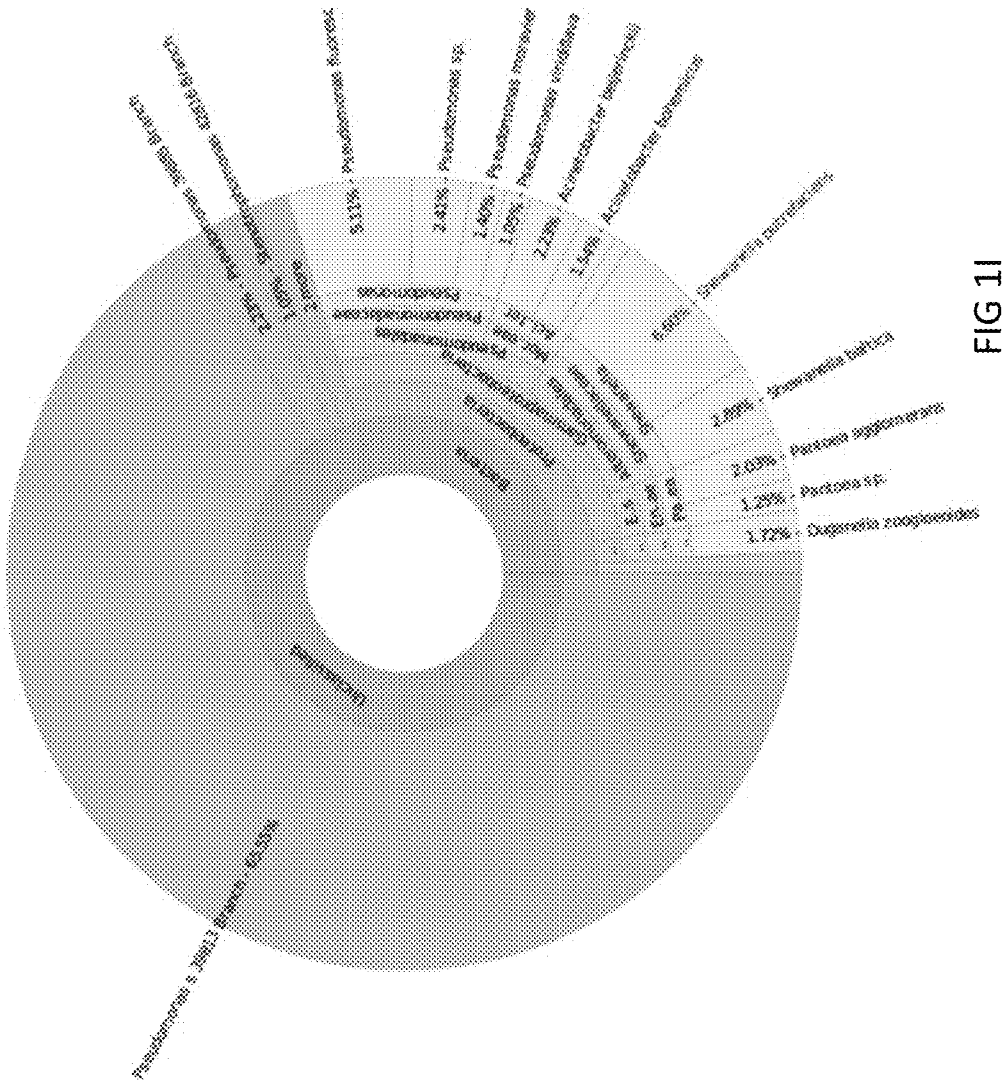
FIG. 1I shows bacterial diversity in green oak leaf lettuce.

FIG. 1I shows bacterial diversity in green oak leaf lettuce. It is dominated *Pseudomonas* species including fluorescens and mostly gamma proteobacteria.

Figure 1J:
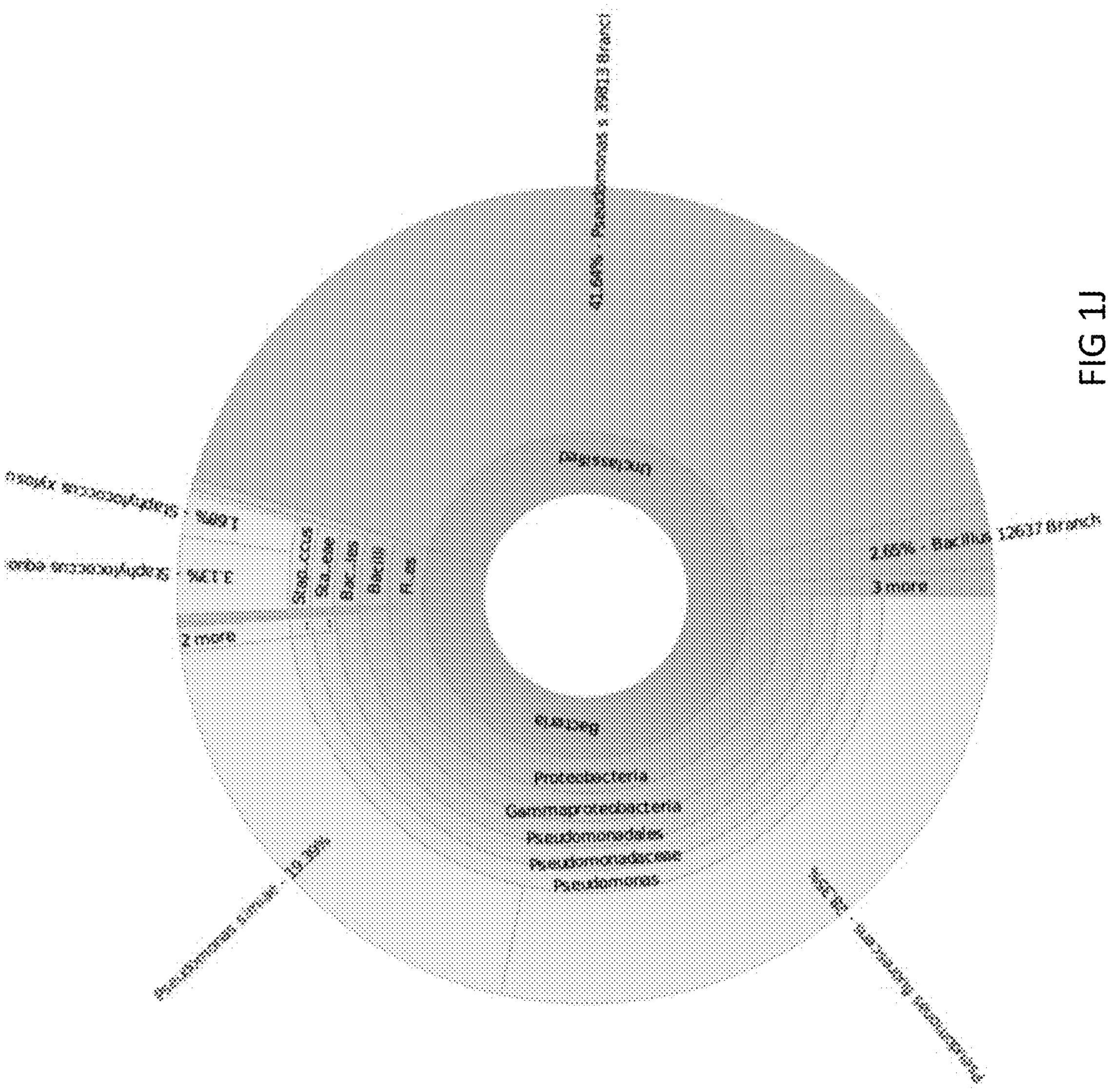
FIG. 1J shows bacterial diversity in cherry tomatoes.

FIG. 1J shows bacterial diversity in cherry tomatoes. It is dominated by three species of *Pseudomonas* comprising more than 85% of the total diversity on which *P. fluorescens* comprises 28% of bacterial diversity.

Figure 1K:
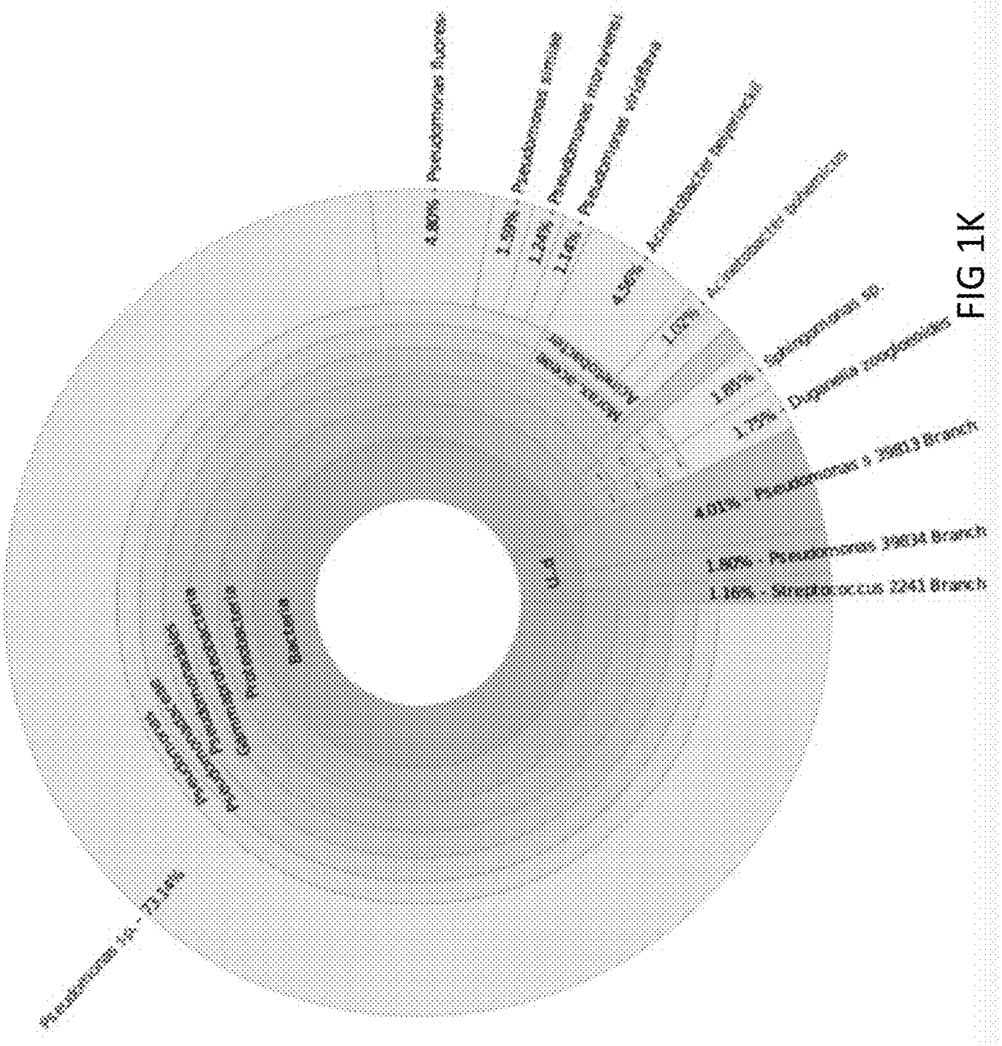
FIG. 1K shows bacterial diversity in crisp red gem lettuce.

FIG. 1K shows bacterial diversity in crisp red gem lettuce. Dominance by *Pseudomonas* species covering 73% of the bacterial diversity, on which *P. fluorescens* comprises 5% of bacterial diversity.

Figure 1L:
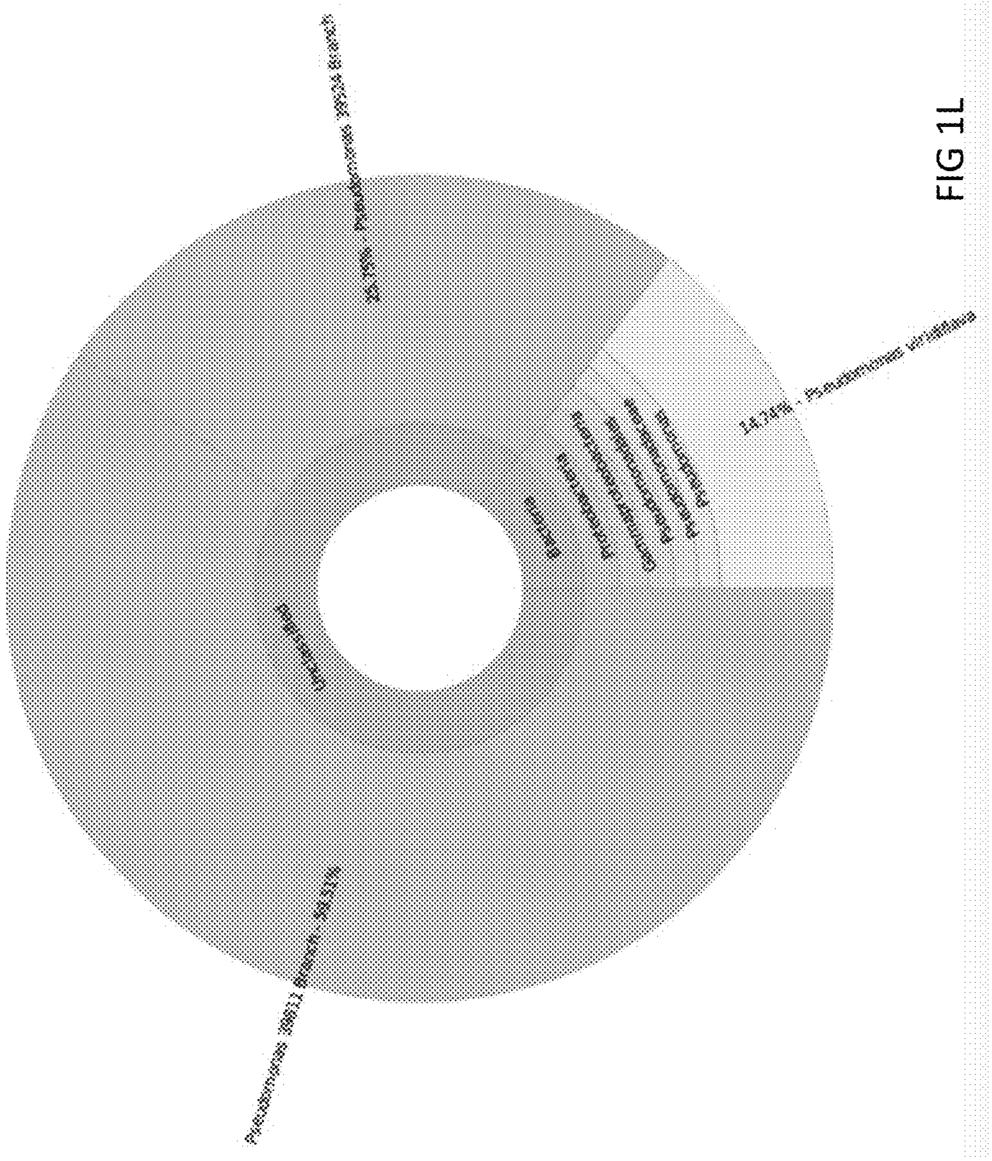
FIG. 1L shows bacterial diversity in broccoli juice.

FIG. 1L shows bacterial diversity in broccoli juice. The sample is absolutely dominated by three varieties of *Pseudomonas.*

Figure 2A:
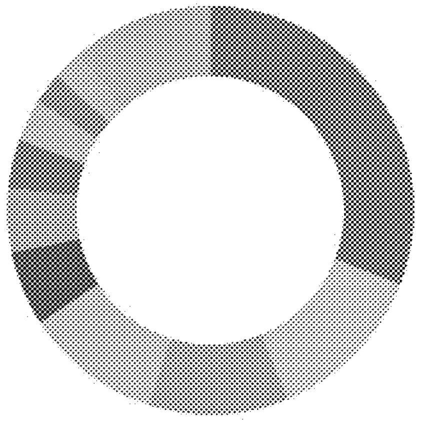
FIG. 2 A-C show graphs depicting the taxonomic composition of microbial samples taken from Broccoli Heads (FIG. 2A), Blueberries (FIG. 2B), and Pickled Green Olives (FIG. 2C).

FIG. 2 shows taxonomic composition of blueberries, pickled olives and broccoli head. More specifically, FIG. 2A shows taxonomic composition of broccoli head showing a diversity of fungi and bacteria distinct from the broccoli juice dominated by few *Pseudomonas* species.

Figure 2C:
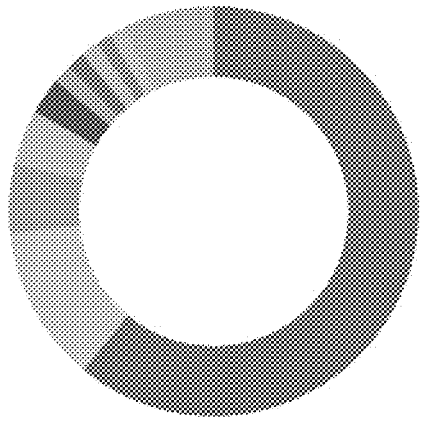

FIG. 2C shows taxonomic composition of blueberries.

FIG. 2C shows taxonomic composition of pickled olives showing a variety of lactic acid bacteria present and dominant. Some of the species are recognized as probiotics.

Figure 3A:
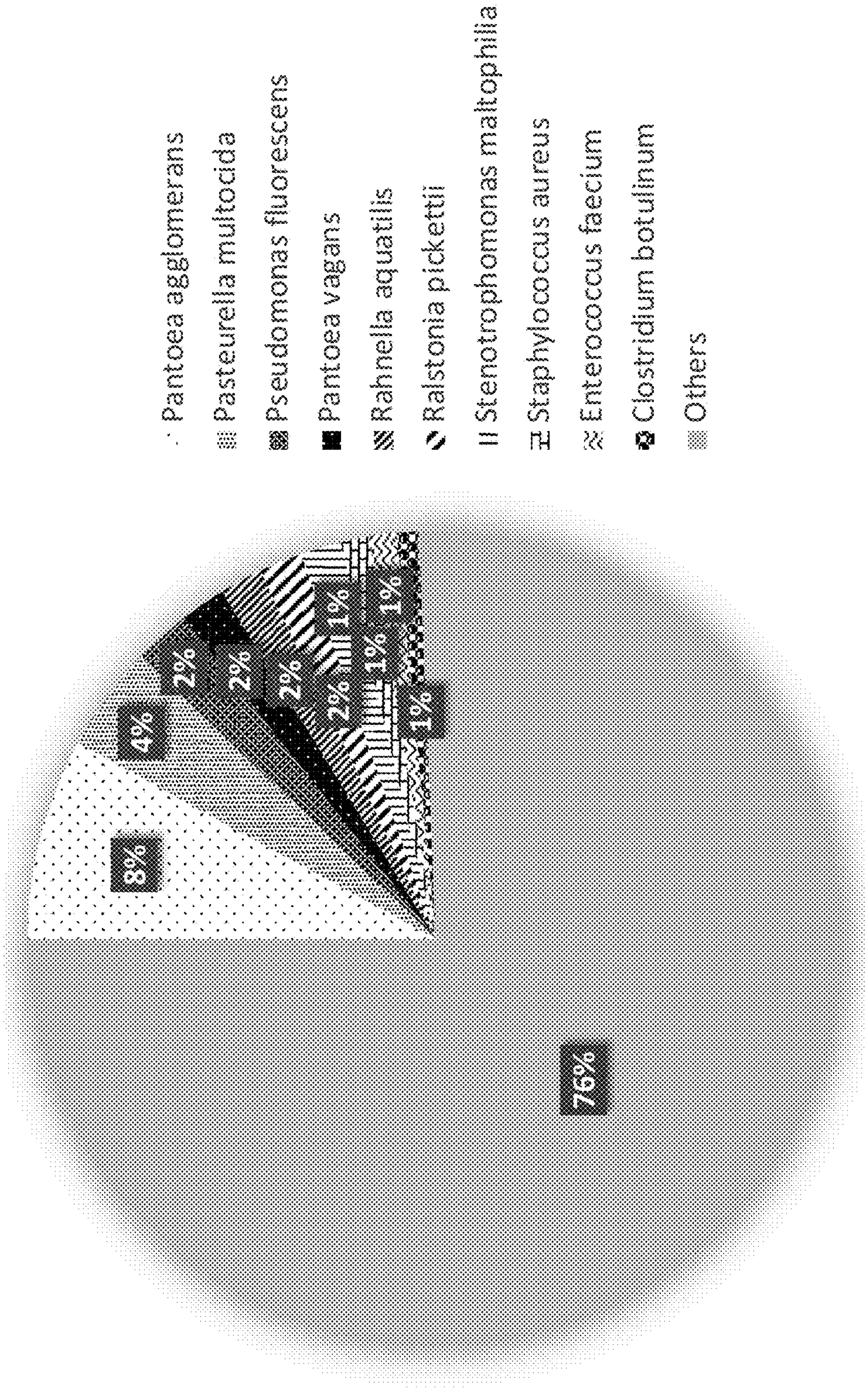
FIG. 3A shows taxonomic composition of *ginseng*. There is a relatively high diversity represented in this sample with members of *Pseudomonas, Pantoea*, and *Stenotrophomonas*.

FIG. 3A shows taxonomic composition of *ginseng*. There is a relatively high diversity represented in this sample with members of *Pseudomonas, Pantoea*, and *Stenotrophomonas.*

Figure 3B:
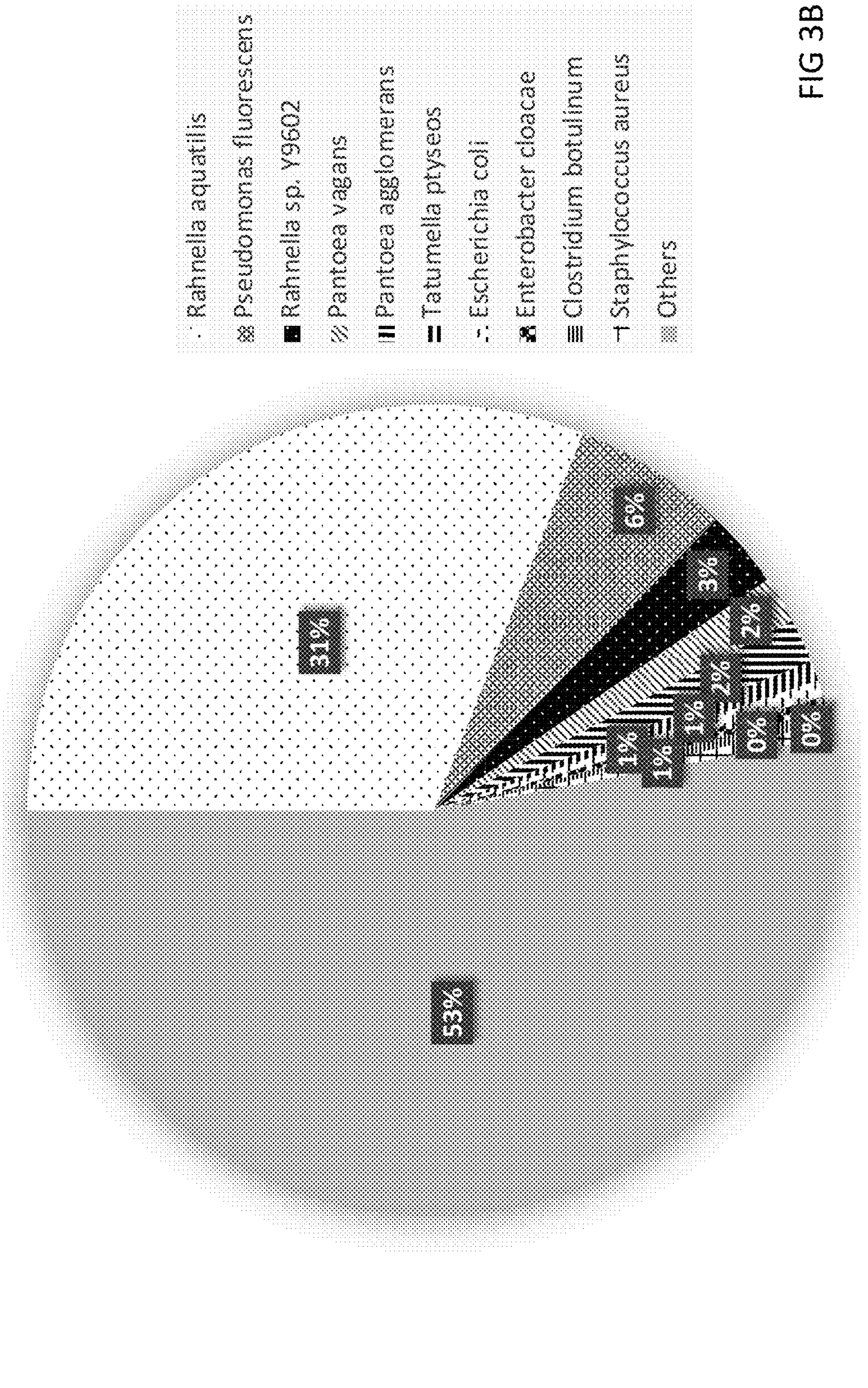
FIG. 3B shows taxonomic composition of blackberries. The most abundant member is *Rahnella aquatilis* covering 31% of total composition.

FIG. 3B shows taxonomic composition of blackberries. The most abundant member is *Rahnella aquatilis* covering 31% of total composition.

Figure 3C:
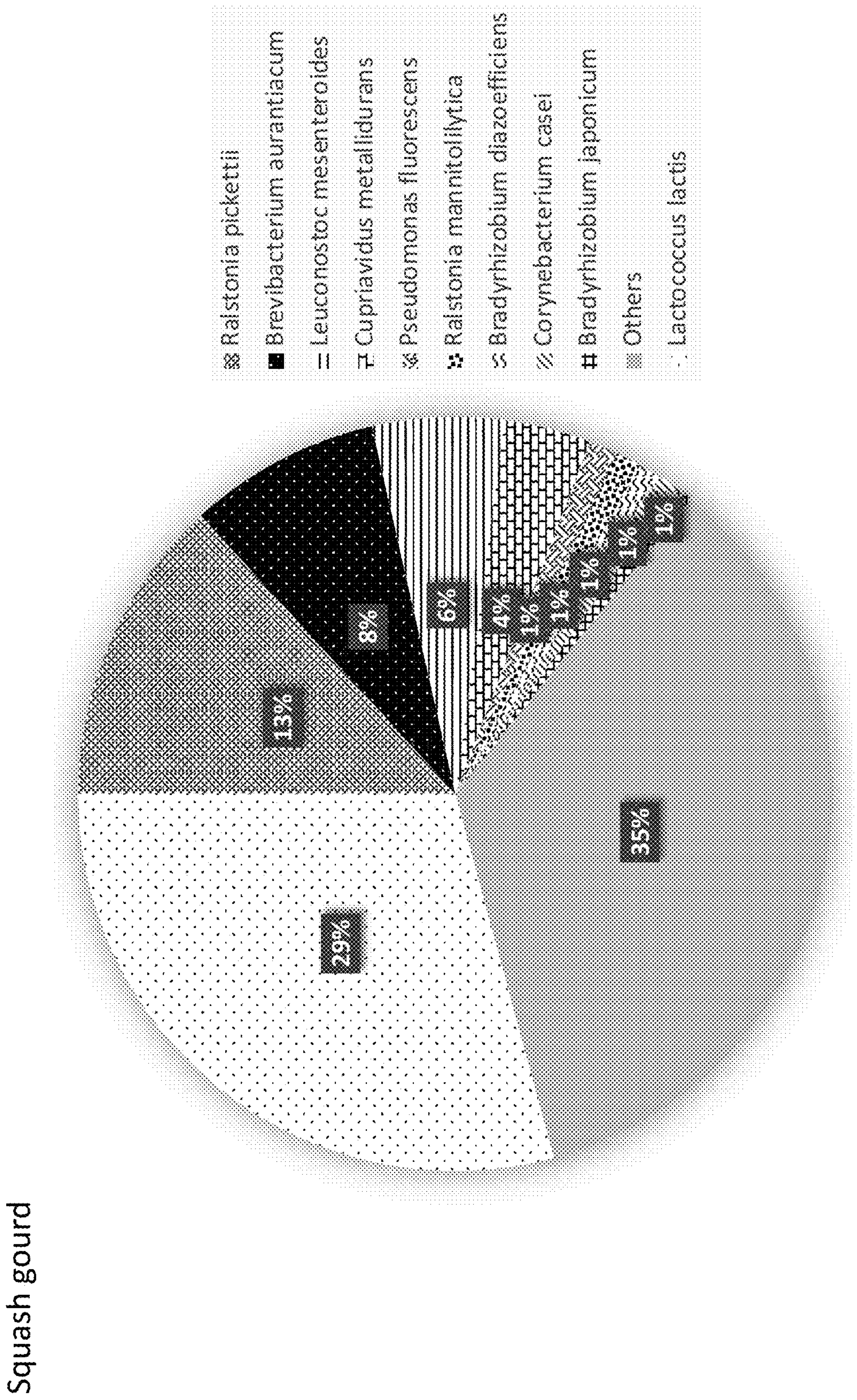
FIG. 3C shows taxonomic composition of squash gourd. The sample is dominated by *Lactococcus lactis* covering 59% of total composition but also *Leuconostoc mesenteroides* was present at 3.3% of the bacterial population.

FIG. 3C shows taxonomic composition of squash gourd. The sample is dominated by *Lactococcus lactis* covering 59% of total composition but also *Leuconostoc mesenteroides* was present at 3.3% of the bacterial population.

Figure 3D:
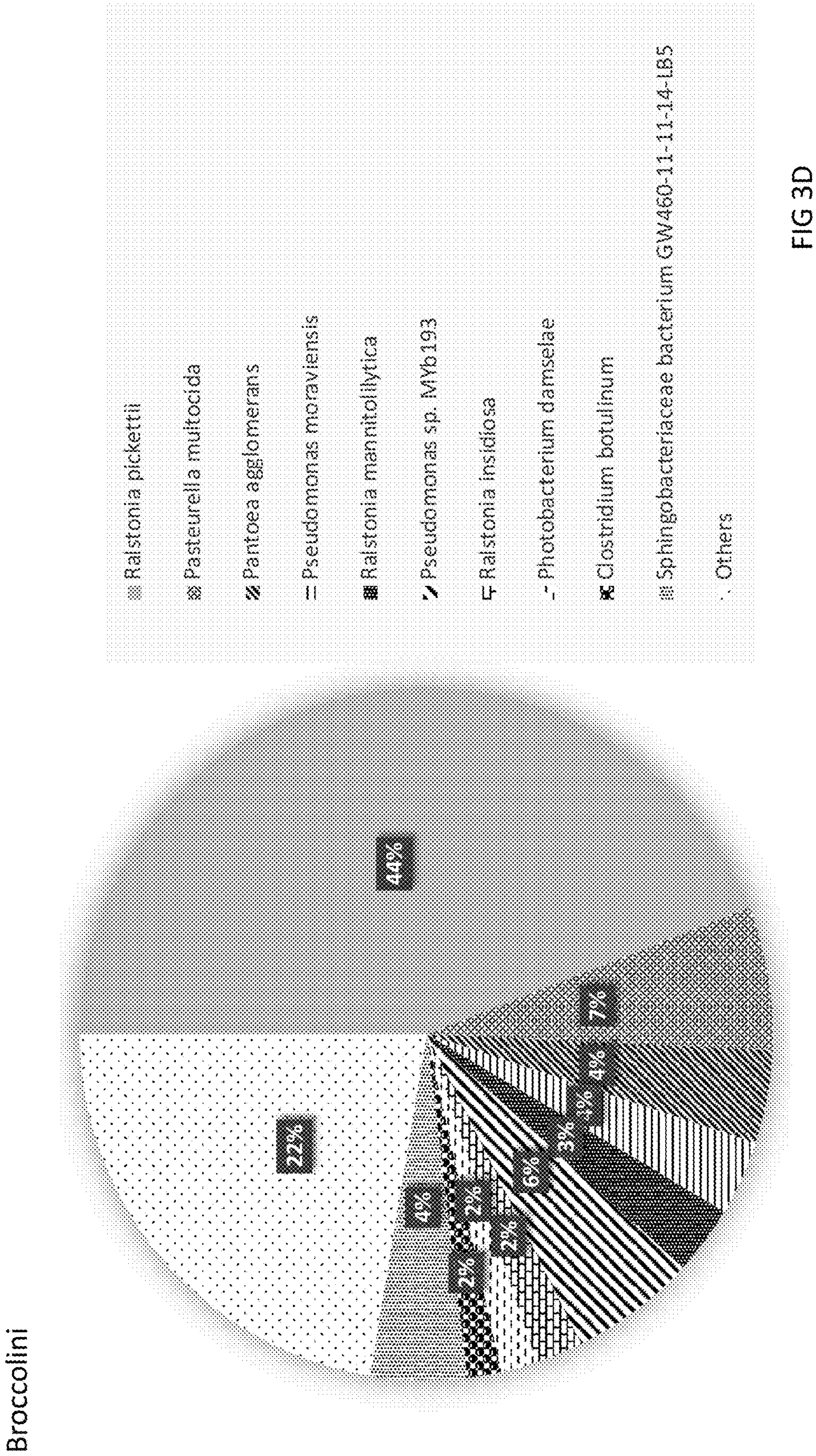
FIG. 3D shows taxonomic composition of broccolini. *Ralstonia pickettii* covers 44% of entire bacterial community.

FIG. 3D shows taxonomic composition of broccolini. *Ralstonia pickettii* covers 44% of entire bacterial community.

Figure 3E:
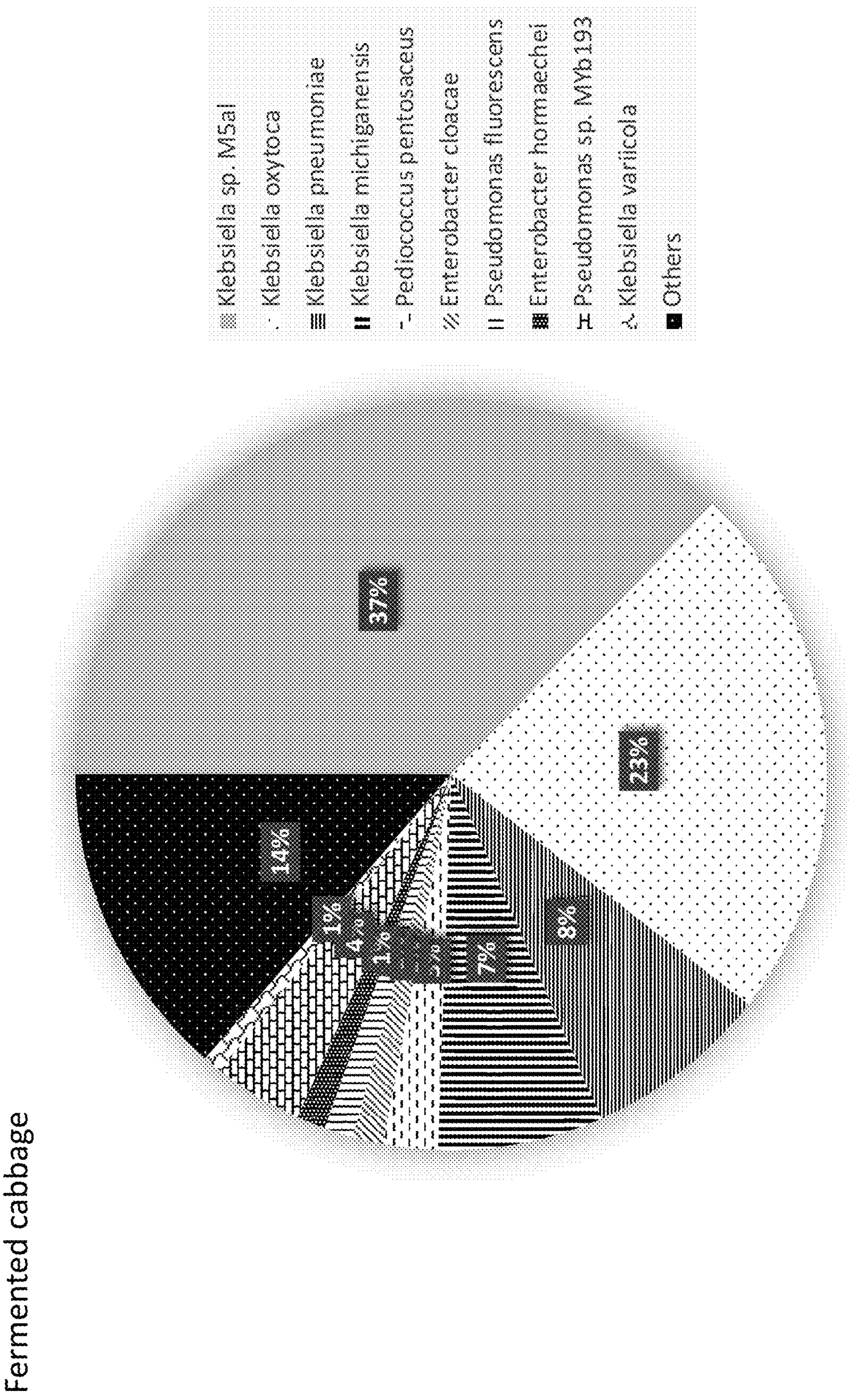
FIG. 3E shows taxonomic composition of fermented cabbage. It contained *Pediococcus pentosaceus* as well as dominant gamma proteobacteria.

FIG. 3E shows taxonomic composition of fermented cabbage. It contained *Pediococcus pentosaceus* as well as dominant gamma proteobacteria.

Figure 3F:
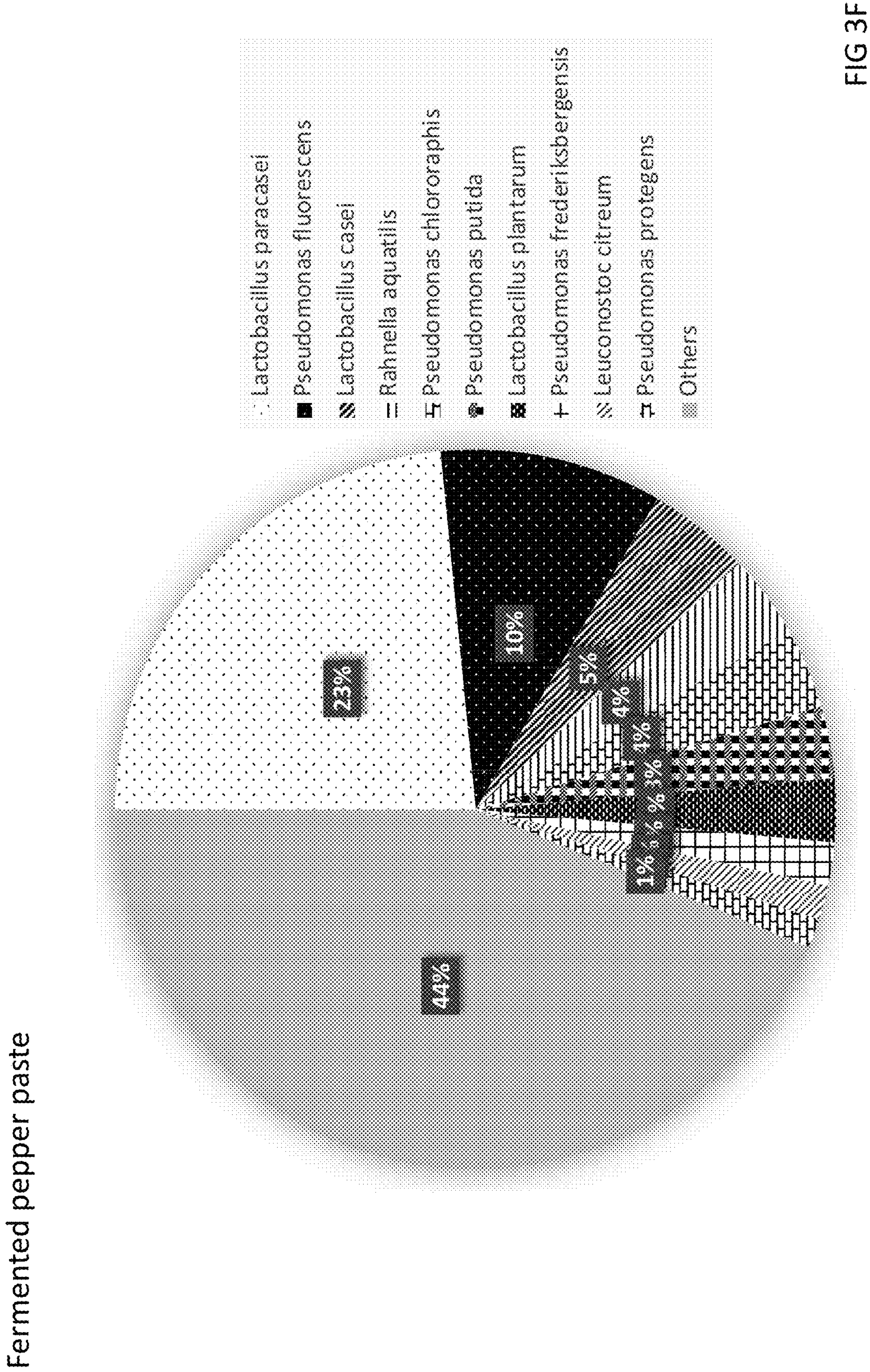
FIG. 3F shows taxonomic composition of fermented pepper paste. The sample enriched many lactic acid bacteria such as *Lactobacillus paracasei, Lactobacillus casei* and *Lactobacillus plantarum.*
Figure 4:
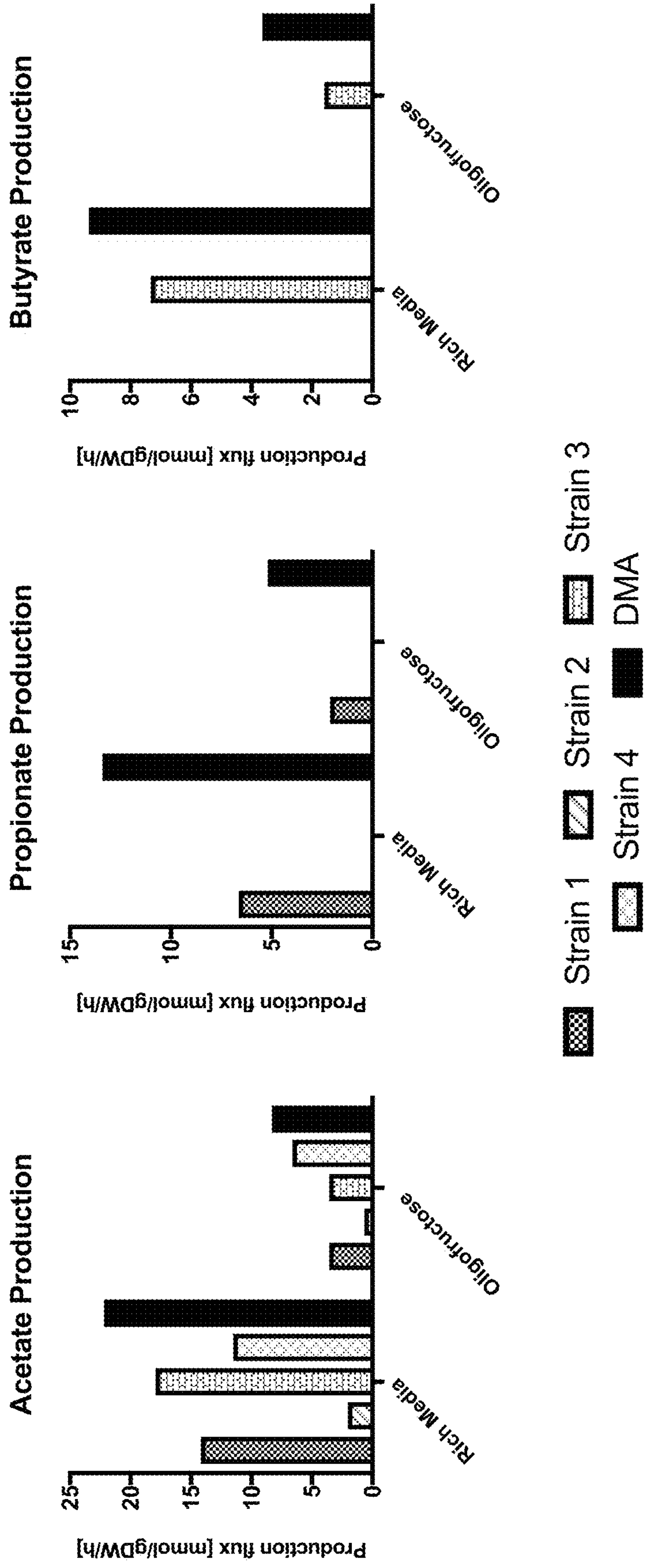
FIG. 4 shows fermentative rates by sample microbes alone or as a community under various conditions in silico. Four microbes were tested in silico for their ability to produce (A) Acetate, (B) Propionate, or (C) Butyrate under rich media or oligofructose conditions alone or as an assembled community.
Figure 5:
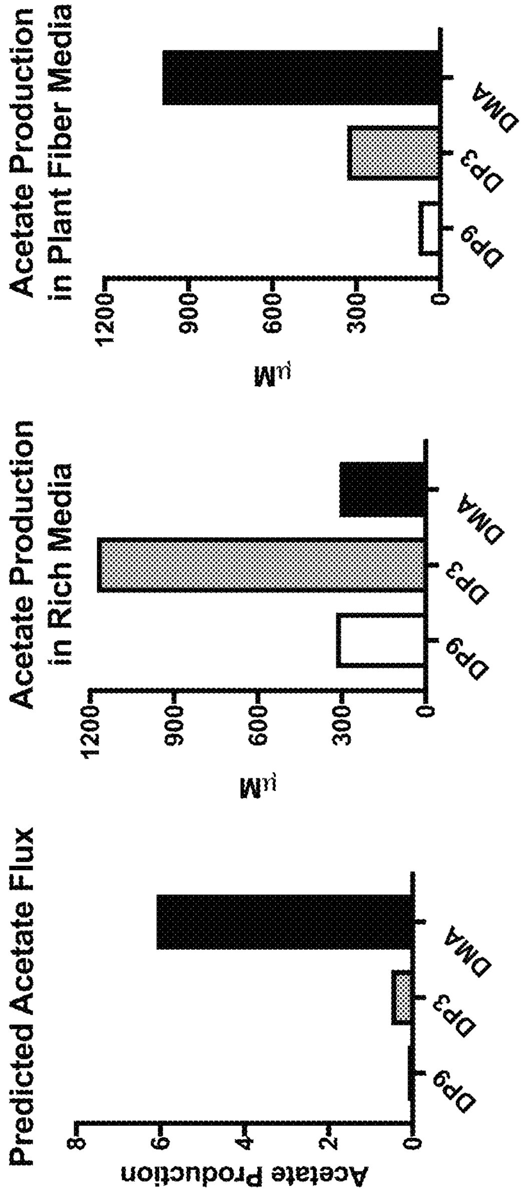
FIG. 5 shows DMA experimental validation for a combination of strains DP3 and DP9 under nutrient replete and plant fiber media showing that the strains show synergy for increased SCFA production only under plant fiber media but not under rich media.
Figure 6:
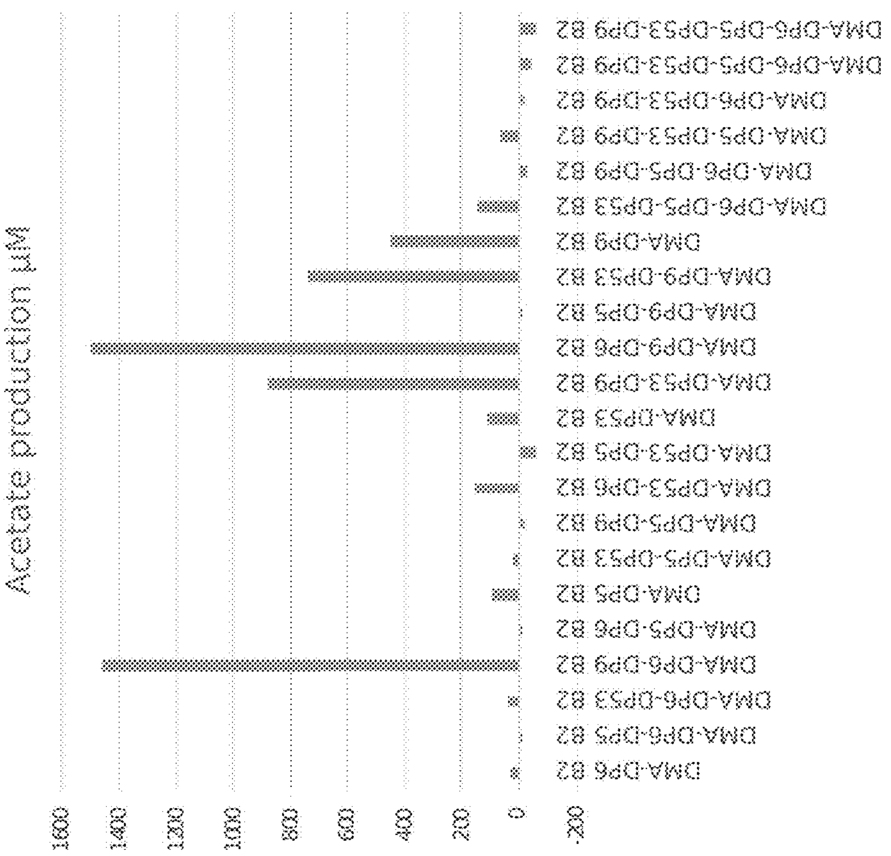
FIG. 6 shows synergistic acetate production for 4 strains tested as singles, pairs or trios. Cells were grown on blueberry extract media for 4 days in a 24 well plate at 300 RPM and 22° C. The pairs in this experiment were run in duplicate. Spent culture broth was extracted with ethyl acetate and analyzed by gas chromatography with a flame ionization detector (GC-FID) and acetate concentrations measured with a standard curve done in sterile media. The strain DP6 does not produce acetate, while strain DP9 produces 448 uM, and when the 2 are grown together the acetate production is 1500 uM and 1457 uM for both duplicate cultures respectively. This indicates the acetate increased by adding strain DP6 to DP9.
Figure 7:
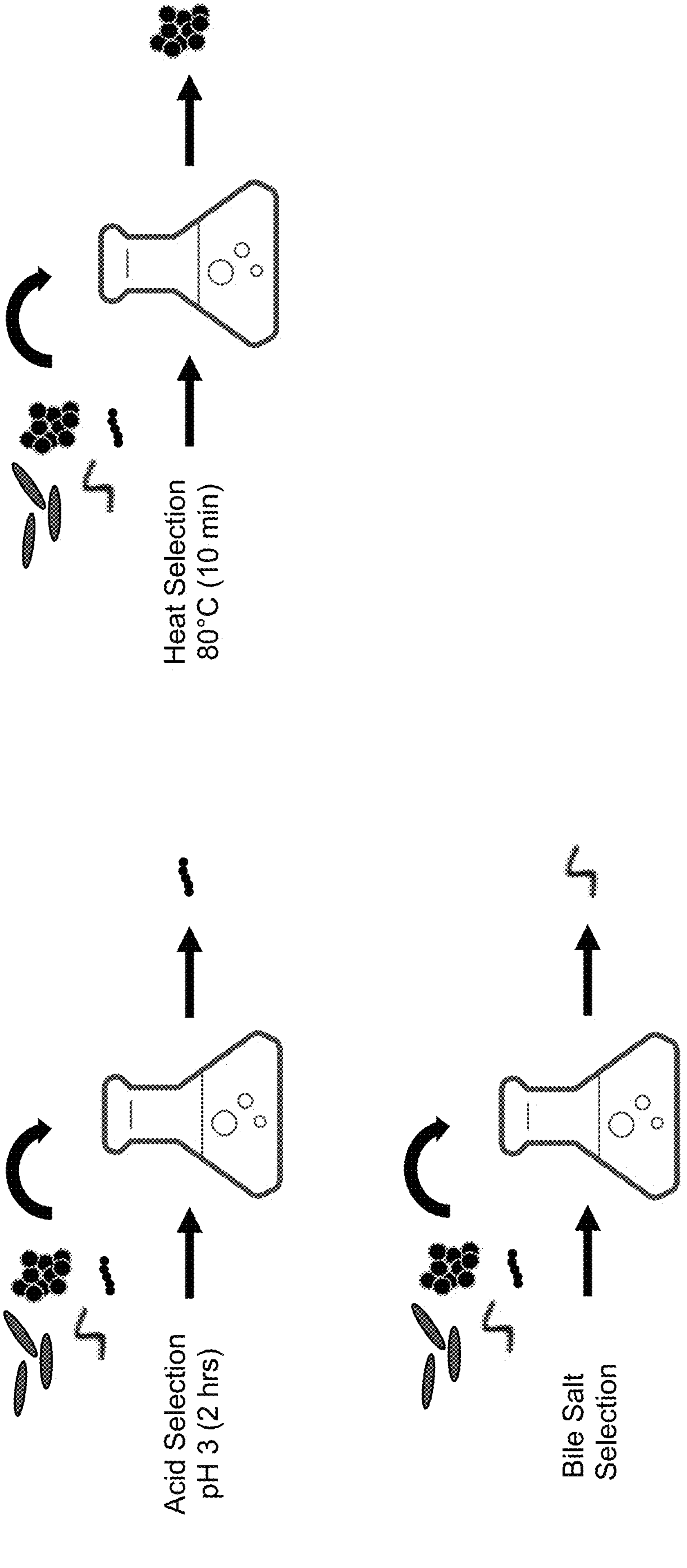
FIG. 7 shows a schematic describing a gut simulator experiment. The experiment comprises an in vitro, system that mimics various sections of the gastrointestinal tract. Isolates of interest are incubated in the presence of conditions that mimic particular stresses in the gastro-intestinal tract (such as low pH or bile salts), heat shock, or metformin. After incubation, surviving populations are recovered. Utilizing this system, the impact of various oral anti-diabetic therapies alone or in combination with probiotic cocktails of interest on the microbial ecosystem can be tested.
Figure 8:
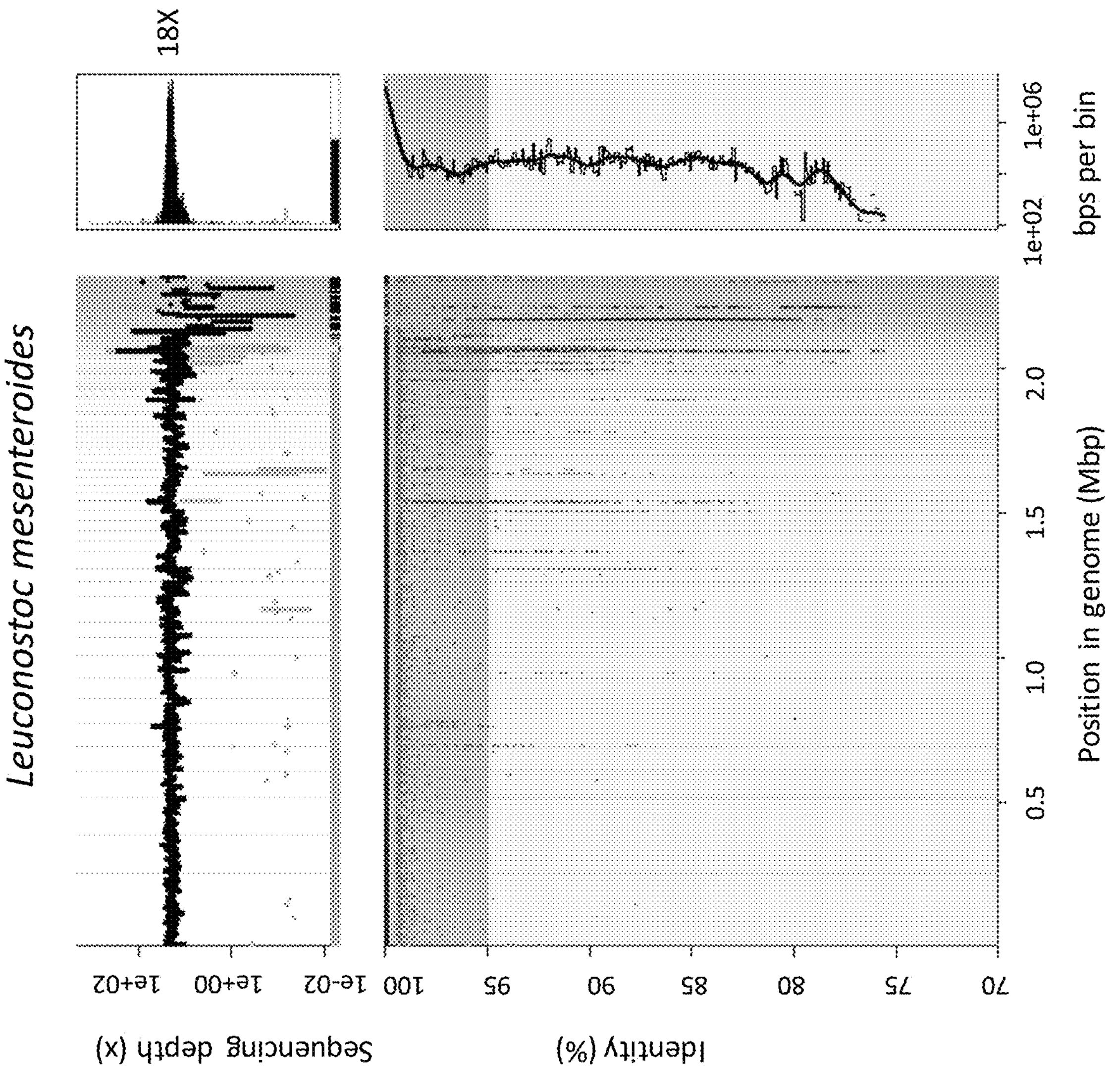
FIG. 8 shows a fragment recruitment plot sample for the shotgun sequencing on sample 22 (fermented cabbage) comparing to the reference genome of strain DP3 *Leuconostoc mesenteroides*-like and the 18× coverage indicating the isolated strain was represented in the environmental sample and it was largely genetically homogeneous.
Figure 9:
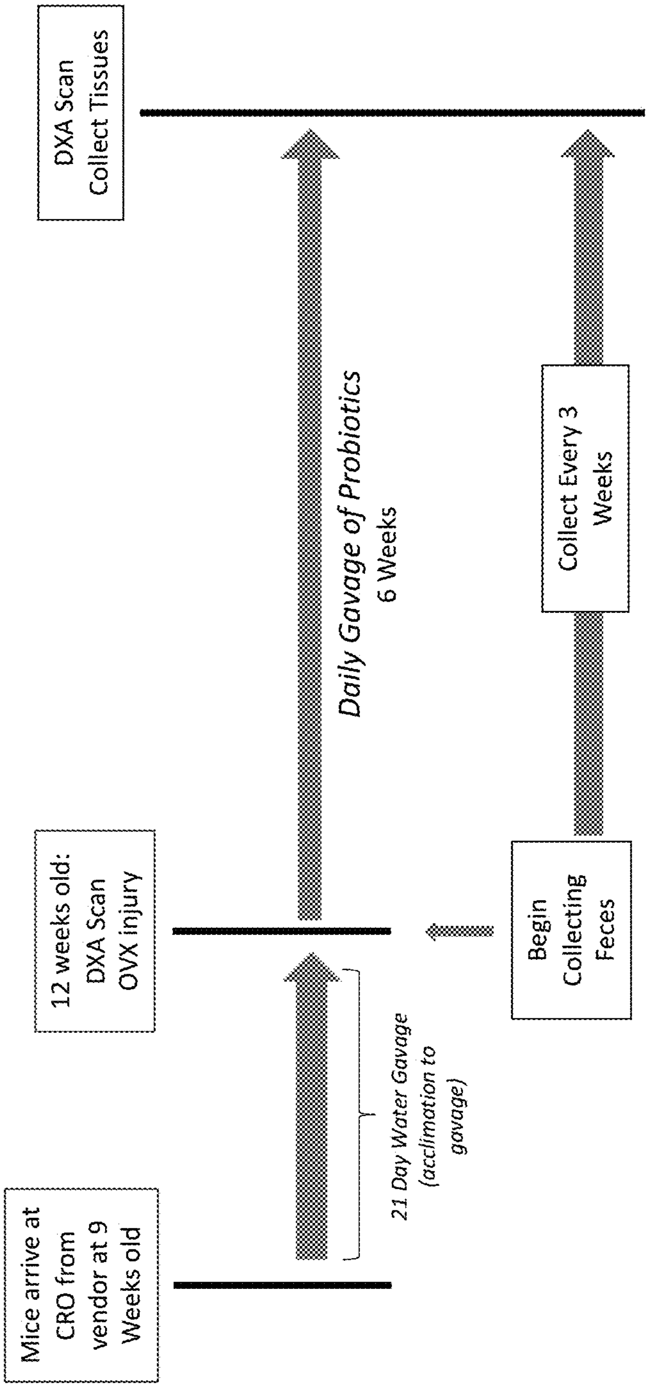
FIG. 9 shows a schematic detailing the experimental procedure for a pre-clinical model testing the disclosed invention. The experimental design is as follows: Candidate DMAs were evaluated for their therapeutic efficacy in an ovariectomized (OVX) mouse model of postmenopausal osteoporosis. All mice were group housed with 5 mice per cage in individually ventilated cages (IVCs) specifically designed for germ free husbandry [59, 60]. At 12-weeks of age, mice were weighed, had baseline feces collected, and underwent OVX (N=20) or sham (N=10) surgery to deplete estrogen levels and commence the bone resorption process as previously described [61]. 1-day post-surgery, mice were randomly divided into experimental groups and mice began a daily oral gavage regimen (200 uL) of saline (negative control), or SBD111 and continued for 6-weeks. Fecal samples were collected every 3 weeks to monitor the composition of the gut microbiome over time. On the last day of the study, mice received a DXA scan to evaluate systemic BMD, followed by euthanasia and collection of uterine weights, serum, cecal material, lumbar spine and femurs for downstream analysis.
Figure 10:
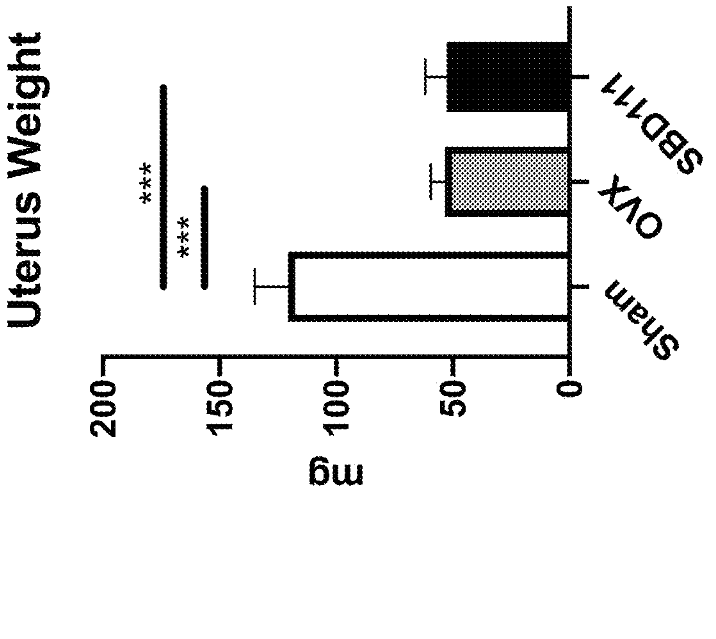
FIG. 10. Shows ovary weights taken from ovariectomized and sham-treated mice. Ovariectomized (OVX) mice were treated with either water (OVX) or DMA SBD111 for six-weeks post-surgery. At sacrifice, the uterus from each animal was removed and weighed. Uterus measurements were also taken from sham-treated mice. Decreased uterus weight in OVX and SBD111 treated animals indicates successful ovariectomy. Significant differences between groups in A were identified via 1-way ANOVA with a Tukey multiple comparison post-test (*$P<0.05$, $P<0.01$ *$P<0.001$, ****$P<0.0001$)

FIG. 3F shows taxonomic composition of fermented pepper paste. The sample enriched many lactic acid bacteria such as *Lactobacillus paracasei, Lactobacillus casei* and *Lactobacillus plantarum.*

Example 2: In Silico Modeling Outputs for Different Assemblages and DMA Formulation To generate in silico predictions for the effect of different microbial assemblages with a human host a genome-wide metabolic analysis was performed with formulated microbial communities selected from the Agora collection (Magbustoddir et al. 2016) and augmented with the genomes of bacterial members detected in the present survey. These simulations predict the "fermentative power" of each assemblage when simulated under different nutritional regimes including relatively high carbon availability (carbon replete) or carbon limited conditions when using plant fibers such as inulin, oligofructose and others as carbon source.

The method used for DNA sequencing the sample-associated microbiomes enabled to search for genes detected in the different vegetables related to propionate, butyrate, acetate and bile salt metabolism. This was done by mapping the reads obtained in the samples to reference genes selected for their intermediate role in the synthesis or degradation of these metabolites. There were organisms present in some of the 15 analyzed samples that matched the target pathways indicating their metabolic potential to produce desirable metabolites. Table 6a shows Metabolites in samples.

TABLE 6a

Metabolites in samples.

| NAME OF ENZYME | ASSOCIATED METABOLITE | GENE SYMBOL | PATHWAY | E.C. NUMBER | COMMENTS |
|---|---|---|---|---|---|
| ACETOLACTATE SYNTHASE I | (S)-2-ACETOLACTATE | | BUTANOATE METABOLISM | 2.2.1.6 | BUTYRATE PRODUCTION |
| ACETATE KINASE | PROPIONATE | ACKA | PROPANOATE METABOLISM | 2.7.2.1 | PROPIONATE |
| ACETYL-COA SYNTHETASE | PROPIONATE | AACS | PROPANOATE METABOLISM | 6.2.1.1 | PROPIONATE |
| ACETYL-COA HYDROLASE | ACETATE | | PYRUVATE METABOLISM | 3.1.2.1 | ACETATE |
| BILE SALT TRANSPORTER | BILE SALTS | ACR3 | BILE SALT TRANSPORT | | BILE SALT TOLERANCE |

amount of SCFA when grown together and when exposed to substrates such as plant fibers.

To illustrate this process, a set of 40 bacterial and fungal strains were isolated from food sources and their genomes were sequenced. The assembled and annotated genomes were then used to formulate in silico assemblages considering the human host as one of the metabolic members. Assuming a diet composed of lipids, different carbohydrates and proteins the metabolic fluxes were predicted using an unconstrained model comparing the individual strain production of acetate, propionate and butyrate and compared to the metabolic fluxes with the assemblage.

In the first model, 4 strains were combined into a DMA. Strains 1-4 are predicted to produce acetate as single cultures but the combination into a DMA predicts the flux will increase when modeled on replete media and the flux decreases when modeled on plant fibers. Strain 4 is predicted to utilize the fibers better than the other 3 to produce acetate. Strain 1 is the only member of the assemblage predicted to produce propionate and when modeled with the other 3 strains the predicted flux doubles in replete media and quadruples in the fiber media illustrating the potential metabolic synergy from the assemblage. Strain 3 is the only member of the assemblage predicted to produce butyrate and when modeled with the other 3 strains the predicted flux increase slightly in replete media and doubled in the fiber media illustrating the potential metabolic synergy from the assemblage.

TABLE 6b

Strains from first DMA model.

| | |
|---|---|
| Strain 1 | DP6 *Bacillus cereus*-like |
| Strain 2 | DP9 *Pediococcus pentosaceus*-like |
| Strain 3 | *Clostridium butyricum* DSM 10702 |
| Strain 4 | DP1 *Pseudomonas fluorescens*-like |

Substrate availability plays an important role in the establishment of synergistic interactions. Carbon limitation in presence of plant fibers favors fiber depolymerization and fermentation to produce SCFA. Conversely, carbon replete conditions will prevent the establishment of synergistic metabolism to degrade fibers as it is not favored thermodynamically when the energy available from simple sugars is available. To illustrate this, a DMA was formulated containing two strains of lactic acid bacteria and run a metabolic prediction assuming a limited media with plant fibers. According to the model, *Leuconostoc* predicted flux is higher than *Pediococcus* and the DMA flux increases five times on the combined strains. When tested in the lab and DMA Formulation Microbes in nature interact with multiple other groups and form consortia that work in synergy exchanging metabolic products and substrates resulting in thermodynamically favorable reactions as compared to the individual metabolism. For example, in the human colon, the process for plant fiber depolymerization, digestion and fermentation into butyrate is achieved by multiple metabolic groups working in concert. This metabolic synergy is reproduced in the DMA concept where strains are selected to be combined based on their ability to synergize to produce an increased measured by gas chromatography, the acetate production increases 3 times compared to the single strains. However, when grown on carbon replete media with available simple sugars, acetate production is correspondingly higher compared to the plant fiber media but there is no benefit of synergistic acetate production when the two strains are grown together into a DMA.

In addition to acetate, propionate, and butyrate some strains produce other isomers. For example, strain DP1 related to *P. fluorescens* and DP5 related to *Debaromyces hansenii* (yeast) produce isobutyrate when grown in carbon-replete media as single strains, however there is metabolic synergy when tested together as DMA measured as an increase in the isobutyric acid production.

To describe experimentally the process of DMA validation the following method is applied to find other candidates applicable to other products:

1. Define a suitable habitat where microbes are with the desirable attributes are abundant based on ecological hypotheses. For example, fresh vegetables are known to have anti-inflammatory effects when consumed in a whole-food plant-based diet, and therefore, it is likely they harbor microbes that can colonize the human gut.
2. Apply a selection filter to isolate and characterize only those microbes capable of a relevant gut function. For example, tolerate acid shock, bile salts and low oxygen. In addition, strains need to be compatible with target therapeutic drugs including but not limited to bisphosphonates (alendronate, risedronate, ibandronate, zolendronate), biologics (denosumab, romosozumab), selective estrogen receptor mediators (Raloxifene), or anabolic agents (teriparatide, abaloparatide).
3. Selected strains are then cultivated in vitro and their genomes sequenced at 100× coverage to assemble, annotate and use in predictive genome-wide metabolic models.
4. Metabolic fluxes are generated with unconstrained models that consider multiple strains and the human host to determine the synergistic effects from multiple strains when it is assumed, they are co-cultured under simulated substrate conditions.
5. Predicted synergistic combinations are then tested in the laboratory for validation. Single strains are grown to produce a biomass and the spent growth media removed after reaching late log phase. The washed cells are then combined in Defined Microbial Assemblages with 2-10 different strains per DMA and incubated using a culture media with plant fibers as substrates to produce short chain fatty acids to promote gut health.
6. The DMAs are then analyzed by gas chromatography to quantify the short chain fatty acid production where the synergistic effect produces an increased production in the combined assemblage as compared to the individual contributions.

Example 3: Gut Simulation Experiments

The experiment comprises an in vitro, system that mimics various sections of the gastrointestinal tract. Isolates of interest are incubated in the presence of conditions that mimic particular stresses in the gastro-intestinal tract (such as low pH or bile salts), or heat shock. After incubation, surviving populations are recovered. Utilizing this system, the impact of various oral anti-diabetic therapies alone or in combination with probiotic cocktails of interest on the microbial ecosystem can be tested. Representative isolates are shown in Table 7.

TABLE 7

| Strains | | | | | |
|---|---|---|---|---|---|
| Strain Number | Heat Shock | Isolation Temperature | Acid Shock (pH 3; 2 hr) | Genus | Species |
| DP1 | No | 25 | No | *Pseudomonas* | *fluorescens* |
| DP2 | No | 37 | No | *Hanseniaspora* | *occidentalis* |
| DP3 | No | 25 | No | *Leuconostoc* | *mesenteroides* |
| DP4 | No | 25 | No | *Aureobasidium* | *pullulans* |
| DP5 | No | 37 | No | *Debaromyces* | *hansenii* |
| DP6 | Yes | 25 | No | *Bacillus* | *wiedmannii* |
| DP7 | No | 25 | No | *Pichia* | *fermentans* |
| DP8 | No | 25 | No | *Hanseniaspora* | *opuntiae* |
| DP9 | No | 25 | No | *Pediococcus* | *pentosaceus* |
| DP10 | Yes | 25 | No | *Bacillus* | *velezensis* |
| DP11 | No | 25 | No | *Pseudomonas* | *putida* |
| DP12 | No | 25 | Yes | *Microbacterium* | sp. |
| DP13 | No | 25 | Yes | *Bacillus* | *mycoides* |
| DP14 | No | 25 | Yes | *Arthrobacter* | *luteolus* |
| DP15 | No | 25 | No | *Curtobacterium* | sp. |
| DP16 | No | 25 | No | *Lacihabitans* | *lacunae* |
| DP17 | No | 25 | No | *Rahnella* | *aquatilis* |
| DP18 | No | 25 | No | *Pseudomonas* | sp. |
| DP19 | No | 25 | No | *Curtobacterium* | *pusilium* |
| DP20 | No | 25 | No | *Stenotrophomonas* | *rhizophila* |
| DP22 | No | 25 | No | *Rahnella* | sp. |
| DP23 | No | 25 | No | *Erwinia* | *billingiae* |
| DP24 | No | 25 | No | *Filobasidium* | *globisporum* |
| DP25 | No | 25 | No | *Penicillium* | *solitum* |
| DP26 | No | 25 | No | *Methylobacterium* | sp. |
| DP27 | No | 25 | No | *Sphingomonas* | sp. |
| DP28 | No | 25 | Yes | *Aureobasidium* | *pullulans* |
| DP29 | No | 25 | Yes | *Pseudoclavibacter* | *helvolus* |
| DP30 | No | 25 | Yes | *Microbacterium* | *testaceum* |
| DP31 | No | 25 | Yes | *Sporisorium* | *reilianum* |
| DP32 | No | 25 | No | *Hafnia* | *paralvei* |
| DP33 | No | 25 | No | *Erwinia* | *persicinus* |

TABLE 7-continued

| Strains | | | | | |
|---|---|---|---|---|---|
| Strain Number | Heat Shock | Isolation Temperature | Acid Shock (pH 3; 2 hr) | Genus | Species |
| DP34 | No | 25 | Yes | *Plantibacter* | *flavus* |
| DP35 | No | 25 | Yes | *Pantoea* | *ananatis* |
| DP36 | No | 25 | Yes | *Pantoea* | *vagans* |
| DP37 | No | 25 | No | *Pseudomonas* | *rhodesiae* |
| DP38 | No | 25 | No | *Rhodococcus* | sp. |
| DP39 | No | 25 | No | *Agrobacterium* | *tumefaciens* |
| DP40 | No | 37 | No | *Pantoea* | sp. |
| DP41 | Yes | 37 | No | *Corynebacterium* | *mucifaciens* |
| DP42 | No | 37 | No | *Pseudomonas* | *lundensis* |
| DP43 | No | 25 | No | *Janthinobacterium* | sp. |
| DP44 | No | 25 | No | *Herbaspirillum* | sp. |
| DP45 | No | 25 | No | *Sanguibacter* | *keddieii* |
| DP46 | No | 25 | Yes | *Pantoea* | *agglomerans* |
| DP47 | No | 25 | Yes | *Cronobacter* | *dublinensis* |
| DP48 | Yes | 25 | No | *Bacillus* | *paralicheniformis* |
| DP49 | Yes | 25 | No | *Bacillus* | *gibsonii* |
| DP50 | No | 25 | No | *Enterobacter* | sp. |
| DP51 | No | 25 | No | *Klebsiella* | *aerogenes* |
| DP52 | No | 25 | No | *Arthrobacter* | sp. |
| DP53 | No | 25 | No | *Pseudomonas* | *fragi* |
| DP54 | No | 25 | No | *Methylobacterium* | *adhaesivum* |
| DP55 | Yes | 25 | No | *Bacillus* | *megaterium* |
| DP56 | Yes | 25 | No | *Paenibacillus* | *lautus* |
| DP57 | Yes | 25 | No | *Bacillus* | *mycoides* |
| DP58 | No | 25 | No | *Janthinobacterium* | *svalbardensis* |
| DP59 | No | 25 | No | *Kosakonia* | *cowanii* |
| DP60 | Yes | 25 | No | *Bacillus* | *simplex* |
| DP61 | No | 25 | No | *Lelliottia* | sp. |
| DP62 | No | 25 | No | *Erwinia* | sp. |
| DP63 | No | 25 | Yes | *Pseudomonas* | *azotoformans* |
| DP64 | No | 25 | No | *Hanseniaspora* | *uvarum* |
| DP65 | No | 25 | No | *Bacillus* | sp. |
| DP66 | No | 25 | No | *Hanseniaspora* | *occidentalis* |
| DP67 | Yes | 25 | No | *Bacillus* | sp. |
| DP68 | Yes | 25 | No | *Bacillus* | *atrophaeus* |
| DP69 | Yes | 25 | No | *Bacillus* | sp. |
| DP70 | No | 25 | No | *Bacillus* | *subtilis* |
| DP71 | No | 25 | No | *Rhodotorula* | sp. |
| DP72 | Yes | 25 | No | *Bacillus* | *zhangzhouensis* |
| DP73 | Yes | 37 | No | *Bacillus* | *clausii* |
| DP74 | Yes | 25 | No | *Bacillus* | *coagulans* |
| DP75 | No | 37 | No | *Pseudomonas* | *gessardii* |
| DP76 | No | 25 | No | *Ochrobactrum* | sp. |
| DP77 | Yes | 25 | No | *Bacillus* | *aryabhattai* |
| DP78 | No | 25 | No | *Erwinia* | *rhapontici* |
| DP79 | No | 25 | No | *Pseudomonas* | *fragi* |
| DP80 | No | 25 | No | *Methylobacterium* | *adhaesivum* |
| DP81 | Yes | 37 | No | *Bacillus* | *clausii* |
| DP82 | Yes | 37 | No | *Bacillus* | *clausii* |
| DP83 | Yes | 37 | No | *Bacillus* | *clausii* |
| DP84 | No | 25 | No | *Microbacterium* | sp. |
| DP85 | No | 30 | No | *Methanolacinia* | *petrolearia* |
| DP86 | No | 30 | No | *Bacillus* | *velezensis* |
| DP87 | No | 30 | No | *Lactobacillus* | *plantarum* |
| DP88 | No | 30 | No | *Bacillus* | *velezensis* |
| DP89 | No | 30 | No | *Bacillus* | *subtilis* |
| DP90 | No | 30 | No | *Lactobacillus* | *plantarum* |
| DP92 | No | 30 | No | *Bacillus* | *subtilis* |
| DP93 | No | 30 | No | *Leuconostoc* | *mesenteroides* |
| DP94 | No | 30 | No | *Lactobacillus* | *brevis* |
| DP95 | No | 30 | No | *Lactobacillus* | *paracasei* |
| DP96 | No | 30 | No | *Lactobacillus* | *casei* |
| DP97 | No | 30 | No | *Lactococcus* | *garvieae* |
| DP98 | No | 30 | No | *Lactococcus* | *garvieae* |
| DP100 | No | 30 | No | *Lactobacillus* | *plantarum* |
| DP101 | No | 30 | No | *Pediococcus* | *pentosaceus* |
| DP102 | No | 30 | No | *Pichia* | *krudriazevii* |

Example 4: Computation of Microbial Average Nucleotide Identity (ANI)

A whole-genome based method was applied, known as the average nucleotide identity (ANI), to estimate the genetic relatedness among bacterial genomes and profile hundreds of microbial species at a higher resolution taxonomic level (i.e., species- and strain-level classification). ANI is based on the average of the nucleotide identity of all orthologous genes shared between a genome pair. Genomes of the same species present ANI values above 95% and of the same genus values above 80% (Jain et al. 2018).

Taxonomic annotation of the strains combined into DMAs using ANI and the NCBI RefSeq database indicated that these microbes represent species not present in the database and most likely are new bacterial species even when the nucleotide identity based on the 16S rRNA gene is 99%:

TABLE 8

Comparative predictive power of 16S rRNA sequence analysis and Average Nucleotide Identity (ANI) analysis. While 16S rRNA sequence percentage indicates a high degree of homology, ANI analysis demonstrates that the overall genome sequence of the microbial entities isolated from plants and described herein as compared to reference strains is different enough in many cases to qualify as a different species.

| ID | Name | 16S rRNA gene (%) | Closest Ref. genome | ANI (%) |
|---|---|---|---|---|
| DP3 | Leuconostoc mesenteroides (NR_074957.1) | 99 | Leuconostoc pseudomesenteroides (JDVA01000001.1) | 91.77 |
| DP9 | Pediococcus pentosaceus (NR_042058.1) | 99 | Pediococcus pentosaceus (NC_022780.1) | 99.6 |
| DP53 | Pseudomonas helleri | 99 | Pseudomonas psychrophila (NZ_LT329795.1) | 86.82 |
| DP1 | Pseudomonas (NR_148763.1) fluorescens (NR_115715.1) | 99 | Pseudomonas antarctica (NZ_CP015600.1) | 94.48 |
| DP22 | Rahnella sp. (NR_025337.1) | 98 | Rahnella sp. (NC_015061.1) | 88.24 |

Example 5: Testing Composition Efficacy in a Mouse Model of Obesity Induced Bone Loss Experimental Design: Male diet induced obese (DIO) and low-fat diet control C57BL/6J mice were purchased from the vendor at 16 weeks of age and were singly housed in individually ventilated cages (IVCs). At 5 weeks of age, mice were placed on either a low-fat diet (10% kcal, D12450B) or high-fat diet (60% kcal, D12492) (Open Source Diets; Research Diets Inc.) and remained on those respective diets for the duration of the experiment. Mice were allowed to acclimate for 2-weeks prior to the experimental initiation. At 18-weeks of age, one cohort of lean mice (N=4) and one cohort of obese mice (n=4) began control supplementation with water by daily oral gavage, while another group of obese mice (N=4) were treated with a daily oral gavage of SBD102 at a dose of $8 \times 10^{10}$ CFUs/kg body weight. Control groups were provided sterile water at a dose of 5 mL/kg body weight. Mice were orally gavaged with control or test article daily for 8-weeks.

Bone mineral density analysis: At the time of sacrifice, mice were anesthetized via intraperitoneal injection of ketamine (60 mg/kg) and xylazine (4 mg/kg) and scanned by Dual Energy x-ray Absorptiometry (DEXA) scan (PIXImus2 Mouse Densitometer; GE) to measure whole body bone mineral density (BMD).

Distal femur trabecular bone analysis: To evaluate trabecular bone volumes at the distal femur, femurs were removed at the time of sacrifice and analyzed by micro computed tomography (microCT) with a Scanco microCT 40 desktop microCT scanner.

Figure 13:
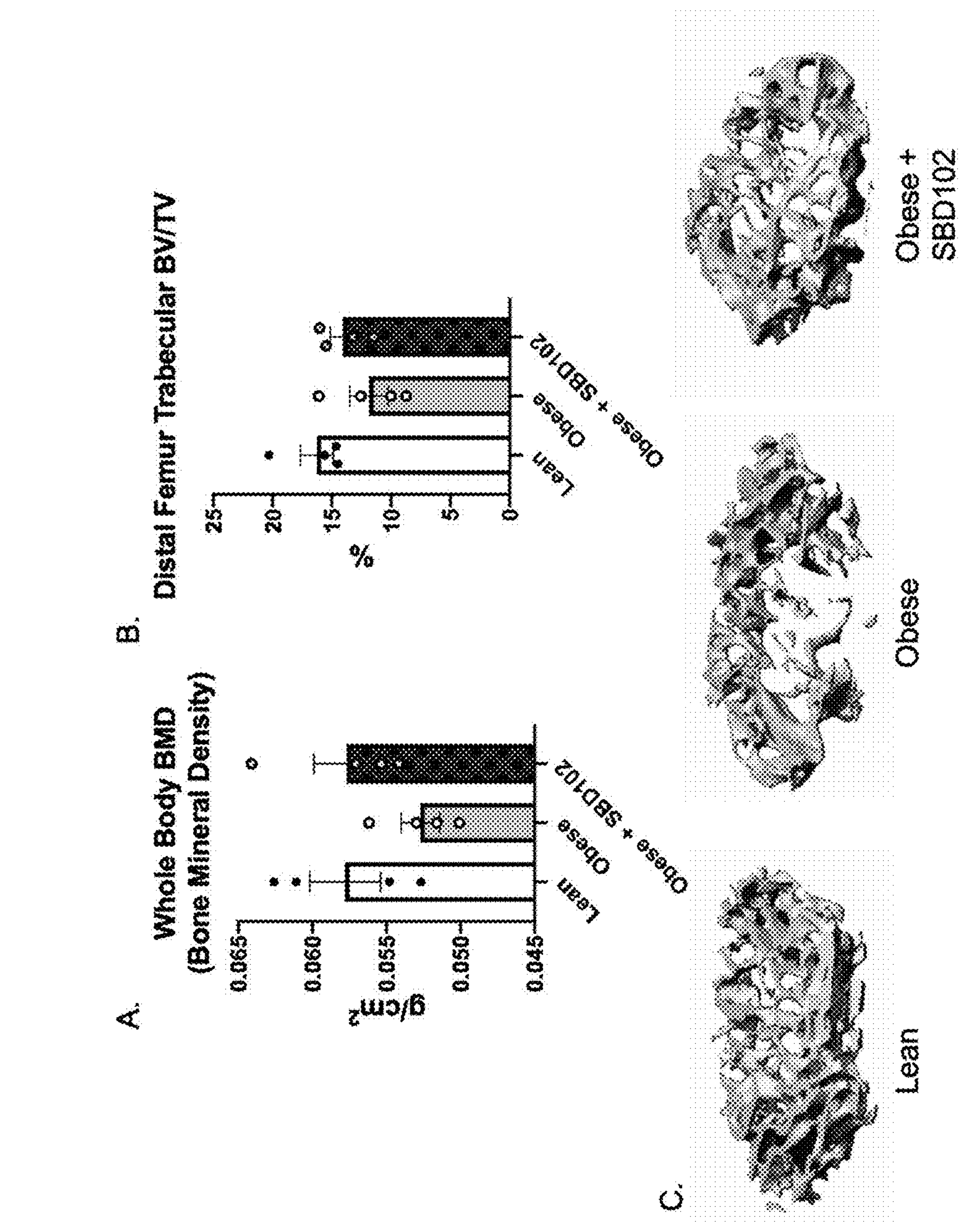
FIG. 13. C57bl/6J mice were placed on a high fat diet (60% kcal fat) for 12 weeks to induce obesity. Mice were then treated with either water control (obese) or SBD102 (obese+SBD102), a DMA consisting of prebiotic plant fibers and probiotic microbes, for 8-weeks. Bone mineral density (BMD) was measured by whole body dual x-ray absorptiometry (DXA) (A), and trabecular bone volume was measured at the distal femur by micro computed tomography (MicroCT) (B). Whole body DXA revealed an 8.5% decrease in BMD in obese mice compared to lean, that was prevented by treatment with SBD102 (A). A similar effect was observed by microCT of the distal femur, were obese mice had lower trabecular bone volume compared to lean mice that was prevented by treatment with SBD102 (B). Representative images of the microCT are depicted in (C).

Conclusion: Compared to lean animals, obese mice lost 8.5% of their total BMD as measured by DXA scan. Obese mice treated with SBD102 were completely protected from this loss of BMD, indicating that SBD102 prevents obesity induced bone loss in a mouse model (FIG. 13A). Substantiating these data, microCT analysis of distal femurs showed similar trends where obesity induced a decrease in trabecular bone volume (BV/TV) compared to lean animals, and treatment with SBD102 prevented that decrease (FIG. 13B, 13C). With this, treatment with DMAs like SBD102 demonstrates a viable therapeutic option for the prevention of obesity induced bone loss.

SBD102 comprised DP9, DP2, and DP53.

Example 6: Testing Composition Efficacy in Mouse Model of Postmenopausal Osteoporosis Experimental Design: DMA compositions were evaluated for therapeutic efficacy in an ovariectomized (OVX) mouse model of postmenopausal osteoporosis. All mice were group-housed with 5 mice per cage in individually ventilated cages (IVCs) specifically designed for germ free husbandry [59, 60]. At 12-weeks of age, mice were weighed, had baseline feces collected, and underwent OVX surgery (N=20) or sham (N=10) surgery to deplete estrogen levels and commence the bone resorption process as previously described (Souza et al., 2019). 1-day post-surgery, mice were randomly divided into experimental groups and mice began a daily oral gavage regimen (200 uL) of saline (negative control), or SBD111 ($5 \times 10^9$ CFU/dose) which continued for 6-weeks. Fecal samples were collected at the beginning of the experiment, at week 3 and week 6 at the end of the experiment to monitor the composition of the gut microbiome over time. Finally, on the last day of the study, mice received a DXA scan to evaluate systemic BMD, followed by euthanasia and collection of lumbar vertebra for analysis.

SBD111 comprised: DP1 (*Pseudomonas* sp.), DP94 (*Lactobacillus brevis*), DP95 (*Leuconostoc mesenteroides*), DP100 (*Lactobacillus plantarum*), and DP102 (*Pichia krudriazevii*).

Tissue collection and analysis: At the time of sacrifice, the uterus was removed and weighed to confirm that the ovaries were successfully removed, and estrogen was depleted following OVX surgery. Tissues were then collected from each mouse to evaluate bone quantity. Cecal contents were removed and flash frozen for downstream metagenomic sequencing and SCFA analysis by GC-FID to determine how our DMA impacted the composition and function of the gut microbiome. Finally, the lumbar spines were removed, processed, and analyzed by micro computed tomography (microCT) with a Scanco microCT 40 desktop microCT scanner.

Figure 11:
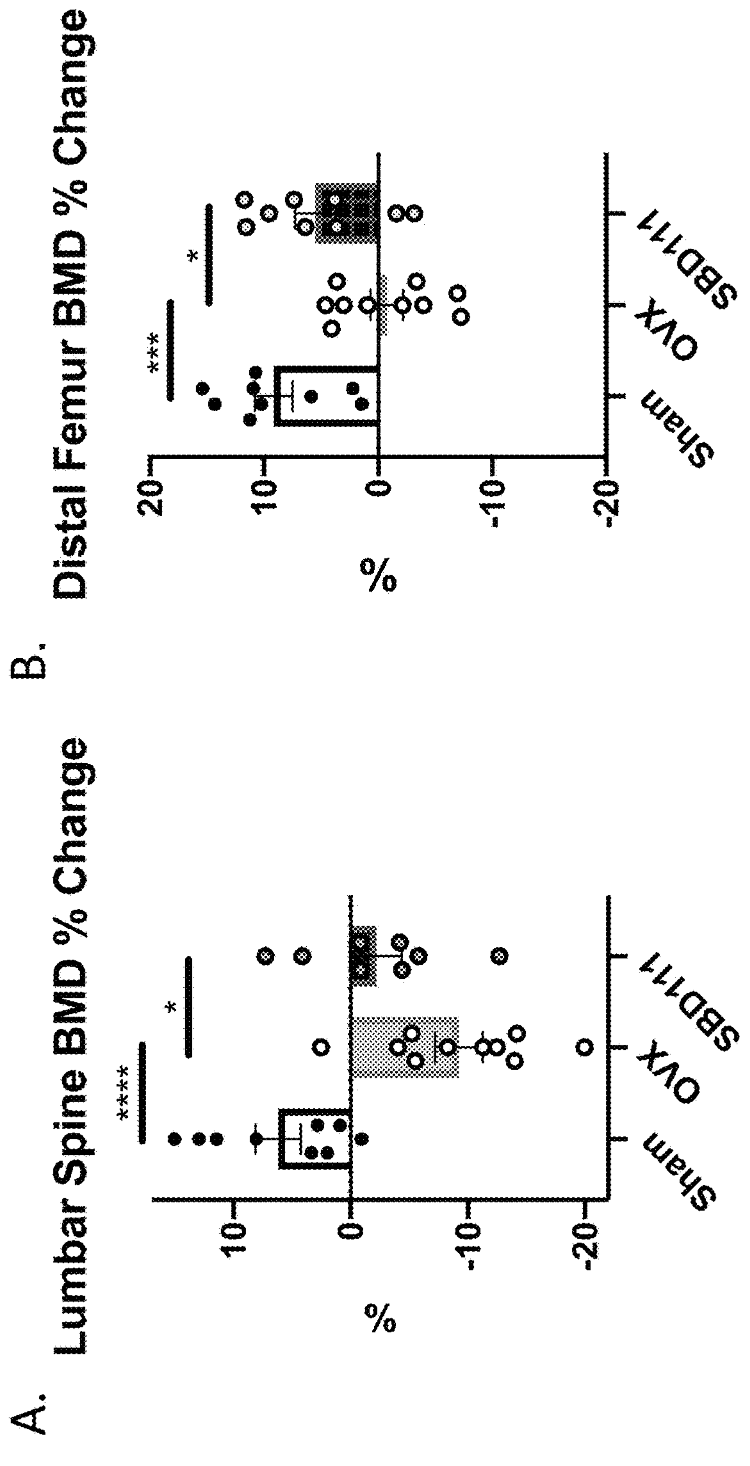
FIG. 11. Ovariectomized (OVX) mice were treated with either water (OVX) or SBD111 for six-weeks post-surgery. Mice received DXA scans before surgery and six-weeks post-surgery to determine the percent change in bone mineral density (BMD). DXA scans reveal a significant protection against OVX-induced bone loss at the lumbar spine (A) and distal femur (B) in mice treated with SBD111. Significant differences between groups in A and B were identified via 1-way ANOVA with a Tukey multiple comparison post-test (*$P<0.05$, $P<0.01$ *$P<0.001$, ****$P<0.0001$)
Figure 12:
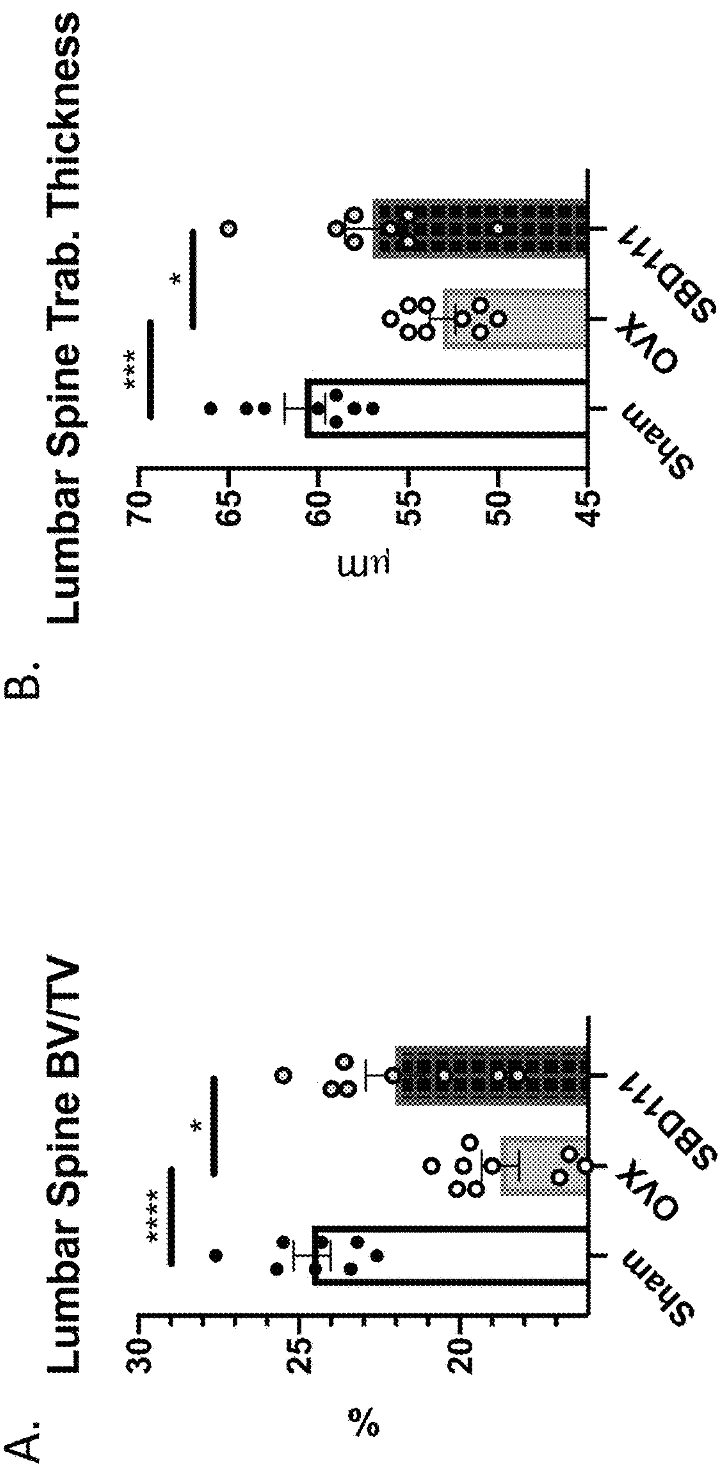
FIG. 12. Ovariectomized (OVX) mice were treated with either water (OVX) or SBD111 for six-weeks post-surgery. At sacrifice, lumbar spine (L1-L4) were removed and analyzed by micro computed tomography (MicroCT) for trabecular bone volume (BV/TV) (A) and trabecular thickness (B). MicroCT scans reveal a significant protection against OVX-induced bone loss at the lumbar spine as indicated by BV/TV (A) and Trabecular Thickness (B) in mice treated with SBD111. Significant differences between groups in A and B were identified via 1-way ANOVA with a Tukey multiple comparison post-test (*$P<0.05$, $P<0.01$ *$P<0.001$, ****$P<0.0001$)

Conclusion: As has been previously described, OVX surgery induced a significant loss of BMD at the lumbar spine and distal femur in comparison to mice receiving sham surgery. Strikingly, OVX mice treated with SBD111 were almost completely protected from this steroid ablation induced bone loss after 6-weeks of daily treatment (FIG. 11A,B). Further, microCT analysis of the lumbar spine revealed significant protection from the loss of trabecular bone that is characteristic of this model in mice treated with SBD111. SBD111 treated animals retained ~70% more trabecular bone volume than OVX controls, and also had thicker trabeculae compared to OVX animals (FIG. 12A, B). With this, DMA treatment demonstrates a potential viable therapeutic option for the protection against postmenopausal bone loss.

Example 7: Orthopaedic Infection

To test the impact of our DMAs on the severity and incidence of implant-associated orthopedic infections, a well-recognized orthopedic implant surgery and infection model is used.

An orthopedic implant coated with *Staphylococcus aureus* (*S. aureus*) is generated by cutting flat stainless steel surgical wire into a 0.02×0.5×4 mm length, and bent at 1 mm to make an L shaped pin that is placed in an overnight culture of USA300 LAC::/uxmethicillin resistants *S. aureus* (2×10^6 CFUs) for 20 minutes. Next, mice are anesthetized with an intraperitoneal injection of ketamine (60 mg/kg) and xylazine (4 mg/kg), and a 4 mm incision is made on the medial aspect of the right tibia. A hole in the medial tibia is then predrilled using successive 30- and 26-gauge needles before the infected pin is placed through the defect. The surgical site is then closed using a 5-0 nylon suture.

After surgery, mice are divided into treatment groups, and daily oral gavages of defined microbial assemblages (DMAs) or saline controls are performed for four weeks. Weekly fecal samples are collected for sequencing to monitor the gut microbiome over time. For each treatment, infections are monitored longitudinally by bioluminescence of the tibia using a Xenogen IVIS® camera system. At 14, 21, and 35 days post-infection, mice are euthanized and tissues are collected including ti bias for analysis of the infection by micro-computed tomography (MicroCT) and histology, serum for cytokine analysis, and colonic tissues for immune cell and cytokine evaluation by histology and qRT-PCR.

The results demonstrate that mice treated with the compositions disclosed herein have a shorter recovery period and milder infection symptoms than mice receiving the saline control.

Example 8: Efficacy of DMAs on Improving Fracture Healing in a Mouse Model

To test the impact of DMAs on fracture healing, a well-recognized mouse model of fracture repair is used, the murine stabilized tibia fracture model. Here, 12-week old male and female mice are anesthetized with an intraperitoneal injection of ketamine (60 mg/kg) and xylazine (4 mg/kg). A 4 mm longitudinal incision is made on the anterior side of the right tibia, and a small hole is then be drilled into the tibial tuberosity using a 26-gauge needle. A transverse osteotomy is then performed with a number 11 scalpel blade at the proximal diaphysis of the tibia. The fibula remains intact. The bone fracture is then fixed with an intramedullary nailing procedure using a 26-gauge Quincke type spinal needle (BD Medical Systems), and the wound is closed using 5-0 nylon sutures. After surgery, mice are divided into treatment groups, and begin daily oral gavages for four weeks of defined microbial assemblages (DMAs) or saline controls. Weekly fecal samples are collected for sequencing to monitor the gut microbiome over time. For each treatment, Fractures are evaluated for strength, fracture callus formation, and union proficiency by X-ray, MicroCT, biomechanical torsion testing of the tibia, and histological/histomorphometric analysis of the tibia at 7, 14, 21, and 35 days post fracture. Additionally, serum, colon, and cecal material are collected from each mouse, from which serum is analyzed for inflammatory cytokine levels, colonic tissues are evaluated by qRT-PCR for immune cell and cytokine levels, and cecal material is shotgun sequenced for microbiome analysis.

The results demonstrate that mice treated with the compositions disclosed herein demonstrate the efficacy of DMAs on improving fracture healing in a mouse model.

Example 9: Evaluation of Anti-Osteoarthritis Efficacy in a Mouse Model

DMAs are evaluated for their therapeutic efficacy in a mouse model of post-traumatic osteoarthritis. All mice are group housed with 3 mice per cage in individually ventilated cages (IVCs) specifically designed for germ free husbandry. At 12-weeks of age, mice have baseline feces collected, and receive either a sham injury (n=12) or a destabilization of the medial meniscus (DMM) (n=72) injury to induce arthritis. Briefly, a 5-mm-long incision is made through the skin on the medial side of the knee. Under a dissecting microscope, another incision through the synovial membrane is made along the medial side of the patellar tendon, opening the joint space. Using a #11 scalpel, the medial meniscotibial ligament (MMTL) is transected, enabling the medial meniscus to move freely. After surgery, 4-0 silk sutures are used to close the incision using an interrupted pattern. 1-week post-surgery, mice are randomly divided into experimental groups and fresh fecal samples are again collected. Mice then begin a daily oral gavage regimen (200 μL) of saline (negative control), DMA #1, DMA #2, DMA #3, DMA #4, or DMA #5 and continue for 12-weeks. Monthly fecal samples are collected to monitor the composition of the gut microbiome over time. On the last day of the study, mice are euthanized, and tissues are collected including serum, colon, cecal material, knees, and synovial membranes for analysis. Serum is analyzed for inflammatory cytokine levels; colonic tissues are evaluated by qRT-PCR for immune cell and cytokine levels; cecal material is shotgun sequenced for microbiome analysis; knees are evaluated by histology for total cartilage area and hypertrophic chondrocyte markers, and synovial membranes are assessed by qRT-PCR for inflammatory cytokine levels.

The results demonstrate that mice treated with the compositions disclosed herein anti-osteoarthritis efficacy in a mouse model.

Example 10: Monitoring the Effect of DMAs on Microbial Flora of a Mammal

Alterations of the gut microbiota have been linked with changes in the host homeostasis such as chronic inflammation. In order to evaluate changes in the gut microbiota composition in OVX mice, fecal pellets were collected from OVX and sham mice during baseline and week 6 of treatment and the gut microbiota was characterized. Briefly, DNA was extracted using the ZymoBIOMICS DNA extraction Kit and quantified using a Qubit 2.0 fluorometer with the dsDNA HS assay kit. Metagenomic libraries were prepared using the Illumina Nextera Flex DNA library preparation kit and an equimolar mixture of the libraries was sequenced on an Illumina NovaSeq Si instrument on a 2×150 bp paired end run. Raw reads from the sequencing run were analyzed using SolexaQA (Cox et al. 2010) for trimming and removing of Illumina adaptors using a Phred score cutoff of 20 and minimum fragment length of 50 bp. Mouse sequencing reads were removed by mapping metagenomic reads against the *Mus musculus* genome GRCm38 using Bowtie2 with default parameters (Langmead et al. 2012). Taxonomic classification of the short-read metagenomes was determined using MetaPhlan2, which uses clade-specific marker genes from approximately 17,000 reference genomes to estimate the relative abundance of microbial members present in the sample (Troung et al. 2015).

Figure 14:
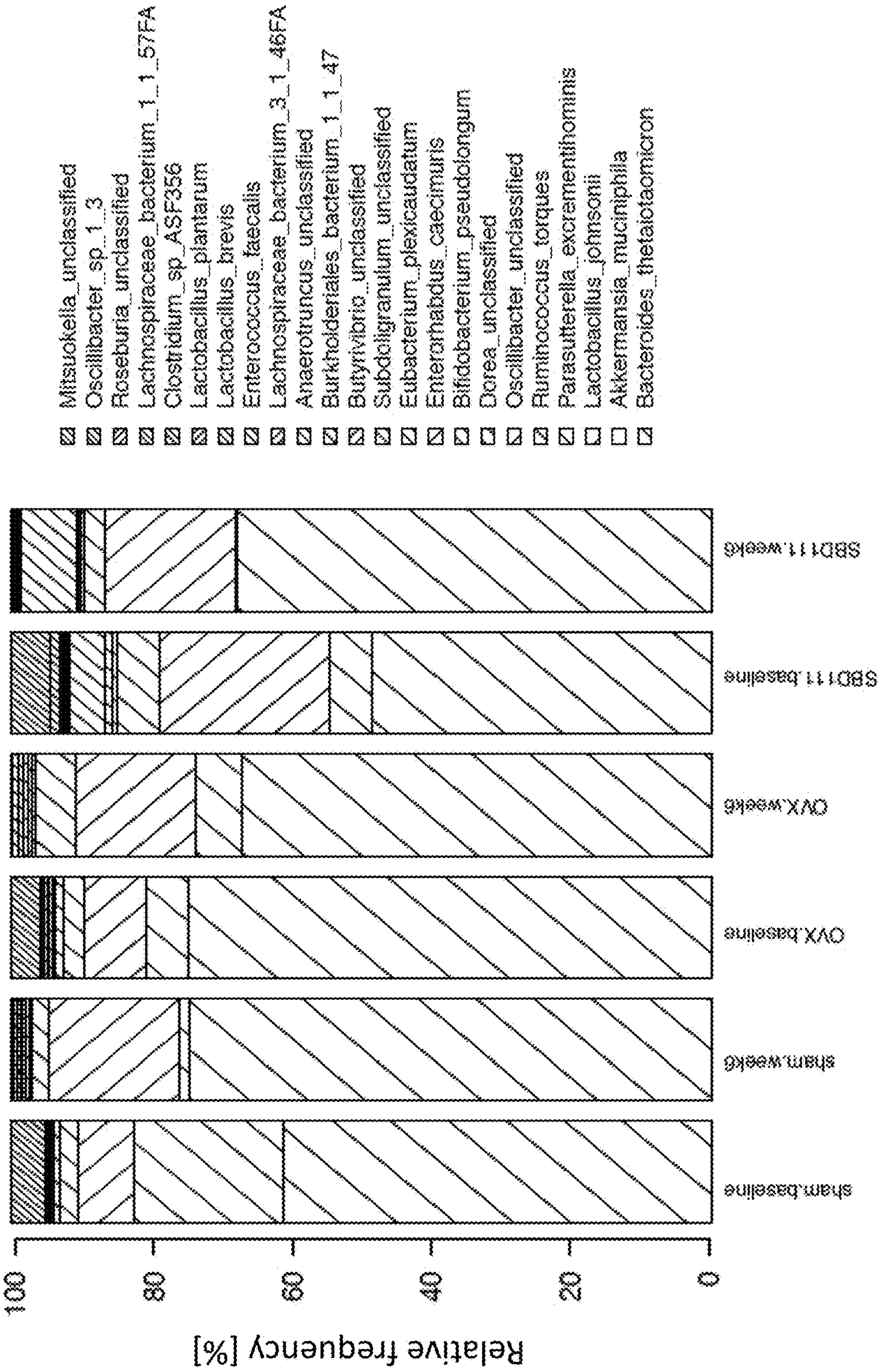
FIG. 14. Shows the composition of the gut microbial community of the sham and OVX mice at the baseline and six-weeks post-surgery time points with SBD111. Overall, *Bacteroides thetaiotaomicron* was the most prevalent taxon detected among the mice groups encompassing more than 50% of the total community on average, followed by *Lactobacillus johnsonii* with abundance values between 8.8% and 24.2%, excepting the sham baseline group where *Akkermansia municiphila* was the second most abundant taxon (21.3% on average). In the case of the SBD111 group, *Bifidobacterium pseudolongum* showed an increase in abundance at week 6 (from 5% to 7.8% of the total community).

FIG. 14 shows the composition of the gut microbial community of the sham and ovx mice at the baseline and week 6 time points with different DMA combinations. Overall, *Bacteroides thetaiotaomicron* was the most prevalent taxon detected among the mice groups encompassing more than 50% of the total community on average, followed by *Lactobacillus johnsonii* with abundance values between 8.8% and 24.2%, excepting the sham baseline group where *Akkermansia municiphila* was the second most abundant taxon (21.3% on average). In the case of the SBD111 group, *Bifidobacterium pseudolongum* showed an increase in abundance at week 6 (from 5% to 7.8% of the total community). *Bifidobacterium pseudolongum* has been shown previously to modulate the immune system and decrease systemic inflammation. Inflammation plays a large role in osteoclastogenesis and the breakdown of bone, so the increased abundance of *Bifidobacterium pseudolongum* likely decreases systemic inflammatory mediators and thus decreases the resorption of bone, leading to improved BMD and trabecular bone volume in mice treated with SBD111 compared to OVX mice.

Further, *Eubacterium plexicaudatum* and *Lactobacillus johnsonii* increase in the sham group after 6 weeks while *Akkermansia* muciniphila decreases. These changes should be considered as part of a growth changes in the microbiome due to age and not associated to a changing phenotype due to the interventions.

In the OVX group there is a decrease in the Burkholderiales bacterium and *Oscillibacter* sp. SBD111 exhibits an increase in *Bacteroides thetaiotaomicron* in Lachnospiracea bacterium and a decrease in Burkholderiales, *Parasutterella excremintihomini* that can be associated to the phenotypes of prevention to bone loss.

Example 11: Functional Profile of the Gut Microbiota Under DMA Treatment L-Rhamnose Degradation In order to compare the rhamnose degradation in each group at week 6, relative abundances of genes related to L-rhamnose degradation pathway in individual mouse were calculated by mapping of sequencing reads against UniRef90 using HuMANN2 and characterizing gene families (Franzosa et al., 2018). Gene families that were annotated to the same MetaCyC reaction ID were averaged in each individual.

Figure 19A:
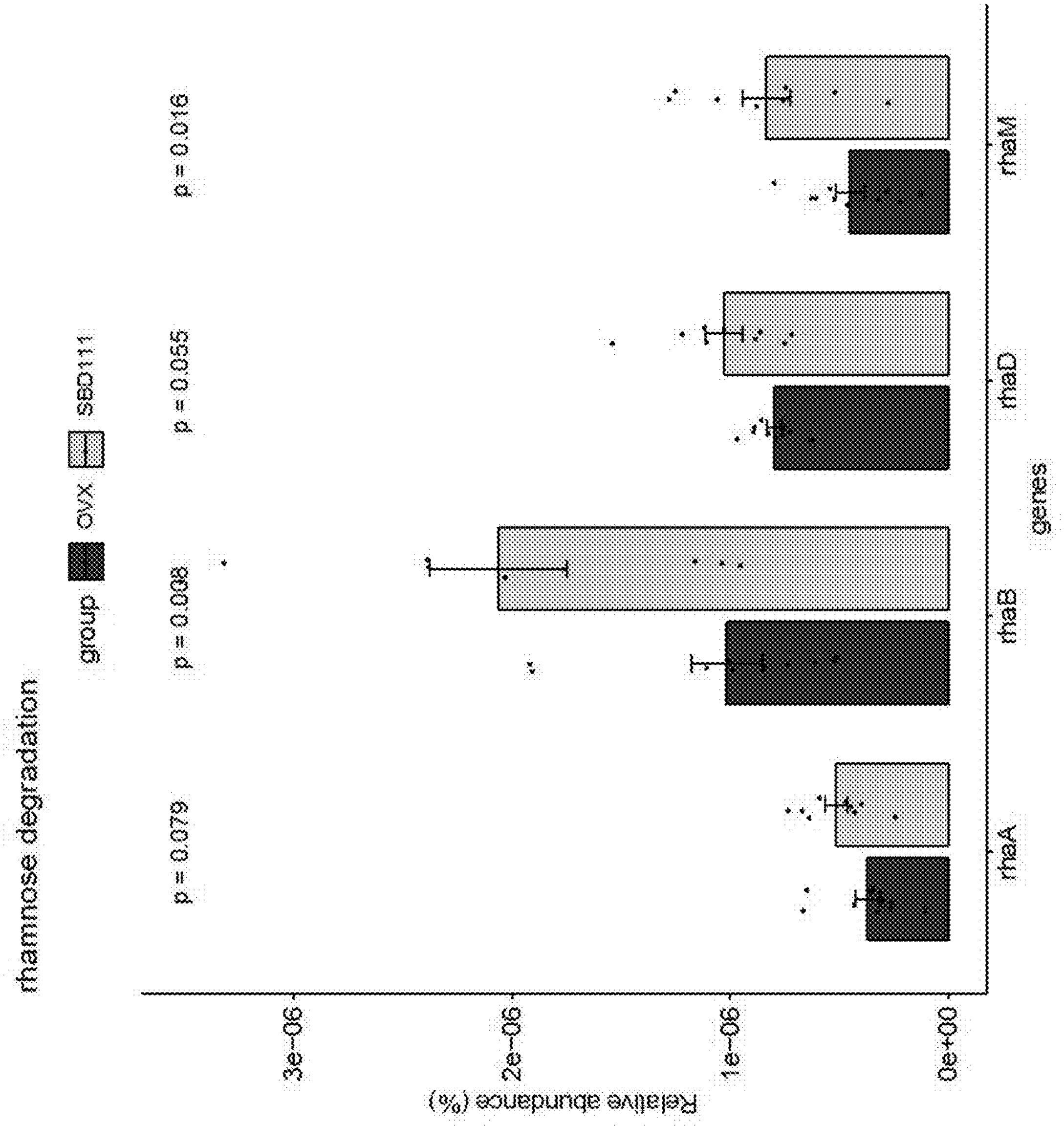
FIG. 19A Comparison of relative abundance of genes related to L-rhamnose degradation between OVX group and SBD111-treated group. Differences between groups were assessed by Mann-Whitney U test (*P<0.05, **P<0.01). rhaD, rhamnulose-1-phosphage aldolase; rhaB, rhamnulokinase; rhaA, L-rhamnose isomerase; rhaM, L-rhamnose mutarotase.

FIG. 19A shows the comparison of relative abundance of genes related to L-rhamnose degradation between OVX group and SBD111-treated group. Differences between groups were assessed by Mann-Whitney U test. Comparison of gene abundance between OVX and SBD111 groups indicated significantly higher abundance at week 6 in the SBD111 group in comparison with the OVX one. The L-rhamnose degradation pathway has been implicated in increased short chain fatty acid production. Further, increased short chain fatty acid production has been shown to improve BMD in OVX mice, and thus an increase in L-rhamnose degradation may partially explain the increased BMD and trabecular bone volume in SBD111 treated mice via increased SCFA production.

rhaD, rhamnulose-1-phosphage aldolase; rhaB, rhamnulokinase; rhaA L-rhamnose isomerase; rhaM, L-rhamnose mutarotase.

TABLE 9

Pathways significantly enriched or depleted after 6 weeks in both SBD111 and OVX in response to ovariectomy surgery and treatment. The mean relative frequency between baseline and six- week time points were compared for each mice group (OVX, sham, and SBD111). Mann-Whitney U test ($P < 0.05$).

| | OVX | sham | p-values |
|---|---|---|---|
| L-rhamnose degradation I | 0.57 | 0.77 | 0.02 |
| | OVX | DMA5 | |
| L-arginine biosynthesis I (via L-ornithine) | 0.80 | 0.58 | 0.01 |
| L-arginine biosynthesis II (acetyl cycle) | 0.41 | 0.26 | 0.02 |
| L-arginine biosynthesis III (via N-acetyl-L-citrulline) | 0.42 | 0.26 | 0.01 |
| L-rhamnose degradation I | 0.57 | 0.82 | 0.03 |
| dTDP-L-rhamnose biosynthesis I | 0.86 | 0.58 | 0.05 |

Short-Chain Fatty Acids (SCFA) Gene Abundance

SCFA, produced mainly from microbial fermentation of dietary fiber, appear to be a major mediator of the beneficial effects induced by the gut microbiome (Tan et al., 2014). In order to compare the potential production level of short-chain fatty acids in each group at week 6, relative abundances of marker genes related to SCFA productions in individual mouse were calculated by mapping of sequencing reads against UniRef90 using HuMANN2 HUMAnN2 and characterizing gene families (Franzosa et al. 2018). Gene families that were annotated to the same MetaCyC reaction ID were averaged in each individual.

Figure 19B:
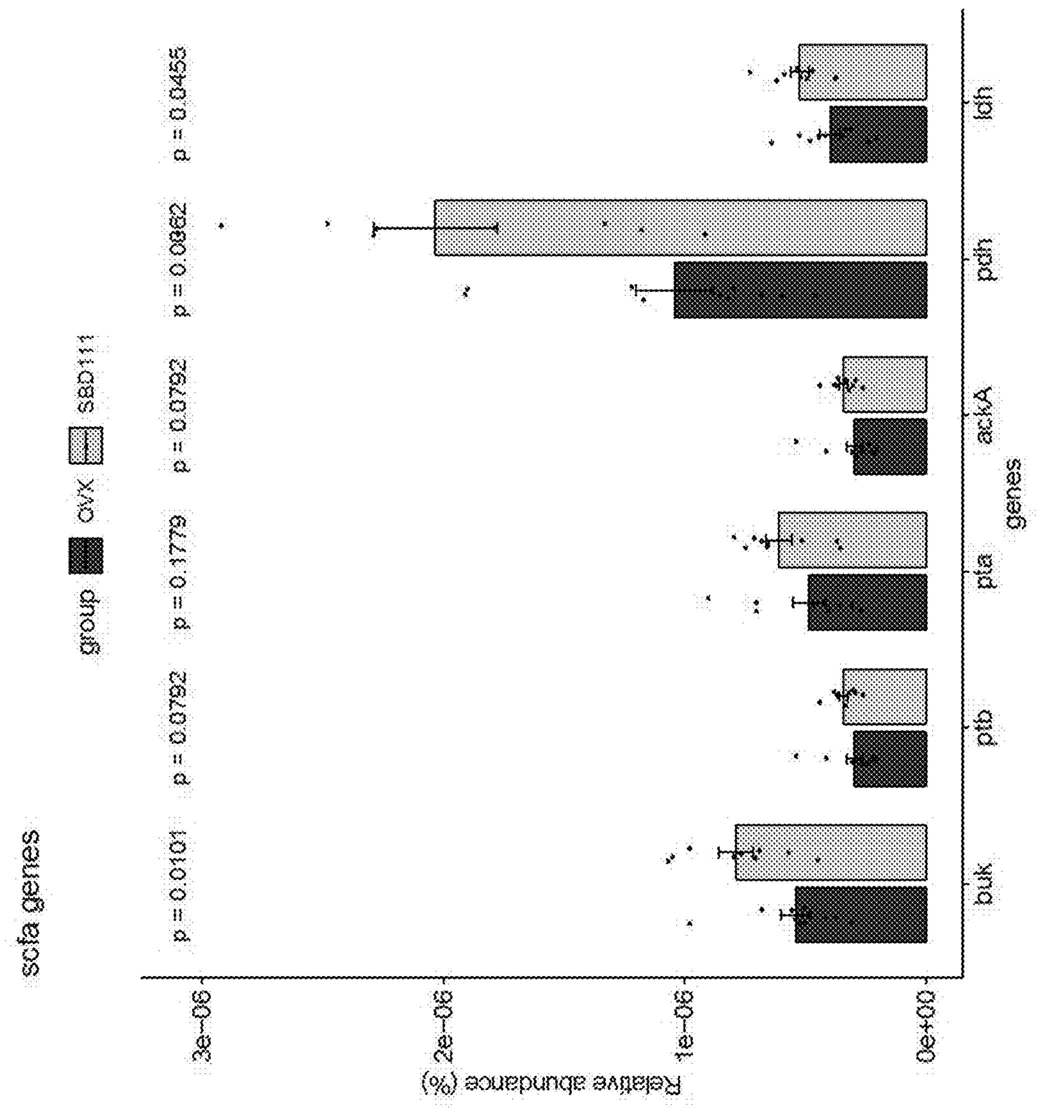
FIG. 19B Comparison of relative abundance of genes related to SCFA production between OVX group and SBD111-treated group. Differences between groups were assessed by Mann-Whitney U test (*P<0.05, **P<0.01). Butyrate kinase (buk) and phosphotransbutyrylase (ptb) were selected as marker genes representing butyrate production. Pyruvate dehydrogenase (pdh), phosphate acetyltransferase (pta) and acetate kinase (ackA) represent acetate production. L-lactate dehydrogenase (ldh) are involved in lactate production pathway.

FIG. 19B shows the comparison of relative abundance of genes related to SCFA production between OVX group and SBD111-treated group. Differences between groups were assessed by Mann-Whitney U test. Butyrate kinase (buk) and phosphotransbutyrylase (ptb) were selected as marker genes representing butyrate production. Pyruvate dehydrogenase (pdh), phosphate acetyltransferase (pta) and acetate kinase (ackA) represent acetate production. L-lactate dehydrogenase (ldh) are involved in lactate production pathway. All genes presented in the figure are significantly more abundant in SBD111-treated groups compared to OVX group. Increased short chain fatty acid production has been shown to improve BMD in OVX mice, and thus an increase in genes related to SCFA biosynthesis may partially explain the increased BMD and trabecular bone volume in SBD111 treated mice.

Glycoside Hydrolase

Microbial fermentation of complex non-digestible dietary carbohydrates and host-derived glycans in human intestines has important health consequences. Bacteria that colonize the mammalian gut possess large number of genes that encode carbohydrate active enzymes, which play an important role in the community by initiating the breakdown of complex substrates such as plant cell walls, starch particles and mucins.

Glycoside hydrolases (GH) are one of the carbohydrate active enzyme families that catalyze the hydrolysis of glycosidic bonds in plant fibers. In order to compare the potential capabilities of glycoside hydrolase activity in each group at week 6, relative abundances of gene families related to glycoside hydrolase in individual mouse were calculated by mapping sequencing reads against UniRef90 using HUMAnN2 and characterizing gene families (Franzosa et al. 2018). UniRef90 gene families that were annotated to the same GH families were averaged in each individual.

Figure 19C:
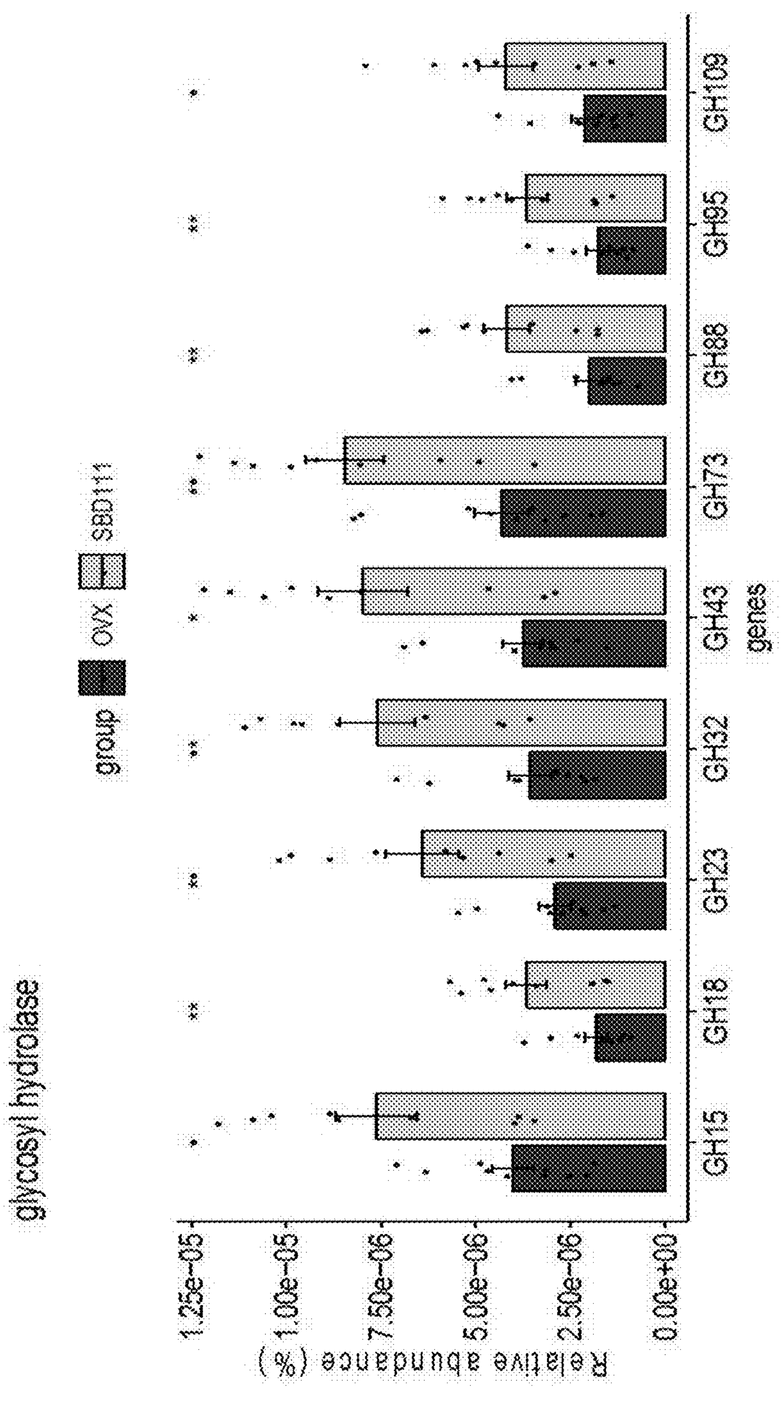
FIG. 19C Comparison of relative abundance of genes related to glycoside hydrolase between OVX group and SBD111-treated group. Differences between groups were assessed by Mann-Whitney U test (*P<0.05, **P<0.01). GH15, glucoamylase; GH18, chitinase; GH23, peptidoglycan lyase; GH32, invertase; GH43, β-xylosidase; GH73, lysozyme; GH88, unsaturated glucuronyl hydrolases; GH95, α-L-fucosidase; GH109, α-N-acetylgalactosaminidase.

FIG. 19C shows the comparison of relative abundance of genes related to glycoside hydrolase between OVX group and SBD111-treated group at week 6. Differences between groups were assessed by Mann-Whitney U test (*P<0.05, P<0.01). Comparison of gene abundance between OVX and SBD111 groups indicated significantly higher abundance at week 6 in the SBD111 group in comparison with the OVX one. Results are shown in FIG. 19**C. Increased abundance of GH genes likely indicates increased fermentation of non-digestible dietary fiber, leading to increased SCFA production. Increased short chain fatty acid production has been shown to improve BMD in OVX mice, and thus an increase in glycoside hydrolase may partially explain the increased BMD and trabecular bone volume in SBD111 treated mice through increased production of SCFA.

GH15, glucoamylase; GH18, chitinase; GH23, peptidoglycan lyase; GH32, invertase; GH43, β-xylosidase; GH73, lysozyme; GH88, unsaturated glucuronyl hydrolases; GH95, α-L-fucosidase; GH109, α-N-acetylgalactosaminidase.

Vitamin K2 Biosynthesis

Figure 19D:
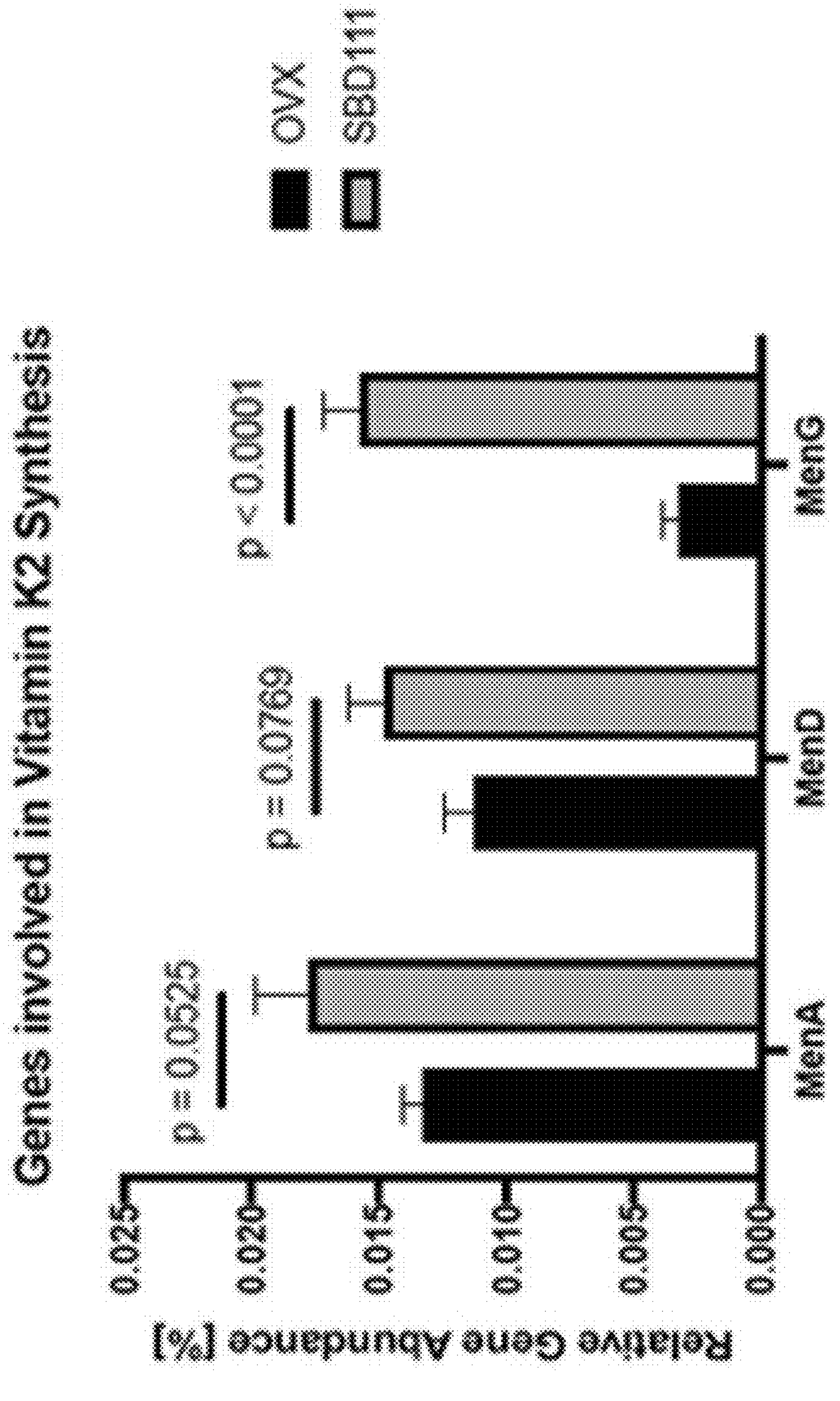
FIG. 19D Comparison of relative abundance of genes related to vitamin K2 biosynthesis between OVX group and SBD111-treated group. Differences between groups were assessed by Mann-Whitney U test (*P<0.05, **P<0.01). MenA, 1,4-dihydroxy-2-naphthoate prenyltransferase; MenD, 2-succinyl-5-enolpyruvyl-6-hydroxy-3-cyclohexene-1-carboxylate synthase, and MenG, demethylmenaquinone methyltransferase.

Functional characterization of the short-read metagenomes was determined using HUMAnN2 (Abubucker et al. 2012) with default parameters and the UniRef90 database (Suzek et al. 2015). Identifying genes involved in vitamin K2 (menaquinone) biosynthesis in the gut metagenomes is useful because vitamin K2 exhibits beneficial effects on human health. Although some studies have reported a positive effect of vitamin K2 consumption on bone health (Hess et al. 2015, Heaney 2013), the mechanism and factors involved in this relation are still unclear. Comparison of changes in gene abundance at the baseline and week 6 between OVX and SBD111 groups indicated higher significant increase in abundance at week 6 in the SBD111 group in comparison with the OVX one. Results are shown in FIG. 19D. As vitamin K2 has been shown to play a role in osteoblast functionality, an increase in Vitamin K2 biosynthesis may in part explain the increased BMD and trabecular bone volume in SBD111 treated mice compared to OVX mice.

Alkaline Phosphatase

Alkaline phosphatase (ALP) is a ubiquitous membrane-bound glycoprotein that catalyzes the hydrolysis of phosphate monoesters at basic pH values and is produced by both eukaryotic and prokaryotic cells. In the intestine, ALP has been shown to improve intestinal barrier integrity, exerting its effects through dephosphorylation of proinflammatory molecules including lipopolysaccharide (LPS), flagellin, and adenosine triphosphate (ATP) released from cells during stressful events. Diminished activity of ALP could increase the risk of disease through changes in the microbiome, intestinal inflammation, and intestinal permeability. With this, the increased gene abundance of ALP In order to compare the potential capabilities of alkaline phosphatase activity in each group at week 6, relative abundances of gene families related to alkaline phosphatase in individual mouse were calculated by mapping sequencing reads against UniRef90 using HUMAnN2 and characterizing gene families (Franzosa et al., 2018).

Figure 19E:
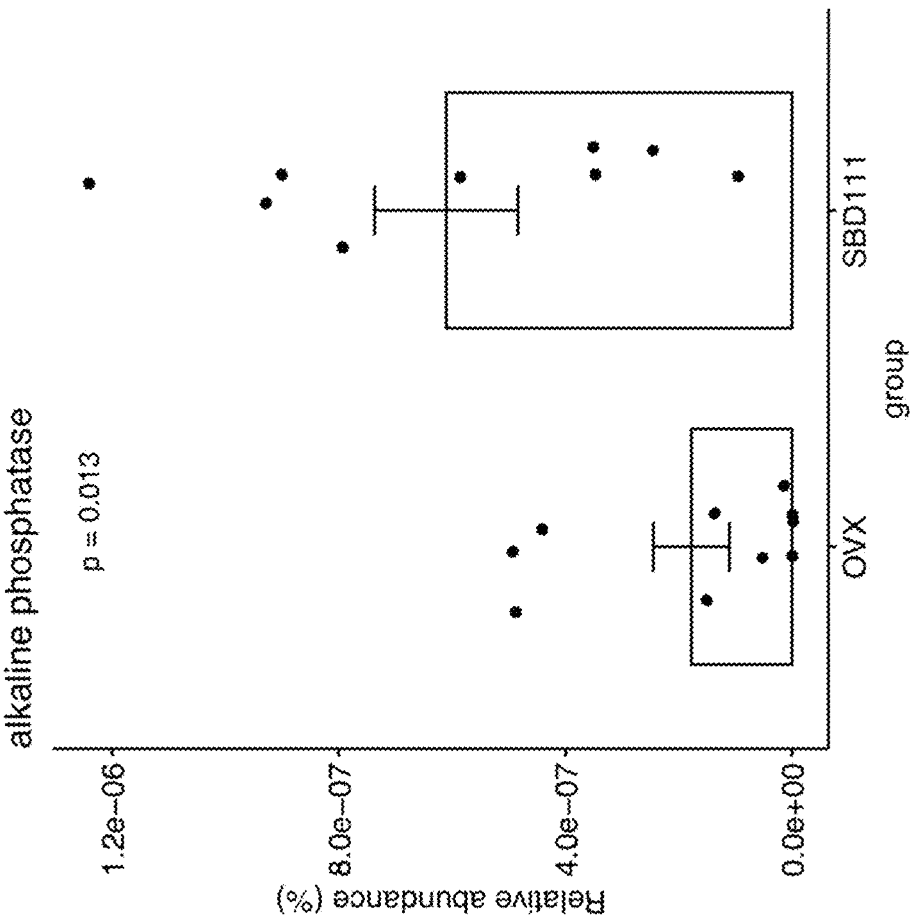
FIG. 19E Comparison of relative abundance of alkaline phosphate gene between OVX group and SBD111-treated group at 6 weeks. Differences between groups were assessed by Mann-Whitney U test (*P<0.05, **P<0.01).

FIG. 19E shows the comparison of relative abundance of alkaline phosphatase between OVX group and SBD111-treated group. Alkaline phosphatase was found to be increased in samples from SBD111 treated mice. Differences between groups were assessed by Mann-Whitney U test. With this, increased ALP in the microbiome could improve gut barrier integrity and decrease systemic inflammation, leading to improved BMD in SBD111 treated mice compared to OVX.

Additional Changes

Changes in additional metabolic pathways were also observed. Some comparisons of interest are displayed in Table 10 and Table 11.

TABLE 10

Comparison of the pathways enriched or depleted in both SBD111 and OVX after 6 weeks with respect to baseline in response to ovariectomy surgery and treatment. Mann-Whitney U test (P < 0.05).

| | Pathway | Baseline mean rel. freq. (%) | 6 Weeks mean rel. freq. (%) | p-values |
|---|---|---|---|---|
| DMA5 | L-arginine biosynthesis I (via L-ornithine) | 0.75 | 0.58 | 0.03 |
| DMA5 | L-arginine biosynthesis III (via N-acetyl-L-citrulline) | 0.36 | 0.26 | 0.04 |

TABLE 10-continued

Comparison of the pathways enriched or depleted in both SBD111 and OVX after 6 weeks with respect to baseline in response to ovariectomy surgery and treatment. Mann-Whitney U test ($P < 0.05$).

| | Pathway | Baseline mean rel. freq. (%) | 6 Weeks mean rel. freq. (%) | p-values |
|---|---|---|---|---|
| DMA5 | L-arginine biosynthesis IV (archaebacteria) | 0.82 | 0.64 | 0.03 |
| DMA5 | L-rhamnose degradation I | 0.48 | 0.82 | 0.01 |
| OVX | L-arginine biosynthesis I (via L-ornithine) | 0.58 | 0.80 | 0.02 |
| OVX | L-arginine biosynthesis II (acetyl cycle) | 0.21 | 0.41 | 0.00 |
| OVX | L-arginine biosynthesis III (via N-acetyl-L-citrulline) | 0.26 | 0.42 | 0.01 |
| OVX | L-arginine biosynthesis IV (archaebacteria) | 0.64 | 0.86 | 0.02 |

TABLE 11

Metabolic pathways of interest and observed changes in both SBD111 and OVX mice in response to ovariectomy surgery and treatment.

| Pathway | Metabolic effect | Observed changes |
|---|---|---|
| UMP biosynthesis | Immune system stimulation humans; DNA, RNA synthesis | Increased in SBD111 at week 6 |
| coenzyme A biosynthesis II (mammalian) | Fatty acid metabolism cofactor | Increased in SBD111 at week 6 |
| adenine and adenosine salvage III | Nucleotide synthesis, immune system | Increased in SBD111 at week 6 |
| 5-aminoimidazole ribonucleotide biosynthesis II | Alternative glucose oxidation | Increased in SBD111 at week 6 |
| pentose phosphate pathway (non-oxidative branch) | Alternative glucose oxidation, active in ovarian tissue, skeletal muscles | Increased in SBD111 at week 6 |
| L-rhamnose degradation I | Bone health, connective tissues, SCFA upregulation | Increased in SBD111 at week 6 |
| superpathway of 5-aminoimidazole ribonucleotide biosynthesis | purine biosynthesis | Increased in SBD111 at week 6 |
| superpathway of L-aspartate and L-asparagine biosynthesis | formation of succinate& fumarate in anaerobic conditions | Increased in SBD111 at week 6 |
| L-arginine biosynthesis IV | BMD, immunomodulatory, anti-aging | Decreased in SBD111 at week 6 |
| L-arginine biosynthesis I (via L-orinthine) | downstream intermediate releases acetate | Decreased in SBD111 at week 6 |
| flavin biosynthesis III (fungi) | energetic metabolism, redox homeostasis and protein folding, vitamin B2 | Increased in SBD111 at week 6 |
| L-histidinedegradation I | catabolite repression, L-glutamate, amino acid degredation | Increased in SBD111 at week 6 |
| D-fructuronate degredation | Female-specific factor, gut microbiota | Decreased in OVX vs SBD111 |
| inosine-5'-phosphate biosynthesis I | RNAand DNA synthesis, IMPDH in T cells, immune system | Decrease in SBD111 vs OVX |
| sulfate reduction I (assimilatory) | Colonic sulfide metabolism, hydrogen sulfide, intestinal disorders | Appeared in OVX |
| dTDP-L-rhamnose biosynthesis I | Enterobacterial common antigen | Increased in OVX vs SBD111 |
| tetrapyrrole biosynthesis I (from glutamate) | production of vitamin B12, antioxidant properties | Decrease in SBD111 vs OVX |
| L-arginine biosynthesis II (acetyl cycle) | inflammation regulation | Increase in OVX |

| Family | Genes | SBD111 mean rel. freq. (%) | OVX mean rel. freq. (%) | p-values |
|---|---|---|---|---|
| UniRef90_D6D0Y9 | D6D0Y9_Alpha-1,2-mannosidase, putative | 0.017 | 0.014 | 0.037 |
| UniRef90_Q8A1H4 | Q8A1H4_Glycosyl hydrolase, family 88 | 0.018 | 0.015 | 0.039 |
| UniRef90_R9KRQ6 | R9KRQ6_Beta-galactosidase | 0.004 | 0.001 | 0.007 |
| UniRef90_Q8A1F2 | Q8A1F2_Phospholipid/glycerol acyltransferase | 0.017 | 0.014 | 0.035 |
| UniRef90_Q8A222 | Q8A222_N-actylgalactosamine-6-sulfatase | 0.017 | 0.013 | 0.033 |
| UniRef90_Q8A9I7 | Q8A9I7_dTDP-4-dehydrorhamnose | 0.014 | 0.010 | 0.017 |
| UniRef90_J9CIK2 | J9CIK2_Tetrapyrrole methylase family protein | 0.016 | 0.012 | 0.032 |
| UniRef90_R7KTS6 | R7KTS6_Zinc ABC transporter zinc-binding | 0.019 | 0.015 | 0.042 |
| UniRef90_R6UVU4 | R6UVU4_GDP-L-fucose synthase | 0.015 | 0.011 | 0.044 |
| UniRef90_Q8A3K1 | Q8A3K1_L-rhamnose-proton symporter | 0.017 | 0.013 | 0.043 |
| UniRef90_Q8A7Q2 | Q8A7Q2_Glycoside transferase family 2 | 0.017 | 0.012 | 0.027 |
| UniRef90_Q8A3K8 | Q8A3K8_Glycoside transferase family 4 | 0.019 | 0.015 | 0.021 |
| UniRef90_Q8A7J9 | Q8A7J9_Phosphatidylglycerophosphatase A | 0.016 | 0.011 | 0.028 |
| UniRef90_R5UG56 | R5UG56_Gliding motility-associated protein | 0.015 | 0.011 | 0.019 |

-continued

| Family | Genes | SBD111 mean rel. freq. (%) | OVX mean rel. freq. (%) | p-values |
|---|---|---|---|---|
| UniRef90_Q8A677 | Q8A677_Guanylate kinase | 0.018 | 0.013 | 0.013 |
| UniRef90_Q8A3L8 | Q8A3L8_Glycoside transferase family 4 | 0.021 | 0.016 | 0.036 |
| UniRef90_Q5LI10 | Q5LI10_Argininosuccinate lyase | 0.017 | 0.013 | 0.043 |
| UniRef90_Q8AAL0 | Q8AAL0_Arabinose-proton symporter | 0.019 | 0.014 | 0.046 |
| UniRef90_Q8A0G3 | Q8A0G3_NADH-quinone oxidoreductase | 0.019 | 0.014 | 0.039 |
| UniRef90_Q8A0F5 | Q8A0F5_NADH-quinone oxidoreductase | 0.018 | 0.013 | 0.050 |
| UniRef90_Q8A3K7 | Q8A3K7_Glycoside transferase family 2 | 0.018 | 0.013 | 0.006 |
| UniRef90_D6D807 | D6D807_Asparaginase | 0.019 | 0.014 | 0.031 |
| UniRef90_R9H5P6 | R9H5P6_Serine acetyltransferase | 0.017 | 0.011 | 0.010 |
| UniRef90_R5B6J1 | R5B6J1_Tyrosine-tRNA ligase | 0.072 | 0.108 | 0.001 |
| UniRef90_R7J544 | R7J544_L-aspartate oxidase | 0.038 | 0.051 | 0.009 |

Figure 15:
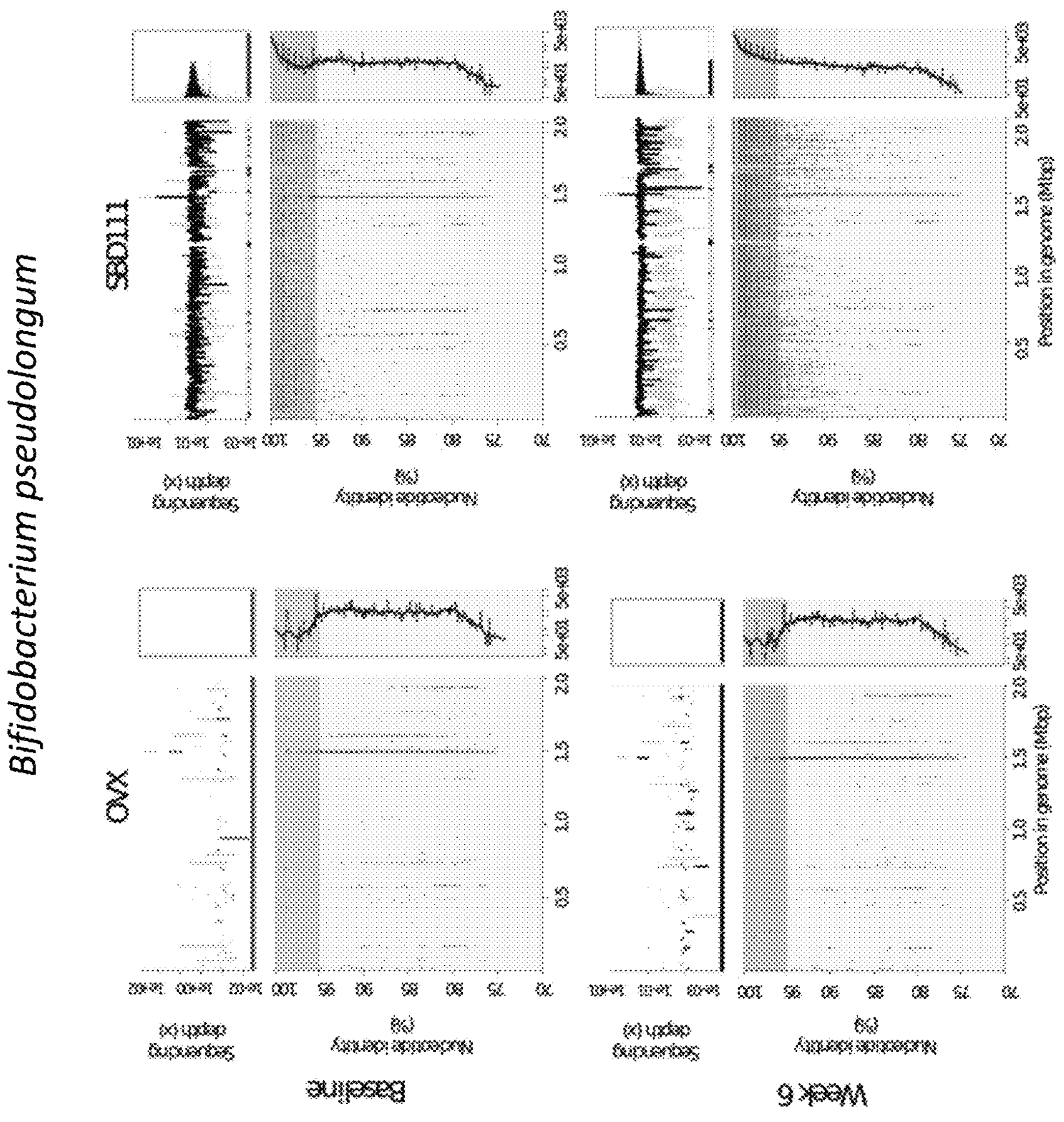
FIG. 15. Fragment recruitment plots showing fragment recruitment of the *Bifidobacterium pseudolongum* reference genome in the gut metagenomes from mice treated with OVX and SBD111 at the baseline and six-weeks post-surgery. Recruitment plots were built using scripts available at the enveomics toolbox (Rodriguez-R and Konstantinidis 2016). Table 13 shows the individuals changes in *B. pseudolongum* as seem by coverage.
Figure 16:
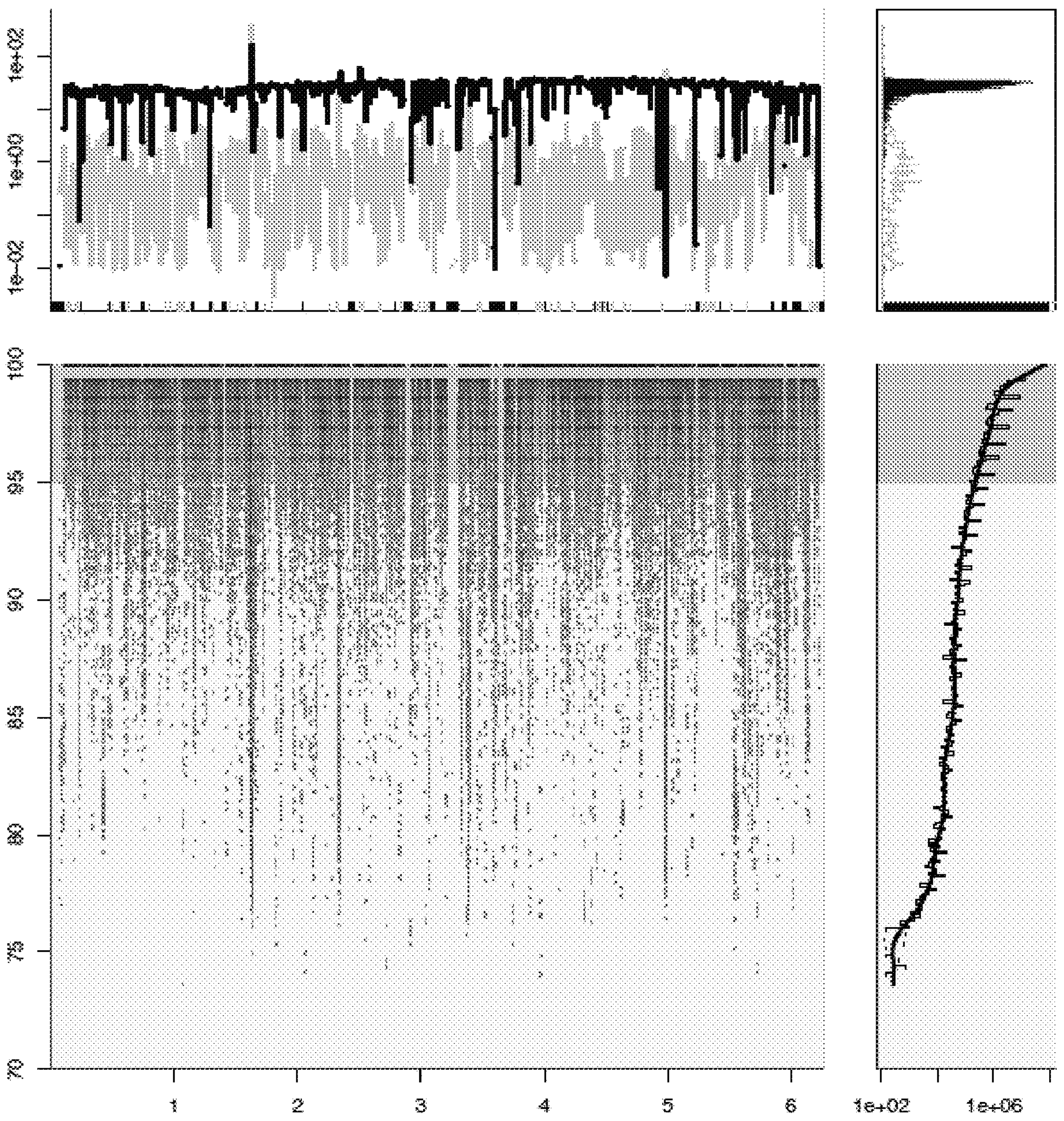
FIG. 16. Fragment recruitment plots showing fragment recruitment of the *Bifidobacterium pseudolongum* and *Lactobacillus johnsonii* reference genomes in the gut metagenomes from mice treated with SBD111 taken at the week 6 time point. These show that the microbes were present at week 6 post-surgery. The recruitment plots were built using scripts available at the enveomics toolbox (Rodriguez-R and Konstantinidis 2016).
Figure 16:
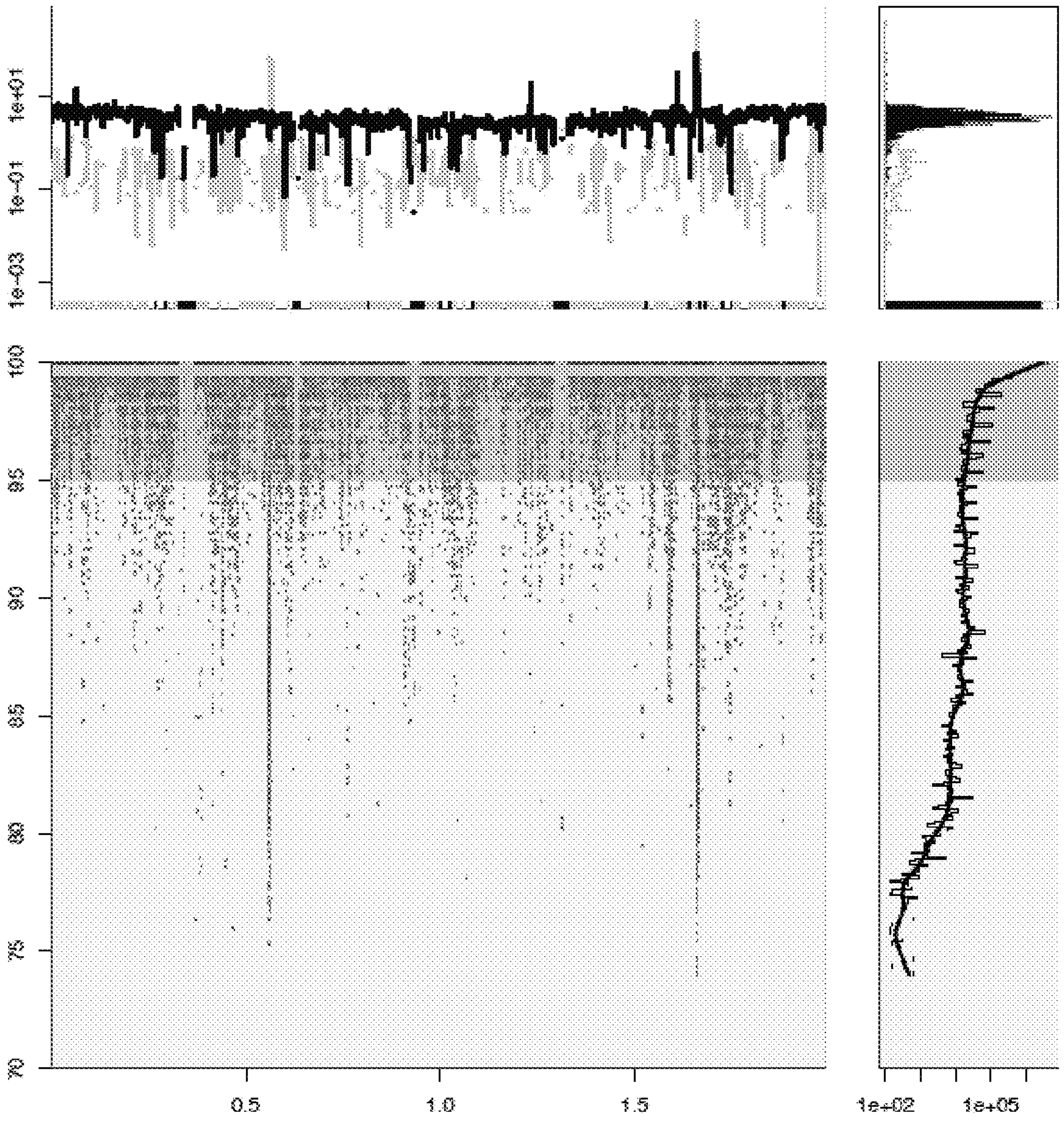
Figure 17:
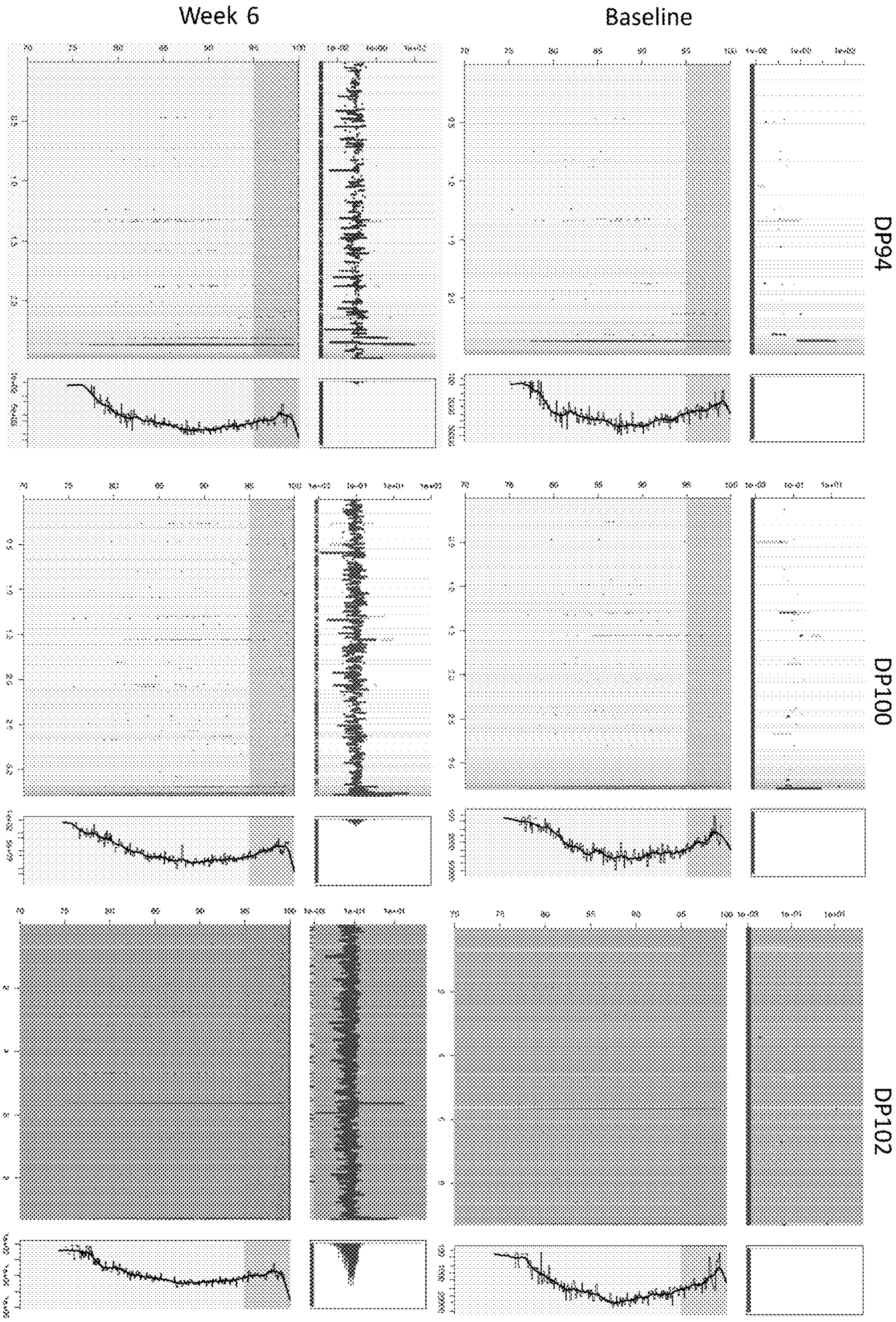
FIG. 17 Fragment recruitment of the genomes from the microbes used in SDB111 in the gut metagenomes from mice treated with SBD111 at the baseline and week 6 time points. Recruitment plots were built using scripts available at the enveomics toolbox (Rodriguez-R and Konstantinidis 2016).
Figure 18A:
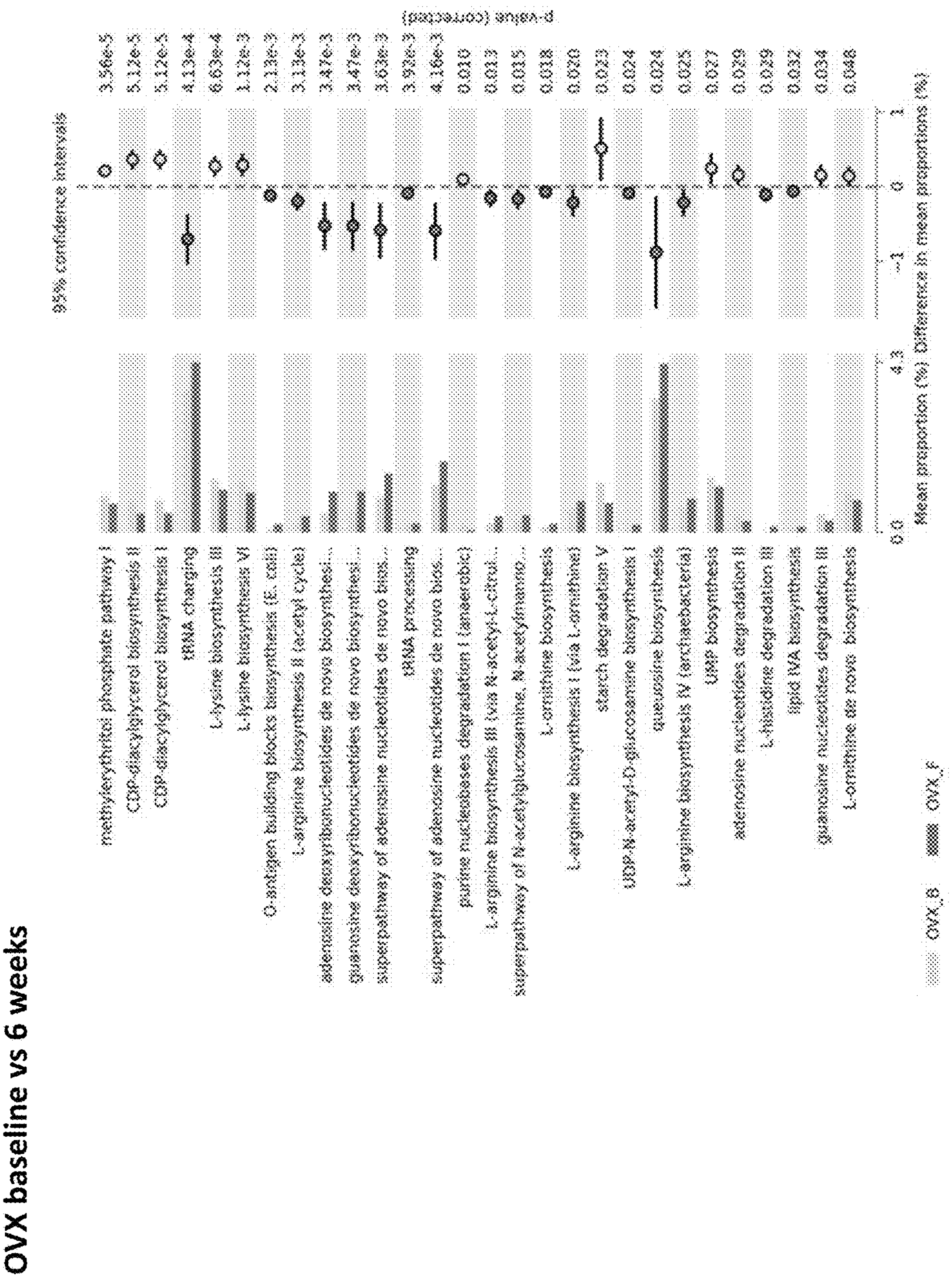
FIG. 18A Metabolic pathways significantly different between baseline and 6 weeks of treatment in OVX mice (Tukey-Kramer post-hoc test, P<0.05).
Figure 18B:
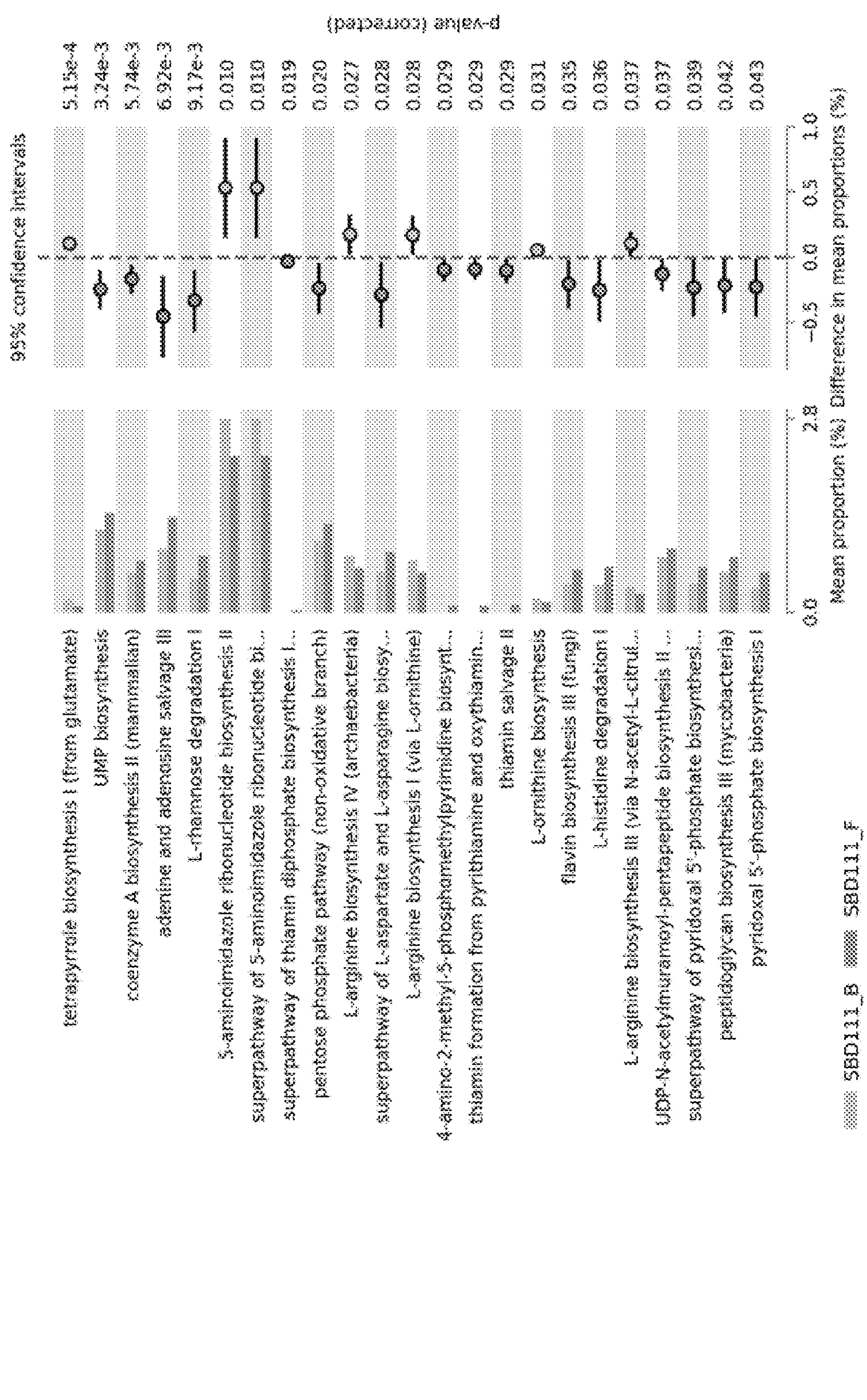
FIG. 18B Metabolic pathways significantly different between baseline and 6 weeks of treatment in SBD111-treated OVX mice (Tukey-Kramer post-hoc test, P<0.05).
Figure 18C:
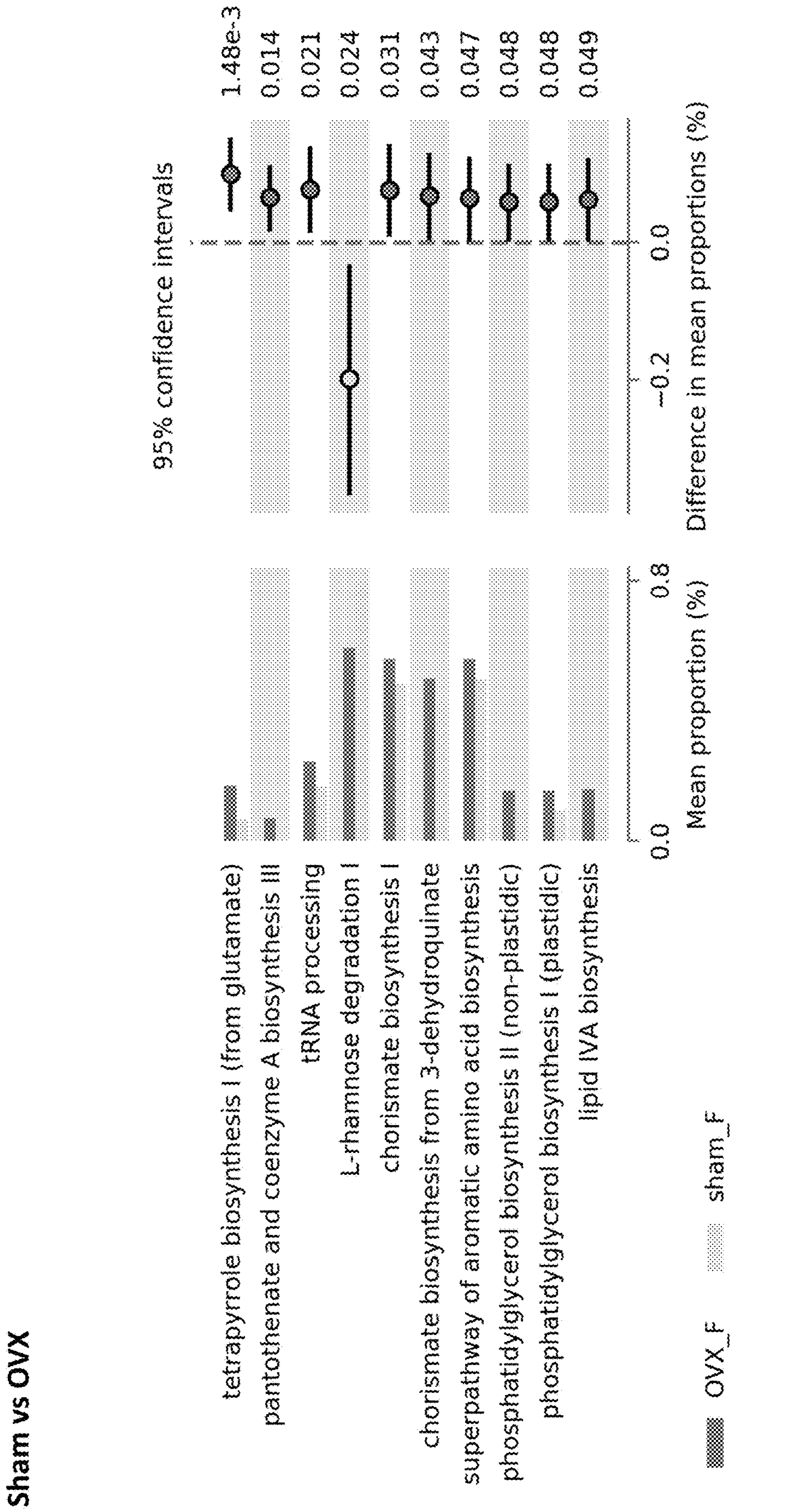
FIG. 18C Metabolic pathways significantly different between untreated OVX mice (OVX) and mice given a sham surgery (sham) after 6 weeks of treatment (Tukey-Kramer post-hoc test, P<0.05).
Figure 18D:
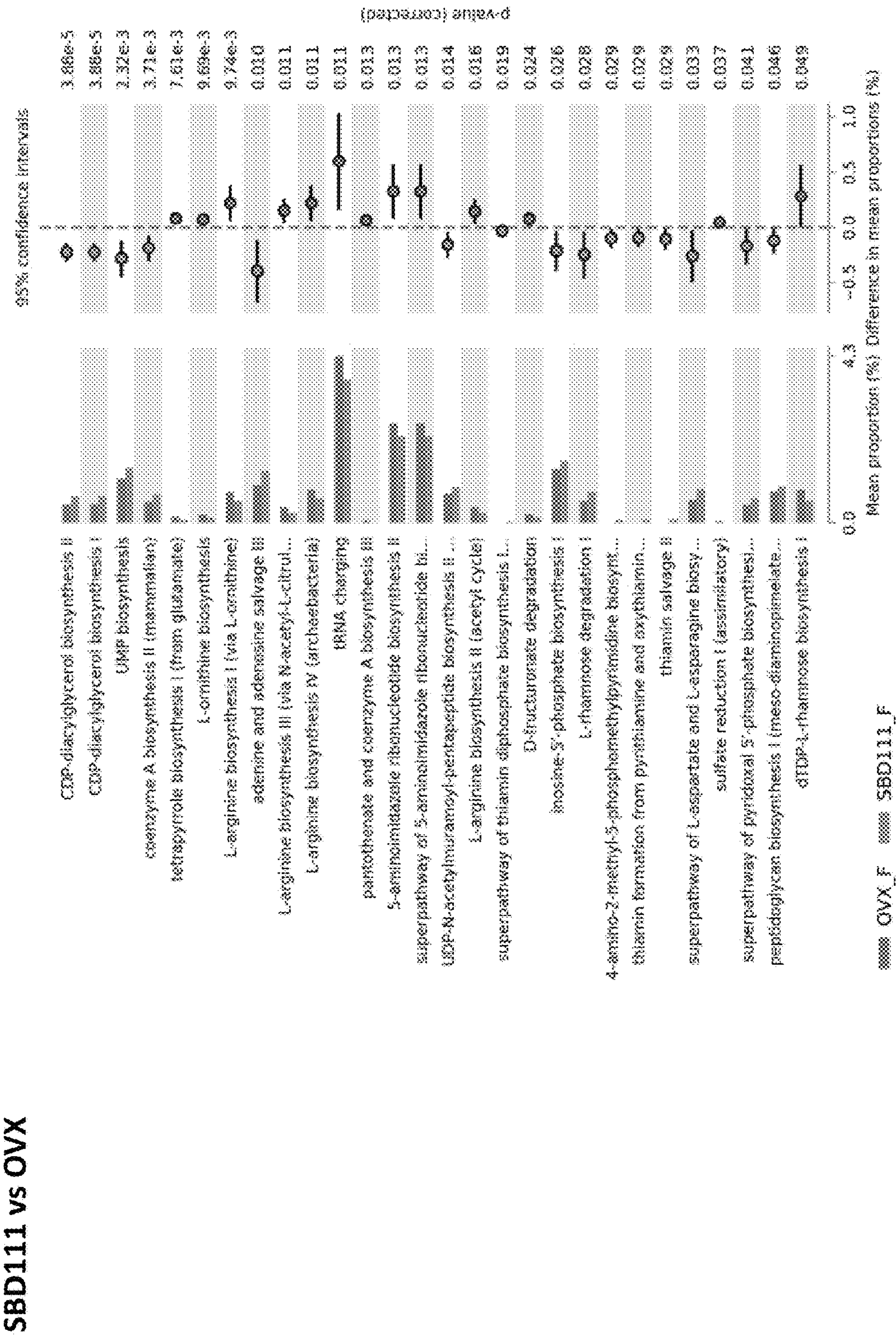
FIG. 18D Metabolic pathways significantly different between untreated OVX (OVX) mice and mice treated with SBD111 after 6 weeks of treatment (Tukey-Kramer post-hoc test, P<0.05).

Example 12: Increase in Relative Abundance and Intra-Population Diversity of *Bifidobacterium pseudolongum* in Week-6 SBD111-Treated Group FIG. 15 shows the fragment recruitment of the *Bifidobacterium pseudolongum* reference genome in the gut from SBD111-treated group at the baseline and week 6 time points. Recruitment plots were built using scripts available at the enveomics toolbox (Rodriguez-R and Konstantinidis 2016).

TABLE 13

Average coverage of *B. pseudolongum* genome in the gut metagenomes of mice treated with SBD111 at the baseline and week 6 time points.

| Subject ID | Baseline | week 6 |
|---|---|---|
| 2266 | 0.95 | 3.19 |
| 2268 | 1.32 | 3.55 |
| 2269 | 1.35 | 2.32 |
| 2270 | 2.7 | 1.37 |
| 2271 | 0.52 | 0.29 |
| 2272 | 0.69 | 3.92 |
| 2273 | 0.37 | 1.75 |
| 2274 | 0.55 | 4.32 |
| 2275 | 2.57 | 1.39 |

The fragment recruitment plot shows that *B. pseudolongum* was not present in the gut microbiome at the baseline and after 6 weeks in the ovx mouse group since metagenomic reads did not map at any nucleotide identity across the genome sequence (left panel of the plot) with an even coverage.

Opposite, the recruitment plot at the baseline of one of the mice treated with SBD111 shows that there is one *B. pseudolongum* population in the gut metagenome with genome coverage values of 0.5× and metagenomic reads mapped more than 98% nucleotide identity (dark thick line, top right panel). After 6 weeks, an increase in the abundance of this population was observed (average coverage values of 4.32×) in addition to the increase of discrete populations (light lines in the bottom panel) indicating an increase in the intra-population diversity (reads mapped between 95% and 98% nucleotide identity) of *B. pseudolongum* in the gut metagenome.

In conclusion, the SDB111-treated group showed an increase in the abundance of *B. pseudolongum* after 6 weeks (table 12) as well as the diversity of *B. pseudolongum* in the gut community. Accordingly, the results demonstrate that the administration of a SDB111 resulted in an increase in abundance and diversity of a beneficial microbial population. *Bifidobacterium pseudolongum* has been shown previously to modulate the immune system and decrease systemic inflammation. Inflammation plays a large role in osteoclastogenesis and the breakdown of bone, so the increased abundance of *Bifidobacterium pseudolongum* likely decreases systemic inflammatory mediators and thus decreases the resorption of bone, leading to improved BMD and trabecular bone volume in mice treated with SBD111 compared to OVX mice.

Example 13: Cryopreservent Demonstrating Improved Shelf Life

Cryopreservation was performed using DP53 (*Pseudomonas fragi*) under conditions using DMSO at 10% or a cryogenic buffer ("Cryobuffer") at 10% and were compared to PBS as negative control to assess viability at different timepoints after cryo storage at −80° C. A cell pellet containing 1×10^9 CFUs/ml measured by colony counts in nutrient agar media were placed in a cryogenic vial and stored at −80° C.

Figure 20:
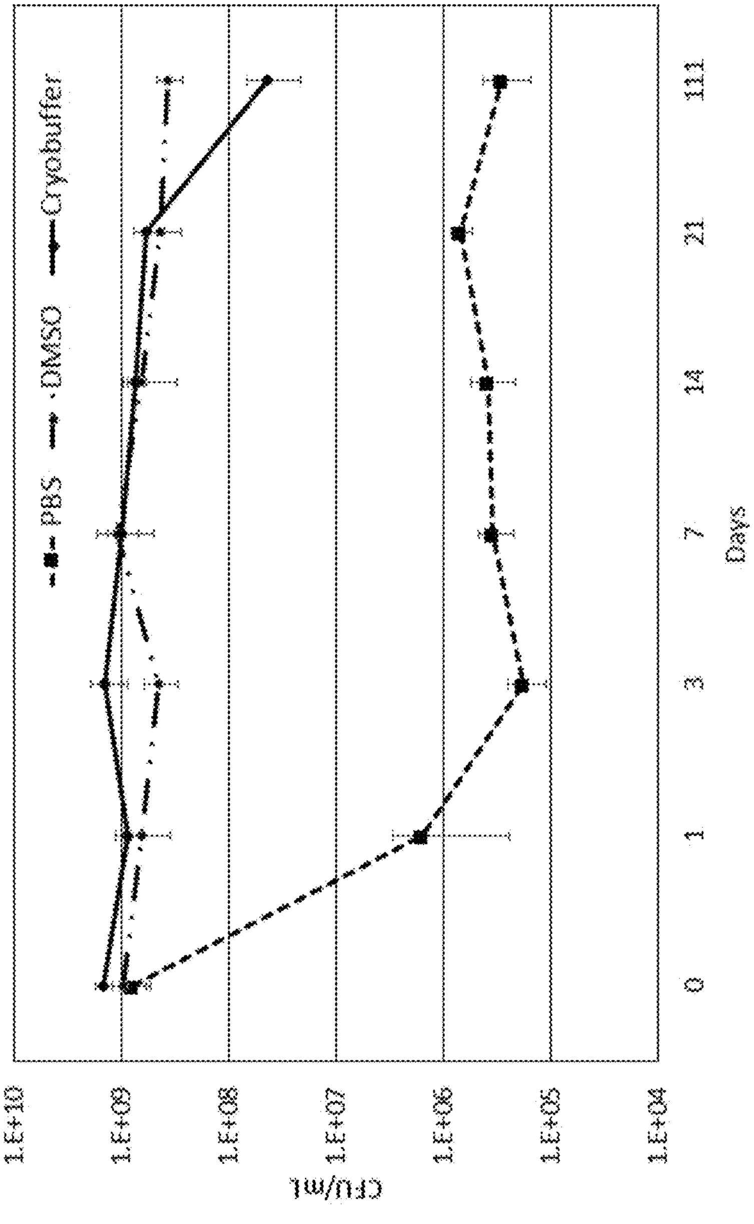
FIG. 20 shows viability at different timepoints after cryopreservation using PBS, DMSO, or Cryobuffer solutions to store bacteria.

As shown in FIG. 20, the vials with PBS without cryoprotectant showed 1×10^6 CFU/ml after 1 day while DMSO and Cryobuffer remained high. After 3 days there was further loss of viability in PBS to 1.75×10^5 CFU/ml while DMSO and Cryobuffer maintained the same titer. The vials containing DMSO generally maintained the same titer out to day 111, while the vials containing the Cryobuffer generally maintained the same titer out to day 21 and about a log difference in viability at day 111. Thus, the results demonstrate the use of cryogenic buffer enables cryopreservation and extension of shelf life. Accordingly, the use of cryogenic buffer enables cryopreservation when conducting preclinical or clinical experiments as the product can have the same amount of viable cells at different time points.

INCORPORATION BY REFERENCE

All references, issued patents, and patent applications cited within the body of the instant specification are hereby incorporated by reference in their entirety, for all purposes. Additionally, Compositions of Oligofructose and Commensal Microorganisms and Methods Thereof, WO2018170034, filed on Mar. 14, 2018 is hereby incorporated by reference.

Sequence Listing

| Seq ID No. | Description | Sequence |
|---|---|---|
| 1 | DP1 16S rRNA | AGTCAGACATGCAAGTCGAGCGGTAGAGAGAAGCTTGCTTCTCTTGA<br>GAGCGGCGGACGGGTGAGTAAAGCCTAGGAATCTGCCTGGTAGTGGG<br>GGATAACGTTCGGAAACGGACGCTAATACCGCATACGTCCTACGGGA<br>GAAAGCAGGGGACCTTCGGGCCTTGCGCTATCAGATGAGCCTAGGTC<br>GGATTAGCTAGTTGGTGAGGTAATGGCTCACCAAGGCGACGATCCGT<br>AACTGGTCTGAGAGGATGATCAGTCACACTGGAACTGAGACACGGTC<br>CAGACTCCTACGGGAGGCAGCAGTGGGGAATATTGGACAATGGGCGA<br>AAGCCTGATCCAGCCATGCCGCGTGTGTGAAGAAGGTCTTCGGATTG<br>TAAAGCACTTTAAGTTGGGAGGAAGGGCATTAACCTAATACGTTAGT<br>GTTTTGACGTTACCGACAGAATAAGCACCGGCTAACTCTGTGCCAGC<br>AGCCGCGGTAATACAGAGGGTGCAAGCGTTAATCGGAATTACTGGGC<br>GTAAAGCGCGCGTAGGTGGTTTGTTAAGTTGGATGTGAAATCCCCGG<br>GCTCAACCTGGGAACTGCATTCAAAACTGACTGACTAGAGTATGGTA<br>GAGGGTGGTGGAATTTCCTGTGTAGCGGTGAAATGCGTAGATATAGG<br>AAGGAACACCAGTGGCGAAGGCGACCACCTGGACTAATACTGACACT<br>GAGGTGCGAAAGCGTGGGGAGCAAACAGGATTAGATACCCTGGTAGT<br>CCACGCCGTAAACGATGTCAACTAGCCGTTGGGAGCCTTGAGCTCTTA<br>GTGGCGCAGCTAACGCATTAAGTTGACCGCCTGGGGAGTACGGCCGC<br>AAGGTTAAAACTCAAATGAATTGACGGGGGCCCGCACAAGCGGTGGA<br>GCATGTGGTTTAATTCGAAGCAACGCGAAGAACCTTACCAGGCCTTG<br>ACATCCAATGAACTTTCTAGAGATAGATTGGTGCCTTCGGGAACATTG<br>AGACAGGTGCTGCATGGCTGTCGTCAGCTCGTGTCGTGAGATGTTGG<br>GTTAAGTCCCGTAACGAGCGCAACCCTTGTCCTTAGTTACCAGCACGT<br>AATGGTGGGCACTCTAAGGAGACTGCCGGTGACAAACCGGAGGAAG<br>GTGGGGATGACGTCAAGTCATCATGGCCCTTACGGCCTGGGCTACAC<br>ACGTGCTACAATGGTCGGTACAGAGGGTTGCCAAGCCGCGAGGTGGA<br>GCTAATCCCATAAAACCGATCGTAGTCCGGATCGCAGTCTGCAACTC<br>GACTGCGTGAAGTCGGAATCGCTAGTAATCGCGAATCAGAATGTCGC<br>GGTGAATACGTTCCCGGGCCTTGTACACACCGCCCGTCACACCATGG<br>GAGTGGGTTGCACCAGAAGTAGCTAGTCTAACCTTCGGGAGGACGGT<br>TACCACGGTGTGATTCATGACTGGGGTGAAGTCGTAACAAGGTAGCC<br>GTAGGGGAACCTGCGGCTGGATCACCTCCTT |
| 2 | DP2 ITS sequence | TTGTTGCTCGAGTTCTTGTTTAGATCTTTTACAATAATGTGTATCTTTA<br>ATGAAGATGNGNGCTTAATTGCGCTGCTTTATTAGAGTGTCGCAGTAG<br>AAGTAGTCTTGCTTGAATCTCAGTCAACGTTTACACACATTGGAGTTT<br>TTTTACTTTAATTTAATTCTTTCTGCTTTGAATCGAAAGGTTCAAGGCA<br>AAAAACAAACACAAACAATTTTATTTTATTATAATTTTTTAAACTAAA<br>CCAAAATTCCTAACGGAAATTTTAAAATAATTTAAAACTTTCAACAAC<br>GGATCTCTTGGTTCTCGCATCGATGAAAAACGTACCGAATTGCGATAA<br>GTAATGTGAATTGCAAATACTCGTGAATCATTGAATTTTTGAACGCAC<br>ATTGCGCCCTTGAGCATTCTCAAGGGCATGCCTGTTTGAGCGTCATTT<br>CCTTCTCAAAAAATAATTTTTTATTTTTTGGTTGTGGGCGATACTCAGG<br>GTTAGCTTGAAATTGGAGACTGTTTCAGTCTTTTTTAATTCAACACTTA<br>NCTTCTTTGGAGACGCTGTTCTCGCTGTGATGTATTTATGGATTTATTC<br>GTTTTACTTTACAAGGGAAATGGTAATGTACCTTAGGCAAAGGGTTGC<br>TTTTAATATTCATCAAGTTTGACCTCAAATCAGGTAGGATTACCCGCT<br>GAACTTAAGCATATCAATAAGCGGAGGAAAAGAAACCAACTGGGATT<br>ACCTTAGTAACGGCGAGTGAAGCGGTAAAAGCTCAAATTTGAAATCT<br>GGTACTTTCAGTGCCCGAGTTGTAATTTGTAGAATTTGTCTTTGATTA<br>GGTCCTTGTCTATGTTCCTTGGAACAGGACGTCATAGAGGGTGAGANT<br>CCCGTTTGNNGAGGATACCTTTTCTCTGTANNACTTTTTCNAAGAGTC<br>GAGTTGNTTGGGAATGCAGCTCAAANNGGGTNGNAAATTCCATCTAA<br>AGCTAAATATTNGNCNAGAGACCGANAGCGACANTACAGNGATGGA<br>AAGANGAAA |
| 3 | DP3 16S rRNA | ATTGAGAGTTTGATCCTGGCTCAGGATGAACGCTGGCGGCGTGCCTA<br>ATACATGCAAGTCGAACGCACAGCGAAAGGTGCTTGCACCTTTCAAG<br>TGAGTGGCGAACGGGTGAGTAACACGTGGACAACCTGCCTCAAGGCT<br>GGGGATAACATTTGGAAACAGATGCTAATACCGAATAAAACTCAGTG<br>TCGCATGACACAAAGTTAAAAGGCGCTTTGGCGTCACCTAGAGATGG<br>ATCCGCGGTGCATTAGTTAGTTGGTGGGGTAAAGGCCTACCAAGACA<br>ATGATGCATAGCCGAGTTGAGAGACTGATCGGCCACATTGGGACTGA<br>GACACGGCCCAAACTCCTACGGGAGGCTGCAGTAGGGAATCTTCCAC<br>AATGGGCGAAAGCCTGATGGAGCAACGCCGCGTGTGTGATGAAGGCT<br>TTCGGGTCGTAAAGCACTGTTGTACGGGAAGAACAGCTAGAATAGGG<br>AATGATTTTAGTTTGACGGTACCATACCAGAAAGGGACGGCTAAATA<br>CGTGCCAGCAGCCGCGGTAATACGTATGTCCCGAGCGTTATCCGGATT<br>TATTGGGCGTAAAGCGAGCGCAGACGGTTGATTAAGTCTGATGTGAA<br>AGCCCGGAGCTCAACTCCGGAATGGCATTGGAAACTGGTTAACTTGA<br>GTGCAGTAGAGGTAAGTGGAACTCCATGTGTAGCGGTGGAATGCGTA<br>GATATATGGAAGAACACCAGTGGCGAAGGCGGCTTACTGGACTGTAA<br>CTGACGTTGAGGCTCGAAAGTGTGGGTAGCAAACAGGATTAGATACC<br>CTGGTAGTCCACACCGTAAACGATGAACACTAGGTGTTAGGAGGTTT<br>CCGCCTCTTAGTGCCGAAGCTAACGCATTAAGTGTTCCGCCTGGGGAG |

-continued

Sequence Listing

| Seq ID No. | Description | Sequence |
|---|---|---|
| | | TACGACCGCAAGGTTGAAACTCAAAGGAATTGACGGGGACCCGCACA<br>AGCGGTGGAGCATGTGGTTTAATTCGAAGCAACGCGAAGAACCTTAC<br>CAGGTCTTGACATCCTTTGAAGCTTTTAGAGATAGAAGTGTTCTCTTC<br>GGAGACAAAGTGACAGGTGGTGCATGGTCGTCGTCAGCTCGTGTCGT<br>GAGATGTTGGGTTAAGTCCCGCAACGAGCGCAACCCTTATTGTTAGTT<br>GCCAGCATTCAGATGGGCACTCTAGCGAGACTGCCGGTGACAAACCG<br>GAGGAAGGCGGGGACGACGTCAGATCATCATGCCCCTTATGACCTGG<br>GCTACACACGTGCTACAATGGCGTATACAACGAGTTGCCAACCCGCG<br>AGGGTGAGCTAATCTCTTAAAGTACGTCTCAGTTCGGATTGTAGTCTG<br>CAACTCGACTACATGAAGTCGGAATCGCTAGTAATCGCGGATCAGCA<br>CGCCGCGGTGAATACGTTCCCGGGTCTTGTACACACCGCCCGTCACAC<br>CATGGGAGTTTGTAATGCCCAAAGCCGGTGGCCTAACCTTTTAGGAA<br>GGAGCCGTCTAAGGCAGGACAGATGACTGGGGTGAAGTCGTAACAA<br>GGTAGCCGTAGGAGAACCTGCGGCTGGATCACCTCCTTT |
| 4 | DP4 16S rRNA | TTGAAGAGTTTGATCATGGCTCAGATTGAACGCTGGCGGCAGGCCTA<br>ACACATGCAAGTCGAGCGGCAGCGGAAAGTAGCTTGCTACTTTGCCG<br>GCGAGCGGCGGACGGGTGAGTAATGTCTGGGAAACTGCCTGATGGAG<br>GGGGATAACTACTGGAAACGGTAGCTAATACCGCATGACCTCGAAAG<br>AGCAAAGTGGGGGATCTTCGGACCTCACGCCATCGGATGTGCCCAGA<br>TGGGATTAGCTAGTAGGTGAGGTAATGGCTCACCTAGGCGACGATCC<br>CTAGCTGGTCTGAGAGGATGACCAGCCACACTGGAACTGAGACACGG<br>TCCAGACTCCTACGGGAGGCAGCAGTGGGGAATATTGCACAATGGGC<br>GCAAGCCTGATGCAGCCATGCCGCGTGTGTGAAGAAGGCCTTAGGGT<br>TGTAAAGCACTTTCAGCGAGGAGGAAGGCATCATACTTAATACGTGT<br>GGTGATTGACGTTACTCGCAGAAGAAGCACCGGCTAACTCCGTGCCA<br>GCAGCCGCGGTAATACGGAGGGTGCAAGCGTTAATCGGAATTACTGG<br>GCGTAAAGCGCACGCAGGCGGTTTGTTAAGTCAGATGTGAAATCCCC<br>GCGCTTAACGTGGGAACTGCATTTGAAACTGGCAAGCTAGAGTCTTG<br>TAGAGGGGGGTAGAATTCCAGGTGTAGCGGTGAAATGCGTAGAGATC<br>TGGAGGAATACCGGTGGCGAAGGCGGCCCCCTGGACAAAGACTGAC<br>GCTCAGGTGCGAAAGCGTGGGGAGCAAACAGGATTAGATACCCTGGT<br>AGTCCACGCCGTAAACGATGTCGACTTGGAGGTTGTTCCCTTGAGGA<br>GTGGCTTCCGGAGCTAACGCGTTAAGTCGACCGCCTGGGGAGTACGG<br>CCGCAAGGTTAAAACTCAAATGAATTGACGGGGGCCCGCACAAGCGG<br>TGGAGCATGTGGTTTAATTCGATGCAACGCGAAGAACCTTACCTACTC<br>TTGACATCCACGGAATTTGGCAGAGATGCCTTAGTGCCTTCGGGAACC<br>GTGAGACAGGTGCTGCATGGCTGTCGTCAGCTCGTGTTGTGAAATGTT<br>GGGTTAAGTCCCGCAACGAGCGCAACCCTTATCCTTTGTTGCCAGCGA<br>TTCGGTCGGGAACTCAAAGGAGACTGCCGGTGATAAACCGGAGGAAG<br>GTGGGGATGACGTCAAGTCATCATGGCCCTTACGAGTAGGGCTACAC<br>ACGTGCTACAATGGCGCATACAAAGAGAAGCGACCTCGCGAGAGCA<br>AGCGGACCTCACAAAGTGCGTCGTAGTCCGGATCGGAGTCTGCAACT<br>CGACTCCGTGAAGTCGGAATCGCTAGTAATCGTGGATCAGAATGCCA<br>CGGTGAATACGTTCCCGGGCCTTGTACACACCGCCCGTCACACCATGG<br>GAGTGGGTTGCAAAAGAAGTAGGTAGCTTAACCTTCGGGAGGGCGCT<br>TACCACTTTGTGATTCATGACTGGGGTGAAGTCGTAACAAGGTAACC<br>GTAGGGGAACCTGCGGTTGGATCACCTCCTT |
| 5 | DP5 ITS sequence | GCGCTTATTGCGCGGCGAAAAAACCTTACACACAGTGTTTTTTGTTAT<br>TACANNAACTTTTGCTTTGGTCTGGACTAGAAATAGTTTGGGCCAGAG<br>GTTACTAAACTAAACTTCAATATTTATATTGAATTGTTATTTATTTAAT<br>TGTCAATTTGTTGATTAAATTCAAAAAATCTTCAAAACTTTCAACAAC<br>GGATCTCTTGGTTCTCGCATCGATGAAGAACGCAGCGAAATGCGATA<br>AGTAATATGAATTGCAGATTTTCGTGAATCATCGAATCTTTGAACGCA<br>CATTGCGCCCTCTGGTATTCCAGAGGGCATGCCTGTTTGAGCGTCATT<br>TCTCTCTCAAACCTTCGGGTTTGGTATTGAGTGATACTCTTAGTCGAA<br>CTAGGCGTTTGCTTGAAATGTATTGGCATGAGTGGTACTGGATAGTGC<br>TATATGACTTTCAATGTATTAGGTTTATCCAACTCGTTGAATAGTTTA<br>ATGGTATATTTCTCGGTATTCTAGGCTCGGCCTTACAATATAACAAAC<br>AAGTTTGACCTCAAATCAGGTAGGATTACCCGCTGAACTTAAGCATAT<br>CAATAAGCGGAGGAAAAGAAACCAACAGGGATTGCCTTAGTAACGG<br>CGAGTGAAGCGGCAAAAGCTCAAATTTGAAATCTGGCACCTTCGGTG<br>TCCGAGTTGTAATTTGAAGAAGGTAACTTTGGAGTTGGCTCTTGTCTA<br>TGTTCCTTGGAACAGGACGTCACAGAGGGTGAGAATCCCGTGCGATG<br>AGATGCCCAATTCTATGTAAAGTGCTTTCGAAGAGTCGAGTTGTTTGG<br>GAATGCAGCTCTAAGTGGGTGGTAAATTCCATCTAAAGCTAAATATT<br>GGCGAGAGACCGATAGCGAACAAGTACAGTGATGGAAAGATGAAAA<br>GAACTTTGAAAAGAGAGTGAAAAAGTACGTGAAATTGTTGAAAGGG<br>AAAGGGCTTGAGATCAGACTTGGTATTTTGCGATCCTTTCCTTCTTGG<br>TTGGGTTCCTCGCAGCTTACTGGGNCAGCATCGGTTTGGATGG |

-continued

Sequence Listing

| Seq ID No. | Description | Sequence |
|---|---|---|
| 6 | DP6 16S rRNA | GAAAGGCGGCTTCGGCTGTCACTTATGGATGGACCCGCGTCGCATTA<br>GCTAGTTGGTGAGGTAACGGCTCACCAAGGCAACGATGCGTAGCCGA<br>CCTGAGAGGGTGATCGGCCACACTGGGACTGAGACACGGCCCAGACT<br>CCTACGGGAGGCAGCAGTAGGGAATCTTCCGCAATGGACGAAAGTCT<br>GACGGAGCAACGCCGCGTGAGTGATGAAGGCTTTCGGGTCGTAAAAC<br>TCTGTTGTTAGGGAAGAACAAGTGCTAGTTGAATAAGCTGCACCTTG<br>ACGGTACCTAACCAGAAAGCCACGGCTAACTACGTGCCAGCAGCCGC<br>GGTAATACGTAGGTGGCAAGCGTTATCCGGAATTATTGGGCGTAAAG<br>CGCGCGCAGGTGGTTTCTTAAGTCTGATGTGAAAGCCCACGGCTCAA<br>CCGTGGAGGGTCATTGGAAACTGGGAGACTTGAGTGCAGAAGAGGA<br>AAGTGGAATTCCATGTGTAGCGGTGAAATGCGTAGAGATATGGAGGA<br>ACACCAGTGGCGAAGGCGACTTTCTGGTCTGTAACTGACACTGAGGC<br>GCGAAAGCGTGGGGAGCAAACAGGATTAGATACCCTGGTAGTCCACG<br>CCGTAAACGATGAGTGCTAAGTGTTAGAGGGTTTCCGCCCTTTAGTGC<br>TGAAGTTAACGCATTAAGCACTCCGCCTGGGGAGTACGGCCGCAAGG<br>CTGAAACTCAAAGGAATTGACGGGGGCCCGCACAAGCGGTGGAGCAT<br>GTGGTTTAATTCGAAGCAACGCGAAGAACCTTACCAGGTCTTGACAT<br>CCTCTGAAAACCCTAGAGATAGGGCTTCTCCTTCGGGAGCAGAGTGA<br>CAGGTGGTGCATGGTTGTCGTCAGCTCGTGTCGTGAGATGTTGGGTTA<br>AGTCCCGCAACGAGCGCAACCCTTGATCTTAGTTGCCATCATTAAGTT<br>GGGCACTCTAAGGTGACTGCCGGTGACAAACCGGAGGAAGGTGGGG<br>ATGACGTCAAATCATCATGCCCCTTATGACCTGGGCTACACACGTGCT<br>ACAATGGACGGTACAAAGAGCTGCAAGACCGCGAGGTGGAGCTAAT<br>CTCATAAAACCGTTCTCAGTTCGGATTGTAGGCTGCAACTCGCCTACA<br>TGAAGCTGGAATCGCTAGTAATCGCGGATCAGCAT |
| 7 | DP7 ITS | CCACNCTGCGTGGGCGACACGAAACACCGAAACCGAACGCACGCCGT<br>CAAGCAAGAAATCCACAAAACTTTCAACAACGGATCTCTTGGTTCTC<br>GCATCGATGAAGAGCGCAGCGAAATGCGATACCTAGTGTGAATTGCA<br>GCCATCGTGAATCATCGAGTTCTTGAACGCACATTGCGCCCGCTGGTA<br>TTCCGGCGGGCATGCCTGTCTGAGCGTCGTTTCCTTCTTGGAGCGGAG<br>CTTCAGACCTGGCGGGCTGTCTTTCGGGACGGCGCGCCCAAAGCGAG<br>GGGCCTTCTGCGCGAACTAGACTGTGCGCGCGGGGCGGCCGGCGAAC<br>TTATACCAAGCTCGACCTCAGATCAGGCAGGAGTACCCGCTGAACTT<br>AAGCATATCAATAAGCGGAGGAAAAGAAACCAACAGGGATTGCCCC<br>AGTAGCGGCGAGTGAAGCGGCAAAAGCTCAGATTTGGAATCGCTTCG<br>GCGAGTTGTGAATTGCAGGTTGGCGCCTCTGCGGCGGCGGCGGTCCA<br>AGTCCCTTGGAACAGGGCGCCATTGAGGGTGAGAGCCCCGTGGGACC<br>GTTTGCCTATGCTCTGAGGCCCTTCTGACGAGTCGAGTTGTTTGGGAA<br>TGCAGCTCTAAGCGGGTGGTAAATTCCATCTAAGGCTAAATACTGGC<br>GAGAGACCGATAGCGAACAAGTACTGTGAAGGAAAGATGAAAAGCA<br>CTTTGAAAAGAGAGTGAAACAGCACGTGAAATTGTTGAAAGGGAAG<br>GGTATTGCGCCCGACATGGAGCGTGCGCACCGCTGCCCCTCGTGGGC<br>GGCGCTCTGGGCGTGCTCTGGGCCAGCATCGGTTTTTGCCGCGGGAG<br>AAGGGCGGCGGGCATGTAGCTCTTC |
| 8 | DP8 ITS | GTTGCTCGAGTTCTTGTTTAGATCTTTTACNATAATGTGTATCTTTAAT<br>GAAGATGTGCGCTTAATTGCGCTGCTTTATTAGAGTGTCGCAGTAGAA<br>GTAGTCTTGCTTGAATCTCAGTCAACGTTTACACACATTGGAGTTTTTT<br>TACTTTAATTTAATTCTTTCTGCTTTGAATCGAAAGGTTCAAGGCAAA<br>AAACAAACACAAACAATTTTATTTTATTATAATTTTTTAAACTAAACC<br>AAAATTCCTAACGGAAATTTTAAAATAATTTAAAACTTTCAACAACG<br>GATCTCTTGGTTCTCGCATCGATGAAAAACGTAGCGAATTGCGATAA<br>GTAATGTGAATTGCAAATACTCGTGAATCATTGAATTTTTGAACGCAC<br>ATTGCGCCCTTGAGCATTCTCAAGGGCATGCCTGTTTGAGCGTCATTT<br>CCTTCTCAAAAGATAATTTTTTATTTTTTGGTTGTGGGCGATACTCAGG<br>GTTAGCTTGAAATTGGAGACTGTTTCAGTCTTTTTTAATTCAACACTTA<br>NCTTCTTTGGAGACGCTGTTCTCGCTGTGATGTATTTATGGATTTATTC<br>GTTTTACTTTACAAGGGAAATGGTAATGTACCTTAGGCAAAGGGTTGC<br>TTTTAATATTCATCAAGTTTGACCTCAAATCAGGTAGGATTACCCGCT<br>GAACTTAAGCATATCAATAAGCGGAGGAAAAGAAACCAACTGGGATT<br>ACCTTAGTAACGGCGAGTGAAGCGGTAAAAGCTCAAATTTGAAATCT<br>GGTACTTTCANNGCCCGAGTTGTAATTTGTAGAATTTGTCTTTGATTA<br>GGTCCTTGTCTATGTTCCTTGGANCAGGACGTCATANAGGGTGANTCC<br>CNTTTGGCGANGANACCTTTTCTCTGTANACTTTTTCNANAGTCGAGT<br>TGTTTNGGATGCAGCTCNAAGTGGGGNGG |
| 9 | DP9 16S rRNA | ATGAGAGTTTGATCTTGGCTCAGGATGAACGCTGGCGGCGTGCCTAA<br>TACATGCAAGTCGAACGAACTTCCGTTAATTGATTATGACGTACTTGT<br>ACTGATTGAGATTTTAACACGAAGTGAGTGGCGAACGGGTGAGTAAC<br>ACGTGGGTAACCTGCCCAGAAGTAGGGGATAACACCTGGAAACAGAT<br>GCTAATACCGTATAACAGAGAAAACCGCATGGTTTTCTTTTAAAAGAT |

-continued

Sequence Listing

| Seq ID No. | Description | Sequence |
|---|---|---|
| | | GGCTCTGCTATCACTTCTGGATGGACCCGCGGCGTATTAGCTAGTTGG<br>TGAGGCAAAGGCTCACCAAGGCAGTGATACGTAGCCGACCTGAGAGG<br>GTAATCGGCCACATTGGGACTGAGACACGGCCCAGACTCCTACGGGA<br>GGCAGCAGTAGGGAATCTTCCACAATGGACGCAAGTCTGATGGAGCA<br>ACGCCGCGTGAGTGAAGAAGGGTTTCGGCTCGTAAAGCTCTGTTGTT<br>AAAGAAGAACGTGGGTAAGAGTAACTGTTTACCCAGTGACGGTATTT<br>AACCAGAAAGCCACGGCTAACTACGTGCCAGCAGCCGCGGTAATACG<br>TAGGTGGCAAGCGTTATCCGGATTTATTGGGCGTAAAGCGAGCGCAG<br>GCGGTCTTTTAAGTCTAATGTGAAAGCCTTCGGCTCAACCGAAGAAGT<br>GCATTGGAAACTGGGAGACTTGAGTGCAGAAGAGGACAGTGGAACTC<br>CATGTGTAGCGGTGAAATGCGTAGATATATGGAAGAACACCAGTGGC<br>GAAGGCGGCTGTCTGGTCTGCAACTGACGCTGAGGCTCGAAAGCATG<br>GGTAGCGAACAGGATTAGATACCCTGGTAGTCCATGCCGTAAACGAT<br>GATTACTAAGTGTTGGAGGGTTTCCGCCCTTCAGTGCTGCAGCTAACG<br>CATTAAGTAATCCGCCTGGGGAGTACGACCGCAAGGTTGAAACTCAA<br>AAGAATTGACGGGGGCCCGCACAAGCGGTGGAGCATGTGGTTTAATT<br>CGAAGCTACGCGAAGAACCTTACCAGGTCTTGACATCTTCTGACAGTC<br>TAAGAGATTAGAGGTTCCCTTCGGGGACAGAATGACAGGTGGTGCAT<br>GGTTGTCGTCAGCTCGTGTCGTGAGATGTTGGGTTAAGTCCCGCAACG<br>AGCGCAACCCTTATTACTAGTTGCCAGCATTAAGTTGGGCACTCTAGT<br>GAGACTGCCGGTGACAAACCGGAGGAAGGTGGGGACGACGTCAAAT<br>CATCATGCCCCTTATGACCTGGGCTACACACGTGCTACAATGGATGGT<br>ACAACGAGTCGCGAGACCGCGAGGTTAAGCTAATCTCTTAAAACCAT<br>TCTCAGTTCGGACTGTAGGCTGCAACTCGCCTACACGAAGTCGGAATC<br>GCTAGTAATCGCGGATCAGCATGCCGCGGTGAATACGTTCCCGGGCC<br>TTGTACACACCGCCCGTCACACCATGAGAGTTTGTAACACCCAAAGC<br>CGGTGGGGTAACCTTTTAGGAGCTAGCCGTCTAAGGTGGGACAGATG<br>ATTAGGGTGAAGTCGTAACAAGGTAGCCGTAGGAGAACCTGCGGCTG<br>GATCACCTCCTT |
| 10 | DP10 16S rRNA | CAGATAGTTGGTGAGGTAACGGCTCACCAAGGCAACGATGCGTAGCC<br>GACCTGAGAGGGTGATCGGCCACACTGGGACTGAGACACGGCCCAGA<br>CTCCTACGGGAGGCAGCAGTAGGGAATCTTCCGCAATGGACGAAAGT<br>CTGACGGAGCAACGCCGCGTGAGTGATGAAGGTTTTCGGATCGTAAA<br>GCTCTGTTGTTAGGGAAGAACAAGTGCCGTTCAAATAGGGCGGCACC<br>TTGACGGTACCTAACCAGAAAGCCACGGCTAACTACGTGCCAGCAGC<br>CGCGGTAATACGTAGGTGGCAAGCGTTGTCCGGAATTATTGGGCGTA<br>AAGGGCTCGCAGGCGGTTTCTTAAGTCTGATGTGAAAGCCCCCGGCT<br>CAACCGGGGAGGGTCATTGGAAACTGGGGAACTTGAGTGCAGAAGA<br>GGAGAGTGGAATTCCACGTGTAGCGGTGAAATGCGTAGAGATGTGGA<br>GGAACACCAGTGGCGAAGGCGACTCTCTGGTCTGTAACTGACGCTGA<br>GGAGCGAAAGCGTGGGGAGCGAACAGGATTAGATACCCTGGTAGTCC<br>ACGCCGTAAACGATGAGTGCTAAGTGTTAGGGGGTTTCCGCCCCTTA<br>GTGCTGCAGCTAACGCATTAAGCACTCCGCCTGGGGAGTACGGTCGC<br>AAGACTGAAACTCAAAGGAATTGACGGGGGCCCGCACAAGCGGTGG<br>AGCATGTGGTTTAATTCGAAGCAACGCGAAGAACCTTACCAGGTCTT<br>GACATCCTCTGACAATCCTAGAGATAGGACGTCCCCTTCGGGGGCAG<br>AGTGACAGGTGGTGCATGGTTGTCGTCAGCTCGTGTCGTGAGATGTTG<br>GGTTAAGTCCCGCAACGAGCGCAACCCTTGATCTTAGTTGCCAGCATT<br>CAGTTGGGCACTCTAAGGTGACTGCCGGTGACAAACCGGAGGAAGGT<br>GGGGATGACGTCAAATCATCATGCCCCTTATGACCTGGGCTACACAC<br>GTGCTACAATGGACAGAACAAAGGGCAGCGAAACCGCGAGGTTAAG<br>CCAATCCCACAAATCTGTTCTCAGTTCGGATCGCAGTCTGCAACTCGA<br>CTGCGTGAAGCTGGAATCGCTAGTAATCGCGGATCAGCATGCCGCGG<br>TGAATACGTTCCCGGGCCTTGTACACACCGCCCGTCACACCACGAGA<br>GTTTGTAACACCCGAAGTCGGTGAGGTAACCTTTTAGGAGCCAGCCG<br>CCGAAGGTGGGACAGATGATTGGGGTGAAGTCGTAACAAGGTAGCCG<br>TATCGGAAGGTGCGGCTGGATCACCTCCTTT |
| 11 | DP11 16S rRNA | TGAAGAGTTTGATCATGGCTCAGATTGAACGCTGGCGGCAGGCCTAA<br>CACATGCAAGTCGAGCGGTAGAGAGAAGCTTGCTTCTCTTGAGAGCG<br>GCGGACGGGTGAGTAATGCCTAGGAATCTGCCTGGTAGTGGGGGATA<br>ACGTTCGGAAACGGACGCTAATACCGCATACGTCCTACGGGAGAAAG<br>CAGGGGACCTTCGGGCCTTGCGCTATCAGATGAGCCTAGGTCGGATT<br>AGCTAGTTGGTGAGGTAATGGCTCACCAAGGCGACGATCCGTAACTG<br>GTCTGAGAGGATGATCAGTCACACTGGAACTGAGACACGGTCCAGAC<br>TCCTACGGGAGGCAGCAGTGGGGAATATTGGACAATGGGCGAAAGCC<br>TGATCCAGCCATGCCGCGTGTGTGAAGAAGGTCTTCGGATTGTAAAG<br>CACTTTAAGTTGGGAGGAAGGGTTGTAGATTAATACTCTGCAATTTTG<br>ACGTTACCGACAGAATAAGCACCGGCTAACTCTGTGCCAGCAGCCGC<br>GGTAATACAGAGGGTGCAAGCGTTAATCGGAATTACTGGGCGTAAAG<br>CGCGCGTAGGTGGTTCGTTAAGTTGGATGTGAAAGCCCCGGGCTCAA<br>CCTGGGAACTGCATTCAAAACTGACGAGCTAGAGTATGGTAGAGGGT |

-continued

Sequence Listing

| Seq ID No. | Description | Sequence |
|---|---|---|
| | | GGTGGAATTTCCTGTGTAGCGGTGAAATGCGTAGATATAGGAAGGAA<br>CACCAGTGGCGAAGGCGACCACCTGGACTGATACTGACACTGAGGTG<br>CGAAAGCGTGGGGAGCAAACAGGATTAGATACCCTGGTAGTCCACGC<br>CGTAAACGATGTCAACTAGCCGTTGGAATCCTTGAGATTTTAGTGGCG<br>CAGCTAACGCATTAAGTTGACCGCCTGGGGAGTACGGCCGCAAGGTT<br>AAAACTCAAATGAATTGACGGGGGCCCGCACAAGCGGTGGAGCATGT<br>GGTTTAATTCGAAGCAACGCGAAGAACCTTACCAGGCCTTGACATCC<br>AATGAACTTTCCAGAGATGGATGGGTGCCTTCGGGAACATTGAGACA<br>GGTGCTGCATGGCTGTCGTCAGCTCGTGTCGTGAGATGTTGGGTTAAG<br>TCCCGTAACGAGCGCAACCCTTGTCCTTAGTTACCAGCACGTTATGGT<br>GGGCACTCTAAGGAGACTGCCGGTGACAAACCGGAGGAAGGTGGGG<br>ATGACGTCAAGTCATCATGGCCCTTACGGCCTGGGCTACACACGTGCT<br>ACAATGGTCGGTACAAAGGGTTGCCAAGCCGCGAGGTGGAGCTAATC<br>CCATAAAACCGATCGTAGTCCGGATCGCAGTCTGCAACTCGACTGCG<br>TGAAGTCGGAATCGCTAGTAATCGCGAATCAGAATGTCGCGGTGAAT<br>ACGTTCCCGGGCCTTGTACACACCGCCCGTCACATCCCACACGAATTG<br>CTTG |
| 12 | DP12 16S rRNA | TACGGAGAGTTTGATCCTGGCTCAGGATGAACGCTGGCGGCGTGCTT<br>AACACATGCAAGTCGAACGGTGAAGCCAAGCTTGCTTGGTGGATCAG<br>TGGCGAACGGGTGAGTAACACGTGAGCAACCTGCCCTGGACTCTGGG<br>ATAAGCGCTGGAAACGGCGTCTAATACTGGATATGAGCCTTCATCGC<br>ATGGTGGGGGTTGGAAAGATTTTTTGGTCTGGGATGGGCTCGCGGCCT<br>ATCAGCTTGTTGGTGAGGTAATGGCTCACCAAGGCGTCGACGGGTAG<br>CCGGCCTGAGAGGGTGACCGGCCACACTGGGACTGAGACACGGCCCA<br>GACTCCTACGGGAGGCAGCAGTGGGGAATATTGCACAATGGGCGAAA<br>GCCTGATGCAGCAACGCCGCGTGAGGGATGACGGCCTTCGGGTTGTA<br>AACCTCTTTTAGCAGGGAAGAAGCGAAAGTGACGGTACCTGCAGAAA<br>AAGCGCCGGCTAACTACGTGCCAGCAGCCGCGGTAATACGTAGGGCG<br>CAAGCGTTATCCGGAATTATTGGGCGTAAAGAGCTCGTAGGCGGTTT<br>GTCGCGTCTGCTGTGAAATCCCGAGGCTCAACCTCGGGCCTGCAGTG<br>GGTACGGGCAGACTAGAGTGCGGTAGGGGAGATTGGAATTCCTGGTG<br>TAGCGGTGGAATGCGCAGATATCAGGAGGAACACCGATGGCGAAGG<br>CAGATCTCTGGGCCGTAACTGACGCTGAGGAGCGAAAGGGTGGGGAG<br>CAAACAGGCTTAGATACCCTGGTAGTCCACCCCGTAAACGTTGGGAA<br>CTAGTTGTGGGGACCATTCCACGGTTTCCGTGACGCAGCTAACGCATT<br>AAGTTCCCCGCCTGGGGAGTACGGCCGCAAGGCTAAAACTCAAAGGA<br>ATTGACGGGGACCCGCACAAGCGGCGGAGCATGCGGATTAATTCGAT<br>GCAACGCGAAGAACCTTACCAAGGCTTGACATACACCAGAACGGGCC<br>AGAAATGGTCAACTCTTTGGACACTGGTGAACAGGTGGTGCATGGTT<br>GTCGTCAGCTCGTGTCGTGAGATGTTGGGTTAAGTCCCGCAACGAGC<br>GCAACCCTCGTTCTATGTTGCCAGCACGTAATGGTGGGAACTCATGGG<br>ATACTGCCGGGGTCAACTCGGAGGAAGGTGGGGATGACGTCAAATCA<br>TCATGCCCCTTATGTCTTGGGCTTCACGCATGCTACAATGGCCGGTAC<br>AAAGGGCTGCAATACCGTGAGGTGGAGCGAATCCCAAAAAGCCGGTC<br>CCAGTTCGGATTGAGGTCTGCAACTCGACCTCATGAAGTCGGAGTCG<br>CTAGTAATCGCAGATCAGCAACGCTGCGGTGAATACGTTCCCGGGTC<br>TTGTACACACCGCCCGTCAAGTCATGAAAGTCGGTAACACCTGAAGC<br>CGGTGGCCCAACCCTTGTGGAGGGAGCCGTCGAAGGTGGGATCGGTA<br>ATTAGGACTAAGTCGTAACAAGGTAGCCGTACCGGAAGGTGCGGCTG<br>GATCACCTCCTTT |
| 13 | DP13 16S rRNA | AGTTAGCGGCGGACGGGTGAGTAACACGTGGGTAACCTGCCTATAAG<br>ACTGGGATAACTCCGGGAAACCGGGGCTAATACCGGATAACATTTTG<br>CACCGCATGGTGCGAAATTGAAAGGCGGCTTCGGCTGTCACTTATAG<br>ATGGACCTGCGGCGCATTAGCTAGTTGGTGAGGTAACGGCTCACCAA<br>GGCGACGATGCGTAGCCGACCTGAGAGGGTGATCGGCCACACTGGGA<br>CTGAGACACGGCCCAGACTCCTACGGGAGGCAGCAGTAGGGAATCTT<br>CCGCAATGGACGAAAGTCTGACGGAGCAACGCCGCGTGAACGATGA<br>AGGCTTTCGGGTCGTAAAGTTCTGTTGTTAGGGAAGAACAAGTGCTA<br>GTTGAATAAGCTGGCACCTTGACGGTACCTAACCAGAAAGCCACGGC<br>TAACTACGTGCCAGCAGCCGCGGTAATACGTAGGTGGCAAGCGTTAT<br>CCGGAATTATTGGGCGTAAAGCGCGCGCAGGTGGTTTCTTAAGTCTG<br>ATGTGAAAGCCCACGGCTCAACCGTGGAGGGTCATTGGAAACTGGGA<br>GACTTGAGTGCAGAAGAGGAAAGTGGAATTCCATGTGTAGCGGTGAA<br>ATGCGTAGAGATATGGAGGAACACCAGTGGCGAAGGCGACTTTCTGG<br>TCTGCAACTGACACTGAGGCGCGAAAGCGTGGGGAGCAAACAGGATT<br>AGATACCCTGGTAGTCCACGCCGTAAACGATGAGTGCTAAGTGTTAG<br>AGGGTTTCCGCCCTTTAGTGCTGAAGTTAACGCATTAAGCACTCCGCC<br>TGGGGAGTACGGCCGCAAGGCTGAAACTCAAAGGAATTGACGGGGG<br>CCCGCACAAGCGGTGGAGCATGTGGTTTAATTCGAAGCAACGCGAAG<br>AACCTTACCAGGTCTTGACATCCTCTGAAAACCCTAGAGATAGGGCTT<br>CCCCTTCGGGGGCAGAGTGACAGGTGGTGCATGGTTGTCGTCAGCTC |

-continued

Sequence Listing

| Seq ID No. | Description | Sequence |
|---|---|---|
| | | GTGTCGTGAGATGTTGGGTTAAGTCCCGCAACGAGCGCAACCCTTGA<br>TCTTAGTTGCCATCATTAAGTTGGGCACTCTAAGGTGACTGCCGGTGA<br>CAAACCGGAGGAAGGTGGGGATGACGTCAAATCATCATGCCCCTTAT<br>GACCTGGGCTACACACGTGCTACAATGGACGGTACAAAGAGTCGCAA<br>GACCGCGAGGTGGAGCTAATCTCATAAAACCGTTCTCAGTTCGGATT<br>GTAGGCTGCAACTCGCCTACATGAAGCTGGAATCGCTAGTAATCGCG<br>GATCAGCATGCCGCGGTGAATACGTTCCCGGGCCTTGTACACACCGC<br>CCGTCACACCACGAGAGTTTGTAACACCCGAAGTCGGTGGGGTAACC<br>TTTTGGAGCCAGCCGCCTAAGGTGGGACAGATGATTGGGGTGAAGTC<br>GTAACAAGGTAGCCGTATCGGAAGGTGCGGCTGGATCACCTCCTTT |
| 14 | DP1416S rRNA | TACGGAGAGTTTGATCCTGGCTCAGGATGAACGCTGGCGGCGTGCTT<br>AACACATGCAAGTCGAACGATGACTTCTGTGCTTGCACAGAATGATT<br>AGTGGCGAACGGGTGAGTAACACGTGAGTAACCTGCCCTTAACTTCG<br>GGATAAGCCTGGGAAACCGGGTCTAATACCGGATACGACCTCCTGGC<br>GCATGCCATGGTGGTGGAAAGCTTTAGCGGTTTTGGATGGACTCGCG<br>GCCTATCAGCTTGTTGGTTGGGGTAATGGCCCACCAAGGCGACGACG<br>GGTAGCCGGCCTGAGAGGGTGACCGGCCACACTGGGACTGAGACACG<br>GCCCAGACTCCTACGGGAGGCAGCAGTGGGGAATATTGCACAATGGG<br>CGAAAGCCTGATGCAGCGACGCCGCGTGAGGGATGACGGCCTTCGGG<br>TTGTAAACCTCTTTCAGCAGGGAAGAAGCGAAAGTGACGGTACCTGC<br>AGAAGAAGCGCCGGCTAACTACGTGCCAGCAGCCGCGGTAATACGTA<br>GGGCGCAAGCGTTATCCGGAATTATTGGGCGTAAAGAGCTCGTAGGC<br>GGTTTGTCGCGTCTGCTGTGAAAGCCCGGGGCTCAACCCCGGGTCTGC<br>AGTGGGTACGGGCAGACTAGAGTGCAGTAGGGGAGACTGGAATTCCT<br>GGTGTAGCGGTGAAATGCGCAGATATCAGGAGGAACACCGATGGCG<br>AAGGCAGGTCTCTGGGCTGTAACTGACGCTGAGGAGCGAAAGCATGG<br>GGAGCGAACAGGATTAGATACCCTGGTAGTCCATGCCGTAAACGTTG<br>GGCACTAGGTGTGGGGGACATTCCACGTTTTCCGCGCCGTAGCTAAC<br>GCATTAAGTGCCCCGCCTGGGGAGTACGGCCGCAAGGCTAAAACTCA<br>AAGGAATTGACGGGGGCCCGCACAAGCGGCGGAGCATGCGGATTAA<br>TTCGATGCAACGCGAAGAACCTTACCAAGGCTTGACATGAACCGGTA<br>AGACCTGGAAACAGGTCCCCCACTTGTGGCCGGTTTACAGGTGGTGC<br>ATGGTTGTCGTCAGCTCGTGTCGTGAGATGTTGGGTTAAGTCCCGCAA<br>CGAGCGCAACCCTCGTTCTATGTTGCCAGCGGGTTATGCCGGGGACTC<br>ATAGGAGACTGCCGGGGTCAACTCGGAGGAAGGTGGGGACGACGTC<br>AAATCATCATGCCCCTTATGTCTTGGGCTTCACGCATGCTACAATGGC<br>CGGTACAAAGGGTTGCGATACTGTGAGGTGGAGCTAATCCCAAAAAG<br>CCGGTCTCAGTTCGGATTGAGGTCTGCAACTCGACCTCATGAAGTTGG<br>AGTCGCTAGTAATCGCAGATCAGCAACGCTGCGGTGAATACGTTCCC<br>GGGCCTTGTACACACCGCCCGTCAAGTCACGAAAGTTGGTAACACCC<br>GAAGCCGGTGGCCTAACCCCTTGTGGGAGGGAGCCGTCGAAGGTGGG<br>ACCGGCGATTGGGACTAAGTCGTAACAAGGTAGCCGTACCGGAAGGT<br>GCGGCTGGATCACCTCCTTT |
| 15 | DP15 16S rRNA | TACGGAGAGTTTGATCCTGGCTCAGGACGAACGCTGGCGGCGTGCTT<br>AACACATGCAAGTCGAACGATGATCAGGAGCTTGCTCCTGTGATTAG<br>TGGCGAACGGGTGAGTAACACGTGAGTAACCTGCCCCTGACTCTGGG<br>ATAAGCGTTGGAAACGACGTCTAATACTGGATATGATCACTGGCCGC<br>ATGGTCTGGTGGTGGAAAGATTTTTTGGTTGGGGATGGACTCGCGGCC<br>TATCAGCTTGTTGGTGAGGTAATGGCTCACCAAGGCGACGACGGGTA<br>GCCGGCCTGAGAGGGTGACCGGCCACACTGGGACTGAGACACGGCCC<br>AGACTCCTACGGGAGGCAGCAGTGGGGAATATTGCACAATGGGCGAA<br>AGCCTGATGCAGCAACGCCGCGTGAGGGATGACGGCCTTCGGGTTGT<br>AAACCTCTTTTAGTAGGGAAGAAGCGAAAGTGACGGTACCTGCAGAA<br>AAAGCACCGGCTAACTACGTGCCAGCAGCCGCGGTAATACGTAGGGT<br>GCAAGCGTTGTCCGGAATTATTGGGCGTAAAGAGCTCGTAGGCGGTT<br>TGTCGCGTCTGCTGTGAAATCCCGAGGCTCAACCTCGGGCTTGCAGTG<br>GGTACGGGCAGACTAGAGTGCGGTAGGGGAGATTGGAATTCCTGGTG<br>TAGCGGTGGAATGCGCAGATATCAGGAGGAACACCGATGGCGAAGG<br>CAGATCTCTGGGCCGTAACTGACGCTGAGGAGCGAAAGCGTGGGGAG<br>CGAACAGGATTAGATACCCTGGTAGTCCACGCCGTAAACGTTGGGCG<br>CTAGATGTAGGGACCTTTCCACGGTTTCTGTGTCGTAGCTAACGCATT<br>AAGCGCCCCGCCTGGGGAGTACGGCCGCAAGGCTAAAACTCAAAGG<br>AATTGACGGGGGCCCGCACAAGCGGCGGAGCATGCGGATTAATTCGA<br>TGCAACGCGAAGAACCTTACCAAGGCTTGACATACACCGGAAACGGC<br>CAGAGATGGTCGCCCCCTTGTGGTCGGTGTACAGGTGGTGCATGGTTG<br>TCGTCAGCTCGTGTCGTGAGATGTTGGGTTAAGTCCCGCAACGAGCGC<br>AACCCTCGTTCTATGTTGCCAGCGCGTTATGGCGGGGACTCATAGGAG<br>ACTGCCGGGGTCAACTCGGAGGAAGGTGGGGATGACGTCAAATCATC<br>ATGCCCCTTATGTCTTGGGCTTCACGCATGCTACAATGGCCGGTACAA<br>AGGGCTGCGATACCGTAAGGTGGAGCGAATCCCAAAAAGCCGGTCTC<br>AGTTCGGATTGAGGTCTGCAACTCGACCTCATGAAGTCGGAGTCGCT |

-continued

Sequence Listing

| Seq ID No. | Description | Sequence |
| --- | --- | --- |
| | | AGTAATCGCAGATCAGCAACGCTGCGGTGAATACGTTCCCGGGCCTT GTACACACCGCCCGTCAAGTCATGAAAGTCGGTAACACCCGAAGCCG GTGGCCTAACCCTTGTGGAAGGAGCCGTCGAAGGTGGGATCGGTGAT TAGGACTAAGTCGTAACAAGGTAGCCGTACCGGAAGGTGCGGCTGGA TCACCTCCTTT |
| 16 | DP16 16S rRNA | GCACTTCATCGTGGTGCACCGTGAAGGGTCTTTGGGCGTTTTACACAT GCAAGCAAGTGTTCTATAATTTAGGTTATGGAACAGCCAAATGGTCA GTACAGCTCAGTCCTAGGCGATGGACTCCGTAAAACGGGGACAGACT ATCCTTTAATAATTAATAGGTTTATTATTTCAATAATAATCTCTAGGA AGGGATATACATATATCCTTATTAGTCTAAAGGTTAATAAACCGCCTT AGTCAGGACTGAGTTCTCAACAGCTACGGGTTAAACCCCAGGCAACG ACGAGTAGGGGATAGTGATAGCTACAACCCCGACACTGGCCGCAAGC CAGGGTACTTAAGTACGCAGCAGTGAAGAATCCTCGGCAATGCATCG CAATTACCGGTGACCCAATATAAAATAATATCAGGGAGGTAGTAGGT GTGACCGGGTGACCCAAAGACGAGTAGTGACATAAGTTATTATTCGC GTATGTCGAACATGATAGTGACGTGTTCAACATCAAGCCCCGTCCAA CCTCTGTGCCAGCAGTCGCGGTAAAACAGGAGGGGCAGCTCTTATGG TCATGAATGGGCGTATAGGGCACGCAGCCAGTTAGTAAAAGCTTGAA TATTTATTTTTTTAAAAAGAATGTTTGAGAGGCTATGAGTTTTTATAA AGTGTACCCACGACACCAGACTTAGGGCTGAGATCCTATGAAGTCTG GGGGCGGTCCTTTAGGGTGCATTGTAAAAACTGACGGTAAGGTGCGA CAGCTGGGATACCGAAGCGGAGTAGAGCCCGCCTAGCCCCAGCCGTA AACGATAGGGGCCGTTGTTGACTACGGTTTTCAATAAGGCTAACGCCT GAGCCCCTCGCCTGTAGGGTATAGCCGCAAGGCCGACATATTAACGA TGAGACCGCTGGTGAGCAAACGGGTGCGGGGCATGCTGTTCAATCAG ACAGTACGCTGACAACCTTACCACTCCTTGAATCTTTTAGATTATATT TCTAAAATGACAGGTGCTGCATGGCCGTCGTCAGTTCGTGGTCGTGAG TCGTCCGGTTGAGTCCATGAACGAACGCAGACCCGTCTGTATACTCAG TGAAAAGAAATTTAGCTGAACTATACAGTTGTACTTCTATAAAAGGT ACCTGTACGGGATTATGACAGGTCGTCATGGCCTTTATGGAGTGGGCT ACAGGCGTGCCACACGAGCCGTTTTAACGAGTTCCTCATTTTTATGAA TAAGGTCTCTTAATCACGGCTAGTATACGGATCGTAGGCTGTAACTCG CCTACGTGAAGTCGGAGTCCCGAGTAATCGCCGATCATCACGCGGCG GTGAATCTACACTCTCACTGGGGTACTAACCGCTCGTCACG |
| 17 | DP17 16S rRNA | GTGATTGACGTTACTCGCAGAAGAAGCACCGGCTAACTCCGTGCCAG CAGCCGCGGTAATACGGAGGGTGCAAGCGTTAATCGGAATTACTGGG CGTAAAGCGCACGCAGGCGGTTTGTTAAGTCAGATGTGAAATCCCCG CGCTTAACGTGGGAACTGCATTTGAAACTGGCAAGCTAGAGTCTTGT AGAGGGGGGTAGAATTCCAGGTGTAGCGGTGAAATGCGTAGAGATCT GGAGGAATACCGGTGGCGAAGGCGGCCCCCTGGACAAAGACTGACG CTCAGGTGCGAAAGCGTGGGGAGCAAACAGGATTAGATACCCTGGTA GTCCACGCTGTAAACGATGTCGACTTGGAGGTTGTGCCCTTGAGGCGT GGCTTCCGGAGCTAACGCGTTAAGTCGACCGCCTGGGGAGTACGGCC GCAAGGTTAAAACTCAAATGAATTGACGGGGGCCCGCACAAGCGGTG GAGCATGTGGTTTAATTCGATGCAACGCGAAGAACCTTACCTACTCTT GACATCCACGGAATTCGCCAGAGATGGCTTAGTGCCTTCGGGAACCG TGAGACAGGTGCTGCATGGCTGTCGTCAGCTCGTGTTGTGAAATGTTG GGTTAAGTCCCGCAACGAGCGCAACCCTTATCCTTTGTTGCCAGCACG TAATGGTGGGAACTCAAAGGAGACTGCCGGTGATAAACCGGAGGAA GGTGGGGATGACGTCAAGTCATCATGGCCCTTACGAGTAGGGCTACA CACGTGCTACAATGGCATATACAAAGAGAAGCGAACTCGCGAGAGCA AGCGGACCTCATAAAGTATGTCGTAGTCCGGATTGGAGTCTGCAACT CGACTCCATGAAGTCGGAATCGCTAGTAATCGTAGATCAGAATGCTA CGG |
| 18 | DP18 16S rRNA | TGAAGAGTTTGATCATGGCTCAGATTGAACGCTGGCGGCAGGCCTAA CACATGCAAGTCGAGCGGATGAAAGGAGCTTGCTCCTGGATTCAGCG GCGGACGGGTGAGTAATGCCTAGGAATCTGCCTGGTAGTGGGGGACA ACGTTTCGAAAGGAACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCAGTAAATTAATACTTTGCTGTTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGAATGTGAAATCCCCGGGCTCAAC CTGGGAACTGCATCCAAAACTGGCAAGCTAGAGTATGGTAGAGGGTG GTGGAATTTCCTGTGTAGCGGTGAAATGCGTAGATATAGGAAGGAAC ACCAGTGGCGAAGGCGACCACCTGGACTGATACTGACACTGAGGTGC |

-continued

Sequence Listing

| Seq ID No. | Description | Sequence |
|---|---|---|
| | | GAAAGCGTGGGGAGCAAACAGGATTAGATACCCTGGTAGTCCACGCC GTAAACGATGTCAACTAGCCGTTGGGAGCCTTGAGCTCTTAGTGGCG CAGCTAACGCATTAAGTTGACCGCCTGGGGAGTACGGCCGCAAGGTT AAAACTCAAATGAATTGACGGGGGCCCGCACAAGCGGTGGAGCATGT GGTTTAATTCGAAGCAACGCGAAGAACCTTACCAGGCCTTGACATCC AATGAACTTTCCAGAGATGGATTGGTGCCTTCGGGAACATTGAGACA GGTGCTGCATGGCTGTCGTCAGCTCGTGTCGTGAGATGTTGGGTTAAG TCCCGTAACGAGCGCAACCCTTGTCCTTAGTTACCAGCACGTTATGGT GGGCACTCTAAGGAGACTGCCGGTGACAAACCGGAGGAAGGTGGGG ATGACGTCAAGTCATCATGGCCCTTACGGCCTGGGCTACACACGTGCT ACAATGGTCGGTACAAAGGGTTGCCAAGCCGCGAGGTGGAGCTAATC CCATAAAACCGATCGTAGTCCGGATCGCAGTCTGCAACTCGACTGCG TGAAGTCGGAATCGCTAGTAATCGCGAATCAGAATGTCGCGGTGAAT ACGTTCCCGGGCCTTGTACACACCGCCCGTCACACCATGGGAGTGGG TTGCACCAGAAGTAGCTAGTCTAACCTTCGGGAGGACGGTTACCACG GTGTGATTCATGACTGGGGTGAAGTCGTAACAAGGTAGCCGTAGGGG AACCTGCGGCTGGATCACCTCCTT |
| 19 | DP19 16S rRNA | TACGGAGAGTTTGATCCTGGCTCAGGACGAACGCTGGCGGCGTGCTT AACACATGCAAGTCGAACGATGATGCCCAGCTTGCTGGGTGGATTAG TGGCGAACGGGTGAGTAACACGTGAGTAACCTGCCCCTGACTCTGGG ATAAGCGTTGGAAACGACGTCTAATACTGGATACGACTGCCGGCCGC ATGGTCTGGTGGTGGAAAGATTTTTTGGTTGGGGATGGACTCGCGGCC TATCAGCTTGTTGGTGAGGTAATGGCTCACCAAGGCGACGACGGGTA GCCGGCCTGAGAGGGTGACCGGCCACACTGGGACTGAGACACGGCCC AGACTCCTACGGGAGGCAGCAGTGGGGAATATTGCACAATGGGCGAA AGCCTGATGCAGCAACGCCGCGTGAGGGATGACGGCCTTCGGGTTGT AAACCTCTTTTAGTAGGGAAGAAGCGAAAGTGACGGTACCTGCAGAA AAAGCACCGGCTAACTACGTGCCAGCAGCCGCGGTAATACGTAGGGT GCAAGCGTTGTCCGGAATTATTGGGCGTAAAGAGCTCGTAGGCGGTT TGTCGCGTCTGCTGTGAAATCCCGAGGCTCAACCTCGGGCTTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGCGTGGGGAG CGAACAGGATTAGATACCCTGGTAGTCCACGCCGTAAACGTTGGGCG CTAGATGTAGGGACCTTTCCACGGTTTCTGTGTCGTAGCTAACGCATT AAGCGCCCCGCCTGGGGAGTACGGCCGCAAGGCTAAAACTCAAAGG AATTGACGGGGGCCCGCACAAGCGGCGGAGCATGCGGATTAATTCGA TGCAACGCGAAGAACCTTACCAAGGCTTGACATACACCGGAAACGGC CAGAGATGGTCGCCCCCTTGTGGTCGGTGTACAGGTGGTGCATGGTTG TCGTCAGCTCGTGTCGTGAGATGTTGGGTTAAGTCCCGCAACGAGCGC AACCCTCGTTCTATGTTGCCAGCGCGTTATGGCGGGGACTCATAGGAG ACTGCCGGGGTCAACTCGGAGGAAGGTGGGGATGACGTCAAATCATC ATGCCCCTTATGTCTTGGGCTTCACGCATGCTACAATGGCCGGTACAA AGGGCTGCGATACCGTAAGGTGGAGCGAATCCCAAAAAGCCGGTCTC AGTTCGGATTGAGGTCTGCAACTCGACCTCATGAAGTCGGAGTCGCT AGTAATCGCAGATCAGCAACGCTGCGGTGAATACGTTCCCGGGCCTT GTACACACCGCCCGTCAAGTCATGAAAGTCGGTAACACCCGAAGCCG GTGGCCTAACCCTTGTGGAAGGAGCCGTCGAAGGTGGGATCGGTGAT TAGGACTAAGTCGTAACAAGGTAGCCGTACCGGAAGGTGCGGCTGGA TCACCTCCTTT |
| 20 | DP20 16S rRNA | TGAAGAGTTTGATCCTGGCTCAGAGTGAACGCTGGCGGTAGGCCTAA CACATGCAAGTCGAACGGCAGCACAGTAAGAGCTTGCTCTTATGGGT GGCGAGTGGCGGACGGGTGAGGAATACATCGGAATCTACCTTTTCGT GGGGGATAACGTAGGGAAACTTACGCTAATACCGCATACGACCTTCG GGTGAAAGCAGGGGACCTTCGGGCCTTGCGCGGATAGATGAGCCGAT GTCGGATTAGCTAGTTGGCGGGGTAAAGGCCCACCAAGGCGACGATC CGTAGCTGGTCTGAGAGGATGATCAGCCACACTGGAACTGAGACACG GTCCAGACTCCTACGGGAGGCAGCAGTGGGGAATATTGGACAATGGG CGCAAGCCTGATCCAGCCATACCGCGTGGGTGAAGAAGGCCTTCGGG TTGTAAAGCCCTTTTGTTGGGAAAGAAAAGCAGTCGGCTAATACCCG GTTGTTCTGACGGTACCCAAAGAATAAGCACCGGCTAACTTCGTGCC AGCAGCCGCGGTAATACGAAGGGTGCAAGCGTTACTCGGAATTACTG GGCGTAAAGCGTGCGTAGGTGGTTGTTTAAGTCTGTTGTGAAAGCCCT GGGCTCAACCTGGGAATTGCAGTGGATACTGGGCGACTAGAGTGTGG TAGAGGGTAGTGGAATTCCCGGTGTAGCAGTGAAATGCGTAGAGATC GGGAGGAACATCCATGGCGAAGGCAGCTACCTGGACCAACACTGACA CTGAGGCACGAAAGCGTGGGGAGCAAACAGGATTAGATACCCTGGTA GTCCACGCCCTAAACGATGCGAACTGGATGTTGGGTGCAATTTGGCA CGCAGTATCGAAGCTAACGCGTTAAGTTCGCCGCCTGGGGAGTACGG TCGCAAGACTGAAACTCAAAGGAATTGACGGGGGCCCGCACAAGCG GTGGAGTATGTGGTTTAATTCGATGCAACGCGAAGAACCTTACCTGGT |

-continued

Sequence Listing

| Seq ID No. | Description | Sequence |
|---|---|---|
| | | CTTGACATGTCGAGAACTTTCCAGAGATGGATTGGTGCCTTCGGGAAC<br>TCGAACACAGGTGCTGCATGGCTGTCGTCAGCTCGTGTCGTGAGATGT<br>TGGGTTAAGTCCCGCAACGAGCGCAACCCTTGTCCTTAGTTGCCAGCA<br>CGTAATGGTGGGAACTCTAAGGAGACCGCCGGTGACAAACCGGAGG<br>AAGGTGGGGATGACGTCAAGTCATCATGGCCCTTACGACCAGGGCTA<br>CACACGTACTACAATGGTAGGGACAGAGGGCTGCAAACCCGCGAGG<br>GCAAGCCAATCCCAGAAACCCTATCTCAGTCCGGATTGGAGTCTGCA<br>ACTCGACTCCATGAAGTCGGAATCGCTAGTAATCGCAGATCAGCATT<br>GCTGCGGTGAATACGTTCCCGGGCCTTGTACACACCGCCCGTCACACC<br>ATGGGAGTTTGTTGCACCAGAAGCAGGTAGCTTAACCTTCGGGAGGG<br>CGCTTGCCACGGTGTGGCCGATGACTGGGGTGAAGTCGTAACAAGGT<br>AGCCGTATCGGAAGGTGCGGCTGGATCACCTCCTTT |
| 22 | DP22 16S rRNA | TTGAAGAGTTTGATCATGGCTCAGATTGAACGCTGGCGGCAGGCCTA<br>ACACATGCAAGTCGAGCGGCAGCGGGAAGTAGCTTGCTACTTTGCCG<br>GCGAGCGGCGGACGGGTGAGTAATGTCTGGGAAACTGCCTGATGGAG<br>GGGGATAACTACTGGAAACGGTAGCTAATACCGCATGACCTCGCAAG<br>AGCAAAGTGGGGGACCTTCGGGCCTCACGCCATCGGATGTGCCCAGA<br>TGGGATTAGCTAGTAGGTGAGGTAATGGCTCACCTAGGCGACGATCC<br>CTAGCTGGTCTGAGAGGATGACCAGCCACACTGGAACTGAGACACGG<br>TCCAGACTCCTACGGGAGGCAGCAGTGGGGAATATTGCACAATGGGC<br>GCAAGCCTGATGCAGCCATGCCGCGTGTGTGAAGAAGGCCTTAGGGT<br>TGTAAAGCACTTTCAGCGAGGAGGAAGGGTTCAGTGTTAATAGCACT<br>GAACATTGACGTTACTCGCAGAAGAAGCACCGGCTAACTCCGTGCCA<br>GCAGCCGCGGTAATACGGAGGGTGCAAGCGTTAATCGGAATTACTGG<br>GCGTAAAGCGCACGCAGGCGGTTTGTTAAGTCAGATGTGAAATCCCC<br>GAGCTTAACTTGGGAACTGCATTTGAAACTGGCAAGCTAGAGTCTTGT<br>AGAGGGGGGTAGAATTCCAGGTGTAGCGGTGAAATGCGTAGAGATCT<br>GGAGGAATACCGGTGGCGAAGGCGGCCCCCTGGACAAAGACTGACG<br>CTCAGGTGCGAAAGCGTGGGGAGCAAACAGGATTAGATACCCTGGTA<br>GTCCACGCTGTAAACGATGTCGACTTGGAGGTTGTGCCCTTGAGGCGT<br>GGCTTCCGGAGCTAACGCGTTAAGTCGACCGCCTGGGGAGTACGGCC<br>GCAAGGTTAAAACTCAAATGAATTGACGGGGGCCCGCACAAGCGGTG<br>GAGCATGTGGTTTAATTCGATGCAACGCGAAGAACCTTACCTACTCTT<br>GACATCCAGAGAATTCGCTAGAGATAGCTTAGTGCCTTCGGGAACTC<br>TGAGACAGGTGCTGCATGGCTGTCGTCAGCTCGTGTTGTGAAATGTTG<br>GGTTAAGTCCCGCAACGAGCGCAACCCTTATCCTTTGTTGCCAGCGAG<br>TAATGTCGGGAACTCAAAGGAGACTGCCGGTGATAAACCGGAGGAA<br>GGTGGGGATGACGTCAAGTCATCATGGCCCTTACGAGTAGGGCTACA<br>CACGTGCTACAATGGCATATACAAAGAGAAGCAAACTCGCGAGAGCA<br>AGCGGACCTCATAAAGTATGTCGTAGTCCGGATTGGAGTCTGCAACT<br>CGACTCCATGAAGTCGGAATCGCTAGTAATCGTAGATCAGAATGCTA<br>CGGTGAATACGTTCCCGGGCCTTGTACACACCGCCCGTCACACCATGG<br>GAGTGGGTTGCAAAAGAAGTAGGTAGCTTAACCTTCGGGAGGGCGCT<br>TACCACTTTGTGATTCATGACTGGGGTGAAGTCGTAACAAGGTAACC<br>GTAGGGGAACCTGCGGTTGGATCACCTCCTT |
| 23 | DP23 16S rRNA | TTGAAGAGTTTGATCATGGCTCAGATTGAACGCTGGCGGCAGGCCTA<br>ACACATGCAAGTCGAACGGTAGCACAGAGAGCTTGCTCTTGGGTGAC<br>GAGTGGCGGACGGGTGAGTAATGTCTGGGAAACTGCCCGATGGAGGG<br>GGATAACTACTGGAAACGGTAGCTAATACCGCATAACGTCTTCGGAC<br>CAAAGTGGGGGACCTTCGGGCCTCACACCATCGGATGTGCCCAGATG<br>GGATTAGCTAGTAGGTGGGGTAATGGCTCACCTAGGCGACGATCCCT<br>AGCTGGTCTGAGAGGATGACCAGCCACACTGGAACTGAGACACGGTC<br>CAGACTCCTACGGGAGGCAGCAGTGGGGAATATTGCACAATGGGCGC<br>AAGCCTGATGCAGCCATGCCGCGTGTATGAAGAAGGCCTTCGGGTTG<br>TAAAGTACTTTCAGCGGGGAGGAAGGCGATACGGTTAATAACCGTGT<br>CGATTGACGTTACCCGCAGAAGAAGCACCGGCTAACTCCGTGCCAGC<br>AGCCGCGGTAATACGGAGGGTGCAAGCGTTAATCGGAATTACTGGGC<br>GTAAAGCGCACGCAGGCGGTCTGTCAAGTCAGATGTGAAATCCCCGG<br>GCTTAACCTGGGAACTGCATTTGAAACTGGCAGGCTTGAGTCTCGTAG<br>AGGGGGGTAGAATTCCAGGTGTAGCGGTGAAATGCGTAGAGATCTGG<br>AGGAATACCGGTGGCGAAGGCGGCCCCCTGGACGAAGACTGACGCTC<br>AGGTGCGAAAGCGTGGGGAGCAAACAGGATTAGATACCCTGGTAGTC<br>CACGCTGTAAACGATGTCGACTTGGAGGTTGTGCCCTTGAGGCGTGG<br>CTTCCGGAGCTAACGCGTTAAGTCGACCGCCTGGGGAGTACGGCCGC<br>AAGGTTAAAACTCAAATGAATTGACGGGGGCCCGCACAAGCGGTGGA<br>GCATGTGGTTTAATTCGATGCAACGCGAAGAACCTTACCTGGCCTTGA<br>CATCCACAGAATTCGGCAGAGATGCCTTAGTGCCTTCGGGAACTGTG<br>AGACAGGTGCTGCATGGCTGTCGTCAGCTCGTGTTGTGAAATGTTGGG<br>TTAAGTCCCGCAACGAGCGCAACCCTTATCCTTTGTTGCCAGCGATTC<br>GGTCGGGAACTCAAAGGAGACTGCCGGTGATAAACCGGAGGAAGGT<br>GGGGATGACGTCAAGTCATCATGGCCCTTACGGCCAGGGCTACACAC |

-continued

Sequence Listing

| Seq ID No. | Description | Sequence |
|---|---|---|
| | | GTGCTACAATGGCGCATACAAAGAGAAGCGACCTCGCGAGAGCAAG CGGACCTCATAAAGTGCGTCGTAGTCCGGATCGGAGTCTGCAACTCG ACTCCGTGAAGTCGGAATCGCTAGTAATCGTAGATCAGAATGCTACG GTGAATACGTTCCCGGGCCTTGTACACACCGCCCGTCACACCATGGG AGTGGGTTGCAAAAGAAGTAGGTAGCTTAACCTTCGGGAGGGCGCTT ACCACTTTGTGATTCATGACTGGGGTGAAGTCGTAACAAGGTAACCG TAGGGGAACCTGCGGTTGGATCACCTCCTT |
| 24 | DP24 16S rRNA | AGCATTTGATTATGGTGCTTACTGATTGCTATCTAGGGGTTTAACACA TGCTAGTCAATGATCTTTTAGATTATGGCGTACGGGCTAGGAATACTT AGAATGATAACTCTATGATCGCAGTAATAGCGTAAAAGGTATAATAC CGCATAGAGGTTCGCTTCGTATCTCAATAGGTAGTTGGTGAGGTAAA GCTCAACAAGCCGATGATGAGTAATATTGGATGAAAGTCTTAAATAT AGCAGTGGAAATGAAAAAGTCCACCGTTATTTATTAACGCAGCAGTG GAGAATCGTCGTAATGTGCAGTATTCATTTATGGATAAGCATGAACG CGCTACCTAGATTCGGATAGGAGATAGCATCTTCTACCGATAAAAGA ACTTAGAATAATGATCTAGTTCTCATTAGTGGGTGACAATCGCCGTGC CAGCATCAGCGGTAAAACGGCTTCCGCAAGCAATAGTAATTTAAATT GGTGTAAAGGGTACGTAGCCGGCCTTATTAGGCTAGAGTTAGATACG GGTAAGTACAATACTTGGAGTAGGGCTGATATCTTATGATCCCAAGG GGAGTGCTAAAGGCGAAGGCAACTTACTGGTAATAACTGACGGTGAG GTACGAAGGTCAGGGCATGGAAAGAGATTAGATACCTCATTACTCCT GACAGTAAACGATGTAGATTAAAGATTGGAATAATTCTGTCTTAACG CTAACGCATTAAATCTACCACCTGTAGAGTATAGTCGCAAGGCCGAA ATACAAATAATTAGACGGCTCTAGAGCAAACGGAGTGAAGCATGTTA TTTAATACGATAACCCGCGTAAAATCTTACCAGTTCTTGAATCTTAGA CAGGTGTTGCATGGTTGTCGTCAGCTCGTGCTAATGGTGTCTGGTTAA TTCCAAATAACGAGCGCAATCCTTACTTCTAGTTTTCTAGGAGTCTCC ATTTGACATACGTGTCAATGGTTTAAGGAATATGACAAACCCTCATGG CCCTTATGGACTGGGCAATAGACGTGCCACAAGAATCTAGACAAAAT GACGCGAAATGGTAACAATGAGCTAATCATCAAAGAAGATTAATGTA CGAATTATGGGCTGGAACTCGCCCATATGAAGTAGGAATTCCGAGTA ATCGCGTATCAGAACGACGCGGTGAACATCATCTCTGGAGTGTACTA ACTGCTCGTCACGGGACGAAAGGGAGTGTATTATGAAGTGGGGCTAA TTGGTTAACTCCGGTGAGTGTCACGAATAATCCTTCCCGATTGTTCTG AAGTCGAAACAAGGTAACCGTAAGGGAACTTGCGGTTGA |
| 25 | DP25 16S rRNA | TACGGAGAGTTTGATCCTGGCTCAGGATGAACGCTGGCGGCGTGCTT AACACATGCAAGTCGAACGGTGAAGCCAAGCTTGCTTGGTGGATCAG TGGCGAACGGGTGAGTAACACGTGAGCAACCTGCCCTGGACTCTGGG ATAAGCGCTGGAAACGGCGTCTAATACTGGATATGAGCTCCTTCCGC ATGGTGGGGGTTGGAAAGATTTTTCGGTCTGGGATGGGCTCGCGGCC TATCAGCTTGTTGGTGAGGTAATGGCTCACCAAGGCGTCGACGGGTA GCCGGCCTGAGAGGGTGACCGGCCACACTGGGACTGAGACACGGCCC AGACTCCTACGGGAGGCAGCAGTGGGGAATATTGCACAATGGGCGGA AGCCTGATGCAGCAACGCCGCGTGAGGGATGACGGCCTTCGGGTTGT AAACCTCTTTTAGCAGGGAAGAAGCGAAAGTGACGGTACCTGCAGAA AAAGCGCCGGCTAACTACGTGCCAGCAGCCGCGGTAATACGTAGGGC GCAAGCGTTATCCGGAATTATTGGGCGTAAAGAGCTCGTAGGCGGTT TGTCGCGTCTGCTGTGAAATCCCGAGGCTCAACCTCGGGCCTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGGGTGGGGAG CAAACAGGCTTAGATACCCTGGTAGTCCACCCCGTAAACGTTGGGAA CTAGTTGTGGGGACCATTCCACGGTTTCCGTGACGCAGCTAACGCATT AAGTTCCCCGCCTGGGGAGTACGGCCGCAAGGCTAAAACTCAAAGGA ATTGACGGGGACCCGCACAAGCGGCGGAGCATGCGGATTAATTCGAT GCAACGCGAAGAACCTTACCAAGGCTTGACATATACGAGAACGGGCC AGAAATGGTCAACTCTTTGGACACTCGTAAACAGGTGGTGCATGGTT GTCGTCAGCTCGTGTCGTGAGATGTTGGGTTAAGTCCCGCAACGAGC GCAACCCTCGTTCTATGTTGCCAGCACGTAATGGTGGGAACTCATGGG ATACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCAATACCGTAAGGTGGAGCGAATCCCAAAAAGCCGGTC CCAGTTCGGATTGAGGTCTGCAACTCGACCTCATGAAGTCGGAGTCG CTAGTAATCGCAGATCAGCAACGCTGCGGTGAATACGTTCCCGGGTC TTGTACACACCGCCCGTCAAGTCATGAAAGTCGGTAACACCTGAAGC CGGTGGCCCAACCCTTGTGGAGGGAGCCGTCGAAGGTGGGATCGGTA ATTAGGACTAAGTCGTAACAAGGTAGCCGTACCGGAAGGTGCGGCTG GATCACCTCCTTT |

-continued

Sequence Listing

| Seq ID No. | Description | Sequence |
|---|---|---|
| 26 | DP26 16S rRNA | CTTGAGAGTTTGATCCTGGCTCAGAGCGAACGCTGGCGGCAGGCTTA ACACATGCAAGTCGAGCGGGCATCTTCGGATGTCAGCGGCAGACGGG TGAGTAACACGTGGGAACGTACCCTTCGGTTCGGAATAACGCTGGGA AACTAGCGCTAATACCGGATACGCCCTTTTGGGGAAAGGTTTACTGCC GAAGGATCGGCCCGCGTCTGATTAGCTAGTTGGTGGGGTAACGGCCT ACCAAGGCGACGATCAGTAGCTGGTCTGAGAGGATGATCAGCCACAC TGGGACTGAGACACGGCCCAGACTCCTACGGGAGGCAGCAGTGGGG AATATTGGACAATGGGCGCAAGCCTGATCCAGCCATGCCGCGTGAGT GATGAAGGCCTTAGGGTTGTAAAGCTCTTTTGTCCGGGACGATAATG ACGGTACCGGAAGAATAAGCCCCGGCTAACTTCGTGCCAGCAGCCGC GGTAATACGAAGGGGGCTAGCGTTGCTCGGAATCACTGGGCGTAAAG GGCGCGTAGGCGGCCATTCAAGTCGGGGGTGAAAGCCTGTGGCTCAA CCACAGAATTGCCTTCGATACTGTTTGGCTTGAGTATGGTAGAGGTTG GTGGAACTGCGAGTGTAGAGGTGAAATTCGTAGATATTCGCAAGAAC ACCGGTGGCGAAGGCGGCCAACTGGACCATTACTGACGCTGAGGCGC GAAAGCGTGGGGAGCAAACAGGATTAGATACCCTGGTAGTCCACGCC GTAAACGATGAATGCCAGCTGTTGGGGTGCTTGCACCTCAGTAGCGC AGCTAACGCTTTAAGCATTCCGCCTGGGGAGTACGGTCGCAAGATTA AAACTCAAAGGAATTGACGGGGGCCCGCACAAGCGGTGGAGCATGT GGTTTAATTCGAAGCAACGCGCAGAACCTTACCATCCCTTGACATGGC ATGTTACCCGGAGAGATTCGGGGTCCACTTCGGTGGCGTGCACACAG GTGCTGCATGGCTGTCGTCAGCTCGTGTCGTGAGATGTTGGGTTAAGT CCCGCAACGAGCGCAACCCACGTCCTTAGTTGCCATCATTCAGTTGGG CACTCTAGGGAGACTGCCGGTGATAAGCCGCGAGGAAGGTGTGGATG ACGTCAAGTCCTCATGGCCCTTACGGGATGGGCTACACACGTGCTAC AATGGCGGTGACAGTGGGACGCGAAGGAGCGATCTGGAGCAAATCC CCAAAAACCGTCTCAGTTCAGATTGCACTCTGCAACTCGAGTGCATGA AGGCGGAATCGCTAGTAATCGTGGATCAGCATGCCACGGTGAATACG TTCCCGGGCCTTGTACACACCGCCCGTCACACCATGGGAGTTGGTCTT ACCCGACGGCGCTGCGCCAACCGCAAGGAGGCAGGCGACCACGGTA GGGTCAGCGACTGGGGTGAAGTCGTAACAAGGTAGCCGTAGGGGAA CCTGCGGCTGGATCACCTCCTTT |
| 27 | DP27 16S rRNA | CTTGAGAGTTTGATCCTGGCTCAGAACGAACGCTGGCGGCATGCCTA ACACATGCAAGTCGAACGATGCTTTCGGGCATAGTGGCGCACGGGTG CGTAACGCGTGGGAATCTGCCCTCAGGTTCGGAATAACAGCTGGAAA CGGCTGCTAATACCGGATGATATCGCAAGATCAAAGATTTATCGCCT GAGGATGAGCCCGCGTTGGATTAGGTAGTTGGTGGGGTAAAGGCCTA CCAAGCCGACGATCCATAGCTGGTCTGAGAGGATGATCAGCCACACT GGGACTGAGACACGGCCCAGACTCCTACGGGAGGCAGCAGTGGGGA ATATTGGACAATGGGCGCAAGCCTGATCCAGCAATGCCGCGTGAGTG ATGAAGGCCCTAGGGTTGTAAAGCTCTTTTACCCGGGAAGATAATGA CTGTACCGGGAGAATAAGCCCCGGCTAACTCCGTGCCAGCAGCCGCG GTAATACGGAGGGGGCTAGCGTTGTTCGGAATTACTGGGCGTAAAGC GCACGTAGGCGGCTTTGTAAGTCAGAGGTGAAAGCCTGGAGCTCAAC TCCAGAACTGCCTTTGAGACTGCATCGCTTGAATCCAGGAGAGGTCA GTGGAATTCCGAGTGTAGAGGTGAAATTCGTAGATATTCGGAAGAAC ACCAGTGGCGAAGGCGGCTGACTGGACTGGTATTGACGCTGAGGTGC GAAAGCGTGGGGAGCAAACAGGATTAGATACCCTGGTAGTCCACGCC GTAAACGATGATAACTAGCTGTCCGGGCACTTGGTGCTTGGGTGGCG CAGCTAACGCATTAAGTTATCCGCCTGGGGAGTACGGCCGCAAGGTT AAAACTCAAAGGAATTGACGGGGGCCTGCACAAGCGGTGGAGCATGT GGTTTAATTCGAAGCAACGCGCAGAACCTTACCAGCGTTTGAC |
| 28 | DP28 16S rRNA | ATAGTCGGGGGCATCAGTATTCAATTGTCAGAGGTGAAATTCTTGGAT TTATTGAAGACTAACTACTGCGAAAGCATTTGCCAAGGATGTTTTCAT TAATCAGTGAACGAAAGTTAGGGGATCGAAGACGATCAGATACCGTC GTAGTCTTAACCATAAACTATGCCGACTAGGGATCGGGCGATGTTATC ATTTTGACTCGCTCGGCACCTTACGAGAAATCAAAGTCTTTGGGTTCT GGGGGGAGTATGGTCGCAAGGCTGAAACTTAAAGAAATTGACGGAA GGGCACCACCAGGCGTGGAGCCTGCGGCTTAATTTGACTCAACACGG GGAAACTCACCAGGTCCAGACACAATAAGGATTGACAGATTGAGAGC TCTTTCTTGATTTTGTGGGTGGTGGTGCATGGCCGTTCTTAGTTGGTGG AGTGATTTGTCTGCTTAATTGCGATAACGAACGAGACCTTAACCTGCT AAATAGCCCGGCCCGCTTTGGCGGGTCGCCGGCTTCTTAGAGGGACT ATCGGCTCAAGCCGATGGAAGTTTGAGGCAATAACAGGTCTGTGATG CCCTTAGATGTTCTGGGCCGCACGCGCGCTACACTGACAGAGCCAAC GAGTTCATTTCCTTGCCCGGAAGGGTTGGGTAATCTTGTTAAACTCTG TCGTGCTGGGGATAGAGCATTGCAATTATTGCTCTTCAACGAGGAATG CCTAGTAAGCGTACGTCATCAGCGTGCGTTGATTACGTCCCTGCCCTT TGTACACACCGCCCGTCGCTACTACCGATTGAATGGCTGAGTGAGGC CTTCGGACTGGCCCAGGGAGGTCGGCAACGACCACCCAGGGCCGGAA |

-continued

Sequence Listing

| Seq ID No. | Description | Sequence |
|---|---|---|
| | | AGTTGGTCAAACTCCGTCATTTAGAGGAAGTAAAAGTCGTAACAAGG |
| | | TTTCCGTAGGTGAACCTGCGGAAGGATCA |
| 29 | DP29 16S rRNA | TACGGAGAGTTTGATCCTGGCTCAGGACGAACGCTGGCGGCGTGCTT |
| | | AACACATGCAAGTCGAACGATGAAGCCCAGCTTGCTGGGTTGATTAG |
| | | TGGCGAACGGGTGAGTAACACGTGAGCAACGTGCCCATAACTCTGGG |
| | | ATAACCTCCGGAAACGGTGGCTAATACTGGATATCTAACACGATCGC |
| | | ATGGTCTGTGTTTGGAAAGATTTTTTGGTTATGGATCGGCTCACGGCC |
| | | TATCAGCTTGTTGGTGAGGTAATGGCTCACCAAGGCGACGACGGGTA |
| | | GCCGGCCTGAGAGGGTGACCGGCCACACTGGGACTGAGACACGGCCC |
| | | AGACTCCTACGGGAGGCAGCAGTGGGGAATATTGCACAATGGGCGAA |
| | | AGCCTGATGCAGCAACGCCGCGTGAGGGATGACGGCATTCGGGTTGT |
| | | AAACCTCTTTTAGTAGGGAAGAAGCGAAAGTGACGGTACCTGCAGAA |
| | | AAAGCACCGGCTAACTACGTGCCAGCAGCCGCTGTAATACGTAGGGT |
| | | GCAAGCGTTGTCCGGAATTATTGGGCGTAAAGAGCTCGTAGGCGGTT |
| | | TGTCGCGTCTGCTGTGAAATCCCGAGGCTCAACCTCGGGTCTGCAGTG |
| | | GGTACGGGCAGACTAGAGTGTGGTAGGGGAGATTGGAATTCCTGGTG |
| | | TAGCGGTGGAATGCGCAGATATCAGGAGGAACACCGATGGCGAAGG |
| | | CAGATCTCTGGGCCATTACTGACGCTGAGGAGCGAAAGCATGGGGAG |
| | | CGAACAGGATTAGATACCCTGGTAGTCCATGCCGTAAACGTTGGGCG |
| | | CTAGATGTGGGGACCATTCCACGGTTTCCGTGTCGTAGCTAACGCATT |
| | | AAGCGCCCCGCCTGGGGAGTACGGCCGCAAGGCTAAAACTCAAAGG |
| | | AATTGACGGGGGCCCGCACAAGCGGCGGAGCATGCGGATTAATTCGA |
| | | TGCAACGCGAAGAACCTTACCAAGGCTTGACATATACCGGAAACGTT |
| | | CAGAAATGTTCGCC |
| 30 | DP30 16S rRNA | TACGGAGAGTTTGATCCTGGCTCAGGATGAACGCTGGCGGCGTGCTT |
| | | AACACATGCAAGTCGAACGGTGAAGCCAAGCTTGCTTGGTGGATCAG |
| | | TGGCGAACGGGTGAGTAACACGTGAGCAACCTGCCCTGGACTCTGGG |
| | | ATAAGCGCTGGAAACGGCGTCTAATACTGGATATGAGACGTGATCGC |
| | | ATGGTCGTGTTTGGAAAGATTTTTCGGTCTGGGATGGGCTCGCGGCCT |
| | | ATCAGCTTGTTGGTGAGGTAATGGCTCACCAAGGCGTCGACGGGTAG |
| | | CCGGCCTGAGAGGGTGACCGGCCACACTGGGACTGAGACACGGCCCA |
| | | GACTCCTACGGGAGGCAGCAGTGGGGAATATTGCACAATGGGCGAAA |
| | | GCCTGATGCAGCAACGCCGCGTGAGGGATGACGGCCTTCGGGTTGTA |
| | | AACCTCTTTTAGCAGGGAAGAAGCGAAAGTGACGGTACCTGCAGAAA |
| | | AAGCGCCGGCTAACTACGTGCCAGCAGCCGCGGTAATACGTAGGGCG |
| | | CAAGCGTTATCCGGAATTATTGGGCGTAAAGAGCTCGTAGGCGGTTT |
| | | GTCGCGTCTGCTGTGAAATCCCGAGGCTCAACCTCGGGCCTGCAGTG |
| | | GGTACGGGCAGACTAGAGTGCGGTAGGGGAGATTGGAATTCCTGGTG |
| | | TAGCGGTGGAATGCGCAGATATCAGGAGGAACACCGATGGCGAAGG |
| | | CAGATCTCTGGGCCGTAACTGACGCTGAGGAGCGAAAGGGTGGGGAG |
| | | CAAACAGGCTTAGATACCCTGGTAGTCCACCCCGTAAACGTTGGGAA |
| | | CTAGTTGTGGGGACCATTCCACGGTTTCCGTGACGCAGCTAACGCATT |
| | | AAGTTCCCCGCCTGGGGAGTACGGCCGCAAGGCTAAAACTCAAAGGA |
| | | ATTGACGGGGACCCGCACAAGCGGCGGAGCATGCGGATTAATTCGAT |
| | | GCAACGCGAAGAACCTTACCAAGGCTTGACATATACGAGAACGGGCC |
| | | AGAAATGGTCAACTCTTTGGACACTCGTAAACAGGTGGTGCATGGTT |
| | | GTCGTCAGCTCGTGTCGTGAGATGTTGGGTTAAGTCCCGCAACGAGC |
| | | GCAACCCTCGTTCTATGTTGCCAGCACGTAATGGTGGGAACTCATGGG |
| | | ATACTGCCGGGGTCAACTCGGAGGAAGGTGGGGATGACGTCAAATCA |
| | | TCATGCCCCTTATGTCTTGGGCTTCACGCATGCTACAATGGCCGGTAC |
| | | AAAGGGCTGCAATACCGTGAGGTGGAGCGAATCCCAAAAAGCCGGTC |
| | | CCAGTTCGGATTGAGGTCTGCAACTCGACCTCATGAAGTCGGAGTCG |
| | | CTAGTAATCGCAGATCAGCAACGCTGCGGTGAATACGTTCCCGGGTC |
| | | TTGTACACACCGCCCGTCAAGTCATGAAAGTCGGTAACACCTGAAGC |
| | | CGGTGGCCCAACCCTTGTGGAGGGAGCCGTCGAAGGTGGGATCGGTA |
| | | ATTAGGACTAAGTCGTAACAAGGTAGCCGTACCGGAAGGTGCGGCTG |
| | | GATCACCTCCTTT |
| 31 | DP31 16SrRNA | CAGCCGGGGGCATTAGTATTTGCACGCTAGAGGTGAAATTCTTGGATT |
| | | GTGCAAAGACTTCCTACTGCGAAAGCATTTGCCAAGAATGTTTTCATT |
| | | AATCAAGAACGAAGGTTAGGGTATCGAAAACGATTAGATACCGTTGT |
| | | AGTCTTAACAGTAAACTATGCCGACTCCGAATCGGTCGATGCTCATTT |
| | | CACTGGCTCGATCGGCGCGGTACGAGAAATCAAAGTTTTTGGGTTCTG |
| | | GGGGGAGTATGGTCGCAAGGCTGAAACTTAAAGAAATTGACGGAAG |
| | | GGCACCACCAGGAGTGGAGCCTGCGGCTTAATTTGACTCAACACGGG |
| | | AAAACTCACCGGGTCCGGACATAGTAAGGATTGACAGATTGATGGCG |
| | | CTTTCATGATTCTATGGGTGGTGGTGCATGGCCGTTCTTAGTTGGTGG |
| | | AGTGATTTGTCTGGTTAATTCCGATAACGAACGAGACCTTGACCTGCT |
| | | AAATAGACGGGTTGACATTTTGTTGGCCCCTTATGTCTTCTTAGAGGG |
| | | ACAATCGACCGTCTAGGTGATGGAGGCAAAAGGCAATAACAGGTCTG |
| | | TGATGCCCTTAGATGTTCCGGGCTGCACGCGCGCTACACTGACAGAG |

-continued

Sequence Listing

| Seq ID No. | Description | Sequence |
|---|---|---|
| | | ACAACGAGTGGGGCCCCTTGTCCGAAATGACTGGGTAAACTTGTGAA ACTTTGTCGTGCTGGGGATGGAGCTTTGTAATTTTTGCTCTTCAACGA GGAATTCCTAGTAAGCGCAAGTCATCAGCTTGCGTTGACTACGTCCCT GCCCTTTGTACACACCGCCCGTCGCTACTACCGATTGAATGGCTTAGT GAGGACTTGGGAGAGTACATCGGGGAGCCAGCAATGGCACCCTGACG GCTCAAACTCTTACAAACTTGGTCATTTAGAGGAAGTAAAAGTCGTA ACAAGGTATCTGTAGGTGAACCTGCAGATGGATCATTTC |
| 32 | DP32 16S rRNA | ACTGAGCATTGACGTTACTCGCAGAAGAAGCACCGGCTAACTCCGTG CCAGCAGCCGCGGTAATACGGAGGGTGCAAGCGTTAATCGGAATTAC TGGGCGTAAAGCGCACGCAGGCGGTTTGTTAAGTCAGATGTGAAATC CCCGAGCTTAACTTGGGAACTGCATTTGAAACTGGCAAGCTAGAGTC TTGTAGAGGGGGGTAGAATTCCAGGTGTAGCGGTGAAATGCGTAGAG ATCTGGAGGAATACCGGTGGCGAAGGCGGCCCCCTGGACAAAGACTG ACGCTCAGGTGCGAAAGCGTGGGGAGCAAACAGGATTAGATACCCTG GTAGTCCACGCTGTAAACGATGTCGACTTGGAGGTTGTGCCCTTGAGG CGTGGCTTCCGGAGCTAACGCGTTAAGTCGACCGCCTGGGGAGTACG GCCGCAAGGTTAAAACTCAAATGAATTGACGGGGGCCCGCACAAGCG GTGGAGCATGTGGTTTAATTCGATGCAACGCGAAGAACCTTACCTACT CTTGACATCCAGAGAATTCGCTAGAGATAGCTTAGTGCCTTCGGGAA CTCTGAGACAGGTGCTGCATGGCTGTCGTCAGCTCGTGTTGTGAAATG TTGGGTTAAGTCCCGCAACGAGCGCAACCCTTATCCTTTGTTGCCAGC GAGTAATGTCGGGAACTCAAAGGAGACTGCCGGTGATAAACCGGAG GAAGGTGGGGATGACGTCAAGTCATCATGGCCCTTACGAGTAGGGCT ACACACGTGCTACAATGGCATATACAAAGAGAAGCGAACTCGCGAGA GCAAGCGGACCTCATAAAGTATGTCGTAGTCCGGATTGGAGTCTGCA ACTCGACTCCATGAAGTCGGAATCGCTAGTAATCGTAGATCAGAATG CTACGGTGAATACGTTCCCGGGCCTTGTACACACCGCCCGTCACACCA TGGGAGTGGGTTGCAAAAGAAGTAGGTAGCTTAACCTTCGGGAGGGC GCTTACCACTTTGTGATTCATGACTGGGGTGAAGTCGTAACAAGGTAA CCGTAGGGGAACCTGCGGTTGGATCACCTCCTT |
| 33 | DP33 16S rRNA | GGAGGAAGGCGTAGAGATCTGGAGGAATACCGGTGGCGAAGGCGGC CCCCTGGACAAAGACTGACGCTCAGGTGCGAAAGCGTGGGGAGCAA ACAGGATTAGATACCCTGGTAGTCCACGCCGTAAACGATGTCGACTT GGAGGTTGTGCCCTTGAGGCGTGGCTTCCGGAGCTAACGCGTTAAGT CGACCGCCTGGGGAGTACGGCCGCAAGGTTAAAACTCAAATGAATTG ACGGGGGCCCGCACAAGCGGTGGAGCATGTGGTTTAATTCGATGCAA CGCGAAGAACCTTACCTGGCCTTGACATCCACGGAATTCGGCAGAGA TGCCTTAGTGCCTTCGGGAACCGTGAGACAGGTGCTGCATGGCTGTCG TCAGCTCGTGTTGTGAAATGTTGGGTTAAGTCCCGCAACGAGCGCAA CCCTTATCCTTTGTTGCCAGCACGTAATGGTGGGAACTCAAAGGAGAC TGCCGGTGATAAACCGGAGGAAGGTGGGGATGACGTCAAGTCATCAT GGCCCTTACGGCCAGGGCTACACACGTGCTACAATGGCGCATACAAA GAGAAGCGACCTCGCGAGAGCAAGCGGACCTCATAAAGTGCGTCGTA GTCCGGATCGGAGTCTGCAACTCGACTCCGTGAAGTCGGAATCGCTA GTAATCGTAGATCAGAATGCTACGGTGAATACGTTCCCGGGCCTTGTA CACACCGCCCGTCACACCATGGGAGTGGGTTGCAAAAGAAGTAGGTA GCTTAACCTTCGGGAGGGCGCTTACCACTTTGTGATTCATGACTGGGG TGAAGTCGTAACAAGGTAACCGTAGGGGAACCTGCGGTTGGATCACC TCCTT |
| 34 | DP34 16S rRNA | TACGGAGAGTTTGATCCTGGCTCAGGACGAACGCTGGCGGCGTGCTT AACACATGCAAGTCGAACGATGAAGCCCAGCTTGCTGGGTGGATTAG TGGCGAACGGGTGAGTAACACGTGAGTAACCTGCCCTTGACTCTGGG ATAAGCGTTGGAAACGACGTCTAATACCGGATACGAGCTTCCACCGC ATGGTGAGTTGCTGGAAAGAATTTTGGTCAAGGATGGACTCGCGGCC TATCAGCTTGTTGGTGAGGTAATGGCTCACCAAGGCGACGACGGGTA GCCGGCCTGAGAGGGTGACCGGCCACACTGGGACTGAGACACGGCCC AGACTCCTACGGGAGGCAGCAGTGGGGAATATTGCACAATGGGCGAA AGCCTGATGCAGCAACGCCGCGTGAGGGACGACGGCCTTCGGGTTGT AAACCTCTTTTAGCAGGGAAGAAGCGAAAGTGACGGTACCTGCAGAA AAAGCACCGGCTAACTACGTGCCAGCAGCCGCGGTAATACGTAGGGT GCAAGCGTTGTCCGGAATTATTGGGCGTAAAGAGCTCGTAGGCGGTT TGTCGCGTCTGCTGTGAAATCCCGAGGCTCAACCTCGGGTCTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGCTACTGACGCTGAGGAGCGAAAGGGTGGGGAG CAAACAGGCTTAGATACCCTGGTAGTCCACCCCGTAAACGTTGGGCG CTAGATGTGGGGACCATTCCACGGTTTCCGTGTCGTAGCTAACGCATT AAGCGCCCCGCCTGGGGAGTACGGCCGCAAGGCTAAAACTCAAAGG AATTGACGGGGGCCCGCACAAGCGGCGGAGCATGCGGATTAATTCGA TGCAACGCGAAGAACCTTACCAAGGCTTGACATATACGAGAACGGGC |

-continued

Sequence Listing

| Seq ID No. | Description | Sequence |
|---|---|---|
| | | CAGAAATGGTCAACTCTTTGGACACTCGTAAACAGGTGGTGCATGGT TGTCGTCAGCTCGTGTCGTGAGATGTTGGGTTAAGTCCCGCAACGAGC GCAACCCTCGTTCTATGTTGCCAGCACGTAATGGTGGGAACTCATGGG ATACTGCCGGGGTCAACTCGGAGGAAGGTGGGGACGACGTCAAATCA TCATGCCCCTTATGTCTTGGGCTTCACGCATGCTACAATGGCCAGTAC AAAGGGCTGCAATACCGTAAGGTGGAGCGAATCCCAAAAAGCTGGTC CCAGTTCGGATTGAGGTCTGCAACTCGACCTCATGAAGTCGGAGTCG CTAGTAATCGCAGATCAGCAACGCTGCGGTGAATACGTTCCCGGGCC TTGTACACACCGCCCGTCAAGTCATGAAAGTCGGTAACACCCGAAGC CAGTGGCCTAACCGCAAGGATGGAGCTGTCTAAGGTGGGATCGGTAA TTAGGACTAAGTCGTAACAAGGTAGCCGTACCGGAAGGTGCGGCTGG ATCACCTCCTTT |
| 35 | DP35 16S rRNA | TTGAAGAGTTTGATCATGGCTCAGATTGAACGCTGGCGGCAGGCCTA ACACATGCAAGTCGGACGGTAGCACAGAGAGCTTGCTCTTGGGTGAC GAGTGGCGGACGGGTGAGTAATGTCTGGGGATCTGCCCGATAGAGGG GGATAACCACTGGAAACGGTGGCTAATACCGCATAACGTCGCAAGAC CAAAGAGGGGGACCTTCGGGCCTCTCACTATCGGATGAACCCAGATG GGATTAGCTAGTAGGCGGGGTAATGGCCCACCTAGGCGACGATCCCT AGCTGGTCTGAGAGGATGACCAGCCACACTGGAACTGAGACACGGTC CAGACTCCTACGGGAGGCAGCAGTGGGGAATATTGCACAATGGGCGC AAGCCTGATGCAGCCATGCCGCGTGTATGAAGAAGGCCTTCGGGTTG TAAAGTACTTTCAGCGGGGAGGAAGGCGATGAGGTTAATAACCGCGT CGATTGACGTTACCCGCAGAAGAAGCACCGGCTAACTCCGTGCCAGC AGCCGCGGTAATACGGAGGGTGCAAGCGTTAATCGGAATTACTGGGC GTAAAGCGCACGCAGGCGGTCTGTTAAGTCAGATGTGAAATCCCCGG GCTTAACCTGGGAACTGCATTTGAAACTGGCAGGCTTGAGTCTTGTAG AGGGGGGTAGAATTCCAGGTGTAGCGGTGAAATGCGTAGAGATCTGG AGGAATACCGGTGGCGAAGGCGGCCCCCTGGACAAAGACTGACGCTC AGGTGCGAAAGCGTGGGGAGCAAACAGGATTAGATACCCTGGTAGTC CACGCCGTAAACGATGTCGACTTGGAGGTTGTTCCCTTGAGGAGTGG CTTCCGGAGCTAACGCGTTAAGTCGACCGCCTGGGGAGTACGGCCGC AAGGTTAAAACTCAAATGAATTGACGGGGGCCCGCACAAGCGGTGGA GCATGTGGTTTAATTCGATGCAACGCGAAGAACCTTACCTACTCTTGA CATCCAGCGAACTTAGCAGAGATGCTTTGGTGCCTTCGGGAACGCTG AGACAGGTGCTGCATGGCTGTCGTCAGCTCGTGTTGTGAAATGTTGGG TTAAGTCCCGCAACGAGCGCAACCCTTATCCTTTGTTGCCAGCGATTC GGTCGGGAACTCAAAGGAGACTGCCGGTGATAAACCGGAGGAAGGT GGGGATGACGTCAAGTCATCATGGCCCTTACGAGTAGGGCTACACAC GTGCTACAATGGCGCATACAAAGAGAAGCGACCTCGCGAGAGCAAG CGGACCTCACAAAGTGCGTCGTAGTCCGGATCGGAGTCTGCAACTCG ACTCCGTGAAGTCGGAATCGCTAGTAATCGTGGATCAGAATGCCACG GTGAATACGTTCCCGGGCCTTGTACACACCGCCCGTCACACCATGGG AGTGGGTTGCAAAAGAAGTAGGTAGCTTAACCTTCGGGAGGGCGCTT ACCACTTTGTGATTCATTACTGGGGTGAAGTCGTAACAAGGTAACCGT AGGGGAACCTGCGGTTGGATCACCTCCTT |
| 36 | DP36 16S rRNA | TTGAAGAGTTTGATCATGGCTCAGATTGAACGCTGGCGGCAGGCCTA ACACATGCAAGTCGGACGGTAGCACAGAGAGCTTGCTCTTGGGTGAC GAGTGGCGGACGGGTGAGTAATGTCTGGGGATCTGCCCGATAGAGGG GGATAACCACTGGAAACGGTGGCTAATACCGCATAACGTCGCAAGAC CAAAGAGGGGGACCTTCGGGCCTCTCACTATCGGATGAACCCAGATG GGATTAGCTAGTAGGCGGGGTAATGGCCCACCTAGGCGACGATCCCT AGCTGGTCTGAGAGGATGACCAGCCACACTGGAACTGAGACACGGTC CAGACTCCTACGGGAGGCAGCAGTGGGGAATATTGCACAATGGGCGC AAGCCTGATGCAGCCATGCCGCGTGTATGAAGAAGGCCTTCGGGTTG TAAAGTACTTTCAGCGGGGAGGAAGGCGATGCGGTTAATAACCGCGT CGATTGACGTTACCCGCAGAAGAAGCACCGGCTAACTCCGTGCCAGC AGCCGCGGTAATACGGAGGGTGCAAGCGTTAATCGGAATTACTGGGC GTAAAGCGCACGCAGGCGGTCTGTTAAGTCAGATGTGAAATCCCCGG GCTTAACCTGGGAACTGCATTTGAAACTGGCAGGCTTGAGTCTTGTAG AGGGGGGTAGAATTCCAGGTGTAGCGGTGAAATGCGTAGAGATCTGG AGGAATACCGGTGGCGAAGGCGGCCCCCTGGACAAAGACTGACGCTC AGGTGCGAAAGCGTGGGGAGCAAACAGGATTAGATACCCTGGTAGTC CACGCCGTAAACGATGTCGACTTGGAGGTTGTTCCCTTGAGGAGTGG CTTCCGGAGCTAACGCGTTAAGTCGACCGCCTGGGGAGTACGGCCGC AAGGTTAAAACTCAAATGAATTGACGGGGGCCCGCACAAGCGGTGGA GCATGTGGTTTAATTCGATGCAACGCGAAGAACCTTACCTACTCTTGA CATC |
| 37 | DP37 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATGCCTAGGAATCTGCCTGGTAGTGGGGGATA |

-continued

Sequence Listing

| Seq ID No. | Description | Sequence |
|---|---|---|
| | | ACGTTCGGAAACGAACGCTAATACCGCATACGTCCTACGGGAGAAAG CAGGGGACCTTCGGGCCTTGCGCTATCAGATGAGCCTAGGTCGGATT AGCTAGTTGGTGGGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCCATTACCTAATACGTGATGGTTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGGATGTGAAATCCCCGGGCTCAAC CTGGGAACTGCATTCAAAACTGACTGACTAGAGTATGGTAGAGGGTG GTGGAATTTCCTGTGTAGCGGTGAAATGCGTAGATATAGGAAGGAAC ACCAGTGGCGAAGGCGACCACCTGGACTGATACTGACACTGAGGTGC GAAAGCGTGGGGAGCAAACAGGATTAGATACCCTGGTAGTCCACGCC GTAAACGATGTCAACTAGCCGTTGGGAGCCTTGAGCTCTTAGTGGCG CAGCTAACGCATTAAGTTGACCGCCTGGGGAGTACGGCCGCAAGGTT AAAACTCAAATGAATTGACGGGGGCCCGCACAAGCGGTGGAGCATGT GGTTTAATTCGAAGCAACGCGAAGAACCTTACCAGGCCTTGACATCC AATGAACTTTCTAGAGATAGATTGGTGCCTTCGGGAACATTGAGACA GGTGCTGCATGGCTGTCGTCAGCTCGTGTCGTGAGATGTTGGGTTAAG TCCCGTAACGAGCGCAACCCTTGTCCTTAGTTACCAGCACGTAATGGT GGGCACTCTAAGGAGACTGCCGGTGACAAACCGGAGGAAGGTGGGG ATGACGTCAAGTCATCATGGCCCTTACGGCCTGGGCTACACACGTGCT ACAATGGTCGGTACAGAGGGTTGCCAAGCCGCGAGGTGGAGCTAATC CCATAAAACCGATCGTAGTCCGGATCGCAGTCTGCAACTCGACTGCG TGAAGTCGGAATCGCTAGTAATCGCGAATCAGAATGTCGCGGTGAAT ACGTTCCCGGGCCTTGTACACACCGCCCGTCACACCATGGGAGTGGG TTGCACCAGAAGTAGCTAGTCTAACCTTCGGGGGGACGGTTACCACG GTGTGATTCATGACTGGGGTGAAGTCGTAACAAGGTAGCCGTAGGGG AACCTGCGGCTGGATCACCTCCTT |
| 38 | DP38 16S rRNA | TACGGAGAGTTTGATCCTGGCTCAGGACGAACGCTGGCGGCGTGCTT AACACATGCAAGTCGAGCGGTAAGGCCTTTCGGGGTACACGAGCGGC GAACGGGTGAGTAACACGTGGGTGATCTGCCCTGCACTCTGGGATAA GCTTGGGAAACTGGGTCTAATACCGGATATGACCACAGCATGCATGT GTTGTGGTGGAAAGATTTATCGGTGCAGGATGGGCCCGCGGCCTATC AGCTTGTTGGTGGGGTAATGGCCTACCAAGGCGACGACGGGTAGCCG ACCTGAGAGGGTGACCGGCCACACTGGGACTGAGACACGGCCCAGAC TCCTACGGGAGGCAGCAGTGGGGAATATTGCACAATGGGCGGAAGCC TGATGCAGCGACGCCGCGTGAGGGATGAAGGCCTTCGGGTTGTAAAC CTCTTTCAGCAGGGACGAAGCGTGAGTGACGGTACCTGCAGAAGAAG CACCGGCTAACTACGTGCCAGCAGCCGCGGTAATACGTAGGGTGCGA GCGTTGTCCGGAATTACTGGGCGTAAAGAGTTCGTAGGCGGTTTGTCG CGTCGTTTGTGAAAACCCGGGGCTCAACTTCGGGCTTGCAGGCGATA CGGGCAGACTTGAGTGTTTCAGGGGAGACTGGAATTCCTGGTGTAGC GGTGAAATGCGCAGATATCAGGAGGAACACCGGTGGCGAAGGCGGG TCTCTGGGAAACAACTGACGCTGAGGAACGAAAGCGTGGGTAGCAAA CAGGATTAGATACCCTGGTAGTCCACGCCGTAAACGGTGGGCGCTAG GTGTGGGTTCCTTCCACGGGATCTGTGCCGTAGCTAACGCATTAAGCG CCCCGCCTGGGGAGTACGGCCGCAAGGCTAAAACTCAAAGGAATTGA CGGGGGCCCGCACAAGCGGCGGAGCATGTGGATTAATTCGATGCAAC GCGAAGAACCTTACCTGGGTTTGACATACACCGGAAAACCGTAGAGA TACGGTCCCCCTTGTGGTCGGTGTACAGGTGGTGCATGGCTGTCGTCA GCTCGTGTCGTGAGATGTTGGGTTAAGTCCCGCAACGAGCGCAACCC TTGTCTTATGTTGCCAGCACGTAATGGTGGGGACTCGTAAGAGACTGC CGGGGTCAACTCGGAGGAAGGTGGGGACGACGTCAAGTCATCATGCC CCTTATGTCCAGGGCTTCACACATGCTACAATGGCCAGTACAGAGGG CTGCGAGACCGTGAGGTGGAGCGAATCCCTTAAAGCTGGTCTCAGTT CGGATCGGGGTCTGCAACTCGACCCCGTGAAGTCGGAGTCGCTAGTA ATCGCAGATCAGCAACGCTGCGGTGAATACGTTCCCGGGCCTTGTAC ACACCGCCCGTCACGTCATGAAAGTCGGTAACACCCGAAGCCGGTGG CCTAACCCCTTACGGGGAGGGAGCCGTCGAAGGTGGGATCGGCGATT GGGACGAAGTCGTAACAAGGTAGCCGTACCGGAAGGTGCGGCTGGAT CACCTCCTTT |
| 39 | DP39 16S rRNA | CTTGAGAGTTTGATCCTGGCTCAGAACGAACGCTGGCGGCAGGCTTA ACACATGCAAGTCGAACGCCCCGCAAGGGGAGTGGCAGACGGGTGA GTAACGCGTGGGAATCTACCGTGCCCTGCGGAATAGCTCCGGGAAAC TGGAATTAATACCGCATACGCCCTACGGGGGAAAGATTTATCGGGGT ATGATGAGCCCGCGTTGGATTAGCTAGTTGGTGGGGTAAAGGCCTAC CAAGGCGACGATCCATAGCTGGTCTGAGAGGATGATCAGCCACATTG GGACTGAGACACGGCCCAAACTCCTACGGGAGGCAGCAGTGGGGAA TATTGGACAATGGGCGCAAGCCTGATCCAGCCATGCCGCGTGAGTGA |

-continued

Sequence Listing

| Seq ID No. | Description | Sequence |
|---|---|---|
| | | TGAAGGCCTTAGGGTTGTAAAGCTCTTTCACCGGAGAAGATAATGAC GGTATCCGGAGAAGAAGCCCCGGCTAACTTCGTGCCAGCAGCCGCGG TAATACGAAGGGGGCTAGCGTTGTTCGGAATTACTGGGCGTAAAGCG CACGTAGGCGGATATTTAAGTCAGGGGTGAAATCCCAGAGCTCAACT CTGGAACTGCCTTTGATACTGGGTATCTTGAGTATGGAAGAGGTAAGT GGAATTCCGAGTGTAGAGGTGAAATTCGTAGATATTCGGAGGAACAC CAGTGGCGAAGGCGGCTTACTGGTCCATTACTGACGCTGAGGTGCGA AAGCGTGGGGAGCAAACAGGATTAGATACCCTGGTAGTCCACGCCGT AAACGATGAATGTTAGCCGTCGGGCAGTATACTGTTCGGTGGCGCAG CTAACGCATTAAACATTCCGCCTGGGGAGTACGGTCGCAAGATTAAA ACTCAAAGGAATTGACGGGGGCCCGCACAAGCGGTGGAGCATGTGGT TTAATTCGAAGCAACGCGCAGAACCTTACCAGCTCTTGACATTCGGG GTTTGGGCAGTGGAGACATTGTCCTTCAGTTAGGCTGGCCCCAGAAC AGGTGCTGCATGGCTGTCGTCAGCTCGTGTCGTGAGATGTTGGGTTAA GTCCCGCAACGAGCGCAACCCTCGCCCTTAGTTGCCAGCATTTAGTTG GGCACTCTAAGGGGACTGCCGGTGATAAGCCGAGAGGAAGGTGGGG ATGACGTCAAGTCCTCATGGCCCTTACGGGCTGGGCTACACACGTGCT ACAATGGTGGTGACAGTGGGCAGCGAGACAGCGATGTCGAGCTAATC TCCAAAAGCCATCTCAGTTCGGATTGCACTCTGCAACTCGAGTGCATG AAGTTGGAATCGCTAGTAATCGCAGATCAGCATGCTGCGGTGAATAC GTTCCCGGGCCTTGTACACACCGCCCGTCACACCATGGGAGTTGGTTT TACCCGAAGGTAGTGCGCTAACCGCAAGGAGGCAGCTAACCACGGTA GGGTCAGCGACTGGGGTGAAGTCGTAACAAGGTAGCCGTAGGGGAA CCTGCGGCTGGATCACCTCCTTT |
| 40 | DP40 16S rRNA | TTGACGTTACCCGCAGAAGAAGCACCGGCTAACTCCGTGCCAGCAGC CGCGGTAATACGGAGGGTGCAAGCGTTAATCGGAATTACTGGGCGTA AAGCGCACGCAGGCGGTCTGTTAAGTCAGATGTGAAATCCCCGGGCT TAACCTGGGAACTGCATTTGAAACTGGCAGGCTTGAGTCTTGTAGAG GGGGGTAGAATTCCAGGTGTAGCGGTGAAATGCGTAGAGATCTGGAG GAATACCGGTGGCGAAGGCGGCCCCCTGGACAAAGACTGACGCTCAG GTGCGAAAGCGTGGGGAGCAAACAGGATTAGATACCCTGGTAGTCCA CGCCGTAAACGATGTCGACTTGGAGGTTGTTCCCTTGAGGAGTGGCTT CCGGAGCTAACGCGTTAAGTCGACCGCCTGGGGAGTACGGCCGCAAG GTTAAAACTCAAATGAATTGACGGGGGCCCGCACAAGCGGTGGAGCA TGTGGTTTAATTCGATGCAACGCGAAGAACCTTACCTACTCTTGACAT CCAGAGAACTTTCCAGAGATGGATTGGTGCCTTCGGGAACTCTGAGA CAGGTGCTGCATGGCTGTCGTCAGCTCGTGTTGTGAAATGTTGGGTTA AGTCCCGCAACGAGCGCAACCCTTATCCTTTGTTGCCAGCGCGTGATG GCGGGAACTCAAAGGAGACTGCCGGTGATAAACCGGAGGAAGGTGG GGATGACGTCAAGTCATCATGGCCCTTACGAGTAGGGCTACACACGT GCTACAATGGCGCATACAAAGAGAAGCGACCTCGCGAGAGCAAGCG GACCTCACAAAGTGCGTCGTAGTCCGGATCGGAGTCTGCAACTCGAC TCCGTGAAGTCGGAATCGCTAGTAATCGTGGATCAGAATGCCACGGT GAATACGT |
| 41 | DP41 16S rRNA | GTGGAGAGTTTGATCCTGGCTCAGGATGAACGCTGGCGGCGTGCTTA ACACATGCAAGTCGAACGGAAAGGCCCAAGCTTGCTTGGGTACTCGA GTGGCGAACGGGTGAGTAACACGTGGGTGATCTGCCCTGCACTTCGG GATAAGCCTGGGAAACTGGGTCTAATACCGGATAGGACGATGGTTTG GATGCCATTGTGGAAAGTTTTTTCGGTGTGGGATGAGCTCGCGGCCTA TCAGCTTGTTGGTGGGGTAATGGCCTACCAAGGCGTCGACGGGTAGC CGGCCTGAGAGGGTGTACGGCCACATTGGGACTGAGATACGGCCCAG ACTCCTACGGGAGGCAGCAGTGGGGAATATTGCACAATGGGCGCAAG CCTGATGCAGCGACGCCGCGTGGGGGATGACGGCCTTCGGGTTGTAA ACTCCTTTCGCTAGGGACGAAGCGTTTTGTGACGGTACCTGGAGAAG AAGCACCGGCTAACTACGTGCCAGCAGCCGCGGTAATACGTAGGGTG CGAGCGTTGTCCGGAATTACTGGGCGTAAAGAGCTCGTAGGTGGTTT GTCGCGTCGTTTGTGTAAGCCCGCAGCTTAACTGCGGGACTGCAGGC GATACGGGCATAACTTGAGTGCTGTAGGGGAGACTGGAATTCCTGGT GTAGCGGTGGAATGCGCAGATATCAGGAGGAACACCGATGGCGAAG GCAGGTCTCTGGGCAGTAACTGACGCTGAGGAGCGAAAGCATGGGTA GCGAACAGGATTAGATACCCTGGTAGTCCATGCCGTAAACGGTGGGC GCTAGGTGTGAGTCCCTTCCACGGGGTTCGTGCCGTAGCTAACGCATT AAGCGCCCCGCCTGGGGAGTACGGCCGCAAGGCTAAAACTCAAAGG AATTGACGGGGGCCCGCACAAGCGGCGGAGCATGTGGATTAATTCGA TGCAACGCGAAGAACCTTACCTGGGCTTGACATACACCAGATCGCCG TAGAGATACGGTTTCCCTTTGTGGTTGGTGTACAGGTGGTGCATGGTT GTCGTCAGCTCGTGTCGTGAGATGTTGGGTTAAGTCCCGCAACGAGC GCAACCCTTGTCTTATGTTGCCAGCACGTGATGGTGGGGACTCGTGAG AGACTGCCGGGGTTAACTCGGAGGAAGGTGGGGATGACGTCAAATCA TCATGCCCCTTATGTCCAGGGCTTCACACATGCTACAATGGTCGGTAC AACGCGCATGCGAGCCTGTGAGGGTGAGCGAATCGCTGTGAAAGCCG |

-continued

Sequence Listing

| Seq ID No. | Description | Sequence |
|---|---|---|
| | | GTCGTAGTTCGGATTGGGGTCTGCAACTCGACCCCATGAAGTCGGAG TCGCTAGTAATCGCAGATCAGCAACGCTGCGGTGAATACGTTCCCGG GCCTTGTACACACCGCCCGTCACACCATGGGAGTGGGTTGCAAAAGA AGTAGGTAGCTTAACCTTCGGGAGGGCGCTTACCACTTTGTGAT |
| 42 | DP42 16S rRNA | TGAAGAGTTTGATCATGGCTCAGATTGAACGCTGGCGGCAGGCCTAA CACATGCAAGTCGAGCGGTAGAGAGGTGCTTGCACCTCTTGAGAGCG GCGGACGGGTGAGTAATACCTAGGAATCTGCCTGATAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCTACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCATTAACCTAATACGTTAGTGTCTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGAATGTGAAATCCCCGGGCTCAAC CTGGGAACTGCATCCAAAACTGGCAAGCTAGAGTATGGTAGAGGGTA GTGGAATTTCCTGTGTAGCGGTGAAATGCGTAGATATAGGAAGGAAC ACCAGTGGCGAAGGCGACTACCTGGACTGATACTGACACTGAGGTGC GAAAGCGTGGGGAGCAAACAGGATTAGATACCCTGGTAGTCCACGCC GTAAACGATGTCAACTAGCCGTTGGGAACCTTGAGTTCTTAGTGGCGC AGCTAACGCATTAAGTTGACCGCCTGGGGAGTACGGCCGCAAGGTTA AAACTCAAATGAATTGACGGGGGCCCGCACAAGCGGTGGAGCATGTG GTTTAATTCGAAGCAACGCGAAGAACCTTACCAGGCCTTGACATCCA ATGAACTTTCCAGAGATGGATTGGTGCCTTCGGGAACATTGAGACAG GTGCTGCATGGCTGTCGTCAGCTCGTGTCGTGAGATGTTGGGTTAAGT CCCGTAACGAGCGCAACCCTTGTCCTTAGTTACCAGCACGTAATGGTG GGCACTCTAAGGAGACTGCCGGTGACAAACCGGAGGAAGGTGGGGA TGACGTCAAGTCATCATGGCCCTTACGGCCTGGGCTACACACGTGCTA CAATGGTCGGTACAAAGGGTTGCCAAGCCGCGAGGTGGAGCTAATCC CATAAAACCGATCGTAGTCCGGATCGCAGTCTGCAACTCGACTGCGT GAAGTCGGAATCGCTAGTAATCGTGAATCAGAATGTCACGGTGAATA CGTTCCCGGGCCTTGTACACACCGCCCGTCACACCATGGGAGTGGGTT GCACCAGAAGTAGCTAGTCTAACCCTCGGGAGGACGGTTACCACGGT GTGATTCATGACTGGGGTGAAGTCGTAACAAGGTAGCCGTAGGGGAA CCTGCGGCTGGATCACCTCCTT |
| 43 | DP43 16S rRNA | CTGAGTTTGATCCTGGCTCAGATTGAACGCTGGCGGCATGCCTTACAC ATGCAAGTCGAACGGCAGCACGGAGCTTGCTCTGGTGGCGAGTGGCG AACGGGTGAGTAATATATCGGAACGTACCCTGGAGTGGGGGATAACG TAGCGAAAGTTACGCTAATACCGCATACGATCTAAGGATGAAAGTGG GGGATCGCAAGACCTCATGCTCGTGGAGCGGCCGATATCTGATTAGC TAGTTGGTAGGGTAAAAGCCTACCAAGGCATCGATCAGTAGCTGGTC TGAGAGGACGACCAGCCACACTGGAACTGAGACACGGTCCAGACTCC TACGGGAGGCAGCAGTGGGGAATTTTGGACAATGGGCGAAAGCCTGA TCCAGCAATGCCGCGTGAGTGAAGAAGGCCTTCGGGTTGTAAAGCTC TTTTGTCAGGGAAGAAACGGTGAGAGCTAATATCTCTTGCTAATGAC GGTACCTGAAGAATAAGCACCGGCTAACTACGTGCCAGCAGCCGCGG TAATACGTAGGGTGCAAGCGTTAATCGGAATTACTGGGCGTAAAGCG TGCGCAGGCGGTTTTGTAAGTCTGATGTGAAATCCCCGGGCTCAACCT GGGAATTGCATTGGAGACTGCAAGGCTAGAATCTGGCAGAGGGGGGT AGAATTCCACGTGTAGCAGTGAAATGCGTAGATATGTGGAGGAACAC CGATGGCGAAGGCAGCCCCCTGGGTCAAGATTGACGCTCATGCACGA AAGCGTGGGGAGCAAACAGGATTAGATACCCTGGTAGTCCACGCCCT AAACGATGTCTACTAGTTGTCGGGTCTTAATTGACTTGGTAACGCAGC TAACGCGTGAAGTAGACCGCCTGGGGAGTACGGTCGCAAGATTAAAA CTCAAAGGAATTGACGGGGACCCGCACAAGCGGTGGATGATGTGGAT TAATTCGATGCAACGCGAAAAACCTTACCTACCCTTGACATGGCTGG AATCCTTGAGAGATCAGGGAGTGCTCGAAAGAGAACCAGTACACAGG TGCTGCATGGCTGTCGTCAGCTCGTGTCGTGAGATGTTGGGTTAAGTC CCGCAACGAGCGCAACCCTTGTCATTAGTTGCTACGAAAGGGCACTC TAATGAGACTGCCGGTGACAAACCGGAGGAAGGTGGGGATGACGTC AAGTCCTCATGGCCCTTATGGGTAGGGCTTCACACGTCATACAATGGT ACATACAGAGCGCCGCCAACCCGCGAGGGGGAGCTAATCGCAGAAA GTGTATCGTAGTCCGGATTGTAGTCTGCAACTCGACTGCATGAAGTTG GAATCGCTAGTAATCGCGGATCAGCATGTCGCGGTGAATACGTTCCC GGGTCTTGTACACACCGCCCGTCACACCATGGGAGCGGGTTTTACCA GAAGTAGGTAGCTTAACCGTAAGGAGGGCGCTTACCACGGTAGGATT CGTGACTGGGGTGAAGTCGTAACAAGGTAGCCGTATCGGAAGGTGCG GCTGGATCACCTCCTTT |

-continued

Sequence Listing

| Seq ID No. | Description | Sequence |
|---|---|---|
| 44 | DP44 16S rRNA | TGGCGGCATGCCTTACACATGCAAGTCGAACGGCAGCATAGGAGCTT GCTCCTGATGGCGAGTGGCGAACGGGTGAGTAATATATCGGAACGTG CCCTAGAGTGGGGGATAACTAGTCGAAAGACTAGCTAATACCGCATA CGATCTACGGATGAAAGTGGGGGATCGCAAGACCTCATGCTCCTGGA GCGGCCGATATCTGATTAGCTAGTTGGTGGGGTAAAAGCTCACCAAG GCGACGATCAGTAGCTGGTCTGAGAGGACGACCAGCCACACTGGGAC TGAGACACGGCCCAGACTCCTACGGGAGGCAGCAGTGGGGAATTTTG GACAATGGGGGCAACCCTGATCCAGCAATGCCGCGTGAGTGAAGAAG GCCTTCGGGTTGTAAAGCTCTTTTGTCAGGGAAGAAACGGTTCTGGAT AATACCTAGGACTAATGACGGTACCTGAAGAATAAGCACCGGCTAAC TACGTGCCAGCAGCCGCGGTAATACGTAGGGTGCAAGCGTTAATCGG AATTACTGGGCGTAAAGCGTGCGCAGGCGGTTGTGTAAGTCAGATGT GAAATCCCCGGGCTCAACCTGGGAATTGCATTTGAGACTGCACGGCT AGAGTGTGTCAGAGGGGGGTAGAATTCCACGTGTAGCAGTGAAATGC GTAGATATGTGGAGGAATACCGATGGCGAAGGCAGCCCCCTGGGATA ACACTGACGCTCATGCACGAAAGCGTGGGGAGCAAACAGGATTAGAT ACCCTGGTAGTCCACGCCCTAAACGATGTCTACTAGTTGTCGGGTCTT AATTGACTTGGTAACGCAGCTAACGCGTGAAGTAGACCGCCTGGGGA GTACGGTCGCAAGATTAAAACTCAAAGGAATTGACGGGGACCCGCAC AAGCGGTGGATGATGTGGATTAATTCGATGCAACGCGAAAAACCTTA CCTACCCTTGACATGGATGGAATCCCGAAGAGATTTGGGAGTGCTCG AAAGAGAACCATCACACAGGTGCTGCATGGCTGTCGTCAGCTCGTGT CGTGAGATGTTGGGTTAAGTCCCGCAACGAGCGCAACCCTTGTCATTA GTTGCTACGAAAGGGCACTCTAATGAGACTGCCGGTGACAAACCGGA GGAAGGTGGGGATGACGTCAAGTCCTCATGGCCCTTATGGGTAGGGC TTCACACGTCATACAATGGTACATACAGAGGGCCGCCAACCCGCGAG GGGGAGCTAATCCCAGAAAGTGTATCGTAGTCCGGATTGGAGTCTGC AACTCGACTCCATGAAGTTGGAATCGCTAGTAATCGCGGATCAGCAT GTCGCGGTGAATACGTTCCCGGGTCTTGTACACACCGCCCGTCACACC ATGGGAGCGGGTTTTACCAGAAGTGGGTAGCCTAACCGCAAGGAGGG CGCTCACCACGGTAGGATTCGTGACTGGGGTGAAGTCGTAACAAGGT AGCCGTATCGGAAGGTGCGGCTGGATCACCTCCTTT |
| 45 | DP45 16S rRNA | TACGGAGAGTTTGATCCTGGCTCAGGACGAACGCTGGCGGCGTGCTT AACACATGCAAGTCGAACGGTGACGCTAGAGCTTGCTCTGGTTGATC AGTGGCGAACGGGTGAGTAACACGTGAGTAACCTGCCCTTGACTCTG GGATAACTCCGGGAAACCGGGGCTAATACCGGATACGAGACGCGACC GCATGGTCGGCGTCTGGAAAGTTTTTCGGTCAAGGATGGACTCGCGG CCTATCAGCTTGTTGGTGAGGTAATGGCTCACCAAGGCGTCGACGGG TAGCCGGCCTGAGAGGGCGACCGGCCACACTGGGACTGAGACACGGC CCAGACTCCTACGGGAGGCAGCAGTGGGGAATATTGCACAATGGGCG AAAGCCTGATGCAGCGACGCCGCGTGAGGGATGAAGGCCTTCGGGTT GTAAACCTCTTTCAGTAGGGAAGAAGCGAAAGTGACGGTACCTGCAG AAGAAGCGCCGGCTAACTACGTGCCAGCAGCCGCGGTAATACGTAGG GCGCAAGCGTTGTCCGGAATTATTGGGCGTAAAGAGCTCGTAGGCGG TTTGTCGCGTCTGGTGTGAAAACTCAAGGCTCAACCTTGAGCTTGCAT CGGGTACGGGCAGACTAGAGTGTGGTAGGGGTGACTGGAATTCCTGG TGTAGCGGTGGAATGCGCAGATATCAGGAGGAACACCGATGGCGAA GGCAGGTCACTGGGCCACTACTGACGCTGAGGAGCGAAAGCATGGGG AGCGAACAGGATTAGATACCCTGGTAGTCCATGCCGTAAACGTTGGG CACTAGGTGTGGGGCTCATTCCACGAGTTCCGCGCCGCAGCTAACGC ATTAAGTGCCCCGCCTGGGGAGTACGGCCGCAAGGCTAAAACTCAAA GGAATTGACGGGGGCCCGCACAAGCGGCGGAGCATGCGGATTAATTC GATGCAACGCGAAGAACCTTACCAAGGCTTGACATACACCGGAATCA TGCAGAGATGTGTGCGTCTTCGGACTGGTGTACAGGTGGTGCATGGTT GTCGTCAGCTCGTGTCGTGAGATGTTGGGTTAAGTCCCGCAACGAGC GCAACCCTCGTCCTATGTTGCCAGCACGTTATGGTGGGGACTCATAGG AGACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCGATACCGCGAGGTGGAGCGAATCCCAAAAAGCCGGT CTCAGTTCGGATTGGGGTCTGCAACTCGACCCCATGAAGTCGGAGTC GCTAGTAATCGCAGATCAGCAACGCTGCGGTGAATACGTTCCCGGGC CTTGTACACACCGCCCGTCAAGTCACGAAAGTCGGTAACACCCGAAG CCGGTGGCCTAACCCCTTGTGGGATGGAGCCGTCGAAGGTGGGATTG GCGATTGGGACTAAGTCGTAACAAGGTAGCCGTACCGGAAGGTGCGG CTGGATCACCTCCTTT |
| 46 | DP46 16S rRNA | TTGAAGAGTTTGATCATGGCTCAGATTGAACGCTGGCGGCAGGCCTA ACACATGCAAGTCGGACGGTAGCACAGAGGAGCTTGCTCCTTGGGTG ACGAGTGGCGGACGGGTGAGTAATGTCTGGGGATCTGCCCGATAGAG GGGGATAACCACTGGAAACGGTGGCTAATACCGCATAACGTCGCAAG ACCAAAGAGGGGGACCTTCGGGCCTCTCACTATCGGATGAACCCAGA TGGGATTAGCTAGTAGGCGGGGTAATGGCCCACCTAGGCGACGATCC |

-continued

Sequence Listing

| Seq ID No. | Description | Sequence |
|---|---|---|
| | | CTAGCTGGTCTGAGAGGATGACCAGCCACACTGGAACTGAGACACGG TCCAGACTCCTACGGGAGGCAGCAGTGGGGAATATTGCACAATGGGC GCAAGCCTGATGCAGCCATGCCGCGTGTATGAAGAAGGCCTTCGGGT TGTAAAGTACTTTCAGCGGGGAGGAAGGCGACAGGGTTAATAACCCT GTCGATTGACGTTACCCGCAGAAGAAGCACCGGCTAACTCCGTGCCA GCAGCCGCGGTAATACGGAGGGTGCAAGCGTTAATCGGAATTACTGG GCGTAAAGCGCACGCAGGCGGTCTGTTAAGTCAGATGTGAAATCCCC GGGCTTAACCTGGGAACTGCATTTGAAACTGGCAGGCTTTAGTCTTGT AGAGTGGGGTAGAATTCCAGGTGTAGCGGTGAAATGCGTAGAGATGT GGAGGAACACCAGTGGCGAAGGCGGCTTTTTGGTCTGTAACTGACGC TGAGGCGCGAAAGCGTGGGGAGCAAACAGGATTAGATACCCTGGTA GTCCACGCCGTAAACGATGAGTGCTAAGTGTT |
| 47 | DP47 16S rRNA | AGGGTGCAAGCGTTAATCGGAATTACTGGGCGTAAAGCGCGCGTAGG TGGTTTGTTAAGTTGAATGTGAAATCCCCGGGCTCAACCTGGGAACTG CATTTGAAACTGGCAAGCTAGAGTCTCGTAGAGGGGGGTAGAATTCC AGGTGTAGCGGTGAAATGCGTAGAGATCTGGAGGAATACCGGTGGCG AAGGCGGCCCCCTGGACGAAGACTGACGCTCAGGTGCGAAAGCGTGG GGAGCAAACAGGATTAGATACCCTGGTAGTCCACGCCGTAAACGATG TCAACTAGCCGTTGGAAGCCTTGAGCTTTTAGTGGCGCAGCTAACGCA TTAAGTTGACCGCCTGGGGAGTACGGCCGCAAGGTTAAAACTCAAAT GAATTGACGGGGGCCCGCACAAGCGGTGGAGCATGTGGTTTAATTCG AAGCAACGCGAAGAACCTTACCAGGCCTTGACATCCAATGAACTTTC TAGAGATAGATTGGTGCCTTCGGGAACATTGAGACAGGTGCTGCATG GCTGTCGTCAGCTCGTGTCGTGAGATGTTGGGTTAAGTCCCGCAACGA GCGCAACCCTTGTCCTGTGTTGCCAGCGCGTAATGGCGGGGACTCGC AGGAGACTGCCGGGGTCAACTCGGAGGAAGGTGGGGATGACGTCAA ATCATCATGCCCCTTATGTCTTGGGCTTCACGCATGCTACAATGGCCG GTACAAAGGGCTGCAATACCGTGAGGTGGAGCGAATCCCAAAAAGCC GGTCCCAGTTCGGATTGAGGTCTGCAACTCGACCTCATGAAGTCGGA GTCGCTAGTAATCGCAGATCAGCAACGCTGCGGTGAATACGTTCCCG GGTCTTGTACACACCGCCCGTCAAGTCATGAAAGTCGGTAACACCTG AAGCCGGTGGCCCAACCCTTGTGGAGGGAGCCGTCGAAGGTGGGATC GGTAATTAGGACTAAGT |
| 48 | DP48 16S rRNA | CATGGAGAGTTTGATCCTGGCTCAGGACGAACGCTGGCGGCGTGCCT AATACATGCAAGTCGAGCGGACAGATGGGAGCTTGCTCCCTGATGTT AGCGGCGGACGGGTGAGTAACACGTGGGTAACCTGCCTGTAAGACTG GGATAACTCCGGGAAACCGGGGCTAATACCGGATGCTTGATTGAACC GCATGGTTCAATTATAAAAGGTGGCTTTTAGCTACCACTTACAGATGG ACCCGCGGCGCATTAGCTAGTTGGTGAGGTAACGGCTCACCAAGGCA ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGATGAAGGTT TTCGGATCGTAAAACTCTGTTGTTAGGGAAGAACAAGTACCGTTCGA ATAGGGCGGTACCTTGACGGTACCTAACCAGAAAGCCACGGCTAACT ACGTGCCAGCAGCCGCGGTAATACGTAGGTGGCAAGCGTTGTCCGGA ATTATTGGGCGTAAAGCGCGCGCAGGCGGTTTCTTAAGTCTGATGTGA AAGCCCCCGGCTCAACCGGGGAGGGTCATTGGAAACTGGGGAACTTG AGTGCAGAAGAGGAGAGTGGAATTCCACGTGTAGCGGTGAAATGCGT AGAGATGTGGAGGAACACCAGTGGCGAAGGCGACTCTCTGGTCTGTA ACTGACGCTGAGGCGCGAAAGCGTGGGGAGCGAACAGGATTAGATA CCCTGGTAGTCCACGCCGTAAACGATGAGTGCTAAGTGTTAGAGGGT TTCCGCCCTTTAGTGCTGCAGCAAACGCATTAAGCACTCCGCCTGGGG AGTACGGTCGCAAGACTGAAACTCAAAGGAATTGACGGGGGCCCGCA CAAGCGGTGGAGCATGTGGTTTAATTCGAAGCAACGCGAAGAACCTT ACCAGGTCTTGACATCCTCTGACAACCCTAGAGATAGGGCTTCCCCTT CGGGGGCAGAGTGACAGGTGGTGCATGGTTGTCGTCAGCTCGTGTCG TGAGATGTTGGGTTAAGTCCCGCAACGAGCGCAACCCTTGATCTTAGT TGCCAGCATTCAGTTGGGCACTCTAAGGTGACTGCCGGTGACAAACC GGAGGAAGGTGGGGATGACGTCAAATCATCATGCCCCTTATGACCTG GGCTACACACGTGCTACAATGGGCAGAACAAAGGGCAGCGAAGCCG CGAGGCTAAGCCAATCCCACAAATCTGTTCTCAGTTCGGATCGCAGTC TGCAACTCGACTGCGTGAAGCTGGAATCGCTAGTAATCGCGGATCAG CATGCCGCGGTGAATACGTTCCCGGGCCTTGTACACACCGCCCGTCAC ACCACGAGAGTTTGTAACACCCGAAGTCGGTGAGGTAACCTTTTGGA GCCAGCCGCCGAAGGTGGGACAGATGATTGGGGTGAAGTCGTAACAA GGTAGCCGTATCGGAAGGTGCGGCTGGATCACCTCCTTT |
| 49 | DP49 16S rRNA | TATGGAGAGTTTGATCCTGGCTCAGGACGAACGCTGGCGGCGTGCCT AATACATGCAAGTCGAGCGGACGTTTTTGAAGCTTGCTTCAAAAACG TTAGCGGCGGACGGGTGAGTAACACGTGGGCAACCTGCCTTATCGAC TGGGATAACTCCGGGAAACCGGGGCTAATACCGGATAATATCTAGCA |

-continued

Sequence Listing

| Seq ID No. | Description | Sequence |
|---|---|---|
| | | CCTCCTGGTGCAAGATTAAAAGAGGGCCTTCGGGCTCTCACGGTGAG<br>ATGGGCCCGCGGCGCATTAGCTAGTTGGAGAGGTAATGGCTCCCCAA<br>GGCGACGATGCGTAGCCGACCTGAGAGGGTGATCGGCCACACTGGGA<br>CTGAGACACGGCCCAGACTCCTACGGGAGGCAGCAGTAGGGAATCTT<br>CCGCAATGGACGAAAGTCTGACGGAGCAACGCCGCGTGAGTGATGAA<br>GGGTTTCGGCTCGTAAAGCTCTGTTATGAGGGAAGAACACGTACCGT<br>TCGAATAGGGCGGTACCTTGACGGTACCTCATCAGAAAGCCACGGCT<br>AACTACGTGCCAGCAGCCGCGGTAATACGTAGGTGGCAAGCGTTGTC<br>CGGAATTATTGGGCGTAAAGCGCGCGCAGGCGGCCTTTTAAGTCTGA<br>TGTGAAATCTTGCGGCTCAACCGCAAGCGGTCATTGGAAACTGGGAG<br>GCTTGAGTACAGAAGAGGAGAGTGGAATTCCACGTGTAGCGGTGAAA<br>TGCGTAGATATGTGGAGGAACACCAGTGGCGAAGGCGACTCTCTGGT<br>CTGTAACTGACGCTGAGGCGCGAAAGCGTGGGGAGCAAACAGGATTA<br>GATACCCTGGTAGTCCACGCCGTAAACGATGAGTGCTAGGTGTTAGG<br>GGTTTCGATGCCCGTAGTGCCGAAGTTAACACATTAAGCACTCCGCCT<br>GGGGAGTACGGCCGCAAGGCTGAAACTCAAAGGAATTGACGGGGGC<br>CCGCACAAGCAGTGGAGCATGTGGTTTAATTCGAAGCAACGCGAAGA<br>ACCTTACCAGGTCTTGACATCCTTTGACCACTCTGGAGACAGAGCTTC<br>CCCTTCGGGGGCAAAGTGACAGGTGGTGCATGGTTGTCGTCAGCTCG<br>TGTCGTGAGATGTTGGGTTAAGTCCCGCAACGAGCGCAACCCTTGAC<br>CTTAGTTGCCAGCATTTAGTTGGGCACTCTAAGGTGACTGCCGGTGAC<br>AAACCGGAGGAAGGTGGGGATGACGTCAAATCATCATGCCCCTTATG<br>ACCTGGGCTACACACGTGCTACAATGGATGGTACAAAGGGTTGCGAA<br>GCCGCGAGGTGAAGCCAATCCCATAAAGCCATTCTCAGTTCGGATTG<br>TAGGCTGCAACTCGCCTGCATGAAGCTGGAATTGCTAGTAATCGCGG<br>ATCAGCATGCCGCGGTGAATACGTTCCCGGGCCTTGTACACACCGCCC<br>GTCACACCACGAGAGTTTGTAACACCCGAAGTCGGTGAGGTAACCTT<br>TTGGAGCCAGCCGCCGAAGGTGGGACAGATGATTGGGGTGAAGTCGT<br>AACAAGGTAGCCGTATCGGAAGGTGCGGCTGGATCACCTCCTTT |
| 50 | DP50 16S rRNA | TTGAAGAGTTTGATCATGGCTCAGATTGAACGCTGGCGGCAGGCCTA<br>ACACATGCAAGTCGAACGGTAGCACAGAGAGCTTGCTCTTGGGTGAC<br>GAGTGGCGGACGGGTGAGTAATGTCTGGGAAACTGCCCGATGGAGGG<br>GGATAACTACTGGAAACGGTAGCTAATACCGCATAACGTCGCAAGAC<br>CAAAGTGGGGGACCTTCGGGCCTCACACCATCGGATGTGCCCAGATG<br>GGATTAGCTAGTAGGTGGGGTAATGGCTCACCTAGGCGACGATCCCT<br>AGCTGGTCTGAGAGGATGACCAGCCACACTGGAACTGAGACACGGTC<br>CAGACTCCTACGGGAGGCAGCAGTGGGGAATATTGCACAATGGGCGC<br>AAGCCTGATGCAGCCATGCCGCGTGTATGAAGAAGGCCTTCGGGTTG<br>TAAAGTACTTTCAGCGAGGAGGAAGGCATTGTGGTTAATAACCGCAG<br>TGATTGACGTTACTCGCAGAAGAAGCACCGGCTAACTCCGTGCCAGC<br>AGCCGCGGTAATACGGAGGGTGCAAGCGTTAATCGGAATTACTGGGC<br>GTAAAGCGCACGCAGGCGGTCTGTCAAGTCGGATGTGAAATCCCCGG<br>GCTCAACCTGGGAACTGCATTCGAAACTGGCAGGCTAGAGTCTTGTA<br>GAGGGGGGTAGAATTCCAGGTGTAGCGGTGAAATGCGTAGAGATCTG<br>GAGGAATACCGGTGGCGAAGGCGGCCCCCTGGACAAAGACTGACGCT<br>CAGGTGCGAAAGCGTGGGGAGCAAACAGGATTAGATACCCTGGTAGT<br>CCACGCCGTAAACGATGTCGACTTGGAGGTTGTGCCCTTGAGGCGTG<br>GCTTCCGGAGCTAACGCGTTAAGTCGACCGCCTGGGGAGTACGGCCG<br>CAAGGTTAAAACTCAAATGAATTGACGGGGGCCCGCACAAGCGGTGG<br>AGCATGTGGTTTAATTCGATGCAACGCGAAGAACCTTACCTACTCTTG<br>ACATCCACGGAATTTAGCAGAGATGCTTTAGTGCCTTCGGGAACCGT<br>GAGACAGGTGCTGCATGGCTGTCGTCAGCTCGTGTTGTGAAATGTTGG<br>GTTAAGTCCCGCAACGAGCGCAACCCTTATCCTTTGTTGCCAGCGGTT<br>CGGCCGGGAACTCAAAGGAGACTGCCAGTGATAAACTGGAGGAAGG<br>TGGGGATGACGTCAAGTCATCATGGCCCTTACGAGTAGGGCTACACA<br>CGTGCTACAATGGCATATACAAAGAGAAGCGACCTCGCGAGAGCAAG<br>CGGACCTCATAAAGTATGTCGTAGTCCGGATCGGAGTCTGCAACTCG<br>ACTCCGTGAAGTCGGAATCGCTAGTAATCGTAGATCAGAATGCTACG<br>GTGAATACGTTCCCGGGCCTTGTACACACCGCCCGTCACACCATGGG<br>AGTGGGTTGCAAAAGAAGTAGGTAGCTTAACCTTCGGGAGGGCGCTT<br>ACCACTTTGTGATTCATGACTGGGGTGAAGTCGTAACAAGGTAACCG<br>TAGGGGAACCTGCGGTTGGATCACCTCCTT |
| 51 | DP51 16S rRNA | TTGAAGAGTTTGATCATGGCTCAGATTGAACGCTGGCGGCAGGCCTA<br>ACACATGCAAGTCGAGCGGTAGCACAGGGAGCTTGCTCCTGGGTGAC<br>GAGCGGCGGACGGGTGAGTAATGTCTGGGAAACTGCCTGATGGAGGG<br>GGATAACTACTGGAAACGGTAGCTAATACCGCATAACGTCGCAAGAC<br>CAAAGAGGGGGACCTTCGGGCCTCTTGCCATCAGATGTGCCCAGATG<br>GGATTAGCTAGTAGGTGAGGTAATGGCTCACCTAGGCGACGATCCCT<br>AGCTGGTCTGAGAGGATGACCAGCCACACTGGAACTGAGACACGGTC<br>CAGACTCCTACGGGAGGCAGCAGTGGGGAATATTGCACAATGGGCGC<br>AAGCCTGATGCAGCCATGCCGCGTGTATGAAGAAGGCCTTCGGGTTG |

-continued

Sequence Listing

| Seq ID No. | Description | Sequence |
|---|---|---|
| | | TAAAGTACTTTCAGCGAGGAGGAAGGCATTAAGGTTAATAACCTTGG<br>TGATTGACGTTACTCGCAGAAGAAGCACCGGCTAACTCCGTGCCAGC<br>AGCCGCGGTAATACGGGGGGTGCAAGCGTTAATCGGAATTACTGGGC<br>GTAAAGCGCACGCAGGCGGTTTGTCAAGTCGGATGTGAAATCCCCGG<br>GCTCAACCTGGGAACTGCATTCGAAACGGGCAAGCTAGAGTCTTGTA<br>GAGGGGGGTAGAATTCCAGGTGTAGCGGTGAAATGCGTAGAGATCTG<br>GAGGAATACCGGTGGCGAAGGCGGCCCCCTGGACAAAGACTGACGCT<br>CAGGTGCGAAAGCGTGGGGAGCAAACAGGATTAGATACCCTGGTAGT<br>CCACGCCGTAAACGATGTCGACTTGGAGGTTGTGCCCTTGAGGCGTG<br>GCTTCCGGAGCTAACGCGTTAAGTCGACCGCCTGGGGAGTACGGCCG<br>CAAGGTTAAAACTCAAATGAATTGACGGGGGCCCGCACAAGCGGTGG<br>AGCATGTGGTTTAATTCGATGCAACGCGAAGAACCTTACCTACTCTTG<br>ACATCCAGAGAACTTTCCAGAGATGGATTGGTGCCTTCGGGAACTCT<br>GAGACAGGTGCTGCATGGCTGTCGTCAGCTCGTGTTGTGAAATGTTGG<br>GTTAAGTCCCGCAACGAGCGCAACCCTTATCCTTTGTTGCCAGCGAGT<br>AATGTCGGGAACTCAAAGGAGACTGCCAGTGACAAACTGGAGGAAG<br>GTGGGGATGACGTCAAGTCATCATGGCCCTTACGAGTAGGGCTACAC<br>ACGTGCTACAATGGCATATACAAAGAGAAGCGACCTCGCGAGAGCAA<br>GCGGACCTCACAAAGTATGTCGTAGTCCGGATCGGAGTCTGCAACTC<br>GACTCCGTGAAGTCGGAATCGCTAGTAATCGTAGATCAGAATGCTAC<br>GGTGAATACGTTCCCGGGCCTTGTACACACCGCCCGTCACACCATGG<br>GAGTGGGTTGCAAAAGAAGTAGGTAGCTTAACCTTCGGGAGGGCGCT<br>TACCACTTTGTGATTCATGACTGGGGTGAAGTCGTAACAAGGTAACC<br>GTAGGGGAACCTGCGGTTGGATCACCTCCTT |
| 52 | DP52 16S rRNA | ACGGAGAGTTTGATCCTGGCTCAGGATGAACGCTGGCGGCGTGCTTA<br>ACACATGCAAGTCGAACGATGATCCCAGCTTGCTGGGGGATTAGTGG<br>CGAACGGGTGAGTAACACGTGAGTAACCTGCCCTTGACTCTGGGATA<br>AGCCTGGGAAACTGGGTCTAATACCGGATATGACTGTCTGACGCATG<br>TCAGGTGGTGGAAAGCTTTTGTGGTTTTGGATGGACTCGCGGCCTATC<br>AGCTTGTTGGTGGGGTAATGGCCTACCAAGGCGACGACGGGTAGCCG<br>GCCTGAGAGGGTGACCGGCCACACTGGGACTGAGACACGGCCCAGAC<br>TCCTACGGGAGGCAGCAGTGGGGAATATTGCACAATGGGCGCAAGCC<br>TGATGCAGCGACGCCGCGTGAGGGATGACGGCCTTCGGGTTGTAAAC<br>CTCTTTCAGTAGGGAAGAAGCGAAAGTGACGGTACCTGCAGAAGAAG<br>CGCCGGCTAACTACGTGCCAGCAGCCGCGGTAATACGTAGGGCGCAA<br>GCGTTATCCGGAATTATTGGGCGTAAAGAGCTCGTAGGCGGTTTGTCG<br>CGTCTGCTGTGAAAGACCGGGGCTCAACTCCGGTTCTGCAGTGGGTA<br>CGGGCAGACTAGAGTGCAGTAGGGGAGACTGGAATTCCTGGTGTAGC<br>GGTGAAATGCGCAGATATCAGGAGGAACACCGATGGCGAAGGCAGG<br>TCTCTGGGCTGTAACTGACGCTGAGGAGCGAAAGCATGGGGAGCGAA<br>CAGGATTAGATACCCTGGTAGTCCATGCCGTAAACGTTGGGCACTAG<br>GTGTGGGGGACATTCCACGTTTTCCGCGCCGTAGCTAACGCATTAAGT<br>GCCCCGCCTGGGGAGTACGGCCGCAAGGCTAAAACTCAAAGGAATTG<br>ACGGGGGCCCGCACAAGCGGCGGAGCATGCGGATTAATTCGATGCAA<br>CGCGAAGAACCTTACCAAGGCTTGACATGAACCGGTAATACCTGGAA<br>ACAGGTGCCCCGCTTGCGGTCGGTTTACAGGTGGTGCATGGTTGTCGT<br>CAGCTCGTGTCGTGAGATGTTGGGTTAAGTCCCGCAACGAGCGCAAC<br>CCTCGTTCTATGTTGCCAGCGCGTTATGGCGGGGACTCATAGGAGACT<br>GCCGGGGTCAACTCGGAGGAAGGTGGGGACGACGTCAAATCATCATG<br>CCCCTTATGTCTTGGGCTTCACGCATGCTACAATGGCCGGTACAAAGG<br>GTTGCGATACTGTGAGGTGGAGCTAATCCCAAAAAGCCGGTCTCAGT<br>TCGGATTGGGGTCTGCAACTCGACCCCATGAAGTCGGAGTCGCTAGT<br>AATCGCAGATCAGCAACGCTGCGGTGAATACGTTCCCGGGCCTTGTA<br>CACACCGCCCGTCAAGTCACGAAAGTTGGTAACACCCGAAGCCGGTG<br>GCCTAACCCTTGTGGGGGGAGCCGTCGAAGGTGGGACCGGCGATTGG<br>GACTAAGTCGTAACAAGGTAGCCGTACCGGAAGGTGCGGCTGGATCA<br>CCTCCTTT |
| 53 | DP53 16S rRNA | TGAAGAGTTTGATCATGGCTCAGATTGAACGCTGGCGGCAGGCCTAA<br>CACATGCAAGTCGAGCGGTAGAGAGAAGCTTGCTTCTCTTGAGAGCG<br>GCGGACGGGTGAGTAATACCTAGGAATCTGCCTGATAGTGGGGGATA<br>ACGTTCGGAAACGGACGCTAATACCGCATACGTCCTACGGGAGAAAG<br>CAGGGGACCTTCGGGCCTTGCGCTATCAGATGAGCCTAGGTCGGATT<br>AGCTAGTTGGTGAGGTAATGGCTCACCAAGGCTACGATCCGTAACTG<br>GTCTGAGAGGATGATCAGTCACACTGGAACTGAGACACGGTCCAGAC<br>TCCTACGGGAGGCAGCAGTGGGGAATATTGGACAATGGGCGAAAGCC<br>TGATCCAGCCATGCCGCGTGTGTGAAGAAGGTCTTCGGATTGTAAAG<br>CACTTTAAGTTGGGAGGAAGGGCAGTTACCTAATACGTGATTGTCTTG<br>ACGTTACCGACAGAATAAGCACCGGCTAACTCTGTGCCAGCAGCCGC<br>GGTAATACAGAGGGTGCAAGCGTTAATCGGAATTACTGGGCGTAAAG<br>CGCGCGTAGGTGGTTTGTTAAGTTGAATGTGAAATCCCCGGGCTCAAC<br>CTGGGAACTGCATCCAAAACTGGCAAGCTAGAGTATGGTAGAGGGTA |

-continued

Sequence Listing

| Seq ID No. | Description | Sequence |
| --- | --- | --- |
| | | GTGGAATTTCCTGTGTAGCGGTGAAATGCGTAGATATAGGAAGGAAC<br>ACCAGTGGCGAAGGCGACTACCTGGACTGATACTGACACTGAGGTGC<br>GAAAGCGTGGGGAGCAAACAGGATTAGATACCCTGGTAGTCCACGCC<br>GTAAACGATGTCAACTAGCCGTTGGGAGTCTTGAACTCTTAGTGGCGC<br>AGCTAACGCATTAAGTTGACCGCCTGGGGAGTACGGCCGCAAGGTTA<br>AAACTCAAATGAATTGACGGGGGCCCGCACAAGCGGTGGAGCATGTG<br>GTTTAATTCGAAGCAACGCGAAGAACCTTACCAGGCCTTGACATCCA<br>ATGAACTTTCTAGAGATAGATTGGTGCCTTCGGGAACATTGAGACAG<br>GTGCTGCATGGCTGTCGTCAGCTCGTGTCGTGAGATGTTGGGTTAAGT<br>CCCGTAACGAGCGCAACCCTTGTCCTTAGTTACCAGCACGTAATGGTG<br>GGCACTCTAAGGAGACTGCCGGTGACAAACCGGAGGAAGGTGGGGA<br>TGACGTCAAGTCATCATGGCCCTTACGGCCTGGGCTACACACGTGCTA<br>CAATGGTCGGTACAAAGGGTTGCCAAGCCGCGAGGTGGAGCTAATCC<br>CATAAAACCGATCGTAGTCCGGATCGCAGTCTGCAACTCGACTGCGT<br>GAAGTCGGAATCGCTAGTAATCGTGAATCAGAATGTCACGGTGAATA<br>CGTTCCCGGGCCTTGTACACACCGCCCGTCACACCATG |
| 54 | DP54 16S rRNA | CTTGAGAGTTTGATCCTGGCTCAGAGCGAACGCTGGCGGCAGGCTTA<br>ACACATGCAAGTCGAGCGGGCACCTTCGGGTGTCAGCGGCAGACGGG<br>TGAGTAACACGTGGGAACGTACCCTTCGGTTCGGAATAACGCTGGGA<br>AACTAGCGCTAATACCGGATACGCCCTTTTGGGGAAAGGTTTACTGCC<br>GAAGGATCGGCCCGCGTCTGATTAGCTAGTTGGTGGGGTAACGGCCT<br>ACCAAGGCGACGATCAGTAGCTGGTCTGAGAGGATGATCAGCCACAC<br>TGGGACTGAGACACGGCCCAGACTCCTACGGGAGGCAGCAGTGGGG<br>AATATTGGACAATGGGCGCAAGCCTGATCCAGCCATGCCGCGTGAGT<br>GATGAAGGCCTTAGGGTTGTAAAGCTCTTTTGTCCGGGACGATAATG<br>ACGGTACCGGAAGAATAAGCCCCGGCTAACTTCGTGCCAGCAGCCGC<br>GGTAATACGAAGGGGGCTAGCGTTGCTCGGAATCACTGGGCGTAAAG<br>GGCGCGTAGGCGGCCATTCAAGTCGGGGGTGAAAGCCTGTGGCTCAA<br>CCACAGAATTGCCTTCGATACTGTTTGGCTTGAGTTTGGTAGAGGTTG<br>GTGGAACTGCGAGTGTAGAGGTGAAATTCGTAGATATTCGCAAGAAC<br>ACCAGTGGCGAAGGCGGCCAACTGGACCAATACTGACGCTGAGGCGC<br>GAAAGCGTGGGGAGCAAACAGGATTAGATACCCTGGTAGTCCACGCC<br>GTAAACGATGAATGCTAGCTGTTGGGGTGCTTGCACCTCAGTAGCGC<br>AGCTAACGCTTTAAGCATTCCGCCTGGGGAGTACGGTCGCAAGATTA<br>AAACTCAAAGGAATTGACGGGGGCCCGCACAAGCGGTGGAGCATGT<br>GGTTTAATTCGAAGCAACGCGCAGAACCTTACCATCCCTTGACATGTC<br>GTGCCATCCGGAGAGATCCGGGGTTCCCTTCGGGGACGCGAACACAG<br>GTGCTGCATGGCTGTCGTCAGCTCGTGTCGTGAGATGTTGGGTTAAGT<br>CCCGCAACGAGCGCAACCCACGTCCTTAGTTGCCATCATTTAGTTGGG<br>CACTCTAGGGAGACTGCCGGTGATAAGCCGCGAGGAAGGTGTGGATG<br>ACGTC |
| 55 | DP55 16S rRNA | TCGGAGAGTTTGATCCTGGCTCAGGATGAACGCTGGCGGCGTGCCTA<br>ATACATGCAAGTCGAGCGAACTGATTAGAAGCTTGCTTCTATGACGTT<br>AGCGGCGGACGGGTGAGTAACACGTGGGCAACCTGCCTGTAAGACTG<br>GGATAACTTCGGGAAACCGAAGCTAATACCGGATAGGATCTTCTCCT<br>TCATGGGAGATGATTGAAAGATGGTTTCGGCTATCACTTACAGATGG<br>GCCCGCGGTGCATTAGCTAGTTGGTGAGGTAACGGCTCACCAAGGCA<br>ACGATGCATAGCCGACCTGAGAGGGTGATCGGCCACACTGGGACTGA<br>GACACGGCCCAGACTCCTACGGGAGGCAGCAGTAGGGAATCTTCCGC<br>AATGGACGAAAGTCTGACGGAGCAACGCCGCGTGAGTGATGAAGGCT<br>TTCGGGTCGTAAAACTCTGTTGTTAGGGAAGAACAAGTACAAGAGTA<br>ACTGCTTGTACCTTGACGGTACCTAACCAGAAAGCCACGGCTAACTA<br>CGTGCCAGCAGCCGCGGTAATACGTAGGTGGCAAGCGTTATCCGGAA<br>TTATTGGGCGTAAAGCGCGCGCAGGCGGTTTCTTAAGTCTGATGTGAA<br>AGCCCACGGCTCAACCGTGGAGGGTCATTGGAAACTGGGGAACTTGA<br>GTGCAGAAGAGAAAAGCGGAATTCCACGTGTAGCGGTGAAATGCGTA<br>GAGATGTGGAGGAACACCAGTGGCGAAGGCGGCTTTTTGGTCTGTAA<br>CTGACGCTGAGGCGCGAAAGCGTGGGGAGCAAACAGGATTAGATAC<br>CCTGGTAGTCCACGCCGTAAACGATGAGTGCTAAGTGTTAGAGGGTT<br>TCCGCCCTTTAGTGCTGCAGCTAACGCATTAAGCACTCCGCCTGGGGA<br>GTACGGTCGCAAGACTGAAACTCAAAGGAATTGACGGGGGCCCGCAC<br>AAGCGGTGGAGCATGTGGTTTAATTCGAAGCAACGCGAAGAACCTTA<br>CCAGGTCTTGACATCCTCTGACAACTCTAGAGATAGAGCGTTCCCCTT<br>CGGGGGACAGAGTGACAGGTGGTGCATGGTTGTCGTCAGCTCGTGTC<br>GTGAGATGTTGGGTTAAGTCCCGCAACGAGCGCAACCCTTGATCTTA<br>GTTGCCAGCATTTAGTTGGGCACTCTAAGGTGACTGCCGGTGACAAA<br>CCGGAGGAAGGTGGGGATGACGTCAAATCATCATGCCCCTTATGACC<br>TGGGCTACACACGTGCTACAATGGATGGTACAAAGGGCTGCAAGACC<br>GCGAGGTCAAGCCAATCCCATAAAACCATTCTCAGTTCGGATTGTAG<br>GCTGCAACTCGCCTACATGAAGCTGGAATCGCTAGTAATCGCGGATC<br>AGCATGCT |

-continued

Sequence Listing

| Seq ID No. | Description | Sequence |
| --- | --- | --- |
| 56 | DP56 16S rRNA | ATTGGAGAGTTTGATCCTGGCTCAGGACGAACGCTGGCGGCGTGCCT<br>AATACATGCAAGTCGAGCGGACCTGATGGAGTGCTTGCACTCCTGAT<br>GGTTAGCGGCGGACGGGTGAGTAACACGTAGGCAACCTGCCCTCAAG<br>ACTGGGATAACTACCGGAAACGGTAGCTAATACCGGATAATTTATTT<br>CACAGCATTGTGGAATAATGAAAGACGGAGCAATCTGTCACTTGGGG<br>ATGGGCCTGCGGCGCATTAGCTAGTTGGTGGGGTAACGGCTCACCAA<br>GGCGACGATGCGTAGCCGACCTGAGAGGGTGAACGGCCACACTGGG<br>ACTGAGACACGGCCCAGACTCCTACGGGAGGCAGCAGTAGGGAATCT<br>TCCGCAATGGGCGAAAGCCTGACGGAGCAACGCCGCGTGAGTGATGA<br>AGGTTtTCGGATCGTAAAGCTCTGTTGCCAAGGAAGAACGTCTTCTAG<br>AGTAACTGCTAGGAGAGTGACGGTACTTGAGAAGAAAGCCCCGGCTA<br>ACTACGTGCCAGCAGCCGCGGTAATACGTAGGGGGCAAGCGTTGTCC<br>GGAATTATTGGGCGTAAAGCGCGCGCAGGCGGTTCTTTAAGTCTGGT<br>GTTTAAACCCGAGGCTCAACTTCGGGTCGCACTGGAAACTGGGGAAC<br>TTGAGTGCAGAAGAGGAGAGTGGAATTCCACGTGTAGCGGTGAAATG<br>CGTAGATATGTGGAGGAACACCAGTGGCGAAGGCGACTCTCTGGGCT<br>GTAACTGACGCTGAGGCGCGAAAGCGTGGGGAGCAAACAGGATTAG<br>ATACCCTGGTAGTCCACGCCGTAAACGATGAATGCTAGGTGTTAGGG<br>GTTTCGATACCCTTGGTGCCGAAGTTAACACATTAAGCATTCCGCCTG<br>GGGAGTACGGTCGCAAGACTGAAACTCAAAGGAATTGACGGGGACC<br>CGCACAAGCAGTGGAGTATGTGGTTTAATTCGAAGCAACGCGAAGAA<br>CCTTACCAAGTCTTGACATCCCTCTGAATCCTCTAGAGATAGAGGCGG<br>CCTTCGGGACAGAGGTGACAGGTGGTGCATGGTTGTCGTCAGCTCGT<br>GTCGTGAGATGTTGGGTTAAGTCCCGCAACGAGCGCAACCCTTGATTT<br>TAGTTGCCAGCACATCATGGTGGGCACTCTAGAATGACTGCCGGTGA<br>CAAACCGGAGGAAGGCGGGGATGACGTCAAATCATCATGCCCCTTAT<br>GACTTGGGCTACACACGTACTACAATGGCTGGTACAACGGGAAGCGA<br>AGCCGCGAGGTGGAGCCAATCCTATAAAAGCCAGTCTCAGTTCGGAT<br>TGCAGGCTGCAACTCGCCTGCATGAAGTCGGAATTGCTAGTAATCGC<br>GGATCAGCATGCCGCGGTGAATACGTTCCCGGGTCTTGTACACACCG<br>CCCGTCACACCACGAGAGTTTACAACACCCGAAGTCGGTGGGGTAAC<br>CCGCAAGGGAGCCAGCCGCCGAAGGTGGGGTAGATGATTGGGGTGA<br>AGTCGTAACAAGGTAGCCGTATCGGAAGGTGCGGCTGGATCACCTCC<br>TTT |
| 57 | DP57 16S rRNA | ATTGGAGAGTTTGATCCTGGCTCAGGATGAACGCTGGCGGCGTGCCT<br>AATACATGCAAGTCGAGCGAATGGATTAAGAGCTTGCTCTTATGAAG<br>TTAGCGGCGGACGGGTGAGTAACACGTGGGTAACCTGCCCATAAGAC<br>TGGGATAACTCCGGGAAACCGGGGCTAATACCGGATAACATTTTGCA<br>CCGCATGGTGCGAAATTCAAAGGCGGCTTCGGCTGTCACTTATGGAT<br>GGACCCGCGTCGCATTAGCTAGTTGGTGAGGTAACGGCTCACCAAGG<br>CAACGATGCGTAGCCGACCTGAGAGGGTGATCGGCCACACTGGGACT<br>GAGACACGGCCCAGACTCCTACGGGAGGCAGCAGTAGGGAATCTTCC<br>GCAATGGACGAAAGTCTGACGGAGCAACGCCGCGTGAGTGATGAAG<br>GCTTTCGGGTCGTAAAACTCTGTTGTTAGGGAAGAACAAGTGCTAGTT<br>GAATAAGCTGGCACCTTGACGGTACCTAACCAGAAAGCCACGGCTAA<br>CTACGTGCCAGCAGCCGCGGTAATACGTAGGTGGCAAGCGTTATCCG<br>GAATTATTGGGCGTAAAGCGCGCGCAGGTGGTTTCTTAAGTCTGATGT<br>GAAAGCCCACGGCTCAACCGTGGAGGGTCATTGGAAACTGGGAGACT<br>TGAGTGCAGAAGAGGAAAGTGGAATTCCATGTGTAGCGGTGAAATGC<br>GTAGAGATATGGAGGAACACCAGTGGCGAAGGCGACTTTCTGGTCTG<br>TAACTGACACTGAGGCGCGAAAGCGTGGGGAGCAAACAGGATTAGA<br>TACCCTGGTAGTCCACGCCGTAAACGATGAGTGCTAAGTGTTAGAGG<br>GTTTCCGCCCTTTAGTGCTGAAGTTAACGCATTAAGCACTCCGCCTGG<br>GGAGTACGGCCGCAAGGCTGAAACTCAAAGGAATTGACGGGGGCCC<br>GCACAAGCGGTGGAGCATGTGGTTTAATTCGAAGCAACGCGAAGAAC<br>CTTACCAGGTCTTGACATCCTCTGACAACCCTAGAGATAGGGCTTCCC<br>CTTCGGGGGCAGAGTGACAGGTGGTGCATGGTTGTCGTCAGCTCGTG<br>TCGTGAGATGTTGGGTTAAGTCCCGCAACGAGCGCAACCCTTGATCTT<br>AGTTGCCATCATTAAGTTGGGCACTCTAAGGTGACTGCCGGTGACAA<br>ACCGGAGGAAGGTGGGGATGACGTCAAATCATCATGCCCCTTATGAC<br>CTGGGCTACACACGTGCTACAATGGACGGTACAAAGAGCTGCAAGAC<br>CGCGAGGTGGAGCTAATCTCATAAAACCGTTCTCAGTTCGGATTGTAG<br>GCTGCAACTCGCCTACATGAAGCTGGAATCGCTAGTAATCGCGGATC<br>AGCATGCCGCGGTGAATACGTTCCCGGGCCTTGTACACACCGCCCGTC<br>ACACCACGAGAGTTTGTAACACCCGAAGTCGGTGGGGTAACCTTTTT<br>GGAGCCAGCCGCCTAAGGTGGGACAGATGATTGGGGTGAAGTCGTAA<br>CAAGGTAGCCGTATCGGAAGGTGCGGCTGGATCACCTCCTTT |
| 58 | DP58 16S rRNA | AATGACGGTACCTGAAGAATAAGCACCGGCTAACTACGTGCCAGCAG<br>CCGCGGTAATACGTAGGGTGCAAGCGTTAATCGGAATTACTGGGCGT<br>AAAGCGTGCGCAGGCGGTTTTGTAAGTCTGATGTGAAATCCCCGGGC |

-continued

Sequence Listing

| Seq ID No. | Description | Sequence |
|---|---|---|
| | | TCAACCTGGGAATTGCATTGGAGACTGCAAGGCTAGAATCTGGCAGA<br>GGGGGGTAGAATTCCACGTGTAGCAGTGAAATGCGTAGATATGTGGA<br>GGAACACCGATGGCGAAGGCAGCCCCCTGGGTCAAGATTGACGCTCA<br>TGCACGAAAGCGTGGGGAGCAAACAGGATTAGATACCCTGGTAGTCC<br>ACGCCCTAAACGATGTCTACTAGTTGTCGGGTCTTAATTGACTTGGTA<br>ACGCAGCTAACGCGTGAAGTAGACCGCCTGGGGAGTACGGTCGCAAG<br>ATTAAAACTCAAAGGAATTGACGGGGACCCGCACAAGCGGTGGATGA<br>TGTGGATTAATTCGATGCAACGCGAAAAACCTTACCTACCCTTGACAT<br>GGCTGGAATCCTCGAGAGATTGGGGAGTGCTCGAAAGAGAACCAGTA<br>CACAGGTGCTGCATGGCTGTCGTCAGCTCGTGTCGTGAGATGTTGGGT<br>TAAGTCCCGCAACGAGCGCAACCCTTGTCATTAGTTGCTACGAAAGG<br>GCACTCTAATGAGACTGCCGGTGACAAACCGGAGGAAGGTGGGGATG<br>ACGTCAAGTCCTCATGGCCCTTATGGGTAGGGCTTCACACGTCATACA<br>ATGGTACATACAGAGCGCCGCCAACCCGCGAGGGGGAGCTAATCGCA<br>GAAAGTGTATCGTAGTCCGGATTGTAGTCTGCAACTCGACTGCATGA<br>AGTTGGAATCGCTAGTAATCGCGGATCAGCATGTCGCGGTGAATACG<br>TTCCCGGGTCTTGTACACACCGCCCGTCACACCATGGGAGCGGGTTTT<br>ACCAGAAGTAGGTAGCTTAACCGTAAGGAGGGCGCTTACCACGGTAG<br>GATTCGTGACTGGGGTGAAGTCGTAACAAGGTAGCCGTATCGGAAGG<br>TGCGGCTGGATCACCTCCTTT |
| 59 | DP59 16S rRNA | TTGAAGAGTTTGATCATGGCTCAGATTGAACGCTGGCGGCAGGCCTA<br>ACACATGCAAGTCGAACGGTAACAGGAAGCAGCTTGCTGCTTTGCTG<br>ACGAGTGGCGGACGGGTGAGTAATGTCTGGGAAACTGCCTGATGGAG<br>GGGGATAACTACTGGAAACGGTAGCTAATACCGCATAACGTCGCAAG<br>ACCAAAGAGGGGGACCTTCGGGCCTCTTGCCATCAGATGTGCCCAGA<br>TGGGATTAGCTAGTAGGTGGGGTAACGGCTCACCTAGGCGACGATCC<br>CTAGCTGGTCTGAGAGGATGACCAGCCACACTGGAACTGAGACACGG<br>TCCAGACTCCTACGGGAGGCAGCAGTGGGGAATATTGCACAATGGGC<br>GCAAGCCTGATGCAGCCATGCCGCGTGTATGAAGAAGGCCTTCGGGT<br>TGTAAAGTACTTTCAGCGGGGAGGAAGGCGATGCGGTTAATAACCGC<br>GTCGATTGACGTTACCCGCAGAAGAAGCACCGGCTAACTCCGTGCCA<br>GCAGCCGCGGTAATACGGAGGGTGCAAGCGTTAATCGGAATTACTGG<br>GCGTAAAGCGCACGCAGGCGGTCTGTCAAGTCGGATGTGAAATCCCC<br>GGGCTCAACCTGGGAACTGCATCCGAAACTGGCAGGCTTGAGTCTCG<br>TAGAGGGGGGTAGAATTCCAGGTGTAGCGGTGAAATGCGTAGAGATC<br>TGGAGGAATACCGGTGGCGAAGGCGGCCCCCTGGACGAAGACTGAC<br>GCTCAGGTGCGAAAGCGTGGGGAGCAAACAGGATTAGATACCCTGGT<br>AGTCCACGCCGTAAACGATGTCGACTTGGAGGTTGTGCCCTTGAGGC<br>GTGGCTTCCGGAGCTAACGCGTTAAGTCGACCGCCTGGGGAGTACGG<br>CCGCAAGGTTAAAACTCAAATGAATTGACGGGGGCCCGCACAAGCGG<br>TGGAGCATGTGGTTTAATTCGATGCAACGCGAAGAACCTTACCTGGTC<br>TTGACATCCACAGAACTTGGCAGAGATGCCTTGGTGCCTTCGGGAACT<br>GTGAGACAGGTGCTGCATGGCTGTCGTCAGCTCGTGTTGTGAAATGTT<br>GGGTTAAGTCCCGCAACGAGCGCAACCCTTATCCTTTGTTGCCAGCGG<br>TTAGGCCGGGAACTCAAAGGAGACTGCCAGTGATAAACTGGAGGAA<br>GGTGGGGATGACGTCAAGTCATCATGGCCCTTACGACCAGGGCTACA<br>CACGTGCTACAATGGCGCATACAAAGAGAAGCGATCTCGCGAGAGCC<br>AGCGGACCTCATAAAGTGCGTCGTAGTCCGGATTGGAGTCTGCAACT<br>CGACTCCATGAAGTCGGAATCGCTAGTAATCGTGAATCAGAATGTCA<br>CGGTGAATACGTTCCCGGGCCTTGTACACACCGCCCGTCACACCATGG<br>GAGTGGGTTGCAAAAGAAGTAGGTAGCTTAACCTTCGGGAGGGCGCT<br>TACCACTTTGTGATTCATGACTGGGGTGAAGTCGTAACAAGGTAACC<br>GTAGGGGAACCTGCGGTTGGATCACCTCCTT |
| 60 | DP60 16S rRNA | TCGGAGAGTTTGATCCTGGCTCAGGACGAACGCTGGCGGCGTGCCTA<br>ATACATGCAAGTCGAGCGAATCGATGGGAGCTTGCTCCCTGAGATTA<br>GCGGCGGACGGGTGAGTAACACGTGGGCAACCTGCCTATAAGACTGG<br>GATAACTTCGGGAAACCGGAGCTAATACCGGATACGTTCTTTTCTCGC<br>ATGAGAGAAGATGGAAAGACGGTTTTGCTGTCACTTATAGATGGGCC<br>CGCGGCGCATTAGCTAGTTGGTGAGGTAATGGCTCACCAAGGCGACG<br>ATGCGTAGCCGACCTGAGAGGGTGATCGGCCACACTGGGACTGAGAC<br>ACGGCCCAGACTCCTACGGGAGGCAGCAGTAGGGAATCTTCCGCAAT<br>GGACGAAAGTCTGACGGAGCAACGCCGCGTGAACGAAGAAGGCCTT<br>CGGGTCGTAAAGTTCTGTTGTTAGGGAAGAACAAGTACCAGAGTAAC<br>TGCTGGTACCTTGACGGTACCTAACCAGAAAGCCACGGCTAACTACG<br>TGCCAGCAGCCGCGGTAATACGTAGGTGGCAAGCGTTGTCCGGAATT<br>ATTGGGCGTAAAGCGCGCGCAGGTGGTTCCTTAAGTCTGATGTGAAA<br>GCCCACGGCTCAACCGTGGAGGGTCATTGGAAACTGGGGAACTTGAG<br>TGCAGAAGAGGAAAGTGGAATTCCAAGTGTAGCGGTGAAATGCGTAG<br>AGATTTGGAGGAACACCAGTGGCGAAGGCGACTTTCTGGTCTGTAAC<br>TGACACTGAGGCGCGAAAGCGTGGGGAGCAAACAGGATTAGATACC<br>CTGGTAGTCCACGCCGTAAACGATGAGTGCTAAGTGTTAGAGGGTTT |

-continued

Sequence Listing

| Seq ID No. | Description | Sequence |
|---|---|---|
| | | CCGCCCTTTAGTGCTGCAGCTAACGCATTAAGCACTCCGCCTGGGGAG TACGGCCGCAAGGCTGAAACTCAAAGGAATTGACGGGGGCCCGCACA AGCGGTGGAGCATGTGGTTTAATTCGAAGCAACGCGAAGAACCTTAC CAGGTCTTGACATCCTCTGACAACCCTAGAGATAGGGCGTTCCCCTTC GGGGGACAGAGTGACAGGTGGTGCATGGTTGTCGTCAGCTCGTGTCG TGAGATGTTGGGTTAAGTCCCGCAACGAGCGCAACCCTTGATCTTAGT TGCCAGCATTCAGTTGGGCACTCTAAGGTGACTGCCGGTGACAAACC GGAGGAAGGTGGGGATGACGTCAAATCATCATGCCCCTTATGACCTG GGCTACACACGTGCTACAATGGATGGTACAAAGGGCTGCAAACCTGC GAAGGTAAGCGAATCCCATAAAGCCATTCTCAGTTCGGATTGTAGGC TGCAACTCGCCTACATGAAGCCGGAATCGCTAGTAATCGCGGATCAG CATGCCGCGGTGAATACGTTCCCGGGCCTTGTACACACCGCCCGTCAC ACCACGAGAGTTTGTAACACCCGAAGTCGGTGAGGTAACCTTTATGG AGCCAGCCGCCTAAGGTGGGACAGATGATTGGGGTGAAGTCGTAACA AGGTAGCCGTATCGGAAGGTGCGGCTGGATCACCTCCTTT |
| 61 | DP61 16S rRNA | GGAAGGCGGTCTGTCAAGTCGGATGTGAAATCCCCGGGCTCAACCTG GGAACTGCATTCGAAACTGGCAGGCTAGAGTCTTGTAGAGGGGGGTA GAATTCCAGGTGTAGCGGTGAAATGCGTAGAGATCTGGAGGAATACC GGTGGCGAAGGCGGCCCCCTGGACAAAGACTGACGCTCAGGTGCGAA AGCGTGGGGAGCAAACAGGATTAGATACCCTGGTAGTCCACGCCGTA AACGATGTCGACTTGGAGGTTGTTCCCTTGAGGAGTGGCTTCCGGAGC TAACGCGTTAAGTCGACCGCCTGGGGAGTACGGCCGCAAGGTTAAAA CTCAAATGAATTGACGGGGGCCCGCACAAGCGGTGGAGCATGTGGTT TAATTCGATGCAACGCGAAGAACCTTACCTACTCTTGACATCCACGGA ATTTAGCAGAGATGCTTTAGTGCCTTCGGGAACCGTGAGACAGGTGC TGCATGGCTGTCGTCAGCTCGTGTTGTGAAATGTTGGGTTAAGTCCCG CAACGAGCGCAACCCTTATCCTTTGTTGCCAGCGGTCCGGCCGGGAA CTCAAAGGAGACTGCCAGTGATAAACTGGAGGAAGGTGGGGATGAC GTCAAGTCATCATGGCCCTTACGAGTAGGGCTACACACGTGCTACAA TGGCGCATACAAAGAGAAGCGACCTCGCGAGAGCAAGCGGACCTCAT AAAGTGCGTCGTAGTCCGGATCGGAGTCTGCAACTCGACTCCGTGAA GTCGGAATCGCTAGTAATCGTAGATCAGAATGCTACGGTGAATACGT TCCCGGGCCTTGTACACACCGCCCGTCACACCATGGGAGTGGGTTGC AAAAGAAGTAGGTAGCTTAACCTTCGGGAGGGCGCTTACCACTTTGT GATTCATGACTGGGGTGAAGTCGTAACAAGGTAACCGTAGGGGAACC TGCGGTTGGATCACCTCCTT |
| 62 | DP62 16S rRNA | TGGCTCAGATTGAACGCTGGCGGCAGGCCTAACACATGCAAGTCGAA CGGTAGCACAGAGGAGCTTGCTCCTTGGGTGACGAGTGGCGGACGGG TGAGTAATGTCTGGGAAACTGCCCGATGGAGGGGGATAACTACTGGA AACGGTAGCTAATACCGCATAACGTCTTCGGACCAAAGTGGGGGACC TTCGGGCCTCACACCATCGGATGTGCCCAGATGGGATTAGCTAGTAG GTGGGGTAATGGCTCACCTAGGCGACGATCCCTAGCTGGTCTGAGAG GATGACCAGCCACACTGGAACTGAGACACGGTCCAGACTCCTACGGG AGGCAGCAGTGGGGAATATTGCACAATGGGCGCAAGCCTGATGCAGC CATGCCGCGTGTATGAAGAAGGCCTTCGGGTTGTAAAGTACTTTCAGT GGGGAGGAAGGCGTTAAGGTTAATAACCTTGGCGATTGACGTTACCC GCAGAAGAAGCACCGGCTAACTCCGTGCCAGCAGCCGCGGTAATACG GAGGGTGCAAGCGTTAATCGGAATTACTGGGCGTAAAGCGCACGCAG GCGGTCTGTCAAGTCGGATGTGAAATCCCCGGGCTCAACCTGGGAAC TGCATTCGAAACTGGCAGGCTAGAGTCTTGTAGAGGGGGGTAGAATT CCAGGTGTAGCGGTGAAATGCGTAGAGATCTGGAGGAATACCGGTGG CGAAGGCGGCCCCCTGGACAAAGACTGACGCTCAGGTGCGAAAGCGT GGGGAGCAAACAGGATTAGATACCCTGGTAGTCCACGCCGTAAACGA TGTCGACTTGGAGGTTGTTCCCTTGAGGAGTGGCTTCCGGAGCTAACG CGTTAAGTCGACCGCCTGGGGAGTACGG |
| 63 | DP63 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATGCCTAGGAATCTGCCTGGTAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGTTGTAGATTAATACTCTGCAATTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGGATGTGAAATCCCCGGGCTCAAC CTGGGAACTGCATTCAAAACTGACTGACTAGAGTATGGTAGAGGGTG GTGGAATTTCCTGTGTAGCGGTGAAATGCGTAGATATAGGAAGGAAC |

-continued

Sequence Listing

| Seq ID No. | Description | Sequence |
|---|---|---|
| | | ACCAGTGGCGAAGGCGACCACCTGGACTAATACTGACACTGAGGTGC GAAAGCGTGGGGAGCAAACAGGATTAGATACCCTGGTAGTCCACGCC GTAAACGATGTCAACTAGCCGTTGGAAGCCTTGAGCTTTTAGTGGCGC AGCTAACGCATTAAGTTGACCGCCTGGGGAGTACGGCCGCAAGGTTA AAACTCAAATGAATTGACGGGGGCCCGCACAAGCGGTGGAGCATGTG GTTTAATTCGAAGCAACGCGAAGAACCTTACCAGGCCTTGACATCCA ATGAACTTTCTAGAGATAGATTGGTGCCTTCGGGAACATTGAGACAG GTGCTGCATGGCTGTCGTCAGCTCGTGTCGTGAGATGTTGGGTTAAGT CCCGTAACGAGCGCAACCCTTGTTCTTAGTTACCAGCACGTTATGGTG GGCACTCTAAGGAGACTGCCGGTGACAAACCGGAGGAAGGTGGGGA TGACGTCAAGTCATCATGGCCCTTACGGCCTGGGCTACACACGTGCTA CAATGGTCGGTACAGAGGGTTGCCAAGCCGCGAGGTGGAGCTAATCC CATAAAACCGATCGTAGTCCGGATCGCAGTCTGCAACTCGACTGCGT GAAGTCGGAATCGCTAGTAATCGCGAATCAGAATGTCGCGGTGAATA CGTTCCCGGGCCTTGTACACACCGCCCGTCACACCATGGGAGTGGGTT GCACCAGAAGTAGCTAGTCTAACCTTCGGGAGGACGGTTACCACGGT GTGATTCATGACTGGGGTGAAGTCGTAACAAGGTAGCCGTAGGGGAA CCTGCGGCTGGATCACCTCCTT |
| 64 | DP64 ITS sequence | TCCGTAGGTGAACCTGCGGAAGGATCATTAAATAATCAATAATTTTG GCTTGTCCATTATTATCTATTTACTGTGAACTGTATTATTACTTGACGC TTGAGGGATGCTCCACTGCTATAAGGATAGGCGGTGGGGATGTTAAC CGAGTCATAGTCAAGCTTAGGCTTGGTATCCTATTATTATTTACCAAA AGAATTCAGAATTAATATTGTAACATAGACCTAAAAAATCTATAAAA CAACTTTTAACAACGGATCTCTTGGTTCTCGCATCGATGAAGAACGTA GCAAAGTGCGATAACTAGTGTGAATTGCATATTCAGTGAATCATCGA GTCTTTGAACGCAACTTGCGCTCATTGGTATTCCAATGAGCACGCCTG TTTCAGTATCAAAACAAACCCTCTATTCAATATTTTTGTTGAATAGGA ATACTGAGAGTCTCTTGATCTTTTCTGATCTCGAACCTCTTGAAATGT ACAAAGGCCTGATCTTGTTTGAATGCCTGAACTTTTTTTTAATATAAA GAGAAGCTCTTGCGGTAAACTGTGCTGGGGCCTCCCAAATAATACTCT TTTTAAATTTGATCTGAAATCAGGCGGGATTACCCGCTGAACTTAAGC ATATCAATAAGCGGAGGAAAAGAAAATAACAATGATTTCCCTAGTAA CGGCGAGTGAAGAGGAAAGAGCTCAAAGTTGGAAACTGTTTGGCTTA GCTAAACCGTATTGTAAACTGTAGAAACATTTTCCTGGCACGCCGGAT TAATAAGTCCTTTGGAACAAGGCATCATGGAGGGTGAGAATCCCGTC TTTGATCCGAGTAGTTGTCTTTTGTGATATGTTTTCAAAGAGTCAGGTT GTTTGGGAATGCAGCCTAAATTGGGTGGTAAATCTCACCTAAAGCTA AATATTTGCGAGAGACCGATAGCGAACAAGTACCGTGAGGGAAAGAT GAAAAGAACTTTGAAAAGAGAGTTAAACAGTATGTGAAATTGTTAAA AGGGAACCGTTTGGAGCCAGACTGGTTTGACTGTAATCAACCTAGAA TTCGTTCTGGGTGCACTTGCAGTCTATACCTGCCAACAACAGTTTGAT TTGGAGGAAAAAATTAGTAGGAATGTAGCCTCTCGAGGTGTTATAGC CTACTATCATACTCTGGATTGGACTGAGGAACGCAGCGAATGCCATT AGGCGAGATTGCTGGGTGCTTTCGCTAATAAATGTTAGAATTTCTGCT TCGGGTGGTGCTAATGTTTAAAGGAGGAACACATCTAGTATATTTTTT ATTCGCTTAGGTTGTTGGCTTAATGACTCTAAATGACCCGTCTTGAAA CACGGACCAAGGAGTCCACCATAAGTGCAAGTATTTGAGTGACAAAC TCATATGCGTAAGGAAACTGATTGATACGAAATCTTTTGATGGCAGTA TCACCCGGCGTTGACGTTTTATACTGAACTGACCGAGGTAAAGCACTT ATGATGGGACCCGAAAGATGGTGAACTATGCCTGAATAGGGTGAAGC CAGAGGAAACTCTGGTGGAGGCTCGTAGCGATTCTGACGTGCAAATC GATCGTCAAATTTGGGTATAGGGGCGAAAGACTAATCGAACCATCTA GTAGCTGGTTCCTGCCGAAGTTTCCCTCAGGA |
| 65 | DP65 ITS sequence | TCCGTAGGTGAACCTGCGGAAGGATCATTATTGAAAACAAGGGTGTC CAATTTAACTTGGAACCCGAACTTCTCAATTCTAACTTTGTGCATCTG TATTATGGCGAGCAGTCTTCGGATTGTGAGCCTTCACTTATAAACACT AGTCTATGAATGTAAAATTTTTATAACAAATAAAAACTTTCAACAACG GATCTCTTGGCTCTCGCATCGATGAAGAACGCAGCGAAATGCGATAC GTAATGTGAATTGCAGAATTCAGTGAATCATCGAATCTTTGAACGCAT CTTGCGCTCTCTGGTATTCCGGAGAGCATGTCTGTTTGAGTGTCATGA ATTCTTCAACCCAATCTTTTCTTGTAATCGATTGGTGTTTGGATTTTGA GCGCTGCTGGCTTCGGCCTAGCTCGTTCGTAATACATTAGCATCCCTA ATACAAGTTTGGATTGACTTGGCGTAATAGACTATTCGCTAAGGATTC GGTGGAAACATCGAGCCAACTTCATTAAGGAAGCTCCTAATTTAAAA GTCTACCTTTTGATTAGATCTCAAATCAGGCAGGATTACCCGCTGAAC TTAAGCATATCAATAAGCGGAGGAAAAGAAACTAACAAGGATTCCCC TAGTAGCGGCGAGCGAAGCGGGAAAAGCTCAAATTTGTAATCTGGCG TCTTCGACGTCCGAGTTGTAATCTCGAGAAGTGTTTTCCGTGATAGAC CGCATACAAGTCTCTTGGAACAGAGCGTCATAGTGGTGAGAACCCAG TACACGATGCGGATGCCTATTACTTTGTGATACACTTTCGAAGAGTCG AGTTGTTTGGGAATGCAGCTCAAATTGGGTGGTAAATTCCATCTAAAG |

-continued

Sequence Listing

| Seq ID No. | Description | Sequence |
|---|---|---|
| | | CTAAATATTGGCGAGAGACCGATAGCGAACAAGTACCGTAAGGGAA<br>AGATGAAAAGCACTTTGGAAAGAGAGTTAACAGTACGTGAAATTGTT<br>GGAAGGGAAACACATGCAGTGATACTTGCTATTCGGGGCAACTCGAT<br>TGGCAGGCCCGCATCAGTTTTTCGGGGCGGAAAAGCGTAGAGAGAAG<br>GTAGCAATTTCGGTTGTGTTATAGCTCTTTACTGGATTCGCCCTGGGG<br>GACTGAGGAACGCAGCGTGCTTTTAGCAATTCCTTCGGGAATTCCACG<br>CTTAGGATGCGGGTTTATGGCTGTATATGACCCGTCTTGAAACACGGA<br>CCAAGGAGTCTAACATGCTTGCGAGTATTTGGGTGTCAAACCCGGAT<br>GCGCAATGAAAGTGAATGGAGGTGGGAAGCGCAAGCTGCACCATCG<br>ACCGATCTGGATTTTTTAAGATGGATTTGAGTAAGAGCAAGTATGTTG<br>GGACCCGAAAGATGGTGAACTATGCCTGAATAGGGCGAAGCCAGAG<br>GAAACTCTGGTGGAGGCTCGTAGCGGTTCTGACGTGCAAATCGATCG<br>TCAAATTTGGGTATAGGGGCGAAAGACTAATCGAACCATCTAGTAGC<br>TGGTTCCTGCCGAAGTTTCCCTCAGGA |
| 66 | DP66 ITS sequence | TCCGTAGGTGAACCTGCGGAAGGATCATTACTGTGATTTATCCACCAC<br>ACTGCGTGGGCGACACGAAACACCGAAACCGAACGCACGCCGTCAA<br>GCAAGAAATCCACAAAACTTTCAACAACGGATCTCTTGGTTCTCGCAT<br>CGATGAAGAGCGCAGCGAAATGCGATACCTAGTGTGAATTGCAGCCA<br>TCGTGAATCATCGAGTTCTTGAACGCACATTGCGCCCGCTGGTATTCC<br>GGCGGGCATGCCTGTCTGAGCGTCGTTTCCTTCTTGGAGCGGAGCTTC<br>AGACCTGGCGGGCTGTCTTTCGGGACGGCGCGCCCAAAGCGAGGGGC<br>CTTCTGCGCGAACTAGACTGTGCGCGCGGGGCGGCCGGCGAACTTAT<br>ACCAAGCTCGACCTCAGATCAGGCAGGAGTACCCGCTGAACTTAAGC<br>ATATCAATAAGCGGAGGAAAAGAAACCAACAGGGATTGCCCCAGTA<br>GCGGCGAGTGAAGCGGCAAAAGCTCAGATTTGGAATCGCTTCGGCGA<br>GTTGTGAATTGCAGGTTGGCGCCTCTGCGGCGGCGGCGGTCCAAGTC<br>CCTTGGAACAGGGCGCCATTGAGGGTGAGAGCCCCGTGGGACCGTTT<br>GCCTATGCTCTGAGGCCCTTCTGACGAGTCGAGTTGTTTGGGAATGCA<br>GCTCTAAGCGGGTGGTAAATTCCATCTAAGGCTAAATACTGGCGAGA<br>GACCGATAGCGAACAAGTACTGTGAAGGAAAGATGAAAAGCACTTTG<br>AAAAGAGAGTGAAACAGCACGTGAAATTGTTGAAAGGGAAGGGTAT<br>TGCGCCCGACATGGAGCGTGCGCACCGCTGCCCCTCGTGGGCGGCGC<br>TCTGGGCGTGCTCTGGGCCAGCATCGGTTTTTGCCGCGGGAGAAGGG<br>CGGCGGGCATGTAGCTCTTCGGAGTGTTATAGCCTGCCGCCGGCGCC<br>GCGAGCGGGGACCGAGGACTGCGACTTTTGTCTCGGATGCTGGCACA<br>ACGGCGCAACACCGCCCGTCTTGAAACATGGACCAAGGAGTCTAACG<br>TCTATGCGAGTGTTTGGGTGTGAAACCCCGGGCGCGTAATGAAAGTG<br>AACGTAGGTCGGACCGCTCCTCTCGGGGGGCGGGCACGATCGACCGA<br>TCCTGATGTCTTCGGATGGATTTGAGTAAGAGCATAGCTGTTGGGACC<br>CGAAAGATGGTGAACTATGCCTGAATAGGGTGAAGCCAGAGGAAACT<br>CTGGTGGAGGCTCGTAGCGGTTCTGACGTGCAAATCGATCGTCGAATT<br>TGGGTATAGGGGCGAAAGACTAATCGAACCATCTAGTAGCTGGTTCC<br>TGCCGAAGTTTCCCTCAGGA |
| 67 | DP53 Glutamine-tRNA ligase | ATGAGCAAGCCCACTGTCGACCCCACTCTGAATCCAAAGGCTGGCCC<br>TGCTGTCCCGGCTAACTTCCTGCGTCCAATCGTTCAGGCGGACCTAGA<br>CTCGGGTAAATACACACAGATCGTGACCCGCTTTCCGCCGGAGCCAA<br>ACGGCTATCTGCACATCGGTCATGCCAAATCCATTTGTGTGAACTTTG<br>GGCTGGCTCAAGAGTTTGGCGGCGTGACGCATTTGCGTTTTGACGACA<br>CCAACCCGGCAAAAGAAGACCAGGAATACATCGACGCCATCGAAAG<br>CGACGTCAAGTGGCTGGGCTTCGAGTGGGCCGGTGAAGTGCGTTACG<br>CGTCGCAATACTTCGATCAACTGCACGAGTGGGCGATTTACCTGATCA<br>AAGAAGGCAAGGCCTACGTCTGCGACCTGACGCCCGAGCAAGCCAAG<br>GAATACCGTGGCAGCCTGACCGAGCCCGGCAAGAACAGCCCGTTCCG<br>CGACCGTAGCGTTGAAGAGAACCTGGATCTGTTCGCCCGCATGACCG<br>CCGGTGAGTTTGAAGACGGCAAGCGTGTGCTGCGCGCCAAGATCGAC<br>ATGACCTCGCCGAACATGAACCTGCGCGACCCGATCATGTACCGCAT<br>CCGTCATGCCCATCACCACCAGACCGGTGACAAGTGGTGCATCTACC<br>CCAACTATGACTTCACCCACGGTCAGTCGGATGCCATTGAAGGCATC<br>ACCCATTCGATCTGCACCCTGGAGTTCGAAAGCCATCGTCCGCTGTAC<br>GAATGGTTCCTGGACAGCCTGCCAGTACCGGCGCGCCCGCGTCAGTA<br>CGAGTTCAGCCGTCTGAACCTCAACTACACCATCACCAGCAAGCGCA<br>AGCTCAAGCAGCTGGTCGATGAAAAGCACGTCAACGGCTGGGATGAC<br>CCGCGCATGTCGACGCTGTCGGGTTTCCGCCGTCGCGGTTACACGCCT<br>AAATCGATTCGTAATTTCTGTGACATGGTCGGCACCAACCGTTCTGAC<br>GGTGTTGTTGACTTCGGCATGCTGGAATTCAGCATTCGTGACGATTTG<br>GACCACAGCGCGCCGCGCGCCATGTGCGTGCTGCGTCCATTGAAGGT<br>GATTATTACCAACTACCCGGAAGGTCAGGTCGAAAACCTCGAGCTGC<br>CTTGCCACCCGAAAGAAGACATGGGTGTGCGGGTGTTGCCGTTTGCC<br>CGTGAAATCTACATCGACCGTGAAGACTTCATGGAAGAGCCGCCAAA<br>AGGCTACAAGCGTCTTGAGCCTGCGGGCGAAGTGCGTTTGCGCGGCA<br>GCTATGTGATCCGTGCCGACGAAGCGATCAAGGATGCCGATGGCAAC |

-continued

Sequence Listing

| Seq ID No. | Description | Sequence |
|---|---|---|
| | | ATCGTTGAACTGCATTGCTCGTACGATCCGCTGACCCTGGGTAAAAAC<br>CCTGAAGGTCGCAAGGTCAAGGGTGTTGTGCACTGGGTGCCGGCGGC<br>GGCCAGCGTCGAATGCGAAGTGCGTTTGTATGATCGTCTGTTCCGCTC<br>GCCGAACCCTGAAAAGGCCGAAGACGGCGCGGGCTTCCTGGAAAAC<br>ATCAACCCTGACTCGCTGCAGGTACTGACCGGTTGTCGTGCTGAACCC<br>TCGCTGGGCAATGCACAGCCGGAAGACCGTTTCCAGTTCGAGCGCGA<br>AGGCTACTTCTGCGCAGATATCAAGGACTCGAAACCCGGTCACCCGG<br>TATTCAACCGTACCGTGACCCTGCGTGATTCGTGGGGCCAGTGA |
| 68 | DP53 DNA gyrase subunit B | TTGAGCGAAGAAAACACGTACGACTCAACGAGCATTAAAGTGCTGAA<br>AGGCCTTGATGCCGTACGCAAACGTCCCGGTATGTACATTGGTGATAC<br>TGACGATGGCAGCGGTCTGCACCACATGGTGTTCGAAGTAGTCGACA<br>ACTCCATCGACGAAGCGCTGGCTGGCCATTGCGACGACATCACCATC<br>ACGATCCACCCGGACGAGTCCATCACCGTGCGCGATAACGGCCGCGG<br>TATTCCGGTTGACGTGCATAAAGAAGAAGGCGTATCTGCAGCCGAGG<br>TCATCATGACCGTGCTGCACGCCGGCGGTAAGTTCGATGACAACTCCT<br>ACAAAGTATCCGGCGGCTTGCACGGTGTAGGTGTTTCGGTGGTAAAC<br>GCCCTGTCCGAACTGCTGGTCTTGACTGTACGCCGCAGCGGCAAGATC<br>TGGGAACAGACCTACGTCCACGGTGTTCCTCAGGCGCCTATGGCTATT<br>GTGGGTGAAAGCGAAACCACGGGTACGCAGATCCACTTCAAGCCTTC<br>GGCTGAAACCTTCAAGAATATCCACTTTAGCTGGGACATCCTGGCCA<br>AGCGGATTCGTGAACTGTCCTTCCTGAACTCCGGTGTGGGTATCGTCC<br>TCAAGGACGAGCGCAGCGGCAAGGAGGAGCTGTTCAAGTACGAAGG<br>TGGCCTGCGTGCATTCGTTGATTACCTGAACACCAACAAGAACGCTGT<br>GAACCAGGTGTTCCACTTCAATGTTCAGCGTGAAGACGGCATCGGCG<br>TAGAAATCGCCCTGCAGTGGAACGACAGCTTCAACGAGAACCTGTTG<br>TGCTTCACCAACAACATTCCACAGCGCGATGGTGGCACGCACTTGGT<br>GGGCTTCCGCTCTGCCCTGACGCGTAACCTCAACACGTACATCGAAGC<br>TGAAGGCCTGGCCAAGAAGCACAAGGTCGCCACCACCGGTGATGACG<br>CCCGTGAAGGCTTGACCGCGATCATCTCGGTGAAAGTGCCGGATCCA<br>AAGTTCAGCTCGCAGACTAAAGACAAGCTGGTGTCTTCCGAAGTGAA<br>GACCGCTGTTGAACAGGAAATGGGCAAGTTCTTCTCCGACTTCCTGCT<br>GGAACACCCGAACGAAGCCAAGTTGATTGTCGGCAAGATGATCGACG<br>CAGCCCGTGCTCGTGAAGCTGCACGTAAAGCCCGTGAGATGACCCGT<br>CGTAAAGGCGCGTTGGACATCGCGGGCTTGCCGGGCAAGCTGGCTGA<br>CTGCCAGGAAAAAGACCCTGCTCTGTCCGAACTGTACCTGGTGGAAG<br>GTGACTCTGCTGGCGGCTCCGCCAAGCAGGGTCGCAACCGTCGTACC<br>CAAGCCATCCTGCCGTTGAAAGGTAAAATCCTCAACGTCGAGAAAGC<br>CCGTTTTGACAAGATGATCTCTTCGCAAGAAGTCGGCACCTTGATCAC<br>TGCGCTGGGCTGTGGCATCGGCCGCGAAGAGTACAACATCGACAAAC<br>TGCGCTATCACAACATCATCATCATGACCGATGCTGACGTTGACGGTT<br>CGCACATCCGTACCCTGCTGCTGACCTTCTTCTTCCGTCAGTTGCCGG<br>AGCTGATCGAGCGTGGCTACATCTACATCGCCCAGCCACCGTTGTACA<br>AAGTGAAAAAGGGCAAGCAAGAGCAGTACATCAAAGACGACGAGGC<br>CATGGAAGAGTACATGACCCAGTCGGCTCTTGAAGATGCCAGCCTGC<br>ACTTGAACGAAGATGCCCCTGGCATCTCCGGTGAGGCACTGGAGCGT<br>CTGGTGTACGACTTCCGCATGGTGATGAAGACCCTCAAGCGTTTGTCG<br>CGCCTGTACCCTCAGGAGCTGACCGAGCACTTCATCTACCTGCCGGCT<br>GTAAGCCTTGAGCAGTTGGGTGACCACGCTGCCATGCAGGACTGGAT<br>GGCCAAGTTTGAAGAGCGTCTGCGTCTGGTTGAGAAATCGGGCCTGG<br>TCTACAAAGCCAGCCTGCGTGAAGACCGTGAGCGTAATGTCTGGTTG<br>CCAGAGGTCGAACTGATCTCCCACGGCCACTCGACGTTCATCACCTTC<br>AACCGCGACTTCTTCGGCAGCAACGATTACAAAACCGTTGTGACCCT<br>GGGCGCTCAACTGAGCACCCTGCTGGATGAAGGCGCCTATATCCAGC<br>GTGGCGAACGTCGCAAGCAAGTGACCGAGTTCAAAGAAGCACTGGAC<br>TGGTTGATGGCTGAAAGCACCAAGCGTCACACCATCCAGCGCTACAA<br>AGGACTGGGTGAAATGAACCCGGATCAGCTCTGGGAAACCACGATGG<br>ACCCAAGCGTGCGTCGCATGCTGAAAGTCACCATCGAAGACGCGATC<br>GGCGCCGATCAGATCTTCAACACCTTGATGGGCGATGCTGTAGAACC<br>ACGTCGTGAATTCATCGAGAGCAACGCACTGGCAGTGTCCAACCTGG<br>ATTTCTGA |
| 69 | DP53 Isoleucine tRNA ligase | ATGACCGACTACAAAGCCACGCTAAACCTCCCGGACACCGCCTTCCC<br>AATGAAGGCCGGCCTGCCACAGCGCGAACCGCAAATTTTGCAGCGCT<br>GGGACAGCATTGGCCTGTACGGGAAGTTGCGCGAGATTGGCAAGGAT<br>CGTCCGAAGTTCGTACTTCACGACGGTCCTCCGTACGCCAACGGCACT<br>ATCCATATCGGTCATGCGCTGAACAAGATTCTGAAAGACATGATCAT<br>CCGCTCCAAGACCCTGTCGGGTTTTGACGCGCCGTATGTGCCGGGCTG<br>GGATTGCCATGGTTTGCCGATTGAACACAAGGTCGAAGTGACCCACG<br>GTAAAAACCTGAGCGCGGATAAAACCCGCGAGCTGTGCCGTGCCTAC<br>GCCACCGAGCAGATCGAGGGGCAGAAGTCCGAGTTCATCCGTCTGGG<br>TGTGCTGGGTGATTTCGCCAACCCGTACAAGACCATGGACTTCAAAA<br>ACGAAGCCGGTGAAATCCGTGCTTTGGCTGAGATCGTCAAGGGCGGT |

-continued

Sequence Listing

| Seq ID No. | Description | Sequence |
|---|---|---|
| | | TTTGTGTTCAAGGGCCTCAAGCCGGTGAACTGGTGCTTCGATTGCGGT<br>TCGGCCCTGGCTGAAGCTGAAGTTGAATACCAGGACAAGAAGTCTGC<br>GGCCATCGACGTTGCCTTCCCGGTTGCCGACGAGGCCAAGCTGGCCG<br>AGGCCTTTGGTCTGGCGGCACTGAGCAAACCTGCTTCGATCGTGATCT<br>GGACCACCACCCCGTGGACCATTCCGGCCAACCAGGCGCTTAACGTA<br>CACCCGGAATTCACCTACGCGCTGGTCGACGTGGGCGACAAGTTGCT<br>GGTACTGGCTGAAGAACTGGTCGAATCGAGTCTGGCGCGTTACAACC<br>TGCAGGGTTCGGTCATCGCCACCACCACTGGCTCAGCGCTTGAACTAA<br>TCAACTTCCGTCACCCGTTCTATGACCGTCTGTCGCCTGTTTATCTGGC<br>CGACTACGTTGAGCTGGGTGCTGGCACTGGTGTGGTTCACTCGGCTCC<br>AGCCTACGGCGTAGACGACTTCGTGACCTGCAAAGCCTATGGCATGG<br>TCAACGACGACATCATCAACCCGGTGCAAAGCAATGGCGTTTACGTG<br>CCGTCGCTGGAGTTCTTCGGTGGCCAGTTCATCTGGAAGGCCAACCAG<br>AACATCATCGACAAGCTGATCGAAGTCGGTTCGCTGATGTTCACCGA<br>GACCATCAGCCACAGCTATATGCACTGCTGGCGCCACAAGACGCCGC<br>TGATCTACCGTGCCACCGCCCAGTGGTTTATCGGTATGGACAAGCAGC<br>CGACTGATGGCGATACCTTGCGCACCCGTGCGCTGCAAGCGATCGAA<br>GACACCCAGTTCGTTCCGGCCTGGGGTCAGGCGCGCCTGCACTCGAT<br>GATCGCCAACCGCCCGGACTGGTGCATCTCGCGTCAACGCAACTGGG<br>GCGTGCCGATCCCGTTTTTCCTGAACAAGGAAAGCGGCGAGCTGCAC<br>CCGCGCACCGTCGAAATGATGGAAGAAGTGGCCAAGCGCGTTGAAGT<br>CGAAGGCATCGAGGCGTGGTTCAAGCTGGATGCTGCCGAGCTGCTGG<br>GCGACGAAGCGCCGCTGTACGACAAGATCAGCGATACCCTCGACGTC<br>TGGTTCGATTCGGGCACCACGCACTGGCATGTCCTTCGCGGTTCGCAC<br>CCGATGGGTCATGAAACCGGCCCACGCGCTGATCTCTACCTTGAAGG<br>CTCCGACCAGCACCGTGGCTGGTTCCACTCGTCGTTGCTGACCGGTTG<br>CGCCATCGACAACCACGCGCCGTACCGCGAGCTGCTGACCCACGGTT<br>TTACCGTGGACGAAGCGGGCCGCAAGATGTCCAAGTCGCTGGGCAAC<br>GTGATTGCACCGCAAAAGGTCAACGACACCCTGGGCGCCGACATCAT<br>GCGTCTGTGGGTTGCTTCGACCGACTACTCGGGCGAAATCGCGGTTTC<br>CGACCAGATCCTGCAGCGCAGTGCGGACGCCTACCGACGTATCCGCA<br>ATACCGCACGCTTCCTGCTGTCGAACCTGACCGGTTTCAATCCAGCCA<br>CCGACATCCTGCCTGCCGAAGAAATGCTGGCACTGGACCGCTGGGCG<br>GTGGATCGTGCGTTGCTGCTGCAACGTGAGCTGGAGCTGCATTACGG<br>CGAATACCGTTTCTGGAACGTGTACTCCAAGGTGCACAACTTCTGCGT<br>TCAGGAGCTGGGCGGTTTCTATCTCGACATCATCAAGGACCGCCAGT<br>ACACCACCGGCGCCAACAGCAAGGCTCGCCGTTCGTGCCAGACCGCG<br>CTGTTCCACATCTCTGAAGCGCTGGTGCGCTGGATCGCTCCGATCCTG<br>GCGTTCACCGCTGATGAGTTGTGGCAGTACCTGCCGGGCGAGCGCAA<br>CGAATCGGTCATGCTCAACACCTGGTACGAAGGCCTGACTGAACTGC<br>CGGAAGGCACCGAACTGGATCGCGCCTACTGGGAGCGAATCATGGCG<br>GTCAAGGTTGCGGTCAACAAGGAAATGGAAAACTTGCGCGCAGCCAA<br>GGCCATTGGCGGTAACTTGCAAGCAGAAGTGACCTTGTTCGCCGAAG<br>ATCAGCTGGCTGCTGATTTGTCCAAGTTGAGCAACGAACTGCGTTTCG<br>TGTTGATCACCTCCACTGCCAGCGTTGCGCCTTTTGCGCAGGCTCCAG<br>CAGATGCCGTGGTTACCGAAGTGGCTGGCCTCAAACTCAAGGTGGTC<br>AAGTCGGCCCATGCCAAGTGCGCCCGTTGCTGGCACTGCCGTGAAGA<br>CGTCGGCGTTAACCCCGAGCACCCTGAAATCTGCGGTCGTTGTGTAGA<br>CAATATCAGCGGCGCTGGTGAGGTACGTCACTATGCCTAA |
| 70 | DP53 NADH-quinone oxidoreductase subunit C/D | ATGACTGCAGGCTCCGCTCTGTACATCCCGCCTTACAAGGCTGACGAC<br>CAAGATGTGGTTGTCGAACTCAATACCCGTTTTGGCCCTGAGGCGTTC<br>ACCGCCCAGGCCACGCGCACCGGCATGCCGGTGCTTTGGGTTAGCCG<br>CGCAAAACTGGTCGAAGTACTGACCTTCCTGCGCAACCTGCCAAAAC<br>CCTACGTCATGCTCTATGACCTGCACGGTGTGGACGAACGTCTGCGTA<br>CCAAGCGTCAGGGCCTGCCATCGGGTGCAGACTTCACCGTCTTCTACC<br>ACCTGATGTCGCTGGAACGTAACAGCGACGTCATGATCAAGGTGGCC<br>CTGTCTGAAAAAGACCTGAGTGTCCCTACCGTGACCGGTATCTGGCCG<br>AACGCCAACTGGTACGAGCGTGAAGTCTGGGACATGTTCGGCATCGA<br>TTTCAAAGGCCACCCGCACCTGTCGCGCATCATGATGCCGCCGACCTG<br>GGAAGGTCACCCGCTGCGCAAGGACTTCCCGGCCCGTGCCACAGAGT<br>TCGATCCGTACAGCCTGACCCTGGCCAAGGTGCAGCTGGAAGAGGAA<br>GCCGCGCGCTTCCGCCCGGAAGACTGGGGCATGAAACGCTCCGGTGA<br>AAACGAGGACTACATGTTCCTCAACCTGGGCCCTAACCACCCCTTCGGC<br>TCACGGTGCCTTCCGCATCATCCTGCAGCTGGACGGTGAAGAGATCGT<br>CGACTGCGTGCCTGACGTCGGTTACCACCACCGTGGCGCCGAGAAAA<br>TGGCCGAACGCCAGTCCTGGCACAGTTTCATCCCGTACACCGACCGG<br>ATCGATTACCTCGGCGGAGTGATGAACAACCTGCCGTACGTGCTCTCG<br>GTCGAGAAGCTGGCCGGTATCAAAGTGCCGGATCGGGTCGACACCAT<br>CCGCATCATGATGGCCGAATTCTTCCGTATCACCAGCCACCTGCTGTT<br>CCTGGGTACCTATATCCAGGACGTGGGCGCCATGACCCCGGTGTTCTT<br>CACGTTCACCGACCGTCAGCGCGCTTACAAGGTGATCGAGGCCATCA<br>CCGGTTTCCGTCTGCACCCGGCCTGGTACCGCATCGGCGGCGTTGCCC |

-continued

Sequence Listing

| Seq ID No. | Description | Sequence |
| --- | --- | --- |
| | | ACGACCTGCCGAACGGCTGGGATCGCCTGGTCAAGGAATTCATCGAC<br>TGGATGCCCAAGCGTCTGGACGAGTACCAGAAAGCCGCTCTGGACAA<br>CAGCATCCTGCGTGGTCGTACCATCGGCGTTGCCGCCTACAACACCAA<br>AGAGGCCCTGGAATGGGGCGTCACCGGTGCCGGCCTGCGCTCCACCG<br>GTTGTGACTTCGATATCCGCAAGGCGCGCCCGTATTCCGGCTACGAGA<br>ACTTCGAATTCGAAGTCCCGCTGGCAGCCAACGGCGATGCCTACGAT<br>CGTTGCATCGTGCGCGTCGAAGAAATGCGCCAGAGCCTGAAAATCAT<br>CGAGCAGTGCATGCGCAACATGCCGGCCGGCCCGTACAAGGCGGATC<br>ACCCGCTGACCACGCCGCCGCCTAAAGAACGCACGCTGCAGCATATC<br>GAGACCTTGATCACGCACTTCCTGCAAGTTTCGTGGGGCCCGGTGATG<br>CCGGCCAACGAATCCTTCCAGATGATCGAAGCGACCAAGGGCATCAA<br>CAGTTATTACCTGACGAGCGATGGCGGCACCATGAGCTACCGCACCC<br>GGATTCGCACCCCAAGCTTCCCGCACCTGCAACAGATCCCTTCGGTGA<br>TCAAAGGTGAAATGGTCGCGGACTTGATTGCGTACCTGGGTAGTATC<br>GATTTCGTTATGGCCGACGTGGACCGCTAA |
| 71 | DP53 Protein RecA | ATGGACGACAACAAGAAGAAAGCCTTGGCTGCGGCCCTGGGTCAGAT<br>CGAACGTCAATTCGGCAAGGGTGCCGTGATGCTGATGGGCGACCAGG<br>AGCGTCAGGCAGTCCCGGCGATCTCCACCGGCTCCCTGGGTCTGGAC<br>ATCGCACTGGGCATTGGCGGTCTGCCAAAAGGCCGTATTGTTGAAAT<br>CTACGGCCCTGAGTCGTCGGGTAAAACCACACTGACCCTGTCCGTGAT<br>TGCCCAGGCGCAAAAGGCCGGTGCTACCTGCGCCTTCGTCGATGCCG<br>AGCACGCCCTTGATCCTGAGTACGCTGCCAAACTGGGCGTAAACGTT<br>GATGACCTGCTGGTTTCACAGCCTGACACCGGCGAACAGGCACTGGA<br>AATCACCGATATGCTGGTGCGTTCCAATGCGGTTGACGTGATCATCAT<br>CGACTCCGTTGCTGCACTGACGCCAAAAGCTGAAATCGAAGGCGACA<br>TGGGCGATACCCACGTTGGCCTGCAAGCCCGTCTGATGTCGCAAGCG<br>CTGCGTAAAATCACCGGTAACATCAAGAACGCCAACTGCCTGGTTAT<br>CTTCATCAACCAGATCCGCATGAAAATCGGCGTGATGTTCGGCAGCC<br>CTGAAACCACCACCGGTGGTAACGCACTGAAGTTCTACGCTTCGGTA<br>CGTCTGGATATCCGCCGCACCGGCGCCGTAAAAGAAGGCGATGTGGT<br>GGTGGGTAGCGAAACCCGCGTGAAAGTGGTCAAGAACAAGGTGGCA<br>CCACCGTTCCGTCAGGCTGAATTCCAGATCCTGTACGGCAAGGGTATC<br>TACCTGAACGGTGAAATGATTGACCTGGGCGTACTGCATGGCTTTGTT<br>GAAAAAGCTGGCGCCTGGTACAGCTACAACGGCAGCAAAATCGGTCA<br>GGGCAAGGCCAACTCCGCCAAGTTCCTGGACGATAACCCGGACATCA<br>AGGATGCGCTGGAGAAGCAGCTGCGTGAGAAGTTGCTCGGGCCAAAA<br>ACCGATGCCGAACTGGCAGCGACGGACTGCAATGGACCTGCTCGCGC<br>GACGCGAGCACGGTCGAGTCGAGCTGACGCGCAAGTTGCGTCAGCGC<br>GGCGCTTGCCCCGACATGATCGACGCTGCCCTTGA |
| 72 | DP53 RNA polymerase sigma factor RpoD | ATGTCCGGAAAAGCGCAACAGCAGTCTCGTATCAAAGAGTTGATCAC<br>CCTCGGCCGTGAGCAGAAGTATCTGACTTACGCAGAGGTCAACGACC<br>ACCTGCCCGAAGATATTTCAGATCCGGAGCAAGTGGAAGACATCATC<br>CGCATGATTAATGACATGGGGATCCCCGTACACGAGAGTGCTCCGGA<br>TGCGGACGCCCTTATGTTGGCCGATGCCGACACCGACGAAGCAGCAG<br>CTGAAGAAGCGGCTGCAGCGTTGGCGGCAGTAGAGACCGACATTGGT<br>CGTACTACCGACCCTGTGCGCATGTATATGCGTGAAATGGGCACGGT<br>AGAACTGCTGACACGTGAAGGCGAAATCGAAATCGCCAAGCGTATCG<br>AAGAAGGCATCCGTGAAGTGATGGGCGCAATCGCGCACTTCCCTGGC<br>ACGGTTGACCATATTCTCTCCGAGTACACTCGCGTCACCACCGAAGGT<br>GGCCGCCTGTCCGACGTTCTGAGCGGTTATATCGACCCGGACGACGG<br>TATTGCGCCGCCCGCAGCCGAAGTACCTCCTCCTGTCGACACCAAGGT<br>GAAAGCCGAAGGTGATGACGAAGAGGACGACAAGGAAGATTCCGGC<br>GAAGACGAGGAAGAGGTCGAAAGCGGCCCTGATCCGATCATCGCGG<br>CCCAGCGCTTTGGCGCTGTTTTCGATCAGATGGAAATCGCTCGCAAGG<br>CCCTGAAAAAGCACGGTCGCGGCAGCAAGCAGGCAATTGCCGAGCTG<br>GTTGCACTGGCTGAGCTGTTCATGCCGATCAAACTGGTTCCGAAGCAA<br>TTCGAAGGCCTGGTTGAGCGTGTTCGCAGCGCCCTGGAGCGTCTGCGT<br>GCACAAGAGCGCGCAATCATGCAGCTGTGTGTACGTGATGCACGCAT<br>GCCGCGCACCGATTTCCTGCGTCTGTTCCCGGGCAACGAAGTCGACG<br>AAAGCTGGAGCGATGCGCTGGCCAAAGGCAAAAGCAAATATGCTGA<br>AGCCATTGGTCGCCTGCAACCGGACATCATCCGTTGCCAGCAAAAGC<br>TCTCTGCTCTGGAAGCAGAAACCGGCTTGAAGATTGCCGAGATCAAG<br>GACATCAACCGTCGCATGTCGATCGGCGAGGCCAAGGCCCGCCGCGC<br>GAAGAAAGAAATGGTTGAAGCCAACTTGCGTCTGGTGATCTCCATCG<br>CCAAGAAGTACACCAACCGTGGCCTGCAGTTCCTCGATCTGATCCAG<br>GAAGGCAACATCGGCTTGATGAAAGCGGTAGACAAGTTTGAATACCG<br>CCGCGGCTACAAATTCTCGACTTATGCCACCTGGTGGATCCGTCAGGC<br>GATCACTCGCTCGATCGCCGACCAGGCCCGCACCATCCGTATTCCGGT<br>GCACATGATCGAGACGATCAACAAGCTCAACCGTATTTCCCGTCAGA<br>TGTTGCAGGAAATGGGCCGTGAACCGACCCCGGAAGAGCTGGGCGAA<br>CGCATGGAAATGCCTGAGGATAAAATCCGCAAGGTATTGAAGATCGC |

-continued

Sequence Listing

| Seq ID No. | Description | Sequence |
|---|---|---|
| | | TAAAGAGCCGATCTCCATGGAAACCCCGATCGGTGATGACGAAGACT<br>CCCATCTGGGTGACTTCATCGAAGACTCGACCATGCAGTCGCCAATCG<br>ATGTTGCTACCGTTGAGAGCCTTAAAGAAGCGACACGCGACGTACTC<br>GGCGGCCTCACAGCCCGTGAAGCCAAGGTACTGCGCATGCGTTTCGG<br>TATCGACATGAATACCGACCACACCCTTGAGGAGGTTGGTAAACAGT<br>TCGACGTTACCCGTGAGCGGATTCGTCAGATCGAAGCCAAGGCGCTG<br>CGCAAGCTGCGCCACCCGACGAGAAGCGAGCATTTGCGCTCCTTCCT<br>CGACGAGTGA |
| 73 | DP53 DNA-directed RNA polymerase subunit beta | ATGGCTTACTCATATACTGAGAAAAAACGTATCCGCAAGGACTTTAG<br>CAAGTTGCCGGACGTCATGGATGTGCCGTATCTCTTGGCAATCCAGCT<br>GGATTCGTATCGTGAATTCTTGCAGGCGGGAGCGACTAAAGATCAGT<br>TCCGCGACGTGGGCCTGCATGCGGCCTTCAAATCCGTTTTCCCGATCA<br>TCAGCTACTCCGGCAATGCTGCGCTGGAGTACGTCGGTTATCGCTTGG<br>GCGAACCGGCATTTGATGTCAAAGAATGCGTGTTGCGTGGCGTAACG<br>TACGCCGTACCTTTGCGGGTAAAAGTTCGTTTGATCATTTTCGACAAA<br>GAATCGTCGAACAAAGCGATCAAGGACATCAAAGAGCAAGAAGTCT<br>ACATGGGTGAAATCCCCCTGATGACTGAAAACGGTACCTTCGTAATC<br>AACGGTACCGAGCGTGTAATTGTTTCCCAGCTGCACCGTTCCCCGGGC<br>GTGTTCTTTGCCACGACCGCGGCAAGACGCACAGCTCCGGTAAGCTG<br>CTTTATTCCGCGCGTATCATTCCTTACCGTGGTTCGTGGCTCGACTTCG<br>AGTTCGACCCGAAAGACTGCGTGTTCGTGCGTATTGACCGTCGTCGCA<br>AGCTGCCTGCATCGGTATTGCTGCGCGCGCTGGGTTATACCACTGAGC<br>AAGTGCTGGACGCGTTCTACACCACCAACGTGTTCCACGTTCAGGGTG<br>AGAGCATCAGCCTGGAGCTGGTTCCACAGCGTCTGCGCGGTGAAATC<br>GCGGCCATCGACATTACCGATGACAAAGGCAAGGTGATTGTTGAGCA<br>GGGTCGTCGTATCACTGCTCGTCATATCAACCAGCTGGAAAAAGCCG<br>GTGTCAAAGAGCTCGTTATGCCTCTGGACTATGTCCTGGGTCGCACAA<br>CGGCCAAGGCTATCGTGCATCCGGCTACTGGCGAAATCATTGCTGAG<br>TGCAACACCGAGCTGACCACTGAAATCCTGGCAAAAGTTGCCAAGGG<br>CCAGGTTGTTCGCATCGAAACGTTGTACACCAACGATATCGACTGCG<br>GTCCGTTCGTCTCCGACACGCTGAAGATCGACTCCACCAGCAACCAA<br>CTGGAAGCGCTGGTCGAAATCTATCGCATGATGCGTCCAGGCGAGCC<br>GCCAACCAAAGACGCTGCCGAGACTCTGTTCAACAACCTGTTCTTCAG<br>CCCTGAGCGCTATGACCTGTCTGCGGTCGGCCGGATGAAGTTCAACC<br>GTCGTATCGGTCGTACCGAGATCGAAGGTTCGGGCGTGTTGTGCAAA<br>GAAGACATCGTTGCCGTGCTGAAGACCCTGGTCGACATCCGTAACGG<br>TAAAGGCATCGTCGATGACATCGACCACCTGGGTAACCGTCGTGTTC<br>GCTGTGTAGGCGAAATGGCCGAGAACCAGTTCCGCGTTGGCCTGGTA<br>CGTGTTGAGCGTGCGGTCAAAGAGCGTCTGTCGATGGCTGAAAGCGA<br>AGGCCTGATGCCGCAAGACCTGATCAACGCCAAGCCTGTGGCTGCGG<br>CGGTGAAAGAGTTCTTCGGTTCCAGCCAGCTGTCCCAGTTCATGGACC<br>AGAACAACCCTCTGTCCGAGATCACCCACAAGCGCCGTGTTTCTGCAC<br>TGGGCCCGGGCGGTCTGACGCGTGAGCGTGCGGGCTTTGAAGTTCGT<br>GACGTACACCCGACTCACTACGGCCGTGTTTGCCCTATTGAGACGCCG<br>GAAGGTCCGAACATCGGTCTGATCAACTCCCTGGCTGCCTATGCGCGC<br>ACCAACCAGTACGGCTTCCTCGAGAGCCCGTACCGTGTAGTGAAAGA<br>CGCACTGGTAACTGACGAGATCGTTTTCCTGTCCGCCATCGAAGAAGC<br>TGATCACGTGATCGCTCAGGCCTCGGCCACGATGAACGACAAGAAAG<br>TGCTGATCGACGAGCTGGTTGCTGTTCGTCACTTGAACGAATTCACCG<br>TCAAGGCGCCGGAAGACGTCACCTTGATGGACGTTTCGCCGAAGCAG<br>GTTGTTTCGGTTGCAGCGTCGCTGATCCCGTTCCTGGAACACGATGAC<br>GCCAACCGTGCGTTGATGGGTTCCAACATGCAGCGTCAAGCTGTACC<br>AACCCTGCGCGCTGACAAGCCGCTGGTAGGTACCGGCATGGAGCGTA<br>ACGTAGCTCGTGACTCCGGCGTTTGCGTCGTGGCTCGTCGTGGCGGCG<br>TGATCGACTCTGTTGATGCCAGCCGTATCGTGGTTCGTGTTGCTGATG<br>ACGAAGTTGAAACTGGCGAAGCCGGTGTCGACATCTACAACCTGACC<br>AAATACACCCGTTCCAACCAGAACACTTGCATCAACCAGCGTCCGCT<br>GGTGCGCAAGGGTGACCGTGTACAGCGTAGCGACATCATGGCTGACG<br>GCCCGTCCACCGATATGGGTGAACTGGCGCTGGGTCAAAACATGCGC<br>ATCGCGTTCATGGCCTGGAACGGTTACAACTTCGAAGACTCCATCTGC<br>TTGTCGGAACGAGTTGTTCAAGAAGACCGCTTTACCACGATCCACATT<br>CAGGAACTGACCTGTGTGGCACGTGACACCAAGCTTGGGCCTGAAGA<br>GATCACTGCAGACATCCCTAACGTGGGTGAAGCTGCACTGAACAAAC<br>TGGACGAAGCCGGTATCGTTTACGTAGGTGCTGAAGTTGGCGCCGGC<br>GACATTCTGGTAGGTAAGGTCACTCCGAAAGGCGAGACCCAGCTGAC<br>TCCGGAAGAGAAGCTGTTGCGTGCCATCTTCGGTGAAAAAGCCAGCG<br>ACGTTAAAGACACCTCCCTGCGCGTACCTACCGGTACCAAAGGTACT<br>GTTATCGACGTGCAGGTCTTCACCCGTGACGGCGTTGAGCGTGATGCT<br>CGTGCACTGTCGATCGAGAAGACCCAGCTGGACGAGATCCGCAAGGA<br>TCTGAACGAAGAGTTCCGTATCGTTGAAGGCGCTACCTTCGAACGTCT<br>GCGCTCTGCTCTGGTTGGCCGCATTGCCGAAGGTGGTGCCGGTCTGAA<br>GAAAGGTCAGGAAATCACCAATGAAATCCTGGACGGTCTTGAGCATG |

-continued

Sequence Listing

| Seq ID No. | Description | Sequence |
|---|---|---|
| | | GTCAGTGGTTCAAACTGCGCATGGCTGAAGATGCTCTGAACGAGCAG<br>CTTGAAAAGGCTCAGGCTTACATCATCGATCGCCGTCGTCTGCTGGAC<br>GACAAGTTCGAAGACAAGAAGCGCAAACTGCAGCAGGGCGATGACC<br>TGGCTCCAGGCGTGCTGAAAATCGTCAAGGTTTACCTGGCAATCCGCC<br>GTCGCATCCAGCCGGGTGACAAGATGGCCGGTCGTCACGGTAACAAG<br>GGTGTGGTCTCCGTGATCATGCCGGTTGAAGACATGCCGTACGATGCC<br>AATGGCACCCCGGTTGATGTGGTCCTCAACCCGTTGGGCGTACCTTCG<br>CGTATGAACGTTGGTCAGATTCTCGAAACTCACCTGGGCCTCGCGGCC<br>AAAGGTCTGGGCGAGAAGATCAACCTCATGATTGAAGAACAACGCAA<br>GGTCGCTGACCTGCGTAAGTTCCTGCATGAGATCTACAACGAAATTG<br>GCGGTCGTCAAGAAAGCCTGGATGACTTCTCCGATCAGGAAATCCTG<br>GATCTGGCGAAGAACCTTCGCGGCGGTGTGCCAATGGCTACCCCGGT<br>GTTCGACGGTGCCAAGGAAAGCGAAATCAAGGCAATGCTTCGTTTGG<br>CAGACCTGCCAGACAGCGGCCAGATGGTGCTGACTGATGGTCGTACC<br>GGCAACAAGTTCGAGCGTCCGGTTACCGTTGGCTACATGTACATGCTG<br>AAGCTGAACCACTTGGTAGACGACAAGATGCACGCTCGTTCTACCGG<br>TTCTTACAGCCTGGTTACCCAGCAGCCGCTGGGTGGTAAGGCGCAGTT<br>CGGTGGTCAGCGTTTCGGGGAGATGGAGGTCTGGGCGCTGGAAGCCT<br>ACGGCGCGGCATACACTCTGCAAGAAATGCTCACAGTGAAGTCGGAC<br>GATGTGAACGGCCGTACCAAGATGTACAAAAACATCGTGGACGGCGA<br>TCACCGTATGGAGCCGGGCATGCCCGAGTCCTTCAACGTGTTGATCAA<br>AGAAATTCGTTCCCTCGGCATCGATATCGATCTGGAAACCGAATAA |
| 74 | DP9 Glycine tRNA ligase beta subunit | ATGGCACATAATTATTTACTAGAAATTGGATTGGAAGAAATTCCGGC<br>CCATGTTGTAACTCCAAGTATCAAACAGTTAGTACAAAAAGTAACAG<br>CCTTCTTAAAAGAAAATCGCTTAACATACGACTCAATTGATCATTTTT<br>CAACTCCTCGTCGTTTGGCAATTCGAATCAATGGGTTAGGCGACCAAC<br>AACCTGATATTGAAGAAGATGCTAAAGGCCCTGCTCGTAAAATTGCT<br>CAAGATGCTGATGGAAATTGGACTAAGGCTGCAATTGGCTTTACACG<br>TGGACAAGGTCTTACGGTTGACGATATTACTTTTAAAACAATCAAAG<br>GTACGGACTATGTGTACGTCCATAAGTTAATCAAAGGAAAGATGACT<br>AAGGAAATCCTTACGGGGATAAAAGAAGTTGTTGAATCAATTAATTT<br>CCCAACAATGATGAAGTGGGCTAACTTTGATTTTAAATATGTACGCCC<br>AATTCGTTGGCTGGTTTCTATTCTAGATGAAGAAGTCCTTCCTTTTAGT<br>ATCTTAGACGTAACTGCGGGACGCCGAACAGAAGGACATCGTTTCTT<br>AGGTGAAGCTGTCGAACTGGCTAATGCTGAAGAATATGAAGCAAAAT<br>TACACGATCAATTTGTGATTGTTGATGCCGACGAGCGTAAACAATTAA<br>TTTCAAACCAAATTAAAGCAATTGCTGAAAGCAATCGTTGGAACGTT<br>ACCCCTAACCCAGGTCTTTTAGAAGAGGTTAACAATTTGGTTGAGTGG<br>CCAACCGCTTTTAATGGGGGATTTGATGAAAAGTATTTAGCTATTCCA<br>GAAGAGGTATTGATAACATCAATGCGTGACCACCAACGCTTCTTCTTT<br>GTCCGCGACCAAGCTGGAAAGCTATTGCCAAACTTCATCTCCGTACG<br>AAATGGGAATGAAGAATTTATTGAAAATGTTGTTCGTGGAAATGAAA<br>AAGTTTTAACTGCACGTTTAGAAGACGCTGCTTTCTTCTACGAAGAAG<br>ATCAAAAACATGATATTAATTATTATGTTGACCGACTTAAAAAGGTTA<br>GTTTCCATGATAAGATTGGTTCAATGTACGAAAAAATGCAACGAGTT<br>AATTCTATTGCTAAAGTTATTGGAAACACCTTAAATCTTAATCAAACG<br>GAACTTGATGATATCGATCGCGCTACAATGATTTATAAATTTGATTTG<br>GTAACTGGTATGGTTGGTGAGTTCTCAGAATTACAAGGAGTAATGGG<br>TGAAAAATATGCTCAACTTAATGGTGAAAACCAAGCAGTAGCCCAAG<br>CCATTCGCGAACATTACATGCCAAATAGCGCAGAAGGTGATTTGCCT<br>GAAAGTGTAACGGGCGCGGTAGTCGCATTAGCTGATAAGTTTGATAA<br>CATCTTTAGTTTTTTCTCAGCTGGTATGATTCCAAGTGGTTCAAACGAT<br>CCATATGCATTACGCCGACATGCATATGGAATTGTTAGAATCTTAAAT<br>AGCCGTGATTGGCAATTAGATTTAAATCAATTCAAATCACAATTTAAG<br>ACTGAATTAGCGGAGAATGGCACAGCGTTTGGTGTGGATGTCGATCA<br>AAACTTTGACCAAGTACTTAACTTCTTTAATGACCGTATTAAACAATT<br>GCTTGATCATCAAAAGATTAGTCATGATATCGTTGAAACGGTGCTTAC<br>AGGTAATAATCATGATGTTACGGAAATTATCGAAGCTGCCCAAGTAC<br>TAGCAGATGCTAAAGCGAGCTCTACATTTAAAGATGATATTGAAGCT<br>TTAACACGAGTTCAAAGAATTGCTACAAAGAATGAAGAAAGTGGAGA<br>ACTTAATGTAGATCCACAATTATTTAATAATGCTTCTGAAGGCGAACT<br>TTTTGATCAAATTATTAAAATTGAAGCTGCAAATAATTTGACAATGAG<br>CCAACTATTTGCTAAATTATGCGAGTTGACTCCTGCGATTAGCAAGTA<br>CTTTGACGCAACGATGGTCATGGACAAAGACGAAAATATTAAGTGTA<br>ATCGTTTGAATATGATGAGTCGGTTAGCTAATTTAATTCTAAAAATTG<br>GGGATCTAACTAACGTACTTGTAAAATAA |
| 75 | DP9 Glutamine synthetase | ATGGCAAAGAAAAATTATTCGCAAGCAGATATTCGTCAGATGGCAAA<br>GGATGAAAATGTACGTTTTCTCCGATTAATGTTTACAGATCTTTTTGG<br>AATAATTAAGAACGTTGAAGTACCAATTAGTCAATTGGACAAACTAT<br>TAGATAATAAATTGATGTTTGATGGTTCCTCAATTGACGGGTTTGTTC<br>GGATTGAAGAAAGTGACATGTATTTATACCCAGATCTTTCTACTTGGA |

-continued

Sequence Listing

| Seq ID No. | Description | Sequence |
|---|---|---|
| | | TGGTTTTCCCATGGGGAAGCGAACATGGCAAGGTGGCTCGCATTATTT GTGAAGTATACTCAAATGATCGTAAACCATTCGTGGGTGATCCACGT AACAATTTAATTCGAGTACTCCAAGAGATGAAGGATGCAGGATTTAC TGATTTTAATATCGGACCTGAACCTGAGTTTTTCTTGTTGAAATTAGA TGAAAATGGTAAACCAACCACTAATTTAAATGATAAAGGTAGTTACT TTGATTTAGCTCCTGTTGATTTAGGTGAAAACTGCCGTCGTGATATTG TTTTGGAACTTGAAAATATGGGCTTTGATGTTGAAGCTTCTCATCATG AAGTTGCTCCAGGACAACACGAAATTGACTTTAAATACGCCGATGCT TTGACCGCTGCCGATAACATTCAAACCTTTAAGTTGGTTGTTAAGACA GTTGCCCGTAAATATAACCTGCATGCTACATTTATGCCTAAACCTATG GATGGAATCAATGGTTCAGGGATGCATTTAAACATGTCACTTTTCAAT AAGGAAGGCAATGCTTTCTATGACGAAAAGGGTGACTTACAACTTTC TCAAAATGCTTACTGGTTCCTTGGTGGACTATTGAAGCATGCTCGTAG TTATACGGCCGTATGTAACCCAATTGTTAACTCGTACAAACGTTTAGT TCCTGGATATGAAGCTCCAGTATACGTTGCTTGGTCAGGTTCAAATCG TTCACCACTTATTCGCGTTCCTTCAAGTAAGGGACTCTCAACTCGTTTT GAAGTTCGAAGCGTCGATCCAGCTGCTAACCCATACTTAGCAATTGC ATCAGTATTGGAAGCAGGCTTAGATGGCATTAGAAACAAGATTGAAC CAGAAGATTCCGTTGATCGTAATATCTATCGAATGAACATTCAAGAA CGTAATGAAGAGCATATTACAGATCTACCTTCAACATTACACAATGCT TTGAAGGAATTCCAAAATGATGATGTAATGCGTAAGGCATTAGGAGA TCACATTTTCCAAAGCTTCCTCGAAGCTAAGAAGTTAGAATGGGCTTC TTACCGTCAAGAAGTGACACAATGGGAACGTGATCAATATCTCGAAA TGTTCTAG |
| 76 | DP9 DNA gyrase subunit B | TTGGCAGACGAAAAAGAAACGAAAGCAGAATTAGCCAGAGAATATG ATGCGAGTCAAATTCAGGTTTTAGAGGGGCTCGAAGCAGTTCGTAAA CGCCCAGGAATGTATATTGGGTCGACTAGTTCTCAAGGACTACACCAT TTGGTTTGGGAAATTATTGATAATGGTATTGATGAAGCTCTTGCAGGA TTTGCAGACAAAATTGATGTGATCGTTGAAAAAGACAATAGTATTAC CGTCACTGATAATGGACGTGGGATTCCGGTTGATATCCAAAAGAAAA CTGGAAAACCAGCTTTAGAAACAGTCTTTACGGTCCTACATGCCGGA GGTAAATTCGGCGGTGGCGGTTATAAAGTTTCTGGAGGATTGCATGG TGTGGGCGCATCCGTTGTAAATGCGTTATCAACGGAATTAGATGCGC GCGTCATGAAGGACGGTAAAATCTATTACATTGATTTTGCGCTAGGA AAAGTAAAAACACCGATGAAAACGATTGGTGATACTGAACATCCTGA CGATCATGGAACTATTGTTCATTTCGTTCCAGATCCAGATATTTTCCA AGAAACTACCACATACGACATTAATATCTTAAAAACACGAATTCGTG AATTAGCCTTTTTGAACAAAGGTCTACGGATTACTTTGAAGGATATGC GTCCTGAAAAGCCAACTGAAGACGACTTCTTGTATGAAGGTGGGATT CGCCACTACGTTGAATATCTAAACGAAGGCAAAGAAGTAATTTTTCCC TGAACCTATCTATGTTGAAGGGGTTACAAAAGGTATCACTGTTGAAGT AGCTATGCAATATATCGAAGGTTATCAAAGTAAATTGTTAACTTTTAC TAACAATATTCATACTTACGAAGGCGGTACCCACGAAGAAGGTTTCA AACGTGCTTTAACACGAGTTATTAACGATTACGCTAAAAACAACAAT ATTTTAAAAGAAAATGATGATAAATTGTCTGGTGATGATGTTCGAGA AGGTTTGACGGCAGTAGTCAGCGTTAAGCATCCTGATCCTCAATTCGA AGGACAAACGAAAACAAAATTGGGTAACTCAGATGCTCGGACAGCTG TTAACGAAGTGTTTGCTGAAACTTTCAATAAATTCTTATTGGAAAATC CTAAGGTTGCACGTCAAATTGTTGATAAGGGAATCTTGGCAGCAAAA GCAAGAGTCGCCGCTAAACGAGCTCGTGAAGTTACGCGTAAGAAGAG TGGCCTAGAACTCAATAATCTTCCTGGTAAATTAGCTGATAATACTTC TAAGGATCCTTCAATTAGTGAATTATTCATTGTCGAGGGTGATTCTGC CGGTGGTAGTGCTAAGTCGGGACGTTCGCGTCTCACACAAGCTATTTT GCCAATTCGTGGGAAGATTTTGAACGTTGAAAAAGCCACTTTGGATC GGGTTTTGGCCAATGAAGAAATTCGTTCACTCTTTACAGCGCTCGGAA CTGGATTTGGTGAGGACTTTGATGTAAGTAAAGCCAACTATCATAAAT TGATTATCATGACCGATGCCGATGTCGATGGTGCTCATATTCGGACAC TATTATTGACGCTGTTCTATCGTTACATGCGTCCAATGATTGATGCAG GATTTGTTTACATTGCTCAACCACCGCTCTACCAAGTACGTCAAGGTA AGATGATTCAATATATCGATTCTGATGAAGAATTAGAAACAGTACTT GGACAATTGTCACCATCACCAAAACCTGTAATTCAACGTTATAAAGG TCTTGGTGAAATGGATGCTGAGCAACTTTGGGAAACAACCATGAATC CAGAAAATCGACGCTTGTTACGAGTTTCAGCCGAAGATGCTGATGCT GCAAGTGGTGATTTTGAAATGTTGATGGGTGACAAGGTTGAACCACG TCGTAAATTCATTGAAGAGAACGCTGTGTTTGTTAAAAACTTGGATAT CTAA |
| 77 | DP9 Leucine tRNA ligase | ATGGCTTATAATCATAAAGATATCGAACAGAAGTGGCAGCAATTCTG GAGCGACAATGAGACTTTTAAGACGGTCGAAGATGCAGACAAACCCA AATATTATGCATTAGACATGTTCCCTTATCCATCAGGTCAAGGACTCC ATGTGGGCCATCCTGAAGGATATACAGCAACAGATATTATGTCACGA ATGAAACGGATGCAAGGTTACAAAGTACTTCATCCAATGGGATGGGA |

-continued

Sequence Listing

| Seq ID No. | Description | Sequence |
|---|---|---|
| | | TGCTTTTGGTCTTCCAGCAGAACAATATGCGATGAAGACGGGTAACA<br>ATCCGCGTGATTTTACAGCTAAGAATATTCAAAACTTTAAGCGTCAAA<br>TCCAATCACTTGGTTTTTCTTATGACTGGTCGCGAGAAGTTAATACAA<br>CTGATCCAGCTTACTACAAGTGGACTCAATGGATTTTTGAGCAACTCT<br>ACAAGAAGGGCTTAGCTTATGAAAAAGAAACGCTGGTAAACTGGGCT<br>CCTGATTTAATGGGTGGAACGGTAGTTGCTAACGAAGAAGTTGTGGA<br>TGGTAAGACAGAACGTGGTGGGTTCCCCGTTTATCGTAAACCAATGA<br>AACAATGGATTCTTAAAATTACAGCTTACGCCGACCGTTTGATTGACG<br>ATTTGGACCTGGTAGATTGGCCCGATAGTATTAAAGAAATGCAAAAA<br>AACTGGATTGGTCGTTCAGTGGGGGCTAGCGTCTTCTTTAATGTTGAA<br>GATAGCGAAAAACAAATTGAAGTATTTACAACGCGTCCAGATACATT<br>ATTTGGCGCAACATACTTGGTAATTTCACCAGAACATGACCTCGTTGA<br>CCAAATTACAACTCCAGAAAGTAAAGCTGCCGTTGAAGAATACAAGA<br>AAGCTGTTGCAACTAAATCAGATCTTGAACGGACGGATTTGAGTAAA<br>GATAAGACGGGAGTCTTTACGGGAGCATACGCGGTTAACCCTGTTAA<br>TGGTAAGAAAATTCCAGTTTGGATTAGTGATTACGTATTGGCTTCATA<br>CGGAACTGGAGCAGTGATGGCTGTTCCTGCTCATGATGGCCGTGACT<br>ACGAATTTGCTAAGAAATTCAAGATAGATATGGTGCCAGTTTATGAA<br>GGTGGCAATCTTGAAGATGGAGTATTGGACAGCGAAGGCGGGCTAAT<br>TAACTCTGGATTCCTAGATGGGATGGATAAGCAGACGGCTATTGATA<br>CCATGATTAGCTGGTTGGAAGAACATGGAGTTGGTCATAAGAAGGTT<br>AACTATCGTCTTCGTGACTGGGTCTTCTCTCGCCAACGCTACTGGGGT<br>GAACCAATCCCTGTAATTCATTGGGAAGATGGAGAAACAACTTTGAT<br>TCCTGAAGATGAATTGCCATTGAGACTCCCGGCTGCAACTGACATTCG<br>TCCTTCCGGTACCGGAGAAAGCCCATTAGCTAACCTAGATGATTGGGT<br>AAACGTAGTTGATGAAAATGGTCGTAAGGGTCGCCGGGAAACTAATA<br>CAATGCCACAATGGGCGGGTAGTTCATGGTACTTCCTCCGTTACGTTG<br>ATCCTAAGAATGATCAAAAGATTGCTGACGAAGATTTACTTAAAGAA<br>TGGTTACCAGTCGACTTATATGTTGGTGGAGCTGAACATGCGGTACTT<br>CATTTACTTTATGCACGTTTCTGGCACAAAGTTTTATATGATCTAGGA<br>GTTGTACCAACTAAGGAACCATTCCAAAAATTGGTCAACCAAGGGAT<br>GATTCTCGGTAGCAATCATGAGAAGATGTCTAAGTCAAAAGGGAACG<br>TGGTTAATCCAGATGATATTGTTGAGCGCTTTGGAGCGGATACTTTAC<br>GATTATACGAAATGTTCATGGGACCTCTGACAGAATCAGTCGCCTGG<br>AGTGAAGATGGGCTTAACGGAAGTCGTAAGTGGATTGACCGCGTCTG<br>GCGCTTGATGATTGACGACGAAAACCAATTGCGTGATCATATTGTTAC<br>TGAAAATGATGGCAGTTTGGATATGATTTATAACCAAACTGTTAAGA<br>AGGTAACTGATGATTATGAAAACATGCGCTTTAACACGGCTATTTCAC<br>AAATGATGGTCTTTGTTAATGAAGCATACAAGGCTGATAAACTTCCA<br>GCAGTATATATGGAAGGATTAGTTAAGATGTTAGCTCCAATTATTCCG<br>CACGTTGCTGAAGAACTTTGGAGTTTGCTAGGTCACGAAGGTGGTATT<br>TCATACGCTGAATGGCCAACATATGATGAAAGTAAGTTAGTAGAAGC<br>TACAGTTCAAGTCATTCTACAAGTTAATGGTAAAGTTCGGAGTAAAAT<br>TACCGTTGACAAGGATATCGCCAAAGAAGAACTTGAAAAATTAGCGT<br>TAGCTGATGCTAAGATTCAACAATGGACGGCAGATAAGACTGTTCGT<br>AAGGTAATTGTTATTCCTAACAAGATTGTTAATATCGTAGTAGGCTAA |
| 78 | DP9 Glucose-6-phosphate isomerase | ATGGCACATATTTCATTTGACAGTTCTAATGTTGCAGATTTTGTACAT<br>GAAAACGAACTTGCAGAAATCCAACCACTTGTTACAGCTGCTGATCA<br>GATTTTACGTGATGGCTCTGGCGCTGGTAGTGATTTCCGTGGATGGAT<br>CGATTTACCATCAAATTATGATAAGGACGAATTTGCCCGTATCAAGA<br>AAGCCGCTGATAAGATCCGCAATGACTCAGAAGTATTCGTTGCTATC<br>GGTATTGGTGGTTCATATTTGGGTGCTCGTGCAGCCATTGATTTCTTG<br>AACAACACTTTCTACAATCTTCTTACTAAAGAACAACGTAATGGTGCT<br>CCTCAAGTAATCTTCGCTGGTAACTCAATTAGTTCAACTTACCTTGCT<br>GACGTATTGAACTTAATCGGGGACCGTGACTTCTCAATTAACGTAATT<br>TCTAAGTCAGGTACAACTACAGAACCAGCTATTGCATTCCGTGTTCTT<br>AAAGAAAAACTAATCAAGAAGTACGGTGAAGAAGAAGCTAAGAAAC<br>GTATCTATGCAACAACTGACCGTGCTAAAGGCGCCCTAAAGACAGAA<br>GCTGATGCAGAAAACTATGAAGAATTCGTAGTTCCTGATGACATTGG<br>TGGTCGTTTCTCTGTTCTTTCAGCTGTTGGTTTATTACCAATCGCGGTT<br>GCCGGTGGCGATATTGACCAATTGATGAAGGGTGCTGAAGATGCAAG<br>CAACGAATACAAGGATGCTGATGTTACAAAGAACGAAGCATACAAGT<br>ACGCTGCTTTACGTAACATCCTTTATCGTAAGGGCTACACAACAGAAC<br>TTCTTGAAAACTACGAACCAACACTTCAATACTTCGGCGAATGGTGG<br>AAGCAATTGATGGGTGAATCAGAAGGTAAAGATCAAAAGGGTATCTA<br>CCCATCTTCTGCTAACTTCTCAACTGACTTACATTCACTAGGACAATA<br>CATCCAAGAAGGTCGTCGCAATTTAATGGAAACAGTTATCAATGTTG<br>AAAAGCCTAACCATGACATCGACATTCCTAAGGCTGACCAAGACCTT<br>GATGGATTACGTTATCTCGAAGGTCGCACAATGGACGAAGTTAACAA<br>GAAAGCTTACCAAGGTGTAACTCTTGCTCATAACGACGGTGGTGTTCC<br>AGTTATGACGGTTAACATTCCTGATCAAACAGCTTACACATTAGGCTA<br>TATGATTTACTTCTTCGAAGCAGCTGTTGCTGTATCTGGTTACTTGAAC |

-continued

Sequence Listing

| Seq ID No. | Description | Sequence |
|---|---|---|
| | | GGAATTAATCCATTCAACCAACCAGGTGTTGAAGCATACAAGTCAAA<br>TATGTTTGCATTACTTGGTAAACCAGGTTATGAAGATAAGACAGCTGA<br>ATTAAACGCTCGTCTATAA |
| 79 | DP9 Phospho-glucomutase | ATGAGTTGGGAAGATTCTGTCAAAGAATGGCAAGATTATGCAGATTT<br>AGATTTTAATTTAAAAAAAGAATTAGCAACTTTAGCTGAAGATAAAG<br>ATGCTTTAAAAGAAGCCTTTTATGCTCCAATGGAATTTGGTACAGCAG<br>GAATGCGTGGCGTAATGGGCCCTGGTATCAACCGGATGAATATCTAT<br>ACGGTTCGTCAAGCAACAGAAGGTTTAGCTAATTTTATGGATACCTTA<br>GATTTTACTGATAAGAAACGGGGAGTGGCGATCAGTTTTGATTCCCGC<br>TATCACTCACAAGAGTTTGCTTTAGCAGCAGCTGGTGTTTTAGGTAAG<br>CATGGTATTCCAAGTTTTGTTTTTGATAGTATGCGTCCCACTCCAGAA<br>TTATCATATACAGTACGTGAGTTAAACACTTATGCTGGAATCATGATT<br>ACTGCTAGTCATAATCCTAAACAATATAATGGATATAAGATTTATGGT<br>CCTGATGGCGGACAAATGCCACCAATGGAATCTGATAAGATTACAGA<br>ATATATTCGCCAAGTAACTGACATCTTTGGTGTTGAAGCTCTTACTCA<br>AAGTGAATTAAGAGCTAAGGGCTTAATGACCATTATTGGTGAAGACA<br>TTGACCTCAAGTATCTTGAGGAAGTTAAGACGGTATCAATTAATCATG<br>AACTAATCCAGCGCTTTGGTGCAGACATGAAGTTGATCTACTCACCAT<br>TACATGGTACTGGAAAAGTAGTTGGTGGACGTGCGTTAGAAAATGCT<br>GGTTTTAAGGATTACACTATGGTCCCTGAACAAGCAATTGCTGACCCA<br>GAATTTATTACAACGCCATTCCCTAACCCAGAATTCCCACAAACTTTT<br>GATTTGGCTATTGAATTAGGTAAAAAGCAAGATGCTGACCTTTTGATT<br>GCCACTGATCCGGATGCCGATCGTTTGGGAGCTGCCGTTCGTTTACCA<br>AATGGTGACTACAAATTATTGACAGGGAACCAAATTGCAGCCTTGAT<br>GTTAGAATACATCTTAACTGCGCATGATGCAGCAGGTGACTTGCCAG<br>GTAACGCAGCTGCCGTTAAGTCAATTGTTTCTAGTGAACTAGCAACCA<br>GAATTGCCGAAGCCCATCATGTAGAAATGATTAACGTTCTAACTGGG<br>TTTAAGTACATTGCTGACCAAATTAAACATTACGAAGAAAATGGCGA<br>CCATACCTTTATGTTTGGTTTCGAAGAAAGTTATGGCTATCTTGTTCG<br>GCCATTTGTTCGCGATAAAGATGCCATCCAAGGAATTGTCCTATTGGC<br>TGAAATTGCTGCTTATTATCGTAGTAAGGGGCAAACCTTATATGACGG<br>TCTTCAAAACTTATTTACTACTTACGGATATCATGAAGAAAAGACCAT<br>TTCAAAAGATTTCCCTGGAGTTGACGGTAAAGAAAAAATGGCTGCCA<br>TTATGGAAAAGGTTCGTGAAGAACGCCCAAGTCAATTTGATCAGTAC<br>AAGGTATTAGAAACTGAAGACTTCTTAGCTCAAACTAAGTATGAAGC<br>AGATGGATCTACCCAAGCTATCAAATTACCAAAAGCGGATGTTTTGA<br>AATTTACATTAGATGATGGTACTTGGATTGCAATTCGTCCTTCTGGAA<br>CAGAACCAAAAATTAAATTCTATATTGGTACAGTTGGCGAAGATGAA<br>AAAGATGCTTTGAATAAGATTGATGTTTTTGAAACAGCTATTAATGAA<br>CTTATAAAATAA |
| 80 | DP9 2-oxoglutarate carboxylase small subunit | ATGCACCGTATTTTAATTGCCAACCGAGGCGAAATTGCGACCCGAATT<br>ATTCGGGCAACGCATGAACTCGGAAAAACAGCTGTAGCAATTTATGC<br>TAAAGCGGATGAATTTTCTATGCATCGTTTTAAAGCAGATGAAGCTTA<br>CCAAGTTGGTGAAGATAGTGATCCAATTGGAGCATATTTAAATATTG<br>ATGACATTATTCGTATTGCAAAAGAAAATAATATTGATGCAATTCACC<br>CCGGCTATGGATTTTTGTCGGAAAATGCTGTATTTGCGCGAGCAGTTG<br>AAGCAGCTGGGATTAAGTTCATTGGACCTCGACCCGAATTACTAGAA<br>ATGTTTGGTGATAAATTACAAGCTAAAAATGCAGCCATTAAGGCCGG<br>TGTACCAACTATTCCGGGAACGGAAAAACCAGTTAAAGATGTCGATG<br>ACGCGCTAAATTTTGCAGAGCAATTTGGCTATCCTATATTTGTTAAGT<br>CAGCGGCAGGTGGCGGCGGAAAAGGGATGCGGATTGTACATCATCAA<br>CAAGAGATGCGCGAAGCATTTAAGATGGCTCAGTCAGAAGCTTCTTC<br>GTCTTTTGGTGACGATGAAATTTACTTAGAACGTTACTTAGTTGATCC<br>AATCCATATTGAGGTTCAAGTAGTTGCGGATGAACACGGTGAGATGG<br>TTCATTTGTATGAACGAAATTCATCGATTCAGCGACGCCATCAAAAAA<br>TCATTGAATTTGCTCCAGCAGTGGGAATTTCTGCCACCGTCCGTGATC<br>AAATAAGAAAAGCTGCTTTAAAATTATTGAAGTCGGTCAATTATAGT<br>AACGCTGCAACCATTGAGTTTTTGGTAGAAGGTAATCAATTTTACTTT<br>ATGGAAGTGAATCCACGAATTCAGGTTGAACATACAGTTACCGAAGA<br>AGTCACGGGAATCGATATTGTGCAAACCCAAATTAAGGTTGCTGAAG<br>GTCAAAGATTACACGAAGAAATCGGTGTTCCTCAACAAGCCCAAATT<br>GAAGCTGTGGGAGTGGCAATTCAAGCCCGAATTACCACTGAAGATCC<br>AATGAATAACTTTATTCCAGATGTCGGTAGAATCCAGACGTATCGTTC<br>ACCTGGTGGAACAGGTGTGAGATTGGATGCTGGAAATGCCTTTGCTG<br>GAGCCATTGTAACTCCGCATTATGATTCACTTCTGACCAAGGCAATTG<br>TCCATGCGCCAACCTTTGACGAAGCCTTGGTAAAGATGGATCGAGTG<br>CTCAATGAATTTGTAATTGCTGGGGTTAAAACTAATATTCCATTTTTA<br>AAGAAATTAATTCATCATCCTATTTTTAGATCGGAATTAGCTCCGACA<br>ACCTTTGTGGATGAGACACCAGAACTCTTTGATTTAAAAGCTGAAACT<br>CCGGTAGTTACTCAACTTTTGAGTTACATTGCTAATACTACTATCAAT<br>GGTTATCCAGGCTTAGAAAAGCAGAATCCAGTAGTGTTAACTCGGCC |

-continued

Sequence Listing

| Seq ID No. | Description | Sequence |
|---|---|---|
| | | AGTCCGTCCACATTTTGAAGCACAAGTACCGCATGAAAATGCGAAAC AGATCTTGGATAGTAAGGGACCTGATGCCATGATCAATTGGCTGTTA AAACAAAAGCAGGTCTTGCTAACCGATACGACCATGCGGGATGCCCA TCAATCATTATTTGCTACGCGAATGCGGACCAAAGACATGGTAGAAA TTGCCGATCAAGTCCAGAAAGGTCTGCCTAACCTATTTTCAGCTGAAG TTTGGGGCGGTGCGACCTTTGATGTTGCTTATCGGTTCCTAGGTGAGG ATCCATGGGAAAGACTCCAACAATTGCGGGCTAAAATGCCAAATACG ATGCTCCAAATGCTTTTACGTGGGTCAAATGCAGTAGGGTATCAAAAT TATCCAGACAACGCCATTGACGAATTTATTCGATTGGCTGCCAAAAAT GGAATTGATGTTTTCCGAATCTTTGATTCTCTTAATTGGGTGCCACAG CTTGAAGAATCTATCCAACGGGTGCGTGATAATGGAAAAGTGGCTGA AGCAGCCATGGCATATACTGGCGATATTTTAGATACTAATCGTACTAA ATATAATTTGAAATATTATGTGGATTTGGCTCAAGAACTCCAAGCAGC AGGTGCTCATATTATTGGAATCAAAGATATGTCAGGAATTTTAAAACC ACAAGCTGCTTATGCATTAATTTCAGAGTTAAAAAATCATCTGGATGT GCCAATTCATTTGCATACGCACGATACTACAGGCAACGGCATTTTCTT ATATTCTGAAGCAATACGAGCTGGAGTTGATGTGGTCGACGTTGCCA CTTCTGCGCTAGCGGGAACGACTTCTCAGCCTTCAATGCAGTCTCTTT ACTATGCGTTGTCTAATAACCAGCGCCAACCAGATTTAGATATTCAAA AAGCAGAAAAACTAGATGAATATTGGGGCGGAATTCGACCATATTAC GAAGGATTTGGCACCCAATTAAATGGACCACAAACTGAAATTTATCG AATTGAAATGCCTGGTGGACAGTATACCAACCTTCGCCAGCAAGCTA ACGCAGTCCATTTGGGTAAGCGTTGGGATGAGATTAAGGAAATGTAC GCAACCGTCAATCAAATGTTTGGCGATATTCCAAAGGTTACGCCTTCT TCTAAAGTAGTTGGCGATATGGCACTATTCATGGTCCAAAATGATTTG ACGCCTGAAATGGTAATGAACGATAAGGGACAATTAAGTTTTCCCGA ATCAGTGGTAAACTTTTTCCGTGGTGATTTAGGACAACCGGCGGGTGG TTTTCCAAAACAGCTCCAAAAGGTGATTCTAAAAGAGCAAGCCCCAT TGACAGTACGACCAGGAGCTTTAGCCGATCCAGTTGATTTTGATCAAG TTCGTAAACAGGCAACTAAGGTTTTAGGTCACCAAGCAAGTGATGAA GAAGTTATGTCGTTTATTATGTATCCAGATGTGATGACCGAATACATT CAACGTCAAAATGAATATGGTCCAGTACCATTATTAGATACTCCAATC TTTTTCCAAGGCATGCATATTGGCCAACGCATTGATTTACAATTGGGA CGCGGAAAATCGGTCATTATTGTCCTTCGAGAAATTAGTGAAGCAGA TGAGGCGGGCCAAAGGTCACTTTTCTTTGATATAAATGGACAAAGTG AAGAAGTGATTGTTTATGATGTTAATGCGCAGGTAACGAAAGTAAAG AAGATTAAAGCTGATCCGACTAAAGCCGAACAGATTGGCGCTACTAT GGCGGGCTCGGTCATTGAAGTCCAAGTAGAAGCGGGCCAAAAGGTCC AGCGAGGTGATAACTTAATTGTCACTGAGGCGATGAAAATGGAGACC GCGTTAAGAGCACCTTTCGACGCAACCATTAAGAAGATTTATGCTACC CCTGAAATGCAAATCGAGACGGGGGATTTATTGATTGAACTAGAAAA GGAGTAA |
| 81 | DP3 Glycine tRNA ligase beta subunit | ATGTCAACATTTTTATTAGAAATTGGACTTGAAGAAATACCAGCTCAT TTGGTAACCAGTTCAGAGAATCAGTTAATTGAAAGAACTAAAAAGTT CTTATCAGAGCATCGTTTAACAGTAGGTGATATTAAACCATATTCAAC ACCGCGACGTCTGGCTGTCGTTTTGACAGATGTTGCTGAAACATCAGA AAGTTTAAGCGAAGAAAAGCGTGGACCATCTGTTGACCGTGCACAAG ACGAAAACGGTAATTGGACAAAGGCAGCATTAGGTTTTGCACGTGGT CAAGGTGCTAATCCTGAAGCATTTGAAATTAAAGATGGATATGTTTG GCTAACAAAACGTACTGCTGGTGTAGCCGCGAATGAAATTTTAGCTA AAATTGGTGATGAAGTTGTCGCCCAAATGAAATTTTCAACTTATATGA AGTGGGCTAATCACAGCTTTTTGTATGTTCGACCTATTCGTTGGCTCG TAGCACTTCTTGATAGTGAAGTCATTTCTTTCAACGTGTTAGATATTA CCACAGATCGTTTCACACGTGGTCATCGTTTTTTGTCTTCAGAACATG TTGAAATATCTTCTGCAGATAATTATGTAACGACTTTGCAGGGTGCTA ACGTGGTTGTTGATGCTACAGTGCGCAAAAATGAAATTCGATCGCAG TTGAATGCAATTGCTGAAGCTAATGGTTGGGTTCTGCAACTTGAGACC GATGCGGCGCAAGATTTGTTGGAAGAAGTTAATAACATTGTTGAGTG GCCAACAGCGTTTGCTGGCAGTTTCGATGAGAAATATTTAGAAATAC CAGATGAAGTTTTGATTACATCAATGCGCGAACATCAGCGTTTCTTCT TTGTGACGAATGAAAAAGGACAATTATTGCCACACTTTTTGTCAATAA GAAATGGTAACCGTGAGCATCTAAACAACGTTATTGCTGGAAATGAA AAAGTATTGGTAGCAAGGTTAGAAGATGCCGAATTCTTCTATCATGA AGACCAAACCAAATCAATTTCTGATTACATGACTAAAGTTAAAAAGT TAGTCTTCCATGAAAAAATTGGTACGGTGTATGAACACATGCAACGC ACTGGTGCTTTGGCTTCAGCAATGGCGGTGGTTTTGAAGTTTGATGAA GTACAACAGGCTGATTTGACCCGTGCATCAGAAATTTATAAATTTGAT TTGATGACCGGTATGGTTGGTGAATTTGATGAACTTCAAGGCATTATG GGTGAGCATTATGCCAAGCTTTTTGGCGAAGATGATGCGGTTGCAAC AGCCATTCGAGAGCATTATATGCCAACTTCAGCTAATGGTGAGGTTGC GCAATCTGAAATTGGTGCTTTGTTGGCCGTTGCGGATAAACTTGATAG CATTGTGACGTTTTTTGCTGCTGGATTAATACCAAGTGGTTCTAATGA |

-continued

Sequence Listing

| Seq ID No. | Description | Sequence |
|---|---|---|
| | | TCCTTATGGCTTACGACGTGCAGCTACTGGCATCGTGCGTACATTGGT<br>GGATAAAAAATGGCATATTGATTTGCGGCCTTTGCTAGCTGATTTTGT<br>GCAACAGCAAGGTAAGGTAACTGACACCGATTTAACGACATTTGTTG<br>ATTTCATGTTGGATCGTGTTCGTAAATTATCGTTGGATGCTGGAATAC<br>GTCAAGATATTGTCATTGCTGGATTAGGCAACGTTGATAGAGCTGATA<br>TCGTATATATTAGTCAGCGAGTCGAAGTTTTGTCCCAACATAGTGGTG<br>ATGGCAATTTCCGAGATGTAATTGAGGCACTGACTCGTGTGGATCGCT<br>TAGCCGTAAAGCAAGTAACTAATGCAACGGTTGATCCTGCTAAGTTT<br>GAAAATCAATCTGAAAAGGACCTATATCAAGCAACGTTAACGCTTGA<br>TTTAAATACTTTGATGCATGACGGTGCAGAAAATCTCTACATGGCCTT<br>AGCAAATTTGCAAAAACCAATTGCGGCTTATTTTGATGAAACCATGGT<br>TAACGCTGAAGATGAATCTGTTAAAGATAATCGATATGCGCAGCTGA<br>ACGTCATACAACGACTAACCAACGGATTAGGAGATTTGACGCAAATC<br>GTCATTAAGTAA |
| 82 | DP3 Glutamine synthetase | ATGGCTCGTAAAACATTTACCAAAGAAGAAATTAAACAAATTGTTGT<br>TGATGAAAATGTAGAATTCATTCGTGTAACATTCACTGATGTCTTAGG<br>TGCGATTAAAAACGTTGAAGTACCAACTTCTCAATTAGATAAGGTGCT<br>TGACAACAATTTAATGTTTGACGGTTCATCAATCGAGGGATTTGTTCG<br>TATCAATGAATCAGATATGTATCTTTACCCCGATTTATCAACATTTAT<br>GATTTTCCCATGGGCAACGGATGGTCATGGTGGTAAAGTGGCCCGCTT<br>GATTGCCGACATTTATACTGCTGATCGTGAGCCATTTGCTGGAGACCC<br>CCGTCATGCGTTACGTTCGGTACTCGCTGACGCGCGTGAAGCTGGGTT<br>TACGGCGTTTAATGTCGGGACAGAACCTGAATTTTTCTTGTTTAAACT<br>TGATGAAAAAGGCAACCCAACCACAGAGTTAAACGACAAAGGTGGTT<br>ATTTTGACCTAGCACCATTGGATATGGGTGAAAATGTTCGTCGTGAAA<br>TTGTTTTGACTTTGGAAAAAATGGGCTTTGAAATTGAAGCTGCTCACC<br>ACGAAGTTGCCGAAGGACAGCATGAAGTAGACTTTAAATACGCTTCA<br>GCTCTTGAAGCCGCTGACAACATTCAGACGTTTAAGTTGGTTGTTAAA<br>ACCATCGCACGCAAGAATGGTTACTATGCTACCTTTATGCCAAAGCCT<br>GTTGCAGGTATTAACGGATCCGGTATGCACACAAACATGTCATTATTT<br>ACAAAAGATGGTAACGCATTTGTTGATACATCGGATGAAATGGGCTT<br>GTCAAAAACAGCATATAACTTCTTGGGTGGTATTTTAGAACATGCGAC<br>TGCGTTTACAGCGCTTGCAAACCCAACAGTTAACTCATACAAGCGCTT<br>GACACCAGGATTCGAAGCACCTGTTTATGTTGCATGGTCAGCATCAA<br>ATCGTTCACCAATGGTTCGAGTTCCGGCCTCACGTGGTAATTCAACAC<br>GTTTGGAACTTCGTTCAGTTGACCCAACAGCTAATCCTTATACTGCAT<br>TGGCAGCCATTTTGGCTTCAGGACTGGATGGGATCAAGCGTGAATTA<br>GAGCCTTTGGCCTCAGTTGATAAAAATATTTATTTGATGGATGAGGTC<br>GAACGGGAAAAGGCAGGCATTACAGACTTACCAGATACTCTGTTGGC<br>TGCAGTTCGTGAGTTGGCGGCTGATGATGTTGTTCGTTCAGCTATTGG<br>AGAACATATTGCTGATAAGTTTATTGAAGCAAAGAAGATTGAATACA<br>CATCATATCGTCAGTTTGTTTCTGAATGGGAAACAGATTCTTATCTTG<br>AAAATTACTAA |
| 83 | DP3 DNA gyrase subunit B | GTGTTCGCAGATTATATCTGTTCACACGCTAATAATATGGCAGAGAAT<br>ATCGAAAATGAAGCATTGGAGAACATTGATGGCATCGTAACCGATGA<br>TACCGAAATCCGTCAAGCAAGCACCGTTCATGCAGCAGCAGGCGCTT<br>ACAATGCTGATCAGATTCAAGTTTTGGAAGGATTGGAAGCTGTCCGC<br>AAACGCCCTGGCATGTACATTGGTACGACCACAGCGCAAGGCTTGCA<br>CCATTTGGTATGGGAAATTGTTGATAACGGGATTGATGAGGCATTAG<br>CAGGGTTTGCGTCACATATTACGGTCACAATCGAAAAGGATAACTCA<br>ATCACGGTAACCGATGACGGCCGTGGTATTCCTGTCGACATTCAAACT<br>AAAACGGGTAAGCCAGCTCTTGAAACTGTCTTTACGGTATTACACGCC<br>GGTGGTAAATTTGGCGGTGGCGGTTATAAAGTATCTGGTGGATTACA<br>CGGTGTTGGAGCTTCTGTTGTCAATGCCTTGTCAACGGATTTGGACGT<br>TAGAGTTGTTCGTGATAATACTGTTTATTACATGGACTTCAAAGTGGG<br>ACGCGTCAACACACCGATGAAACAATTGACGGAAAAGCCCACTATTG<br>AGCGTGGTACAATTGTTCATTTTAAGCCCGATGCAGATATTTTCCGTG<br>AAACAACAGTTTATAACTACAACACATTACTAACACGTGTGCGCGAA<br>TTGGCCTTTTTGAATAAAGGTTTGCGCATTTCGATTACAGATAATCGA<br>CCTGAAGAAGCTGTTTCTGAAAGCTTTCATTTTGAAGGTGGGATTAAA<br>GAATACGTCAGCTATTTGAATAAGGACAAGACTGCTATTTTCCCTGAA<br>CCTGTTTACGTTGAGGGTGAAGAAAATGGCATTGTAGTGGAAGCTGC<br>CTTACAGTACACTACCGATATTAAAGACAATCTGCGGACGTTTACTAA<br>CAATATCAATACCTATGAAGGTGGGACGCACGAAACTGGCTTTAAAA<br>CAGCCTTAACACGTGTAATCAATGATTACGCTCGTAAAAATGGTCAG<br>CTCAAAGATAATGCAGAAAGTTTGACAGGGGAAGATGTGCGCGAAG<br>GCATGACTGCTATCGTGTCAATCAAGCACCCAGATCCACAATTTGAA<br>GGACAAACCAAAACTAAATTAGGTAACTCCGATGCACGTCAAGCAAC<br>GGATCGGATGTTCTCAGAAACGTTCAGTCGTTTCATGATGGAAAATCC<br>AGCAGTTGCCAAGCAAATTGTTGAAAAAGGTGTCTTAGCCCAAAAAG<br>CACGATTGGCTGCCAAGCGTGCACGCGAAATGACACGCAAACAATCT |

-continued

Sequence Listing

| Seq ID No. | Description | Sequence |
|---|---|---|
| | | GGTTTGGAAATTGGTAATTTGCCAGGTAAATTAGCTGATAATACCTCA AATGATCCTGAAATTTCAGAATTATTTATTGTTGAGGGTGATTCAGCC GGTGGTTCAGCTAAGCAAGGACGTAACCGTTTGACGCAAGCTATTTT GCCAATTCGAGGCAAAATTTTAAATGTTGGGAAAGCCTCATTGGATC GGGTGTTAGCCAACGAAGAAATTCGATCATTGTTTACAGCAATGGGA ACTGGATTTGGTGAGGACTTTAATGTTGAAAAAGCCAATTATCACAA AGTCATTATTATGACAGATGCCGATGTCGATGGCGCCCATATTCGAAC ACTATTGTTAACGCTATTTTATCGTTATATGCGACCACTTGTTGACGC AGGCTATATTTATATTGCGCAGCCACCGCTTTACGGTGTTGCCTTAGG CAATAATAAATCAATGACGTACATTGATTCTGATGAAGAACTTGAAG ACTATTTGTCACAATTGCCATCTAATATTAAACCAAAAGTTCAACGTT ATAAGGGACTAGGGGAAATGGATTACGATCAACTAGCAGATACAACC ATGGATCCGCAGAATCGTCGTTTGCTACGTGTTGACCCAACTGATGCT GAAGAAGCCGAAGCAGTTATTGATATGTTAATGGGTGGGGATGTACC ACCACGTCGTAAGTTTATTGAAGACAATGCTGTCTTTGTTGAGAACTT GGATATTTAA |
| 84 | DP3 Leucine tRNA ligase | ATGATTTTCGTCAACGAAGCTTACAAAACCGATGCTGTGCCGAAAGC GGCGGCGGAAAACTTCGTACAGATGCTGTCCCCACTGGCACCGCATT TGGCAGAAGAACTGTGGGAACGACTTGGTCATACCGATACGATTACG TATGAACCATGGCCAACGTACGATGAGGCTTGGACCATAGAATCCGA AGTGGAAATCGTCGTGCAAGTGAACGGCAAAATCGTAGAACGCACGA AAATTTCCAAAGACCTGGATCAAGCAGCGATGCAAGAACACAGCTTA AGCCTGCCGAATGTTCAGCAGGCTGTGGCTGGGAAGACGATCCGCAA AGTGATTGCGGTGCCAGGCAAGCTGGTGAATATCGTCGTTGGATAA |
| 85 | DP3 Glucose-6-phosphate isomerase | ATGGCACACATTACATTTGACACAAAGAACATTGAGAATTTTGTTGCA CCATACGAATTGGACGAAATGCAACCATTAATTACGATGGCTGACCA ACAATTGCGCAATCGTACGGGCGCTGGTGCAGAATATTCTGATTGGTT GACTCTACCTACTGATTACGACAAGGAAGAATTTGCACGTATTCAAA AGGCGGCGCAACAAATTCAATCTGATTCAAAGATTTTGGTTGTCATTG GTATTGGTGGTTCATATTTGGGCGCGAAGATGGCGGTTGATTTCTTGA ATCCAATGTTTAATAATGAATTGTCGGATGACCAACGTCAAGGTGTTA AAATTTATTTTGCTGGTAACTCAACTTCTGCAGCTTACTTAAATGATTT AGTTCGTGTCATTGGTGATCAAGACTTTTCTGTCAACGTTATCTCAAA GTCTGGCACAACAACGGAACCATCAATCGCTTTCCGTGTGTTTAAACA ATTGTTAGAGAAAAAGTATGGTTCTGATGCTGCTAAGAAGCGTATCT ATGCCACAACAGATGCCAATCGTGGTGCTTTGCACGATGAAGCAGCG GCTTCAGGTTATGAAACATTCACAATTCCTGATGGTGTCGGTGGTCGC TTCTCTGTTTTGACAGCTGTTGGCTTGTTGCCAATTGCTGCTTCAGGCG CTGATATCCAAAAATTGATGGACGGCGCTCGTGATGCGCAAAACGAA TATACTGATTCTGATTTGAAAAAGAACGAGGCATATAAATATGCAGC CGTTCGTCGTATTTTGTATGATAAGGGTTATACAACAGAATTGTTGAT TAACTGGGAACCTTCAATGCAATATTTGTCAGAGTGGTGGAAGCAAT TGATGGGCGAGTCTGAAGGTAAAAATCAAAAGGGTATCTATCCATCT TCAGCTAACTTCTCAACCGACTTGCACTCACTTGGACAATATATTCAA GAAGGACGCCGTGATTTGTTTGAGACGGTGGTTAAGTTAGACAATCC TGTATCTAATTTGGACCTACCACATGAAGAAGGCAACAATGATGGTTT GCAATATTTGGAAGGTATCACGATCGATGAAGTGAACACCAAAGCAT CTCAAGGGGTTACTTTGGCTCACGTTGATGGTGGTGTGCCTAACTTGG CTGTTCACTTGCCAGCACAAGATGCTTATTCACTCGGTTACATGATTT ACTTCTTTGAAATGGCTGTTGGGGCGTCTGGTTATACGTTTGGTATTA ACCCATTCAACCAACCGGGTGTCGAAGCCTATAAGACAGCTATGTTT GCACTATTAGGTAAGCCTGGCTATGAGGAAGCGACAAAAGCATTCCG TGCCCGCTTAGACAAATAA |
| 86 | DP3 Beta-phospho-glucomutase | ATGACTAAATTTTCAGATATTAAAGGTTTTGCCTTTGATTTAGATGGG GTTATTGCTGATACGGCGCGTTTCCATGGTGAAGCTTGGCATCAAACA GCTGATGAGGTTGGCACAACTTGGACACCAGAATTGGCTGAAGGTTT GAAGGGCATTAGTCGTATGGCTTCCTTGCAAATGATTTTGGATGCTGG GGATCATGCCGATGATTTTTCGCAAGCAGATAAAGAAGCATTAGCAG AAAAGAAAAATCATAATTATCAACAACTTATTTCAACATTGACGGAA GATGATATTTTGCCTGGCATGAAAGATTTTATTCAATCAGCCAAGGCA GCCGGCTATACAATGTCGGTGGCATCAGCTTCTAAAAACGCACCAAT GATTCTAGATCATTTGGGATTGACCAAGTATTTTGTCGGCATTGTTGA TCCCGCCACTTTGACAAAGGGAAAACCTGATCCTGAAATCTTCGTTCG TGCTGCGGAAGTCTTACATTTAAATCCAGAAAATGTTATTGGATTGGA AGATTCAGCTGCTGGTATTGTGTCAATCAATGGCGCAGGTGAGACAT CACTAGCCATTGGTAACGCAGATGTTTTGTCAGGAGCGGACTTGAATT TTGCGTCTACTTCAGAAGTGACCTTAGCAAATATTGAAGCTAAAATGC AATAG |

-continued

Sequence Listing

| Seq ID No. | Description | Sequence |
|---|---|---|
| 87 | DP3 2-oxoglutarate carboxylase small subunit | ATGTTTAAAAAAGTGCTTGTTGCTAATCGTGGTGAAATTGCGGTTCGC ATCATTCGAACGCTCAAAGAAATGGGGATTGCTTCAGTCGCTATTTAC TCGACAGCCGATAAAGATAGTTTACACGTACAAATCGCTGACGAAGC GATTGCTGTGGGGGGACCGAAACCTAAAGATTCATACTTAAATATGA AAAATATTTTAAGTGCAGCCCTGCTGTCGGGAGCAGAGGCAATTCAT CCAGGATATGGCTTTTTAGCTGAAAATACATTGTTTGCTGAAATGGTT GGCGAAGTTGGTATTAAATGGATTGGGCCTAGGCCAGAAACAATTGA GTTAATGGGTAACAAAGCTAACGCACGTGAAGAAATGCGGCGTGCCG GCGTACCAGTAATTCCAGGTTCAGAGGGATTTATCCGTGATTTTCATG AAGCAAAAACGGTTGCTGATAAAATTGGCTATCCTTTGTTGCTAAAA GCTGCCGCTGGTGGTGGTGGTAAAGGCATGCGTTTTGTTTACGGTGAG GATGAGTTATCAGATAAATTTGATGATGCTCAAAACGAAGCGCGTGC TTCGTTTGGCGATGATCACATGTATATTGAAAAAGTTATGTCACGTGT TCGCCACATTGAAATGCAAGTGTTTCGTGATGAGAATGGTCATGTTGT TTACTTGCCAGAACGAAATTGCTCATTGCAACGCAATAATCAAAAGG TGATTGAAGAATCACCAGCTACGGGTGTAACGCCTGAAATGCGTGCG CATCTTGGCGAAATTGTTACTAAAGCCGCAAAAGCATTGGCGTATGA AAATACTGGAACCATTGAATTTTTGCAAGATCGCGATGGTCATTTCTA CTTTATGGAAATGAACACACGTATTCAAGTAGAACATCCAGTTTCTGA AATGGTAACGGGATTAGATTTAATTAAGTTACAAATTCAAGTTGCTGC AGGCTTAGATTTACCGGTGGTTCAAGATGACGTGATCGTTCAAGGCC ACTCTATCGAAGTACGTTTGACGGCTGAGCAGCCAGAAAAACACTTT GCACCTAGTGCTGGAACGATTGATTTTGTTTTTTTGCCAACTGGTGGA CCGGGTGTTCGTATTGATTCAGCCTTATTTAATGGCGATAAAATTCAA CCATTTTACGATTCTATGATTGGCAAATTAATTGTTAAGGCCGATGAT CGTGAAACAGCCATGAGAAAGATTCAACGTGTGGTTGATGAAACTGT TGTACGTGGTGTAGCAACGAGCCGTAATTTTCAAAAAGCTCTGTTAGC TGATCCACAGGTTCAACGTGGCGAATTTGACACACGTTATTTGGAAAC TGAATTTTTACCGAGATGGACACAAACATTGCCAGATAATCAATAA |
| 88 | DP1 Glutamine-tRNA ligase | ATGAGCAAGCCCACTGTCGACCCTACCTCGAATTCCAAGGCCGGACC TGCCGTCCCGGTCAATTTCCTGCGCCCGATCATCCAGGCGGACCTGGA TTCGGGCAAGCATACGCAGATCGTCACCCGCTTCCCGCCAGAGCCCA ACGGCTACCTGCACATCGGTCATGCCAAGTCGATTTGTGTGAACTTCG GCCTGGCTCAGGAGTTCGGTGGCGTTACGCACCTGCGTTTCGACGACA CCAACCCGGCCAAGGAAGACCAGGAATACATCGACGCCATCGAAAG CGACATCAAGTGGCTGGGCTTCGAATGGTCCGGTGAAGTGCGCTATG CATCCAAGTATTTCGACCAGCTGTTCGACTGGGCCGTCGAGTTGATCA AGGCCGGCAAGGCCTACGTTGACGACCTGACCCCCGAGCAAGCCAAG GAATACCGTGGCAGCCTGACCGAGCCGGGCAAGAACAGCCCGTTCCG CGACCGTTCGGTCGAAGAGAACCTCGACTGGTTCAACCGCATGCGCG CCGGTGAGTTCCCGGACGGCGCCCGCGTGCTGCGCGCCAAGATCGAC ATGGCCTCGCCGAACATGAACCTGCGCGACCCGATCATGTACCGCAT TCGCCATGCCCATCACCACCAGACCGGTGACAAGTGGTGCATCTACC CCAACTACGACTTCACCCACGGTCAGTCGGACGCCATCGAAGGCATC ACCCACTCCATCTGCACCCTGGAGTTCGAAAGCCATCGCCCTCTGTAC GAATGGTTCCTGGACAGCCTGCCGGTGCCGGCGCACCCGCGTCAGTA CGAATTCAGCCGCCTGAACCTGAACTACACCATCACCAGCAAGCGCA AGCTCAAGCAACTGGTCGATGAAAGCACGTGCATGGCTGGGACGAC CCGCGCATGTCGACGCTCTCGGGTTTCCGTCGTCGTGGCTACACCCCG GCGTCGATCCGCAATTTCTGCGACATGGTCGGCACCAACCGTTCTGAC GGTGTGGTCGATTACGGCATGCTTGAGTTCAGCATCCGTCAGGATCTG GACGCGAACGCGCCGCGCGCCATGTGCGTGCTGCGTCCGTTGAAAGT CGTGATCACCAACTACCCGGAAGACAAGGTCGACCACCTTGAGCTGC CGCGTCACCCGCAGAAAGAAGAGCTGGGCGTGCGCAAGCTGCCGTTC GCGCGCGAAATCTACATCGACCGTGACGACTTCATGGAAGAGCCGCC GAAGGGTTACAAGCGCCTGGAGCCGAACGGCGAAGTGCGCCTGCGTG GCAGCTACGTGATCCGCGCCGACGAAGCAATCAAGGACGCCGAAGGC AACATCGTCGAACTGCGCTGCTCGTACGATCCGGAAACACTCGGCAA GAACCCTGAAGGCCGTAAGGTCAAGGGCGTGATCCACTGGGTGCCGG CCGCTGCCAGCATCGAGTGCGAAGTGCGTCTGTACGATCGTCTGTTCC GATCGCCGAACCCGGAGAAGGCCGAAGACAGCGCCAGCTTCCTGGAC AACATCAACCCTGACTCGCTGCAAGTGCTTACAGGTTGTCGTGCTGAG CCATCGCTTGGCGACGCACAGCCGGAAGACCGTTTCCAGTTCGAGCG CGAAGGTTACTTCTGCGCGGATATCAAGGACTCGAAACCCGGTGCTC CGGTATTCAACCGTACCGTGACCTTGCGTGATTCGTGGGGCCAGTGA |
| 89 | DP1 DNA gyrase subunit B | ATGAGCGAAGAAAACACGTACGACTCGACCAGCATTAAAGTGCTGAA AGGTTTGGATGCCGTACGCAAACGTCCCGGTATGTACATCGGCGACA CCGATGATGGTAGCGGTCTGCACCACATGGTGTTCGAGGTGGTCGAC AACTCCATCGACGAAGCTTTGGCCGGTCACTGCGACGACATCAGCAT TATCATCCACCCGGATGAGTCCATCACGGTGCGCGACAACGGTCGCG |

-continued

Sequence Listing

| Seq ID No. | Description | Sequence |
|---|---|---|
| | | GCATTCCGGTCGATGTGCACAAAGAAGAAGGCGTTTCGGCGGCTGAG<br>GTCATCATGACCGTGCTGCACGCCGGCGGTAAGTTCGATGACAACTCT<br>TATAAAGTCTCCGGCGGTCTGCACGGTGTAGGTGTGTCGGTAGTGAA<br>CGCACTGTCCGAAGAGCTGATCCTGACCGTTCGCCGTAGCGGCAAGA<br>TTTGGGAGCAGACGTACGTCCATGGTGTGCCACAAGAGCCGATGAAA<br>ATCGTTGGCGACAGTGAATCCACGGGTACGCAGATCCACTTCAAGCC<br>ATCGGCTGAAACCTTCAAGAACATCCACTTTAGCTGGGACATCCTGGC<br>CAAGCGGATTCGCGAACTGTCCTTCCTCAACTCCGGTGTGGGTATCGT<br>CCTCAAGGACGAGCGCAGCGGCAAGGAAGAACTGTTCAAGTACGAA<br>GGCGGTCTGCGCGCGTTCGTTGAATACCTGAACACCAATAAGACCGC<br>GGTCAACCAGGTGTTCCACTTCAACATTCAGCGTGAAGACGGCATCG<br>GCGTGGAAATCGCCCTGCAGTGGAACGACAGCTTCAACGAGAACTTG<br>TTGTGCTTCACCAACAACATTCCACAGCGCGATGGCGGTACTCACTTG<br>GTGGGTTTCCGTTCCGCACTGACGCGTAACCTGAACACTTACATCGAA<br>GCCGAAGGCTTGGCCAAGAAGCACAAAGTCGCCACCACCGGTGACGA<br>TGCGCGTGAAGGCCTGACCGCGATTATCTCGGTGAAAGTGCCGGATC<br>CCAAGTTCAGCTCCCAGACCAAAGACAAGCTGGTTTCTTCCGAGGTG<br>AAGACCGCCGTGGAACAGGAGATGGGCAAGTACTTCTCCGACTTCCT<br>GCTGGAGAACCCGAACGAAGCCAAGCTGGTCGTCGGCAAGATGATCG<br>ACGCTGCACGTGCTCGCGAAGCGGCGCGTAAAGCCCGTGAGATGACC<br>CGTCGTAAAGGCGCGCTGGATATTGCTGGCTTGCCTGGCAAGTTGGCT<br>GACTGCCAGGAGAAGGACCCAGCGCTCTCCGAGCTATATCTTGTGGA<br>AGGTGACTCTGCTGGCGGTTCCGCCAAGCAGGGTCGTAACCGTCGCA<br>CCCAGGCGATCCTGCCGTTGAAAGGCAAGATTCTCAACGTAGAGAAG<br>GCCCGCTTCGACAAGATGATTTCCTCCCAGGAAGTCGGCACCTTGATT<br>ACGGCGTTGGGTTGCGGCATTGGCCGCGATGAGTACAACATCGACAA<br>GCTGCGCTACCACAACATCATCATCATGACCGATGCTGACGTCGACG<br>GTTCGCACATCCGTACCTTGCTGCTGACCTTCTTCTTCCGTCAGTTGCC<br>TGAGCTGATTGAGCGTGGCTACATCTATATCGCGCAGCCGCCGTTGTA<br>CAAAGTGAAAAAGGGCAAGCAAGAGCAGTACATCAAAGACGACGAC<br>GCCATGGAAGAGTACATGACGCAGTCGGCCCTGGAAGATGCAAGCCT<br>GCACTTGAACGACGAAGCACCGGGTATCTCCGGTGAGGCGTTGGAGC<br>GTCTGGTTAACGACTTCCGTATGGTGATGAAGACCCTCAAGCGTCTAT<br>CGCGTCTGTACCCTCAGGAACTGACCGAGCACTTCATCTACCTGCCGG<br>CCGTCAGTCTGGAGCAGTTGGGTGATCATGCAGCGATGCAAGAGTGG<br>CTGGCTCAGTACGAAGTACGCCTGCGCACTGTTGAGAAGTCTGGCCT<br>GGTGTACAAAGCCAGTCTGCGTGAAGACCGTGAACGTAACGTGTGGC<br>TGCCGGAGGTTGAGTTGATCTCCCACGGCCTGTCGAATTACGTCACCT<br>TCAACCGCGACTTCTTCGGCAGTAATGACTACAAGACGGTCGTGACC<br>CTCGGCGCGCAGTTGAGCACCTTGCTGGATGATGGTGCTTACATTCAA<br>CGTGGCGAGCGTAAGAAAGCGGTCAAGGAGTTCAAGGAAGCCTTGG<br>ACTGGCTGATGGCGGAAAGCACCAAGCGTCATACCATTCAGCGATAC<br>AAAGGTCTGGGCGAGATGAACCCTGATCAGTTGTGGGAAACCACCAT<br>GGATCCAGCACAGCGTCGCATGCTGCGCGTGACCATCGAAGACGCCA<br>TTGGCGCAGATCAGATCTTCAACACCCTGATGGGTGATGCGGTCGAA<br>CCTCGCCGTGACTTCATCGAGAGCAATGCCTTGGCGGTGTCCAACCTG<br>GACTTCTGA |
| 90 | DP1 Isoleucine--tRNA ligase | ATGACCGACTATAAAGCCACGCTAAACCTTCCGGACACCGCCTTCCC<br>AATGAAGGCCGGCCTGCCACAGCGCGAACCGCAGATCCTGCAGCGCT<br>GGGACAGTATTGGCCTGTACGGAAAGTTGCGCGAAATTGGCAAGGAT<br>CGTCCGAAGTTCGTCCTGCACGACGGCCCTCCTTATGCCAACGGCACG<br>ATTCACATCGGTCATGCGCTGAACAAAATTCTCAAGGACATGATCCTG<br>CGCTCGAAAACCCTGTCGGGTTTTGACGCGCCGTATGTCCCGGGCTGG<br>GACTGCCATGGCCTGCCGATCGAACACAAAGTCGAAGTGACCTACGG<br>CAAAAACCTGGGCGCGGATAAAACCCGCGAACTGTGCCGTGCCTACG<br>CCACTGAGCAGATCGAAGGGCAGAAGTCCGAATTCATCCGCCTGGGC<br>GTGCTGGGCGAGTGGGACAACCCGTACAAGACCATGAACTTCAAGAA<br>CGAGGCCGGTGAAATCCGTGCCTTGGCTGAAATCGTCAAAGGCGGTT<br>TTGTGTTCAAGGGCCTCAAGCCCGTGAACTGGTGCTTCGACTGCGGTT<br>CGGCCCTGGCTGAGGCGGAAGTCGAATACGAAGACAAGAAGTCCTCG<br>ACCATCGACGTGGCCTTCCCGATCGCCGACGACGCCAAGTTGGCCCA<br>GGCTTTCGGCCTGGCAAGCCTGAGCAAGCCGGCGGCCATCGTGATCT<br>GGACCACCACCCCGTGGACCATCCCGGCCAACCAGGCGCTGAACGTG<br>CACCCGGAATTCACCTACGCCCTGGTGGACGTCGGTGATCGCCTGCTG<br>GTGCTGGCCGAGGAAATGGTCGAGGCCTGTCTGGCGCGCTACGAACT<br>GCAAGGTTCGGTGATCGCCACCACCACCGGCTCCGCGCTGGAACTGA<br>TCAACTTCCGTCACCCGTTCTATGACCGCCTGTCGCCGGTTTACCTGG<br>CTGACTACGTCGAACTGGGTTCGGGTACGGGTGTGGTTCACTCCGCAC<br>CGGCCTACGGCGTTGACGACTTCGTGACCTGCAAAGCCTACGGTATG<br>GTCAACGATGACATCCTCAACCCGGTGCAGAGCAATGGTGTGTACGC<br>GCCATCGCTGGAGTTCTTCGGCGGCCAGTTCATCTTCAAGGCTAACGA<br>GCCGATCATCGACAAACTGCGTGAAGTCGGTGCGCTGCTGCACACCG |

-continued

Sequence Listing

| Seq ID No. | Description | Sequence |
|---|---|---|
| | | AAACCATCAAGCACAGCTACATGCACTGCTGGCGCCACAAAACCCCG<br>CTGATCTACCGCGCCACCGCGCAGTGGTTTATCGGCATGGACAAAGA<br>GCCGACCAGCGGCGACACCCTGCGTGTGCGCTCGCTCAAAGCCATCG<br>AAGACACCAAGTTCGTCCCGGCCTGGGGCCAGGCGCGCCTGCACTCG<br>ATGATCGCCAATCGTCCGGACTGGTGCATCTCCCGCCAGCGTAACTGG<br>GGCGTACCGATCCCGTTCTTCCTGAACAAGGAAAGCGGCGAGCTGCA<br>CCCACGCACCGTCGAGCTGATGGAAGCCGTGGCCTTGCGCGTTGAAC<br>AGGAAGGCATCGAAGCCTGGTTCAAGCTGGACGCCGCCGAGCTGCTG<br>GGCGACGAAGCGCCGCTGTACGACAAGAAGGCTCGGACCAACACCGT<br>GGCTGGTTCCACTCGTCGCTGCTGA |
| 91 | DP1 NADH-quinone oxidoreductase subunit C/D | ATGACTACAGGCAGTGCTCTGTACATCCCGCCTTATAAGGCAGACGA<br>CCAGGATGTGGTTGTCGAACTCAATAACCGTTTTGGCCCTGACGCCTT<br>TACCGCCCAGGCCACACGTACCGGCATGCCGGTGCTGTGGGTGGCGC<br>GCGCCAGGCTCGTCGAAGTCCTGACCTTCCTGCGCAACCTGCCCAAGC<br>CGTACGTCATGCTCTATGACCTGCATGGCGTGGACGAGCGTCTGCGG<br>ACCAAGCGCCAGGGCCTGCCGAGCGGCGCCGATTTCACCGTGTTCTA<br>TCACCTGCTGTCGATCGAACGTAACAGCGACGTGATGATCAAGGTCG<br>CCCTCTCCGAAAGCGACCTGAGCGTCCCGACCGTGACCGGCATCTGG<br>CCCAACGCCAGTTGGTACGAGCGTGAAGTCTGGGACATGTTCGGTAT<br>CGACTTCCCTGGCCACCCGCACCTGACGCGCATCATGATGCCGCCGA<br>CCTGGGAAGGTCACCCGCTGCGCAAGGACTTCCCTGCGCGCGCCACC<br>GAATTCGACCCGTTCAGCCTGAACCTCGCCAAGCAACAGCTTGAAGA<br>AGAGGCTGCACGCTTCCGGCCGGAAGACTGGGGCATGAAACGCTCCG<br>GCACCAACGAGGACTACATGTTCCTCAACCTGGGCCCGAACCACCCT<br>TCGGCGCACGGTGCCTTCCGTATCATCCTGCAACTGGACGGCGAAGA<br>AATCGTCGACTGCGTGCCGGACATCGGTTACCACCACCGTGGTGCCG<br>AGAAGATGGCCGAGCGCCAGTCGTGGCACAGCTTCATCCCGTACACC<br>GACCGTATCGACTACCTCGGCGGCGTGATGAACAATCTGCCGTACGT<br>GCTCTCGGTCGAGAAGCTGGCCGGTATCAAGGTGCCGGACCGCGTCG<br>ACACCATCCGCATCATGATGGCCGAGTTCTTCCGGATCACCAGCCACC<br>TGCTGTTCCTGGGTACCTACATCCAGGACGTCGGCGCCATGACCCCGG<br>TGTTCTTCACCTTCACCGACCGTCAGCGCGCCTACAAGGTCATCGAAG<br>CCATCACCGGCTTCCGCCTGCACCCGGCCTGGTACCGCATCGGCGGTG<br>TCGCGCACGACCTGCCAAATGGCTGGGAACGCCTGGTCAAGGAATTC<br>ATCGACTGGATGCCCAAGCGTCTGGACGAGTACCAGAAAGCCGCCCT<br>GGACAACAGCATCCTCAAGGGCCGGACCATTGGGGTCGCGGCCTACA<br>ACACCAAAGAGGCCCTGGAATGGGGCGTCACCGGTGCTGGCCTGCGT<br>TCCACCGGTTGCGATTTCGACCTGCGTAAAGCGCGCCCGTACTCCGGC<br>TACGAGAACTTCGAATTCGAAGTGCCGTTGGCGGCCAATGGCGATGC<br>CTACGACCGTTGCATCGTGCGCGTCGAAGAAATGCGCCAGAGCCTGA<br>AGATCATCGAGCAATGCATGCGCAACATCCGGCAGGCCCGTACAAGG<br>CGGACCACCCGCTGACCACGCCGCCGCCGAAAGAGCGCACGCTGCAA<br>CACATCGAAACCCTGATCACGCACTTCCTGCAGGTTTCGTGGGGCCCG<br>GTGATGCCGGCCAACGAATCCTTCCAGATGATCGAAGCGACCAAGGG<br>TATCAACAGTTATTACCTGACGAGCGATGGCGGCACCATGAGCTACC<br>GCACCCGGATTCGCACTCCAAGCTTCCCGCACCTGCAGCAGATCCCTT<br>CGGTGATCAAAGGTGAAATGGTCGCGGACTTGATTGCGTACCTGGGT<br>AGTATCGATTTCGTTATGGCCGACGTGGACCGCTAA |
| 92 | DP1 Protein RecA | ATGGACGACAACAAGAAGAAAGCCTTGGCTGCGGCCCTGGGTCAGAT<br>CGAACGTCAATTCGGCAAGGGTGCCGTAATGCGTATGGGCGATCACG<br>ACCGTCAGGCGATCCCGGCTATTTCCACTGGCTCTCTGGGTCTGGACA<br>TCGCACTCGGCATTGGCGGCCTGCCAAAAGGCCGTATCGTTGAAATCT<br>ACGGCCCTGAATCTTCCGGTAAAACCACCCTGACCCTGTCGGTGATTG<br>CCCAGGCGCAAAAAATGGGCGCCACTTGTGCGTTCGTCGATGCCGAG<br>CACGCTCTTGACCCTGAATACGCCGGCAAGCTGGGCGTCAACGTTGA<br>CGACCTGCTGGTTTCCCAACCGGACACCGGTGAGCAAGCCTTGGAAA<br>TCACCGACATGCTGGTGCGCTCCAACGCCATCGACGTGATCGTGGTCG<br>ACTCCGTGGCTGCCCTGGTGCCGAAAGCTGAAATCGAAGGCGAAATG<br>GGCGACATGCACGTGGGCCTGCAAGCCCGTCTGATGTCCCAGGCGCT<br>GCGTAAAATCACCGGTAACATCAAGAACGCCAACTGCCTGGTGATCT<br>TCATCAACCAGATCCGTATGAAGATTGGCGTGATGTTCGGCAGCCCG<br>GAAACCACCACCGGTGGTAACGCGTTGAAGTTCTACGCTTCGGTCCGT<br>CTGGATATCCGCCGTACTGGCGCGGTGAAGGAAGGCGACGAGGTGGT<br>GGGTAGCGAAACCCGCGTTAAAGTTGTGAAGAACAAGGTGGCCCCGC<br>CATTCCGTCAGGCTGAGTTCCAGATTCTCTACGGCAAGGGTATCTACC<br>TGAACGGCGAGATGATCGACCTGGGCGTACTGCACGGTTTCGTCGAG<br>AAGTCCGGTGCCTGGTATGCCTACAACGGCAGCAAGATCGGTCAGGG<br>CAAGGCCAACTCGGCCAAGTTCCTGGCGGACAACCCGGATATCGCTG<br>CCACGCTTGAGAAGCAGATTCGCGACAAGCTGCTGACCCCGGCACCA<br>GACGTGAAAGCTGCTGCCAACCGCGAGCCGGTTGAAGAAGTAGAAG<br>AAGTCGACACTGACATCTGA |

-continued

Sequence Listing

| Seq ID No. | Description | Sequence |
|---|---|---|
| 93 | DP1 RNA polymerase sigma factor RpoD | ATGGAAATCACCCGCAAGGCTCTGAAAAAGCACGGTCGCGGCAACAA GCTGGCAATTGCCGAGCTGGTGGCCCTGGCTGAGCTGTTCATGCCAAT CAAGCTGGTGCCGAAGCAATTTGAAGGCCTGGTTGAGCGTGTGCGCA GTGCTCTTGAGCGTCTGCGTGCCCAAGAGCGCGCAATCATGCAGCTCT GCGTACGTGATGCACGCATGCCGCGTGCCGACTTCCTGCGCCAGTTCC CGGGCAACGAAGTGGATGAAAGCTGGACCGACGCACTGGCCAAAGG CAAGGCGAAGTACGCCGAAGCCATTGGTCGCCTGCAGCCGGACATCA TCCGTTGCCAGCAGAAGCTGACCGCGCTTCAAACCGAAACCGGTCTG ACGATTGCTGAGATCAAGGACATCAACCGTCGCATGTCGATCGGTGA GGCCAAGGCCCGCCGCGCGAAGAAAGAGATGGTTGAAGCGAACTTG CGTCTGGTGATCTCCATCGCCAAGAAGTACACCAACCGTGGCCTGCA ATTCCTCGATCTGATCCAGGAAGGCAACATCGGCTTGATGAAGGCTG TGGACAAGTTCGAATACCGTCGCGGCTACAAGTTCTCGACTTATGCCA CCTGGTGGATCCGTCAGGCGATCACTCGCTCGATCGCAGACCAGGCC CGCACCATCCGTATTCCGGTGCACATGATCGAGACCATCAACAAGCT CAACCGTATTTCCCGGCAGATGTTGCAGGAAATGGGTCGCGAACCGA CGCCGGAAGAGCTGGGCGAACGCATGGAAATGCCTGAGGATAAAAT CCGTAAGGTATTGAAGATCGCTAAAGAGCCGATCTCCATGGAAACGC CGATTGGTGATGACGAAGACTCCCATCTGGGTGACTTCATCGAAGAC TCGACCATGCAGTCGCCCATCGATGTGGCTACCGTTGAGAGCCTTAAA GAAGCGACTCGCGACGTACTGTCCGGCCTCACTGCCCGTGAAGCCAA GGTACTGCGCATGCGTTTCGGCATCGACATGAATACCGACCACACCCT TGAGGAAGTCGGTAAGCAGTTTGACGTGACCCGTGAACGGATCCGTC AGATCGAAGCCAAGGCACTGCGCAAGTTGCGCCACCCGACGCGAAGC GAGCATCTACGCTCCTTCCTCGACGAGTGA |
| 94 | DP1 DNA-directed RNA polymerase subunit beta | ATGGCTTACTCATATACTGAGAAAAAACGTATCCGCAAGGACTTTAG CAAGTTGCCGGACGTCATGGATGTCCCGTACCTTCTGGCTATCCAGCT GGATTCGTATCGTGAATTCTTGCAAGCGGGAGCGACTAAAGATCAGT TCCGCGACGTGGGCCTGCATGCGGCCTTCAAATCCGTTTTCCCGATCA TCAGCTACTCCGGCAATGCTGCGCTGGAGTACGTGGGTTATCGCCTGG GCGAACCGGCATTTGATGTCAAAGAATGCGTGTTGCGCGGTGTTACG TACGCCGTACCTTTGCGGGTAAAAGTCCGTCTGATCATTTTCGACAAA GAATCGTCGAACAAAGCGATCAAGGACATCAAAGAGCAAGAAGTCT ACATGGGCGAAATCCCATTGATGACTGAAAACGGTACCTTCGTTATC AACGGTACCGAGCGCGTTATCGTTTCCCAGCTGCACCGTTCCCCGGGC GTGTTCTTCGACCACGACCGCGGCAAGACGCACAGCTCCGGTAAGCT CCTGTACTCCGCGCGGATCATTCCGTACCGCGGCTCGTGGTTGGACTT CGAGTTCGACCCGAAAGACTGCGTGTTCGTGCGTATCGACCGTCGTCG TAAGCTGCCGGCCTCGGTACTGCTGCGCGCGCTCGGCTATACCACTGA GCAAGTGCTTGATGCTTTCTACACCACCAACGTATTCAGCCTGAAGGA TGAAACCCTCAGCCTGGAACTGATTGCTTCGCGTCTGCGTGGTGAAAT TGCCGTCCTGGATATCCAGGATGAAAACGGCAAGGTCATCGTTGAAG CTGGCCGCCGTATTACCGCGCGCCACATCAACCAGATCGAAAAAGCC GGTATCAAGTCGCTGGACGTGCCGCTGGACTACGTCCTGGGTCGCAC CACTGCCAAGGTCATCGTTCACCCGGCTACAGGCGAAATCCTGGCTG AGTGCAACACCGAGCTGAACACCGAGATCCTGGCAAAAATCGCCAAG GCCCAGGTTGTTCGCATCGAGACCCTGTACACCAACGACATCGACTG CGGTCCGTTCATCTCCGACACGCTGAAGATCGACTCCACCAGCAACC AATTGGAAGCGCTGGTCGAGATCTATCGCATGATGCGTCCTGGTGAG CCACCGACCAAAGACGCTGCCGAGACCCTGTTCAACAACCTGTTCTTC AGCCCTGAGCGCTATGACCTGTCTGCGGTCGGCCGGATGAAGTTCAA CCGTCGTATCGGTCGTACCGAGATCGAAGGTTCGGGCGTGCTGTGCA AGGAAGACATCGTCGCGGTACTGAAGACCTTGGTCGACATCCGTAAC GGTAAAGGCATCGTCGATGACATCGACCACTTGGGTAACCGTCGTGT TCGCTGCGTAGGCGAAATGGCCGAGAACCAGTTCCGCGTTGGCCTGG TACGTGTTGAGCGTGCGGTCAAAGAGCGTCTGTCGATGGCTGAAAGC GAAGGCCTGATGCCGCAAGATCTGATCAACGCCAAGCCAGTGGCTGC GGCGGTGAAAGAGTTCTTCGGTTCCAGCCAGCTCTCGCAGTTCATGGA CCAGAACAACCCGCTCTCCGAGATCACCCACAAGCGCCGTGTTTCCG CACTGGGCCCGGGCGGTCTGACCCGTGAGCGTGCAGGCTTTGAAGTT CGTGACGTACACCCAACGCACTACGGTCGTGTTTGCCCGATCGAAAC GCCGGAAGGTCCGAACATCGGTCTGATCAACTCCCTTGCCGCTTATGC ACGCACTAACCAGTACGGCTTCCTCGAGAGCCCGTACCGTGTAGTGA AAGATGCACTGGTCACCGACGAGATCGTGTTCCTGTCCGCCATCGAA GAAGCCGATCACGTGATCGCTCAGGCTTCGGCCACGATGAACGACAA GAAAGTCCTGATCGACGAGCTGGTAGCTGTTCGTCACTTGAACGAGTT CACCGTTAAGGCGCCGGAAGACGTCACCTTGATGGACGTTTCGCCGA AGCAGGTAGTTTCGGTTGCAGCGTCGCTGATCCCGTTCCTGGAGCACG ATGACGCCAACCGTGCGTTGATGGGTTCCAACATGCAGCGTCAAGCT GTACCCACCCTGCGTGCCGACAAGCCGCTGGTAGGTACCGGCATGGA GCGTAACGTAGCCCGTGACTCCGGCGTTTGCGTCGTGGCTCGTCGTGG |

-continued

Sequence Listing

| Seq ID No. | Description | Sequence |
|---|---|---|
| | | CGGCGTGATCGACTCTGTTGATGCCAGCCGTATCGTGGTTCGTGTTGC<br>CGATGACGAAGTTGAGACTGGCGAAGCCGGTGTCGACATCTACAACC<br>TGACCAAATACACCCGCTCGAACCAGAACACCTGCATCAACCAGCGC<br>CCGCTGGTGAGCAAGGGTGATCGCGTTCAGCGTAGCGACATCATGGC<br>CGACGGCCCGTCCACCGATATGGGTGAGCTGGCACTGGGTCAGAACA<br>TGCGCATCGCGTTCATGGCATGGAACGGCTTCAACTTCGAAGACTCCA<br>TCTGCCTGTCCGAGCGTGTTGTTCAAGAAGACCGCTTCACCACGATCC<br>ACATTCAGGAGCTGACCTGTGTGGCGCGTGACACCAAGCTTGGGCCA<br>GAGGAAATCACTGCAGACATCCCGAACGTGGGTGAAGCTGCACTGAA<br>CAAACTGGACGAAGCCGGTATCGTTTACGTAGGTGCTGAAGTTGGCG<br>CAGGCGACATCCTGGTTGGTAAGGTCACTCCGAAAGGCGAGACCCAA<br>CTGACTCCGGAAGAGAAGCTGTTGCGTGCCATCTTCGGTGAAAAAGC<br>CAGCGACGTTAAAGACACTTCCCTGCGCGTACCTACCGGTACCAAGG<br>GTACTGTCATCGACGTACAGGTCTTCACCCGTGACGGCGTTGAGCGTG<br>ATGCTCGTGCACTGTCCATCGAGAAGACTCAACTCGACGAGATCCGC<br>AAGGACCTGAACGAAGAGTTCCGTATCGTTGAAGGCGCGACCTTCGA<br>ACGTCTGCGTTCCGCTCTGGTAGGCCACAAGGCTGAAGGCGGCGCAG<br>GTCTGAAGAAAGGTCAGGACATCACCGACGAAATCCTCGACGGTCTT<br>GAGCACGGCCAGTGGTTCAAACTGCGCATGGCTGAAGACGCTCTGAA<br>CGAGCAGCTCGAGAAGGCCCAGGCCTATATCGTTGATCGCCGCCGTC<br>TGCTGGACGACAAGTTCGAAGACAAGAAGCGCAAACTGCAGCAGGG<br>CGATGACCTGGCTCCAGGCGTGCTGAAAATCGTCAAGGTTTACCTGG<br>CAATCCGTCGCCGCATTCAGCCGGGCGACAAGATGGCCGGTCGTCAC<br>GGTAACAAGGGTGTGGTCTCCGTGATCATGCCGGTTGAAGACATGCC<br>GCACGATGCCAATGGCACCCCGGTCGACGTCGTCCTCAACCCGTTGG<br>GCGTACCTTCGCGTATGAACGTTGGTCAGATCCTTGAAACCCACCTGG<br>GCCTCGCGGCCAAAGGTCTGGGCGAGAAGATCAACCGTATGATCGAA<br>GAGCAGCGCAAGGTCGCAGACCTGCGTAAGTTCCTGCACGAGATCTA<br>CAACGAGATCGGCGGTCGCAACGAAGAGCTGGACACCTTCTCCGACC<br>AGGAAATCCTGGATCTGGCGAAGAACCTGCGCGGCGGCGTTCCAATG<br>GCTACCCCGGTATTCGACGGTGCCAAGGAAAGCGAAATCAAGGCCAT<br>GCTGAAACTGGCAGACCTGCCGGAAAGTGGCCAGATGCAGCTGTTCG<br>ACGGCCGTACCGGCAACAAGTTTGAGCGCCCGGTTACTGTTGGCTAC<br>ATGTACATGCTGAAGCTGAACCACTTGGTAGACGACAAGATGCACGC<br>TCGTTCTACCGGTTCGTACAGCCTGGTTACCCAGCAGCCGCTGGGTGG<br>TAAGGCTCAGTTCGGTGGTCAGCGTTTCGGGGAGATGGAGGTCTGGG<br>CACTGGAAGCATACGGTGCTGCTTACACTCTGCAAGAAATGCTCACA<br>GTGAAGTCGGACGATGTGAACGGTCGGACCAAGATGTACAAAAACAT<br>CGTGGACGGCGATCACCGTATGGAGCCGGGCATGCCCGAGTCCTTCA<br>ACGTGTTGATCAAAGAAATTCGTTCCCTCGGCATCGATATCGATCTGG<br>AAACCGAATAA |
| 95 | DP22 Glutamine-tRNA ligase | ATGAGTGAGGCTGAAGCCCGCCCAACAAATTTTATCCGTCAGATTATT<br>GATGAAGATCTGGCGACCGGGAAACACAATACCGTTCATACCCGTTT<br>CCCGCCTGAGCCAAATGGCTATCTGCATATCGGTCATGCGAAATCTAT<br>CTGCCTGAACTTCGGCATTGCGCAAGACTATCAGGGGCAGTGCAACC<br>TGCGTTTTGACGATACCAACCCGGCAAAAGAAGACATCGAATTCGTT<br>GAGTCGATCAAACACGACGTCCAGTGGTTAGGTTTCGACTGGAGCGG<br>TGATATTCACTACTCTTCAGACTATTTTGATCAACTGCACGCTTATGC<br>GCTGGAACTGATCAACAAAGGTCTGGCGTACGTTGACGAACTGTCAC<br>CGGATCAGATCCGTGAATACCGCGGCTCGCTGACGTCTCCGGGCAAA<br>AACAGCCCGTACCGTGACCGTTCAGTGGAAGAGAACATCGCGCTGTT<br>TGAGAAAATGCGTAACGGTGAATTTGCCGAAGGCGCTGCCTGTCTGC<br>GTGCAAAAATCGATATGGCGTCGCCTTTCTTCGTGATGCGCGATCCGG<br>TTCTGTACCGTATTAAGTTTGCAGAACACCACCAGACCGGCAAAAAA<br>TGGTGCATCTATCCGATGTACGATTTCACCCACTGCATTTCCGATGCG<br>CTGGAAGGGATCACCCATTCGCTGTGTACGCTGGAATTCCAGGACAA<br>CCGCCGTCTGTACGACTGGGTTCTGGATAACATCTCCATTCCATGCCA<br>CCCGCGTCAGTACGAGTTCTCCCGTCTGAATCTCGAGTACTCCATCAT<br>GTCTAAGCGTAAGCTGAACCAGCTGGTGACCGAGAAGATTGTGGAAG<br>GCTGGGACGACCCGCGTATGCCGACTGTTTCAGGTCTGCGTCGTCGTG<br>GTTACACCGCCGCGTCTATCCGTGAATTCTGCCGTCGTATCGGCGTCA<br>CCAAGCAAGACAACAACGTCGAAATGATGGCGCTGGAATCCTGTATC<br>CGTGACGATCTGAACGAAAATGCACCGCGCGCCATGGCGGTGATCAA<br>CCCGGTTAAAGTGATCATTGAAAACTTTACCGGTGATGACGTGCAGA<br>GGGTGAAAATGCCGAACCACCCGAGCAAACCGGAAATGGGCACCCG<br>CGAAGTGCCATTTACCCGTGAGATTTATATCGATCAGGCAGATTTCCG<br>CGAAGAAGCGAACAAGCAATACAAGCGTCTGGTGCTCGGCAAAGAA<br>GTGCGTCTGCGCAATGCGTATGTGATCAAAGCAGAACGTATCGAGAA<br>AGATGCAGAAGGCAATATCACCACGATCTTCTGTTCTTACGATATCGA<br>TACACTGAGCAAAGATCCTGCCGATGGCCGCAAGGTGAAAGGCGTGA<br>TCCACTGGGTTTCGGCGTCAGAAGGCAAACCGGCGGAGTTCCGCCTG<br>TATGACCGTCTGTTCAGCGTCGCCAACCCGGGTCAGGCAGAAGATTTC |

-continued

Sequence Listing

| Seq ID No. | Description | Sequence |
|---|---|---|
| | | CTGACCACCATCAACCCGGAATCTCTGGTGATTTCCCACGGTTTCGTG<br>GAGCCATCACTGGTGGCTGCACAGGCTGAAATCAGCCTGCAGTTCGA<br>GCGTGAAGGTTACTTCTGCGCCGACAGCCGCTACTCAAGCGCTGAAC<br>ATCTGGTGTTTAACCGTACCGTTGGCCTGCGCGATACCTGGGAAAGCA<br>AACCCGTCGTGTAA |
| 96 | DP22 DNA gyrase subunit B | ATGTCGAATTCTTATGACTCCTCAAGTATCAAGGTATTAAAAGGGCTG<br>GACGCGGTGCGTAAGCGCCCCGGCATGTATATCGGCGATACCGATGA<br>CGGCACTGGTCTGCACCACATGGTATTCGAGGTTGTGGACAACGCTAT<br>CGACGAAGCCCTCGCGGGCCACTGTAAAGAGATTCAGGTCACGATCC<br>ATGCGGATAACTCTGTGTCCGTACAGGATGATGGTCGTGGCATTCCGA<br>CCGGTATTCATGAAGAAGAGGGCGTTTCTGCTGCTCAGGTCATCATGA<br>CCGTTCTTCACGCCGGCGGTAAATTTGACGATAACTCGTATAAAGTCT<br>CCGGCGGTCTGCATGGCGTGGGTGTTTCCGTCGTTAACGCCCTGTCAG<br>AAAAACTGGAACTGGTTATCCGCCGCGAAGGCAAAGTGCACACCCAG<br>ACTTACGTGCATGGCGAACCTCAGGATCCGCTGAAAGTGATTGGCGA<br>TACTGACGTGACCGGTACCACGGTACGTTTCTGGCCAAGCTTCAACAC<br>CTTCACCAATCACACTGAATTCGAGTATGACATTCTGGCGAAACGCCT<br>GCGTGAACTGTCATTCCTGAACTCCGGCGTGGCGATCCGCCTGCTGGA<br>TAAACGTGATGGTAAAAACGATCACTTCCATTATGAAGGCGGTATCA<br>AAGCTTTCGTGGAATATCTGAACAAAAACAAAACCCCAATCCATCCG<br>ACCGTATTCTATTTCTCCACGGTCAAAGATGACATTGGCGTTGAAGTG<br>GCGTTGCAGTGGAACGACGGTTTCCAGGAAAACATTTACTGCTTCACC<br>AACAACATTCCACAGCGCGATGGCGGGACTCACTTAGCCGGTTTCCG<br>TTCGGCAATGACCCGTACCCTGAACGCGTACATGGATAAAGAAGGCT<br>ACAGCAAGAAATCCAAAATCAGCGCCACCGGTGATGATGCCCGTGAA<br>GGCCTGATTGCTGTGGTGTCGGTGAAGGTGCCGGATCCTAAGTTCTCT<br>TCTCAGACCAAAGACAAACTGGTGTCTTCTGAAGTGAAAACAGCGGT<br>TGAAACGCTGATGAACGAGAAGCTGGTGGATTACCTGATGGAAAACC<br>CGTCAGACGCCAAAATCGTTGTCGGTAAAATCATCGACGCAGCGCGT<br>GCCCGTGAAGCAGCACGTAAAGCGCGTGAAATGACCCGCCGTAAAGG<br>CGCGCTGGATCTGGCTGGCTTGCCAGGCAAACTGGCGGACTGTCAGG<br>AACGCGATCCGGCACATTCCGAACTGTACTTAGTGGAAGGGGACTCA<br>GCGGGCGGCTCTGCAAAACAAGGCCGTAACCGTAAGAACCAGGCGAT<br>TCTGCCGTTGAAAGGTAAAATCCTCAACGTGGAGAAAGCGCGCTTCG<br>ACAAAATGCTCTCTTCTCAGGAAGTGGCAACGCTGATTACAGCACTC<br>GGTTGCGGCATTGGCCGTGACGAATACAACCCGGACAAACTGCGCTA<br>TCACAGCATCATCATCATGACCGATGCCGACGTCGATGGTTCGCACAT<br>CCGTACCCTGTTGCTGACATTCTTCTACCGTCAGATGCCTGAAATTGT<br>AGAACGTGGCCACGTGTTTATCGCCCAGCCGCCGTTGTACAAAGTGA<br>AAAAAGGCAAGCAGGAACAGTACATTAAAGATGACGAAGCGATGGA<br>TCAGTATCAGATTTCCATTGCGATGGACGGGGCAACGTTACACGCCA<br>ACGCTCATGCGCCAGCCCTGGCGGGTGAACCGCTGGAGAAACTGGTC<br>GCTGAACATCACAGCGTGCAGAAAATGATTGGCCGCATGGAACGTCG<br>TTATCCGCGTGCGCTGCTGAATAACCTGATCTATCAGCCGACCCTGCC<br>GGGTGCAGATCTGGCCGATCAGGCGAAAGTGCAGGCCTGGATGGAAT<br>CGCTGGTGGCGCGTCTCAACGAGAAAGAGCAGCACGGCAGTTCTTAC<br>AGCGCGATCGTGCGTGAAAACCGCGAACATCAGCTGTTCGAACCGGT<br>TCTGCGTATCCGCACCCACGGTGTTGATACCGATTACGATCTGGATGC<br>CGACTTCATCAAAGGCGGCGAATACCGCAAAATCTGTGCGCTGGGTG<br>AACAGCTGCGCGGCCTGATCGAAGAAGATGCCTTCATCGAACGTGGC<br>GAACGCCGTCAGCCCGTCACCAGCTTCGAACAGGCGCTGGAATGGCT<br>GGTGAAAGAGTCCCGTCGTGGTCTGTCGATTCAGCGATACAAAGGTC<br>TGGGTGAAATGAACCCTGAACAGCTGTGGGAAACCACCATGGATCCT<br>GAGCAACGTCGCATGTTACGTGTGACCGTGAAGGATGCCATCGCCGC<br>TGACCAGTTGTTCACGACGCTGATGGGCGATGCGGTTGAACCGCGCC<br>GCGCCTTTATCGAAGAGAACGCCCTGAAAGCCGCCAATATCGATATC<br>TGA |
| 97 | DP22 Isoleucine tRNA ligase | ATGAGTGACTACAAGAACACCCTGAATTTGCCGGAAACAGGGTTCCC<br>GATGCGTGGCGATCTGGCCAAGCGTGAACCTGACATGCTGAAAAATT<br>GGTATGACCAGGATCTGTACGGGATTATTCGTGCTGCCAAGAAAGGC<br>AAAAAAACCTTTATTTTGCATGACGGCCCTCCGTATGCGAACGGCAG<br>CATTCATATTGGTCACTCAGTAAACAAAATTCTTAAAGACATGATTAT<br>CAAGTCCAAAGGACTTGCGGGCTTTGATGCGCCGTATGTGCCGGGCT<br>GGGATTGTCATGGTCTGCCGATCGAGCTGAAAGTCGAACAACTGATC<br>GGTAAGCCGGGCGAGAAAGTTACGGCGGCGGAATTCCGTGAAGCCTG<br>CCGTAAATATGCCGCAGAACAGGTTGAAGGCCAGAAGAAAGACTTCA<br>TCCGTCTGGGCGTGCTGGGCGACTGGGATCATCCGTACCTGACGATG<br>GATTTCAAAACCGAAGCCAACATCATCCGTGCGCTGGGCAAAATCAT<br>CGGTAACGGCCACCTGCATAAAGGCGCCAAGCCGGTGCACTGGTGTA<br>CAGATTGCGGTTCGTCGCTGGCCGAAGCCGAAGTCGAATATTACGAC<br>AAAGCCTCGCCTTCTATTGATGTGGCGTTCAACGCGACGGATGCCGCA |

-continued

Sequence Listing

| Seq ID No. | Description | Sequence |
|---|---|---|
| | | GCCGTGGCAGCGAAATTTGGCGTTACTGCCTTTAATGGCCCGATCTCG<br>CTGGTTATCTGGACCACAACACCGTGGACTATGCCCGCTAACCGCGCC<br>ATTTCACTGAATCCTGAGTTTGCTTATCAGCTGGTTCAGGTCGAAGGT<br>CAGTGTCTGATCCTGGCAACCGATCTGGTTGAAAGCGTCATGAAACG<br>TGCCGGTATTGCCGGATGGACCGTTCTGGGCGAGTGCAAAGGCGCAG<br>ACCTCGAACTGCTGCGCTTCAAACACCCGTTCCTCGGTTTCGACGTTC<br>CGGCGATCCTGGGCGATCACGTGACGCTCGATGCGGGTACCGGTGCC<br>GTGCATACCGCACCAGGCCACGGCCCTGACGACTTTGTTATCGGCCA<br>GAAATACGGTCTGGAAGTGGCGAATCCGGTAGGGCCGAACGGTTGCT<br>ACCTGCCGGGCACTTACCCGACGCTGGACGGTAAATTTGTCTTTAAAG<br>CCAACGACCTGATCGTTGAGTTGCTGCGTGAAAAAGGCGCATTGCTG<br>CACGTTGAGAAAATCACGCACAGCTATCCTTGCTGCTGGCGCCACAA<br>AACGCCAATCATCTTCCGCGCGACGCCGCAATGGTTCATCAGCATGG<br>ATCAGAAGGGCCTGCGTCAGCAGTCGCTGGAAGAGATCAAAGGCGTG<br>CAGTGGATCCCGGACTGGGGTCAGGCACGTATCGAAAACATGGTCGC<br>TAACCGTCCTGACTGGTGTATCTCCCGTCAGCGTACCTGGGGCGTGCC<br>GATGTCTCTGTTCGTTCACAAAGACACTGAGCAGCTGCATCCGCGCAG<br>CCTTGAGCTGATGGAAGAAGTGGCGAAACGTGTTGAGGTGGATGGCA<br>TTCAGGCGTGGTGGGATCTGAATCCGGAAGACATTCTGGGTGCAGAC<br>GCCGCAGATTACGTCAAAGTACCGGACACGCTGGACGTCTGGTTTGA<br>CTCCGGTTCAACGCATTCTTCCGTTGTGGATGTGCGTCCTGAGTTCAA<br>CGGGCATTCTCCTGATCTGTATCTGGAAGGTTCTGACCAGCATCGCGG<br>CTGGTTCATGTCTTCCCTGATGATTTCGACGGCAATGAAAGGCAAAGC<br>GCCTTACAAACAAGTGCTGACTCACGGTTTCACCGTGGATGGTCAGG<br>GCCGCAAAATGTCTAAATCCATCGGCAATACCATCGCGCCGCAAGAC<br>GTGATGAACAAGCTGGGTGGCGACATTCTGCGTCTGTGGGTCGCGTC<br>GACGGATTACACCGGCGAAATCGCCGTGTCCGACGAAATCCTCAAAC<br>GTGCTGCTGATTCTTACCGCCGTATCCGTAACACCGCGCGCTTCCTGC<br>TGGCGAACCTTAACGGTTTCGATCCGGCGCTGCACAGCGTGGCTCCG<br>GAAGACATGGTGGTGCTGGACCGCTGGGCGGTTGGCCGTGCGAAAGC<br>CGCTCAGGAAGAAATCATTGCTGCGTATGAAGCCTATGATTTCCATGG<br>CGTTGTTCAGCGTCTGATGCAGTTCTGCTCGATCGAAATGGGTTCCTT<br>CTATCTGGATATCATTAAAGATCGTCAGTACACCGCGAAAAGCGACA<br>GCGTTGCACGTCGCAGCTGTCAGACCGCGCTGTATCACATCAGTGAA<br>GCGCTGGTTCGCTGGATGGCACCGATCATGTCGTTCACAGCCGATGA<br>AATCTGGGCGGAACTGCCGGGAAGCCGTGAGAAATTCGTCTTCACCG<br>AAGAGTGGTACGACGGTCTGTTCGGTCTCGCAGGCAACGAATCCATG<br>AACGATGCGTTCTGGGATGAACTGCTGAAAGTGCGTGGCGAAGTGAA<br>CAAAGTGATCGAACAGGCGCGTGCGGATAAACGTCTGGGCGGTTCTC<br>TGGAAGCAGCGGTTACGCTGTTTGCTGATGATGCGCTGGCAACAGAC<br>CTGCGTTCTCTGGGCAATGAACTGCGCTTTGTGCTGCTGACGTCAGGG<br>GCGAAAGTTGCCGCACTGAGTGATGCAGATGACGCGGCTCAGTCGAG<br>TGAATTGCTGAAAGGCCTGAAGATTGGTCTGGCGAAAGCAGAAGGCG<br>ACAAGTGCCCGCGCTGCTGGCATTACACTACCGATTAA |
| 98 | DP22 NADH-quinone oxidoreductase subunit C/D | ATGACAGATTTGACGACGCAAGATTCCGCCCTGCCAGCATGGCATAC<br>CCGTGATCATCTCGATGATCCGGTTATCGGCGAATTGCGTAACCGTTT<br>TGGGCCAGAGGCCTTTACTGTCCAGGCAACCCGCACCGGAATTCCCG<br>TGGTGTGGTTCAAGCGTGAACAGTTACTGGAAGCGATTACCTTTTTAC<br>GAAAACAGCCAAAACCTTACGTCATGCTTTTCGATTTGCATGGCTTTG<br>ATGAGCGTTTACGTACACACCGCGACGGTTTACCGGCTGCGGATTTTT<br>CCGTTTTCTACCACCTGATCTCCGTCGAGCGTAACCGCGACATCATGA<br>TCAAAGTGGCGTTGTCAGAAAACGATCTTCATGTTCCGACGATCACCA<br>AAGTGTTCCCGAACGCTAACTGGTACGAACGCGAAACATGGGAAATG<br>TTCGGTATTACCTTCGACGGCCATCCGCACCTGACGCGCATCATGATG<br>CCGCAGACCTGGGAAGGGCATCCGCTGCGTAAAGACTATCCGGCGCG<br>CGCCACCGAGTTCGATCCTTATGAGCTGACTAAGCAAAAAGAAGAAC<br>TCGAGATGGAATCGCTGACCTTCAAGCCGGAAGACTGGGGCATGAAG<br>CGCGGTACCGATAACGAGGACTTTATGTTCCTCAACCTCGGTCCTAAC<br>CACCCGTCAGCGCATGGTGCATTCCGTATTATCCTGCAGCTGGATGGC<br>GAAGAGATTGTCGACTGCGTGCCTGACGTCGGTTACCACCACCGTGG<br>TGCGGAGAAAATGGGCGAACGCCAGTCATGGCACAGCTACATTCCGT<br>ATACTGACCGTATCGAATATCTCGGCGGTTGTGTTAACGAAATGCCTT<br>ACGTGCTGGCTGTTGAAAAACTCGCCGGTATCGTGACGCCGGATCGC<br>GTTAACACCATCCGTGTGATGCTGTCTGAACTGTTCCGTATCAACAGC<br>CATCTGCTGTACATCTCTACGTTTATTCAGGACGTGGGTGCGATGACG<br>CCGGTATTCTTCGCCTTTACCGATCGTCAGAAAATTTACGATCTGGTG<br>GAAGCGATCACCGGTTTCCGTATGCACCCGGCCTGGTTCCGTATCGGT<br>GGCGTAGCGCATGACCTGCCGAAAGGCTGGGACCGCCTGCTGCGTGA<br>ATTCCTTGACTGGATGCCAGCCCGTTTGGATTCCTACGTCAAAGCGGC<br>GCTGAGAAACACCATTCTGATTGGCCGTTCCAAAGGCGTGGCCGCGT<br>ATAACGCCGACGACGCACTGGCCTGGGGCACCACCGGTGCTGGCCTG<br>CGCGCAACGGGTATCCCGTTCGATGTGCGTAAATGGCGTCCGTATTCA |

-continued

Sequence Listing

| Seq ID No. | Description | Sequence |
|---|---|---|
| | | GGTTATGAAAACTTTGACTTTGAAGTGCCGACCGGTGATGGCGTCAGT<br>GACTGCTATTCCCGCGTGATGCTGAAAGTGGAAGAACTTCGTCAGAG<br>CCTGCGCATTCTGGAACAGTGCTACAAAAACATGCCGGAAGGCCCGT<br>TCAAGGCGGATCACCCGCTGACCACGCCGCCACCGAAAGAGCGCACG<br>CTGCAACACATCGAGACCCTGATCACGCACTTCCTGCAAGTGTCGTGG<br>GGGCCGGTCATGCCTGCACAAGAATCTTTCCAGATGGTTGAAGCAAC<br>CAAAGGGATCAACAGCTACTACCTGACCAGTGACGGCAGCACCATGA<br>GCTACCGCACCCGTGTCCGTACGCCGAGCTTCCCGCATTTGCAGCAGA<br>TCCCGTCCGTAATCCGTGGCAGCCTGGTATCCGACCTGATCGTGTATC<br>TGGGCAGTATCGATTTTGTAATGTCAGATGTGGACCGCTAA |
| 99 | DP22 Protein RecA | ATGGCTATTGATGAGAACAAGCAAAAAGCGTTAGCTGCAGCACTGGG<br>CCAGATTGAAAAGCAATTCGGTAAAGGCTCCATCATGCGTCTGGGTG<br>AAGATCGCTCCATGGACGTTGAAACGATCTCTACCGGCTCTTTGTCTC<br>TGGATATCGCGTTAGGTGCCGGCGGTTTGCCAATGGGCCGTATCGTTG<br>AGATCTATGGCCCGGAATCTTCCGGTAAAACAACGCTGACCTTGCAA<br>GTTATCGCGGCTGCACAGCGTGAAGGCAAAACCTGTGCGTTCATCGA<br>TGCAGAACACGCCCTGGACCCGATCTACGCTAAAAAACTGGGCGTGG<br>ATATCGATAACCTGCTGTGTTCTCAGCCAGATACCGGCGAACAGGCTC<br>TGGAAATCTGTGACGCGCTGACCCGTTCAGGCGCTGTTGACGTGATCA<br>TCGTTGACTCCGTTGCCGCACTGACACCGAAAGCGGAAATCGAAGGC<br>GAAATTGGTGACTCTCACATGGGCCTCGCGGCACGTATGATGAGCCA<br>GGCGATGCGTAAGCTGGCCGGTAACCTGAAAAACGCCAACACCTTGC<br>TGATCTTCATCAACCAGATCCGTATGAAAATTGGTGTGATGTTCGGTA<br>ACCCGGAAACCACCACCGGCGGTAACGCCCTGAAATTCTACGCTTCT<br>GTGCGTCTGGATATCCGCCGTATCGGCGCGATCAAAGAAGGCGATGT<br>GGTTGTCGGTAGCGAAACGCGTGTGAAAGTGGTGAAGAACAAAATCG<br>CTGCGCCATTTAAACAAGCTGAATTCCAGATCATGTACGGCGAAGGC<br>ATCAATATCAACGGCGAGCTGATTGATCTCGGCGTGAAGCACAAGCT<br>GATCGAAAAAGCCGGTGCATGGTATAGCTACAACGGTGAGAAGATTG<br>GTCAGGGTAAAGCGAACTCCTGCAACTTCCTGAAAGAAAACCCGAAA<br>GTGGCTGCCGAGCTGGATAAAAAACTGCGTGATATGCTGTTGAGCGG<br>TACCGGTGAACTGAGTGCTGCGACCACGGCTGAAGATGCTGACGACA<br>ACATGGAAACCAGCGAAGAGTTTTAA |
| 100 | DP22 RNA polymerase sigma factor RpoD | ATGGAGCAAAACCCGCAGTCACAGCTTAAGCTACTTGTCACCCGTGG<br>TAAGGAGCAAGGCTATCTGACCTATGCTGAGGTCAATGACCATCTGC<br>CGGAAGATATCGTCGATTCCGACCAGATCGAAGACATCATCCAGATG<br>ATTAACGACATGGGCATCCAGGTACTTGAAGAAGCACCGGACGCCGA<br>TGATTTGATGCTGGCCGAAAACCGCCCTGATACCGATGAAGACGCTG<br>CAGAAGCCGCGGCGCAGGTGCTTTCCAGCGTTGAATCCGAAATTGGC<br>CGTACCACCGACCCTGTGCGTATGTATATGCGCGAGATGGGTACCGTT<br>GAGTTGCTGACCCGTGAAGGCGAAATCGACATCGCCAAACGTATCGA<br>AGACGGTATCAATCAGGTCCAGTGCTCCGTTGCTGAATATCCTGAAGC<br>TATCACTTATTTGTTAGAGCAATATGACCGTGTGGAAGCAGGCGAAG<br>TACGTCTGTCTGACCTGATCACCGGTTTTGTTGACCCGAACGCCGAAG<br>AAGAAATCGCACCAACTGCGACTCACGTGGGTTCTGAACTGACCACT<br>GAAGAGCAGAATGATGACGACGAAGACGAAGATGAAGACGACGACG<br>CTGAAGACGACAACAGCATCGATCCGGAACTGGCTCGCCAGAAGTTC<br>ACCGAACTGCGTGAACAGCATGAAGCGACGCGTCTGGTCATCAAGAA<br>AAACGGCCGTAGTCACAAGAGCGCAGCAGAAGAAATCCTGAAGCTGT<br>CCGATGTGTTCAAACAGTTCCGTCTGGTGCCAAAACAGTTCGATTTCC<br>TGGTTAACAGCATGCGTTCCATGATGGATCGCGTTCGTGCTCAGGAAC<br>GTCTGATCATGAAAGTGTGCGTTGAACAGTGCAAAATGCCGAAGAAA<br>AACTTCGTCAATCTGTTCGCCGGTAACGAAACCAGCGATACCTGGTTT<br>GATGCCGCTCTGGCAATGGGTAAACCATGGTCCGAGAAGCTGAAAGA<br>AGTCACCGAAGACGTGCAACGCGGCCTGATGAAACTGCGTCAGATCG<br>AAGAAGAAACCGGCCTGACTATCGAACAGGTTAAAGACATCAACCGT<br>CGCATGTCGATCGGCGAAGCGAAAGCCCGTCGCGCGAAGAAAGAGA<br>TGGTTGAAGCAAACTTACGTCTGGTTATTTCTATCGCCAAGAAATACA<br>CCAACCGTGGTCTGCAGTTCCTTGACCTGATCCAGGAAGGTAACATCG<br>GCCTGATGAAAGCCGTTGATAAGTTTGAATATCGCCGTGGTTATAAGT<br>TCTCAACTTATGCGACCTGGTGGATCCGTCAGGCTATCACCCGCTCCA<br>TCGCCGACCAGGCGCGTACCATCCGTATCCCGGTACATATGATTGAG<br>ACGATCAACAAACTCAACCGTATCTCCCGTCAGATGCTGCAAGAGAT<br>GGGCCGCGAACCGACACCGGAAGAGCTGGCTGAGCGTATGTTGATGC<br>CGGAAGACAAAATCCGCAAAGTGCTGAAAATTGCCAAAGAGCCAATC<br>TCCATGGAAACGCCAATCGGCGACGATGAAGATTCGCATCTGGGCGA<br>TTTCATCGAGGATACCACCCTCGAGCTGCCACTGGATTCTGCGACGTC<br>TGAAAGCCTGCGTTCTGCAACGCATGACGTTCTGGCTGGCCTGACTGC<br>ACGTGAAGCGAAAGTTCTGCGTATGCGTTTCGGTATCGATATGAACA<br>CTGACCACACGCTGGAAGAAGTGGGCAAACAGTTCGACGTGACCCGT |

-continued

Sequence Listing

| Seq ID No. | Description | Sequence |
|---|---|---|
| | | GAGCGTATCCGTCAGATCGAAGCGAAAGCGTTGCGTAAACTGCGCCA<br>CCCGAGCCGCTCCGAAGTACTGCGCAGCTTCCTGGACGATTAA |
| 101 | DP22 DNA-directed RNA polymerase subunit beta' | GTGAAAGACTTACTAAAGTTTCTGAAAGCGCAAACTAAGACCGAAGA<br>GTTTGATGCGATCAAAATTGCTCTGGCATCGCCAGACATGATCCGTTC<br>TTGGTCTTTTGGTGAAGTTAAGAAGCCAGAAACCATTAACTACCGTAC<br>GTTCAAACCAGAACGTGACGGCCTTTTCTGTGCCCGTATTTTCGGACC<br>AGTAAAAGACTACGAATGCCTGTGCGGTAAGTACAAGCGTTTAAAAC<br>ATCGCGGCGTGATCTGCGAGAAGTGCGGCGTTGAAGTGACCCAGACT<br>AAAGTACGCCGTGAGCGTATGGGCCACATCGAACTGGCTTCCCCGAC<br>TGCACACATCTGGTTCCTGAAATCGCTGCCATCGCGCATCGGTTTGCT<br>GCTGGATATGCCACTGCGTGACATCGAACGTGTTCTGTACTTCGAATC<br>CTATGTGGTTATCGAAGGCGGCATGACTAACCTCGAAAAACGCCAGA<br>TCCTGACTGAAGAGCAGTATCTGGATGCGTTGGAAGAGTTTGGTGAT<br>GAGTTCGACGCGAAGATGGGTGCGGAAGCTATTCAGGCCCTGTTGAA<br>AAACATGGATCTGGAAGCAGAGTGCGAGCAACTGCGTGAAGAGTTGA<br>ACGAAACCAACTCCGAAACCAAACGTAAGAAGCTGACCAAGCGTATC<br>AAGCTGCTGGAAGCGTTCGTTCAGTCTGGTAACAAACCAGAGTGGAT<br>GATCCTGACTGTGCTGCCGGTACTGCCACCAGACTTGCGTCCATTGGT<br>TCCGTTGGACGGCGGCCGTTTCGCAACGTCGGATCTGAACGATCTGTA<br>TCGTCGCGTGATCAACCGTAACAACCGTCTGAAACGCCTGCTGGATCT<br>GGCTGCGCCAGACATCATCGTACGTAACGAAAAACGTATGCTGCAAG<br>AAGCGGTAGATGCTTTGCTGGATAACGGCCGTCGCGGTCGTGCTATC<br>ACCGGCTCTAACAAGCGTCCGCTGAAATCTCTGGCAGACATGATTAA<br>AGGTAAACAGGGTCGTTTCCGTCAGAACTTGCTGGGTAAACGTGTCG<br>ACTACTCTGGTCGTTCCGTTATCACCGTAGGTCCATACCTGCGTCTGC<br>ACCAGTGTGGTCTGCCGAAGAAAATGGCACTGGAACTGTTCAAACCG<br>TTCATCTACGGCAAGCTGGAACTGCGTGGCCTGGCCACCACCATCAA<br>AGCCGCGAAGAAAATGGTTGAGCGCGAAGAAGCTGTCGTTTGGGACA<br>TCCTGGACGAAGTTATCCGCGAACACCCGGTACTGCTGAACCGTGCA<br>CCAACCCTGCACCGTTTGGGTATCCAGGCGTTTGAACCGGTTCTGATC<br>GAAGGTAAAGCAATCCAGCTGCACCCGCTGGTTTGTGCGGCATATAA<br>CGCCGACTTCGATGGTGACCAGATGGCTGTTCACGTACCGTTGACGCT<br>GGAAGCCCAGCTGGAAGCGCGTGCGTTGATGATGTCTACCAACAACA<br>TCCTGTCACCTGCGAACGGCGAGCCAATCATCGTTCCTTCTCAGGACG<br>TTGTATTGGGTCTGTACTACATGACCCGTGACTGTGTTAACGCCAAAG<br>GCGAAGGCATGGTTCTGACCGGTCCTAAAGAAGCTGAGCGTATTTAC<br>CGCGCCGGTTTGGCCTCTCTGCATGCGCGTGTCAAAGTGCGTATTACA<br>GAAGAGATCAAAAATACCGAAGGCGAAGTTACGCACAAGACGTCGA<br>TTATCGACACGACAGTTGGTCGCGCCATCCTTTGGATGATCGTACCTA<br>AAGGTCTGCCGTTCTCTATCGTCAACCAGCCTCTGGGCAAAAAAGCTA<br>TCTCCAAAATGCTGAACACCTGTTACCGCATTTTGGGCCTGAAGCCGA<br>CCGTTATTTTTGCTGACCAGATCATGTACACCGGTTTTGCTTACGCTGC<br>CCGTTCAGGCGCGTCAGTAGGTATCGATGACATGGTAATCCCTGCGA<br>AGAAAGCAGAGATCATCGAAGAAGCAGAAACCGAAGTTGCTGAAAT<br>CCAGGAACAGTTCCAGTCTGGTCTGGTCACTGCTGGCGAACGCTATA<br>ACAAAGTGATCGACATCTGGGCTGCGGCCAACGAACGTGTTGCTAAG<br>GCAATGATGGAAAACTTGTCTGTTGAAGACGTCGTCAACCGTGACGG<br>TGTTGTTGAACAGCAGGTTTCCTTCAACAGTATCTTTATGATGGCCGA<br>CTCCGGTGCGCGTGGTTCTGCTGCACAGATTCGTCAGCTGGCCGGTAT<br>GCGTGGCCTGATGGCGAAACCAGATGGTTCCATCATTGAAACGCCAA<br>TCACCGCGAACTTCCGTGAAGGTCTGAACGTACTCCAGTACTTCATCT<br>CTACTCACGGTGCTCGTAAAGGTTTGGCGGATACCGCACTTAAAACG<br>GCTAACTCCGGTTATCTGACCCGTCGTCTGGTTGACGTCGCGCAGGAT<br>CTGGTTGTGACCGAAGACGACTGTGGGACTCACGAAGGCATCATGAT<br>GACTCCGGTCATCGAAGGTGGCGACGTTAAAGAACCACTGCGTGAGC<br>GTGTACTGGGTCGTGTGACTGCAGAAGATATCCTCAAGCCGGGTACG<br>GCGGATATCCTGGTTCCACGTAACACCCTGCTTCACGAGAAGACGTGT<br>GATCTGTTAGAAGAGAACTCAGTCGACAGCGTGAAAGTACGTTCAGT<br>CGTAAGTTGCGAAACCGACTTTGGTGTGTGTGCAAACTGCTACGGTCG<br>CGACCTGGCACGTGGTCACATCATCAACAAAGGTGAAGCGATCGGTG<br>TTATTGCAGCACAGTCCATCGGTGAGCCGGGTACCCAGCTGACGATG<br>CGTACGTTCCACATCGGTGGTGCGGCATCTCGTGCGGCAGCGGAATC<br>CAGCATCCAGGTTAAGAACACTGGTACCATTAAACTGAGCAACCACA<br>AGCACGTTAGCAACTCTAACGGCAAACTGGTGATCACTTCCCGTAAC<br>ACTGAGCTGAAATTGATCGACGAATTCGGTCGTACCAAAGAAAGCTA<br>TAAAGTGCCTTACGGTTCCGTGATGGGCAAAGGCGATGGCGCATCAG<br>TTAACGGCGGCGAAACCGTTGCTAACTGGGATCCGCACACCATGCCA<br>GTTATCAGTGAAGTGAGTGGTTTCATTCGCTTTGCCGATATGGTGGAT<br>ACTCAGACCATCACACGCCAGACCGACGACCTGACCGGTTTGTCTTCT<br>CTGGTTGTTCTGGACTCTGCAGAGCGTACCGGTAGCGGTAAAGACCT<br>GCGTCCGGCACTGAAAATCGTTGACGCTAAAGGCGACGACGTATTGA<br>TTCCAGGTACTGATATGCCTGCTCAATACTTCCTGCCAGGTAAAGCGA |

-continued

Sequence Listing

| Seq ID No. | Description | Sequence |
|---|---|---|
| | | TTGTTCAGCTGGAAGATGGTACTCAGATCCACTCTGGTGACACCCTGG<br>CGCGTATTCCTCAGGAATCCGGCGGTACCAAGGACATCACCGGTGGT<br>CTGCCACGCGTTGCTGACCTGTTCGAAGCACGTCGTCCGAAAGAGCCT<br>GCAATCCTTGCTGAAATCAGCGGGATCATCTCCTTCGGTAAAGAAAC<br>CAAAGGCAAACGTCGTCTGGTAATTTCTCCGTTAGATGGCAGCGATG<br>CTTACGAAGAAATGATCCCTAAATGGCGTCAGCTGAACGTGTTCGAA<br>GGCGAAGTTGTGGAACGTGGTGACGTCGTATCCGACGGCCCTGAGTC<br>TCCGCACGACATCTTGCGTTTACGTGGTGTTCACGCGGTTACCCGCTA<br>CATCACCAACGAAGTGCAGGAAGTTTACCGTCTGCAAGGCGTTAAGA<br>TTAACGATAAGCACATCGAAGTTATCGTTCGTCAGATGTTGCGTAAAG<br>GCACCATCGTTAGCGCTGGTGGCACTGACTTCCTGGAAGGCGAGCAG<br>GCAGAAATGTCTCGCGTTAAAATCGCTAACCGTAAGCTGGAAGCTGA<br>AGGCAAAATCACGGCAACATTCAGCCGTGACCTGCTCGGTATCACCA<br>AGGCATCCCTGGCGACCGAATCCTTCATCTCTGCAGCGTCGTTCCAGG<br>AAACCACGCGTGTTCTTACCGAAGCGGCTGTTGCCGGTAAACGTGAT<br>GAACTGCGTGGCCTGAAAGAGAACGTTATCGTTGGCCGTCTGATCCC<br>AGCCGGTACCGGTTACGCTTATCATCAGGATCGTGCACGCCGTAAAG<br>CACAAGGCGAAGTGCCAGTTGTACCGCAAGTCAGCGCGGATGAAGCA<br>ACGGCTAACCTGGCTGAACTGCTGAACGCAGGTTTCGGTAACAGCGA<br>CGATTAA |
| 102 | DP67 Glutamine-tRNA ligase | ATGAGTGAGGCTGAAGCCCGCCCAACTAACTTTATTCGTCAGATTATC<br>GACGAAGATCTGGCGAACGGTAAGCACAGTTCAGTGCACACCCGCTT<br>CCCGCCTGAGCCGAATGGCTATCTGCATATTGGCCATGCGAAATCAAT<br>CTGCCTGAACTTTGGTATCGCTCAGGATTATCAGGGGCAGTGTAACCT<br>GCGCTTTGATGACACTAACCCGGTGAAAGAAGATCTGGAGTTTGTTG<br>AATCAATCAAGCGTGATGTGCAGTGGCTGGGCTTTAAGTGGAGTGGT<br>GACGTACGCTACTCATCTGACTATTTCGAGCAACTGCACAATTATGCC<br>GTTGAGCTGATTAGTAAAGGGCTGGCGTACGTTGATGAACTGTCACC<br>GGAGCAGATCCGTGAATACCGTGGCAGCCTGACCTCAGCGGGTAAAA<br>ACAGCCCCTTCCGCGATCGCAGCGTGGACGAAAACCTTGCGCTCTTTG<br>CAAAAATGCGCGCGGGCGGCTTTGCCGAGGGCACCGCGTGTTTACGA<br>GCCAAAATTGATATGGCTTCCAACTTTATCGTTCTGCGCGATCCGGTG<br>ATCTACCGCATCAAATTTGCCGAACATCATCAGACCGGCAATAAGTG<br>GTGCATCTATCCGATGTATGACTTTACCCACTGCATCTCTGATGCGCT<br>GGAAGGCATTACTCACTCACTGTGTACGCTGGAATTCCAGGATAACC<br>GTCGCCTGTACGACTGGGTGCTGGATAACATCACCATTCCGGTTCATC<br>CGCGTCAGTATGAATTCTCTCGCCTGAATCTTGAATATGCCATCATGT<br>CCAAGCGTAAGTTGAGTCAGTTGGTGACCGAGAACGTGGTGGAAGGT<br>TGGGATGATCCCCGTATGCTGACTGTTTCGGGTTTGCGCCGCCGTGGC<br>TACACTGCGGAATCCATCCGTGAATTCTGCCGCCGCATTGGGGTGACC<br>AAGCAGGACAATATTGTTGAAATGGCCGCTCTGGAATCCTGTATCCGT<br>GACGACCTCAATGAGAATGCCCCGCGTGCCATGGCAGTGATGGATCC<br>GGTAAAAGTGGTGATAGAAAATCTGCCTGCGCATCACGATGAGGTGA<br>TCACCATGCCGAATCATCCGAGCAAGCCGGAAATGGGTACCCGCGAA<br>GTCCCGTTCAGTCGTGAGATCTACATCGATCGTGCTGACTTCCGTGAG<br>GAAGCAAACAAGCAGTACAAGCGGCTGGTGCTGGGCAAAGAAGTGC<br>GTCTGCGTAACGCTTATGTGATCAAAGCCGAGCGCGTGGCAAAGGAC<br>GATGAAGGCAACATTACCTGCCTGTTCTGTACCTGTGATGTGGATACT<br>CTGAGCAAGGATCCGGCCGACGGGCGTAAAGTGAAGGGCGTTATCCA<br>CTGGGTGTCAGCTGTTCATGCCCTTCCGGCAGAGTTCCGTCTGTACGA<br>TCGGCTGTTCAGCGTACCGAATCCGGGGGCGGCAGAAGACTTCCTGG<br>CCAGCATCAACCCGGAATCTCTGGTGATCCGTCAGGGCTTCGTGGAG<br>CCCGGGATGCAGCAGGCGGAGGCGTCAGCCCCGTATCAGTTTGAGCG<br>TGAAGGCTACTTCTGCGCTGACAGTGTCTACTCCAGTGCCAGCAATCT<br>GGTGTTCAACCGCACCGTTGGCCTGCGTGACACCTGGGCGAAAGTCG<br>GCGAGTAA |
| 103 | DP67 DNA gyrase subunit B | ATGTCGAATTCTTATGACTCCTCCAGTATCAAAGTTCTGAAAGGGCTC<br>GATGCTGTACGCAAACGCCCGGGTATGTATATCGGCGATACGGATGA<br>CGGTACCGGTCTGCATCACATGGTATTTGAGGTCGTGGATAACGCCAT<br>TGACGAAGCGCTCGCCGGTCACTGTTCCGATATTCTTGTCACTATTCA<br>TGCCGATAACTCTGTTTCCGTTGTGGATGATGGCCGTGGTATTCCGAC<br>CGGTATTCACGAAGAAGAAGGCATCTCAGCCGCTGAAGTGATCATGA<br>CCGTGCTGCACGCCGGCGGTAAGTTCGACGATAACTCTTATAAAGTCT<br>CCGGCGGCCTGCACGGCGTGGGCGTGTCAGTGGTGAACGCCCTGTCG<br>GAAAAACTGGAGCTGACCATTCGTCGCGAAGGGAAAGTTCACCAGCA<br>GACTTACGTCCACGGCGTGCCACAGGCCCCGTTGAGTGTGAGCGGTG<br>AAACTGACCTGACGGGAACGCGCGTGCGTTTCTGGCCCAGCCATCAG<br>ACGTTCACTAACGTCGTGGAGTTCGAGTACGAAATTTTGGCAAAGCG<br>CCTGCGTGAGCTGTCGTTCCTGAACTCCGGTGTATCAATCAAGCTGGA<br>AGATAAGCGCGACGGTAAAAGCGACCATTACCACTATGAAGGTGGTA<br>TCAAGGCGTTTGTTGAGTACCTCAACAAGAACAAAACCCCGATCCAC |

-continued

Sequence Listing

| Seq ID No. | Description | Sequence |
|---|---|---|
| | | CCGAATGTGTTCTATTTCTCAACCGAGAAAGACGGCATTGGTGTGGA<br>AGTGGCGCTGCAGTGGAACGATGGTTTCCAGGAAAATATCTACTGCT<br>TTACCAACAACATCCCACAGCGGGATGGGGGCACGCACCTCGTTGGT<br>TTCCGTACCGCGATGACCCGTACCCTGAATGCCTACATGGATAAAGA<br>AGGCTACAGCAAGAAAGCCAAAGTCAGCGCCACCGGTGACGACGCG<br>CGTGAAGGCCTGATTGCTGTGGTGTCGGTGAAAGTGCCGGATCCGAA<br>ATTCTCTTCACAGACCAAAGATAAACTGGTCTCTTCTGAAGTGAAAAC<br>CGCCGTTGAGCAGCAGATGAACGAGCTGCTGGCAGAATACCTGCTGG<br>AAAACCCGACCGATGCCAAAATCGTCGTCGGTAAAATCATTGATGCG<br>GCCCGCGCCCGTGAAGCGGCCCGTCGTGCACGTGAAATGACCCGCCG<br>TAAAGGCGCGCTGGATCTGGCAGGCCTGCCGGGCAAACTGGCGGACT<br>GCCAGGAGCGTGATCCGGCTCTGTCCGAAATTTACCTGGTGGAAGGG<br>GACTCTGCGGGCGGCTCTGCCAAGCAGGGACGTAACCGTAAAAACCA<br>GGCCATCCTGCCGCTGAAGGGTAAAATCCTCAACGTCGAGAAGGCGC<br>GCTTTGACAAGATGCTCGCGTCGCAGGAAGTCGCTACGCTGATCACC<br>GCGCTGGGCTGTGGTATCGGTCGTGATGAGTACAACCCCGACAAACT<br>GCGCTATCACAGCATCATTATCATGACCGATGCCGACGTGGATGGCTC<br>GCATATCCGTACCCTGCTGCTGACCTTCTTCTACCGTCAGATGCCAGA<br>AATCATTGAGCGTGGTCATGTCTATATTGCCCAGCCACCGCTGTACAA<br>GGTGAAAAAAGGCAAGCAGGAGCAGTATATTAAAGACGACGATGCG<br>ATGGATCAGTACCAGATCGCCATCGCGCTGGACGGTGCCACGCTGCA<br>TGCGAACGCCAGCGCCCCGGCCCTTGGCGGTAAGCCACTGGAAGATC<br>TGGTGTCTGAGTTCAACAGCACGCGCAAGATGATCAAGCGCATGGAG<br>CGCCGTTACCCGGTGGCCTTGCTGAATGCGCTGGTCTACAACCCGACC<br>CTGAGCGATTTGACCGCCGAAGCGCCGGTACAGAGCTGGATGGATGT<br>GCTGGTGAAGTATCTGAACGACAACGACCAGCACGGCAGCACCTACA<br>GCGGTCTGGTACGCGAAAATCTGGAGCTGCATATCTTTGAGCCGGTA<br>CTGCGTATCAAAACCCACGGCGTGGATACCGATTATCCGCTCGACAG<br>CGAGTTTATGCTCGGCGGCGAATACCGTAAGCTCTGCGCGCTGGGTG<br>AGAAGCTGCGTGGCCTGATCGAAGAAGACGCGTTCATCGAACGTGGT<br>GAGCGGCGTCAGCCGATTGCCAGCTTTGAGCAGGCGATGGAGTGGCT<br>GGTTAAAGAGTCACGCCGTGGCCTGACGGTTCAGCGTTATAAAGGTC<br>TGGGCGAGATGAACCCGGATCAGCTGTGGGAAACCACCATGGATCCG<br>GACAGCCGCCGTATGCTGCGCGTGACCATCAAAGATGCCGTGGCCGC<br>CGACCAGCTGTTCACCACCCTGATGGGGGATGCGGTAGAGCCCCGTC<br>GTGCCTTTATTGAAGAGAACGCCCTGCGCGCGGCAAACATCGATATC<br>TGA |
| 104 | DP67 Isoleucine 1RNA ligase | ATGAGTGACTATAAATCTACCCTGAATTTGCCGGAAACGGGGTTCCC<br>GATGCGTGGCGATCTGGCCAAACGCGAACCGGGTATGCTGCAACGTT<br>GGTATGATGACAAGCTGTACGGCATCATTCGCGAAGCCAAGAAAGGG<br>AAAAAAACCTTTATCCTGCACGATGGCCCTCCTTACGCCAACGGCAG<br>CATTCATATTGGTCACTCCGTTAACAAGATTCTGAAAGACATTATCGT<br>TAAGTCGAAAGGCATGGCGGGCTATGACTCGCCTTATGTACCGGGTT<br>GGGACTGCCACGGTCTGCCTATCGAGCATAAAGTTGAGCAGATGATC<br>GGTAAGCCGGGAGAGAAAGTCAGCGCCGCTGAGTTCCGTGCTGCCTG<br>CCGCAAATACGCTGCCGAGCAGGTGGAAGGGCAGAAAGCCGACTTTA<br>TCCGTCTGGGTGTGTTGGGTGACTGGGATCGTCCGTATCTGACAATGA<br>ACTTCCAGACCGAAGCCAATATTATCCGTGCGCTGGGTAAAATCATC<br>GGTAACGGGCACCTGCACAAAGGGGCCAAGCCGGTACACTGGTGCCT<br>GGACTGCCGTTCTGCCCTGGCTGAGGCGGAAGTGGAGTACTACGATA<br>AAACCTCTCCGTCTATCGATGTCATGTTCAATGCGACTGATAAAGAGG<br>GGGTACAGGCCAAATTTGCGGCAACGAATGTTGACGGCCCGATCTCG<br>CTGGTGATCTGGACTACCACGCCGTGGACCATGCCGGCTAACCGCGC<br>TATCTCACTGCATCCTGAATTCGACTACCAGCTGGTACAGATTGAAGG<br>CCGTGCTCTGATCCTCGCCAAAGAGATGGTTGAGAGCGTGATGCAGC<br>GCGTTGGTGTTGCCGCCTGGACCGTGCTGGGCGAAGCGAAAGGGGCA<br>GACCTGGAGCTGATGGGCTTCCAGCATCCGTTCCTCGACCATACCTCT<br>CCGGTTGTGCTGGGTGAGCATGTCACGCTGGAAGCCGGTACCGGTGC<br>GGTCCATACCGCACCAGGCCATGGCCCGGACGACTATGTTATCGGTC<br>AGAAATACGGTATCGAAGTGGCTAACCCGGTCGGCCCGGATGGCTGC<br>TACCTGCCGGGAACCTACCCGACGCTGGATGGTGTGAACGTCTTTAA<br>AGCCAACGATATGATCGTTGAACTGCTGCGTGAAAAGGGTGCTCTGC<br>TGCACGTTGAGAAACTGTTCCACAGCTATCCACACTGCTGGCGTCATA<br>AAACGCCCATCATCTTCCGCGCTACGCCACAGTGGTTTATCAGCATGG<br>ATCAGAAGGGCCTGCGTGCGCAGTCGCTGAAAGAGATCAAGGGCGTG<br>CAGTGGATCCCGGACTGGGGTCAGGCACGTATTGAATCGATGGTCGC<br>GAACCGTCCTGACTGGTGTATTTCCCGTCAGCGTACCTGGGGCGTGCC<br>GATGGCGCTGTTCGTCCATAAAGACACCGAACAGCTGCACCCGGATT<br>CGCTGGAGCTGATGGAGAAAGTGGCGAAGCGGGTTGAGCAGGACGG<br>CATTCAGGCATGGTGGGATCTTGATGCCCGCGACCTGATGGGCGCCG<br>ATGCTGACAACTACGTTAAAGTCCCGGATACCCTGGACGTCTGGTTTG<br>ACTCCGGTTCAACCAGCTACTCGGTCGTCGATGCCCGCCCTGAATTTG |

-continued

Sequence Listing

| Seq ID No. | Description | Sequence |
|---|---|---|
| | | ACGGCAATGCCCCTGACCTGTATCTGGAAGGATCGGATCAGCACCGC<br>GGCTGGTTTATGTCCTCACTGATGATCTCGACCGCGATGAAAGGCAA<br>AGCGCCTTACCGTCAGGTACTGACGCACGGCTTCACCGTCGATGGTCA<br>GGGCCGTAAGATGTCCAAGTCACTGGGCAATACTGTCAGCCCGCAGG<br>ATGTGATGAACAAACTGGGCGCCGATATTCTGCGCCTGTGGGTCGCCT<br>CTACGGACTACTCCGGTGAGATCGCCGTATCCGACGAGATCCTTAAA<br>CGCTCTGCCGACAGCTATCGCCGCATCCGTAACACCGCACGTTTCCTG<br>CTGGCAAACCTTGCCGGTTTTAATCCGGAAACCGATAGGGTGAAACC<br>GGAAGAGATGGTGGTGGATCGCTGGGCCGTTGGCCGTGCGCTGG<br>CGGCACAGAATGATATCGTAGCCTCGTATGAAGCTTATGACTTCCATG<br>AAGTCGTGCAGCGTCTGATGCAGTTCTGTTCGGTTGAGATGGGCTCCT<br>TCTACCTGGATATCATCAAGGATCGTCAGTACACCGCGAAGGCCGAT<br>GGCCTGGCGCGTCGCAGCTGTCAGACGGCGCTGTGGTATATCGTGGA<br>AGCGCTGGTGCGCTGGATGGCACCGATTATGTCCTTCACTGCCGATGA<br>AATCTGGGGTTACCTGCCGGGTAAACGCAGCCAGTATGTCTTTACCGA<br>AGAGTGGTTTGACGGGCTGTTCAGCCTGGAGGACAATCAGCCGATGA<br>ACGACAGTTACTGGGCAGAACTGCTGAAAGTACGCGGTGAAGTCAAC<br>AAGGTGATCGAGCAGGCCCGCGCTGATAAGCGGATTGGCGGGTCTCT<br>GGAAGCCAGCGTGACGCTGTATGCTGACGCAGACCTGGCCGCGAAGC<br>TGACCAGCCTGGGTGAGGAGCTGCGCTTTGTGTTGCTGACTTCCGGGG<br>CGCAGGTTGCGGATTATGCGCAGGCCACCGCTGATGCACAGCAAAGC<br>GAAGGGGTAAAAGGTCTGAAAATTGCCCTGAGCAAAGCGGAAGGCG<br>AGAAGTGCCCGCGCTGCTGGCATTACACTAACGATATCGGCCAGAAT<br>GCTGAACACGCTGACGTGTGCGGCCGTTGTGTCACTAACGTCGCGGG<br>CAGCGGCGAACAGCGTAAGTTTGCATGA |
| 105 | DP67 NADH-quinone oxidoreductase subunit C/D | GTGATCGGCGAGCTGCGTAATCGTTTTGGGCCTGATGCCTTTACAGTA<br>CAAGCGACCCGTACCGGCGTGCCGGTGGTCTGGGTAAAACGTGAGCA<br>GTTGCTTGAGATTATTGAGTTCCTGCGCAAGCTGCCTAAACCCTATGT<br>GATGCTGTATGACCTGCATGGCATGGATGAGCGCCTGCGTACTCACC<br>GTGCCGGTTTACCGGCGGCGGATTTTTCCGTTTTCTATCACTTCATCTC<br>CATTGAACGTAACCGCGACATCATGCTCAAGGTGGCGTTGTCTGAAA<br>ACGATTTGAATGTGCCCACCATCACCAAAATTTTCCCGAATGCCAACT<br>GGTATGAGCGTGAAACCTGGGAGATGTTTGGTATCAATGTTGAAGGC<br>CACCCGCACCTGACGCGCATTATGATGCCGCAGAGCTGGGAAGGGCA<br>TCCGCTGCGCAAAGATTACCCTGCGCGTGCGACCGAGTTCGATCCGTT<br>TGAACTGACCAAGCAGAAAGAAGATCTGGAGATGGAATCTCTGACCT<br>TCAAGCCTGAAGACTGGGGCATGAAGCGTTCGACCAACAATGAGGAC<br>TTCATGTTCCTCAACCTGGGCCCGAACCACCCTTCTGCGCACGGCGCG<br>TTCCGTATCATCCTGCAACTGGACGGTGAAGAGATCGTCGACTGCGTG<br>CCGGATATCGGATACCACCATCGTGGTGCCGAAAAAATGGGTGAACG<br>CCAGTCCTGGCACAGCTACATTCCGTATACCGACCGTATTGAGTATCT<br>CGGCGGCTGCGTAAACGAAATGCCGTACGTGCTGGCGGTAGAAAAGC<br>TGGCTGGTATCAAAGTCCCTGAGCGCGTGGAAGTCATTCGCGTGATG<br>CTATCAGAGCTGTTCCGTATAAACAGCCACCTGCTGTACATCTCTACG<br>TTTATCCAGGACGTCGGTGCTATGTCCCCGGTGTTCTTTGCCTTTACTG<br>ACCGCCAGAAAATTTACGACGTGGTAGAAGCCATTACCGGCTTCCGT<br>ATGCATCCGGCCTGGTTCCGCATTGGTGGCGTGGCGCATGATCTGCCT<br>AAAGGCTGGGAGCGCCTGCTGCGTGAGTTCCTGGATTGGATGCCTAA<br>GCGTCTGAAAGCCTATGAGCAGACCGCACTGAAAAACTCCGTGCTTA<br>TTGCCCGTTCCAAAGGGGTTTCTGCCTATAACATGGAAGAAGCACTG<br>GCCTGGGGCACGACGGGGGCTGGCCTGCGTGGTACCGGTCTGGACTT<br>TGATGTGCGTAAATGGCGTCCATATTCCGGTTATGAAAACTTCGATTT<br>CGAAGTGCCAATCGGAGATGGCGTAAGCTGTGCTTACACCCGTGTCA<br>TGCTGAAGATGGAAGAGATGCGCCAGAGTATGCGCATCCTGGAACAG<br>TGCCTGAAGAACATGCCAGCAGGCCCGTTCAAGGCTGACCATCCGCT<br>GACCACGCCGCCGCCGAAAGAGCGCACGCTGCAGCATATCGAAACCC<br>TGATCACTCACTTCCTGCAGGTTTCGTGGGGCCCGGTAATGCCGGCAA<br>ACGAATCCTTCCAGATGATTGAAGCGACCAAAGGGATCAACAGTTAC<br>TACCTGACCAGTGATGGCAGCACGATGAGCTACCGCACCCGCGTGCG<br>TACGCCGAGCTTCCCGCATTTGCAACAGATCCCATCGGTGATCAACGG<br>CAGCCTGGTATCCGATCTGATCGTATACCTCGGTAGTATCGATTTTGT<br>TATGTCAGACGTGGACCGCTAA |
| 106 | DP67 Protein RecA | ATGGCTATCGACGAAAACAAGCAAAAAGCACTGGCAGCAGCGCTGG<br>GCCAGATTGAAAAGCAGTTTGGTAAAGGCTCCATCATGCGCCTGGGT<br>GAAGACCGCACCATGGATGTGGAAACCATCTCAACCGGTTCTTTATC<br>ACTGGATATCGCGCTGGGTGCCGGTGGTTTACCAATGGGCCGTATCGT<br>TGAAATCTATGGCCCGGAGTCTTCCGGTAAAACCACCCTGACGCTGC<br>AGGTTATCGCTTCTGCACAGCGTAAAGGGAAAACCTGTGCATTTATCG<br>ATGCCGAGCATGCTCTGGACCCGGTCTACGCTAAAAAACTGGGCGTG<br>GATATCGATAACTTGCTGTGTTCTCAGCCGGATACCGGTGAGCAGGC<br>GCTGGAAATCTGTGATGCGCTGGCCCGTTCCGGTGCGGTTGACGTCAT |

-continued

Sequence Listing

| Seq ID No. | Description | Sequence |
|---|---|---|
| | | CATCGTCGACTCCGTAGCGGCGTTGACACCAAAAGCAGAAATCGAAG GTGAAATCGGTGACTCTCATATGGGCCTTGCGGCACGTATGATGAGC CAGGCGATGCGTAAGCTGGCCGGTAACCTGAAGAACTCCGGTACGCT GCTGATCTTTATCAACCAGATCCGTATGAAAATTGGCGTGATGTTCGG TAACCCGGAAACCACTACCGGTGGTAACGCTCTGAAATTCTACGCTTC TGTCCGTCTGGATATTCGCCGCATCGGCGCGATCAAAGAGGGTGATG AAGTGGTGGGTAGCGAAACCCGCGTTAAAGTGGTGAAAAACAAAATC GCAGCACCGTTTAAACAGGCTGAGTTCCAGATCATGTACGGCGAAGG TATCAACGTTTACGGTGAGCTGGTCGACCTGGGCGTGAAGCACAAGC TGATCGAAAAAGCCGGTGCCTGGTACAGCTATAACGGTGACAAGATT GGTCAGGGTAAAGCCAACTCAGGTAACTTCCTGAAAGAGAACCCGGC TATCGCTAACGAAATCGAAGCAAAACTGCGTGAAATGCTGTTGAACA GCCCGGACGATAAGCCTGATTTTGTTCCGGCTCCGCATGAAGCCGATA GTGAAGTTAACGAAGATATCTAA |
| 107 | RNA polymerase sigma factor RpoD | ATGGAGCAAAACCCGCAGTCACAGCTTAAGCTACTTGTCACCCGTGG TAAGGAGCAAGGCTATCTGACCTATGCCGAGGTCAATGACCATCTGC CGGAAGATATCGTCGACTCCGATCAGATTGAAGACATCATTCAGATG ATCAACGACATGGGCATTCAGGTTGTAGAAGAAGCGCCTGATGCCGA TGATTTGATGCTGAATGAGAACAACAACGACACGGACGAAGACGCTG CCGAAGCGGCTGCTCAGGTATTATCCAGCGTAGAATCTGAAATCGGA CGTACCACCGACCCGGTGCGCATGTACATGCGCGAAATGGGACGGT TGAACTGCTGACGCGTGAAGGCGAGATCGATATCGCCAAACGCATCG AAGAGGGTATCAACCAGGTACAGTGTTCCGTTGCTGAATATCCTGAA GCGATTACTTACCTGCTTGAGCAATATGACCGTGTTGAAGCGGGCGA AGCGCGCCTGTCGGATCTGATCACCGGTTTTGTCGACCCGAATGCCGA AGCAGAGATCGCCCCTACTGCGACTCACGTGGGTTCAGAACTTTCCGC TGAAGAGCGTGATGACGAAGAAGAAGACGAAGAGTCTGACGACGAC AGCTCGGATGATGACAACAGCATCGATCCGGAACTGGCGCGGGAAAA ATTCAACGACCTGCGCGTTCAGTACGAAACCACCCGTACCGTTATCAA AGCGAAAAGCCGCAGCCACGCTGATGCCATCGCTGAGATCCAGAATC TGTCCGACGTGTTCAAGCAGTTCCGCCTGGTGCCGAAGCAGTTCGACT TCCTGGTGAACAGCATGCGCACCATGATGGATCGCGTCCGTACTCAG GAACGCCTGATCCTCAAGCTGTGCGTAGAAATCTGTAAGATGCCGAA GAAGAACTTCATTACCCTGTTCACCGGTAATGAAACCAGCGAAACCT GGTTCAAAGCGGCACTGGCAATGAATAAGCCGTGGTCAGAGAAGCTG AACGATGTGTCAGATGACGTACACCGTAGCCTGATGAAGCTGCAGCA GATCGAAACGGAAACTGGCCTGACGATTGAACAGGTAAAAGACATCA ACCGTCGTATGTCGATCGGCGAAGCGAAAGCGCGCCGTGCGAAGAAA GAGATGGTTGAGGCTAACCTGCGTCTGGTTATCTCTATCGCCAAGAAG TACACCAACCGTGGCCTGCAGTTCCTGGATCTGATTCAGGAAGGTAA CATCGGTCTGATGAAAGCGGTGGATAAGTTTGAATATCGCCGTGGTT ATAAGTTCTCGACTTATGCCACCTGGTGGATCCGTCAGGCGATCACCC GTTCAATCGCTGACCAGGCGCGTACCATCCGTATTCCGGTGCACATGA TTGAGACGATTAACAAGCTCAACCGTATTTCCCGCCAGATGCTGCAA GAGATGGGCCGTGAGCCGACGCCGGAAGAGCTGGCCGAGCGTATGCT GATGCCGGAAGATAAGATCCGTAAGGTGCTGAAAATTGCCAAAGAGC CGATCTCTATGGAGACGCCGATTGGTGATGATGAAGATTCACATCTG GGTGATTTTATCGAAGACACCACGCTGGAGCTGCCGCTGGACTCCGC GACGTCAGAGAGCCTGCGTTCTGCCACGCACGACGTGCTGGCCGGTC TGACCGCGCGTGAAGCCAAAGTACTGCGTATGCGTTTCGGTATCGAT ATGAATACCGACCACACGCTGGAAGAAGTGGGCAAACAGTTCGACGT AACGCGTGAGCGTATTCGTCAGATTGAGGCGAAAGCGCTGCGTAAGC TGCGTCACCCAAGCCGCTCTGAAGTGCTGCGCAGCTTCCTCGACGATT AA |
| 108 | DNA-directed RNA polymerase subunit beta | ATGGTTTACTCCTATACCGAGAAAAAACGTATTCGTAAGGATTTTGGA AAGCGTCCACAAGTTCTGGACATTCCATATCTCCTTTCTATCCAGCTT GACTCGTTCCAGAAGTTCATCGAGCAAGATCCGGAAGGTCAATATGG TCTGGAAGCAGCATTCCGCTCCGTATTTCCAATCCAAAGCTATAGCGG TAATTCTGAGCTGCAGTACGTCAGCTACCGTTTAGGCGAACCCGTCTT TGATGTGAAAGAGTGTCAGATTCGTGGCGTCACGTATTCTGCTCCTCT GCGCGTAAAACTGCGCCTGGTGATCTACGAGCGCGAAGCGCCGGAAG GCACCGTTAAAGACATCAAAGAACAAGAAGTTTACATGGGCGAAATT CCGCTCATGACGGATAACGGTACCTTTGTTATCAACGGTACTGAGCGC GTTATCGTTTCTCAGCTCCACCGTAGTCCTGGTGTCTTCTTCGACAGCG ATAAGGGTAAAACCCACTCGTCCGGTAAAGTGCTGTATAACGCACGT ATCATCCCTTACCGTGGTTCATGGCTGGACTTCGAGTTCGACCCGAAA GACAACCTGTTCGTCCGTATTGACCGTCGCCGTAAACTGCCAGCGACC ATCATTCTGCGCGCGTTGAATTACACCACTGAACAGATCCTCGACCTG TTCTTCGATAAAGTGGTTTACCAAATTCGCGACAACAAGCTGCAGATG GAGCTTATTCCTGAGCGCCTGCGTGGTGAGACCGCTTCATTTGATATT GAAGCGAACGGCACCGTTTACGTCGAAAAAGGCCGCCGTATTACTGC |

-continued

Sequence Listing

| Seq ID No. | Description | Sequence |
|---|---|---|
| | | GCGCCATATTCGCCAGCTTGAGAAAGATGCTGTTGCCCACATCGAAG<br>TGCCGGTTGAGTATATTGCCGGTAAAGTGGTCGCTAAAGACTACGTTG<br>ATGAGAGCACCGGTGAACTGCTGATCGCAGCGAACATGGAACTGTCA<br>CTGGATCTGCTGGCTAAACTCAGCCAGTCCGGTCACAAGCGCATTGA<br>AACCCTGTTCACCAACGATCTGGATCACGGTGCGTACATGTCTGAGAC<br>GGTACGTGTCGACCCAACCAGCGATCGCCTGAGCGCTCTGGTTGAGA<br>TCTACCGCATGATGCGTCCTGGTGAGCCACCAACGCGTGAAGCGGCT<br>GAAAACCTGTTTGAGAACCTGTTCTTCTCTGAAGACCGCTATGATCTG<br>TCTGCGGTTGGTCGTATGAAGTTCAACCGTTCTCTGCTGCGCGACGAG<br>ATCGAAGGTTCCGGTATCCTGAGCAAAGACGACATCATTCAGGTGAT<br>GAAGAAGCTCATCGGTATCCGTAACGGTATTGGCGAAGTGGATGATA<br>TCGACCACCTCGGCAACCGTCGTATCCGTTCCGTTGGCGAAATGGCTG<br>AAAACCAGTTCCGTGTTGGCCTTGTGCGCGTAGAGCGTGCGGTGAAA<br>GAGCGTCTGTCCCTGGGCGATCTGGATACCCTGATGCCACAGGACAT<br>GATCAACGCCAAGCCAATTTCTGCGGCAGTGAAAGAGTTCTTCGGCT<br>CCAGCCAGCTGTCACAGTTTATGGACCAGAACAACCCGTTGTCTGAG<br>ATCACGCATAAGCGTCGTATCTCTGCACTGGGTCCGGGCGGTCTGACG<br>CGTGAGCGTGCAGGCTTCGAAGTTCGAGACGTACACCCGACGCACTA<br>CGGTCGCGTATGTCCAATCGAAACGCCGGAAGGTCCAAACATCGGTC<br>TGATCAACTCCTTGTCTGTGTATGCACAGACCAATGAGTACGGTTTCC<br>TGGAAACCCCATACCGTCGCGTTCGCGAAGGCGTGGTGACCGACGAA<br>ATTCATTACCTCTCTGCTATTGAAGAGGGTAACTACGTTATCGCTCAG<br>GCAAACACCAATCTCGACGACGAAGGTCACTTCGTAGACGACCTGGT<br>CACCTGCCGTAGCAAAGGCGAATCGAGTCTCTTCAACCGCGATCAAG<br>TTGACTACATGGACGTTTCCACCCAGCAGGTGGTTTCCGTCGGTGCGT<br>CACTGATCCCGTTCCTGGAGCACGATGACGCCAACCGCGCATTGATG<br>GGTGCAAACATGCAACGTCAGGCGGTTCCTACTCTGCGTGCTGATAA<br>GCCGCTGGTAGGTACCGGTATGGAGCGTGCGGTTGCGGTTGACTCCG<br>GTGTTACTGCCGTAGCGAAACGTGGTGGTACCGTGCAGTACGTGGAT<br>GCATCCCGTATCGTTATTAAAGTTAACGAAGACGAAATGTATCCGGG<br>CGAAGCCGGTATCGACATTTACAACCTGACCAAATATACCCGTTCTAA<br>CCAGAACACCTGCATCAACCAGATGCCTTGCGTGAACCTGGGTGAGC<br>CAATCGAACGTGGTGATGTGCTGGCTGATGGCCCTTCAACCGATCTCG<br>GCGAACTGGCACTCGGTCAGAACATGCGCGTCGCGTTCATGCCGTGG<br>AACGGCTACAACTTCGAAGACTCCATTCTGGTCTCGGAGCGCGTTGTT<br>CAGGAAGATCGCTTCACCACTATCCACATTCAGGAACTGGCGTGTGT<br>GTCTCGTGACACCAAGCTGGGGCCAGAAGAGATCACCGCTGACATCC<br>CTAACGTGGGTGAAGCTGCGCTCTCTAAACTGGATGAGTCCGGTATC<br>GTGTATATCGGTGCGGAAGTGACCGGTGGGGACATTCTGGTTGGTAA<br>GGTAACACCTAAAGGTGAAACCCAGCTGACGCCAGAAGAGAAACTG<br>CTGCGTGCGATCTTCGGTGAAAAAGCGTCTGACGTTAAAGACTCTTCT<br>CTGCGCGTACCAAACGGTGTGTCAGGGACAATCATCGACGTTCAGGT<br>CTTTACCCGCGATGGCGTGGAAAAAGACAAGCGTGCGCTGGAAATCG<br>AAGAGATGCAGCTGAAGCAGGCGAAGAAAGACCTGTCTGAAGAATT<br>GCAGATCCTCGAAGCCGGCTTGTTCAGCCGTATTAACTACCTGCTGGT<br>TGCCGGCGGTGTTGAAGCGGAAAAACTGGAGAAGCTGCCACGTGAGC<br>GCTGGCTCGAACTGGGCCTGACCGACGAAGAGAAGCAAAATCAGCTG<br>GAACAGCTGGCCGAGCAGTACGACGAGCTGAAGCACGAGTTTGAGA<br>AAAAACTTGAAGCCAAGCGCCGTAAAATCACTCAGGGCGATGACCTG<br>GCACCTGGCGTGCTGAAAATCGTGAAAGTGTATCTGGCCGTTAAACG<br>TCAGATCCAGCCTGGTGACAAAATGGCAGGTCGTCACGGGAACAAAG<br>GTGTTATCTCCAAGATCAACCCGATCGAAGATATGCCATACGATGAG<br>TTCGGTACGCCGGTCGACATCGTACTGAACCCGCTGGGCGTTCCATCA<br>CGTATGAACATTGGTCAGATTCTTGAAACCCACCTGGGTATGGCTGCG<br>AAAGGCATTGGCGAGAAAATTAACGCTATGCTTAAGAAGCAGGAAG<br>AAGTGTCCAAGCTGCGTGAATTCATTCAGCGTGCTTACGATCTGGGCA<br>GCGATCTGCGTCAGAAAGTTGACCTGAACACCTTCACCGATGACGAA<br>GTGCTGCGCCTGGCAGAGAATCTGAAAAAAGGTATGCCAATTGCAAC<br>ACCAGTGTTTGACGGCGCGAAAGAGAGCGAAATCAAAGAGCTGTTAC<br>AGCTCGGCGGCCTGCCTTCTTCTGGCCAGATCACGCTGTTTGATGGTC<br>GTACCGGTGAGCAGTTCGAACGTCAGGTTACCGTTGGCTACATGTAC<br>ATGCTGAAGCTGAACCACCTGGTTGATGACAAAATGCATGCGCGTTC<br>TACCGGTTCTTACAGCCTCGTTACTCAGCAGCCGCTGGGTGGTAAGGC<br>GCAGTTCGGTGGTCAGCGCTTCGGTGAGATGGAAGTGTGGGCACTGG<br>AAGCATACGGTGCCGCGTATACCCTGCAGGAAATGCTGACCGTGAAG<br>TCTGATGACGTTAACGGCCGTACCAAGATGTATAAAAACATCGTTGA<br>CGGCAACCATCAGATGGAACCGGGCATGCCGGAATCTTTCAACGTAC<br>TGTTGAAAGAGATCCGCTCGCTGGGTATCAACATCGAGCTGGAAGAC<br>GAGTAA |
| 109 | DP68 Glutamine-tRNA ligase | ATGAGCAAGCCCACTGTCGACCCTACCTCGAATTCCAAGGCCGGACC<br>TGCCGTCCCGGTCAATTTCCTGCGCCCGATCATCCAGGCGGACCTGGA<br>TTCGGGCAAGCACACGCAGATCGTCACCCGCTTCCCGCCAGAGCCCA |

-continued

Sequence Listing

| Seq ID No. | Description | Sequence |
|---|---|---|
| | | ACGGCTACCTGCACATCGGTCACGCCAAGTCGATCTGTGTGAACTTCG<br>GCCTGGCCCAGGAGTTCGGTGGCGTCACGCACCTGCGTTTCGACGAC<br>ACCAACCCGGCCAAGGAAGACCAGGAATACATCGACGCCATCGAAA<br>GCGACATCAAGTGGCTGGGCTTCGAATGGTCCGGTGAAGTGCGCTAT<br>GCGTCCAAGTATTTCGACCAGTTGTTCGACTGGGCCGTCGAGCTGATC<br>AAGGCCGGCAAGGCCTACGTCGACGACCTGACCCCGGAGCAGGCCAA<br>GGAATACCGTGGCACGCTGACCGAGCCGGGCAAGAACAGCCCGTTCC<br>GTGACCGTTCGGTAGAAGAGAACCTCGACTGGTTCAACCGCATGCGC<br>GCCGGTGAGTTCCCGGACGGCGCCCGCGTGCTGCGCGCCAAGATCGA<br>CATGGCCTCGCCGAACATGAACCTGCGCGACCCGATCATGTACCGCA<br>TCCGCCACGCCCATCACCACCAGACCGGTGACAAGTGGTGCATCTAC<br>CCGAACTATGACTTCACCCACGGTCAGTCGGACGCCATCGAAGGCAT<br>CACCCACTCCATCTGCACCCTGGAGTTCGAAAGCCATCGCCCGCTGTA<br>TGAGTGGTTCCTCGACAGCCTGCCGGTTCCGGCGCACCCGCGTCAGTA<br>CGAGTTCAGCCGCCTGAACCTGAACTACACCATCACCAGCAAGCGCA<br>AGCTCAAGCAGTTGGTGGACGAAAAGCACGTGCATGGCTGGGATGAC<br>CCGCGCATGTCCACCCTGTCGGGTTTCCGCCGTCGCGGCTACACCCCG<br>GCGTCGATCCGCAGCTTCTGCGACATGGTCGGCACCAACCGCTCCGA<br>CGGCGTGGTCGATTACGGCATGCTCGAGTTCAGCATCCGTCAGGACCT<br>GGACGCCAACGCGCCGCGTGCCATGTGCGTATTGCGCCCGTTGAAAG<br>TCGTGATCACCAACTATCCGGAAGACAAGGTCGACCACCTCGAACTG<br>CCGCGTCACCCGCAGAAAGAAGAACTTGGCGTGCGCAAGCTGCCGTT<br>CGCGCGTGAAATCTACATCGACCGTGATGACTTCATGGAAGAGCCGC<br>CGAAAGGCTACAAGCGCCTGGAGCCTAACGGCGAAGTGCGCCTGCGC<br>GGCAGCTACGTGATCCGTGCCGATGAAGCGATCAAGGACGCCGATGG<br>CAACATCGTCGAACTGCGATGCTCCTACGACCCGGAAACCCTGGGCA<br>AGAACCCTGAAGGCCGCAAGGTCAAAGGCGTCGTTCACTGGGTGCCG<br>GCTGCTGCCAGCATCGAGTGCGAAGTGCGCCTGTACGATCGTCTGTTC<br>CGTTCGCCGAACCCTGAGAAGGCTGAAGACAGCGCCAGCTTCCTGGA<br>CAACATCAACCCTGACTCCCTGCAAGTTCTCACGGGTTGTCGTGCCGA<br>GCCATCGCTTGGCGACGCACAGCCGGAAGACCGTTTCCAGTTCGAGC<br>GCGAAGGTTACTTCTGCGCGGATATCAAGGACTCCAAACCTGGTCAT<br>CCGGTCTTCAACCGTACCGTGACCTTGCGTGATTCGTGGGGCCAGTG |
| 110 | DP68 DNA gyrase subunit B | ATGAGCGAAGAAAACACGTACGACTCGACCAGCATTAAAGTGCTGAA<br>AGGTTTGGATGCCGTACGCAAACGTCCCGGTATGTACATCGGCGACA<br>CCGATGATGGTAGCGGTCTGCACCACATGGTGTTCGAGGTGGTCGAC<br>AACTCCATCGACGAAGCTTTGGCCGGTCACTGCGACGACATCAGCAT<br>TATCATCCACCCGGATGAGTCCATCACCGTGCGCGACAACGGTCGCG<br>GTATTCCGGTCGATGTGCACAAAGAAGAAGGCGTATCGGCGGCAGAG<br>GTCATCATGACCGTGCTTCACGCCGGCGGTAAGTTCGACGACAACTCC<br>TATAAAGTTTCCGGCGGTTTGCACGGTGTAGGTGTGTCGGTGGTGAAC<br>GCTCTGTCCGAAGAGCTTATCCTGACTGTTCGCCGTAGCGGCAAGATC<br>TGGGAACAGACCTACGTGCATGGTGTTCCACAAGAACCGATGAAAAT<br>CGTTGGCGACAGTGAATCCACCGGTACGCAGATCCACTTCAAGCCTTC<br>GGCAGAAACCTTCAAGAATATCCACTTCAGTTGGGACATCCTGGCCA<br>AGCGTATTCGTGAACTGTCGTTCCTTAACTCCGGTGTGGGTATCGTCC<br>TCAAGGACGAGCGCAGCGGCAAGGAAGAGTTGTTCAAGTACGAAGG<br>CGGCTTGCGTGCGTTCGTTGAGTACCTGAACACCAACAAGACTGCGG<br>TCAACCAGGTGTTCCACTTCAACATCCAGCGTGAAGACGGTATCGGC<br>GTTGAAATCGCCCTGCAGTGGAACGACAGCTTCAACGAGAACCTGTT<br>GTGCTTCACCAACAACATTCCACAGCGCGACGGCGGTACTCACTTGGT<br>GGGTTTCCGTTCCGCACTGACGCGTAACCTGAACACCTACATCGAAGC<br>GGAAGGCTTGGCCAAGAAGCACAAAGTGGCCACTACCGGTGACGATG<br>CGCGTGAAGGCCTGACGGCGATTATCTCGGTGAAAGTGCCGGATCCA<br>AAGTTCAGCTCCCAGACCAAAGACAAGCTGGTGTCTTCCGAAGTGAA<br>GACCGCAGTGGAACAGGAGATGGGCAAGTACTTCTCCGACTTCCTGC<br>TGGAAAACCCGAACGAAGCCAAGTTGGTTGTCGGCAAGATGATCGAC<br>GCGGCGCGTGCCCGTGAAGCGGCGCGTAAAGCCCGTGAGATGACCCG<br>CCGTAAAGGCGCGTTGGATATCGCCGGCCTGCCGGGCAAACTGGCTG<br>ACTGCCAGGAGAAGGACCCTGCCCTCTCCGAACTGTACCTGGTGGAA<br>GGTGACTCTGCTGGCGGTTCCGCCAAGCAGGGTCGTAACCGTCGCAC<br>CCAGGCTATCCTGCCGTTGAAGGGTAAGATCCTCAACGTCGAGAAGG<br>CCCGCTTCGACAAGATGATTTCCTCTCAGGAAGTCGGCACCTTGATCA<br>CGGCGTTGGGCTGCGGTATTGGCCGCGATGAGTACAACATCGACAAA<br>CTGCGTTACCACAACATCATCATCATGACCGATGCTGACGTCGACGGT<br>TCGCACATCCGTACCCTGCTGCTGACCTTCTTCTTCCGTCAGTTGCCGG<br>AGCTGATCGAGCGTGGCTACATCTACATCGCTCAGCCGCCGTTGTACA<br>AAGTGAAAAAGGGCAAGCAAGAGCAGTACATCAAAGACGACGACGC<br>CATGGAAGAGTACATGACGCAGTCGGCCCTGGAAGATGCCAGCCTGC<br>ACTTGAACGACGAAGCCCCGGGCATTTCCGGTGAGGCGCTGGAGCGT<br>TTGGTTAACGACTTCCGCATGGTAATGAAGACCCTCAAGCGTCTGTCG<br>CGCCTGTACCCTCAGGAGCTGACCGAGCACTTCATCTACCTGCCTTCC |

-continued

Sequence Listing

| Seq ID No. | Description | Sequence |
| --- | --- | --- |
| | | GTGAGCCTGGAGCAGTTGGGCGATCACGCCCACATGCAGAATTGGCT<br>GGCTCAGTACGAAGTACGTCTGCGCACCGTCGAGAAGTCTGGCCTGG<br>TTTACAAAGCCAGCTTGCGTGAAGACCGTGAACGTAACGTGTGGCTG<br>CCGGAGGTTGAACTGATCTCCCACGGCCTGTCGAACTACGTCACCTTC<br>AACCGCGACTTCTTCGGCAGCAACGACTACAAGACCGTGGTTACCCT<br>CGGCGCGCAATTGAGCACCCTGTTGGACGACGGTGCTTACATCCAGC<br>GTGGCGAGCGTAAGAAAGCGGTCAAGGAGTTCAAGGAAGCCCTGGA<br>CTGGTTGATGGCTGAAAGCACCAAGCGCCACACCATCCAGCGATACA<br>AAGGTCTGGGCGAGATGAACCCGGATCAACTGTGGGAAACCACCATG<br>GATCCTGCTCAGCGTCGCATGCTACGCGTGACCATCGAAGACGCCATT<br>GGCGCAGACCAGATCTTCAACACCCTGATGGGTGATGCGGTCGAGCC<br>TCGCCGTGACTTCATCGAGAGCAACGCCTTGGCGGTGTCTAACCTGGA<br>TTTCTGA |
| 111 | DP68 Isoleucine 1RNA ligase | ATGACCGACTATAAAGCCACGCTAAACCTTCCGGACACCGCCTTCCC<br>AATGAAGGCCGGCCTGCCACAGCGCGAACCGCAGATCCTGCAGCGCT<br>GGGACAGTATTGGCCTGTACGGAAAGTTGCGCGAAATTGGCAAGGAT<br>CGTCCGAAGTTCGTCCTGCACGACGGCCCTCCTTATGCCAACGGCACG<br>ATTCACATCGGTCATGCGCTGAACAAAATTCTCAAGGACATGATCCTG<br>CGTTCGAAAACCCTGTCGGGCTTCGACGCGCCTTATGTTCCGGGCTGG<br>GACTGCCACGGCCTGCCGATCGAACACAAAGTCGAAGTGACCTACGG<br>CAAGAACCTGGGCGCGGATAAAACCCGCGAACTGTGCCGTGCCTACG<br>CCACCGAGCAGATCGAAGGGCAGAAGTCCGAATTCATCCGCCTGGGC<br>GTGCTGGGCGAGTGGGACAACCCGTACAAGACCATGAACTTCAAGAA<br>CGAGGCCGGTGAAATCCGTGCCTTGGCTGAAATCGTCAAAGGCGGTT<br>TCGTGTTCAAGGGCCTCAAGCCCGTGAACTGGTGCTTCGACTGCGGTT<br>CGGCCCTGGCTGAAGCGGAAGTCGAGTACGAAGACAAGAAGTCCTCG<br>ACCATCGACGTGGCCTTCCCGATCGCCGACGACGACAAGCTGGCTCA<br>AGCCTTTGGCCTGTCCAGCCTGCCAAAGCCTGCAGCCATCGTGATCTG<br>GACCACCACCCCGTGGACCATCCCGGCCAACCAGGCGCTGAACGTGC<br>ACCCGGAATTCACCTACGCCCTGGTGGACGTCGGTGATCGCCTGCTGG<br>TGCTGGCTGAAGAAATGGTCGAGGCCTGCCTGGCGCGCTACGAGCTG<br>CAAGGTTCGGTCATCGCCACCACCACCGGCACTGCGCTGGAGCTGAT<br>CAATTTCCGTCACCCGTTCTATGACCGTCTGTCGCCGGTGTACCTGGC<br>TGACTACGTAGAGCTGGGTTCGGGTACTGGTGTGGTTCACTCCGCGCC<br>GGCCTACGGCGTTGATGACTTTGTGACCTGCAAAGCCTACGGCATGGT<br>CAACGATGACATCCTCAACCCGGTGCAGAGCAATGGCGTGTACGCGC<br>CGTCGCTGGAGTTCTTTGGCGGCCAGTTCATCTTCAAGGCCAACGAGC<br>CGATCATCGACAAACTGCGTGAAGTCGGTTCGCTGCTGCACACCGAA<br>ACCATCAAGCACAGCTACATGCACTGCTGGCGTCACAAGACCCCGCT<br>GATCTACCGCGCTACCGCGCAGTGGTTTATCGGCATGGACAAAGAGC<br>CGACCAGCGGCGACACCCTGCGTGTGCGCTCGCTCAAAGCGATCGAA<br>GAGACCAAGTTTGTCCCGGCCTGGGGCCAGGCGCGCCTGCACTCGAT<br>GATCGCCAACCGCCCGGACTGGTGCATCTCCCGCCAGCGCAACTGGG<br>GCGTGCCGATTCCGTTCTTCCTGAACAAGGAAAGCGGCGAGCTGCAC<br>CCACGTACCGTTGAACTGATGGAAGCAGTGGCGCTGCGCGTTGAGCA<br>GGAAGGCATCGAAGCCTGGTTCAAGCTGGACGCCGCCGAACTGCTGG<br>GCGACGAAGCGCCGCTGTACGACAAGATCAGCGACACCCTCGACGTG<br>TGGTTCGACTCGGGTACCACCCACTGGCACGTGCTGCGCGGTTCGCAC<br>CCGATGGGTCACGCCACCGGCCCGCGTGCCGACCTGTACCTGGAAGG<br>CTCGGACCAACACCGTGGCTGGTTCCACTCGTCGTTGCTGACCGGCTG<br>CGCCATCGACAACCACGCGCCGTACCGCGAACTGCTGACCCACGGCT<br>TCACCGTCGACGAGACGGGCCGCAAGATGTCCAAGTCGCTGAAAAAC<br>GTGATCGAGCCGAAAAAGATCAACGACACCCTGGGCGCCGATATCAT<br>GCGTCTGTGGGTCGCCTCGACCGATTACTCGGGCGAAATCGCCGTGTC<br>GGACCAGATCCTGGCCCGTAGCGCCGATGCCTACCGCCGTATCCGTA<br>ATACCGCACGCTTCCTGCTGTCGAACCTGACCGGTTTCAACCCGGCCA<br>CCGACATCCTGCCGGCCGAGGACATGCTCGCCCTGGACCGTTGGGCC<br>GTGGACCGTACGCTGTTGCTGCAGCGCGAGTTGCAGGAACACTACGG<br>CGAATACCGTTTCTGGAACGTGTACTCCAAGATCCACAACTTCTGCGT<br>GCAGGAGCTGGGTGGTTTCTACCTCGATATCATCAAGGACCGCCAGT<br>ACACCACCGGCGCCAACAGCAAGGCGCGCCGCTCGGCGCAGACCGC<br>GCTGTACCACATCTCTGAAGCGCTGGTGCGCTGGATCGCACCGATCCT<br>GGCCTTCACCGCTGACGAACTGTGGGAATACCTGCCGGGCGAGCGTA<br>ACGAATCGGTGATGCTCAACACCTGGTACGAAGGCCTGACCGAATTG<br>CCGGCCAACTTCGAACTGGGCCGCGAGTACTGGGAAGGCGTGATGGC<br>CGTCAAGGTTGCGGTGAACAAGGAGCTGGAAGTTCAGCGCGCGGCCA<br>AGGCCGTCGGTGGCAACCTGCAAGCCGAAGTCACCCTGTTTGCCGAG<br>GAAGGCCTGACCGCCGACCTGGCCAAGCTGAGCAACGAACTGCGCTT<br>CGTACTGATCACCTCGACCGCGAGCCTGGCACCGTTTGCCCAGGCACC<br>TGCGGACGCAGTGGCCACCGAAGTGCCGGGCCTCAAGCTCAAAGTGG<br>TCAAGTCGGCCTTTCCTAAGTGCGCCCGTTGCTGGCACTGCCGTGAAG<br>ACGTCGGCGTGAACCCAGAGCATCCGGAAATCTGCGGTCGTTGCGTC |

-continued

Sequence Listing

| Seq ID No. | Description | Sequence |
|---|---|---|
| | | GACAACATCAGCGGTGCTGGCGAGGTTCGCCACTATGCCTAA |
| 112 | DP68 NADH-quinone oxidoreductase subunit C/D | ATGACTACAGGCAGTGCTCTGTACATCCCGCCTTACAAGGCAGACGA CCAGGATGTGGTTGTCGAACTCAATAACCGTTTTGGCCCTGACGCCTT CACCGCCCAGGCCACACGCACCGGTATGCCGGTGCTGTGGGTGGCGC GCGCCAAGCTCGTCGAAGTCCTGAGCTTCCTGCGCAACCTGCCCAAG CCGTACGTCATGCTTTATGACCTGCATGGCGTGGACGAGCGTCTGCGC ACCAAGCGTCAAGGTTTGCCGAGCGGTGCCGATTTCACCGTGTTCTAC CACTTGATGTCGCTGGAACGTAACAGCGACGTGATGATCAAGGTCGC GCTGTCCGAAAGCGACTTGAGCATCCCGACCGTCACCGGTATCTGGC CGAATGCCAGCTGGTACGAGCGCGAAGTTTGGGACATGTTCGGTATC GACTTCCCGGGCCACCCGCACCTGACGCGCATCATGATGCCGCCGAC CTGGGAAGGTCACCCGCTGCGCAAGGACTTTCCTGCCCGCGCAACCG AATTCGACCCGTTCAGCCTCAACCTCGCCAAGCAGCAGCTTGAAGAA GAAGCTGCACGCTTCCGTCCGGAAGACTGGGGCATGAAACGCTCCGG CACCAACGAGGACTACATGTTCCTCAACCTGGGCCCGAACCACCCTTC GGCTCACGGTGCCTTCCGTATCATCCTGCAACTGGACGGCGAAGAAA TCGTCGACTGTGTGCCGGACATCGGTTACCACCACCGTGGTGCCGAG AAGATGGCCGAGCGCCAGTCCTGGCACAGCTTCATCCCGTACACCGA CCGTATCGACTACCTCGGCGGCGTGATGAACAACCTGCCGTACGTGCT GTCGGTCGAGAAGCTGGCCGGTATCAAGGTGCCGGACCGCGTCGACA CCATCCGCATCATGATGGCCGAGTTCTTCCGCATCACCAGCCACCTGC TGTTCCTGGGTACCTATATCCAGGACGTTGGCGCCATGACCCCGGTGT TCTTCACCTTCACCGACCGTCAACGCGCCTACAAGGTGATCGAAGCCA TCACCGGTTTCCGCCTGCACCCGGCCTGGTATCGCATCGGCGGCGTGG CGCACGACCTGCCGAACGGCTGGGAGCGCCTGGTCAAGGAATTCATC GACTGGATGCCCAAGCGTCTGGACGAGTACCAAAAGGCTGCGCTGGA CAACAGCATCCTCAAGGGTCGTACCATCGGCGTCGCGCAGTACAACA CCAAAGAAGCCCTGGAATGGGGCGTCACTGGTGCCGGCCTGCGTTCG ACCGGCTGCGACTTCGACCTGCGTAAAGCACGGCCGTACTCGGGCTA CGAGAACTTCGAGTTCGAAGTGCCGCTGGCCGCCAATGGCGATGCCT ACGACCGGTGCATCGTGCGCGTTGAAGAAATGCGCCAGAGCCTGAAG ATCATCGAGCAGTGCATGCGCAACATGCCGGCTGGCCCGTACAAGGC GGATCATCCGCTGACCACACCGCCGCCGAAAGAGCGCACGCTGCAGC ACATCGAAACCCTGATCACGCACTTCCTGCAAGTTTCGTGGGGCCCGG TGATGCCGGCCAACGAATCCTTCCAGATGATCGAAGCGACCAAGGGT ATCAACAGTTATTACCTGACGAGCGATGGCGGCACCATGAGCTACCG CACCCGGATTCGTACCCCAAGCTTTGCCCACTTGCAGCAGATCCCTTC GGTGATCAAAGGCGAGATGGTCGCGGACTTGATTGCGTACCTGGGTA GTATCGATTTCGTTATGGCCGACGTGGACCGCTAA |
| 113 | DP68 Protein RecA | ATGGACGACAACAAGAAGAAAGCCTTGGCTGCGGCCCTGGGTCAGAT CGAACGTCAATTCGGCAAGGGTGCCGTAATGCGTATGGGCGATCACG ACCGTCAGGCGATCCCGGCTATTTCCACTGGCTCTCTGGGTCTGGACA TCGCACTCGGCATTGGCGGCCTGCCAAAAGGCCGTATCGTTGAAATCT ACGGTCCTGAATCTTCCGGTAAAACCACCCTGACCCTGTCGGTGATTG CCCAGGCGCAAAAAATGGGCGCCACCTGTGCGTTCGTCGACGCCGAG CACGCCCTGGACCCGGAATACGCCGGTAAGCTGGGCGTCAACGTTGA CGACCTGCTGGTTTCCCAGCCGGACACCGGTGAGCAAGCCCTGGAAA TCACCGACATGCTGGTGCGCTCCAACGCCATCGACGTGATCGTGGTCG ACTCCGTGGCTGCCCTGGTACCGAAAGCTGAAATCGAAGGCGAAATG GGCGACATGCACGTGGGCCTGCAAGCCCGCCTGATGTCCCAGGCGCT GCGTAAAATTACCGGTAACATCAAGAACGCCAACTGCCTGGTGATCT TCATCAACCAGATCCGTATGAAGATCGGCGTAATGTTCGGCAGCCCG GAAACCACTACCGGTGGTAACGCGCTGAAGTTCTACGCTTCGGTCCGT CTGGACATCCGCCGTACCGGCGCGGTGAAGGAAGGTGACGAAGTTGT TGGTAGCGAAACTCGCGTTAAAGTCGTGAAGAACAAGGTCGCTCCGC CTTTCCGTCAGGCAGAGTTCCAGATTCTCTACGGCAAGGGTATCTACC TGAACGGCGAGATGATTGACCTGGGCGTACTGCACGGTTTCGTCGAG AAGTCCGGTGCCTGGTATGCCTACAACGGCAGCAAGATCGGTCAGGG CAAGGCCAACTCGGCCAAGTTCCTGGCAGACAACCCGGATATCGCTG CCACGCTTGAGAAGCAGATTCGCGACAAGCTGCTGACCCCAGCGCCA GACGTGAAAGCTGCCGCCAACCGCGAGCCGGTTGAAGAAGTGGAAG AAGCTGACACTGATATCTGA |
| 114 | DP68 RNA polymerase sigma factor RpoD | ATGTCCGGAAAAGCGCAACAACAGTCTCGTATTAAAGAGTTGATCAC CCTTGGTCGTGAGCAGAAATATCTGACTTACGCAGAGGTCAACGATC ACCTGCCTGAGGATATTTCAGATCCTGAGCAGGTGGAAGACATCATC CGCATGATTAATGACATGGGGATCCCCGTACACGAGAGTGCTCCGGA TGCGGACGCCCTTATGTTGGCCGACTCCGATACCGACGAGGCAGCTG CTGAAGAAGCGGCTGCTGCGCTGGCAGCGGTGGAGACCGACATCGGT CGTACGACTGACCCTGTGCGCATGTATATGCGTGAAATGGGTACCGTC GAGCTGCTGACACGTGAAGGCGAAATCGAAATCGCCAAACGTATTGA |

-continued

Sequence Listing

| Seq ID No. | Description | Sequence |
|---|---|---|
| | | AGAGGGTATCCGTGAAGTGATGGGCGCAATCGCGCACTTCCCTGGCA CGGTTGACCACATTCTCTCCGAGTACACTCGCGTCACCACCGAAGGTG GCCGCCTGTCTGACGTTCTGAGCGGCTACATCGACCCGGACGACGGC ATTGCGCCGCCTGCCGCCGAAGTACCGCCGCCCGTCGATGCGAAAGC CGCGAAGGCTGACGACGACACCGAAGACGACGATGCTGAAGCCAGC AGCGACGACGAAGATGAAGTTGAAAGCGGCCCGGACCCGATCATCGC AGCCCAGCGTTTCGGTGCGGTTTCCGATCAAATGGAAATCACCCGCA AGGCCCTGAAAAAGCACGGTCGCTCCAACAAGCTGGCGATTGCCGAG CTGGTGGCCCTGGCTGAGCTGTTCATGCCGATCAAGCTGGTACCGAA GCAATTCGAAGGCTTGGTTGAGCGTGTTCGCAGTGCCCTTGAACGTCT GCGTGCGCAAGAACGCGCAATCATGCAGCTGTGTGTACGTGATGCAC GTATGCCGCGGGCTGACTTCCTGCGCCAGTTCCCGGGCAACGAAGTA GACGAAAGCTGGACCGACGCACTGGCCAAAGGCAAGGCGAAATACG CCGAAGCCATTGGTCGCCTGCAGCCGGACATCATCCGTTGCCAGCAG AAGCTGACCGCGCTTGAGACCGAAACCGGTCTGACGATTGCTGAAAT CAAAGACATCAACCGTCGCATGTCGATCGGTGAGGCCAAGGCCCGCC GCGCGAAGAAAGAGATGGTTGAAGCGAACTTGCGTCTGGTGATCTCG ATCGCCAAGAAGTACACCAACCGTGGTCTGCAATTCCTCGATCTGATC CAGGAAGGCAACATCGGCTTGATGAAGGCGGTGGACAAGTTCGAATA CCGTCGCGGCTACAAGTTCTCGACTTATGCCACCTGGTGGATCCGTCA GGCGATCACTCGCTCGATCGCCGACCAGGCTCGCACCATCCGTATTCC GGTGCACATGATCGAGACGATCAACAAGCTCAACCGTATTTCCCGGC AGATGTTGCAGGAAATGGGTCGCGAACCGACCCCGGAAGAGCTGGGC GAACGCATGGAAATGCCTGAGGATAAAATCCGCAAGGTATTGAAGAT CGCTAAAGAGCCGATCTCCATGGAAACGCCGATTGGTGATGACGAAG ACTCCCACCTGGGTGACTTCATCGAAGACTCGACCATGCAGTCGCCA ATCGATGTCGCCACTGTTGAGAGCCTTAAAGAAGCGACTCGCGACGT ACTGTCCGGCCTCACTGCCCGTGAAGCCAAGGTACTGCGCATGCGTTT CGGCATCGACATGAATACCGACCACACCCTTGAGGAAGTCGGTAAGC AGTTTGACGTGACCCGCGAGCGGATCCGTCAGATCGAAGCCAAGGCG CTGCGCAAGTTGCGCCACCCGACGCGAAGCGAGCATCTGCGCTCCTT CCTCGACGAGTGA |
| 115 | DP68 DNA-directed RNA polymerase subunit beta | ATGGCTTACTCATATACTGAGAAAAAACGTATCCGCAAGGACTTTAG CAAGTTGCCGGACGTCATGGATGTCCCGTACCTTCTGGCTATCCAGCT GGATTCGTATCGTGAATTCTTGCAGGCGGGAGCGACCAAAGATCAGT TCCGCGACGTGGGCCTGCATGCGGCCTTCAAATCCGTTTTCCCGATCA TCAGCTACTCCGGCAATGCTGCGCTGGAGTACGTGGGTTATCGCCTGG GCGAACCGGCATTTGATGTCAAAGAATGCGTGTTGCGCGGTGTTACG TACGCCGTACCTTTGCGGGTAAAAGTCCGCCTGATCATTTTCGACAAA GAATCGTCGAACAAAGCGATCAAGGACATCAAAGAGCAAGAAGTCT ACATGGGCGAAATCCCACTGATGACTGAAAACGGTACCTTCGTAATC AACGGTACCGAGCGTGTTATTGTTTCCCAGCTGCACCGTTCCCCGGGC GTGTTCTTCGACCACGACCGCGGCAAGACGCACAGCTCCGGTAAACT CCTGTACTCCGCGCGGATCATTCCGTACCGCGGTTCGTGGTTGGACTT CGAGTTCGACCCGAAAGACTGCGTGTTCGTGCGTATCGACCGTCGTCG CAAGCTGCCGGCCTCGGTACTGCTGCGCGCGCTCGGTTACACCACTGA GCAGGTGCTGGACGCTTTCTACACCACCAACGTATTCAGCCTGAAGG ATGAAACCCTCAGCCTGGAGCTGATTGCTTCGCGTCTGCGTGGTGAAA TTGCCGTTCTGGACATTCAGGACGAAAACGGCAAAGTGATCGTTGAA GCGGGTCGTCGTATTACTGCGCGCCACATCAACCAGATCGAAAAAGC CGGCATCAAGTCGCTGGAAGTGCCTCTGGACTACGTCCTGGGTCGCA CCACCGCCAAGGTTATCGTTCACCCGGCTACAGGCGAAATCCTGGCT GAGTGCAACACCGAGCTGAACACCGAAATCCTGGCAAAAATCGCCAA GGCCCAGGTTGTTCGCATCGAGACCCTGTACACCAACGACATCGACT GCGGTCCGTTCATCTCCGACACACTGAAGATCGACTCCACCAGCAAC CAATTGGAAGCGCTGGTCGAGATCTATCGCATGATGCGTCCTGGTGA GCCACCGACCAAAGACGCTGCCGAGACCCTGTTCAACAACCTGTTCTT CAGCCCTGAGCGTTATGACCTGTCTGCGGTCGGCCGGATGAAGTTCA ACCGTCGTATCGGTCGTACCGAGATCGAAGGTTCGGGCGTGCTGTGC AAGGAAGATATCGTCGCGGTACTGAAGACTCTGGTCGACATCCGTAA CGGTAAAGGCATCGTCGATGACATCGACCACCTGGGTAACCGTCGTG TTCGCTGCGTAGGCGAAATGGCCGAAAACCAGTTCCGCGTTGGCCTT GTGCGTGTTGAACGTGCGGTCAAAGAGCGTCTGTCGATGGCTGAAAG CGAAGGCCTGATGCCGCAAGACCTGATCAACGCCAAGCCAGTGGCTG CGGCAGTGAAAGAGTTCTTCGGTTCCAGCCAGCTTTCCCAGTTCATGG ACCAGAACAACCCGCTCTCCGAGATCACCCACAAGCGCCGTGTTTCT GCACTGGGCCCGGGCGGTCTGACCCGTGAGCGTGCTGGCTTTGAAGT TCGTGACGTACACCCGACGCACTACGGTCGTGTTTGCCCGATCGAAAC GCCGGAAGGTCCGAACATCGGTCTGATCAACTCCCTGGCCGCTTATGC GCGCACCAACCAGTACGGCTTCCTCGAGAGCCCGTACCGCGTGGTGA AAGACGCTCTGGTCACCGACGAGATCGTATTCCTGTCCGCCATCGAA GAAGCTGATCACGTGATCGCTCAGGCTTCGGCCACGATGAACGACAA |

-continued

Sequence Listing

| Seq ID No. | Description | Sequence |
|---|---|---|
| | | GAAAGTCCTGATCGACGAGCTGGTAGCTGTTCGTCACTTGAACGAGTT CACCGTCAAGGCGCCGGAAGACGTCACCTTGATGGACGTTTCGCCGA AGCAGGTAGTTTCGGTTGCAGCGTCGCTGATCCCGTTCCTGGAACACG ATGACGCCAACCGTGCGTTGATGGGTTCCAACATGCAGCGTCAAGCT GTACCAACCCTGCGCGCTGACAAGCCGCTGGTAGGTACCGGCATGGA GCGTAACGTAGCCCGTGACTCCGGCGTTTGCGTCGTAGCCCGTCGTGG CGGCGTGATCGACTCCGTTGATGCCAGCCGTATCGTGGTTCGTGTTGC CGATGATGAAGTTGAAACTGGCGAAGCCGGTGTCGACATCTACAACC TGACCAAATACACCCGCTCGAACCAGAACACCTGCATCAACCAGCGT CCGCTGGTGAGCAAGGGTGACCGCGTTCAGCGTAGCGACATCATGGC CGACGGCCCGTCCACTGACATGGGTGAACTGGCTCTGGGTCAGAACA TGCGCATCGCGTTCATGGCATGGAACGGCTTCAACTTCGAAGACTCCA TCTGCCTGTCCGAGCGTGTTGTTCAAGAAGACCGTTTCACCACGATCC ACATTCAGGAACTGACCTGTGTGGCACGTGATACCAAGCTTGGGCCA GAGGAAATCACTGCAGACATCCCGAACGTGGGTGAAGCTGCACTGAA CAAGCTGGACGAAGCCGGTATCGTTTACGTAGGTGCTGAAGTTGGCG CAGGCGACATCCTGGTAGGTAAGGTCACTCCGAAAGGCGAGACCCAA CTGACTCCGGAAGAGAAGCTGCTGCGTGCCATCTTCGGTGAAAAAGC CAGCGACGTTAAAGACACCTCCCTGCGTGTACCTACCGGTACCAAGG GTACTGTTATCGACGTACAGGTCTTCACCCGTGACGGCGTTGAGCGTG ATGCTCGTGCACTGTCCATCGAGAAGACTCAACTCGACGAGATCCGC AAGGACCTGAACGAAGAGTTCCGTATCGTTGAAGGCGCGACCTTCGA ACGTCTGCGTTCCGCTCTGGTAGGCCACAAGGCTGAAGGCGGCGCAG GTCTGAAGAAAGGTCAGGACATCACCGACGAAGTACTCGACGGTCTT GAGCACGGCCAGTGGTTCAAACTGCGCATGGCTGAAGATGCTCTGAA CGAGCAGCTCGAGAAGGCCCAGGCCTACATCGTTGATCGCCGTCGTC TGCTGGACGACAAGTTCGAAGACAAGAAGCGCAAACTGCAGCAGGG CGATGACCTGGCTCCAGGCGTGCTGAAAATCGTCAAGGTTTACCTGG CAATCCGTCGCCGCATCCAGCCGGGCGACAAGATGGCCGGTCGTCAC GGTAACAAAGGTGTGGTCTCCGTGATCATGCCGGTTGAAGACATGCC GCACGATGCCAATGGCACCCCGGTCGACGTCGTCCTCAACCCGTTGG GCGTACCTTCGCGTATGAACGTTGGTCAGATCCTCGAAACCCACCTGG GCCTCGCGGCCAAAGGTCTGGGCGAGAAGATCAACCGTATGATCGAA GAGCAGCGCAAGGTTGCTGACCTGCGTAAGTTCCTGCACGAGATCTA CAACGAGATCGGCGGTCGCAACGAAGAGCTGGACACCTTCTCCGACC AGGAAATCCTGGACTTGGCGAAGAACCTGCGCGGCGGCGTTCCAATG GCTACCCCGGTGTTCGACGGTGCCAAGGAAAGCGAAATCAAGGCCAT GCTGAAACTGGCAGACCTGCCGGAAAGCGGCCAGATGCAGCTGTTCG ACGGCCGTACCGGCAACAAGTTTGAGCGCCCGGTTACTGTTGGCTAC ATGTACATGCTGAAGCTGAACCACTTGGTAGACGACAAGATGCACGC TCGTTCTACCGGTTCGTACAGCCTGGTTACCCAGCAGCCGCTGGGTGG TAAGGCTCAGTTCGGTGGTCAGCGTTTCGGGGAGATGGAGGTCTGGG CACTGGAAGCATACGGTGCTGCATACACTCTGCAAGAAATGCTCACA GTGAAGTCGGACGATGTGAACGGTCGGACCAAGATGTACAAAAACAT CGTGGACGGCGATCACCGTATGGAGCCGGGCATGCCCGAGTCCTTCA ACGTGTTGATCAAAGAAATTCGTTCCCTCGGCATCGATATCGATCTGG AAACCGAATAA |
| 116 | DP69 Glutamine-IRNA ligase | GTGCGCGAGGACCTGGCCAGCGGAAAGCACCAGGCGATCAAGACCC GCTTCCCGCCGGAGCCGAACGGCTACCTGCACATCGGCCACGCCAAG TCGATCTGCCTGAACTTCGGCATCGCCGGTGAGTTCAGCGGCGTCTGC AACCTGCGTTTCGACGACACCAATCCGGCCAAGGAAGACCCGGAGTA CGTGGCCGCGATCCAGGACGACGTGCGCTGGCTGGGCTTTGAATGGA ACGAGCTGCGCCACGCCTCGGACTACTTCCAGACCTATTACCTGGCCG CCGAGAAGCTGATCGAACAGGGCAAGGCCTACGTCTGCGACCTGTCG GCCGAGGAAGTGCGCGCCTACCGCGGCACCCTGACCGAGCCGGGCCG CCCGTCGCCGTGGCGTGACCGCAGCGTCGAGGAGAACCTCGACCTGT TCCGCCGCATGCGTGCCGGTGAATTCCCCGATGGCGCGCGCACCGTG CGCGCCAAGATCGACATGGCCAGCGGCAACATCAACCTGCGTGATCC GGCGCTGTACCGCATCAAGCACGTCGAGCACCAGAACACCGGCAACG CGTGGCCGATCTACCCGATGTACGACTTCGCCCATGCGCTGGGCGATT CGATCGAGGGCATCACCCACTCGCTGTGCACGCTGGAATTCGAAGAC CACCGCCCGCTGTACGACTGGTGCGTGGACAACGTCGACTTCGCCCA CGATGACGCGCTGACCCAGCCGCTGGTCGACGCCGGCCTGCCGCGCG AAGCGGCCAAACCGCGCCAGATCGAGTTCTCGCGCCTGAACATCAAC TACACGGTGATGAGCAAGCGCAAGCTGATGGCGCTGGTCACCGAACA GCTGGTGGACGGCTGGGAAGACCCGCGCATGCCGACCCTGCAGGGCC TGCGTCGCCGTGGCTACACCCCGGCAGCGATGCGCCTGTTCGCCGAG CGCGTGGGCATCAGCAAGCAGAATTCGCTGATCGATTTCAGCGTGCT GGAAGGCGCGCTGCGCGAAGACCTGGACAGCGCCGCACCGCGCCGC ATGGCCGTGGTCGACCCGGTCAAGCTGGTGCTGACCAACCTGGCCGA AGGCCACGAAGAGCAGCTGACCTTCAGCAACCACCCGAAGGACGAG AGCTTCGGTACCCGCGAAGTGCCGTTCGCACGTGAAGTGTGGATCGA |

-continued

Sequence Listing

| Seq ID No. | Description | Sequence |
|---|---|---|
| | | CCGCGAGGACTTCGCCGAAGTGCCGCCGAAGGGCTGGAAGCGCCTGG<br>TTCCCGGTGGTGAAGTGCGCCTGCGCGGCGCCGGCATCATCCGCTGC<br>GACGACGTGATCAAGGATGCCGACGGCACCATCACCGAGCTGCGCGG<br>CTGGCTGGATCCGGAATCGCGCCCGGGCATGGAAGGCGCCAACCGCA<br>AGGTCAAGGGCACCATCCACTGGGTCAGCGCGGTGCACGGTGTGCCG<br>GCCGAGATCCGCCTGTATGACCGCCTGTTCTCGGTGCCGAACCCGGAC<br>GATGAATCGGAAGGCAAGACCTACCGCGACTACCTCAATCCGGACTC<br>GCGCCGCACCGTCACCGGCTATGTCGAGCCGGCGGCTGCCAGCGCTG<br>CGCCGGAACAGTCGTTCCAGTTCGAGCGCACCGGCTACTTCGTTGCCG<br>ACCGCCGCGACCACACCGAAGCCAAGCCGGTGTTCAACCGCAGCGTG<br>ACCCTGCGCGACACCTGGTCGGCCTGA |
| 117 | DP69 DNA gyrase subunit B | ATGACCGACGAACAGAACACCCCGGCAAACAACGGCAACTACGACG<br>CCAACAGCATTACGGCCCTGGAAGGCCTGGAGGCTGTCCGCAAGCGC<br>CCAGGCATGTACATCGGCGACGTCCATGACGGCACCGGCCTGCATCA<br>CATGGTGTTCGAGGTCGTCGACAACTCAATCGACGAAGCCCTCGCCG<br>GCCATGCCGACCACGTCTCGGTGACGATCCATGCCGATGGCTCGGTA<br>GGCGTGTCCGACAACGGTCGCGGCATCCCGACGGGCAAGCACGAGCA<br>GATGAGCAAGAAGCTCGACCGCGATGTGTCTGCAGCCGAAGTGGTGA<br>TGACGGTCCTGCACGCAGGCGGCAAGTTCGACGACAACAGCTACAAG<br>GTTTCCGGCGGCCTGCACGGCGTGGGCGTCAGCGTGGTCAACGCGCT<br>GTCGCAGAAGCTGGTCCTGGATATCTACCAGGGTGGCTTCCACTACCA<br>GCAGGAGTACGCCGACGGCGCAGCACTGCATCCGCTGAAGCAGATCG<br>GCCCCAGCACCAAGCGCGGGACCACCCTGCGCTTCTGGCCCTCGGTA<br>AAGGCTTTCCACGACAACGTGGAATTCCACTACGACATCCTGGCCCG<br>GCGCCTGCGCGAACTGTCCTTCCTCAATTCCGGCGTCAAGATCGTGCT<br>GGTGGACGAGCGTGGTGATGGCCGCCGCGACGACTTCCATTACGAGG<br>GCGGCATCCGCAGCTTCGTGGAGCATCTGGCGCAGTTGAAGACGCCG<br>TTGCACCCGAACGTGATCTCGGTGACCGGCGAATCCAATGGCATCAC<br>CGTGGAAGTGGCGCTGCAGTGGACCGACTCCTACCAGGAGACGATGT<br>ACTGCTTCACCAACAACATTCCGCAGAAGGACGGCGGTACCCACCTG<br>GCCGGCTTCCGTGGCGCATTGACCCGCGTGCTCAACAACTACATCGA<br>GCAGAACGGCATCGCCAAGCAGGCCAAGATCAACCTGACCGGCGATG<br>ACATGCGCGAAGGCATGATCGCGGTGCTGTCGGTGAAGGTGCCGGAT<br>CCCAGCTTCTCCAGCCAGACCAAGGAAAAGCTGGTCAGCTCGGATGT<br>GCGCCCGGCCGTGGAAAGCGCGTTCGGCCAGCGCCTGGAAGAGTTCC<br>TGCAGGAAAACCCGAACGAAGCCAAGGCCATCGCCGGCAAGATCGTC<br>GACGCTGCCCGTGCCCGCGAAGCGGCGCGCAAGGCCCGCGACCTGAC<br>CCGCCGCAAGGGTGCGCTGGATATCGCCGGCCTGCCGGGCAAGCTGG<br>CCGACTGCCAGGAAAAGGATCCGGCGCTGTCCGAACTGTTCATCGTC<br>GAGGGTGACTCGGCAGGTGGTTCGGCCAAGCAGGGTCGCAACCGCAA<br>GAACCAGGCGGTGCTGCCGCTGCGCGGCAAGATCCTCAACGTGGAAC<br>GTGCGCGCTTCGACCGCATGCTGGCGTCCGACCAGGTGGGTACGCTG<br>ATCACCGCGCTGGGTACCGGCATCGGTCGTGACGAGTACAACCCGGA<br>CAAGCTGCGGTACCACAAGATCATCATCATGACCGACGCCGACGTCG<br>ACGGCGCGCACATCCGCACCCTGCTGCTGACGTTCTTCTACCGTCAGA<br>TGCCGGAGCTGATCGAGCGCGGTTATGTCTATATCGGCCTGCCGCCGT<br>TGTACAAGATCAAGCAGGGCAAGCAGGAGCTGTACCTGAAGGACGA<br>CCCGGCGCTGGACAGCTATCTGGCCAGCAGCGCGGTGGAGAACGCTG<br>GGCTGGTGCCGGCCAGCGGCGAGCCGCCGATCGACGGCGTGGCACTG<br>GAAAAGCTGCTGCTCGCCTACGCTGCCGCGCAGGACACGATCAACCG<br>CAATACCCACCGCTACGACCGCAACCTGCTCGAAGCGCTGGTCGACT<br>TCATGCCGCTGGAGCTGGAAAACCTGCGCACTGCAGGTCCTGGCGAA<br>GGTCTGGACGCGTTGGCCAAGCACCTCAACCAGGGCAACCTCGGCAG<br>CGCCCGCTTCACCCTGGAACTGCAGGAACCCAACGAGCAGCGTCCGG<br>CGGCCGTACTGGTGACCCGCAGCCACATGGGCGAACAGCACATCCAG<br>GTGCTGCCGCTGTCCGCGCTGGAAAGCGGCGAACTGCGCGGCATCCA<br>TCAGGCAGCGCAGCTGCTGCACGGTCTGGTCCGCGAAGGCGCGGTCA<br>TCACCCGTGGCGCCAAGTCGATCGAGATCGACTCGTTCGCACAGGCC<br>CGCAACTGGCTGTTGGACGAAGCCAAGCGCGGCCGGCAGATCCAGCG<br>ATTCAAGGGTCTGGGCGAAATGAATCCGGAACAGCTGTGGGATACCA<br>CCGTCAATCCCGATACCCGTCGCCTGCTGCAGGTGCGCATCGAAGAC<br>GCGGTGGCCGCTGACCAGATCTTCAGCACCCTGATGGGTGATGTGGT<br>CGAACCGCGTCGTGACTTCATCGAAGACAACGCGTTGAAGGTCGCCA<br>ACCTGGATATCTGA |
| 118 | DP69 Isoleucine tRNA ligase | GTGAGCCAGGACTACAAGACCACCCTCAACCTGCCGGCCACCGAATT<br>CCCGATGCGCGGCGACCTGCCCAAGCGCGAGCCGGGCATTCTGGCGC<br>GCTGGGAAGAGCAGGGGCTCTACCAGCAGCTGCGCGACAACGCCGCC<br>GGCCGCCCGCTGTTCGTGCTGCATGACGGCCCGCCGTACGCCAATGC<br>GCGCATCCACCTGGGCCATGCGGTCAACAAGATCCTCAAGGACATCA<br>TCGTCAAGTCGCGCTACCTGGCCGGCTTCGATGCGCCCTACGTGCCGG<br>GCTGGGACTGCCATGGCCTGCCGATCGAAATCGCGGTGGAAAAGAAG |

-continued

Sequence Listing

| Seq ID No. | Description | Sequence |
|---|---|---|
| | | TGGGGCAAGGTCGGGGTGAAGCTCGATGCGGTCGAGTTCCGGCAGAA GTGCCGCGAGTTCGCCGAAGAACAGATCGACATCCAGCGTGCCGACT TCAAGCGCCTGGGCGTCACCGGCGACTGGGACAACCCGTACAAGACC CTAAGCTTCGATTTCGAGGCCAACGAGATCCGTGCGCTGTCCAAGATC GTGGCCAACGGCCATCTGCTGCGTGGCGCCAAGCCGGTCTACTGGTG CTTCGACTGCGGCTCGGCACTGGCCGAGGCCGAGATCGAGTACCACG AGAAGACCTCGCCGGCGATCGACGTGGCCTACACCGCGCGTGATCCG CAGGCGGTGGCGCAGGCGTTCGGCGTCAGCCTGCCGGCCGATGTCGA AGTGGCGGTGCCGATCTGGACCACCACTCCGTGGACGCTGCCGGCTT CGCTGGCGGTGTCGCTGGGCGCGGACATCCGCTACGTGCTGGCCGAA GGCCCGGCGCACAACGGCAAGCGCCGTTGGCTGGTGCTGGCTGCTGC GCTGGCCGAACGGTCGCTGCAGCGCTACGGCGTGGACGCGGTGGTGC TGCACGGTGAAGCCGAAGGTTCGGCGCTGGAAAACCAGCTGCTGGCG CACCCGTTCTACCCGGAGCGCGAGATCCCCGTGCTCAACGGCGAACA CGTGTCCGACGAGGACGGTACCGGTGCGGTGCACACTGCCCCCGGCC ACGGCCAGGAAGACTACGTGGTCAGCCAGAAGTACGGCCTGCTGGAG AAGTACAACGCCGGCCAGATCAATCCGGTCGACGGTGCGGGCGTGTA CCTGGCGTCCACCCCGCCCGCCGGTGACCTGGTGCTGGCCGGTACCC ACATCTGGAAGGCGCAGCAGCCGATCATCGAAGTGCTGGCCGCCAGC GGCGCGCTGCTCAAGGCCGTGGAGATCGTGCACAGTTATCCGCATTG TTGGCGCCACAAGAAGACCCCGCTGGTGTTCCGCGCCACCCCGCAGT GGTTCATTTCGATGGACAAGGCCAACCTGCGCAACGATGCGCTGGCC GCGATCGATACCGTCGGCTGGTTCCCGAGCTGGGGCAAGGCGCGCAT CCAAAGCATGATCGACGGCCGCCCGGACTGGACCATCTCGCGCCAGC GCACCTGGGGCGTGCCGATCGCGCTGTTCACCCACCGCCAGACCGGC GAGATCCACCCGCGTTCGGTGGAGCTGATGCAGCAGGTGGCCGACCG CGTTGAAGCCGAAGGCATCGACGTGTGGTACTCGCTGGATGCGGCTG AACTGCTGGGCGCTGAAGCGGCCGACTACGAGAAGGTCACCGACATC CTCGATGTCTGGTTCGATTCCGGCGTGACCCACGAAGCCGTGCTGGCT GCCCGTGGCTTCGGCAAGCCGGCCGATCTGTACCTGGAAGGTTCGGA CCAGCATCGCGGCTGGTTCCAGTCCTCGCTGCTGACCGGCGTGGCCAT CGACAAGCGCGCGCCGTACAAGCAGTGCCTCACCCACGGTTTCACCG TGGACGAGCACGGCCGCAAGATGTCCAAGTCGCTGGGCAACGGCATC GAACCGCAGGAAATCATGAACAAGCTGGGCGCGGACATCCTGCGCCT GTGGATCGCCTCGGCCGACTACAGCAACGAGATGTCGCTGTCGCAGG AAATCCTCAAGCGCACCGCCGACGCCTACCGCCGCCTGCGCAACACC GCCCGCTTCCTGCTGGGCAACCTGGACGGTTTCGATCCGGCCCAGCAC CTGCGCCCGCTCAACGAGATGGTCGCGCTGGACCGCTGGATCGTGCA TCGCGCCTGGGAGCTGCAGGAGAAGATCAAGGCGGCGTATGACAACT ACGACATGGCCGAGATCGTGCAGTTGCTGCTGAACTTCTGCAGCGTG GACCTGGGCTCGCTGTACCTGGACGTGACCAAGGATCGCCTGTATAC GATGCCGACCGATTCGGATGGTCGTCGTTCGGCGCAGAGCGCGATGT ACCACATCGCCGAAGCGTTCACCCGCTGGGTGGCGCCGATCCTGACC TTCACCGCCGACGAGCTGTGGGGCTACCTGCCGGGCGATCGTGCCGG CCACGTGCTGTTCACTACCTGGTACGAGGGCCTGGCACCGCTGCCGAC CGATGCACAGCTCAACGCTGCCGACTTCGATCAGCTGCTGGCCGTGC GCGAGCAGGTGGCCAAGGTGCTGGAGCCGATGCGCGCCAATGGTGCG ATCGGTGCCGCGCTGGAAGCGGAGATCACCATCGCCGCCAGCGAAGA GCAGGCCGCGCGCTGGCAGCCGCTGGCCGATGAACTGCGTTTCCTGTT CATCAGTGGTGACGTGCAGGTGCGTCCGGCGACCACCGACGAGGTGT TCGTCAGCGCGCAGCCGACGCAGAAGTCCAAGTGCGTGCGCTGCTGG CACCACCGTGCCGACGTTGGCAGCAATGCCGACCACCCGGAACTGTG CGGCCGCTGCGTGACCAACATCGCCGGTGCCGGCGAAGCGCGGAGCT GGTTCTGA |
| 119 | DP69 Glycine tRNA ligase beta subunit | ATGAGCCACTTGTCTCCCCTGCTGATTGAACTGGGCACCGAAGAGTTG CCGGTCAAGGCGCTGCCGGGCCTGGCCCAGGCCTTCTTCGACGGTGTT GTCGATGGCCTGCGCAAGCGCGGCGTCGAACTGGAGCTGGGCGATGC CCGCCCGCTGTCGACCCCGCGCCGCCTGGCCGTGCTGCTGCCGGGCGT TGGCCTGGAACAGCCGGAACAACACAGCGAAGTGCTGGGCCCGTACC TGAACATCGCGCTGGACGCCGAAGGCCAGCCGACCAAGGCGCTGCAG GGTTTCGCGGCCAAGGCCGGGATCGACTGGACCGCGCTGGAGAAGAC CACCGACAACAAGGGTGAGCGCTTCGTGCACCGTGCGGTGACTCCGG GCGCGCGCACCGCTGCGCTGCTGCCGGAGATCCTGCGCGAGGCCATC GCCGGCATGCCGATTCCCAAGCCGATGCGCTGGGGCGACCACAGCTG GGGCTTCGCCCGCCCGGTGCACTGGCTGGTGCTGCTGCATGGCGGCG ACGTGGTCGAGGCCGAACTGTTTGGCCTGAAGGCCGACCGCATGAGC CGCGGCCACCGCTTCCTGCACGACAAGACCGTGTGGCTGACCCAGCC GCAGGACTATGTCGAATCGCTGCGCGCCGCCTTCGTGCTGGTCGATCC GGCCGAGCGCCGCCGGCGCATCGTTGCCGAAGTGGAAGCCGCTGCCG CCACCGCCGGTGGCAGCGCACGCATCACCGAGGACAACCTGGAGCAG GTGGTGAACCTGGTCGAGTGGCCGGCGGCAGTGTTGTGCAGCTTCGA GCGCGCGTTCCTGGCGGTACCGCAGGAAGCGCTGATCGAGACGATGG |

-continued

Sequence Listing

| Seq ID No. | Description | Sequence |
|---|---|---|
| | | AGATCAACCAGAAGTTCTTCCCGGTGCTGGATGACGGCGGCAAGCTG ACCGAGAAGTTCATCGGCATCGCCAACATCGAGTCCAAGGACGTGGC CGAAGTGGCCAAGGGCTACGAGCGCGTGATCCGCCCGCGCTTCGCCG ATGCCAAGTTCTTCTTCGACGAAGACCTGAAGCAGGGCCTGCAGGCG ATGGGCGAGGGCCTGAAGACGGTGACCTACCAGGCCAAGCTGGGCA GCGTGGCCGACAAGGTCGCGCGCGTGGCGGCGCTGGCCGAGGTGATC GCTGCGCAGGTGGGGGCCGACCCGGTGCTGGCCAAGCGTGCCGCGCA GCTGGCCAAGAACGACCTGCAGTCGCGCATGGTCAATGAGTTCCCGG AACTGCAGGGCATCGCTGGCCGCCACTACGCGGTGGCCGGTGGCGAG TCGCCGGAGGTGGCGCTGGCCATCGACGAGGCCTACCAGCCGCGCTT CGGTGGCGATGACATCGCGCTGTCGCCGCTGGGCAAGGTGCTGGCGA TCGCCGAGCGTGTGGACACGCTGGCCGGCGGTTTCGCCGCGGGCCTG AAGCCGACCGGCAACAAGGACCCGTTCGCCCTGCGCCGCAACGCGCT GGGCCTGGCCCGCACGATTATCGAAAGTGGCTTCGAGCTGGACCTGC GCGCGCTGCTGGCCAGCGCCAATGCCGGGCTGACCGTGCGCAACGTG CAGGCCGACGTGGCTGAGCTGTACGACTTCATCCTCGACCGCCTGAA GGGCTACTACAGCGACAAGGGCGTGCCGGCCAGCCACTTCAATGCGG TGGCTGAGCTGAAGCCGGTCTCGCTGTACGATTTCGACCGTCGCCTGG ACGCCATCGGTATCTTCGCGGCGCTGCCGGAGGCCGAGGCGCTGGCA GCGGCCAACAAGCGCATCCGCAACATCCTGCGCAAGGCCGAAGGCGA TATTCCGGGCCAGATCGATGCGGCCCTGTTGCAGGAAGATGCCGAGC GCGCGCTGGCGGAAGCCGTGACTGCAGCCATCGACGACACCGGCGCC AGCCTGCACCAGAAGGACTACGTGGCCGTGCTGGCGCGCCTGGCCCG CCTGCGTCCGCAGGTCGATGCGTTCTTCGATGGGGTGATGGTCAATGC CGAGGATCCGGCACTGCGCGGCAACCGCCTGGCGCTGCTGACGATGC TGGGCGAGCGCTTGGGCAAGGTCGCGGCGATCGAGCATCTGTCGAGC TGA |
| 120 | DP69 Glutamine synthetase | ATGTCCGTGGAAACCGTAGAGAAGCTGATCAAGGACAACCAGATCGA GTTCGTCGATCTGCGCTTCGTCGACATGCGTGGTGTCGAACAGCATGT GACCTTCCCGGTCAGCATCGTCGAGCCGTCGCTGTTTGAAGAAGGCA AGATGTTCGATGGCAGCTCGATCGCCGGCTGGAAGGGCATCAACGAG TCGGACATGGTGCTGCTGCCGGACACCGCCAGCGCCTACGTCGACCC GTTCTACGCCGATCCGACCATCGTGATCAGCTGCGACATCCTCGACCC GGCCACCATGCAGCCGTATGGCCGTTGCCCGCGCGGCATCGCCAAGC GCGCCGAGTCCTACCTGAAGTCCTCGGGCATCGCCGAAACCGCGTTCT TCGGCCCGGAGCCGGAGTTCTTCATCTTCGACTCGGTGCGTTTCGCCA ATGAAATGGGCAACACCTTCTTCAAGGTCGACTCGGAAGAAGCGGCG TGGAACAGCGGCGCCAAGTACGACGGCGCCAACAGCGGCTACCGTCC GGGCGTGAAGGGCGGTTATTTCCCCGTTCCGCCGACCGACACCCTGC ACGACCTGCGTGCGGAGATGTGCAAGACCCTGGAACAGGTCGGCATC GAAGTGGAAGTGCAGCACCACGAAGTGGCCACCGCCGGCCAGTGCG AGATCGGCACCAAGTTCAGCACCCTGGTGCAGAAGGCCGACGAACTG CTGCGGATGAAGTACGTCATCAAGAACGTCGCCCACCGCAACGGCAA GACCGTCACCTTCATGCCCAAGCCGATCGTCGGCGACAACGGCAGCG GCATGCACGTGCACCAGTCGCTGTCCAAGGGCGGCACCAACCTGTTC TCCGGTGACGGCTACGGTGGCCTGAGCCAGATGGCGCTGTGGTACAT CGGCGGCATCTTCAAGCATGCCAAGGCGATCAACGCCTTTGCCAACT CGGGTACCAACAGCTACAAGCGCCTGGTGCCGGGCTTCGAAGCCCCG GTGATGCTGGCCTACTCGGCGCGCAACCGTTCGGCCTCGTGCCGCATT CCGTGGGTGTCCAACCCGAAGGCGCGTCGCATTGAAATGCGCTTCCC CGATCCGATCCAGTCGGGCTACCTGACCTTCACCGCGCTGATGATGGC CGGCCTGGACGGCATCAAGAACCAGATCGACCCGGGCGCACCGAGCG ACAAGGATCTGTACGACCTGCCGCCGGAAGAAGAGAAGCTGATTCCG CAGGTCTGCTCCTCGCTGGACCAGGCCCTGGAAGCGCTGGACAAGGA CCGTGAGTTCCTCAAGGCCGGTGGCGTGATGAGCGATGACTTCATCG ACGGCTACATCGCGCTGAAGATGCAGGAAGTGACCAAGTTCCGCGCG GCGACCCACCCGCTGGAATACCAGTTGTACTACGCCAGCTGA |
| 121 | DP69 Glucose-6-phosphate isomerase | ATGACAACGAACAACGGATTCGACTCGCTGCATTCCCACGCCCAGCG CCTGAAGGGCGCAAGCATCCCCAGCCTGCTCGCCGCCGAACCCGGCC GCGTACAGGACCTGGCGCTGCGGGTCGGTCCGTTGTATGTCAACTTCG CCCGGCAGAAATACGATGCCGCGGCGTTGCAGGCGCTGTTGGCGCTG GCTGCCGAACGTGATGTCGGCGGCGCCATCACGCGCCTGTTCCGTGG CGAGCAGGTCAATCTGACCGAAGGCCGCGCCGCACTGCACACCGCAC TGCGCGGCGACGTGGTCGATGCGCCGGTTGCCGCCGAGGCCTATGCC ACGGCCCGCGAAATCCGCCAGCGCATGGGCGTGCTGGTGCGCGCACT GGAAGACAGTGGCGTGACCGATGTGGTCAGTGTCGGCATCGGCGGTT CCGATCTCGGTCCGCGTCTGGTCGCCGACGCACTGCGTCCAGTCACTG GCGCTCGCCTGCGCGTGCATTTCGTGTCTAACGTGGACGGCGCTGCCA TGCAGCGCACGCTGGCCACGCTGGATCCGGCGAAGACCGCCGGCATC CTCATTTCCAAGACCTTCGGTACCCAGGAAACCCTGCTCAACGGCCAG ATCCTGCACGATTGGCTGGGTGGCAGCGAGCGCCTGTACGCGGTCAG |

-continued

Sequence Listing

| Seq ID No. | Description | Sequence |
|---|---|---|
| | | CGCCAATCCGGAACGCGCCGCCAAGGCCTTCGCCATCGCCGCCGAGC<br>GCGTGCTGCCGATGTGGGACTGGGTAGGGGGCGCTATTCGCTGTGG<br>TCGGCCGTCGGTTTCCCGATCGCACTGGCCATCGGCTTCGAGCGTTTC<br>GAGCAGTTGCTGGAAGGCGCCGCGCAGATGGATGCGCATGCGCTGGA<br>CGCGCCGCTGGAGCGCAACCTGCCGGTGCTGCACGGCCTGACCGACA<br>TCTGGAACCGCAATCTGCTGGGCTCTGCCACGCATGCGGTGATGACCT<br>ACGACCAGCGCTTGGCGCTGCTGCCGGCCTACCTGCAGCAGCTGGTG<br>ATGGAAAGCCTGGGCAAGCGCGTGCAGCGCGATGGCCAGCCGGTCAC<br>CACCGACACCGTGCCGGTGTGGTGGGGCGGTGCCGGCACCGATGTGC<br>AGCACAGCTTCTTCCAGGCCCTGCACCAGGGCACCAGCATCATTCCG<br>GCCGATTTCATCGGCTGCGTGCACAACGACGATCCGTATACGGTCAA<br>CCACCAGGCGTTGATGGCCAACCTGCTGGCGCAGACCGAAGCGCTGG<br>CCAACGGCCAGGGCAGTGACGATCCGCACCGCGATTATCCGGGTGGC<br>CGCCCGAGCACGATGATCCTGCTCGACGCGCTCACCCCGCAGGCGCT<br>GGGCGCCTTGATCGCGATGTACGAACACGCCGTGTACGTGCAGTCGG<br>TGATCTGGAACATCAACGCCTTCGACCAGTTCGGTGTCGAGCTGGGC<br>AAGCAGCTGGCCAGTGGCCTGCTGCCCGCTCTGCAGGGTGAGGATGT<br>CGAGGTCAACGACCCGCTGACCCGTGAGCTGCTGGCCCAGCTGAAGG<br>GCTGA |
| 122 | DP69 Leucine tRNA ligase | ATGACCAGCGTCGAACCCAACGTTTACGATCCGCAGCAGGTTGAATC<br>CGCCGCCCAGAAGTACTGGGACGCTACCCGTGCCTTCGAGGTCGATG<br>AAGCCTCGGACAAGCCGAAGTACTACTGCCTGTCGATGCTTCCGTATC<br>CGTCCGGTGCGCTGCACATGGGCCACGTGCGCAATTACACGATCGGC<br>GACGTGATCAGCCGCTACAAGCGCATGACCGGCCACAACGTGCTGCA<br>GCCGATGGGCTGGGACGCGTTTGGCCTGCCGGCGGAAAACGCTGCGA<br>TCAAGAACAAGACCGCGCCGGCCGCCTGGACCTACAAGAACATCGAC<br>CACATGCGCAGCCAGCTGCAGTCGCTGGGCTATGCCATCGACTGGTC<br>GCGCGAGTTCGCCACCTGCCGCCCGGACTATTACGTCCACGAGCAGC<br>GCATGTTCACCCGCCTGATGCGCAAGGGCCTGGCCTACCGCCGCAAC<br>GCGGTGGTGAACTGGGACCCGGTCGACCAGACCGTGCTGGCCAACGA<br>GCAGGTCATCGACGGCCGTGGCTGGCGCTCCGGCGCGCTTGTGGAAA<br>AGCGCGAGATCCCGCAGTGGTTCCTGCGCATCACCGACTACGCCCAG<br>GAACTGCTGGACGGCCTGGATGAGCTGGACGGCTGGCCGGAGTCGGT<br>CAAGACCATGCAGCGCAACTGGATCGGCCGCTCCGAAGGGCTGGAAA<br>TCCAGTTCGACGTGCGCGACGTCGATGGTGCCGCACTGGATCCGCTGC<br>GCGTGTTCACCACCCGCCCGGACACCGTGATGGGCGTGACTTTCGTGT<br>CGATCGCGGCCGAACATCCGCTGGCGCTGCATGCCGCGAAGAACAAC<br>CCGGAACTGGCTGCGCTGCTGTCGGAAATGAAGCAGGGCGGCGTGTC<br>CGAGGCCGAGCTGGAGACCCAGGAAAAGCGCGGCATGGATACCGGC<br>CTGCGCGCCGTGCATCCGGTTACCGGTGCCCAGGTGCCGGTGTGGGTC<br>GCCAACTTCGTGCTGATGGGCTACGGCACTGGCGCGGTGATGGCCGT<br>ACCGGGCCACGACCAGCGCGACAATGAATTCGCCAACAAGTACAACC<br>TGCCGATCCGCCAGGTCATCGCGCTGAAGTCGCTGCGCAAGGACGAA<br>GGCGCCTACGACGCGACGCGCTGGCAGGACTGGTACGGCGACAAGAC<br>CCGCGAGACCGAACTGGTCAACTCCGAAGAGTTCGACGGCCTGGACT<br>TCCAGGGCGCTTTCGAGGCGCTGGCCGAACGGTTCGAGCGCAAGGCC<br>CAGGGACAGCGCCGGGTGAACTACCGCCTGCGCGACTGGGGCGTGAG<br>CCGCCAGCGCTACTGGGGCTGCCCGATTCCGGTGATCTACTGCGACA<br>AGTGTGGCGCGGTACCGGTGCCGGAAGACCAGCTGCCGGTGGTGCTG<br>CCGGAAGACGTGGCGTTCGCCGGTACCGGTTCGCCGATCAAGACCGA<br>TCCGGAATGGCGCAAGACCACCTGCCCGGACTGCGGCGGTGCGGCCG<br>AGCGTGAGACCGACACCTTCGACACCTTCATGGAGTCGAGCTGGTAC<br>TACGCCCGCTACACCTCGCCGGGCGCCCGCGATGCGGTCGACAAGCG<br>CGGCAACTACTGGCTGCCGGTGGACCAGTACATCGGTGGCATCGAAC<br>ACGCGATCCTGCACCTGATGTATTTCCGCTTCTACCACAAGCTGCTGC<br>GCGACGCGCGGATGGTGGACAGCAACGAACCCGCGCGGAACCTGCTG<br>TGCCAGGGCATGGTGATCGCTGAGACCTACTACCGCCCGAACCCGGA<br>CGGCTCGAAGGACTGGATCAACCCGGCCGATGTGGAAGTGCAGCGCG<br>ACGAGCGCGGCCGCATCACCGGCGCCACCCTGATCGCCGACGGTCAG<br>CCGGTGGTGGTCGGTGGTACCGAGAAGATGTCCAAGTCGAAGAACAA<br>CGGCGTGGACCCGCAGGCGATGGTCGGCAAGTACGGCGCCGATACCG<br>TGCGCCTGTTCTCGATGTTCGCTGCACCGCCGGAACAGTCGCTGGAAT<br>GGAACGAAGCCGGCGTGGACGGCATGGCCCGCTTCCTGCGCCGCCTG<br>TGGGCACAGGTGCAGAAGCACGCTGCCGAGGGTGCCGCACCGGCGCT<br>CGACGCGGCCGCGCTGGATGCCGGCCAGAAGGCCCTGCGCCGCAAGA<br>CCCACGAGACCATCGGCAAGGTCGGCGACGACTACGGCCGCCGCCAC<br>AGCTTCAACACCGCCATTGCCGCGGTGATGGAGCTGATGAACGCGCT<br>GGCCAAGTTCGAGGACGGCAGTGAACAGGGGCGCGCCGTGCGCCAG<br>GAAGCACTGCAGGCCATCGTGCTGCTGCTCAACCCGATCACCCCGCA<br>TGCCAGCCACGCCCTGTGGCAGGTACTGGGCCATGGCGAAACGCTGC<br>TGGAAGATCAGCCGTTCCCGCAGGCCGACAGCAGTGCGCTGGTGCGC<br>GATGCGCTGACTTTGGCCGTGCAGGTCAATGGCAAGCTGCGTGGCAC |

-continued

Sequence Listing

| Seq ID No. | Description | Sequence |
|---|---|---|
| | | CATCGAGGTCGCCGCCGATGCCGCGCGCGAGCAGATCGAAGCGCTGG<br>CCCTGGCCGAGCCGAACGCGGCCAAGTTCCTGGAAGGCCTGACGGTG<br>CGCAAGATCATCATCGTTCCCGGCAAGATCGTGAACATCGTCGCTGCC<br>TGA |
| 123 | DP70 Glycine tRNA ligase beta subunit | ATGTCTAAACATACAGTATTGTTCGAATTGGGCTGTGAAGAACTTCCA<br>CCTAAAAGCCTCAAAAAATTACGTGATGCACTGCATGCTGAAACGGT<br>AAAAGGCTTAAAAGATGCAGGCTTAGCATTCGACTCAATCGAAGCTT<br>ATGCAGCACCGCGTCGTTTGGCACTTAAAATTGTGAATATCGATGGCG<br>CTCAGCCTGATACACAAAAACGCTTTGACGGCCCTGCAAAAGAAGCG<br>GCTTATGATGCTGAAGGCAAACCAAGCAAAGCATTAGAAGGCTTTAT<br>GCGTGGTCAAGGCATCACTGCGGATCAAGTCACCACGTTCCAAGCGG<br>GTAAAGTTGAAAAGGTTTGCTATTTAAAAGATGTTAAAGGTCAAAGC<br>CTTGAGGTTTTACTGCCACAAATTCTACAAGCAGCTTTGGACAATCTT<br>CCAATTGCAAAACGTATGCGTTCAGCGGCAAGCCGTACTGAATTCGT<br>GCGTCCTGTAAAATGGGTGGTGTTGCTCAAAGACAATGATGTGATTG<br>CAGCCACTATTCAAGATCACAAAGCAGGCAATGTGACTTATGGTCAT<br>CGTTTCCATGCCCCTGAAGCGATTACTTTGGCTCATGCAGATGAATAT<br>CTTGCCAAGTTAAAAGCGGCTTATGTGGTTGCTGACTTTGCAGAACGC<br>CAAGCCATCATTGACCAACAAGTCAAAGCGTTGGCTGATGAAGTTAA<br>TGCGATTGCGATTGTACCAAGCGACCTGCGTGATGAAGTGACCGCAT<br>TGGTGGAATGGCCTGTTGCGCTACGTGCCAGCTTTGAGGAGCGTTTCC<br>TTGCTGTACCGCAAGAAGCTTTGATTACCACGATGCAAGACAACCAA<br>AAATACTTCTGTTTGGTGAATAGTGATAACAAGCTACAGCCTTATTTC<br>ATTACTGTTTCAAATATTGAGTCTAAAGATCCGATTCAAATTATTGAA<br>GGCAATGAAAAAGTGGTTCGTCCACGTTTGTCGGATGCTGAATTCTTC<br>TTCTTGCAAGATCAAAAGCAACCACTAGCTTCTCGTAAAGAAAAACT<br>GGCTAACATGGTGTTCCAAGCACAATTGGGTACGCTGTGGGATAAGT<br>CACAACGTATTGCAAAATTGGCTGTGGCTTTATCGAACATCACGGGTG<br>CAACTGCGGCTGATGCTGAAAAAGCAGCATTGCTGGCAAAATGTGAC<br>TTAACCTCTGAATTGGTGGGTGAATTCCCTGAACTTCAAGGCATTGCG<br>GGAACCTATTACGCACGCATTGAAGGTGAAAACCATGAAGTGGCTGA<br>AGCTTTAGGCGAACAGTATTTACCTAAATTTGCAGGCGATGTTTTACC<br>GCAAACAAAAACAGGCACAACCATTGCCCTTGCCGACCGTTTAGACA<br>CGCTCACGGGTATTTTTGGTATTGGTCAAGCACCTACAGGTTCTAAAG<br>ATCCGTTTGCATTACGTCGTTCTGCAATCGGTATTTTACGTTTGGTGAC<br>TGAAAACAATCTTGATGTGTCGATTGAAGATTTAATCCAGCTGGCATT<br>AAACGCTTATGGCGATGTTGTAGCGGATCATGCGAAGACTTTAGCGG<br>ATGCTGTTGCATTCCTTGAAGGTCGTTACCGTGCCAAGTATGAAGACC<br>AAGGCGTTGCAGTTGATGTGATTCAAGCGGTTCAAGCATTATCACCA<br>AAATCACCTTTAGATTTTGATAAGCGTGTGACTGCGGTAAATCATTTC<br>CGTGCATTGCCTGAAGCTGCTGCACTGGCTGCTGCAAATAAGCGTGTT<br>GCCAACATTCTTGCCAAAGAAGCAGAACTAACAGGCGCAGTGGTTGA<br>AGCAAACTTGGTTGAAGAGGCTGAAAAAGCATTATTCGCTGTACTTG<br>CTAAAATTACGCCTGAAGTTGAACCATTATTTGCTGCCAAAGATTACA<br>CCACTGCATTGTCTAAGCTTGCTGCTTTACGTGCGCCTGTGGATGCAT<br>TCTTTGAAGGCGTCATGGTCATGGCAGATGATGCAGAATTGAAAGCC<br>AACCGTTTACGTTTATTGGCTCAATTACGTGGTTTGTTTACAAGTGTTG<br>CGGATATTTCGGTGTTGCAGCACTAA |
| 124 | DP70 DNA gyrase subunit B | ATGAGTTCAGAAGATCAAGCTGCTTCTCAAACAGAACAAACCAATGA<br>AAAGGCTTATGATTCCTCTAGTATCAAAGTATTACGTGGCCTAGATGC<br>TGTTCGTAAGCGTCCGGGTATGTATATTGGTGATACGGACGATGGTTC<br>AGGTTTACATCACATGGTGTTTGAGGTGGTCGATAATGCGATTGATGA<br>AGCCTTAGCGGGTCACTGTGATGAAATCTTAGTCACCATCCATGAAG<br>ATGAGTCTGTAAGTGTTGCAGATAACGGTCGTGGGATTCCAACGGAT<br>ATTCACCCTGAAGAAGGGGTATCTGCCGCTGAAGTGATTTTAACCATT<br>TTGCATGCTGGCGGTAAGTTTGATGATAATAGCTATAAAGTTTCCGGT<br>GGTTTACACGGGGTAGGTGTTTCTGTTGTAAATGCCTTGTCGAGTAAA<br>TTATTACTAAATATTCGTCGTGCAGGAAAAGTATATGAACAGGAATA<br>TCACCATGGTGATCCTGTCTATCCATTACGCGCGATTGGTGATACTGA<br>AGAAACCGGTACCACCGTTCGTTTCTATCCGAGTGAATTAACCTTCTC<br>TCAAACGATTTTTAATGTTGATATTTTAGCGCGTCGTTTGCGCGAACT<br>TTCATTCTTAAATGCAGGGGTTCGTATTGTATTACGTGATGAACGTAT<br>CAATGCTGAACATGTATTTGATTATGAAGGTGGTTTGTCTGAATTTGT<br>AAAATATATCAATCAAGGTAAAACCCACTTGAATGAGATTTTTCATTT<br>TACCAGTGAAGTTGTGGAAACAGGAATTACTGTTGAAGTAGCATTAC<br>AGTGGAATGATACTTATCAAGAAAATGTCCGTTGCTTTACCAATAACA<br>TCCCACAAAAAGATGGTGGTACGCATTTAGCCGGTTTCCGTGCCGCGT<br>TAACACGGGGTTTAAACCAGTATCTTGATAGTGAAAATATTCTTAAGA<br>AAGAAAAAGTTGCTGTCACAGGTGATGATGCCCGTGAAGGTTTAACG<br>GCGATTGTTTCAGTGAAAGTGCCTGATCCAAAATTCTCATCACAAACC<br>AAAGAAAAAATTGGTTTCCAGTGAAGTGAAAACTGCTGTAGAGCAGGC |

-continued

Sequence Listing

| Seq ID No. | Description | Sequence |
|---|---|---|
| | | GATGAACAAGTCTTTTTCTGAATATCTTTTAGAAAATCCACAAGCGGC<br>TAAATCGATTGCCGGCAAAATTATTGATGCTGCACGTGCACGTGATGC<br>TGCGCGTAAAGCACGTGAAATGACACGTCGTAAGAGTGCATTAGATA<br>TTGCTGGTCTGCCTGGTAAACTGGCGGATTGCCAAGAAAAAGATCCA<br>GCATTGTCTGAACTTTACTTGGTCGAAGGTGACTCGGCGGGCGGTTCT<br>GCAAAACAGGGTCGTAACCGTAAGATGCAAGCTATTCTGCCGCTTAA<br>AGGTAAAATCTTAAACGTAGAACGTGCACGTTTTGACAAAATGATTT<br>CATCGCAAGAAGTGGGCACGCTGATTACTGCACTGGGCTGTGGTATT<br>GGTCGTGAGGAATACAATCCTGATAAATTGCGTTATCACAAAATCATT<br>ATCATGACCGATGCCGACGTCGATGGTTCGCACATTCGTACGCTCCTG<br>TTGACCTTCTTCTTCCGTCAAATGCCAGAACTTGTGGAACGTGGTTAT<br>ATTTATATTGCACAGCCACCGTTGTATAAGTTGAAAAAAGGTAAGCA<br>AGAGCAATATCTTAAAGATAATGATGCTTTAGAAACCTATCTTATTTC<br>GAATGCCATTGATGAGCTTGAACTGCATATTAGTGCTGAGGCACCTGC<br>GATTCGTGGTGAATCTTTGGCTAAAGTGATTGCTGATTATCAAACCTC<br>ACAAAAAAGTTTAAATCGTTTAACGCTACGTTATCCTGCAAGCTTGCT<br>GGATGGTTTACTTGGTTTGGATGCATTTAAACTTGATCAAAATCATGA<br>TGAAGATTATGTAAAACAATGGTCTGAACAATTGCGTGCAGCAATTG<br>AACAACACCAACCAAGTTTGCGTCCTGAAATCACCTTAGAAGCTTTTG<br>AAAAAGAGCATGCAGATGGTGAGAAAGTGACGCATTATTGGCCACGT<br>GTAACGGTCTATGTACATAACTTGCCGCATCATTATTTACTTGATTCT<br>GGATTATTGGCTTCAAGTGAATACAAGCGTTTACTGCAAAATTCGAA<br>GAGTTGGTTCACATTGCTTGAAGATGGCGCTTATTTGCAAAAAGGTGA<br>GCGTAAAATTCATGTCGCCACTTTCCATCAAGTTTGGCAACATATTTT<br>ATCCGACTCGCGTCGTGGCATGATGATCCAGCGCTATAAAGGTTTGG<br>GTGAGATGAACGCGGAACAGCTTTGGGAAACCACCATGGATCCTGAA<br>AACCGTAACATGTTGCAAGTCACCATTAATGATGCGATTGAAGCGGA<br>TCGTATGTTCTCTTGTTTGATGGGAGATGATGTGGAACCACGTCGTGC<br>CTTCATTGAAGAAAATGCTTTAAATGCGGATATTGACGCTTAA |
| 125 | DP70 Leucine tRNA ligase | ATGACTACTTCTCACATTGACCCTGAATATCAAGCGAGCGCGATTGAA<br>TCCACTGTCCAACAAGACTGGGAAACTCGCAAAGCCTTTAAAGTTGC<br>CGACACTGTAGAAGGTAAACATCGTTATATCCTCTCGATGTTCCCTTA<br>TCCAAGTGGCAAGCTGCATATGGGTCATGTGCGTAACTACACCATTG<br>GCGACGTGATTAGCCGTTTCCACCGTCTCAAAGGTGAAACTGTCCTAC<br>AACCGATGGGTTGGGATGCTTTTGGTCTGCCTGCGGAAAATGCAGCG<br>ATTGCACACCAAGTTGCCCCTGCAAAATGGACCTTTGAAAACATCGC<br>GTACATGCGTGACCAGTTAAAAAAATTGGGTCTGTCAGTCGATTGGG<br>ATCGTGAATTTGCGACCTGTACGCCAGAGTATTATCACTGGGAACAAT<br>GGTTATTTGTACAGCTGTATAAAAAAGGGCTGATTTATCGCAAACTTT<br>CAACGGTAAACTGGGATCCTGTCGATCAGACTGTACTTGCTAATGAA<br>CAAGTTGAAAATGGTCGTGGTTGGCGTTCGGGTGCATTGGTTGAAAA<br>ACGTGATATTCCAATGTATTACTTCCGTATTACCGATTATGCACAAGA<br>ATTATTAGACGATTTAGATTCGCTTAAAGATGGTTGGCCGCAACAAGT<br>CTTGACCATGCAACGCAACTGGATTGGTCGTTCACAAGGCATGGAAA<br>TCACCTTTCCATCTGCGAACCCTGAAATCTATGCAGATGATTTAACGG<br>TTTATACCACACGTGGTGACACCTTGATGGGCGTGACGTATGTTGCGG<br>TTGCCGCTGAACATCCAATGGCGCTTAAAGCGGCTGAAACAAATCCC<br>GAATTGGCTGCATTTATTGAAGAATGCCGTATGGGTTCAGTGGCTGAA<br>GCAGATCTTGCCACTGCCGAGAAAAAAGGCATGGCCACTGGTTTGTC<br>TGTGAAGCATCCTGTAACGGGTGAAGTGGTTCCAGTGTGGATTGCGA<br>ACTATGTATTGATGTCATACGGTTCAGGTGCGGTGATGGCAGTTCCAG<br>CACACGACGAACGTGATTTCGAATTTGCCAACAAATATGGTTTAACCC<br>TCCAGCAAGTGATTGATGCCAAAGGTGCAGACGATGCTGAATTTTCT<br>GCAACTGAATGGCAGGAATGGTATGGCTCGAAAGAAGGCAAACTGGT<br>TAATTCTGGCGAATTTGACGGTTTAGACTTCCAAGCTGCATTTGATGC<br>ATTCATTGCAAAATTAGAACCACAAAAACTGGCAAATACGAAAGTTC<br>AGTTCCGTCTACGTGACTGGGGTGTTTCGCGTCAGCGTTATTGGGGTT<br>GTCCAATTCCAATGATCAACTGTGAAACTTGTGGTCAAGTACCTGTAC<br>CTGAAGAACAACTTCCAGTAATTTTACCAACTGACGTGGTGCCAGAT<br>GGTTCAGGCAATCCGTTAAATAAAATGCCTGAATTTTATGAAACCCA<br>ATGTCCATGTTGTGGTGCAGGTGCACGCCGTGAAACCGATACTTTGGA<br>TACGTTCGTAGAGTCATCTTGGTACTATGCACGTTATGCATCTCCAGA<br>TTTCACTGGCGGTTTAGTTAAACCTGAAGCTGCAAAATCATGGCTACC<br>AGTCAACCAATATATTGGCGGTGTGGAACATGCAATTTTGCATTTATT<br>GTATGCCCGTTTCTTCCATAAATTGATGCGTGATGAAGGCGTCGTTGA<br>AGGCAATGAACCTTTCGCTAACTTACTGACTCAAGGTATGGTTTTAGC<br>TGATACCTTCTACCGTGAAGCCGAATCAGGTAAGAAAACATGGTTTA<br>ATCCTGCGGATATTGAATTAGAAAAAGACGAAAAAGGTCGTGTTCTT<br>TCTGCTAAATACACAGGTGATGGCCAAGAAGTTGTGGTTGGCGGTCA<br>AGAAAAAATGTCGAAATCGAAAAATAATGGCATCGACCCGCAATCGA<br>TTATTGATCAATACGGCGCAGATACTGCACGTGTATTTATGATGTTTG<br>CGGCCCCACCCGATCAATCGCTTGAATGGTCTGATGCCGGTGTGGAA |

-continued

Sequence Listing

| Seq ID No. | Description | Sequence |
|---|---|---|
| | | GGTGCAAACCGTTTCTTGAAACGTGTATGGCGTTTAACCACAGGTTTC TTAGAAAAAGGCAACCATGCTGCTGTAATTGATGTTGCGAATTTGTCA TCAGCGGCACAAGACTTACGTCGTAAAACCCACGAAACCATTCAAAA AGTCGGTGATGACATTGAACGTCGTCATGCCTTCAATACTGCCATTGC AGCGCAAATGGAATTATTGAATGCTTGCAATAAATTTGAAGCCAAAG ATGATAATGACGTTGCGGTTGAACGCGATGCTATTGTTAGCTTACTCA CTTTACTTGCACCATTTGCACCACATTTAAGTCAGACCCTATTGGCTC AATTCGGTATTGAGTTAACTGAAACCTTGTTCCCTACTGTGGATGAGT CTGCGCTAACCCGCAACACACAAACTATTGTGGTACAGGTCAATGGT AAACTTCGTGGCAAGTTGGAAGTGTCTGTTGATCTCTCTAAAGAAGAT ATTTTGGATCAAGCCAAAGCATTGCCTGAAGTACAACAATTCTTAACC GGTCCAACCAAGAAAGAAATTGTGGTGCCGAATAAATTGGTCAATTT GGTGGTTTAA |
| 126 | DP70 Glucose-6-phosphate isomerase | ATGAATAGTATTGAAAAATTTCCCTTGCATGATACGGATCTGATTCAG GAAAAACTAAAAAGTTTTGCCCAACAAGAGCAAGAGATTAATTTAAA TTATTTATTTAAAAAAAATAAAAAACGTTTTGATGAATATTCCGTTCA TGCGGGTCAGTTATGTTTTGATTATAGTAAGCACCGTGTTGATGAGCG TATTATTAACGAGCTTATTTGTTATGCGGAATCACAACATTTGGGTAA CTGGATTCAGCGCTTATTTTCTTTAGAAAAAATTAATTACACTGAAAA TCGCGCAGCGATGCATTGGGCTTTGCGTTTGCCGAAGCAAGATAGTA CACATGCAGATTTGGCAGCGCAGGTACATAGTCAGCTTGATCGTATGT ATCAATTGGTCGAGAAAATTCATCAGGGGCAGTATCGAGGAGCTACA GGTGAGGTCATCCATGATGTGGTCAATATTGGTGTCGGTGGATCAGAT CTTGGTCCTTTAATGGTGTCTCAAGCGCTGACTGATTTTAAAGTTCAA ACGGCTCAAAAATTAAAAGTCCATTTTGTTTCGACGATGGATGGCAG CCAACTTTCAGATCTTTTACATCAGTTTCGCCCAGAAACCACCTTGTTT ATTATTTCATCCAAGTCTTTTGGCACCATTGATACGCTTTCCAATGCAC AAACGGCAAAATGCTGGCTTGAGCAATCTTTAGGAACGTCGAAATCA GTTCTAAGATGTCACTTTGTTGGTGTTTCAACCAAGCCCGATAAGATG ACCGAGTGGGGAATCAGCACTGAAAATCAATTCTTATTGTGGGATTG GGTCGGTGGGCGCTATTCACTATGGTCGTGTATTGGTTTGCCTATTGC ATTAAGTATTGGGGTCGAGGGCTTTAAACAGTTGCTTGCTGGTGCTTA TGAAATGGATCAGCATTTTCAGAACACACCACTTGAACAAAATATTC CTGTGTTGATGGGTTTACTGGGAATATGGAATAACAACTTCCTGAATA TTCAAACTCATGCGGTACTTCCTTATGATGGTCGGCTGAAATATTTTG CGGCTTATTTACAGCAATTGGAAATGGAGTCGAATGGTAAGTCGATT CAGCGTTCTGGTGAAAAAGTCGTATTAGATACCTGCCCAATTTTATGG GGTGAAGTTGGACCAAATGCACAACATGCTTTTTATCAGCTGCTGCAT CAAGGTACACATGCTGTGAGTTGTGACTTTATTGCACCTGTGAAACGC TATAATGCCAATCAATTTACCTATGTTGAAAATGCAGAGGCTTTAGTT GAACAACACCATTTAGCCTTATCGAATTGTTTGGCACAATCACGTCTA TTGGCCTTTGGTAATCATGTTCTAGATCCGAAAGAAGTAGAAAGTTCA CCGAAATATAAACAATATGCAGGCAACCAACCGACCACAACAATTTT GTTAAAAGAGTTGAATCCGCGCAGTTTAGGTATGCTCATTGCGATGTA TGAGCACAAGGTATTTGTGCAATCCGTGATGTGGAATATTAATCCATT TGACCAATGGGGCGTAGAAAAAGGTAAAGAAATTGCCAATCAACTGT TACCGATTCTCAATCAAGAGCAAGCTGATGTTTCTGATCTTGATTCTT CAACGCAAGGTCTATTAAGAATTTTACTGGGAAAAGCTGATGGCTAA |
| 127 | DP70 NADH-quinone oxidoreductase subunit C/D | ATGGCTGAAACTGACATTGCTATGCCAGAATCAACGCCTGTTGATTCA CGCCCAGCATTTGCAATTGTAGAAGAGCTCAAAGCCAAATTTGGTGA GAACTTCTATGTGCAAGCGACTTTTGAAGATTTTCCAACGGTCTGGGT TGAGCGCGCGCGCGTACAAGATGTTTTAATGTTCTTGCGTAAAGTATC ACGTCCATACGTGATGCTGTTCGACTTGTCTGCGGTAGATGAGCGTTT ACGTACCCACCGTGACGGTTTACCTGCATCAGACTTCACTGTGTTTTA TCATTTGTTGTCGCTAGAGCGCAACAGTGATATTCGTATTAAAGTTGC GTTGAGTGAGAGTGATCTCAATCTTCCAACCGCAACCAACATTTGGCC AAATGCCAACTGGTACGAACGTGAAGCTTACGATATGTTCGGGATCA ATTTCGAAGGGCATCCAATGCTCCGTCGTATTTTGTTGCCAACCTATT GGGAAGGTCACCCACTGCGTAAAGAATATTCTGCACGTGCGACTGAA TATACACCGTATATGCAGAACCAAGCGAAGCAGGATTTCGAGCAAGA ACATTTACGTTTTGTTCCTGAAGATTGGGGTCTATCACGCGGTAATGC CGATGAAGATTTCATGTTCTTGAACTTAGGTCCAAACCATCCATCTGC GCACGGTGCATTCCGTATCATTTTGCAGTTGGACGGTGAAGAAGTGA AAGACTGTGTGCCTGATATTGGCTATCACCACCGTGGTGTGGAAAAG ATGGCTGAACGTCAAACTTGGCATTCATTCATTCCATATACCGACCGT GTTGACTACTTGGGTGGTTGTGCGCAAAACATGCCTTATGTGATGGGT GTGGAGCAAATGGCAGGAATTACTGTTCCTGACCGTGCACAATGTAT CCGTGTCATGATGTCTGAATTATTCCGTATCAATAACCATTTATTGTTT ATTGGTACTGCAATTCAAGATGCCGGCGGTATGACGCCAGTCTTCTAT ATGTTTGCCGATCGTCAAAAGATCTATGATGCGATTGAAGCGATTACA GGCTACCGTATGCATCCAGCATGGTTCCGTATTGGCGGGACTGCGCAC |

-continued

Sequence Listing

| Seq ID No. | Description | Sequence |
| --- | --- | --- |
| | | GACCTTCCAAACAATTGGCAACATCTGATTCGTGAAATTCTCGAATGG<br>ATGCCGAAGCGTATGAATGAATACTATACAGCTGCACTACGCAACTC<br>AGTATTTATTGGTCGTACCCGTAATGTTGCACAATACGATGCAAAATC<br>TGCATTGGCTTGGGGTGTAACAGGTACAGGTCTACGCGCGACAGGGA<br>TTGATTTCGACGTGCGTAAATACCGTCCGTATAGCGGTTATGAAAACT<br>ACGACTTCGACGTGCCTTTAGAATACGAAGGCGATGCTTACGCTCGTG<br>TGATGGTTCACTTCCGTGAAATTGAAGAATCACTGAAAATTGTGAAG<br>CAGTGCTTGGATAACATGCCATCTGGTCCATATAAAGCGGATCATCCT<br>TTGGCTGTTCCACCACCAAAAGACAAGACATTACAAGATATTGAAAC<br>TTTGATTACGCACTTCTTGAGCGTGTCATGGGGTCCTGTGATGCCTGC<br>GGGTGAAGCGTCTGTAATGGCTGAAGTGGTAAAAGGTGCATCGAACT<br>ACTACTTGACTTCAGACAAGTCAACCATGAGTTATCGTACCCGTATTC<br>GTACACCAACTTTCACGCACTTACAGCAAATGCCTTCTGTGATTAATG<br>GCAGTCTTGTATCTGACTTGATCATTTATTTAGCGACCATTGACGTCG<br>TAATGGCTGACGTGGATCGCTAG |
| 128 | DP70 Protein RecA | ATGGATGATAATAAAAGTAAGGCGCTTAATGCTGCCCTAAGCCAGAT<br>TGAAAAACAATTTGGTAAAAATACCGTAATGCGTCTTGGTGATAATA<br>CCGTATTGGCCGTTGAAGCGGTCTCTACAGGTTCTTTAACACTAGACA<br>TTGCACTTGGTATTGGTGGCTTACCAAAAGGTCGTATCGTTGAAATTT<br>ACGGTCCTGAATCTTCTGGTAAAACCACAATGACATTGCAAGCGATT<br>GCACAATGTCAAAAAGCCGGTGGTACTTGTGCTTTTATCGATGCAGA<br>ACATGCACTCGATCCTCAGTATGCACGTAAGCTTGGTGTCGACCTTGA<br>CAACCTGTTGGTTTCTCAACCAGACCACGGTGAACAAGCCCTTGAAAT<br>TGCAGACATGTTAGTCCGCTCTGGTGCTATTGACATGATCGTTGTCGA<br>TTCCGTGGCTGCACTGACACCTCGCGCTGAAATTGAAGGTGAAATGG<br>GCGACTCACATATGGGCTTACAAGCACGTTTGATGAGTCAGGCATTA<br>CGTAAAATTACTGGTAATGCAAAACGCTCAAACTGTATGGTGATCTTC<br>ATTAACCAAATCCGTATGAAGATTGGTGTAATGTTTGGTAGCCCTGAA<br>ACCACAACAGGTGGTAATGCACTCAAATTCTACGCTTCTGTACGTTTG<br>GATATCCGTCGTATTGGTCAAGTGAAAGAAGGCGATGAAATTGTCGG<br>TTCAGAAACCCGCGTTAAAGTCGTAAAAAATAAAATGGCACCTCCTT<br>TTAAGGAAGCGTTATTCCAAATTTTATATGGCAAAGGTGTCAATCAAC<br>TGGGTGAACTGGTTGATCTTGCTGTTGCGCAAGAACTGGTACAAAAA<br>GCAGGTGCTTGGTATTCATATCAAGGCAATAAAATTGGTCAAGGTAA<br>AAACAACGTGATCCGCCATTTAGAGGAAAATCCTCAAATTGCACAAG<br>AACTTGATCGCCTGATTCGTGAAAAATTGTTGACACCAACGACCACG<br>CCTATTGAAGAAAAAGATGAAGTAGAACCAGACTTTCTAGATGCTTA<br>A |
| 129 | DP70 RNA polymerase sigma factor RpoD | ATGAGCGATATGACTTCCCCTACTTCGCAAGTAGCGGCTCTGATTAGC<br>CGAGGCAAAGAGCAAGGTTACTTAACTTACGCTGAGGTTAACGATCA<br>TCTCCCAGACTCGATCACGGAAAGCGAACAGATTGAAGACATTATTC<br>AAATGCTTCAAGATGTCGGCATTCCAGTGCATGAACGTGCGCCTGAA<br>TCTGATGACACCATGTTCGACGGTAACAATGCAGAAGCAACCGATGA<br>AGTCGCTGAAGAAGAAGCGGCAGCTGTTCTTGCTTCAGTTGAAAGCG<br>AACCTGGTCGTACCACCGATCCAGTACGTATGTACATGCGTGAAATG<br>GGAACGGTTGAACTATTAACGCGTGAAGGCGAAATTAGCATTGCAAA<br>ACGCATTGAAGAAGGTATTCGTGACGTTCTTCATTCGATTGCGTACTG<br>GCCAAATGCAGTTGAAGTTGTATTAAAAGAATATAGCGATGTTGCTG<br>AAGGCGAACGTCGTCTTGCTGATATTTTATCTGGTTATTTAGACCCAG<br>AATCTGACGAAGAAATTCCAGAAGTTTTAGAAGAAGAAGCTGAAATT<br>GTTGAAGATGATGAAGCGACGACTAAAACCACTAAAGATGTAAAATT<br>GGACGATGACGAAGAAGAAGAATCTGAAAGTGATGATGATTCTGAA<br>GGTGAGTCTGGTCCAGATCCAGAAATTGCACGTGTTCGTTTCACTGAA<br>TTAGAAGATGCGTGGAAAGTAACCAAAGCCACCATTGAAAAGCATGG<br>CCGTAACAGCAAACAAGCAGATGAAGCGCTTGAAGCTCTTGCAACTG<br>TGTTTATGATGTTCAAATTTACACCACGTTTATTTGAAATCATTTCAGA<br>AATGATTCGTGGCACGCATGAACAAATTCGTACAGCAGAACGTGAAG<br>TGATGCGTTACGCAGTTCGTCGTGGTCGTATGGACCGTACCCAATTCC<br>GTACATCGTTCCCAGGCCAAGAGTCAAATCCAGCTTGGTTAGATGAA<br>CAAATTGCTAAAGCACCTGCGGATCAAAAAGGTTATTTAGAAAAAGT<br>ACGTCCAGATGTTGTTGCATTCCAGCAAAAGATTGCCGATATCGAAA<br>AAGAATTGGGCTTAGATGTTAAAGACATCAAAGACATTTCTAAACGT<br>ATGGCTGTGGGTGAAGCGAAAGCACGTCGCGCGAAAAAAGAAATGG<br>TTGAAGCAAACTTACGTTTGGTGATTTCGATTGCGAAAAAATATACCA<br>ACCGTGGTTTACAATTCCTTGACTTGATTCAAGAAGGTAACATCGGTT<br>TGATGAAAGCCGTAGACAAGTTTGAATACCGTCGTGGTTATAAATTCT<br>CGACTTATGCAACTTGGTGGATTCGTCAGGCGATTACCCGTTCGATTG<br>CCGATCAAGCACGTACCATCCGTATTCCAGTACACATGATCGAAACC<br>ATTAACAAGATCAACCGTGTATCTCGTCAACTTCTTCAAGAAATGGGC<br>CGTGAGCCTACCCCTGAAGAATTAGGCGAACGTCTGGAAATGGACGA<br>AGTTAAAGTACGTAAAGTGCTGAAAATTGCCAAAGAACCGATTTCGA |

-continued

Sequence Listing

| Seq ID No. | Description | Sequence |
|---|---|---|
| | | TGGAAACACCGATTGGTGATGACGAAGATTCGCATCTTGGTGACTTC<br>ATTGAAGATGGTAACATTACCTCTCCAATTGATGCCGCGACTTCTGAA<br>GGCTTAAAAGAAGCAACACGTGAAGTGCTGGAAAACTTGACCGAACG<br>TGAAGCGAAAGTCTTAAAAATGCGTTTTGGTATTGATATGCCAACCG<br>ACCATACTTTAGAAGAAGTGGGTAAACAATTTGATGTAACACGTGAA<br>CGTATTCGTCAGATTGAAGCCAAAGCTTTACGTAAATTACGTCACCCT<br>TCTCGTTCTGAACACTTACGTTCATTCCTAGAAAATGACTAA |
| 130 | DP71 Glutamine-IRNA ligase | ATGAGTGAGGCTGAAGCCCGCCCAACAAATTTTATCCGTCAGATTATT<br>GATGAAGATCTGGCGACCGGGAAACACAATACCGTTCACACCCGTTT<br>CCCGCCTGAGCCTAATGGCTATTTGCATATCGGCCATGCGAAGTCTAT<br>CTGCCTGAATTTCGGCATTGCGCAAGACTACCAGGGTCAGTGCAATCT<br>GCGTTTTGACGATACTAACCCGGCAAAAGAAGACATCGAATTCGTTG<br>AGTCGATCAAATACGACGTCCAGTGGCTGGGCTTCGACTGGAGCGGT<br>GATATTCACTACTCCTCAGACTATTTCGATCAACTGCACGCATACGCG<br>CTGGAGCTAATCAACAAAGGTCTGGCGTACGTTGACGAACTGTCTCC<br>CGATCAAATTCGCGAATACCGTGGTTCGCTGACCGCACCGGGCAAAA<br>ACAGCCCGTATCGCGATCGCAGCGTGGAAGAAAATATCGCGCTGTTT<br>GAAAAAATGCGTAACGGTGAATTCGCCGAAGGTGCCGCTTGCCTGCG<br>TGCCAAAATCGATATGGCGTCGCCATTCTTCGTGATGCGCGATCCGGT<br>CATCTACCGTATTAAGTTTGCCGAACATCATCAGACTGGCACAAAATG<br>GTGCATCTACCCGATGTACGATTTCACTCACTGCATTTCCGATGCGCT<br>GGAAGGGATCACCCATTCACTGTGTACGCTGGAATTCCAGGACAACC<br>GCCGTCTGTACGACTGGGTACTGGATAACATCACTATTCCATGCCATC<br>CGCGTCAGTATGAGTTCTCCCGTCTGAATCTTGAATACTCCATCATGT<br>CCAAGCGTAAGCTGAACCTGCTGGTGACGGATAAGATTGTAGAAGGT<br>TGGGACGATCCGCGTATGCCGACGGTTTCCGGTCTGCGTCGCCGTGGT<br>TATACCGCCGCGTCTATCCGCGAATTCTGCCGTCGTATCGGCGTGACC<br>AAGCAGGACAACAACGTTGAAATGATGGCGCTGGAATCCTGTATTCG<br>TGACGATCTGAACGAAAACGCACCGCGCGCCATGGCCGTTATTAACC<br>CGGTTAAAGTTGTCATTGAGAACTTCACCGGTGATGACGTGCAAATG<br>GTGAAAATGCCGAATCATCCGAGCAAACCGGAAATGGGCACCCGCGA<br>AGTGCCGTTCACCCGTGAGATTTACATCGATCAGGCTGATTTCCGCGA<br>AGAAGCGAACAAACAGTACAAACGTCTGGTGCTGGGCAAAGAAGTTC<br>GCCTGCGCAATGCGTATGTGATCAAAGCGGAACACATCGAGAAAGAC<br>GCGGAAGGGAATATCACCACCATCTTCTGTTCTTACGATATCGATACG<br>CTGAGCAAAGATCCCGCTGATGGCCGTAAGGTGAAAGGCGTGATTCA<br>CTGGGTTTCTGCTTCTGAAGGTAAACCGGCAGAATTTCGCCTGTATGA<br>CCGTCTGTTCAGTGTTGCGAACCCTGGCCAGGCTGAAGATTTCCTGAC<br>CACCATCAACCCGGAATCTCTGGTGATTGCTCAGGGCTTCGTTGAGCC<br>GTCTCTGGTCGCTGCTCAGGCAGAAGTCAGTGTGCAGTTCGAACGTG<br>AAGGTTACTTCTGTGCCGACAGCCGCTATTCAAGTGCTGAGCATCTGG<br>TGTTCAACCGCACCGTCGGCCTTCGCGACACCTGGGAAAGCAAACCC<br>GTCGCCTGA |
| 131 | DP71 DNA gyrase subunit B | ATGTCGAATTCTTATGACTCCTCAAGTATCAAGGTATTAAAAGGGCTG<br>GACGCGGTGCGTAAGCGCCCCGGCATGTATATCGGCGATACCGATGA<br>CGGCACTGGTCTGCACCACATGGTATTCGAGGTTGTGGACAACGCTAT<br>CGACGAAGCCCTCGCGGGCCACTGTAAAGAGATTCAGGTCACGATCC<br>ATGCGGATAACTCTGTTTCCGTACAGGATGATGGTCGTGGTATTCCTA<br>CCGGCATTCACGAAGAAGAGGGCGTTTCTGCTGCTCAGGTCATCATG<br>ACCGTACTTCATGCCGGCGGTAAATTTGACGATAACTCGTACAAAGTC<br>TCCGGCGGTCTGCATGGCGTGGGTGTTTCCGTCGTTAACGCCCTGTCG<br>GAAAAACTGGAGCTGGTTATCCGCCGTGAAGGCAAAGTGCACACCCA<br>GACTTACGTCCACGGTGAGCCGCAGGATCCGCTGAAAGTGGTTGGCG<br>ATACCGAGGCGACCGGTACGACCGTGCGCTTCTGGCCAAGCTACGCC<br>ACCTTCACCAATCAAACAGAATTCGAGTATGACATTCTGGCGAAACG<br>CCTCCGTGAGCTGTCATTCCTGAACTCTGGTGTGGCGATCCGCCTGCT<br>CGACAAACGCGATGGCAAGAACGATCACTTCCATTATGAAGGCGGTA<br>TCAAAGCTTTCGTGGAATACCTGAACAAAAACAAAACCCCAATCCAC<br>CCAACCGTGTTCTATTTCTCCACCGTGAAAGACGATATCGGTGTGGAA<br>GTGGCGTTGCAGTGGAATGATGGTTTCCAGGAAAATATTTACTGCTTT<br>ACCAACAATATCCCTCAGCGCGACGGCGGCACCCATCTGGTAGGCTT<br>CCGTTCTGCGATGACCCGTACGCTTAACGCGTATATGGATAAAGAAG<br>GCTACAGCAAGAAATCCAAAATCAGCGCCACCGGTGATGATGCCCGT<br>GAAGGCCTGATCGCCGTGGTTTCGGTAAAAGTGCCGGATCCTAAGTT<br>CTCCTCTCAGACCAAAGACAAACTGGTTTCTTCCGAAGTGAAGACCG<br>CCGTTGAGTCTCTGATGAACGAGAAGCTGGTTGATTATCTGATGGAA<br>AACCCGGCCGACGCGAAAATCGTTGTCGGTAAAATCATCGATGCAGC<br>CCGTGCGCGTGAAGCCGCGCGTAAAGCACGTGAAATGACCCGTCGTA<br>AAGGCGCGCTCGATCTGGCCGGTCTGCCAGGCAAACTGGCTGACTGT<br>CAGGAACGCGACCCGGCACATTCCGAACTGTACTTAGTGGAAGGGGA<br>CTCAGCGGGCGGCTCTGCAAAACAAGGCCGTAACCGTAAGAACCAGG |

-continued

Sequence Listing

| Seq ID No. | Description | Sequence |
|---|---|---|
| | | CGATTCTGCCGTTGAAAGGGAAAATCCTCAACGTTGAGAAAGCGCGC<br>TTCGACAAAATGCTCTCTTCTCAGGAAGTGGCGACGCTGATTACCGCG<br>CTCGGTTGCGGTATCGGCCGTGACGAATACAACCCGGATAAACTGCG<br>TTATCACAGCATCATCATCATGACCGATGCCGACGTCGATGGTTCGCA<br>CATCCGTACCCTGTTACTGACATTCTTCTACCGTCAGATGCCTGAAAT<br>TGTAGAGCGTGGCCACGTGTTTATCGCGCAGCCTCCGCTGTACAAAGT<br>GAAAAAAGGCAAACAGGAACAGTACATTAAAGATGATGAAGCGATG<br>GATCAGTATCAAATCTCTATCGCGATGGACGGGGCAACGTTACACGC<br>CAACGCCCATGCACCAGCACTGGCGGGCGAACCGCTGGAGAAACTGG<br>TGGCTGAACATCACAGCGTGCAGAAAATGATTGGCCGTATGGAACGT<br>CGTTATCCGCGTGCGCTGCTGAATAATCTGGTCTATCAGCCAACGCTG<br>GCGGGTGCTGAACTTGCCGACGAAGCGAAAGTGAAGGAATGGATTGA<br>AACGCTGGTGTCTCGTCTGAACGAGAAAGAGCAGCACGGCAGCAGCT<br>ACAGTGCGATCGTGCGCGAAAATCTTGAACACCAGCTGTTCGAGCCA<br>ATCCTGCGCATTCGTACTCACGGTGTGGATACCGACTACGATCTCGAT<br>GCAGACTTCATTCAGGGCGGCGAATACCGCAAAATCTGTACCCTGGG<br>TGAAAAACTGCGCGGCCTGATCGAAGAAGATGCTTACATCGAACGTG<br>GCGAACGCCGTCAGCCAGTGACCAGCTTCGAGCAGGCGCTGGAATGG<br>CTGGTGAAAGAGTCGCGTCGCGGTCTGTCGATTCAGCGTTATAAAGG<br>TCTGGGTGAAATGAACCCTGAGCAATTGTGGGAAACCACGATGGATC<br>CGACACAACGCCGCATGCTGCGCGTGACGGTGAAAGATGCTATCGCG<br>GCGGACCAGCTGTTCACCACGCTGATGGGCGATGCGGTTGAACCGCG<br>CCGCGCCTTCATCGAAGAGAACGCCCTTAAAGCTGCCAATATCGATA<br>TCTGA |
| 132 | DP71 Isoleucine tRNA ligase | ATGAGTGACTACAAGAACACCCTGAATTTGCCGGAAACAGGGTTCCC<br>GATGCGTGGCGATCTGGCCAAGCGTGAACCTGACATGCTGAAGAATT<br>GGTATGACCAGGATCTGTACGGGATTATTCGTGCTGCCAAGAAAGGC<br>AAGAAAACCTTTATCTTGCATGACGGCCCTCCGTATGCGAACGGCAG<br>CATTCATATTGGTCACTCAGTAAACAAAATTCTTAAAGACATGATCGT<br>TAAGTCCAAAGGACTGGCGGGCTTTGATGCGCCGTATGTTCCGGGCT<br>GGGATTGTCATGGTCTGCCGATTGAACTGAAAGTTGAACAGCTGATC<br>GGTAAGCCGGGCGAAAAAGTCACGGCGGCGGAATTCCGTGAAGCCTG<br>CCGCAAGTACGCTGCTGAACAGGTTGAAGGTCAGAAGAAAGACTTCA<br>TCCGTCTGGGCGTGCTCGGTGACTGGGATCATCCGTACCTGACCATGG<br>ACTTCAAAACAGAAGCCAACATCATTCGTGCCCTGGGTAAAATCATC<br>GGCAACGGTCACCTGCATAAAGGTGCGAAACCTGTTCACTGGTGTAC<br>CGATTGCGGATCTTCACTGGCTGAAGCCGAAGTCGAATATTACGACA<br>AAGTGTCTCCGTCTATCGACGTGACGTTTAATGCGACGGATGCCGCCG<br>CTGTTGCTGCGAAATTCGGTGCCACTGCTTTCAATGGCCCGGTTTCTC<br>TGGTCATCTGGACCACCACCCCGTGGACCATGCCAGCTAACCGCGCG<br>ATTTCACTCAACGCTGAGTTCTCTTATCAGCTGGTGCAGATTGAAGGT<br>CAGTGCCTGATCCTGGCTACCGATCTGGTAGAAAGCGTGATGAATCG<br>CGCCGGTATCGCTGAGTGGACTGTGCTGGGCGAATGTAAAGGTGCGG<br>ATCTTGAATTGCTTCGATTCCAGCATCCGTTCCTCGGTTTCGATGTTCC<br>GGCGATCCTCGGCGATCACGTTACTCTCGATGCCGGTACCGGTGCTGT<br>ACATACCGCACCTGGCCACGGTCCTGATGACTTTGTCATTGGCCAGAA<br>ATACGGTCTGGAAGTCGCAAACCCGGTTGGACCGAACGGCTGCTACC<br>TGCCGGGCACTTATCCGACGCTGGATGGCAAATTCGTCTTTAAAGCGA<br>ATGATCTGATCGTTGAATTGCTGCGTGAGAAGGGCGCACTGCTGCAC<br>GTTGAGAAAATGAACCACAGCTATCCGTGCTGCTGGCGTCACAAAAC<br>GCCGATCATCTTCCGCGCTACGCCACAATGGTTCATCAGCATGGATCA<br>GAAAGGTTTGCGTCAGAAGTCTCTGGAAGAGATCAAAGGCGTGCAGT<br>GGATCCCTGACTGGGGTCAGGCGCGTATCGAAAACATGGTCGCTAAC<br>CGTCCTGACTGGTGTATCTCCCGCCAGCGTACGTGGGGCGTACCGATG<br>TCTCTGTTCGTGCATAAAGATACCGAACAGCTTCATCCGCGCAGCCTT<br>GAGCTGATGGAAGAAGTGGCAAAACGCGTGGAAGCCGATGGCATTC<br>AGGCATGGTGGGATCTGAACCCTGAAGAGATTTTGGGTGCAGACGCT<br>GCCGATTACGTCAAAGTGCCGGATACGCTGGACGTCTGGTTTGACTCC<br>GGTTCCACGCACTCCTCCGTTGTGGATGTGCGCCCTGAGTTCAACGGT<br>CATTCACCGGATCTGTATCTGGAAGGTTCTGACCAGCATCGCGGCTGG<br>TTCATGTCTTCTCTGATGATTTCTACGGCGATGAAAGGCAAAGCGCCT<br>TACAAACAAGTACTGACTCACGGTTTCACCGTCGATGGTCAGGGCCG<br>TAAAATGTCTAAATCCATCGGTAACACCATCGCGCCTCAGGATGTGAT<br>GAATAAGCTGGGTGGCGACATCCTGCGTTTGTGGGTGGCATCTACGG<br>ATTACACCGGCGAAATCGCCGTGTCCGACGAAATCCTCAAACGTGCT<br>GCCGATTCTTATCGCCGTATCCGTAACACCGCGCGCTTCCTGCTGGCG<br>AACCTTAACGGTTTCGATCCGGCGCTGCACAGCGTGGCACCGGAAGA<br>GATGGTTGTGCTGGATCGCTGGGCGGTTGGCCGCGCGAAAGCTGCAC<br>AAGACGAGATCATTGCTGCGTACGAAGCCTATGATTTCCACGGCGTT<br>GTTCAGCGTCTGATGCAGTTCTGCTCGATCGAAATGGGTTCGTTCTAT<br>CTGGATATCATTAAAGATCGCCAGTACACCGCGAAGAGCGACAGCGT<br>TGCGCGCCGCAGCTGCCAGACCGCGCTGTATCACATCTGCGAAGCAC |

-continued

| Seq ID No. | Description | Sequence |
|---|---|---|
| | | TGGTTCGCTGGATGGCGCCAATCATGTCCTTCACTGCCGATGAAATCT GGGCTGAACTGCCAGGTCATCGCGAGAAGTTCGTCTTTACTGAAGAA TGGTACGACGGTCTGTTTGGCCTGATCGGTAACGAATCCATGAACGAT GCGTTCTGGGATGAGCTGCTGAAAGTGCGTGGTGAAGTGAACAAAGT GATCGAACAGGCGCGTGCTGATAAACGTCTGGGCGGTTCTCTGGAAG CAGCCGTGACCTTATATGCAGACGACGCGCTGGCAACAGACCTGCGT TCTCTGGGTAACGAACTGCGCTTTGTGCTCCTGACTTCCGGTGCGAAA GTCGCCGCGCTGTCTGAAGCTGATGACTCAGCGCAGGCCAGCGAATT GTTGAAAGGACTGAAAATTGGTCTGGCGAAAGCAGAAGGCGAGAAG TGCCCGCGCTGCTGGCATTTCACCACTGATATCGGCCAGAATGCGGA ACACAGTGACATCTGTGGCCGTTGTGTGACTAACATTGCCGGTGACG GCGAAGAGCGTAAGTTTGCATAA |
| 133 | DP71 NADH-quinone oxidoreductase subunit C/D | ATGTCAGAACTTACTCATATTAATGCTTCCGGCGACGCCCACATGGTG GATGTCTCCGGTAAAGACGACACCGTTCGTGAAGCCCGTGCCGAAGC CTTTGTTGAAATGGCCGAAAGCACGCTGGCGATGATCATCGGCGGTA ATCACCATAAGGGTGACGTGTTCGCGACCGCGCGGATTGCCGGTATT CAGGCAGCGAAGAAAACCTGGGATCTGATCCCGCTGTGTCATCCGCT GTTGCTGACCAAGGTGGAAGTGAATCTTGAAGCGCAGCCAGAATTTA ATCGTGTACGTATTGAATCCCGCTGCCGCCTGAGCGGTAAAACCGGC GTCGAGATGGAAGCGCTGACCTTCAAGCCTGAAGACTGGGGAATGAA GCGCGGCACCGAAAACGAGGACTTCATGTTCCTCAACCTCGGACCTA ACCATCCGTCTGCGCACGGTGCGTTCCGCATCATCCTGCAGCTTGATG GCGAAGAAATTGTCGACTGTGTACCGGACGTCGGTTACCACCACCGT GGTGCTGAGAAGATGGGCGAGCGCCAGTCATGGCACAGCTACATTCC ATACACGGACCGTATCGAATACCTCGGCGGTTGCGTTAACGAGATGC CATACGTACTGGCTGTTGAAAAACTGGCGGGTATCGTCGTGCCGGAT CGCGTTAACACCATCCGCGTGATGCTGTCTGAACTGTTCCGTATCAAC AGCCACCTGCTGTACATCTCTACGTTTATTCAGGACGTGGGCGCGATG ACGCCAGTGTTCTTCGCCTTTACCGATCGTCAGAAAATTTACGATCTG GTGGAAGCGATCACCGGTTTCCGTATGCACCCGGCCTGGTTCCGTATT GGTGGCGTTGCACACGACCTGCCGAAAGGCTGGGAGCGTCTGCTGCG TGAATTCCTTGACTGGATGCCAGCCCGTCTGGATTCCTACGTCAAGGC AGCGCTGAAAAACACCATTCTGATTGGACGTTCCAAAGGCGTAGCAG CATACAACGCCGATGATGCGCTGGCGTGGGGCACCACCGGTGCTGGC CTGCGTGCGACCGGGATCGACTTCGATGTCCGCAAATGGCGTCCATAT TCAGGTTACGAAAACTTCGATTTTGAAGTGCCGGTCGGCGATGGCGTC AGTGATTGCTATTCCCGCGTGATGCTAAAAGTGGAAGAGCTTCGTCA GAGCCTGCGCATTCTGGAACAGTGCTACAAAAACATGCCGGAAGGCC CGTTCAAGGCGGATCACCCGCTGACCACGCCGCCACCGAAAGAGCGT ACGCTGCAACACATCGAAACCCTGATCACTCACTTCCTGCAAGTGTCG TGGGGTCCGATCATGCCTGCGCAAGAATCTTTCCAGATGGTTGAAGCC ACCAAAGGGATCAACAGCTACTACCTGACCAGTGACGGCAGCACCAT GAGCTACCGCACGCGCGTCCGTACGCCAAGCTTCCCGCATTTGCAGC AGATCCCGTCCGTAATCCGTGGCAGCCTGGTATCCGACCTGATCGTGT ATCTGGGCAGTATCGATTTTGTAATGTCAGATGTGGACCGCTAA |
| 134 | DP71 Protein RecA | ATGGCTATTGATGAGAACAAGCAAAAAGCGTTAGCTGCAGCACTGGG CCAGATTGAAAAGCAATTCGGTAAAGGCTCCATCATGCGTCTGGGTG AAGATCGCTCTATGGACGTGGAAACGATCTCTACCGGCTCTTTGTCTC TGGATATCGCGTTAGGCGCCGGTGGTTTGCCGATGGGCCGTATCGTTG AGATTTATGGCCCGGAATCCTCCGGTAAAACTACGCTGACCCTTCAGG TTATTGCTGCCGCACAGCGCGAAGGCAAAACCTGTGCGTTCATCGAT GCGGAACATGCACTTGACCCTATCTACGCGAAGAAATTGGGCGTAGA TATCGACAACCTGTTGTGTTCTCAGCCGGATACCGGCGAACAGGCTCT GGAAATCTGTGACGCGCTGACCCGTTCAGGCGCGGTCGACGTTATCA TCGTCGACTCCGTTGCTGCACTGACGCCAAAAGCAGAAATCGAAGGC GAAATCGGTGACTCTCACATGGGCCTTGCGGCACGTATGATGAGCCA GGCAATGCGTAAGCTTGCCGGTAACCTGAAAAACGCCAACACCTTGC TGATCTTCATCAACCAGATCCGTATGAAAATCGGTGTGATGTTCGGTA ACCCGGAAACCACCACCGGTGGTAACGCCCTGAAATTCTACGCCTCT GTGCGTCTGGATATCCGCCGCATCGGCGCTATCAAAGAAGGCGACGT GGTGATCGGCAGTGAAACGCGCGTGAAAGTTGTGAAGAACAAAATCG CTGCGCCTTTCAAACAGGCTGAATTCCAGATCCTATACGGCGAAGGC ATCAACATTAACGGCGAGCTGATCGATTTGGGCGTTAAGCACAAACT GGTCGAAAAAGCCGGTGCATGGTACAGCTACAACGGCGAGAAGATTG GTCAGGGTAAATCTAACTCCTGCAACTATCTGAAAGAAAACCCGAAA ATCGCTGCTGAACTGGATAAAAAACTGCGTGATATGTTGTTGAGTGG CACTGGTGAACTGGCCGCTGCAACCACAGCAGAACTTGCAGACGACG ATATGGAAACCAGCGAAGAGTTTTAA |

-continued

Sequence Listing

| Seq ID No. | Description | Sequence |
|---|---|---|
| 135 | DP71 RNA polymerase sigma factor RpoD | GGTAAGGAGCAAGGCTATCTGACCTTTGCTGAGGTCAATGACCATCT GCCGGAAGATATCGTCGACTCCGACCAGATCGAAGACATCATCCAGA TGATTAACGACATGGGCATCCAGGTTCTTGAAGAAGCGCCGGACGCC GATGATTTGATGCTGGCCGAAAACCGCCCTGATACCGATGAAGATGC TGCAGAAGCAGCGGCTCAGGTGCTTTCCAGCGTTGAATCTGAAATTG GCCGTACCACCGACCCTGTGCGTATGTATATGCGCGAAATGGGTACC GTTGAGCTCCTGACCCGTGAAGGCGAAATCGACATCGCCAAACGTAT CGAAGACGGTATCAATCAGGTCCAGTGCTCCGTTGCTGAATATCCTGA AGCTATCACCTATTTGTTAGAGCAATATGACCGTGTTGAAGCAGGCG AAGCACGTCTGTCTGATTTGATCACCGGTTTTGTTGATCCGAACGCCG AAGAAGAAATCGCGCCGACTGCGACTCACGTGGGTTCTGAACTGACC ACTGAAGAGCAAAATGATACCGACGACGATGAAGAAGACGACGACG ATGCTGAAGACGACAACAGCATCGACCCGGAACTGGCGCGTCAGAAG TTCACCGATCTGCGTGAGCAACATGAAGCGACCCGTGCCGTCATCAA GAAAAATGGCCGTAGCCACAAAAGCGCCGCAGAAGAAATTCTGAAG CTGTCCGATGTGTTTAAACAGTTCCGTCTGGTACCAAAACAGTTCGAT TTCCTGGTGAACAGCATGCGCTCCATGATGGATCGCGTCCGTACTCAG GAACGTCTGATCATGAAAGTGTGCGTTGAACAGTGCAAAATGCCGAA GAAAAACTTCGTCAATCTGTTCGCCGGTAACGAAACCAGCAGTACCT GGTTTGATGCTGCTCTGGCAATGGGTAAACCATGGTCTGAGAAGCTG AAAGAAGTGACCGAAGACGTGCAGCGCGGCCTGATGAAACTGCGCC AAATCGAAGAAGAAACTGGCCTGACTATCGAACAGGTAAAAGACATT AACCGTCGCATGTCGATCGGCGAAGCGAAAGCACGCCGCGCGAAGA AAGAGATGGTTGAAGCGAACTTACGTCTGGTTATCTCTATCGCGAAG AAATACACCAACCGTGGCTTGCAGTTCCTTGACCTGATTCAGGAAGGT AACATCGGCCTGATGAAAGCCGTTGATAAGTTTGAATATCGCCGTGG TTATAAGTTCTCTACTTATGCGACCTGGTGGATCCGTCAGGCTATCAC CCGCTCCATCGCCGACCAGGCACGTACCATCCGTATTCCGGTGCATAT GATTGAGACCATCAACAAACTCAACCGTATTTCGCGCCAGATGTTGC AGGAGATGGGCCGTGAGCCGACGCCGGAAGAGCTGGCTGAACGCAT GCTGATGCCGGAAGACAAGATCCGTAAAGTGCTGAAAATTGCTAAAG AGCCAATCTCCATGGAAACGCCAATCGGCGACGATGAAGATTCGCAT CTGGGTGATTTCATCGAGGATACTACCCTCGAGCTGCCGCTGGATTCT GCGACCTCTGAAAGCCTGCGTTCTGCAACGCACGACGTTCTGGCTGGC CTGACCGCACGTGAAGCGAAAGTTCTGCGTATGCGTTTCGGTATCGAT ATGAACACTGACCACACTCTGGAAGAAGTGGGCAAACAGTTCGACGT AACCCGTGAACGTATCCGTCAGATCGAAGCCAAAGCGTTGCGTAAAC TACGCCACCCAAGCCGCTCCGAAGTGCTGCGCAGCTTCCTCGACGACT AG |
| 136 | DP71 DNA-directed RNA polymerase subunit beta | ATGGACCAGAACAACCCGTTGTCTGAGATCACGCACAAACGTCGTAT CTCTGCACTGGGCCCGGGCGGTTTGACCCGTGAACGTGCTGGCTTTGA AGTTCGAGACGTACACCCGACGCACTACGGTCGCGTATGTCCAATCG AAACGCCAGAAGGTCCAAACATCGGTCTGATCAACTCATTATCTGTCT ATGCACAGACAAATGAGTATGGTTTCCTGGAAACCCCTTACCGCCGT GTGCGTGAAGGTATGGTTACCGATGAAATTAACTACCTGTCTGCCATC GAAGAAGGCAACTTTGTTATCGCTCAGGCGAACTCCAACCTGGATGA CGAAGGCCACTTCCTGGAAGATTTAGTCACTTGTCGTAGCAAAGGCG AATCAAGCCTGTTCAGCCGCGACCAGGTTGACTACATGGACGTTTCTA CCCAGCAGATCGTATCCGTTGGTGCTTCACTGATTCCATTCCTGGAAC ACGATGACGCCAACCGTGCATTGATGGGTGCGAACATGCAACGTCAG GCAGTTCCTACTCTGCGTGCTGATAAGCCGCTGGTAGGTACTGGTATG GAACGTGCTGTTGCGGTTGACTCCGGTGTTACTGCCGTTGCCAAACGT GGTGGTACTGTTCAGTACGTAGATGCATCCCGTATCGTTATTCGTGTT AACGAAGAAGAGATGAATCCAGGCGAAGCAGGTATCGACATTTATAA CCTGACTAAGTACACCCGTTCTAACCAGAACACCTGCATCAACCAGA TGCCGTGTGTGAATCTGGGCGAGCCAATCGAGCGCGGCGACGTGCTG GCAGATGGTCCGTCAACAGATCTGGGCGAACTGGCACTGGGTCAGAA CATGCGTGTCGCGTTCATGCCTTGGAACGGTTACAACTTCGAAGACTC CATCTTGGTCTCCGAACGTGTTGTGCAGGAAGATCGCTTCACGACCAT CCATATCCAGGAACTGGCATGTGTGTCCCGTGACACAAAGTTAGGGC CTGAAGAGATCACTGCTGATATCCCTAACGTGGGTGAAGCTGCGCTCT CCAAACTGGATGAGTCCGGTATTGTGTATATCGGTGCTGAAGTGACC GGTGGTGACATTCTGGTCGGTAAAGTTACGCCTAAAGGCGAAACCCA GCTGACTCCAGAAGAGAAACTGCTGCGTGCGATCTTCGGTGAGAAAG CGTCTGACGTTAAAGATTCTTCTCTGCGTGTACCAAACGGCGTTTCCG GTACGATTATTGACGTGCAAGTCTTTACCCGCGATGGCGTGGAAAAA GATAAGCGTGCGTTAGAAATCGAAGAAATGCAGCTGAAACAGGCTAA GAAAGACCTGACTGAAGAGCTGCAAATTCTGGAAGCTGGTCTGTTTG CACGTATCCAGTCCGCGCTGGTTGCTGGCGGTGTTGAAGCCGATAAG CTGGGCAAATTGCCACGCGATCGTTGGCTTGAACTGTCACTGACTGAC GAAGACAAACAGAATCAGTTGGAACAGCTTGCTGAACAGTACGACGA |

-continued

Sequence Listing

| Seq ID No. | Description | Sequence |
|---|---|---|
| | | ACTGAAATCCGAGTTTGAGAAAAAACTCGAAGCTAAACGTCGTAAAA TCACTCAGGGCGATGACCTAGCACCAGGTGTGCTGAAAATCGTTAAA GTGTACCTGGCCGTTAAACGTCAGATCCAACCTGGTGACAAAATGGC AGGCCGCCACGGTAACAAAGGTGTTATCTCCAAGATCAACCCGATCG AAGATATGCCTTACGATGAAAACGGGACTCCTGTTGACATCGTACTG AACCCGCTGGGCGTTCCATCACGTATGAACATTGGTCAGATTTTAGAA ACCCACCTGGGTATGGCCGCGAAAGGTATTGGTGAAAAAATCAATGC CATGCTTAAGAAACATGAAGAAGTTTCTAAGCTGCGCGAGTTCATCC AGCGTGCCTATGATCTGGGCGACGACGTACGTCAGAAAGTTGATCTG ACCACCTTCACCGATGATGAAGTATTGCGTTTGGCTGAAAACCTGAA AAAGGGTATGCCAATTGCAACACCAGTCTTCGACGGTGCGAAAGAGA CAGAGATCAAGCAACTGCTTGAAATGGGCGGCGTCCCAACCTCTGGC CAGATCACACTGTTTGACGGCCGTACCGGCGAGCAATTCGAGCGCCA GGTTACCGTCGGCTACATGTACATGCTGAAACTGAACCACCTGGTTGA CGATAAGATGCATGCGCGTTCTACCGGTTCTTACAGCCTTGTTACTCA GCAGCCGCTGGGTGGTAAAGCTCAGTTCGGTGGTCAGCGCTTCGGTG AGATGGAAGTGTGGGCACTGGAAGCATACGGTGCCGCTTATACCCTG CAGGAAATGCTGACTGTTAAGTCCGATGACGTGAACGGCCGTACTAA GATGTATAAAAACATCGTAGATGGCGATCACCGGATGGAACCAGGCA TGCCGGAATCATTCAACGTACTGTTGAAAGAAATCCGCTCTCTGGGTA TCAACATCGAGCTGGAAGACGAGTAA |
| 137 | DP72 16S rRNA | TTCGGAGAGTTTGATCCTGGCTCAGGACGAACGCTGGCGGCGTGCCT AATACATGCAAGTCGAGCGGACAGAAGGGAGCTTGCTCCCGGATGTT AGCGGCGGACGGGTGAGTAACACGTGGGTAACCTGCCTGTAAGACTG GGATAACTCCGGGAAACCGGAGCTAATACCGGATAGTTCCTTGAACC GCATGGTTCAAGGATGAAAGACGGTTTCGGCTGTCACTTACAGATGG ACCCGCGGCGCATTAGCTAGTTGGTGGGGTAATGGCTCACCAAGGCG ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGATGAAGGTT TTCGGATCGTAAAGCTCTGTTGTTAGGGAAGAACAAGTGCGAGAGTA ACTGCTCGCACCTTGACGGTACCTAACCAGAAAGCCACGGCTAACTA CGTGCCAGCAGCCGCGGTAATACGTAGGTGGCAAGCGTTGTCCGGAA TTATTGGGCGTAAAGGGCTCGCAGGCGGTTTCTTAAGTCTGATGTGAA AGCCCCCGGCTCAACCGGGGAGGGTCATTGGAAACTGGGAAACTTGA GTGCAGAAGAGGAGAGTGGAATTCCACGTGTAGCGGTGAAATGCGTA GAGATGTGGAGGAACACCAGTGGCGAAGGCGACTCTCTGGTCTGTAA CTGACGCTGAGGAGCGAAAGCGTGGGGAGCGAACAGGATTAGATAC CCTGGTAGTCCACGCCGTAAACGATGAGTGCTAAGTGTTAGGGGGTT TCCGCCCCTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAACCCTAGAGATAGGGCTTTCCCTTC GGGGACAGAGTGACAGGTGGTGCATGGTTGTCGTCAGCTCGTGTCGT GAGATGTTGGGTTAAGTCCCGCAACGAGCGCAACCCTTGATCTTAGTT GCCAGCATTTAGTTGGGCACTCTAAGGTGACTGCCGGTGACAAACCG GAGGAAGGTGGGGATGACGTCAAATCATCATGCCCCTTATGACCTGG GCTACACACGTGCTACAATGGACAGAACAAAGGGCTGCGAGACCGCA AGGTTTAGCCAATCCCATAAATCTGTTCTCAGTTCGGATCGCAGTCTG CAACTCGACTGCGTGAAGCTGGAATCGCTAGTAATCGCGGATCAGCA TGCCGCGGTGAATACGTTCCCGGGCCTTGTACACACCGCCCGTCACAC CACGAGAGTTTGCAACACCCGAAGTCGGTGAGGTAACCTTTATGGAG CCAGCCGCCGAAGGTGGGGCAGATGATTGGGGTGAAGTCGTAACAAG GTAGCCGTATCGGAAGGTGCGGCTGGATCACCTCCTTT |
| 138 | DP73 16S rRNA | AACGGAGAGTTTGATCCTGGCTCAGGACGAACGCTGGCGGCGTGCCT AATACATGCAAGTCGAGCGGACAGAAGGGAGCTTGCTCCCGGACGTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAAGGGATGG GCCCGCGGCGCATTAGCTAGTTGGTAAGGTAACGGCTTACCAAGGCG ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGAGGAAGGC CTTCGGGTCGTAAAGCTCTGTTGTGAGGGAAGAAGCGGTGCCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG |

-continued

Sequence Listing

| Seq ID No. | Description | Sequence |
|---|---|---|
| | | TAACTGACGCTGAGGCGCGAAAGCGTGGGGAGCAAACAGGATTAGA TACCCTGGTAGTCCACGCCGTAAACGATGAGTGCTAGGTGTTAG |
| 139 | DP74 16S rRNA | GCCTAATACATGCAAGTCGTGCGGACCTTTTAAAAGCTTGCTTTTAAA AGGTTAGCGGCGAACGGGTGAGTAACACGTGGGCAACCTGCCTGTAA GATCGGGATAATGCCGGGAAACCGGGGCTAATACCGGATAGTTTTTT CCTCCGCATGGAGGAAAAAGGAAAGACGGCTTCGGCTGTCACTTACA GATGGGCCCGCGGCGCATTAGCTTGTTGGTGGGGTAACGGCTCACCA AGGCAACGATGCGTAGCCGACCTGAGAGGGTGATCGGCCACATTGGG ACTGAGACACGGCCCAAACTCCTACGGGAGGCAGCAGTAGGGAATCT TCCGCAATGGACGAAAGTCTGACGGAGCAACGCCGCGTGAGTGAAGA AGGCCTTCGGGTCGTAAAACTCTGTTGCCGGGGAAGAACAAGTGCCG TTCGAACAGGGCGGCGCCTTGACGGTACCCGGCCAGAAAGCCACGGC TAACTACGTGCCAGCAGCCGCGGTAATACGTAGGTGGCAAGCGTTGT CCGGAATTATTGGGCGTAAAGCGCGCGCAGGCGGCTTCTTAAGTCTG ATGTGAAATCTTGCGGCTCAACCGCAAGCGGTCATTGGAAACTGGGA GGCTTGAGTGCAGAAGAGGAGAGTGGAATTCCACGTGTAGCGGTGAA ATGCGTAGAGATGTGGAGGAACACCAGTGGCGAAGGCGGCTCTCTGG TCTGTAACTGACGCTGAGGCGCGAAAGCGTGGGGAGCAAACAGGATT AGATACCCTGGTAGTCCACGCCGTAAACGATGAGTGCTAAGTGTTAG AGGGTTTCCGCCCTTTAGTGCTGCAGCTAACGCATTAAGCACTCCGCC TGGGGAGTACGGCCGCAAGGCTGAAACTCAAAGGAATTGACGGGGG CCCGCACAAGCGGTGGAGCATGTGGTTTAATTCGAAGCAACGCGAAG AACCTTACCAGGTCTTGACATCCTCTGACCTCCCTGGAGACAGGGCCT TCCCCTTCGGGGGACAGAGTGACAGGTGGTGCATGGTTGTCGTCAGC TCGTGTCGTGAGATGTTGGGTTAAGTCCCGCAACGAGCGCAACCCTTG ACCTTAGTTGCCAGCATTCAG |
| 140 | DP75 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATGCCTAGGAATCTGCCTGGTAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCGACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGTTGTAGATTAATACTCTGCAATTTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTCGTTAAGTTGGATGTGAAAGCCCCGGGCTCAA CCTGGGAACTGCATTCAAAACTGACGAGCTAGAGTATGGTAGAGGGT GGTGGAATTTCCTGTGTAGCGGTGAAATGCGTAGATATAGGAAGGAA CACCAGTGGCGAAGGCGACCACCTGGACTGATACTGACACTGAGGTG CGAAAGCGTGGGGAGCAAACAGGATTAGATACCCTGGTAGTCCACGC CGTAAACGATGTCAACTAGCCGTTGGAATCCTTGAGATTTTAGTGGCG CAGCTAACGCATTAAGTTGACCGCCTGGGGAGTACGGCCGCAAGGTT AAAACTCAAATGAATTGACGGGGGCCCGCACAAGCGGTGGAGCATGT GGTTTAATTCGAAGCAACGCGAAGAACCTTACCAGGCCTTGACATCC AATGAACTTTCCAGAGATGGATGGGTGCCTTCGGGAACATTGAGACA GGTGCTGCATGGCTGTCGTCAGCTCGTGTCGTGAGATGTTGGGTTAAG TCCCGTAACGAGCGCAACCCTTGTCCTTAGTTACCAGCACGTTATGGT GGGCACTCTAAGGAGACTGCCGGTGACAAACCGGAGGAAGGTGGGG ATGACGTCAAGTCATCATGGCCCTTACGGCCTGGGCTACACACGTGCT ACAATGGTCGGTACAAAGGGTTGCCAAGCCGCGAGGTGGAGCTAATC CCATAAAACCGATCGTAGTCCGGATCGCAGTCTGCAACTCGACTGCG TGAAGTCGGAATCGCTAGTAATCGCGAATCAGAATGTCGCGGTGAAT ACGTTCCCGGGCCTTGTACACACCGCCCGTCACACCATGGGAGTGGG TTGCACCAGAACGGGAGGACGGTTACCACGGTGTGATTCATGACTGG GGTGAAGTCGTAACAAGGTAGCCGTAGGGGAACCTGCGGCTGGATCA CCTCCTT |
| 141 | DP76 16S rRNA | CTTGAGAGTTTGATCCTGGCTCAGAACGAACGCTGGCGGCAGGCTTA ACACATGCAAGTCGAGCGCCCCGCAAGGGGAGCGGCAGACGGGTGA GTAACGCGTGGGAATCTACCTTTTGCTACGGAACAACAGTTGGAAAC GACTGCTAATACCGTATGTGCCCTTCGGGGGAAAGATTTATCGGCAA AGGATGAGCCCGCGTTGGATTAGCTAGTTGGTGAGGTAAAGGCTCAC CAAGGCGACGATCCATAGCTGGTCTGAGAGGATGATCAGCCACACTG GGACTGAGACACGGCCCAGACTCCTACGGGAGGCAGCAGTGGGGAA TATTGGACAATGGGCGCAAGCCTGATCCAGCCATGCCGCGTGAGTGA TGAAGGCCCTAGGGTTGTAAAGCTCTTTCACCGGTGAAGATAATGAC GGTAACCGGAGAAGAAGCCCCGGCTAACTTCGTGCCAGCAGCCGCGG TAATACGAAGGGGGCTAGCGTTGTTCGGATTTACTGGGCGTAAAGCG |

-continued

Sequence Listing

| Seq ID No. | Description | Sequence |
|---|---|---|
| | | CACGTAGGCGGATTTTTAAGTCAGGGGTGAAATCCCGGGGCTCAACC<br>CCGGAACTGCCTTTGATACTGGAAGTCTTGAGTATGGTAGAGGTGAG<br>TGGAATTCCGAGTGTAGAGGTGAAATTCGTAGATATTCGGAGGAACA<br>CCAGTGGCGAAGGCGGCTCACTGGACCATTACTGACGCTGAGGTGCG<br>AAAGCGTGGGGAGCAAACAGGATTAGATACCCTGGTAGTCCACGCCG<br>TAAACGATGAATGTTAGCCGTCGGGGGGTTTACCTTTCGGTGGCGCA<br>GCTAACGCATTAAACATTCCGCCTGGGGAGTACGGTCGCAAGATTAA<br>AACTCAAAGGAATTGACGGGGGCCCGCACAAGCGGTGGAGCATGTG<br>GTTTAATTCGAAGCAACGCGCAGAACCTTACCAGCCCTTGACATACC<br>GGTCGCGGACACAGAGATGTGTCTTTCAGTTCGGCTGGACCGGATAC<br>AGGTGCTGCATGGCTGTCGTCAGCTCGTGTCGTGAGATGTTGGGTTAA<br>GTCCCGCAACGAGCGCAACCCTCGCCTTTAGTTGCCAGCATTTAGTTG<br>GGCACTCTAAAGGGACTGCCAGTGATAAGCTGGAGGAAGGTGGGGAT<br>GACGTCAAGTCCTCATGGCCCTTACGGGCTGGGCTACACACGTGCTAC<br>AATGGTGGTGACAGTGGGCAGCAAGCACGCGAGTGTGAGCTAATCTC<br>CAAAAGCCATCTCAGTTCGGATTGCACTCTGCAACTCGAGTGCATGA<br>AGTTGGAATCGCTAGTAATCGCGGATCAGCATGCCGCGGTGAATACG<br>TTCCCGGGCCTTGTACACACCGCCCGTCACACCATGGGAGTTGGTTTT<br>ACCCGAAGGCACTGTGCTAACCGCAAGGAGGCAGGTGACCACGGTAG<br>GGTCAGCGACTGGGGTGAAGTCGTAACAAGGTAGCCGTAGGGGAACC<br>TGCGGCTGGATCACCTCCTTT |
| 142 | DP77 16S rRNA | TCGGAGAGTTTGATCCTGGCTCAGGATGAACGCTGGCGGCGTGCCTA<br>ATACATGCAAGTCGAGCGAACTGATTAGAAGCTTGCTTCTATGACGTT<br>AGCGGCGGACGGGTGAGTAACACGTGGGCAACCTGCCTGTAAGACTG<br>GGATAACTTCGGGAAACCGAAGCTAATACCGGATAGGATCTTCTCCT<br>TCATGGGAGATGATTGAAAGATGGTTTCGGCTATCACTTACAGATGG<br>GCCCGCGGTGCATTAGCTAGTTGGTGAGGTAACGGCTCACCAAGGCA<br>ACGATGCATAGCCGACCTGAGAGGGTGATCGGCCACACTGGGACTGA<br>GACACGGCCCAGACTCCTACGGGAGGCAGCAGTAGGGAATCTTCCGC<br>AATGGACGAAAGTCTGACGGAGCAACGCCGCGTGAGTGATGAAGGCT<br>TTCGGGTCGTAAAACTCTGTTGTTAGGGAAGAACAAGTACAAGAGTA<br>ACTGCTTGTACCTTGACGGTACCTAACCAGAAAGCCACGGCTAACTA<br>CGTGCCAGCAGCCGCGGTAATACGTAGGTGGCAAGCGTTATCCGGAA<br>TTATTGGGCGTAAAGCGCGCGCAGGCGGTTTCTTAAGTCTGATGTGAA<br>AGCCCACGGCTCAACCGTGGAGGGTCATTGGAAACTGGGGAACTTGA<br>GTGCAGAAGAGAAAAGCGGAATTCCACGTGTAGCGGTGAAATGCGTA<br>GAGATGTGGAGGAACACCAGTGGCGAAGGCGGCTTTTTGGTCTGTAA<br>CTGACGCTGAGGCGCGAAAGCGTGGGGAGCAAACAGGATTAGATAC<br>CCTGGTAGTCCACGCCGTAAACGATGAGTGCTAAGTGTTAGAGGGTT<br>TCCGCCCTTTAGTGCTGCAGCTAACGCATTAAGCACTCCGCCTGGGGA<br>GTACGGTCGCAAGACTGAAACTCAAAGGAATTGACGGGGGCCCGCAC<br>AAGCGGTGGAGCATGTGGTTTAATTCGAAGCAACGCGAAGAACCTTA<br>CCAGGTCTTGACATCCTCTGACAACTCTAGAGATAGAGCGTTCCCCTT<br>CGGGGGACAGAGTGACAGGTGGTGCATGGTTGTCGTCAGCTCGTGTC<br>GTGAGATGTTGGGTTAAGTCCCGCAACGAGCGCAACCCTTGATCTTA<br>GTTGCCAGCATTCAGTTGGGCACTCTAAGGTGACTGCCGGTGACAAA<br>CCGGAGGAAGGTGGGGATGACGTCAAATCATCATGCCCCTTATGACC<br>TGGGCTACACACGTGCTACAATGGATGGTACAAAGGGCTGCAAGACC<br>GCGAGGTCAAGCCAATCCCATAAAACCATTCTCAGTTCGGATTGTAG<br>GCTGCAACTCGCCTACATGAAGCTGGAATCGCTAGTAATCGCGGATC<br>AGCATGCCGCGGTGAATACGTTCCCGGGCCTTGTACACACCGCCCGTC<br>ACACCACGAGAGTTTGTAACACCCGAAGTCGGTGGAGTAACCGTAAG<br>GAGCTAGCCGCCTAAGGTGGGACAGATGATTGGGGTGAAGTCGTAAC<br>AAGGTAGCCGTATCGGAAGGTGCGGCTGGATCACCTCCTTT |
| 143 | DP78 16S rRNA | TTGAAGAGTTTGATCATGGCTCAGATTGAACGCTGGCGGCAGGCCTA<br>ACACATGCAAGTCGGACGGTAGCACAGAGAGCTTGCTCTTGGGTGAC<br>GAGTGGCGGACGGGTGAGTAATGTCTGGGGATCTGCCCGATAGAGGG<br>GGATAACCACTGGAAACGGTGGCTAATACCGCATAACGTCGCAAGAC<br>CAAAGAGGGGGACCTTCGGGCCTCTCACTATCGGATGAACCCAGATG<br>GGATTAGCTAGTAGGCGGGGTAATGGCCCACCTAGGCGACGATCCCT<br>AGCTGGTCTGAGAGGATGACCAGCCACACTGGAACTGAGACACGGTC<br>CAGACTCCTACGGGAGGCAGCAGTGGGGAATATTGCACAATGGGCGC<br>AAGCCTGATGCAGCCATGCCGCGTGTATGAAGAAGGCCTTCGGGTTG<br>TAAAGTACTTTCAGCGGGGAGGAAGGCGACGGGGTTAATAACCCTGT<br>CGATTGACGTTACCCGCAGAAGAAGCACCGGCTAACTCCGTGCCAGC<br>AGCCGCGGTAATACGGAGGGTGCAAGCGTTAATCGGAATTACTGGGC<br>GTAAAGCGCACGCAGGCGGTCTGTTAAGTCAGATGTGAAATCCCCGG<br>GCTTAACCTGGGAACTGCATTTGAAACTGGCAGGCTTGAGTCTTGTAG<br>AGGGGGGTAGAATTCCAGGTGTAGCGGTGAAATGCGTAGAGATCTGG<br>AGGAATACCGGTGGCGAAGGCGGCCCCCTGGACAAAGACTGACGCTC<br>AGGTGCGAAAGCGTGGGGAGCAAACAGGATTAGATACCCTGGTAGTC |

-continued

Sequence Listing

| Seq ID No. | Description | Sequence |
|---|---|---|
| | | CACGCCGTAAACGATGTCGACTTGGAGGTTGTTCCCTTGAGGAGTGG CTTCCGGAGCTAACGCGTTAAGTCGACCGCCTGGGGAGTACGGCCGC AAGGTTAAAACTCAAATGAATTGACGGGGGCCCGCACAAGCGGTGGA GCATGTGGTTTAATTCGATGCAACGCGAAGAACCTTACCTACTCTTGA CATCCAGCGAACTTAGCAGAGATGCTTTGGTGCCTTCGGGAACGCTG AGACAGGTGCTGCATGGCTGTCGTCAGCTCGTGTTGTGAAATGTTGGG TTAAGTCCCGCAACGAGCGCAACCCTTATCCTTTGTTGCCAGCGATTC GGTCGGGAACTCAAAGGAGACTGCCGGTGATAAACCGGAGGAAGGT GGGGATGACGTCAAGTCATCATGGCCCTTACGAGTAGGGCTACACAC GTGCTACAATGGCGCATACAAAGAGAAGCGACCTCGCGAGAGCAAG CGGACCTCACAAAGTGCGTCGTAGTCCGGATCGGAGTCTGCAACTCG ACTCCGTGAAGTCGGAATCGCTAGTAATCGTGGATCAGAATGCCACG GTGAATACGTTCCCGGGCCTTGTACACACCGCCCGTCACACCATGGG AGTGGGTTGCAAAAGAAGTAGGTAGCTTAACCTTCGGGAGGGCGCTT ACCACTTTGTGATTCATGACTGGGGTGAAGTCGTAACAAGGTAACCG TAGGGGAACCTGCGGTTGGATCACCTCCTT |
| 144 | DP79 16S rRNA | TGAAGAGTTTGATCATGGCTCAGATTGAACGCTGGCGGCAGGCCTAA CACATGCAAGTCGAGCGGTAGAGAGAAGCTTGCTTCTCTTGAGAGCG GCGGACGGGTGAGTAATACCTAGGAATCTGCCTGATAGTGGGGGATA ACGTTCGGAAACGGACGCTAATACCGCATACGTCCTACGGGAGAAAG CAGGGGACCTTCGGGCCTTGCGCTATCAGATGAGCCTAGGTCGGATT AGCTAGTTGGTGAGGTAATGGCTCACCAAGGCTACGATCCGTAACTG GTCTGAGAGGATGATCAGTCACACTGGAACTGAGACACGGTCCAGAC TCCTACGGGAGGCAGCAGTGGGGAATATTGGACAATGGGCGAAAGCC TGATCCAGCCATGCCGCGTGTGTGAAGAAGGTCTTCGGATTGTAAAG CACTTTAAGTTGGGAGGAAGGGCAGTTACCTAATACGTGACTGTCTTG ACGTTACCGACAGAATAAGCACCGGCTAACTCTGTGCCAGCAGCCGC GGTAATACAGAGGGTGCAAGCGTTAATCGGAATTACTGGGCGTAAAG CGCGCGTAGGTGGTTTGTTAAGTTGAATGTGAAATCCCCGGGCTCAAC CTGGGAACTGCATCCAAAACTGGCAAGCTAGAGTATGGTAGAGGGTA GTGGAATTTCCTGTGTAGCGGTGAAATGCGTAGATATAGGAAGGAAC ACCAGTGGCGAAGGCGACTACCTGGACTGATACTGACACTGAGGTGC GAAAGCGTGGGGAGCAAACAGGATTAGATACCCTGGTAGTCCACGCC GTAAACGATGTCAACTAGCCGTTGGGAGTCTTGAACTCTTAGTGGCGC AGCTAACGCATTAAGTTGACCGCCTGGGGAGTACGGCCGCAAGGTTA AAACTCAAATGAATTGACGGGGGCCCGCACAAGCGGTGGAGCATGTG GTTTAATTCGAAGCAACGCGAAGAACCTTACCAGGCCTTGACATCCA ATGAACTTTCTAGAGATAGATTGGTGCCTTCGGGAACATTGAGACAG GTGCTGCATGGCTGTCGTCAGCTCGTGTCGTGAGATGTTGGGTTAAGT CCCGTAACGAGCGCAACCCTTGTCCTTAGTTACCAGCACGTAATGGTG GGCACTCTAAGGAGACTGCCGGTGACAAACCGGAGGAAGGTGGGGA TGACGTCAAGTCATCATGGCCCTTACGGCCTGGGCTACACACGTGCTA CAATGGTCGGTACAAAGGGTTGCCAAGCCGCGAGGTGGAGCTAATCC CATAAAACCGATCGTAGTCCGGATCGCAGTCTGCAACTCGACTGCGT GAAGTCGGAATCGCTAGTAATCGTGAATCAGAATGTCACGGTGAATA CGTTCCCGGGCCTTGTACACACCGCCCGTCACACCATGGGAGTGGGTT GCACCAGAAGTAGCTAGTCTAACCTTCGGGAGGACGGTTACCACGGT GTGATTCATGACTGGGGTGAAGTCGTAACAAGGTAGCCGTAGGGGAA CCTGCGGCTGGATCACCTCCTT |
| 145 | DP80 16S rRNA | CTTGAGAGTTTGATCCTGGCTCAGAGCGAACGCTGGCGGCAGGCTTA ACACATGCAAGTCGAGCGGGCACCTTCGGGTGTCAGCGGCAGACGGG TGAGTAACACGTGGGAACGTACCCTTCGGTTCGGAATAACGCTGGGA AACTAGCGCTAATACCGGATACGCCCTTTTGGGGAAAGGTTTACTGCC GAAGGATCGGCCCGCGTCTGATTAGCTAGTTGGTGGGGTAACGGCCT ACCAAGGCGACGATCAGTAGCTGGTCTGAGAGGATGATCAGCCACAC TGGGACTGAGACACGGCCCAGACTCCTACGGGAGGCAGCAGTGGGG AATATTGGACAATGGGCGCAAGCCTGATCCAGCCATGCCGCGTGAGT GATGAAGGCCTTAGGGTTGTAAAGCTCTTTTGTCCGGGACGATAATG ACGGTACCGGAAGAATAAGCCCCGGCTAACTTCGTGCCAGCAGCCGC GGTAATACGAAGGGGGCTAGCGTTGCTCGGAATCACTGGGCGTAAAG GGCGCGTAGGCGGCCATTCAAGTCGGGGGTGAAAGCCTGTGGCTCAA CCACAGAATTGCCTTCGATACTGTTTGGCTTGAGTTTGGTAGAGGTTG GTGGAACTGCGAGTGTAGAGGTGAAATTCGTAGATATTCGCAAGAAC ACCAGTGGCGAAGGCGGCCAACTGGACCAATACTGACGCTGAGGCGC GAAAGCGTGGGGAGCAAACAGGATTAGATACCCTGGTAGTCCACGCC GTAAACGATGAATGCTAGCTGTTGGGGTGCTTGCACCTCAGTAGCGC AGCTAACGCTTTAAGCATTCCGCCTGGGGAGTACGGTCGCAAGATTA AAACTCAAAGGAATTGACGGGGGCCCGCACAAGCGGTGGAGCATGT GGTTTAATTCGAAGCAACGCGCAGAACCTTACCATCCCTTGACATGTC GTGCCATCCGGAGAGATCCGGGGTTCCCTTCGGGGACGCGAACACAG GTGCTGCATGGCTGTCGTCAGCTCGTGTCGTGAGATGTTGGGTTAAGT |

-continued

| Seq ID No. | Description | Sequence |
|---|---|---|
| | | CCCGCAACGAGCGCAACCCACGTCCTTAGTTGCCATCATTTAGTTGGG CACTCTAGGGAGACTGCCGGTGATAAGCCGCGAGGAAGGTGTGGATG ACGTC |
| 146 | DP81 16S rRNA | AACGGAGAGTTTGATCCTGGCTCAGGACGAACGCTGGCGGCGTGCCT AATACATGCAAGTCGAGCGGACAGAAGGGAGCTTGCTCCCGGACGTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAGGGGATGG GCCCGCGGCGCATTAGCTAGTTGGTAAGGTAACGGCTTACCAAGGCG ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGAGGAAGGC TTTCGGGTCGTAAAGCTCTGTTGTGAGGGAAGAAGCGGTACCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG TAACTGACGCTGAGGCGCGAAAGCGTGGGGAGCAAACAGGATTAGA TACCCTGGTAGTCCACGCCGTAAACGATGAGTGCTAGGTGTTAGGGG TTTCGATGCCCGTAGTGCCGAAGTTAACACATTAAGCACTCCGCCTGG GGAGTACGGCCGCAAGGCTGAAACTCAAAGGAATTGACGGGGACCC GCACAAGCAGTGGAGCATGTGGTTTAATTCGAAGCAACGCGAAGAAC CTTACCAGGTCTTGACATCCTTTGACCACCCAAGAGATTGGGCTTCCC CTTCGGGGGCAAAGTGACAGGTGGTGCATGGTTGTCGTCAGCTCGTG TCGTGAGATGTTGGGTTAAGTCCCGCAACGAGCGCAACCCTTGATCTT AGTTGCCAGCATTGAGTTGGGCACTCTAAGGTGACTGCCGGTGACAA ACCGGAGGAAGGTGGGGATGACGTCAAATCATCATGCCCCTTATGAC CTGGGCTACACACGTGCTACAATGGATGGTACAAAGGGCAGCGAAAC CGCGAGGTGAAGCCAATCCCATAAAGCCATTCTCAGTTCGGATTGCA GGCTGCAACTCGCCTGCATGAAGCCGGAATTGCTAGTAATCGCGGAT CAGCATGCCGCGGTGAATACGTTCCCGGGTCTTGTACACACCGCCCGT CACACCACGAGAGTTTGTAACACCCGAAGTCGGTGAGGCAACCTTTT GGAGCCAGCCGCCTAAGGTGGGACAAATGATTGGGGTGAAGTCGTAA CAAGGTAGCCGTATCGGAAGGTGCGGCTGGATCACCTCCTTT |
| 147 | DP82 16S rRNA | AACGGAGAGTTTGATCCTGGCTCAGGACGAACGCTGGCGGCGTGCCT AATACATGCAAGTCGAGCGGACAGAAGGGAGCTTGCTCCCGGACGTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAAGGGATGG GCCCGCGGCGCATTAGCTAGTTGGTAAGGTAACGGCTTACCAAGGCA ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGAGGAAGGC CTTCGGGTCGTAAAGCTCTGTTGTGAGGGAAGAAGCGGTACCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG TAACTGACGCTGAGGCGCGAAAGCGTGGGGAGCAAACAGGATTAGA TACCCTGGTAGTCCACGCCGTAAACGATGAGTGCTAGGTGTTAGGGG TTTCGATGCCCGTAGTGCCGAAGTTAACACATTAAGCACTCCGCCTGG GGAGTACGGCCGCAAGGCTGAAACTCAAAGGAATTGACGGGGACCC GCACAAGCAGTGGAGCATGTGGTTTAATTCGAAGCAACGCGAAGAAC CTTACCAGGTCTTGACATCCTTTGACCACCCAAGAGATTGGGCTTCCC CTTCGGGGGCAAAGTGACAGGTGGTGCATGGTTGTCGTCAGCTCGTG TCGTGAGATGTTGGGTTAAGTCCCGCAACGAGCGCAACCCTTGATCTT AGTTGCCAGCATTCAGTTGGGCACTCTAAGGTGACTGCCGGTGACAA ACCGGAGGAAGGTGGGGATGACGTCAAATCATCATGCCCCTTATGAC CTGGGCTACACACGTGCTACAATGGATGGTACAAAGGGCAGCGAAAC CGCGAGGTGAAGCCAATCCCATAAAGCCATTCTCAGTTCGGATTGCA GGCTGCAACTCGCCTGCATGAAGCCGGAATTGCTAGTAATCGCGGAT CAGCATGCCGCGGTGAATACGTTCCCGGGTCTTGTACACACCGCCCGT CACACCACGAGAGTTTGTAACACCCGAAGTCGGTGAGGCAACCTTTT GGAGCCAGCCGCCTAAGGTGGGACAAATGATTGGGGTGAAGTCGTAA CAAGGTAGCCGTATCGGAAGGTGCGGCTGGATCACCTCCTTT |

-continued

Sequence Listing

| Seq ID No. | Description | Sequence |
|---|---|---|
| 148 | DP83 16S rRNA | ACGGAGAGTTTGATCCTGGCTCAGGACGAACGCTGGCGGCGTGCCTA ATACATGCAAGTCGAGCGGAGTTTCAAGAAGCTTGCTTTTTGAAACTT AGCGGCGGACGGGTGAGTAACACGTGGGCAACCTGCCCCTTAGACTG GGATAACTCCGGGAAACCGGAGCTAATACCGGATAATCCCTTTCTCC ACCTGGAGAGAGGGTGAAAGATGGCTTCGGCTATCACTAAGGGATGG GCCCGCGGCGCATTAGCTAGTTGGTAAGGTAACGGCTTACCAAGGCA ACGATGCGTAGCCGACCTGAGAGGGTGATCGGCCACACTGGGACTGA GACACGGCCCAGACTCCTACGGGAGGCAGCAGTAGGGAATCTTCCGC AATGGACGAAAGTCTGACGGAGCAACGCCGCGTGAGTGAGGAAGGC CTTCGGGTCGTAAAGCTCTGTTGTGAGGGAAGAAGCGGTACCGTTCG AATAGGGCGGTACCTTGACGGTACCTCACCAGAAAGCCACGGCTAAC TACGTGCCAGCAGCCGCGGTAATACGTAGGTGGCAAGCGTTGTCCGG AATTATTGGGCGTAAAGCGCGCGCAGGCGGCTTCTTAAGTCTGATGT GAAATCTCGGGGCTCAACCCCGAGCGGCCATTGGAAACTGGGGAGCT TGAGTGCAGAAGAGGAGAGTGGAATTCCACGTGTAGCGGTGAAATGC GTAGAGATGTGGAGGAACACCAGTGGCGAAGGCGACTCTCTGGTCTG TAACTGACGCTGAGGCGCGAAAGCGTGGGGAGCAAACAGGATTAGA TACCCTGGTAGTCCACGCCGTAAACGATGAGTGCTAGGTGTTAGGGG TTTCGATGCCCGTAGTGCCGAAGTTAACACATTAAGCACTCCGCCTGG GGAGTACGGCCGCAAGGCTGAAACTCAAAGGAATTGACGGGGACCC GCACAAGCAGTGGAGCATGTGGTTTAATTCGAAGCAACGCGAAGAAC CTTACCAGGTCTTGACATCCTTTGACCACCCAAGAGATTGGGCTTCCC CTTCGGGGGCAAAGTGACAGGTGGTGCATGGTTGTCGTCAGCTCGTG TCGTGAGATGTTGGGTTAAGTCCCGCAACGAGCGCAACCCTTGATCTT AGTTGCCAGCATTCAGTTGGGCACTCTAAGGTGACTGCCGGTGACAA ACCGGAGGAAGGTGGGGATGACGTCAAATCATCATGCCCCTTATGAC CTGGGCTACACACGTGCTACAATGGATGGTACAAAGGGCAGCGAAGC CGCGAGGTGAAGCCAATCCCATAAAGCCATTCTCAGTTCGGATTGCA GGCTGCAACTCGCCTGCATGAAGCCGGAATTGCTAGTAATCGCGGAT CAGCATGCCGCGGTGAATACGTTCCCGGGTCTTGTACACACCGCCCGT CACACCACGAGAGTTTGTAACACCCGAAGTCGGTGAGGCAACCTTTT GGAGCCAGCCGCCTAAGGTGGGACAAATGATTGGGGTGAAGTCGTAA CAAGGTAGCCGTATCGGAAGGTGCGGCTGGATCACCTCCTTT |
| 149 | DP84 16S rRNA | TACGGAGAGTTTGATCCTGGCTCAGGATGAACGCTGGCGGCGTGCTT AACACATGCAAGTCGAACGGTGAAGCCAAGCTTGCTTGGTGGATCAG TGGCGAACGGGTGAGTAACACGTGAGCAACCTGCCCTGGACTCTGGG ATAAGCGCTGGAAACGGCGTCTAATACTGGATATGAGCTCTCATCGC ATGGTGGGGGTTGGAAAGATTTTTTGGTCTGGGATGGGCTCGCGGCCT ATCAGCTTGTTGGTGAGGTAATGGCTCACCAAGGCGTCGACGGGTAG CCGGCCTGAGAGGGTGACCGGCCACACTGGGACTGAGACACGGCCCA GACTCCTACGGGAGGCAGCAGTGGGGAATATTGCACAATGGGCGAAA GCCTGATGCAGCAACGCCGCGTGAGGGATGACGGCCTTCGGGTTGTA AACCTCTTTTAGCAGGGAAGAAGCGAAAGTGACGGTACCTGCAGAAA AAGCGCCGGCTAACTACGTGCCAGCAGCCGCGGTAATACGTAGGGCG CAAGCGTTATCCGGAATTATTGGGCGTAAAGAGCTCGTAGGCGGTTT GTCGCGTCTGCTGTGAAATCCCGAGGCTCAACCTCGGGCCTGCAGTG GGTACGGGCAGACTAGAGTGCGGTAGGGGAGATTGGAATTCCTGGTG TAGCGGTGGAATGCGCAGATATCAGGAGGAACACCGATGGCGAAGG CAGATCTCTGGGCCGTAACTGACGCTGAGGAGCGAAAGGGTGGGGAG CAAACAGGCTTAGATACCCTGGTAGTCCACCCCGTAAACGTTGGGAA CTAGTTGTGGGGACCATTCCACGGTTTCCGTGACGCAGCTAACGCATT AAGTTCCCCGCCTGGGGAGTACGGCCGCAAGGCTAAAACTCAAAGGA ATTGACGGGGACCCGCACAAGCGGCGGAGCATGCGGATTAATTCGAT GCAACGCGAAGAACCTTACCAAGGCTTGACATACACCAGAACGGGCC AGAAATGGTCAACTCTTTGGACACTGGTGAACAGGTGGTGCATGGTT GTCGTCAGCTCGTGTCGTGAGATGTTGGGTTAAGTCCCGCAACGAGC GCAACCCTCGTTCTATGTTGCCAGCACGTAATGGTGGGAACTCATGGG ATACTGCCGGGGTCAACTCGGAGGAAGGTGGGGATGACGTCAAATCA TCATGCCCCTTATGTCTTGGGCTTCACGCATGCTACAATGGCCGGTAC AAAGGGCTGCAATACCGTGAGGTGGAGCGAATCCCAAAAAGCCGGTC CCAGTTCGGATTGAGGTCTGCAACTCGACCTCATGAAGTCGGAGTCG CTAGTAATCGCAGATCAGCAACGCTGCGGTGAATACGTTCCCGGGTC TTGTACACACCGCCCGTCAAGTCATGAAAGGAGCCGTCGAAGGTGGG ATCGGTAATTAGGACTAAGTCGTAACAAGGTAGCCGTACCGGAAGGT GCGGCTGGATCACCTCCTTT |
| 150 | DP85 16S rRNA | ACGGTCGGGGGCATCAGTATTCAGTCGTCAGAGGTGAAATTCTTGGA TTGACTGAAGACTAACTACTGCGAAAGCATTTGCCAAGGACGTTTTCA TTAATCAAGAACGAAAGTTAGGGGATCGAAGATGATCAGATACCGTC GTAGTCTTAACCATAAACTATGCCGACTAGAGATCGGGTGGTGCTTTT TGCGCACTCGGCATCTTACGAGAAATCAAAGTCTTTGGGTTCTGGGGG |

-continued

Sequence Listing

| Seq ID No. | Description | Sequence |
|---|---|---|
| | | GAGTATGGTCGCAAGGCTGAAACTTAAAGGAATTGACGGAGGGGCAC<br>CACCAGGAGTGGAGCCTGCGGCTTAATTTGACTCAACACGGGGAAAC<br>TCACCAGGTCCAGACGTAATAAGGATTGACAAGTTAGAGACTTCTCTT<br>GATCTTACGGGTGGTGGTGCATGGCCGTTTTTAGTCCTTGGAGTGATT<br>TGTCTGCTTAATTGCGATAACGGACGAGACCTTAACCTGCTAAATAGG<br>GCTGCGAGCATCTGCTCGTGGGCTCTTCTTAGAGGGACTATGGGTATC<br>AAACCCATGGAAGTTTGAGGCAACAACAGGTCTGTGATGCCCTTAGA<br>CGTTCTGGGCCGCACGCGCGCTACACTGACGGAGCCAGCAAGCATAA<br>CCTTGGTCGAGAGGCCTGGGTAATCTCGTGAAACTCCGTCGTGCTGGG<br>GATAGAGCATTGTAATTTTTGCTCTTCAACGAGGAATTCCTAGTAAGC<br>GCAAGTCATCAGCTTGCGTTGATTACGTCCCTGCCCCTTGTACACACC<br>GCCCGTCGCTACTACCGATTGAATGGCTTAGTGAGGCTTCAAGACCG<br>GCGCGGCCTGCGGGGCAACTCGCGCGCTGCGCTGGGAATTTAGTCAA<br>ACTTGGTCATTTAGAGGTCGTAAAAGTCGTAACAAGGTTTCCGTAGGT<br>GAACCTGCGGAAGGATCATT |
| 151 | DP86 16S rRNA | CGATGCGTAGCCGACCTGAGAGGGTGATCGGCCACACTGGGACTGAG<br>ACACGGCCCAGACTCCTACGGGAGGCAGCAGTAGGGAATCTTCCGCA<br>ATGGACGAAAGTCTGACGGAGCAACGCCGCGTGAGTGATGAAGGTTT<br>TCGGATCGTAAAGCTCTGTTGTTAGGGAAGAACAAGTGCCGTTCAAA<br>TAGGGCGGCACCTTGACGGTACCTAACCAGAAAGCCACGGCTAACTA<br>CGTGCCAGCAGCCGCGGTAATACGTAGGTGGCAAGCGTTGTCCGGAA<br>TTATTGGGCGTAAAGGGCTCGCAGGCGGTTTCTTAAGTCTGATGTGAA<br>AGCCCCCGGCTCAACCGGGGAGGGTCATTGGAAACTGGGGAACTTGA<br>GTGCAGAAGAGGAGAGTGGAATTCCACGTGTAGCGGTGAAATGCGTA<br>GAGATGTGGAGGAACACCAGTGGCGAAGGCGACTCTCTGGTCTGTAA<br>CTGACGCTGAGGAGCGAAAGCGTGGGGAGCGAACAGGATTAGATAC<br>CCTGGTAGTCCACGCCGTAAACGATGAGTGCTAAGTGTTAGGGGGTT<br>TCCGCCCCTTAGTGCTGCAGCTAACGCATTAAGCACTCCGCCTGGGGA<br>GTACGGTCGCAAGACTGAAACTCAAAGGAATTGACGGGGGCCCGCAC<br>AAGCGGTGGAGCATGTGGTTTAATTCGAAGCAACGCGAAGAACCTTA<br>CCAGGTCTTGACATCCTCTGACAATCCTAGAGATAGGACGTCCCCTTC<br>GGGGGCAGAGTGACAGGTGGTGCATGGTTGTCGTCAGCTCGTGTCGT<br>GAGATGTTGGGTTAAGTCCCGCAACGAGCGCAACCCTTGATCTTAGTT<br>GCCAGCATTCAGTTGGGTGTTCTTTGAAAACT |
| 152 | DP87 16S rRNA | TTTGAGAGTTTGATCCTGGCTCAGGACGAACGCTGGCGGCGTGCCTA<br>ATACATGCAAGTCGAACGAACTCTGGTATTGATTGGTGCTTGCATCAT<br>GATTTACATTTGAGTGAGTGGCGAACTGGTGAGTAACACGTGGGAAA<br>CCTGCCCAGAAGCGGGGGATAACACCTGGAAACAGATGCTAATACCG<br>CATAACAACTTGGACCGCATGGTCCGAGCTTGAAAGATGGCTTCGGC<br>TATCACTTTTGGATGGTCCCGCGGCGTATTAGCTAGATGGTGGGGTAA<br>CGGCTCACCATGGCAATGATACGTAGCCGACCTGAGAGGGTAATCGG<br>CCACATTGGGACTGAGACACGGCCCAAACTCCTACGGGAGGCAGCAG<br>TAGGGAATCTTCCACAATGGACGAAAGTCTGATGGAGCAACGCCGCG<br>TGAGTGAAGAAGGGTTTCGGCTCGTAAAACTCTGTTGTTAAAGAAGA<br>ACATATCTGAGAGTAACTGTTCAGGTATTGACGGTATTTAACCAGAA<br>AGCCACGGCTAACTACGTGCCAGCAGCCGCGGTAATACGTAGGTGGC<br>AAGCGTTGTCCGGATTTATTGGGCGTAAAGCGAGCGCAGGCGGTTTTT<br>TAAGTCTGATGTGAAAGCCTTCGGCTCAACCGAAGAAGTGCATCGGA<br>AACTGGGAAACTTGAGTGCAGAAGAGGACAGTGGAACTCCATGTGTA<br>GCGGTGAAATGCGTAGATATATGGAAGAACACCAGTGGCGAAGGCG<br>GCTGTCTGGTCTGTAACTGACGCTGAGGCTCGAAAGTATGGGTAGCA<br>AACAGGATTAGATACCCTGGTAGTCCATACCGTAAACGATGAATGCT<br>AAGTGTTGGAGGGTTTCCGCCCTTCAGTGCTGCAGCTAACGCATTAAG<br>CATTCCGCCTGGGGAGTACGGCCGCAAGGCTGAAACTCAAAGGAATT<br>GACGGGGGCCCGCACAAGCGGTGGAGCATGTGGTTTAATTCGAAGCT<br>ACGCGAAGAACCTTACCAGGTCTTGACATACTATGCAAATCTAAGAG<br>ATTAGACGTTCCCTTCGGGGACATGGATACAGGTGGTGCATGGTTGTC<br>GTCAGCTCGTGTCGTGAGATGTTGGGTTAAGTCCCGCAACGAGCGCA<br>ACCCTTATTATCAGTTGCCAGCATTAAGTTGGGCACTCTGGTGAGACT<br>GCCGGTGACAAACCGGAGGAAGGTGGGGATGACGTCAAATCATCATG<br>CCCCTTATGACCTGGGCTACACACGTGCTACAATGGATGGTACAACG<br>AGTTGCGAACTCGCGAGAGTAAGCTAATCTCTTAAAGCCATTCTCAGT<br>TCGGATTGTAGGCTGCAACTCGCCTACATGAAGTCGGAATCGCTAGT<br>AATCGCGGATCAGCATGCCGCGGTGAATACGTTCCCGGGCCTTGTAC<br>ACACCGCCCGTCACACCATGAGAGTTTGTAACACCCAAAGTCGGTGG<br>GGTAACCTTTTAGGAACCAGCCGCCTAAGGTGGGACAGATGATTAGG<br>GTGAAGTCGTAACAAGGTAGCCGTAGGAGAACCTGCGGCTGGATCAC<br>CTCCTT |

-continued

Sequence Listing

| Seq ID No. | Description | Sequence |
| --- | --- | --- |
| 153 | DP88 16S rRNA | TAGTGGGTTTGATCCTGGCTCAGGACGAACGCTGGCGGCGTGCCTAA TACATGCAAGTCGAGCGGACAGATGGGAGCTTGCTCCCTGATGTTAG CGGCGGACGGGTGAGTAACACGTGGGTAACCTGCCTGTAAGACTGGG ATAACTCCGGGAAACCGGGGCTAATACCGGATGGTTGTCTGAACCGC ATGGTTCAGACATAAAAGGTGGCTTCGGCTACCACTTACAGATGGAC CCGCGGCGCATTAGCTAGTTGGTGAGGTAACGGCTCACCAAGGCGAC GATGCGTAGCCGACCTGAGAGGGTGATCGGCCACACTGGGACTGAGA CACGGCCCAGACTCCTACGGGAGGCAGCAGTAGGGAATCTTCCGCAA TGGACGAAAGTCTGACGGAGCAACGCCGCGTGAGTGATGAAGGTTTT CGGATCGTAAAGCTCTGTTGTTAGGGAAGAACAAGTGCCGTTCAAAT AGGGCGGCACCTTGACGGTACCTAACCAGAAAGCCACGGCTAACTAC GTGCCAGCAGCCGCGGTAATACGTAGGTGGCAAGCGTTGTCCGGAAT TATTGGGCGTAAAGGGCTCGCAGGCGGTTTCTTAAGTCTGATGTGAA AGCCCCCGGCTCAACCGGGGAGGGTCATTGGAAACTGGGGAACTTGA GTGCAGAAGAGGAGAGTGGAATTCCACGTGTAGCGGTGAAATGCGTA GAGATGTGGAGGAACACCAGTGGCGAAGGCGACTCTCTGGTCTGTAA CTGACGCTGAGGAGCGAAAGCGTGGGGAGCGAACAGGATTAGATAC CCTGGTAGTCCACGCCGTAAACGATGAGTGCTAAGTGTTAGGGGGTT TCCGCCCCTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAATCCTAGAGATAGGACGTCCCCTTC GGGGGCAGAGTGACAGGTGGTGCATGGTTGTCGTCAGCTCGTGTCGT GAGATGTTGGGTTAAGTCCCGCAACGAGCGCAACCCTTGATCTTAGTT GCCAGCATTCAGTTGGGCACTCTAAGGTGACTGCCGGTGACAAACCG GAGGAAGGTGGGGATGACGTCAAATCATCATGCCCCTTATGACCTGG GCTACACACGTGCTACAATGGACAGAACAAAGGGCAGCGAAACCGC GAGGTTAAGCCAATCCCACAAATCTGTTCTCAGTTCGGATCGCAGTCT GCAACTCGACTGCGTGAAGCTGGAATCGCTAGTAATCGCGGATCAGC ATGCCGCGGTGAATACGTTCCCGGGCCTTGTACACACCGCCCGTCACA CCACGAGAGTTTGTAACACCCGAAGTCGGTGAGGTAACCTTTATGGA GCCAGCCGCCGAAGGTGGGACAGATGATTGGGGTGAAGTCGTAACAA GGTAGCCGTATCGGAAGGTGCGGCTGGATCACCTCCTTT |
| 154 | DP89 16S rRNA | GTAACGGCTCACCAAGGCAACGATGCGTAGCCGACCTGAGAGGGTGA TCGGCCACACTGGGACTGAGACACGGCCCAGACTCCTACGGGAGGCA GCAGTAGGGAATCTTCCGCAATGGACGAAAGTCTGACGGAGCAACGC CGCGTGAGTGATGAAGGTTTTCGGATCGTAAAGCTCTGTTGTTAGGGA AGAACAAGTACCGTTCGAATAGGGCGGTACCTTGACGGTACCTAACC AGAAAGCCACGGCTAACTACGTGCCAGCAGCCGCGGTAATACGTAGG TGGCAAGCGTTGTCCGGAATTATTGGGCGTAAAGGGCTCGCAGGCGG TTTCTTAAGTCTGATGTGAAAGCCCCCGGCTCAACCGGGGAGGGTCAT TGGAAACTGGGGAACTTGAGTGCAGAAGAGGAGAGTGGAATTCCAC GTGTAGCGGTGAAATGCGTAGAGATGTGGAGGAACACCAGTGGCGA AGGCGACTCTCTGGTCTGTAACTGACGCTGAGGAGCGAAAGCGTGGG GAGCGAACAGGATTAGATACCCTGGTAGTCCACGCCGTAAACGATGA GTGCTAAGTGTTAGGGGGTTTCCGCCCCTTAGTGCTGCAGCTAACGCA TTAAGCACTCCGCCTGGGGAGTACGGTCGCAAGACTGAAACTCAAAG GAATTGACGGGGGCCCGCACAAGCGGTGGAGCATGTGGTTTAATTCG AAGCAACGCGAAGAACCTTACCAGGTCTTGACATCCTCTGACAATCC TAGAGATAGGACGTCCCCTTCGGGGGCAGAGTGACAGGTGGTGCATG GTTGTCGTCAGCTCGTGTCGTGAGATGTTGGGTTAAGTCCCGCAACGA GCGCAACCCTTGATCTTAGTTGCCAGCATTCAGTTGGGCACTCTAAGG TGACTGCCGGTGACAAACCGGAGGAAGGTGGGGATGACGTCAAATCA TCATGCCCCTTATGACCTGGGCTACACACGTGCTACAATGGACAGAA CAAAGGGCAGCGAAACCGCGAGGTTAAGCCAATCCCACAAATCTGTT CTCAGTTCGGATCGCAGTCTGCAACTCGACTGCGTGAAGCTGGAATC GCTAGTAATCGCGGATCAGCATGCCGCGGTGAATACGTTCCCGGGCC TTGTACACACCGCCCGTCACACCACGAGAGTTTGTAACACCCGAAGT CGGTGAGGTAACCTTTTAGGAGCCAGCCGCCGAAGGTGGGACAGATG ATTGGGGTGAAGTCGTAACAAGGTAGCCGTATCGGAAGGTGCGGCTG GATCACCTCCTTT |
| 155 | DP90 16S rRNA | TTTGAGAGTTTGATCCTGGCTCAGGACGAACGCTGGCGGCGTGCCTA ATACATGCAAGTCGAACGAACTCTGGTATTGATTGGTGCTTGCATCAT GATTTACATTTGAGTGAGTGGCGAACTGGTGAGTAACACGTGGGAAA CCTGCCCAGAAGCGGGGGATAACACCTGGAAACAGATGCTAATACCG CATAACAACTTGGACCGCATGGTCCGAGCTTGAAAGATGGCTTCGGC TATCACTTTTGGATGGTCCCGCGGCGTATTAGCTAGATGGTGGGGTAA CGGCTCACCATGGCAATGATACGTAGCCGACCTGAGAGGGTAATCGG CCACATTGGGACTGAGACACGGCCCAAACTCCTACGGGAGGCAGCAG TAGGGAATCTTCCACAATGGACGAAAGTCTGATGGAGCAACGCCGCG |

-continued

Sequence Listing

| Seq ID No. | Description | Sequence |
|---|---|---|
| | | TGAGTGAAGAAGGGTTTCGGCTCGTAAAACTCTGTTGTTAAAGAAGA ACATATCTGAGAGTAACTGTTCAGGTATTGACGGTATTTAACCAGAA AGCCACGGCTAACTACGTGCCAGCAGCCGCGGTAATACGTAGGTGGC AAGCGTTGTCCGGATTTATTGGGCGTAAAGCGAGCGCAGGCGGTTTTT TAAGTCTGATGTGAAAGCCTTCGGCTCAACCGAAGAAGTGCATCGGA AACTGGGAAACTTGAGTGCAGAAGAGGACAGTGGAACTCCATGTGTA GCGGTGAAATGCGTAGATATATGGAAGAACACCAGTGGCGAAGGCG GCTGTCTGGTCTGTAACTGACGCTGAGGCTCGAAAGTATGGGTAGCA AACAGGATTAGATACCCTGGTAGTCCATACCGTAAACGATGAATGCT AAGTGTTGGAGGGTTTCCGCCCTTCAGTGCTGCAGCTAACGCATTAAG CATTCCGCCTGGGGAGTACGGCCGCAAGGCTGAAACTCAAAGGAATT GACGGGGGCCCGCACAAGCGGTGGAGCATGTGGTTTAATTCGAAGCT ACGCGAAGAACCTTACCAGGTCTTGACATACTATGCAAATCTAAGAG ATTAGACGTTCCCTTCGGGGACATGGATACAGGTGGTGCATGGTTGTC GTCAGCTCGTGTCGTGAGATGTTGGGTTAAGTCCCGCAACGAGCGCA ACCCTTATTATCAGTTGCCAGCATTAAGTTGGGCACTCTGGTGAGACT GCCGGTGACAAACCGGAGGAAGGTGGGGATGACGTCAAATCATCATG CCCCTTATGACCTGGGCTACACACGTGCTACAATGGATGGTACAACG AGTTGCGAACTCGCGAGAGTAAGCTAATCTCTTAAAGCCATTCTCAGT TCGGATTGTAGGCTGCAACTCGCCTACATGAAGTCGGAATCGCTAGT AATCGCGGATCAGCATGCCGCGGTGAATACGTTCCCGGGCCTTGTAC ACACCGCCCGTCACACCATGAGAGTTTGTAACACCCAAAGTCGGTGG GGTAACCTTTTAGGAACCAGCCGCCTAAGGTGGGACAGATGATTAGG GTGAAGTCGTAACAAGGTAGCCGTAGGAGAACCTGCGGCTGGATCAC CTCCTT |
| 156 | DP92 16S rRNA | CGATGCGTAGCCGACCTGAGAGGGTGATCGGCCACACTGGGACTGAG ACACGGCCCAGACTCCTACGGGAGGCAGCAGTAGGGAATCTTCCGCA ATGGACGAAAGTCTGACGGAGCAACGCCGCGTGAGTGATGAAGGTTT TCGGATCGTAAAGCTCTGTTGTTAGGGAAGAACAAGTACCGTTCGAA TAGGGCGGTACCTTGACGGTACCTAACCAGAAAGCCACGGCTAACTA CGTGCCAGCAGCCGCGGTAATACGTAGGTGGCAAGCGTTGTCCGGAA TTATTGGGCGTAAAGGGCTCGCAGGCGGTTTCTTAAGTCTGATGTGAA AGCCCCCGGCTCAACCGGGGAGGGTCATTGGAAACTGGGGAACTTGA GTGCAGAAGAGGAGAGTGGAATTCCACGTGTAGCGGTGAAATGCGTA GAGATGTGGAGGAACACCAGTGGCGAAGGCGACTCTCTGGTCTGTAA CTGACGCTGAGGAGCGAAAGCGTGGGGAGCGAACAGGATTAGATAC CCTGGTAGTCCACGCCGTAAACGATGAGTGCTAAGTGTTAGGGGGTT TCCGCCCCTTAGTGCTGCAGCTAACGCATTAAGCACTCCGCCTGGGGA GTACGGTCGCAAGACTGAAACTCAAAGGAATTGACGGGGGCCCGCAC AAGCGGTGGAGCATGTGGTTTAATTCGAAGCAACGCGAAGAACCTTA CCAGGTCTTGACATCCTCTGACAATCCTAGAGATAGGACGTCCCCTTC GGGGGCAGAGTGACAGGTGGTGCATGGTTGTCGTCAGCTCGTGTCGT GAGATGTTGGGTTAAGTCCCGCAACGAGCGCAACCCTTGATCTTAGTT GCCAGCATTCAGTTGGGCACTCTAAGGTGACTGCCGGTGACAAACCG GAGGAAGGTGGGGATGACGTCAAATCATCATGCCCCTTATGACCTGG GCTACACACGTGCTACAATGGACAGAACAAAGGGCAGCGAAACCGC GAGGTTAAGCCAATCCCACAAATCTGTTCTCAGTTCGGATCGCAGTCT GCAACTCGACTGCGTGAAGCTGGAATCGCTAGTAATCGCGGATCAGC ATGCCGCGGTGAATACGTTCCCGGGCCTTGTACACACCGCCCGTCACA CCACGAGAGTTTGTAACACCCGAAGTCGGTGAGGTAACCTTTTAGGA GCCAGCCGCCGAAGGTGGGACAGATGATTGGGGTGAAGTCGTAACAA GGTAGCCGTATCGGAAGGTGCGGCTGGATCACCTCCTTT |
| 157 | DP93 16S rRNA | ATTGAGAGTTTGATCCTGGCTCAGGATGAACGCTGGCGGCGTGCCTA ATACATGCAAGTCGAACGCACAGCGAAAGGTGCTTGCACCTTTCAAG TGAGTGGCGAACGGGTGAGTAACACGTGGACAACCTGCCTCAAGGCT GGGGATAACATTTGGAAACAGATGCTAATACCGAATAAAACTTAGTG TCGCATGACAAAAAGTTAAAAGGCGCTTCGGCGTCACCTAGAGATGG ATCCGCGGTGCATTAGTTAGTTGGTGGGGTAAAGGCCTACCAAGACA ATGATGCATAGCCGAGTTGAGAGACTGATCGGCCACATTGGGACTGA GACACGGCCCAAACTCCTACGGGAGGCTGCAGTAGGGAATCTTCCAC AATGGGCGAAAGCCTGATGGAGCAACGCCGCGTGTGTGATGAAGGCT TTCGGGTCGTAAAGCACTGTTGTATGGGAAGAACAGCTAGAATAGGA AATGATTTTAGTTTGACGGTACCATACCAGAAAGGGACGGCTAAATA CGTGCCAGCAGCCGCGGTAATACGTATGTCCCGAGCGTTATCCGGATT TATTGGGCGTAAAGCGAGCGCAGACGGTTTATTAAGTCTGATGTGAA AGCCCGGAGCTCAACTCCGGAATGGCATTGGAAACTGGTTAACTTGA GTGCAGTAGAGGTAAGTGGAACTCCATGTGTAGCGGTGGAATGCGTA GATATATGGAAGAACACCAGTGGCGAAGGCGGCTTACTGGACTGCAA CTGACGTTGAGGCTCGAAAGTGTGGGTAGCAAACAGGATTAGATACC CTGGTAGTCCACACCGTAAACGATGAACACTAGGTGTTAGGAGGTTT CCGCCTCTTAGTGCCGAAGCTAACGCATTAAGTGTTCCGCCTGGGGAG |

-continued

Sequence Listing

| Seq ID No. | Description | Sequence |
|---|---|---|
| | | TACGACCGCAAGGTTGAAACTCAAAGGAATTGACGGGGACCCGCACA AGCGGTGGAGCATGTGGTTTAATTCGAAGCAACGCGAAGAACCTTAC CAGGTCTTGACATCCTTTGAAGCTTTTAGAGATAGAAGTGTTCTCTTC GGAGACAAAGTGACAGGTGGTGCATGGTCGTCGTCAGCTCGTGTCGT GAGATGTTGGGTTAAGTCCCGCAACGAGCGCAACCCTTATTGTTAGTT GCCAGCATTCAGATGGGCACTCTAGCGAGACTGCCGGTGACAAACCG GAGGAAGGCGGGGACGACGTCAGATCATCATGCCCCTTATGACCTGG GCTACACACGTGCTACAATGGCGTATACAACGAGTTGCCAACCCGCG AGGGTGAGCTAATCTCTTAAAGTACGTCTCAGTTCGGATTGTAGTCTG CAACTCGACTACATGAAGTCGGAATCGCTAGTAATCGCGGATCAGCA CGCCGCGGTGAATACGTTCCCGGGTCTTGTACACACCGCCCGTCACAC CATGGGAGTTTGTAATGCCCAAAGCCGGTGGCCTAACCTTTTAGGAA GGAGCCGTCTAAGGCAGGACAGATGACTGGGGTGAAGTCGTAACAA GGTAGCCGTAGGAGAACCTGCGGCTGGATCACCTCCTTT |
| 158 | DP94 16S rRNA | ATCTGCCCAGAAGCAGGGGATAACACTTGGAAACAGGTGCTAATACC GTATAACAACAAAATCCGCATGGATTTTGTTTGAAAGGTGGCTTCGGC TATCACTTCTGGATGATCCCGCGGCGTATTAGTTAGTTGGTGAGGTAA AGGCCCACCAAGACGATGATACGTAGCCGACCTGAGAGGGTAATCGG CCACATTGGGACTGAGACACGGCCCAAACTCCTACGGGAGGCAGCAG TAGGGAATCTTCCACAATGGACGAAAGTCTGATGGAGCAATGCCGCG TGAGTGAAGAAGGGTTTCGGCTCGTAAAACTCTGTTGTTAAAGAAGA ACACCTTTGAGAGTAACTGTTCAAGGGTTGACGGTATTTAACCAGAA AGCCACGGCTAACTACGTGCCAGCAGCCGCGGTAATACGTAGGTGGC AAGCGTTGTCCGGATTTATTGGGCGTAAAGCGAGCGCAGGCGGTTTTT TAAGTCTGATGTGAAAGCCTTCGGCTTAACCGGAGAAGTGCATCGGA AACTGGGAGACTTGAGTGCAGAAGAGGACAGTGGAACTCCATGTGTA GCGGTGGAATGCGTAGATATATGGAAGAACACCAGTGGCGAAGGCG GCTGTCTAGTCTGTAACTGACGCTGAGGCTCGAAAGCATGGGTAGCG AACAGGATTAGATACCCTGGTAGTCCATGCCGTAAACGATGAGTGCT AAGTGTTGGAGGGTTTCCGCCCTTCAGTGCTGCAGCTAACGCATTAAG CACTCCGCCTGGGGAGTACGACCGCAAGGTTGAAACTCAAAGGAATT GACGGGGGCCCGCACAAGCGGTGGAGCATGTGGTTTAATTCGAAGCT ACGCGAAGAACCTTACCAGGTCTTGACATCTTCTGCCAATCTTAGAGA TAAGACGTTCCCTTCGGGGACAGAATGACAGGTGGTGCATGGTTGTC GTCAGCTCGTGTCGTGAGATGTTGGGTTAAGTCCCGCAACGAGCGCA ACCCTTATTATCAGTTGCCAGCATTCAGTTGGGCACTCTGGTGAGACT GCCGGTGACAAACCGGAGGAAGGTGGGGATGACGTCAAATCATCATG CCCCTTATGACCTGGGCTACACACGTGCTACAATGGACGGTACAACG AGTTGCGAAGTCGTGAGGCTAAGCTAATCTCTTAAAGCCGTTCTCAGT TCGGATTGTAGGCTGCAACTCGCCTACATGAAGTTGGAATCGCTAGTA ATCGCGGATCAGCATGCCGCGGTGAATACGTTCCCGGGCCTTGTACA CACCGCCCGTCACACCATGAGAGTTTGTAACACCCAAAGCCGGTGAG ATAACCTTCGGGAGTCAGCCGTCTAAGGTGGGACAGATGATTAGGGT GAAGTCGTAACAAGGTAGCCGTAGGAGAACCTGCGGCTGGATCACCT CCTT |
| 159 | DP95 16S rRNA | TGCTAATACCGCATAGATCCAAGAACCGCATGGTTCTTGGCTGAAAG ATGGCGTAAGCTATCGCTTTTGGATGGACCCGCGGCGTATTAGCTAGT TGGTGAGGTAATGGCTCACCAAGGCGATGATACGTAGCCGAACTGAG AGGTTGATCGGCCACATTGGGACTGAGACACGGCCCAAACTCCTACG GGAGGCAGCAGTAGGGAATCTTCCACAATGGACGCAAGTCTGATGGA GCAACGCCGCGTGAGTGAAGAAGGCTTTCGGGTCGTAAAACTCTGTT GTTGGAGAAGAATGGTCGGCAGAGTAACTGTTGTCGGCGTGACGGTA TCCAACCAGAAAGCCACGGCTAACTACGTGCCAGCAGCCGCGGTAAT ACGTAGGTGGCAAGCGTTATCCGGATTTATTGGGCGTAAAGCGAGCG CAGGCGGTTTTTTAAGTCTGATGTGAAAGCCCTCGGCTTAACCGAGGA AGCGCATCGGAAACTGGGAAACTTGAGTGCAGAAGAGGACAGTGGA ACTCCATGTGTAGCGGTGAAATGCGTAGATATATGGAAGAACACCAG TGGCGAAGGCGGCTGTCTGGTCTGTAACTGACGCTGAGGCTCGAAAG CATGGGTAGCGAACAGGATTAGATACCCTGGTAGTCCATGCCGTAAA CGATGAATGCTAGGTGTTGGAGGGTTTCCGCCCTTCAGTGCCGCAGCT AACGCATTAAGCATTCCGCCTGGGGAGTACGACCGCAAGGTTGAAAC TCAAAGGAATTGACGGGGGCCCGCACAAGCGGTGGAGCATGTGGTTT AATTCGAAGCAACGCGAAGAACCTTACCAGGTCTTGACATCTTTTGAT CACCTGAGAGATCAGGTTTCCCCTTCGGGGGCAAAATGACAGGTGGT GCATGGTTGTCGTCAGCTCGTGTCGTGAGATGTTGGGTTAAGTCCCGC AACGAGCGCAACCCTTATGACTAGTTGCCAGCATTTAGTTGGGCACTC TAGTAAGACTGCCGGTGACAAACCGGAGGAAGGTGGGGATGACGTC AAATCATCATGCCCCTTATGACCTGGGCTACACACGTGCTACAATGGA TGGTACAACGAGTTGCGAGACCGCGAGGTCAAGCTAATCTCTTAAAG CCATTCTCAGTTCGGACTGTAGGCTGCAACTCGCCTACACGAAGTCGG AATCGCTAGTAATCGCGGATCAGCACGCCGCGGTGAATACGTTCCCG |

-continued

Sequence Listing

| Seq ID No. | Description | Sequence |
|---|---|---|
| | | GGCCTTGTACACACCGCCCGTCACACCATGAGAGTTTGTAACACCCG AAGCCGGTGGCGTAACCCTTTTAGGGAGCGAGCCGTCTAAGGTGGGA CAAATGATTAGGGTGAAGTCGTAACAAGGTAGCCGTAGGAGAACCTG CGGCTGGATCACCTCCTTT |
| 160 | DP96 16S rRNA | ACACGGCCCAAACTCCTACGGGAGGCAGCAGTAGGGAATCTTCCACA ATGGACGCAAGTCTGATGGAGCAACGCCGCGTGAGTGAAGAAGGCTT TCGGGTCGTAAAACTCTGTTGTTGGAGAAGAATGGTCGGCAGAGTAA CTGTTGTCGGCGTGACGGTATCCAACCAGAAAGCCACGGCTAACTAC GTGCCAGCAGCCGCGGTAATACGTAGGTGGCAAGCGTTATCCGGATT TATTGGGCGTAAAGCGAGCGCAGGCGGTTTTTTAAGTCTGATGTGAA AGCCCTCGGCTTAACCGAGGAAGCGCATCGGAAACTGGGAAACTTGA GTGCAGAAGAGGACAGTGGAACTCCATGTGTAGCGGTGAAATGCGTA GATATATGGAAGAACACCAGTGGCGAAGGCGGCTGTCTGGTCTGTAA CTGACGCTGAGGCTCGAAAGCATGGGTAGCGAACAGGATTAGATACC CTGGTAGTCCATGCCGTAAACGATGAATGCTAGGTGTTGGAGGGTTTC CGCCCTTCAGTGCCGCAGCTAACGCATTAAGCATTCCGCCTGGGGAGT ACGACCGCAAGGTTGAAACTCAAAGGAATTGACGGGGGCCCGCACA AGCGGTGGAGCATGTGGTTTAATTCGAAGCAACGCGAAGAACCTTAC CAGGTCTTGACATCTTTTGATCACCTGAGAGATCAGGTTTCCCCTTCG GGGGCAAAATGACAGGTGGTGCATGGTTGTCGTCAGCTCGTGTCGTG AGATGTTGGGTTAAGTCCCGCAACGAGCGCAACCCTTATGACTAGTT GCCAGCATTTAGTTGGGCACTCTAGTAAGACTGCCGGTGACAAACCG GAGGAAGGTGGGGATGACGTCAAATCATCATGCCCCTTATGACCTGG GCTACACACGTGCTACAATGGATGGTACAACGAGTTGCGAGACCGCG AGGTCAAGCTAATCTCTTAAAGCCATTCTCAGTTCGGACTGTAGGCTG CAACTCGCCTACACGAAGTCGGAATCGCTAGTAATCGCGGATCAGCA CGCCGCGGTGAATACGTTCCCGGGCCTTGTACACACCGCCCGTCACAC CATGAGAGTTTGTAACACCCGAAGCCGGTGGCGTAACCCTTTTAGGG AGCGAGCCGTCTAAGGTGGGACAAATGATTAGGGTGAAGTCGTAACA AGGTAGCCGTAGGAGAACCTGCGGCTGGATCACCTCCTTT |
| 161 | DP97 16S rRNA | AATGAGAGTTTGATCCTGGCTCAGGACGAACGCTGGCGGCGTGCCTA ATACATGCAAGTCGAGCGATGATTAAAGATAGCTTGCTATTTTTATGA AGAGCGGCGAACGGGTGAGTAACGCGTGGGAAATCTGCCGAGTAGC GGGGGACAACGTTTGGAAACGAACGCTAATACCGCATAACAATGAGA ATCGCATGATTCTTATTTAAAAGAAGCAATTGCTTCACTACTTGATGA TCCCGCGTTGTATTAGCTAGTTGGTAGTGTAAAGGACTACCAAGGCG ATGATACATAGCCGACCTGAGAGGGTGATCGGCCACACTGGGACTGA GACACGGCCCAGACTCCTACGGGAGGCAGCAGTAGGGAATCTTCGGC AATGGGGGCAACCCTGACCGAGCAACGCCGCGTGAGTGAAGAAGGTT TTCGGATCGTAAAACTCTGTTGTTAGAGAAGAACGTTAAGTAGAGTG GAAAATTACTTAAGTGACGGTATCTAACCAGAAAGGGACGGCTAACT ACGTGCCAGCAGCCGCGGTAATACGTAGGTCCCAAGCGTTGTCCGGA TTTATTGGGCGTAAAGCGAGCGCAGGTGGTTTCTTAAGTCTGATGTAA AAGGCAGTGGCTCAACCATTGTGTGCATTGGAAACTGGGAGACTTGA GTGCAGGAGAGGAGAGTGGAATTCCATGTGTAGCGGTGAAATGCGTA GATATATGGAGGAACACCGGAGGCGAAAGCGGCTCTCTGGCCTGTAA CTGACACTGAGGCTCGAAAGCGTGGGGAGCAAACAGGATTAGATACC CTGGTAGTCCACGCCGTAAACGATGAGTGCTAGCTGTAGGGAGCTAT AAGTTCTCTGTAGCGCAGCTAACGCATTAAGCACTCCGCCTGGGGAG TACGACCGCAAGGTTGAAACTCAAAGGAATTGACGGGGGCCCGCACA AGCGGTGGAGCATGTGGTTTAATTCGAAGCAACGCGAAGAACCTTAC CAGGTCTTGACATACTCGTGATATCCTTAGAGATAAGGAGTTCCTTCG GGACACGGGATACAGGTGGTGCATGGTTGTCGTCAGCTCGTGTCGTG AGATGTTGGGTTAAGTCCCGCAACGAGCGCAACCCTTATTACTAGTTG CCATCATTAAGTTGGGCACTCTAGTGAGACTGCCGGTGATAAACCGG AGGAAGGTGGGGATGACGTCAAATCATCATGCCCCTTATGACCTGGG CTACACACGTGCTACAATGGATGGTACAACGAGTCGCCAACCCGCGA GGGTGCGCTAATCTCTTAAAACCATTCTCAGTTCGGATTGCAGGCTGC AACTCGCCTGCATGAAGTCGGAATCGCTAGTAATCGCGGATCAGCAC GCCGCGGTGAATACGTTCCCGGGCCTTGTACACACCGCCCGTCACACC ACGGAAGTTGGGAGTACCCAAAGTAGGTTGCCTAACCGCAAGGAGGG CGCTTCCTAAGGTAAGACCGATGACTGGGGTGAAGTCGTAACAAGGT AGCCGTATCGGAAGGTGCGGCTGGATCACCTCCTTT |
| 162 | DP98 16S rRNA | AATGAGAGTTTGATCCTGGCTCAGGACGAACGCTGGCGGCGTGCCTA ATACATGCAAGTCGAGCGATGATTAAAGATAGCTTGCTATTTTTATGA AGAGCGGCGAACGGGTGAGTAACGCGTGGGAAATCTGCCGAGTAGC GGGGGACAACGTTTGGAAACGAACGCTAATACCGCATAACAATGAGA ATCGCATGATTCTTATTTAAAAGAAGCAATTGCTTCACTACTTGATGA TCCCGCGTTGTATTAGCTAGTTGGTAGTGTAAAGGACTACCAAGGCG ATGATACATAGCCGACCTGAGAGGGTGATCGGCCACACTGGGACTGA |

-continued

Sequence Listing

| Seq ID No. | Description | Sequence |
|---|---|---|
| | | GACACGGCCCAGACTCCTACGGGAGGCAGCAGTAGGGAATCTTCGGC AATGGGGGCAACCCTGACCGAGCAACGCCGCGTGAGTGAAGAAGGTT TTCGGATCGTAAAACTCTGTTGTTAGAGAAGAACGTTAAGTAGAGTG GAAAATTACTTAAGTGACGGTATCTAACCAGAAAGGGACGGCTAACT ACGTGCCAGCAGCCGCGGTAATACGTAGGTCCCAAGCGTTGTCCGGA TTTATTGGGCGTAAAGCGAGCGCAGGTGGTTTCTTAAGTCTGATGTAA AAGGCAGTGGCTCAACCATTGTGTGCATTGGAAACTGGGAGACTTGA GTGCAGGAGAGGAGAGTGGAATTCCATGTGTAGCGGTGAAATGCGTA GATATATGGAGGAACACCGGAGGCGAAAGCGGCTCTCTGGCCTGTAA CTGACACTGAGGCTCGAAAGCGTGGGGAGCAAACAGGATTAGATACC CTGGTAGTCCACGCCGTAAACGATGAGTGCTAGCTGTAGGGAGCTAT AAGTTCTCTGTAGCGCAGCTAACGCATTAAGCACTCCGCCTGGGGAG TACGACCGCAAGGTTGAAACTCAAAGGAATTGACGGGGGCCCGCACA AGCGGTGGAGCATGTGGTTTAATTCGAAGCAACGCGAAGAACCTTAC CAGGTCTTGACATACTCGTGATATCCTTAGAGATAAGGAGTTCCTTCG GGACACGGGATACAGGTGGTGCATGGTTGTCGTCAGCTCGTGTCGTG AGATGTTGGGTTAAGTCCCGCAACGAGCGCAACCCTTATTACTAGTTG CCATCATTAAGTTGGGCACTCTAGTGAGACTGCCGGTGATAAACCGG AGGAAGGTGGGGATGACGTCAAATCATCATGCCCCTTATGACCTGGG CTACACACGTGCTACAATGGATGGTACAACGAGTCGCCAACCCGCGA GGGTGCGCTAATCTCTTAAAACCATTCTCAGTTCGGATTGCAGGCTGC AACTCGCCTGCATGAAGTCGGAATCGCTAGTAATCGCGGATCAGCAC GCCGCGGTGAATACGTTCCCGGGCCTTGTACACACCGCCCGTCACACC ACGGAAGTTGGGAGTACCCAAAGTAGGTTGCCTAACCGCAAGGAGGG CGCTTCCTAAGGTAAGACCGATGACTGGGGTGAAGTCGTAACAAGGT AGCCGTATCGGAAGGTGCGGCTGGATCACCTCCTTT |
| 163 | DP100 16S rRNA | TTTGAGAGTTTGATCCTGGCTCAGGACGAACGCTGGCGGCGTGCCTA ATACATGCAAGTCGAACGAACTCTGGTATTGATTGGTGCTTGCATCAT GATTTACATTTGAGTGAGTGGCGAACTGGTGAGTAACACGTGGGAAA CCTGCCCAGAAGCGGGGGATAACACCTGGAAACAGATGCTAATACCG CATAACAACTTGGACCGCATGGTCCGAGCTTGAAAGATGGCTTCGGC TATCACTTTTGGATGGTCCCGCGGCGTATTAGCTAGATGGTGGGGTAA CGGCTCACCATGGCAATGATACGTAGCCGACCTGAGAGGGTAATCGG CCACATTGGGACTGAGACACGGCCCAAACTCCTACGGGAGGCAGCAG TAGGGAATCTTCCACAATGGACGAAAGTCTGATGGAGCAACGCCGCG TGAGTGAAGAAGGGTTTCGGCTCGTAAAACTCTGTTGTTAAAGAAGA ACATATCTGAGAGTAACTGTTCAGGTATTGACGGTATTTAACCAGAA AGCCACGGCTAACTACGTGCCAGCAGCCGCGGTAATACGTAGGTGGC AAGCGTTGTCCGGATTTATTGGGCGTAAAGCGAGCGCAGGCGGTTTTT TAAGTCTGATGTGAAAGCCTTCGGCTCAACCGAAGAAGTGCATCGGA AACTGGGAAACTTGAGTGCAGAAGAGGACAGTGGAACTCCATGTGTA GCGGTGAAATGCGTAGATATATGGAAGAACACCAGTGGCGAAGGCG GCTGTCTGGTCTGTAACTGACGCTGAGGCTCGAAAGTATGGGTAGCA AACAGGATTAGATACCCTGGTAGTCCATACCGTAAACGATGAATGCT AAGTGTTGGAGGGTTTCCGCCCTTCAGTGCTGCAGCTAACGCATTAAG CATTCCGCCTGGGGAGTACGGCCGCAAGGCTGAAACTCAAAGGAATT GACGGGGGCCCGCACAAGCGGTGGAGCATGTGGTTTAATTCGAAGCT ACGCGAAGAACCTTACCAGGTCTTGACATACTATGCAAATCTAAGAG ATTAGACGTTCCCTTCGGGGACATGGATACAGGTGGTGCATGGTTGTC GTCAGCTCGTGTCGTGAGATGTTGGGTTAAGTCCCGCAACGAGCGCA ACCCTTATTATCAGTTGCCAGCATTAAGTTGGGCACTCTGGTGAGACT GCCGGTGACAAACCGGAGGAAGGTGGGGATGACGTCAAATCATCATG CCCCTTATGACCTGGGCTACACACGTGCTACAATGG |
| 164 | DP101 16S rRNA | ATGAGAGTTTGATCTTGGCTCAGGATGAACGCTGGCGGCGTGCCTAA TACATGCAAGTCGAACGAACTTCCGTTAATTGATTATGACGTACTTGT ACTGATTGAGATTTTAACACGAAGTGAGTGGCGAACGGGTGAGTAAC ACGTGGGTAACCTGCCCAGAAGTAGGGGATAACACCTGGAAACAGAT GCTAATACCGTATAACAGAGAAAACCGCATGGTTTTCTTTTAAAAGAT GGCTCTGCTATCACTTCTGGATGGACCCGCGGCGTATTAGCTAGTTGG TGAGGCAAAGGCTCACCAAGGCAGTGATACGTAGCCGACCTGAGAGG GTAATCGGCCACATTGGGACTGAGACACGGCCCAGACTCCTACGGGA GGCAGCAGTAGGGAATCTTCCACAATGGACGCAAGTCTGATGGAGCA ACGCCGCGTGAGTGAAGAAGGGTTTCGGCTCGTAAAGCTCTGTTGTT AAAGAAGAACGTGGGTAAGAGTAACTGTTTACCCAGTGACGGTATTT AACCAGAAAGCCACGGCTAACTACGTGCCAGCAGCCGCGGTAATACG TAGGTGGCAAGCGTTATCCGGATTTATTGGGCGTAAAGCGAGCGCAG GCGGTCTTTTAAGTCTAATGTGAAAGCCTTCGGCTCAACCGAAGAAGT GCATTGGAAACTGGGAGACTTGAGTGCAGAAGAGGACAGTGGAACTC CATGTGTAGCGGTGAAATGCGTAGATATATGGAAGAACACCAGTGGC GAAGGCGGCTGTCTGGTCTGCAACTGACGCTGAGGCTCGAAAGCATG GGTAGCGAACAGGATTAGATACCCTGGTAGTCCATGCCGTAAACGAT |

-continued

Sequence Listing

| Seq ID No. | Description | Sequence |
|---|---|---|
| | | GATTACTAAGTGTTGGAGGGTTTCCGCCCTTCAGTGCTGCAGCTAACG CATTAAGTAATCCGCCTGGGGAGTACGACCGCAAGGTTGAAACTCAA AAGAATTGACGGGGGCCCGCACAAGCGGTGGAGCATGTGGTTTAATT CGAAGCTACGCGAAGAACCTTACCAGGTCTTGACATCTTCTGACAGTC TAAGAGATTAGAGGTTCCCTTCGGGGACAGAATGACAGGTGGTGCAT GGTTGTCGTCAGCTCGTGTCGTGAGATGTTGGGTTAAGTCCCGCAACG AGCGCAACCCTTATTACTAGTTGCCAGCATTAAGTTGGGCACTCTAGT GAGACTGCCGGTGACAAACCGGAGGAAGGTGGGGACGACGTCAAAT CATCATGCCCCTTATGACCTGGGCTACACACGTGCTACAATGGATGGT ACAACGAGTCGCGAGACCGCGAGGTTAAGCTAATCTCTTAAAACCAT TCTCAGTTCGGACTGTAGGCTGCAACTCGCCTACACGAAGTCGGAATC GCTAGTAATCGCGGATCAGCATGCCGCGGTGAATACGTTCCCGGGCC TTGTACACACCGCCCGTCACACCATGAGAGTTTGTAAC |
| 165 | DP101 ITS sequence | TCCGTAGGTGAACCTGCGGAAGGATCATTACTGTGATTTAGTACTACA CTGCGTGAGCGGAACGAAAACAACAACACCTAAAATGTGGAATATAG CATATAGTCGACAAGAGAAATCTACGAAAAACAAACAAAACTTTCAA CAACGGATCTCTTGGTTCTCGCATCGATGAAGAGCGCAGCGAAATGC GATACCTAGTGTGAATTGCAGCCATCGTGAATCATCGAGTTCTTGAAC GCACATTGCGCCCCTCGGCATTCCGGGGGGCATGCCTGTTTGAGCGTC GTTTCCATCTTGCGCGTGCGCAGAGTTGGGGGAGCGGAGCGGACGAC GTGTAAAGAGCGTCGGAGCTGCGACTCGCCTGAAAGGGAGCGAAGCT GGCCGAGCGAACTAGACTTTTTTTCAGGGACGCTTGGCGGCCGAGAG CGAGTGTTGCGAGACAACAAAAAGCTCGACCTCAAATCAGGTAGGAA TACCCGCTGAACTTAAGCATATCAATAAGCGGAGGAAAAGAAACCAA CAGGGATTGCCTCAGTAGCGGCGAGTGAAGCGGCAAGAGCTCAGATT TGAAATCGTGCTTTGCGGCACGAGTTGTAGATTGCAGGTTGGAGTCTG TGTGGAAGGCGGTGTCCAAGTCCCTTGGAACAGGGCGCCCAGGAGGG TGAGAGCCCCGTGGGATGCCGGCGGAAGCAGTGAGGCCCTTCTGACG AGTCGAGTTGTTTGGGAATGCAGCTCCAAGCGGGTGGTAAATTCCAT CTAAGGCTAAATACTGGCGAGAGACCGATAGCGAACAAGTACTGTGA AGGAAAGATGAAAAGCACTTTGAAAAGAGAGTGAAACAGCACGTGA AATTGTTGAAAGGGAAGGGTATTGCGCCCGACATGGGGATTGCGCAC CGCTGCCTCTCGTGGGCGGCGCTCTGGGCTTTCCCTGGGCCAGCATCG GTTCTTGCTGCAGGAGAAGGGGTTCTGGAACGTGGCTCTTCGGAGTGT TATAGCCAGGGCCAGATGCTGCGTGCGGGGACCGAGGACTGCGGCCG TGTAGGTCACGGATGCTGGCAGAACGGCGCAACACCGCCCGTCTTGA AACATGGACCAAGGAGTCTAACGTCTATGCGAGTGTTTGGGTGTGAA ACCCGTACGCGTAATGAAAGTGAACGTAGGTCGGACCCCCTGCCCTC GGGGAGGGGAGCACGATCGACCGATCCCGATGTTTATCGGAAGGATT TGAGTAGGAGCATAGCTGTTGGGACCCGAAAGATGGTGAACTATGCC TGAATAGGGTGAAGCCAGAGGAAACTCTGGTGGAGGCTCGTAGCGGT TCTGACGTGCAAATCGATCGTCGAATTTGGGTATAGGGGCGAAAGAC TAATCGAACCATCTAGTAGCTGGTTCCTGCCGAAGTTTCCCTCAGGA |

What is claimed is:

1. A method for dietary management of a musculoskeletal disease in a subject, the method comprising administering to the subject an effective amount of a synthetic microbial consortium comprising each of *Lactobacillus brevis, Lactobacillus plantarum, Leuconostoc mesenteroides*, and *Pichia kudriavzevii*.

2. The method of claim 1, wherein the synthetic microbial consortium is co-formulated in a unit dose formulated for oral administration to the subject.

3. The method of claim 2, wherein the unit dose is formulated as a dietary supplement or a medical food.

4. The method of claim 2, wherein the unit dose further comprises an effective amount of a cryoprotectant, wherein the effective amount of the cryoprotectant extends survival of the synthetic microbial consortium after thawing the composition from a cryogenic temperature as compared to survival of the synthetic microbial consortium in an otherwise identical composition that lacks the effective amount of the cryoprotectant, assayed under identical conditions.

5. The method of claim 2, wherein the unit dose comprises at least 1×10^7 colony forming units (CFUs) of each of *Lactobacillus brevis, Lactobacillus plantarum, Leuconostoc mesenteroides*, and *Pichia kudriavzevii*, and the total of all microbes present in the unit dose is less than 1×10^12 CFUs.

6. The method of claim 2, wherein the unit dose comprises a prebiotic polysaccharide.

7. The method of claim 1, wherein the dietary management comprises reducing bone loss in the subject, wherein the reduction of bone loss is relative to a control group not administered the composition.

8. The method of claim 7, wherein reducing bone loss comprises maintaining, improving, or lessening a decrease in bone mineral density (BMD) in a subject.

9. The method of claim 1, wherein the subject has, is diagnosed with, or is at risk for one or more of the musculoskeletal diseases selected from the group consisting of: osteoporosis, osteopenia, osteoarthritis, suboptimal fracture healing, osteomyelitis, Paget's disease, stunting, and delayed or non-union fractures.

10. The method of claim 1, wherein the subject is postmenopausal.

11. The method of claim 1, wherein (a) the *Lactobacillus brevis* has a 16S rRNA having at least 97% similarity to SEQ ID NO: 158, (b) the *Lactobacillus plantarum* has a 16S rRNA having at least 97% similarity to SEQ ID NO: 163, (c) the *Leuconostoc mesenteroides* has a 16S rRNA having at least 97% similarity to SEQ ID NO: 157, and (d) the *Pichia kudriavzevii* has a fungal ITS sequence having at least 97% similarity to SEQ ID NO: 165.

12. The method of claim 1, wherein the method further comprises administering an additional agent for treatment of the musculoskeletal disease.

13. The method of claim 12, wherein the synthetic microbial consortium supplements or increases the efficacy of the additional agent.

14. The method of claim 12, wherein the synthetic microbial consortium is administered together with the additional agent.

15. The method of claim 1, wherein the dietary management comprises altering the microbial content of the subject's microbiota, wherein the alteration comprises an increase in abundance of *Lactobacillus brevis, Lactobacillus plantarum, Leuconostoc mesenteroides*, and/or *Pichia kudriavzevii* by between 3 to 6 weeks following administration, and wherein the increase is relative to the microbial content of the control group and/or the microbial content of the subject prior to administration of the synthetic microbial consortium.

16. The method of claim 15, wherein the increase is assessed by genomic sequencing of the subject's microbiota in a fecal sample of the subject.

17. The method of claim 1, wherein the dietary management comprises altering a microbiome associated with the microbiota of the subject.

18. The method of claim 15, wherein altering the microbiome comprises increasing gene abundance of vitamin K2 biosynthesis pathways assessed by genomic sequencing of the subject's microbiota in a fecal sample of the subject.

19. A method for dietary management of a musculoskeletal disease in a postmenopausal subject, the method comprising administering to the subject at least 9×10^10 CFUs of each of *Lactobacillus brevis, Lactobacillus plantarum, Leuconostoc mesenteroides*, and *Pichia kudriavzevii* co-formulated in a unit dose formulated for oral administration to the subject, wherein the unit dose is formulated as a medical food, wherein the unit dosage form of the medical food is an effective amount to reduce loss of bone mineral density (BMD) in the subject, and wherein the subject has, is diagnosed with, or is at risk for one or more of the group consisting of: osteoporosis, osteopenia, osteoarthritis, suboptimal fracture healing, osteomyelitis, Paget's disease, stunting, and delayed or non-union fractures.

20. The method of claim 19, wherein (a) the *Lactobacillus brevis* has a 16S rRNA having at least 97% similarity to SEQ ID NO: 158, (b) the *Lactobacillus plantarum* has a 16S rRNA having at least 97% similarity to SEQ ID NO: 163, (c) the *Leuconostoc mesenteroides* has a 16S rRNA having at least 97% similarity to SEQ ID NO: 157, and (d) the *Pichia*

*kudriavzevii* has a fungal ITS sequence having at least 97% similarity to SEQ ID NO: 165.

* * * * *

SEQUENCE LISTING

```
Sequence total quantity: 165
SEQ ID NO: 1           moltype = RNA  length = 1490
FEATURE                Location/Qualifiers
source                 1..1490
                       mol_type = rRNA
                       organism = unidentified
                       note = DP1 16S rRNA sequence
SEQUENCE: 1
agtcagacat gcaagtcgag cggtagagag aagcttgctt ctcttgagag cggcggacgg  60
gtgagtaaag cctaggaatc tgcctggtag tgggggataa cgttcggaaa cggacgctaa  120
taccgcatac gtcctacggg agaaagcagg ggaccttcgg gccttgcgct atcagatgag  180
cctaggtcgg attagctagt tggtgaggta atggctcacc aaggcgacga tccgtaactg  240
gtctgagagg atgatcagtc acactggaac tgagacacgg tccagactcc tacgggaggc  300
agcagtgggg aatattggac aatgggcgaa agcctgatcc agccatgccg cgtgtgtgaa  360
gaaggtcttc ggattgtaaa gcactttaag ttgggaggaa gggcattaac ctaatacgtt  420
agtgttttga cgttaccgac agaataagca ccggctaact ctgtgccagc agccgcggta  480
atacagaggg tgcaagcgtt aatcggaatt actgggcgta aagcgcgcgt aggtggtttg  540
ttaagttgga tgtgaaatcc ccgggctcaa cctgggaact gcattcaaaa ctgactgact  600
agagtatggt agagggtggt ggaatttcct gtgtagcggt gaaatgcgta gatataggaa  660
ggaacaccag tggcgaaggc gaccacctgg actaatactg acactgaggt gcgaaagcgt  720
ggggagcaaa caggattaga taccctggta gtccacgccg taaacgatgt caactagccg  780
ttgggagcct tgagctctta gtggcgcagc taacgcatta agttgaccgc ctggggagta  840
```

-continued

```
cggccgcaag gttaaaactc aaatgaattg acgggggccc gcacaagcgg tggagcatgt  900
ggtttaattc gaagcaacgc gaagaacctt accaggcctt gacatccaat gaactttcta  960
gagatagatt ggtgccttcg ggaacattga gacaggtgct gcatggctgt cgtcagctcg  1020
tgtcgtgaga tgttgggtta agtcccgtaa cgagcgcaac ccttgtcctt agttaccagc  1080
acgtaatggt gggcactcta aggagactgc cggtgacaaa ccggaggaag gtggggatga  1140
cgtcaagtca tcatggccct tacggcctgg gctacacacg tgctacaatg gtcggtacag  1200
agggttgcca agccgcgagg tggagctaat cccataaaac cgatcgtagt ccggatcgca  1260
gtctgcaact cgactgcgtg aagtcggaat cgctagtaat cgcgaatcag aatgtcgcgg  1320
tgaatacgtt cccgggcctt gtacacaccg cccgtcacac catgggagtg ggttgcacca  1380
gaagtagcta gtctaacctt cgggaggacg gttaccacgg tgtgattcat gactggggtg  1440
aagtcgtaac aaggtagccg taggggaacc tgcggctgga tcacctcctt             1490

SEQ ID NO: 2            moltype = DNA  length = 1017
FEATURE                 Location/Qualifiers
source                  1..1017
                        mol_type = genomic DNA
                        organism = unidentified
                        note = DP2 ITS sequence
SEQUENCE: 2
ttgttgctcg agttcttgtt tagatctttt acaataatgt gtatctttaa tgaagatgng  60
ngcttaattg cgctgcttta ttagagtgtc gcagtagaag tagtcttgct tgaatctcag  120
tcaacgttta cacacattgg agttttttta ctttaattta attctttctg ctttgaatcg  180
aaaggttcaa ggcaaaaaac aaacacaaac aattttattt tattataatt ttttaaacta  240
aaccaaaatt cctaacggaa attttaaaat aatttaaaac tttcaacaac ggatctcttg  300
gttctcgcat cgatgaaaaa cgtaccgaat tgcgataagt aatgtgaatt gcaaatactc  360
gtgaatcatt gaatttttga acgcacattg cgcccttgag cattctcaag ggcatgcctg  420
tttgagcgtc atttccttct caaaaaaataa tttttttattt tttggttgtg ggcgatactc  480
agggttagct tgaaattgga gactgtttca gtctttttta attcaacact tancttcttt  540
ggagacgctg ttctcgctgt gatgtattta tggatttatt cgttttactt tacaagggaa  600
atggtaatgt accttaggca aagggttgct tttaatattc atcaagtttg acctcaaatc  660
aggtaggatt acccgctgaa cttaagcata tcaataagcg gaggaaaaga aaccaactgg  720
gattacctta gtaacggcga gtgaagcggt aaaagctcaa atttgaaatc tggtactttc  780
agtgcccgag ttgtaatttg tagaatttgt ctttgattag gtccttgtct atgttccttg  840
gaacaggacg tcatagaggg tgagantccc gtttgnngag gataccttttt ctctgtanna  900
ctttttcnaa gagtcgagtt gnttgggaat gcagctcaaa nngggtngna aattccatct  960
aaagctaaat attngncnag agaccganag cgacantaca gngatggaaa gangaaa     1017

SEQ ID NO: 3            moltype = RNA  length = 1548
FEATURE                 Location/Qualifiers
source                  1..1548
                        mol_type = rRNA
                        organism = unidentified
                        note = DP3 16S rRNA sequence
SEQUENCE: 3
attgagagtt tgatcctggc tcaggatgaa cgctggcggc gtgcctaata catgcaagtc  60
gaacgcacag cgaaaggtgc ttgcaccttt caagtgagtg gcgaacgggt gagtaacacg  120
tggacaacct gcctcaaggc tggggataac atttggaaac agatgctaat accgaataaa  180
actcagtgtc gcatgacaca aagttaaaag gcgctttggc gtcacctaga gatggatccg  240
cggtgcatta gttagttggt ggggtaaagg cctaccaaga caatgatgca tagccgagtt  300
gagagactga tcggccacat tgggactgag acacggccca aactcctacg ggaggctgca  360
gtagggaatc ttccacaatg ggcgaaagcc tgatggagca acgccgcgtg tgtgatgaag  420
gctttcgggt cgtaaagcac tgttgtacgg gaagaacagc tagaataggg aatgatttta  480
gtttgacggt accataccag aaagggacgg ctaaatacgt gccagcagcc gcggtaatac  540
gtatgtcccg agcgttatcc ggatttattg ggcgtaaagc gagcgcagac ggttgattaa  600
gtctgatgtg aaagcccgga gctcaactcc ggaatggcat tggaaactgg ttaacttgag  660
tgcagtagag gtaagtggaa ctccatgtgt agcggtggaa tgcgtagata tatggaagaa  720
caccagtggc gaaggcggct tactggactg taactgacgt tgaggctcga aagtgtgggt  780
agcaaacagg attagatacc ctggtagtcc acaccgtaaa cgatgaacac taggtgttag  840
gaggtttccg cctcttagtg ccgaagctaa cgcattaagt gttccgcctg gggagtacga  900
ccgcaaggtt gaaactcaaa ggaattgacg gggacccgca caagcggtgg agcatgtggt  960
ttaattcgaa gcaacgcgaa gaaccttacc aggtcttgac atcctttgaa gcttttagag  1020
atagaagtgt tctcttcgga gacaaagtga caggtggtgc atggtcgtcg tcagctcgtg  1080
tcgtgagatg ttgggttaag tcccgcaacg agcgcaaccc ttattgttag ttgccagcat  1140
tcagatgggc actctagcga gactgccggt gacaaaccgg aggaaggcgg ggacgacgtc  1200
agatcatcat gccccttatg acctgggcta cacacgtgct acaatggcgt atacaacgag  1260
ttgccaaccc gcgagggtga gctaatctct taaagtacgt ctcagttcgg attgtagtct  1320
gcaactcgac tacatgaagt cggaatcgct agtaatcgcg gatcagcacg ccgcggtgaa  1380
tacgttcccg ggtcttgtac acaccgcccg tcacaccatg ggagtttgta atgcccaaag  1440
ccggtggcct aacctttag gaaggagccg tctaaggcag gacagatgac tggggtgaag  1500
tcgtaacaag gtagccgtag gagaacctgc ggctggatca cctccttt               1548

SEQ ID NO: 4            moltype = RNA  length = 1538
FEATURE                 Location/Qualifiers
source                  1..1538
                        mol_type = rRNA
                        organism = unidentified
                        note = DP4 16S rRNA sequence
SEQUENCE: 4
ttgaagagtt tgatcatggc tcagattgaa cgctggcggc aggcctaaca catgcaagtc  60
```

```
gagcggcagc ggaaagtagc ttgctacttt gccggcgagc ggcggacggg tgagtaatgt  120
ctgggaaact gcctgatgga gggggataac tactggaaac ggtagctaat accgcatgac  180
ctcgaaagag caaagtgggg gatcttcgga cctcacgcca tcggatgtgc ccagatggga  240
ttagctagta ggtgaggtaa tggctcacct aggcgacgat ccctagctgg tctgagagga  300
tgaccagcca cactggaact gagacacggt ccagactcct acgggaggca gcagtgggga  360
atattgcaca atgggcgcaa gcctgatgca gccatgccgc gtgtgtgaag aaggccttag  420
ggttgtaaag cactttcagc gaggaggaag gcatcatact taatacgtgt ggtgattgac  480
gttactcgca gaagaagcac cggctaactc cgtgccagca gccgcggtaa tacggagggt  540
gcaagcgtta atcggaatta ctgggcgtaa agcgcacgca ggcggtttgt taagtcagat  600
gtgaaatccc cgcgcttaac gtgggaactg catttgaaac tggcaagcta gagtcttgta  660
gaggggggta gaattccagg tgtagcggtg aaatgcgtag agatctggag gaataccggt  720
ggcgaaggcg gcccccctgga caaagactga cgctcaggtg cgaaagcgtg gggagcaaac  780
aggattagat accctggtag tccacgccgt aaacgatgtc gacttggagg ttgttccctt  840
gaggagtggc ttccggagct aacgcgttaa gtcgaccgcc tggggagtac ggccgcaagg  900
ttaaaactca aatgaattga cgggggcccg cacaagcggt ggagcatgtg gtttaattcg  960
atgcaacgcg aagaacctta cctactcttg acatccacgg aatttggcag agatgcctta  1020
gtgccttcgg gaaccgtgag acaggtgctg catggctgtc gtcagctcgt gttgtgaaat  1080
gttgggttaa gtcccgcaac gagcgcaacc cttatccttt gttgccagcg attcggtcgg  1140
gaactcaaag gagactgccg gtgataaacc ggaggaaggt ggggatgacg tcaagtcatc  1200
atggccctta cgagtagggc tacacacgtg ctacaatggc gcatacaaag agaagcgacc  1260
tcgcgagagc aagcggacct cacaaagtgc gtcgtagtcc ggatcggagt ctgcaactcg  1320
actccgtgaa gtcggaatcg ctagtaatcg tggatcagaa tgccacggtg aatacgttcc  1380
cgggccttgt acacaccgcc cgtcacacca tgggagtggg ttgcaaaaga agtaggtagc  1440
ttaaccttcg ggagggcgct taccactttg tgattcatga ctggggtgaa gtcgtaacaa  1500
ggtaaccgta ggggaacctg cggttggatc acctcctt                         1538

SEQ ID NO: 5            moltype = DNA  length = 1042
FEATURE                 Location/Qualifiers
source                  1..1042
                        mol_type = genomic DNA
                        organism = unidentified
                        note = DP5 ITS sequence
SEQUENCE: 5
gcgcttattg cgcggcgaaa aaaccttaca cacagtgttt tttgttatta cannaacttt  60
tgctttggtc tggactagaa atagtttggg ccagaggtta ctaaactaaa cttcaatatt  120
tatattgaat tgttatttat ttaattgtca atttgttgat taaattcaaa aaatcttcaa  180
aactttcaac aacggatctc ttggttctcg catcgatgaa gaacgcagcg aaatgcgata  240
agtaatatga attgcagatt ttcgtgaatc atcgaatctt tgaacgcaca ttgcgccctc  300
tggtattcca gagggcatgc ctgtttgagc gtcatttctc tctcaaacct tcgggtttgg  360
tattgagtga tactcttagt cgaactaggc gtttgcttga aatgtattgg catgagtggt  420
actggatagt gctatatgac tttcaatgta ttaggtttat ccaactcgtt gaatagttta  480
atggtatatt tctcggtatt ctaggctcgg ccttacaata taacaaacaa gtttgacctc  540
aaatcaggta ggattacccg ctgaacttaa gcatatcaat aagcggagga aaagaaacca  600
acagggattg ccttagtaac ggcgagtgaa gcggcaaaag ctcaaatttg aaatctggca  660
ccttcggtgt ccgagttgta atttgaagaa ggtaactttg gagttggctc ttgtctatgt  720
tccttggaac aggacgtcac agagggtgag aatcccgtgc gatgagatgc ccaattctat  780
gtaaagtgct ttcgaagagt cgagttgttt gggaatgcag ctctaagtgg gtggtaaatt  840
ccatctaaag ctaaatattg gcgagagacc gatagcgaac aagtacagtg atggaaagat  900
gaaaagaact ttgaaaagag agtgaaaaag tacgtgaaat tgttgaaagg gaaagggctt  960
gagatcagac ttggtatttt gcgatccttt ccttcttggt tggttcctc gcagcttact  1020
gggncagcat cggtttggat gg                                          1042

SEQ ID NO: 6            moltype = RNA  length = 1165
FEATURE                 Location/Qualifiers
source                  1..1165
                        mol_type = rRNA
                        organism = unidentified
                        note = DP6 16S rRNA sequence
SEQUENCE: 6
gaaaggcggc ttcggctgtc acttatggat ggacccgcgt cgcattagct agttggtgag  60
gtaacggctc accaaggcaa cgatgcgtag ccgacctgag agggtgatcg gccacactgg  120
gactgagaca cggcccagac tcctacggga ggcagcagta gggaatcttc cgcaatggac  180
gaaagtctga cggagcaacg ccgcgtgagt gatgaaggct ttcgggtcgt aaaactctgt  240
tgttagggaa gaacaagtgc tagttgaata agctgcacct tgacggtacc taaccagaaa  300
gccacggcta actacgtgcc agcagccgcg gtaatacgta ggtggcaagc gttatccgga  360
attattgggc gtaaagcgcg cgcaggtggt ttcttaagtc tgatgtgaaa gcccacggct  420
caaccgtgga gggtcattgg aaactgggag acttgagtgc agaagaggaa agtggaattc  480
catgtgtagc ggtgaaatgc gtagagatat ggaggaacac cagtggcgaa ggcgactttc  540
tggtctgtaa ctgacactga ggcgcgaaag cgtggggagc aaacaggatt agataccctg  600
gtagtccacg ccgtaaacga tgagtgctaa gtgttagagg gtttccgccc tttagtgctg  660
aagttaacgc attaagcact ccgcctgggg agtacggccg caaggctgaa actcaaagga  720
attgacgggg gcccgcacaa gcggtggagc atgtggttta attcgaagca acgcgaagaa  780
ccttaccagg tcttgacatc ctctgaaaac cctagagata gggcttctcc ttcgggagca  840
gagtgacagg tggtgcatgg ttgtcgtcag ctcgtgtcgt gagatgttgg gttaagtccc  900
gcaacgagcg caacccttga tcttagttgc catcattaag ttgggcactc taaggtgact  960
gccggtgaca aaccggagga aggtggggat gacgtcaaat catcatgccc cttatgacct  1020
gggctacaca cgtgctacaa tggacggtac aaagagctgc aagaccgcga ggtggagcta  1080
atctcataaa accgttctca gttcggattg taggctgcaa ctcgcctaca tgaagctgga  1140
atcgctagta atcgcggatc agcat                                       1165
```

```
SEQ ID NO: 7            moltype = DNA  length = 871
FEATURE                 Location/Qualifiers
source                  1..871
                        mol_type = genomic DNA
                        organism = unidentified
                        note = DP7 ITS sequence
SEQUENCE: 7
ccacnctgcg tgggcgacac gaaacaccga aaccgaacgc acgccgtcaa gcaagaaatc  60
cacaaaactt tcaacaacgg atctcttggt tctcgcatcg atgaagagcg cagcgaaatg  120
cgatacctag tgtgaattgc agccatcgtg aatcatcgag ttcttgaacg cacattgcgc  180
ccgctggtat tccggcgggc atgcctgtct gagcgtcgtt tccttcttgg agcggagctt  240
cagacctggc gggctgtctt tcgggacggc gcgcccaaag cgaggggcct tctgcgcgaa  300
ctagactgtg cgcgcggggc ggccggcgaa cttataccaa gctcgacctc agatcaggca  360
ggagtacccg ctgaacttaa gcatatcaat aagcggagga aaagaaacca acagggattg  420
ccccagtagc ggcgagtgaa gcggcaaaag ctcagatttg gaatcgcttc ggcgagttgt  480
gaattgcagg ttggcgcctc tgcggcggcg gcggtccaag tcccttggaa cagggcgcca  540
ttgagggtga gagccccgtg ggaccgtttg cctatgctct gaggcccttc tgacgagtcg  600
agttgtttgg gaatgcagct ctaagcgggt ggtaaattcc atctaaggct aaatactggc  660
gagagaccga tagcgaacaa gtactgtgaa ggaaagatga aaagcacttt gaaaagagag  720
tgaaacagca cgtgaaattg ttgaaaggga agggtattgc gcccgacatg gagcgtgcgc  780
accgctgccc ctcgtgggcg gcgctctggg cgtgctctgg gccagcatcg gtttttgccg  840
cgggagaagg gcggcgggca tgtagctctt c                                 871

SEQ ID NO: 8            moltype = DNA  length = 942
FEATURE                 Location/Qualifiers
source                  1..942
                        mol_type = genomic DNA
                        organism = unidentified
                        note = DP8 ITS sequence
SEQUENCE: 8
gttgctcgag ttcttgttta gatcttttac nataatgtgt atctttaatg aagatgtgcg  60
cttaattgcg ctgctttatt agagtgtcgc agtagaagta gtcttgcttg aatctcagtc  120
aacgtttaca cacattggag tttttttact ttaatttaat tctttctgct ttgaatcgaa  180
aggttcaagg caaaaaacaa acacaaacaa ttttatttta ttataatttt ttaaactaaa  240
ccaaaattcc taacggaaat tttaaaataa tttaaaactt tcaacaacgg atctcttggt  300
tctcgcatcg atgaaaaacg tagcgaattg cgataagtaa tgtgaattgc aaatactcgt  360
gaatcattga atttttgaac gcacattgcg cccttgagca ttctcaaggg catgcctgtt  420
tgagcgtcat ttccttctca aaagataatt ttttattttt tggttgtggg cgatactcag  480
ggttagcttg aaattggaga ctgtttcagt cttttttaat tcaacactta ncttctttgg  540
agacgctgtt ctcgctgtga tgtatttatg gatttattcg ttttacttta caagggaaat  600
ggtaatgtac cttaggcaaa gggttgcttt taatattcat caagtttgac ctcaaatcag  660
gtaggattac ccgctgaact taagcatatc aataagcgga ggaaaagaaa ccaactggga  720
ttaccttagt aacggcgagt gaagcggtaa aagctcaaat ttgaaatctg gtactttcan  780
ngcccgagtt gtaatttgta gaatttgtct ttgattaggt ccttgtctat gttccttgga  840
ncaggacgtc atanagggtg antcccnttt ggcgangana ccttttctct gtanactttt  900
tcnanagtcg agttgtttng gatgcagctc naagtggggn gg                      942

SEQ ID NO: 9            moltype = RNA  length = 1572
FEATURE                 Location/Qualifiers
source                  1..1572
                        mol_type = rRNA
                        organism = unidentified
                        note = DP9 16S rRNA sequence
SEQUENCE: 9
atgagagttt gatcttggct caggatgaac gctggcggcg tgcctaatac atgcaagtcg  60
aacgaacttc cgttaattga ttatgacgta cttgtactga ttgagatttt aacacgaagt  120
gagtggcgaa cgggtgagta acacgtgggt aacctgccca gaagtagggg ataacacctg  180
gaaacagatg ctaataccgt ataacagaga aaaccgcatg gttttctttt aaaagatggc  240
tctgctatca cttctggatg gacccgcggc gtattagcta gttggtgagg caaaggctca  300
ccaaggcagt gatacgtagc cgacctgaga gggtaatcgg ccacattggg actgagacac  360
ggcccagact cctacgggag gcagcagtag ggaatcttcc acaatggacg caagtctgat  420
ggagcaacgc cgcgtgagtg aagaagggtt tcggctcgta aagctctgtt gttaaagaag  480
aacgtgggta agagtaactg tttacccagt gacggtattt aaccagaaag ccacggctaa  540
ctacgtgcca gcagccgcgg taatacgtag gtggcaagcg ttatccggat ttattgggcg  600
taaagcgagc gcaggcggtc ttttaagtct aatgtgaaag ccttcggctc aaccgaagaa  660
gtgcattgga aactgggaga cttgagtgca gaagaggaca gtggaactcc atgtgtagcg  720
gtgaaatgcg tagatatatg gaagaacacc agtggcgaag gcggctgtct ggtctgcaac  780
tgacgctgag gctcgaaagc atgggtagcg aacaggatta gataccctgg tagtccatgc  840
cgtaaacgat gattactaag tgttggaggg tttccgccct tcagtgctgc agctaacgca  900
ttaagtaatc cgcctgggga gtacgaccgc aaggttgaaa ctcaaaagaa ttgacggggg  960
cccgcacaag cggtggagca tgtggtttaa ttcgaagcta cgcgaagaac cttaccaggt  1020
cttgacatct tctgacagtc taagagatta gaggttccct tcggggacag aatgacaggt  1080
ggtgcatggt tgtcgtcagc tcgtgtcgtg agatgttggg ttaagtcccg caacgagcgc  1140
aacccttatt actagttgcc agcattaagt tgggcactct agtgagactg ccggtgacaa  1200
accggaggaa ggtggggacg acgtcaaatc atcatgcccc ttatgacctg ggctacacac  1260
gtgctacaat ggatggtaca acgagtcgcg agaccgcgag gttaagctaa tctcttaaaa  1320
ccattctcag ttcggactgt aggctgcaac tcgcctacac gaagtcggaa tcgctagtaa  1380
tcgcggatca gcatgccgcg gtgaatacgt tcccgggcct tgtacacacc gcccgtcaca  1440
```

-continued

```
ccatgagagt ttgtaacacc caaagccggt ggggtaacct tttaggagct agccgtctaa  1500
ggtgggacag atgattaggg tgaagtcgta acaaggtagc cgtaggagaa cctgcggctg  1560
gatcacctcc tt                                                      1572

SEQ ID NO: 10           moltype = RNA  length = 1300
FEATURE                 Location/Qualifiers
source                  1..1300
                        mol_type = rRNA
                        organism = unidentified
                        note = DP10 16S rRNA sequence
SEQUENCE: 10
cagatagttg gtgaggtaac ggctcaccaa ggcaacgatg cgtagccgac ctgagagggt  60
gatcggccac actgggactg agacacggcc cagactccta cgggaggcag cagtagggaa  120
tcttccgcaa tggacgaaag tctgacggag caacgccgcg tgagtgatga aggttttcgg  180
atcgtaaagc tctgttgtta gggaagaaca agtgccgttc aaatagggcg gcaccttgac  240
ggtacctaac cagaaagcca cggctaacta cgtgccagca gccgcggtaa tacgtaggtg  300
gcaagcgttg tccggaatta ttgggcgtaa agggctcgca ggcggtttct taagtctgat  360
gtgaaagccc ccggctcaac cggggagggt cattggaaac tggggaactt gagtgcagaa  420
gaggagagtg gaattccacg tgtagcggtg aaatgcgtag agatgtggag gaacaccagt  480
ggcgaaggcg actctctggt ctgtaactga cgctgaggag cgaaagcgtg gggagcgaac  540
aggattagat accctggtag tccacgccgt aaacgatgag tgctaagtgt tagggggttt  600
ccgcccctta gtgctgcagc taacgcatta agcactccgc ctggggagta cggtcgcaag  660
actgaaactc aaaggaattg acgggggccc gcacaagcgg tggagcatgt ggtttaattc  720
gaagcaacgc gaagaacctt accaggtctt gacatcctct gacaatccta gagataggac  780
gtccccttcg ggggcagagt gacaggtggt gcatggttgt cgtcagctcg tgtcgtgaga  840
tgttgggtta agtcccgcaa cgagcgcaac ccttgatctt agttgccagc attcagttgg  900
gcactctaag gtgactgccg gtgacaaacc ggaggaaggt ggggatgacg tcaaatcatc  960
atgcccctta tgacctgggc tacacacgtg ctacaatgga cagaacaaag ggcagcgaaa  1020
ccgcgaggtt aagccaatcc cacaaatctg ttctcagttc ggatcgcagt ctgcaactcg  1080
actgcgtgaa gctggaatcg ctagtaatcg cggatcagca tgccgcggtg aatacgttcc  1140
cgggccttgt acacaccgcc cgtcacacca cgagagtttg taacacccga agtcggtgag  1200
gtaacctttt aggagccagc cgccgaaggt gggacagatg attggggtga agtcgtaaca  1260
aggtagccgt atcggaaggt gcggctggat cacctccttt                        1300

SEQ ID NO: 11           moltype = RNA  length = 1419
FEATURE                 Location/Qualifiers
source                  1..1419
                        mol_type = rRNA
                        organism = unidentified
                        note = DP11 16S rRNA sequence
SEQUENCE: 11
tgaagagttt gatcatggct cagattgaac gctggcggca ggcctaacac atgcaagtcg  60
agcggtagag agaagcttgc ttctcttgag agcggcggac gggtgagtaa tgcctaggaa  120
tctgcctggt agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggcgac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggttgta gattaatact ctgcaatttt gacgttaccg  480
acagaataag caccggctaa ctctgtgcca gcagccgcgg taatacagag ggtgcaagcg  540
ttaatcggaa ttactgggcg taaagcgcgc gtaggtggtt cgttaagttg gatgtgaaag  600
ccccgggctc aacctgggaa ctgcattcaa aactgacgag ctagagtatg gtagagggtg  660
gtggaatttc ctgtgtagcg gtgaaatgcg tagatatagg aaggaacacc agtggcgaag  720
gcgaccacct ggactgatac tgacactgag gtgcgaaagc gtggggagca aacaggatta  780
gataccctgg tagtccacgc cgtaaacgat gtcaactagc cgttggaatc cttgagattt  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc cagagatgga tgggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgttatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac atcccacacg aattgcttg                         1419

SEQ ID NO: 12           moltype = RNA  length = 1520
FEATURE                 Location/Qualifiers
source                  1..1520
                        mol_type = rRNA
                        organism = unidentified
                        note = DP12 16S rRNA sequence
SEQUENCE: 12
tacggagagt ttgatcctgg ctcaggatga acgctggcgg cgtgcttaac acatgcaagt  60
cgaacggtga agccaagctt gcttggtgga tcagtggcga acgggtgagt aacacgtgag  120
caacctgccc tggactctgg gataagcgct ggaaacggcg tctaatactg gatatgagcc  180
ttcatcgcat ggtgggggtt ggaaagattt tttggtctgg gatgggctcg cggcctatca  240
gcttgttggt gaggtaatgg ctcaccaagg cgtcgacggg tagccggcct gagagggtga  300
ccggccacac tgggactgag acacggccca gactcctacg ggaggcagca gtggggaata  360
```

-continued

```
ttgcacaatg ggcgaaagcc tgatgcagca acgccgcgtg agggatgacg gccttcgggt  420
tgtaaacctc ttttagcagg gaagaagcga aagtgacggt acctgcagaa aaagcgccgg  480
ctaactacgt gccagcagcc gcggtaatac gtagggcgca agcgttatcc ggaattattg  540
ggcgtaaaga gctcgtaggc ggtttgtcgc gtctgctgtg aaatcccgag gctcaacctc  600
gggcctgcag tgggtacggg cagactagag tgcggtaggg gagattggaa ttcctggtgt  660
agcggtggaa tgcgcagata tcaggaggaa caccgatggc gaaggcagat ctctgggccg  720
taactgacgc tgaggagcga aagggtgggg agcaaacagg cttagatacc ctggtagtcc  780
accccgtaaa cgttgggaac tagttgtggg gaccattcca cggtttccgt gacgcagcta  840
acgcattaag ttccccgcct ggggagtacg gccgcaaggc taaaactcaa aggaattgac  900
ggggacccgc acaagcggcg gagcatgcgg attaattcga tgcaacgcga agaaccttac  960
caaggcttga catacaccag aacgggccag aaatggtcaa ctctttggac actggtgaac  1020
aggtggtgca tggttgtcgt cagctcgtgt cgtgagatgt tgggttaagt cccgcaacga  1080
gcgcaaccct cgttctatgt tgccagcacg taatggtggg aactcatggg atactgccgg  1140
ggtcaactcg gaggaaggtg gggatgacgt caaatcatca tgccccttat gtcttgggct  1200
tcacgcatgc tacaatggcc ggtacaaagg gctgcaatac cgtgaggtgg agcgaatccc  1260
aaaaagccgg tcccagttcg gattgaggtc tgcaactcga cctcatgaag tcggagtcgc  1320
tagtaatcgc agatcagcaa cgctgcggtg aatacgttcc cgggtcttgt acacaccgcc  1380
cgtcaagtca tgaaagtcgg taacacctga agccggtggc ccaacccttg tggagggagc  1440
cgtcgaaggt gggatcggta attaggacta agtcgtaaca aggtagccgt accggaaggt  1500
gcggctggat cacctccttt                                             1520

SEQ ID NO: 13          moltype = RNA  length = 1457
FEATURE                Location/Qualifiers
source                 1..1457
                       mol_type = rRNA
                       organism = unidentified
                       note = DP13 16S rRNA sequence
SEQUENCE: 13
agttagcggc ggacgggtga gtaacacgtg ggtaacctgc ctataagact gggataactc  60
cgggaaaccg gggctaatac cggataacat tttgcaccgc atggtgcgaa attgaaaggc  120
ggcttcggct gtcacttata gatggacctg cggcgcatta gctagttggt gaggtaacgg  180
ctcaccaagg cgacgatgcg tagccgacct gagagggtga tcggccacac tgggactgag  240
acacggccca gactcctacg ggaggcagca gtagggaatc ttccgcaatg gacgaaagtc  300
tgacggagca acgccgcgtg aacgatgaag gctttcgggt cgtaaagttc tgttgttagg  360
gaagaacaag tgctagttga ataagctggc accttgacgg tacctaacca gaaagccacg  420
gctaactacg tgccagcagc cgcggtaata cgtaggtggc aagcgttatc cggaattatt  480
gggcgtaaag cgcgcgcagg tggtttctta agtctgatgt gaaagcccac ggctcaaccg  540
tggagggtca ttggaaactg ggagacttga gtgcagaaga ggaaagtgga attccatgtg  600
tagcggtgaa atgcgtagag atatggagga acaccagtgg cgaaggcgac tttctggtct  660
gcaactgaca ctgaggcgcg aaagcgtggg gagcaaacag gattagatac cctggtagtc  720
cacgccgtaa acgatgagtg ctaagtgtta gagggtttcc gccctttagt gctgaagtta  780
acgcattaag cactccgcct ggggagtacg gccgcaaggc tgaaactcaa aggaattgac  840
gggggcccgc acaagcggtg gagcatgtgg tttaattcga agcaacgcga agaaccttac  900
caggtcttga catcctctga aaaccctaga gatagggctt ccccttcggg ggcagagtga  960
caggtggtgc atggttgtcg tcagctcgtg tcgtgagatg ttgggttaag tcccgcaacg  1020
agcgcaaccc ttgatcttag ttgccatcat taagttgggc actctaaggt gactgccggt  1080
gacaaaccgg aggaaggtgg ggatgacgtc aaatcatcat gccccttatg acctgggcta  1140
cacacgtgct acaatggacg gtacaaagag tcgcaagacc gcgaggtgga gctaatctca  1200
taaaaccgtt ctcagttcgg attgtaggct gcaactcgcc tacatgaagc tggaatcgct  1260
agtaatcgcg gatcagcatg ccgcggtgaa tacgttcccg ggccttgtac acaccgcccg  1320
tcacaccacg agagtttgta acacccgaag tcggtggggt aaccttttgg agccagccgc  1380
ctaaggtggg acagatgatt ggggtgaagt cgtaacaagg tagccgtatc ggaaggtgcg  1440
gctggatcac ctccttt                                                1457

SEQ ID NO: 14          moltype = RNA  length = 1526
FEATURE                Location/Qualifiers
source                 1..1526
                       mol_type = rRNA
                       organism = unidentified
                       note = DP1416S rRNA sequence
SEQUENCE: 14
tacggagagt ttgatcctgg ctcaggatga acgctggcgg cgtgcttaac acatgcaagt  60
cgaacgatga cttctgtgct tgcacagaat gattagtggc gaacgggtga gtaacacgtg  120
agtaacctgc ccttaacttc gggataagcc tgggaaaccg ggtctaatac cggatacgac  180
ctcctggcgc atgccatggt ggtggaaagc tttagcggtt ttggatggac tcgcggccta  240
tcagcttgtt ggttggggta atggcccacc aaggcgacga cgggtagccg gcctgagagg  300
gtgaccggcc acactgggac tgagacacgg cccagactcc tacgggaggc agcagtgggg  360
aatattgcac aatgggcgaa agcctgatgc agcgacgccg cgtgagggat gacggccttc  420
gggttgtaaa cctctttcag cagggaagaa gcgaaagtga cggtacctgc agaagaagcg  480
ccggctaact acgtgccagc agccgcggta atacgtaggg cgcaagcgtt atccggaatt  540
attgggcgta aagagctcgt aggcggtttg tcgcgtctgc tgtgaaagcc cggggctcaa  600
ccccgggtct gcagtgggta cgggcagact agagtgcagt aggggagact ggaattcctg  660
gtgtagcggt gaaatgcgca gatatcagga ggaacaccga tggcgaaggc aggtctctgg  720
gctgtaactg acgctgagga gcgaaagcat ggggagcgaa caggattaga taccctggta  780
gtccatgccg taaacgttgg gcactaggtg tgggggacat tccacgtttt ccgcgccgta  840
gctaacgcat taagtgcccc gcctggggag tacggccgca aggctaaaac tcaaaggaat  900
tgacgggggc ccgcacaagc ggcggagcat gcggattaat tcgatgcaac gcgaagaacc  960
ttaccaaggc ttgacatgaa ccggtaagac ctggaaacag gtcccccact tgtggccggt  1020
ttacaggtgg tgcatggttg tcgtcagctc gtgtcgtgag atgttgggtt aagtcccgca  1080
```

```
acgagcgcaa ccctcgttct atgttgccag cgggttatgc cggggactca taggagactg  1140
ccggggtcaa ctcggaggaa ggtggggacg acgtcaaatc atcatgcccc ttatgtcttg  1200
ggcttcacgc atgctacaat ggccggtaca aagggttgcg atactgtgag gtggagctaa  1260
tcccaaaaag ccggtctcag ttcggattga ggtctgcaac tcgacctcat gaagttggag  1320
tcgctagtaa tcgcagatca gcaacgctgc ggtgaatacg ttcccgggcc ttgtacacac  1380
cgcccgtcaa gtcacgaaag ttggtaacac ccgaagccgg tggcctaacc ccttgtggga  1440
gggagccgtc gaaggtggga ccggcgattg ggactaagtc gtaacaaggt agccgtaccg  1500
gaaggtgcgg ctggatcacc tccttt                                      1526

SEQ ID NO: 15          moltype = RNA  length = 1520
FEATURE                Location/Qualifiers
source                 1..1520
                       mol_type = rRNA
                       organism = unidentified
                       note = DP15 16S rRNA sequence
SEQUENCE: 15
tacggagagt ttgatcctgg ctcaggacga acgctggcgg cgtgcttaac acatgcaagt  60
cgaacgatga tcaggagctt gctcctgtga ttagtggcga acgggtgagt aacacgtgag  120
taacctgccc ctgactctgg gataagcgtt ggaaacgacg tctaatactg gatatgatca  180
ctggccgcat ggtctggtgg tggaaagatt ttttggttgg ggatggactc gcggcctatc  240
agcttgttgg tgaggtaatg gctcaccaag gcgacgacgg gtagccggcc tgagagggtg  300
accggccaca ctgggactga gacacggccc agactcctac gggaggcagc agtggggaat  360
attgcacaat gggcgaaagc ctgatgcagc aacgccgcgt gagggatgac ggccttcggg  420
ttgtaaacct cttttagtag ggaagaagcg aaagtgacgg tacctgcaga aaaagcaccg  480
gctaactacg tgccagcagc cgcggtaata cgtagggtgc aagcgttgtc cggaattatt  540
gggcgtaaag agctcgtagg cggtttgtcg cgtctgctgt gaaatcccga ggctcaacct  600
cgggcttgca gtgggtacgg gcagactaga gtgcggtagg ggagattgga attcctggtg  660
tagcggtgga atgcgcagat atcaggagga acaccgatgg cgaaggcaga tctctgggcc  720
gtaactgacg ctgaggagcg aaagcgtggg gagcgaacag gattagatac cctggtagtc  780
cacgccgtaa acgttgggcg ctagatgtag ggacctttcc acggtttctg tgtcgtagct  840
aacgcattaa gcgccccgcc tggggagtac ggccgcaagg ctaaaactca aaggaattga  900
cgggggcccg cacaagcggc ggagcatgcg gattaattcg atgcaacgcg aagaacctta  960
ccaaggcttg acatacaccg gaaacggcca gagatggtcg cccccttgtg gtcggtgtac  1020
aggtggtgca tggttgtcgt cagctcgtgt cgtgagatgt tgggttaagt cccgcaacga  1080
gcgcaaccct cgttctatgt tgccagcgcg ttatggcggg gactcatagg agactgccgg  1140
ggtcaactcg gaggaaggtg gggatgacgt caaatcatca tgccccttat gtcttgggct  1200
tcacgcatgc tacaatggcc ggtacaaagg gctgcgatac cgtaaggtgg agcgaatccc  1260
aaaaagccgg tctcagttcg gattgaggtc tgcaactcga cctcatgaag tcggagtcgc  1320
tagtaatcgc agatcagcaa cgctgcggtg aatacgttcc cgggccttgt acacaccgcc  1380
cgtcaagtca tgaaagtcgg taacacccga agccggtggc ctaacccttg tggaaggagc  1440
cgtcgaaggt gggatcggtg attaggacta agtcgtaaca aggtagccgt accggaaggt  1500
gcggctggat cacctccttt                                             1520

SEQ ID NO: 16          moltype = RNA  length = 1368
FEATURE                Location/Qualifiers
source                 1..1368
                       mol_type = rRNA
                       organism = unidentified
                       note = DP16 16S rRNA sequence
SEQUENCE: 16
gcacttcatc gtggtgcacc gtgaagggtc tttgggcgtt ttacacatgc aagcaagtgt  60
tctataattt aggttatgga acagccaaat ggtcagtaca gctcagtcct aggcgatgga  120
ctccgtaaaa cggggacaga ctatccttta ataattaata ggtttattat ttcaataata  180
atctctagga agggatatac atatatcctt attagtctaa aggttaataa accgccttag  240
tcaggactga gttctcaaca gctacgggtt aaaccccagg caacgacgag taggggatag  300
tgatagctac aaccccgaca ctggccgcaa gccagggtac ttaagtacgc agcagtgaag  360
aatcctcggc aatgcatcgc aattaccggt gacccaatat aaaataatat cagggaggta  420
gtaggtgtga ccgggtgacc caaagacgag tagtgacata agttattatt cgcgtatgtc  480
gaacatgata gtgacgtgtt caacatcaag ccccgtccaa cctctgtgcc agcagtcgcg  540
gtaaaacagg aggggcagct cttatggtca tgaatgggcg tatagggcac gcagccagtt  600
agtaaaagct tgaatattta ttttttttaaa aagaatgttt gagaggctat gagtttttat  660
aaagtgtacc cacgacacca gacttagggc tgagatccta tgaagtctgg gggcggtcct  720
ttagggtgca ttgtaaaaac tgacggtaag gtgcgacagc tgggataccg aagcggagta  780
gagcccgcct agccccagcc gtaaacgata ggggccgttg ttgactacgg ttttcaataa  840
ggctaacgcc tgagcccctc gcctgtaggg tatagccgca aggccgacat attaacgatg  900
agaccgctgg tgagcaaacg ggtgcggggc atgctgttca atcagacagt acgctgacaa  960
ccttaccact ccttgaatct tttagattat atttctaaaa tgacaggtgc tgcatggccg  1020
tcgtcagttc gtggtcgtga gtcgtccggt tgagtccatg aacgaacgca gacccgtctg  1080
tatactcagt gaaaagaaat ttagctgaac tatacagttg tacttctata aaaggtacct  1140
gtacgggatt atgacaggtc gtcatggcct ttatggagtg ggctacaggc gtgccacacg  1200
agccgtttta acgagttcct catttttatg aataaggtct cttaatcacg gctagtatac  1260
ggatcgtagg ctgtaactcg cctacgtgaa gtcggagtcc cgagtaatcg ccgatcatca  1320
cgcggcggtg aatctacact ctcactgggg tactaaccgc tcgtcacg              1368

SEQ ID NO: 17          moltype = RNA  length = 898
FEATURE                Location/Qualifiers
source                 1..898
                       mol_type = rRNA
                       organism = unidentified
```

```
                         note = DP17 16S rRNA sequence
SEQUENCE: 17
gtgattgacg ttactcgcag aagaagcacc ggctaactcc gtgccagcag ccgcggtaat  60
acggagggtg caagcgttaa tcggaattac tgggcgtaaa gcgcacgcag gcggtttgtt  120
aagtcagatg tgaaatcccc gcgcttaacg tgggaactgc atttgaaact ggcaagctag  180
agtcttgtag aggggggtag aattccaggt gtagcggtga aatgcgtaga gatctggagg  240
aataccggtg gcgaaggcgg ccccctggac aaagactgac gctcaggtgc gaaagcgtgg  300
ggagcaaaca ggattagata ccctggtagt ccacgctgta aacgatgtcg acttggaggt  360
tgtgcccttg aggcgtggct tccggagcta acgcgttaag tcgaccgcct ggggagtacg  420
gccgcaaggt taaaactcaa atgaattgac gggggcccgc acaagcggtg gagcatgtgg  480
tttaattcga tgcaacgcga agaaccttac ctactcttga catccacgga attcgccaga  540
gatggcttag tgccttcggg aaccgtgaga caggtgctgc atggctgtcg tcagctcgtg  600
ttgtgaaatg ttgggttaag tcccgcaacg agcgcaaccc ttatcctttg ttgccagcac  660
gtaatggtgg gaactcaaag gagactgccg gtgataaacc ggaggaaggt ggggatgacg  720
tcaagtcatc atggccctta cgagtagggc tacacacgtg ctacaatggc atatacaaag  780
agaagcgaac tcgcgagagc aagcggacct cataaagtat gtcgtagtcc ggattggagt  840
ctgcaactcg actccatgaa gtcggaatcg ctagtaatcg tagatcagaa tgctacgg    898

SEQ ID NO: 18            moltype = RNA  length = 1532
FEATURE                  Location/Qualifiers
source                   1..1532
                         mol_type = rRNA
                         organism = unidentified
                         note = DP18 16S rRNA sequence
SEQUENCE: 18
tgaagagttt gatcatggct cagattgaac gctggcggca ggcctaacac atgcaagtcg  60
agcggatgaa aggagcttgc tcctggattc agcggcggac gggtgagtaa tgcctaggaa  120
tctgcctggt agtgggggac aacgtttcga aaggaacgct aataccgcat acgtcctacg  180
ggagaaagca ggggaccttc gggccttgcg ctatcagatg agcctaggtc ggattagcta  240
gttggtgagg taatggctca ccaaggcgac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggcagta aattaatact ttgctgtttt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg aatgtgaaat  600
ccccgggctc aacctgggaa ctgcatccaa aactggcaag ctagagtatg gtagagggtg  660
gtggaatttc ctgtgtagcg gtgaaatgcg tagatatagg aaggaacacc agtggcgaag  720
gcgaccacct ggactgatac tgacactgag gtgcgaaagc gtggggagca aacaggatta  780
gataccctgg tagtccacgc cgtaaacgat gtcaactagc cgttgggagc cttgagctct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc cagagatgga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgttatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac accatgggag tgggttgcac cagaagtagc tagtctaacc  1440
ttcgggagga cggttaccac ggtgtgattc atgactgggg tgaagtcgta acaaggtagc  1500
cgtaggggaa cctgcggctg gatcacctcc tt                               1532

SEQ ID NO: 19            moltype = RNA  length = 1520
FEATURE                  Location/Qualifiers
source                   1..1520
                         mol_type = rRNA
                         organism = unidentified
                         note = DP19 16S rRNA sequence
SEQUENCE: 19
tacggagagt ttgatcctgg ctcaggacga acgctggcgg cgtgcttaac acatgcaagt  60
cgaacgatga tgcccagctt gctgggtgga ttagtggcga acgggtgagt aacacgtgag  120
taacctgccc ctgactctgg gataagcgtt ggaaacgacg tctaatactg gatacgactg  180
ccggccgcat ggtctggtgg tggaaagatt ttttggttgg ggatggactc gcggcctatc  240
agcttgttgg tgaggtaatg gctcaccaag gcgacgacgg gtagccggcc tgagagggtg  300
accggccaca ctgggactga gacacggccc agactcctac gggaggcagc agtggggaat  360
attgcacaat gggcgaaagc ctgatgcagc aacgccgcgt gagggatgac ggccttcggg  420
ttgtaaacct cttttagtag ggaagaagcg aaagtgacgg tacctgcaga aaaagcaccg  480
gctaactacg tgccagcagc cgcggtaata cgtagggtgc aagcgttgtc cggaattatt  540
gggcgtaaag agctcgtagg cggtttgtcg cgtctgctgt gaaatcccga ggctcaacct  600
cgggcttgca gtgggtacgg gcagactaga gtgcggtagg ggagattgga attcctggtg  660
tagcggtgga atgcgcagat atcaggagga acaccgatgg cgaaggcaga tctctgggcc  720
gtaactgacg ctgaggagcg aaagcgtggg gagcgaacag gattagatac cctggtagtc  780
cacgccgtaa acgttgggcg ctagatgtag ggacctttcc acggtttctg tgtcgtagct  840
aacgcattaa gcgccccgcc tggggagtac ggccgcaagg ctaaaactca aaggaattga  900
cgggggcccg cacaagcggc ggagcatgcg gattaattcg atgcaacgcg aagaacctta  960
ccaaggcttg acatacaccg gaaacggcca gagatggtcg cccccttgtg gtcggtgtac  1020
aggtggtgca tggttgtcgt cagctcgtgt cgtgagatgt tgggttaagt cccgcaacga  1080
gcgcaaccct cgttctatgt tgccagcgcg ttatggcggg gactcatagg agactgccgg  1140
ggtcaactcg gaggaaggtg gggatgacgt caaatcatca tgccccttat gtcttgggct  1200
```

-continued

```
tcacgcatgc tacaatggcc ggtacaaagg gctgcgatac cgtaaggtgg agcgaatccc  1260
aaaaagccgg tctcagttcg gattgaggtc tgcaactcga cctcatgaag tcggagtcgc  1320
tagtaatcgc agatcagcaa cgctgcggtg aatacgttcc cgggccttgt acacaccgcc  1380
cgtcaagtca tgaaagtcgg taacacccga agccggtggc ctaacccttg tggaaggagc  1440
cgtcgaaggt gggatcggtg attaggacta agtcgtaaca aggtagccgt accggaaggt  1500
gcggctggat cacctccttt                                              1520

SEQ ID NO: 20          moltype = RNA  length = 1543
FEATURE                Location/Qualifiers
source                 1..1543
                       mol_type = rRNA
                       organism = unidentified
                       note = DP20 16S rRNA sequence
SEQUENCE: 20
tgaagagttt gatcctggct cagagtgaac gctggcggta ggcctaacac atgcaagtcg  60
aacggcagca cagtaagagc ttgctcttat gggtggcgag tggcggacgg gtgaggaata  120
catcggaatc tacctttcg  tgggggataa cgtagggaaa cttacgctaa taccgcatac  180
gaccttcggg tgaaagcagg ggaccttcgg gccttgcgcg gatagatgag ccgatgtcgg  240
attagctagt tggcggggta aaggcccacc aaggcgacga tccgtagctg gtctgagagg  300
atgatcagcc acactggaac tgagacacgg tccagactcc tacgggaggc agcagtgggg  360
aatattggac aatgggcgca agcctgatcc agccataccg cgtgggtgaa gaaggccttc  420
gggttgtaaa gcccttttgt tgggaaagaa aagcagtcgg ctaatacccg gttgttctga  480
cggtacccaa agaataagca ccggctaact tcgtgccagc agccgcggta atacgaaggg  540
tgcaagcgtt actcggaatt actgggcgta aagcgtgcgt aggtggttgt ttaagtctgt  600
tgtgaaagcc ctgggctcaa cctgggaatt gcagtggata ctgggcgact agagtgtggt  660
agagggtagt ggaattcccg gtgtagcagt gaaatgcgta gagatcggga ggaacatcca  720
tggcgaaggc agctacctgg accaacactg acactgaggc acgaaagcgt ggggagcaaa  780
caggattaga taccctggta gtccacgccc taaacgatgc gaactggatg ttgggtgcaa  840
tttggcacgc agtatcgaag ctaacgcgtt aagttcgccg cctggggagt acggtcgcaa  900
gactgaaact caaaggaatt gacgggggcc cgcacaagcg gtggagtatg tggtttaatt  960
cgatgcaacg cgaagaacct tacctggtct tgacatgtcg agaactttcc agagatggat  1020
tggtgccttc gggaactcga acacaggtgc tgcatggctg tcgtcagctc gtgtcgtgag  1080
atgttgggtt aagtcccgca acgagcgcaa cccttgtcct tagttgccag cacgtaatgg  1140
tgggaactct aaggagaccg ccggtgacaa accggaggaa ggtggggatg acgtcaagtc  1200
atcatggccc ttacgaccag ggctacacac gtactacaat ggtagggaca gagggctgca  1260
aacccgcgag ggcaagccaa tcccagaaac cctatctcag tccggattgg agtctgcaac  1320
tcgactccat gaagtcggaa tcgctagtaa tcgcagatca gcattgctgc ggtgaatacg  1380
ttcccgggcc ttgtacacac cgcccgtcac accatgggag tttgttgcac cagaagcagg  1440
tagcttaacc ttcgggaggg cgcttgccac ggtgtggccg atgactgggg tgaagtcgta  1500
acaaggtagc cgtatcggaa ggtgcggctg gatcacctcc ttt                    1543

SEQ ID NO: 21          moltype =   length =
SEQUENCE: 21
000

SEQ ID NO: 22          moltype = RNA  length = 1539
FEATURE                Location/Qualifiers
source                 1..1539
                       mol_type = rRNA
                       organism = unidentified
                       note = DP22 16S rRNA sequence
SEQUENCE: 22
ttgaagagtt tgatcatggc tcagattgaa cgctggcggc aggcctaaca catgcaagtc  60
gagcggcagc gggaagtagc ttgctacttt gccggcgagc ggcggacggg tgagtaatgt  120
ctgggaaact gcctgatgga gggggataac tactggaaac ggtagctaat accgcatgac  180
ctcgcaagag caaagtgggg gaccttcggg cctcacgcca tcggatgtgc ccagatggga  240
ttagctagta ggtgaggtaa tggctcacct aggcgacgat ccctagctgg tctgagagga  300
tgaccagcca cactggaact gagacacggt ccagactcct acgggaggca gcagtgggga  360
atattgcaca atgggcgcaa gcctgatgca gccatgccgc gtgtgtgaag aaggccttag  420
ggttgtaaag cactttcagc gaggaggaag ggttcagtgt taatagcact gaacattgac  480
gttactcgca gaagaagcac cggctaactc cgtgccagca gccgcggtaa tacggagggt  540
gcaagcgtta atcggaatta ctgggcgtaa agcgcacgca ggcggtttgt taagtcagat  600
gtgaaatccc cgagcttaac ttgggaactg catttgaaac tggcaagcta gagtcttgta  660
gaggggggta gaattccagg tgtagcggtg aaatgcgtag agatctggag gaataccggt  720
ggcgaaggcg gccccctgga caaagactga cgctcaggtg cgaaagcgtg gggagcaaac  780
aggattagat accctggtag tccacgctgt aaacgatgtc gacttggagg ttgtgccctt  840
gaggcgtggc ttccggagct aacgcgttaa gtcgaccgcc tggggagtac ggccgcaagg  900
ttaaaactca aatgaattga cgggggcccg cacaagcggt ggagcatgtg gtttaattcg  960
atgcaacgcg aagaacctta cctactcttg acatccagag aattcgctag agatagctta  1020
gtgccttcgg gaactctgag acaggtgctg catggctgtc gtcagctcgt gttgtgaaat  1080
gttgggttaa gtcccgcaac gagcgcaacc cttatccttt gttgccagcg agtaatgtcg  1140
ggaactcaaa ggagactgcc ggtgataaac cggaggaagg tggggatgac gtcaagtcat  1200
catggccctt acgagtaggg ctacacacgt gctacaatgg catatacaaa gagaagcaaa  1260
ctcgcgagag caagcggacc tcataaagta tgtcgtagtc cggattggag tctgcaactc  1320
gactccatga agtcggaatc gctagtaatc gtagatcaga atgctacggt gaatacgttc  1380
ccgggccttg tacacaccgc ccgtcacacc atgggagtgg gttgcaaaag aagtaggtag  1440
cttaaccttc gggagggcgc ttaccacttt gtgattcatg actggggtga agtcgtaaca  1500
aggtaaccgt aggggaacct gcggttggat cacctcctt                         1539
```

-continued

```
SEQ ID NO: 23           moltype = RNA  length = 1536
FEATURE                 Location/Qualifiers
source                  1..1536
                        mol_type = rRNA
                        organism = unidentified
                        note = DP23 16S rRNA sequence
SEQUENCE: 23
ttgaagagtt tgatcatggc tcagattgaa cgctggcggc aggcctaaca catgcaagtc  60
gaacggtagc acagagagct tgctcttggg tgacgagtgg cggacgggtg agtaatgtct  120
gggaaactgc ccgatggagg gggataacta ctggaaacgg tagctaatac cgcataacgt  180
cttcggacca aagtggggga ccttcgggcc tcacaccatc ggatgtgccc agatgggatt  240
agctagtagg tggggtaatg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagcgg ggaggaaggc gatacggtta ataaccgtgt cgattgacgt  480
tacccgcaga agaagcaccg gctaactccg tgccagcagc cgcggtaata cggagggtgc  540
aagcgttaat cggaattact gggcgtaaag cgcacgcagg cggtctgtca agtcagatgt  600
gaaatccccg ggcttaacct gggaactgca tttgaaactg gcaggcttga gtctcgtaga  660
ggggggtaga attccaggtg tagcggtgaa atgcgtagag atctggagga ataccggtgg  720
cgaaggcggc cccctggacg aagactgacg ctcaggtgcg aaagcgtggg gagcaaacag  780
gattagatac cctggtagtc cacgctgtaa acgatgtcga cttggaggtt gtgcccttga  840
ggcgtggctt ccggagctaa cgcgttaagt cgaccgcctg gggagtacgg ccgcaaggtt  900
aaaactcaaa tgaattgacg ggggcccgca caagcggtgg agcatgtggt ttaattcgat  960
gcaacgcgaa gaaccttacc tggccttgac atccacagaa ttcggcagag atgccttagt  1020
gccttcggga actgtgagac aggtgctgca tggctgtcgt cagctcgtgt tgtgaaatgt  1080
tgggttaagt cccgcaacga gcgcaaccct tatcctttgt tgccagcgat tcggtcggga  1140
actcaaagga gactgccggt gataaaccgg aggaaggtgg ggatgacgtc aagtcatcat  1200
ggcccttacg gccagggcta cacacgtgct acaatggcgc atacaaagag aagcgacctc  1260
gcgagagcaa gcggacctca taaagtgcgt cgtagtccgg atcggagtct gcaactcgac  1320
tccgtgaagt cggaatcgct agtaatcgta gatcagaatg ctacggtgaa tacgttcccg  1380
ggccttgtac acaccgcccg tcacaccatg ggagtgggtt gcaaaagaag taggtagctt  1440
aaccttcggg agggcgctta ccactttgtg attcatgact ggggtgaagt cgtaacaagg  1500
taaccgtagg ggaacctgcg gttggatcac ctcctt                            1536

SEQ ID NO: 24           moltype = RNA  length = 1316
FEATURE                 Location/Qualifiers
source                  1..1316
                        mol_type = rRNA
                        organism = unidentified
                        note = DP24 16S rRNA sequence
SEQUENCE: 24
agcatttgat tatggtgctt actgattgct atctaggggt ttaacacatg ctagtcaatg  60
atcttttaga ttatggcgta cgggctagga atacttagaa tgataactct atgatcgcag  120
taatagcgta aaaggtataa taccgcatag aggttcgctt cgtatctcaa taggtagttg  180
gtgaggtaaa gctcaacaag ccgatgatga gtaatattgg atgaaagtct taaatatagc  240
agtggaaatg aaaaagtcca ccgttattta ttaacgcagc agtggagaat cgtcgtaatg  300
tgcagtattc atttatggat aagcatgaac gcgctaccta gattcggata ggagatagca  360
tcttctaccg ataaaagaac ttagaataat gatctagttc tcattagtgg gtgacaatcg  420
ccgtgccagc atcagcggta aaacggcttc cgcaagcaat agtaatttaa attggtgtaa  480
agggtacgta gccggcctta ttaggctaga gttagatacg ggtaagtaca atacttggag  540
tagggctgat atcttatgat cccaagggga gtgctaaagg cgaaggcaac ttactggtaa  600
taactgacgg tgaggtacga aggtcagggc atggaaagag attagatacc tcattactcc  660
tgacagtaaa cgatgtagat taaagattgg aataattctg tcttaacgct aacgcattaa  720
atctaccacc tgtagagtat agtcgcaagg ccgaaataca aataattaga cggctctaga  780
gcaaacggag tgaagcatgt tatttaatac gataacccgc gtaaaatctt accagttctt  840
gaatcttaga caggtgttgc atggttgtcg tcagctcgtg ctaatggtgt ctggttaatt  900
ccaaataacg agcgcaatcc ttacttctag ttttctagga gtctccattt gacatacgtg  960
tcaatggttt aaggaatatg acaaaccctc atggccctta tggactgggc aatagacgtg  1020
ccacaagaat ctagacaaaa tgacgcgaaa tggtaacaat gagctaatca tcaaagaaga  1080
ttaatgtacg aattatgggc tggaactcgc ccatatgaag taggaattcc gagtaatcgc  1140
gtatcagaac gacgcggtga acatcatctc tggagtgtac taactgctcg tcacgggacg  1200
aaagggagtg tattatgaag tggggctaat tggttaactc cggtgagtgt cacgaataat  1260
ccttcccgat tgttctgaag tcgaaacaag gtaaccgtaa gggaacttgc ggttga      1316

SEQ ID NO: 25           moltype = RNA  length = 1520
FEATURE                 Location/Qualifiers
source                  1..1520
                        mol_type = rRNA
                        organism = unidentified
                        note = DP25 16S rRNA sequence
SEQUENCE: 25
tacggagagt ttgatcctgg ctcaggatga acgctggcgg cgtgcttaac acatgcaagt  60
cgaacggtga agccaagctt gcttggtgga tcagtggcga acgggtgagt aacacgtgag  120
caacctgccc tggactctgg gataagcgct ggaaacggcg tctaatactg gatatgagct  180
ccttccgcat ggtgggggtt ggaaagattt ttcggtctgg gatgggctcg cggcctatca  240
gcttgttggt gaggtaatgg ctcaccaagg cgtcgacggg tagccggcct gagagggtga  300
ccggccacac tgggactgag acacggccca gactcctacg ggaggcagca gtggggaata  360
ttgcacaatg ggcggaagcc tgatgcagca acgccgcgtg agggatgacg gccttcgggt  420
tgtaaacctc ttttagcagg gaagaagcga aagtgacggt acctgcagaa aaagcgccgg  480
```

```
ctaactacgt gccagcagcc gcggtaatac gtagggcgca agcgttatcc ggaattattg  540
ggcgtaaaga gctcgtaggc ggtttgtcgc gtctgctgtg aaatcccgag gctcaacctc  600
gggcctgcag tgggtacggg cagactagag tgcggtaggg gagattggaa ttcctggtgt  660
agcggtggaa tgcgcagata tcaggaggaa caccgatggc gaaggcagat ctctgggccg  720
taactgacgc tgaggagcga aagggtgggg agcaaacagg cttagatacc ctggtagtcc  780
accccgtaaa cgttgggaac tagttgtggg gaccattcca cggtttccgt gacgcagcta  840
acgcattaag ttccccgcct ggggagtacg gccgcaaggc taaaactcaa aggaattgac  900
ggggacccgc acaagcggcg gagcatgcgg attaattcga tgcaacgcga agaaccttac  960
caaggcttga catatacgag aacgggccag aaatggtcaa ctctttggac actcgtaaac  1020
aggtggtgca tggttgtcgt cagctcgtgt cgtgagatgt tgggttaagt cccgcaacga  1080
gcgcaaccct cgttctatgt tgccagcacg taatggtggg aactcatggg atactgccgg  1140
ggtcaactcg gaggaaggtg gggatgacgt caaatcatca tgccccttat gtcttgggct  1200
tcacgcatgc tacaatggcc ggtacaaagg gctgcaatac cgtaaggtgg agcgaatccc  1260
aaaaagccgg tcccagttcg gattgaggtc tgcaactcga cctcatgaag tcggagtcgc  1320
tagtaatcgc agatcagcaa cgctgcggtg aatacgttcc cgggtcttgt acacaccgcc  1380
cgtcaagtca tgaaagtcgg taacacctga agccggtggc ccaacccttg tggagggagc  1440
cgtcgaaggt gggatcggta attaggacta agtcgtaaca aggtagccgt accggaaggt  1500
gcggctggat cacctccttt                                              1520

SEQ ID NO: 26          moltype = RNA  length = 1482
FEATURE                Location/Qualifiers
source                 1..1482
                       mol_type = rRNA
                       organism = unidentified
                       note = DP26 16S rRNA sequence
SEQUENCE: 26
cttgagagtt tgatcctggc tcagagcgaa cgctggcggc aggcttaaca catgcaagtc  60
gagcgggcat cttcggatgt cagcggcaga cgggtgagta acacgtggga acgtaccctt  120
cggttcggaa taacgctggg aaactagcgc taataccgga tacgcccttt tggggaaagg  180
tttactgccg aaggatcggc ccgcgtctga ttagctagtt ggtggggtaa cggcctacca  240
aggcgacgat cagtagctgg tctgagagga tgatcagcca cactgggact gagacacggc  300
ccagactcct acgggaggca gcagtgggga atattggaca atgggcgcaa gcctgatcca  360
gccatgccgc gtgagtgatg aaggccttag ggttgtaaag ctcttttgtc cgggacgata  420
atgacggtac cggaagaata agccccggct aacttcgtgc cagcagccgc ggtaatacga  480
agggggctag cgttgctcgg aatcactggg cgtaaagggc gcgtaggcgg ccattcaagt  540
cgggggtgaa agcctgtggc tcaaccacag aattgccttc gatactgttt ggcttgagta  600
tggtagaggt tggtggaact gcgagtgtag aggtgaaatt cgtagatatt cgcaagaaca  660
ccggtggcga aggcggccaa ctggaccatt actgacgctg aggcgcgaaa gcgtggggag  720
caaacaggat tagataccct ggtagtccac gccgtaaacg atgaatgcca gctgttgggg  780
tgcttgcacc tcagtagcgc agctaacgct ttaagcattc cgcctgggga gtacggtcgc  840
aagattaaaa ctcaaaggaa ttgacggggg cccgcacaag cggtggagca tgtggtttaa  900
ttcgaagcaa cgcgcagaac cttaccatcc cttgacatgg catgttaccc ggagagattc  960
ggggtccact tcggtggcgt gcacacaggt gctgcatggc tgtcgtcagc tcgtgtcgtg  1020
agatgttggg ttaagtcccg caacgagcgc aacccacgtc cttagttgcc atcattcagt  1080
tgggcactct agggagactg ccggtgataa gccgcgagga aggtgtggat gacgtcaagt  1140
cctcatggcc cttacgggat gggctacaca cgtgctacaa tggcggtgac agtgggacgc  1200
gaaggagcga tctggagcaa atccccaaaa accgtctcag ttcagattgc actctgcaac  1260
tcgagtgcat gaaggcggaa tcgctagtaa tcgtggatca gcatgccacg gtgaatacgt  1320
tcccgggcct tgtacacacc gcccgtcaca ccatgggagt tggtcttacc cgacggcgct  1380
gcgccaaccg caaggaggca ggcgaccacg gtagggtcag cgactggggt gaagtcgtaa  1440
caaggtagcc gtaggggaac ctgcggctgg atcacctcct tt                     1482

SEQ ID NO: 27          moltype = RNA  length = 935
FEATURE                Location/Qualifiers
source                 1..935
                       mol_type = rRNA
                       organism = unidentified
                       note = DP27 16S rRNA sequence
SEQUENCE: 27
cttgagagtt tgatcctggc tcagaacgaa cgctggcggc atgcctaaca catgcaagtc  60
gaacgatgct ttcgggcata gtggcgcacg ggtgcgtaac gcgtgggaat ctgccctcag  120
gttcggaata acagctggaa acggctgcta ataccggatg atatcgcaag atcaaagatt  180
tatcgcctga ggatgagccc gcgttggatt aggtagttgg tggggtaaag gcctaccaag  240
ccgacgatcc atagctggtc tgagaggatg atcagccaca ctgggactga gacacggccc  300
agactcctac gggaggcagc agtggggaat attggacaat gggcgcaagc ctgatccagc  360
aatgccgcgt gagtgatgaa ggccctaggg ttgtaaagct cttttacccg ggaagataat  420
gactgtaccg ggagaataag ccccggctaa ctccgtgcca gcagccgcgg taatacggag  480
ggggctagcg ttgttcggaa ttactgggcg taaagcgcac gtaggcggct ttgtaagtca  540
gaggtgaaag cctggagctc aactccagaa ctgcctttga gactgcatcg cttgaatcca  600
ggagaggtca gtggaattcc gagtgtagag gtgaaattcg tagatattcg gaagaacacc  660
agtggcgaag gcggctgact ggactggtat tgacgctgag gtgcgaaagc gtggggagca  720
aacaggatta gataccctgg tagtccacgc cgtaaacgat gataactagc tgtccgggca  780
cttggtgctt gggtggcgca gctaacgcat taagttatcc gcctggggag tacggccgca  840
aggttaaaac tcaaaggaat tgacgggggc ctgcacaagc ggtggagcat gtggtttaat  900
tcgaagcaac gcgcagaacc ttaccagcgt ttgac                             935

SEQ ID NO: 28          moltype = RNA  length = 931
FEATURE                Location/Qualifiers
source                 1..931
```

```
                        mol_type = rRNA
                        organism = unidentified
                        note = DP28 16S rRNA sequence
SEQUENCE: 28
atagtcgggg gcatcagtat tcaattgtca gaggtgaaat tcttggattt attgaagact  60
aactactgcg aaagcatttg ccaaggatgt tttcattaat cagtgaacga aagttagggg  120
atcgaagacg atcagatacc gtcgtagtct taaccataaa ctatgccgac tagggatcgg  180
gcgatgttat cattttgact cgctcggcac cttacgagaa atcaaagtct ttgggttctg  240
gggggagtat ggtcgcaagg ctgaaactta aagaaattga cggaagggca ccaccaggcg  300
tggagcctgc ggcttaattt gactcaacac ggggaaactc accaggtcca gacacaataa  360
ggattgacag attgagagct ctttcttgat tttgtgggtg gtggtgcatg gccgttctta  420
gttggtggag tgatttgtct gcttaattgc gataacgaac gagaccttaa cctgctaaat  480
agcccggccc gctttggcgg gtcgccggct tcttagaggg actatcggct caagccgatg  540
gaagtttgag gcaataacag gtctgtgatg cccttagatg ttctgggccg cacgcgcgct  600
acactgacag agccaacgag ttcatttcct tgcccggaag ggttgggtaa tcttgttaaa  660
ctctgtcgtg ctggggatag agcattgcaa ttattgctct tcaacgagga atgcctagta  720
agcgtacgtc atcagcgtgc gttgattacg tccctgccct ttgtacacac cgcccgtcgc  780
tactaccgat tgaatggctg agtgaggcct tcggactggc ccagggaggt cggcaacgac  840
cacccagggc cggaaagttg gtcaaactcc gtcatttaga ggaagtaaaa gtcgtaacaa  900
ggtttccgta ggtgaacctg cggaaggatc a                                 931

SEQ ID NO: 29           moltype = RNA  length = 1002
FEATURE                 Location/Qualifiers
source                  1..1002
                        mol_type = rRNA
                        organism = unidentified
                        note = DP29 16S rRNA sequence
SEQUENCE: 29
tacggagagt ttgatcctgg ctcaggacga acgctggcgg cgtgcttaac acatgcaagt  60
cgaacgatga agcccagctt gctgggttga ttagtggcga acgggtgagt aacacgtgag  120
caacgtgccc ataactctgg gataacctcc ggaaacggtg gctaatactg gatatctaac  180
acgatcgcat ggtctgtgtt tggaaagatt ttttggttat ggatcggctc acggcctatc  240
agcttgttgg tgaggtaatg gctcaccaag gcgacgacgg gtagccggcc tgagagggtg  300
accggccaca ctgggactga gacacggccc agactcctac gggaggcagc agtggggaat  360
attgcacaat gggcgaaagc ctgatgcagc aacgccgcgt gagggatgac ggcattcggg  420
ttgtaaacct cttttagtag ggaagaagcg aaagtgacgg tacctgcaga aaaagcaccg  480
gctaactacg tgccagcagc cgctgtaata cgtagggtgc aagcgttgtc cggaattatt  540
gggcgtaaag agctcgtagg cggtttgtcg cgtctgctgt gaaatcccga ggctcaacct  600
cgggtctgca gtgggtacgg gcagactaga gtgtggtagg ggagattgga attcctggtg  660
tagcggtgga atgcgcagat atcaggagga acaccgatgg cgaaggcaga tctctgggcc  720
attactgacg ctgaggagcg aaagcatggg gagcgaacag gattagatac cctggtagtc  780
catgccgtaa acgttgggcg ctagatgtgg ggaccattcc acggtttccg tgtcgtagct  840
aacgcattaa gcgccccgcc tggggagtac ggccgcaagg ctaaaactca aaggaattga  900
cgggggcccg cacaagcggc ggagcatgcg gattaattcg atgcaacgcg aagaacctta  960
ccaaggcttg acatataccg gaaacgttca gaaatgttcg cc                     1002

SEQ ID NO: 30           moltype = RNA  length = 1520
FEATURE                 Location/Qualifiers
misc_feature            1..1520
                        note = DP30 16S rRNA sequence
source                  1..1520
                        mol_type = rRNA
                        organism = unidentified
                        note = DP30 16S rRNA sequence
SEQUENCE: 30
tacggagagt ttgatcctgg ctcaggatga acgctggcgg cgtgcttaac acatgcaagt  60
cgaacggtga agccaagctt gcttggtgga tcagtggcga acgggtgagt aacacgtgag  120
caacctgccc tggactctgg gataagcgct ggaaacggcg tctaatactg gatatgagac  180
gtgatcgcat ggtcgtgttt ggaaagattt ttcggtctgg gatgggctcg cggcctatca  240
gcttgttggt gaggtaatgg ctcaccaagg cgtcgacggg tagccggcct gagagggtga  300
ccggccacac tgggactgag acacggccca gactcctacg ggaggcagca gtggggaata  360
ttgcacaatg ggcgaaagcc tgatgcagca acgccgcgtg agggatgacg gccttcgggt  420
tgtaaacctc ttttagcagg gaagaagcga aagtgacggt acctgcagaa aaagcgccgg  480
ctaactacgt gccagcagcc gcggtaatac gtagggcgca agcgttatcc ggaattattg  540
ggcgtaaaga gctcgtaggc ggtttgtcgc gtctgctgtg aaatcccgag gctcaacctc  600
gggcctgcag tgggtacggg cagactagag tgcggtaggg gagattggaa ttcctggtgt  660
agcggtggaa tgcgcagata tcaggaggaa caccgatggc gaaggcagat ctctgggccg  720
taactgacgc tgaggagcga aagggtgggg agcaaacagg cttagatacc ctggtagtcc  780
accccgtaaa cgttgggaac tagttgtggg gaccattcca cggtttccgt gacgcagcta  840
acgcattaag ttccccgcct ggggagtacg gccgcaaggc taaaactcaa aggaattgac  900
ggggacccgc acaagcggcg gagcatgcgg attaattcga tgcaacgcga agaaccttac  960
caaggcttga catatacgag aacgggccag aaatggtcaa ctctttggac actcgtaaac  1020
aggtggtgca tggttgtcgt cagctcgtgt cgtgagatgt tgggttaagt cccgcaacga  1080
gcgcaaccct cgttctatgt tgccagcacg taatggtggg aactcatggg atactgccgg  1140
ggtcaactcg gaggaaggtg gggatgacgt caaatcatca tgccccttat gtcttgggct  1200
tcacgcatgc tacaatggcc ggtacaaagg gctgcaatac cgtgaggtgg agcgaatccc  1260
aaaaagccgg tcccagttcg gattgaggtc tgcaactcga cctcatgaag tcggagtcgc  1320
tagtaatcgc agatcagcaa cgctgcggtg aatacgttcc cgggtcttgt acacaccgcc  1380
cgtcaagtca tgaaagtcgg taacacctga agccggtggc ccaacccttg tggagggagc  1440
```

```
cgtcgaaggt gggatcggta attaggacta agtcgtaaca aggtagccgt accggaaggt  1500
gcggctggat cacctccttt                                              1520

SEQ ID NO: 31          moltype = RNA  length = 941
FEATURE                Location/Qualifiers
source                 1..941
                       mol_type = rRNA
                       organism = unidentified
                       note = DP31 16S rRNA sequence
SEQUENCE: 31
cagccggggg cattagtatt tgcacgctag aggtgaaatt cttggattgt gcaaagactt  60
cctactgcga aagcatttgc caagaatgtt ttcattaatc aagaacgaag gttagggtat  120
cgaaaacgat tagataccgt tgtagtctta acagtaaact atgccgactc cgaatcggtc  180
gatgctcatt tcactggctc gatcggcgcg gtacgagaaa tcaaagtttt tgggttctgg  240
ggggagtatg gtcgcaaggc tgaaacttaa agaaattgac ggaagggcac caccaggagt  300
ggagcctgcg gcttaatttg actcaacacg ggaaaactca ccgggtccgg acatagtaag  360
gattgacaga ttgatggcgc tttcatgatt ctatgggtgg tggtgcatgg ccgttcttag  420
ttggtggagt gatttgtctg gttaattccg ataacgaacg agaccttgac ctgctaaata  480
gacgggttga cattttgttg gccccttatg tcttcttaga gggacaatcg accgtctagg  540
tgatggaggc aaaaggcaat aacaggtctg tgatgccctt agatgttccg ggctgcacgc  600
gcgctacact gacagagaca acgagtgggg ccccttgtcc gaaatgactg ggtaaacttg  660
tgaaactttg tcgtgctggg gatggagctt tgtaattttt gctcttcaac gaggaattcc  720
tagtaagcgc aagtcatcag cttgcgttga ctacgtccct gccctttgta cacaccgccc  780
gtcgctacta ccgattgaat ggcttagtga ggacttggga gagtacatcg gggagccagc  840
aatggcaccc tgacggctca aactcttaca aacttggtca tttagaggaa gtaaaagtcg  900
taacaaggta tctgtaggtg aacctgcaga tggatcattt c                      941

SEQ ID NO: 32          moltype = RNA  length = 1072
FEATURE                Location/Qualifiers
source                 1..1072
                       mol_type = rRNA
                       organism = unidentified
                       note = DP32 16S rRNA sequence
SEQUENCE: 32
actgagcatt gacgttactc gcagaagaag caccggctaa ctccgtgcca gcagccgcgg  60
taatacggag ggtgcaagcg ttaatcggaa ttactgggcg taaagcgcac gcaggcggtt  120
tgttaagtca gatgtgaaat ccccgagctt aacttgggaa ctgcatttga aactggcaag  180
ctagagtctt gtagaggggg gtagaattcc aggtgtagcg gtgaaatgcg tagagatctg  240
gaggaatacc ggtggcgaag gcggccccct ggacaaagac tgacgctcag gtgcgaaagc  300
gtggggagca aacaggatta gataccctgg tagtccacgc tgtaaacgat gtcgacttgg  360
aggttgtgcc cttgaggcgt ggcttccgga gctaacgcgt taagtcgacc gcctggggag  420
tacggccgca aggttaaaac tcaaatgaat tgacgggggc ccgcacaagc ggtggagcat  480
gtggtttaat tcgatgcaac gcgaagaacc ttacctactc ttgacatcca gagaattcgc  540
tagagatagc ttagtgcctt cgggaactct gagacaggtg ctgcatggct gtcgtcagct  600
cgtgttgtga aatgttgggt taagtcccgc aacgagcgca acccttatcc tttgttgcca  660
gcgagtaatg tcgggaactc aaaggagact gccggtgata aaccggagga aggtggggat  720
gacgtcaagt catcatggcc cttacgagta gggctacaca cgtgctacaa tggcatatac  780
aaagagaagc gaactcgcga gagcaagcgg acctcataaa gtatgtcgta gtccggattg  840
gagtctgcaa ctcgactcca tgaagtcgga atcgctagta atcgtagatc agaatgctac  900
ggtgaatacg ttcccgggcc ttgtacacac cgcccgtcac accatgggag tgggttgcaa  960
aagaagtagg tagcttaacc ttcgggaggg cgcttaccac tttgtgattc atgactgggg  1020
tgaagtcgta acaaggtaac cgtaggggaa cctgcggttg gatcacctcc tt          1072

SEQ ID NO: 33          moltype = RNA  length = 853
FEATURE                Location/Qualifiers
source                 1..853
                       mol_type = rRNA
                       organism = unidentified
                       note = DP33 16S rRNA sequence
SEQUENCE: 33
ggaggaaggc gtagagatct ggaggaatac cggtggcgaa ggcggccccc tggacaaaga  60
ctgacgctca ggtgcgaaag cgtggggagc aaacaggatt agataccctg gtagtccacg  120
ccgtaaacga tgtcgacttg gaggttgtgc ccttgaggcg tggcttccgg agctaacgcg  180
ttaagtcgac cgcctgggga gtacggccgc aaggttaaaa ctcaaatgaa ttgacggggg  240
cccgcacaag cggtggagca tgtggtttaa ttcgatgcaa cgcgaagaac cttacctggc  300
cttgacatcc acggaattcg gcagagatgc cttagtgcct tcgggaaccg tgagacaggt  360
gctgcatggc tgtcgtcagc tcgtgttgtg aaatgttggg ttaagtcccg caacgagcgc  420
aacccttatc ctttgttgcc agcacgtaat ggtgggaact caaaggagac tgccggtgat  480
aaaccggagg aaggtgggga tgacgtcaag tcatcatggc ccttacggcc agggctacac  540
acgtgctaca atggcgcata caaagagaag cgacctcgcg agagcaagcg gacctcataa  600
agtgcgtcgt agtccggatc ggagtctgca actcgactcc gtgaagtcgg aatcgctagt  660
aatcgtagat cagaatgcta cggtgaatac gttcccgggc cttgtacaca ccgcccgtca  720
caccatggga gtgggttgca aaagaagtag gtagcttaac cttcgggagg gcgcttacca  780
ctttgtgatt catgactggg gtgaagtcgt aacaaggtaa ccgtagggga acctgcggtt  840
ggatcacctc ctt                                                     853

SEQ ID NO: 34          moltype = RNA  length = 1519
FEATURE                Location/Qualifiers
source                 1..1519
```

```
                        mol_type = rRNA
                        organism = unidentified
                        note = DP34 16S rRNA sequence
SEQUENCE: 34
tacggagagt ttgatcctgg ctcaggacga acgctggcgg cgtgcttaac acatgcaagt  60
cgaacgatga agcccagctt gctgggtgga ttagtggcga acgggtgagt aacacgtgag  120
taacctgccc ttgactctgg gataagcgtt ggaaacgacg tctaataccg gatacgagct  180
tccaccgcat ggtgagttgc tggaaagaat tttggtcaag gatggactcg cggcctatca  240
gcttgttggt gaggtaatgg ctcaccaagg cgacgacggg tagccggcct gagagggtga  300
ccggccacac tgggactgag acacggccca gactcctacg ggaggcagca gtggggaata  360
ttgcacaatg ggcgaaagcc tgatgcagca acgccgcgtg agggacgacg gccttcgggt  420
tgtaaacctc ttttagcagg gaagaagcga aagtgacggt acctgcagaa aaagcaccgg  480
ctaactacgt gccagcagcc gcggtaatac gtagggtgca agcgttgtcc ggaattattg  540
ggcgtaaaga gctcgtaggc ggtttgtcgc gtctgctgtg aaatcccgag gctcaacctc  600
gggtctgcag tgggtacggg cagactagag tgcggtaggg gagattggaa ttcctggtgt  660
agcggtggaa tgcgcagata tcaggaggaa caccgatggc gaaggcagat ctctgggccg  720
ctactgacgc tgaggagcga aagggtgggg agcaaacagg cttagatacc ctggtagtcc  780
accccgtaaa cgttgggcgc tagatgtggg gaccattcca cggtttccgt gtcgtagcta  840
acgcattaag cgccccgcct ggggagtacg gccgcaaggc taaaactcaa aggaattgac  900
gggggcccgc acaagcggcg gagcatgcgg attaattcga tgcaacgcga agaaccttac  960
caaggcttga catatacgag aacgggccag aaatggtcaa ctctttggac actcgtaaac  1020
aggtggtgca tggttgtcgt cagctcgtgt cgtgagatgt tgggttaagt cccgcaacga  1080
gcgcaaccct cgttctatgt tgccagcacg taatggtggg aactcatggg atactgccgg  1140
ggtcaactcg gaggaaggtg gggacgacgt caaatcatca tgccccttat gtcttgggct  1200
tcacgcatgc tacaatggcc agtacaaagg gctgcaatac cgtaaggtgg agcgaatccc  1260
aaaaagctgg tcccagttcg gattgaggtc tgcaactcga cctcatgaag tcggagtcgc  1320
tagtaatcgc agatcagcaa cgctgcggtg aatacgttcc cgggccttgt acacaccgcc  1380
cgtcaagtca tgaaagtcgg taacacccga agccagtggc ctaaccgcaa ggatggagct  1440
gtctaaggtg ggatcggtaa ttaggactaa gtcgtaacaa ggtagccgta ccggaaggtg  1500
cggctggatc acctcctttt                                             1519

SEQ ID NO: 35           moltype = RNA  length = 1536
FEATURE                 Location/Qualifiers
source                  1..1536
                        mol_type = rRNA
                        organism = unidentified
                        note = DP35 16S rRNA sequence
SEQUENCE: 35
ttgaagagtt tgatcatggc tcagattgaa cgctggcggc aggcctaaca catgcaagtc  60
ggacggtagc acagagagct tgctcttggg tgacgagtgg cggacgggtg agtaatgtct  120
ggggatctgc ccgatagagg gggataacca ctggaaacgg tggctaatac cgcataacgt  180
cgcaagacca aagaggggga ccttcgggcc tctcactatc ggatgaaccc agatgggatt  240
agctagtagg cggggtaatg gcccacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagcgg ggaggaaggc gatgaggtta ataaccgcgt cgattgacgt  480
tacccgcaga agaagcaccg gctaactccg tgccagcagc cgcggtaata cggagggtgc  540
aagcgttaat cggaattact gggcgtaaag cgcacgcagg cggtctgtta agtcagatgt  600
gaaatccccg ggcttaacct gggaactgca tttgaaactg gcaggcttga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gttcccttga  840
ggagtggctt ccggagctaa cgcgttaagt cgaccgcctg gggagtacgg ccgcaaggtt  900
aaaactcaaa tgaattgacg ggggcccgca caagcggtgg agcatgtggt ttaattcgat  960
gcaacgcgaa gaaccttacc tactcttgac atccagcgaa cttagcagag atgctttggt  1020
gccttcggga acgctgagac aggtgctgca tggctgtcgt cagctcgtgt tgtgaaatgt  1080
tgggttaagt cccgcaacga gcgcaaccct tatcctttgt tgccagcgat tcggtcggga  1140
actcaaagga gactgccggt gataaaccgg aggaaggtgg ggatgacgtc aagtcatcat  1200
ggcccttacg agtagggcta cacacgtgct acaatggcgc atacaaagag aagcgacctc  1260
gcgagagcaa gcggacctca caaagtgcgt cgtagtccgg atcggagtct gcaactcgac  1320
tccgtgaagt cggaatcgct agtaatcgtg gatcagaatg ccacggtgaa tacgttcccg  1380
ggccttgtac acaccgcccg tcacaccatg ggagtgggtt gcaaaagaag taggtagctt  1440
aaccttcggg agggcgctta ccactttgtg attcattact ggggtgaagt cgtaacaagg  1500
taaccgtagg ggaacctgcg gttggatcac ctcctt                            1536

SEQ ID NO: 36           moltype = RNA  length = 993
FEATURE                 Location/Qualifiers
source                  1..993
                        mol_type = rRNA
                        organism = unidentified
                        note = DP36 16S rRNA sequence
SEQUENCE: 36
ttgaagagtt tgatcatggc tcagattgaa cgctggcggc aggcctaaca catgcaagtc  60
ggacggtagc acagagagct tgctcttggg tgacgagtgg cggacgggtg agtaatgtct  120
ggggatctgc ccgatagagg gggataacca ctggaaacgg tggctaatac cgcataacgt  180
cgcaagacca aagaggggga ccttcgggcc tctcactatc ggatgaaccc agatgggatt  240
agctagtagg cggggtaatg gcccacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
```

-continued

```
ttgtaaagta ctttcagcgg ggaggaaggc gatgcggtta ataaccgcgt cgattgacgt  480
tacccgcaga agaagcaccg gctaactccg tgccagcagc cgcggtaata cggagggtgc  540
aagcgttaat cggaattact gggcgtaaag cgcacgcagg cggtctgtta agtcagatgt  600
gaaatccccg ggcttaacct gggaactgca tttgaaactg gcaggcttga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gttcccttga  840
ggagtggctt ccggagctaa cgcgttaagt cgaccgcctg gggagtacgg ccgcaaggtt  900
aaaactcaaa tgaattgacg ggggcccgca caagcggtgg agcatgtggt ttaattcgat  960
gcaacgcgaa gaaccttacc tactcttgac atc                                 993

SEQ ID NO: 37          moltype = RNA  length = 1532
FEATURE                Location/Qualifiers
source                 1..1532
                       mol_type = rRNA
                       organism = unidentified
                       note = DP37 16S rRNA sequence
SEQUENCE: 37
tgaagagttt gatcatggct cagattgaac gctggcggca ggcctaacac atgcaagtcg  60
agcggtagag agaagcttgc ttctcttgag agcggcggac gggtgagtaa tgcctaggaa  120
tctgcctggt agtgggggat aacgttcgga aacgaacgct aataccgcat acgtcctacg  180
ggagaaagca ggggaccttc gggccttgcg ctatcagatg agcctaggtc ggattagcta  240
gttggtgggg taatggctca ccaaggcgac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggccatt acctaatacg tgatggtttt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg gatgtgaaat  600
ccccgggctc aacctgggaa ctgcattcaa aactgactga ctagagtatg gtagagggtg  660
gtggaatttc ctgtgtagcg gtgaaatgcg tagatatagg aaggaacacc agtggcgaag  720
gcgaccacct ggactgatac tgacactgag gtgcgaaagc gtggggagca aacaggatta  780
gataccctgg tagtccacgc cgtaaacgat gtcaactagc cgttgggagc cttgagctct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc tagagataga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgtaatg gtgggcactc  1140
taaggagact gccggtgaca aaccggagga aggtggggat gacgtcaagt catcatggcc  1200
cttacggcct gggctacaca cgtgctacaa tggtcggtac agagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac accatgggag tgggttgcac cagaagtagc tagtctaacc  1440
ttcgggggga cggttaccac ggtgtgattc atgactgggg tgaagtcgta acaaggtagc  1500
cgtaggggaa cctgcggctg gatcacctcc tt                                  1532

SEQ ID NO: 38          moltype = RNA  length = 1517
FEATURE                Location/Qualifiers
source                 1..1517
                       mol_type = rRNA
                       organism = unidentified
                       note = DP38 16S rRNA sequence
SEQUENCE: 38
tacggagagt ttgatcctgg ctcaggacga acgctggcgg cgtgcttaac acatgcaagt  60
cgagcggtaa ggcctttcgg ggtacacgag cggcgaacgg gtgagtaaca cgtgggtgat  120
ctgccctgca ctctgggata agcttgggaa actgggtcta ataccggata tgaccacagc  180
atgcatgtgt tgtggtggaa agatttatcg gtgcaggatg ggcccgcggc ctatcagctt  240
gttggtgggg taatggccta ccaaggcgac gacgggtagc cgacctgaga gggtgaccgg  300
ccacactggg actgagacac ggcccagact cctacgggag gcagcagtgg ggaatattgc  360
acaatgggcg gaagcctgat gcagcgacgc cgcgtgaggg atgaaggcct tcgggttgta  420
aacctctttc agcagggacg aagcgtgagt gacggtacct gcagaagaag caccggctaa  480
ctacgtgcca gcagccgcgg taatacgtag ggtgcgagcg ttgtccggaa ttactgggcg  540
taaagagttc gtaggcggtt tgtcgcgtcg tttgtgaaaa cccggggctc aacttcgggc  600
ttgcaggcga tacgggcaga cttgagtgtt tcaggggaga ctggaattcc tggtgtagcg  660
gtgaaatgcg cagatatcag gaggaacacc ggtggcgaag gcgggtctct gggaaacaac  720
tgacgctgag gaacgaaagc gtgggtagca aacaggatta gataccctgg tagtccacgc  780
cgtaaacggt gggcgctagg tgtgggttcc ttccacggga tctgtgccgt agctaacgca  840
ttaagcgccc cgcctgggga gtacggccgc aaggctaaaa ctcaaaggaa ttgacggggg  900
cccgcacaag cggcggagca tgtggattaa ttcgatgcaa cgcgaagaac cttacctggg  960
tttgacatac accggaaaac cgtagagata cggtccccct tgtggtcggt gtacaggtgg  1020
tgcatggctg tcgtcagctc gtgtcgtgag atgttgggtt aagtcccgca acgagcgcaa  1080
cccttgtctt atgttgccag cacgtaatgg tggggactcg taagagactg ccggggtcaa  1140
ctcggaggaa ggtggggacg acgtcaagtc atcatgcccc ttatgtccag ggcttcacac  1200
atgctacaat ggccagtaca gagggctgcg agaccgtgag gtggagcgaa tcccttaaag  1260
ctggtctcag ttcggatcgg ggtctgcaac tcgaccccgt gaagtcggag tcgctagtaa  1320
tcgcagatca gcaacgctgc ggtgaatacg ttcccgggcc ttgtacacac cgcccgtcac  1380
gtcatgaaag tcggtaacac ccgaagccgg tggcctaacc ccttacgggg agggagccgt  1440
cgaaggtggg atcggcgatt gggacgaagt cgtaacaagg tagccgtacc ggaaggtgcg  1500
gctggatcac ctccttt                                                   1517
```

-continued

```
SEQ ID NO: 39           moltype = RNA  length = 1482
FEATURE                 Location/Qualifiers
source                  1..1482
                        mol_type = rRNA
                        organism = unidentified
                        note = DP39 16S rRNA sequence
SEQUENCE: 39
cttgagagtt tgatcctggc tcagaacgaa cgctggcggc aggcttaaca catgcaagtc  60
gaacgccccg caaggggagt ggcagacggg tgagtaacgc gtgggaatct accgtgccct  120
gcggaatagc tccgggaaac tggaattaat accgcatacg ccctacgggg gaaagattta  180
tcggggtatg atgagcccgc gttggattag ctagttggtg gggtaaaggc ctaccaaggc  240
gacgatccat agctggtctg agaggatgat cagccacatt gggactgaga cacggcccaa  300
actcctacgg gaggcagcag tggggaatat tggacaatgg gcgcaagcct gatccagcca  360
tgccgcgtga gtgatgaagg ccttagggtt gtaaagctct ttcaccggag aagataatga  420
cggtatccgg agaagaagcc ccggctaact tcgtgccagc agccgcggta atacgaaggg  480
ggctagcgtt gttcggaatt actgggcgta aagcgcacgt aggcggatat ttaagtcagg  540
ggtgaaatcc cagagctcaa ctctggaact gcctttgata ctgggtatct tgagtatgga  600
agaggtaagt ggaattccga gtgtagaggt gaaattcgta gatattcgga ggaacaccag  660
tggcgaaggc ggcttactgg tccattactg acgctgaggt gcgaaagcgt ggggagcaaa  720
caggattaga taccctggta gtccacgccg taaacgatga atgttagccg tcgggcagta  780
tactgttcgg tggcgcagct aacgcattaa acattccgcc tggggagtac ggtcgcaaga  840
ttaaaactca aaggaattga cgggggcccg cacaagcggt ggagcatgtg gtttaattcg  900
aagcaacgcg cagaacctta ccagctcttg acattcgggg tttgggcagt ggagacattg  960
tccttcagtt aggctggccc cagaacaggt gctgcatggc tgtcgtcagc tcgtgtcgtg  1020
agatgttggg ttaagtcccg caacgagcgc aaccctcgcc cttagttgcc agcatttagt  1080
tgggcactct aaggggactg ccggtgataa gccgagagga aggtggggat gacgtcaagt  1140
cctcatggcc cttacgggct gggctacaca cgtgctacaa tggtggtgac agtgggcagc  1200
gagacagcga tgtcgagcta atctccaaaa gccatctcag ttcggattgc actctgcaac  1260
tcgagtgcat gaagttggaa tcgctagtaa tcgcagatca gcatgctgcg gtgaatacgt  1320
tcccgggcct tgtacacacc gcccgtcaca ccatgggagt tggttttacc cgaaggtagt  1380
gcgctaaccg caaggaggca gctaaccacg gtagggtcag cgactggggt gaagtcgtaa  1440
caaggtagcc gtaggggaac ctgcggctgg atcacctcct tt                    1482

SEQ ID NO: 40           moltype = RNA  length = 903
FEATURE                 Location/Qualifiers
source                  1..903
                        mol_type = rRNA
                        organism = unidentified
                        note = DP40 16S rRNA sequence
SEQUENCE: 40
ttgacgttac ccgcagaaga agcaccggct aactccgtgc cagcagccgc ggtaatacgg  60
agggtgcaag cgttaatcgg aattactggg cgtaaagcgc acgcaggcgg tctgttaagt  120
cagatgtgaa atccccgggc ttaacctggg aactgcattt gaaactggca ggcttgagtc  180
ttgtagaggg gggtagaatt ccaggtgtag cggtgaaatg cgtagagatc tggaggaata  240
ccggtggcga aggcggcccc ctggacaaag actgacgctc aggtgcgaaa gcgtggggag  300
caaacaggat tagataccct ggtagtccac gccgtaaacg atgtcgactt ggaggttgtt  360
cccttgagga gtggcttccg gagctaacgc gttaagtcga ccgcctgggg agtacggccg  420
caaggttaaa actcaaatga attgacgggg gcccgcacaa gcggtggagc atgtggttta  480
attcgatgca acgcgaagaa ccttacctac tcttgacatc cagagaactt tccagagatg  540
gattggtgcc ttcgggaact ctgagacagg tgctgcatgg ctgtcgtcag ctcgtgttgt  600
gaaatgttgg gttaagtccc gcaacgagcg caacccttat cctttgttgc cagcgcgtga  660
tggcgggaac tcaaaggaga ctgccggtga taaaccggag gaaggtgggg atgacgtcaa  720
gtcatcatgg cccttacgag tagggctaca cacgtgctac aatggcgcat acaaagagaa  780
gcgacctcgc gagagcaagc ggacctcaca aagtgcgtcg tagtccggat cggagtctgc  840
aactcgactc cgtgaagtcg gaatcgctag taatcgtgga tcagaatgcc acggtgaata  900
cgt                                                               903

SEQ ID NO: 41           moltype = RNA  length = 1457
FEATURE                 Location/Qualifiers
source                  1..1457
                        mol_type = rRNA
                        organism = unidentified
                        note = DP41 16S rRNA sequence
SEQUENCE: 41
gtggagagtt tgatcctggc tcaggatgaa cgctggcggc gtgcttaaca catgcaagtc  60
gaacggaaag gcccaagctt gcttgggtac tcgagtggcg aacgggtgag taacacgtgg  120
gtgatctgcc ctgcacttcg ggataagcct gggaaactgg gtctaatacc ggataggacg  180
atggtttgga tgccattgtg gaaagttttt tcggtgtggg atgagctcgc ggcctatcag  240
cttgttggtg gggtaatggc ctaccaaggc gtcgacgggt agccggcctg agagggtgta  300
cggccacatt gggactgaga tacggcccag actcctacgg gaggcagcag tggggaatat  360
tgcacaatgg gcgcaagcct gatgcagcga cgccgcgtgg gggatgacgg ccttcgggtt  420
gtaaactcct ttcgctaggg acgaagcgtt ttgtgacggt acctggagaa gaagcaccgg  480
ctaactacgt gccagcagcc gcggtaatac gtagggtgcg agcgttgtcc ggaattactg  540
ggcgtaaaga gctcgtaggt ggtttgtcgc gtcgtttgtg taagcccgca gcttaactgc  600
gggactgcag gcgatacggg cataacttga gtgctgtagg ggagactgga attcctggtg  660
tagcggtgga atgcgcagat atcaggagga acaccgatgg cgaaggcagg tctctgggca  720
gtaactgacg ctgaggagcg aaagcatggg tagcgaacag gattagatac cctggtagtc  780
catgccgtaa acggtgggcg ctaggtgtga gtcccttcca cggggttcgt gccgtagcta  840
acgcattaag cgccccgcct ggggagtacg gccgcaaggc taaaactcaa aggaattgac  900
```

```
gggggcccgc acaagcggcg gagcatgtgg attaattcga tgcaacgcga agaaccttac  960
ctgggcttga catacaccag atcgccgtag agatacggtt tccctttgtg gttggtgtac  1020
aggtggtgca tggttgtcgt cagctcgtgt cgtgagatgt tgggttaagt cccgcaacga  1080
gcgcaaccct tgtcttatgt tgccagcacg tgatggtggg gactcgtgag agactgccgg  1140
ggttaactcg gaggaaggtg gggatgacgt caaatcatca tgccccttat gtccagggct  1200
tcacacatgc tacaatggtc ggtacaacgc gcatgcgagc ctgtgagggt gagcgaatcg  1260
ctgtgaaagc cggtcgtagt tcggattggg gtctgcaact cgaccccatg aagtcggagt  1320
cgctagtaat cgcagatcag caacgctgcg gtgaatacgt tcccgggcct tgtacacacc  1380
gcccgtcaca ccatgggagt gggttgcaaa agaagtaggt agcttaacct tcgggagggc  1440
gcttaccact ttgtgat                                                 1457

SEQ ID NO: 42          moltype = RNA  length = 1532
FEATURE                Location/Qualifiers
source                 1..1532
                       mol_type = rRNA
                       organism = unidentified
                       note = DP42 16S rRNA sequence
SEQUENCE: 42
tgaagagttt gatcatggct cagattgaac gctggcggca ggcctaacac atgcaagtcg  60
agcggtagag aggtgcttgc acctcttgag agcggcggac gggtgagtaa tacctaggaa  120
tctgcctgat agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggctac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggcatta acctaatacg ttagtgtctt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg aatgtgaaat  600
ccccgggctc aacctgggaa ctgcatccaa aactggcaag ctagagtatg gtagagggta  660
gtggaatttc ctgtgtagcg gtgaaatgcg tagatatagg aaggaacacc agtggcgaag  720
gcgactacct ggactgatac tgacactgag gtgcgaaagc gtggggagca aacaggatta  780
gataccctgg tagtccacgc cgtaaacgat gtcaactagc cgttgggaac cttgagttct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc cagagatgga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgtaatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgtgaatc agaatgtcac ggtgaatacg ttcccgggcc  1380
ttgtacacac cgcccgtcac accatgggag tgggttgcac cagaagtagc tagtctaacc  1440
ctcgggagga cggttaccac ggtgtgattc atgactgggg tgaagtcgta acaaggtagc  1500
cgtaggggaa cctgcggctg gatcacctcc tt                                1532

SEQ ID NO: 43          moltype = RNA  length = 1525
FEATURE                Location/Qualifiers
source                 1..1525
                       mol_type = rRNA
                       organism = unidentified
                       note = DP43 16S rRNA sequence
SEQUENCE: 43
ctgagtttga tcctggctca gattgaacgc tggcggcatg ccttacacat gcaagtcgaa  60
cggcagcacg gagcttgctc tggtggcgag tggcgaacgg gtgagtaata tatcggaacg  120
taccctggag tgggggataa cgtagcgaaa gttacgctaa taccgcatac gatctaagga  180
tgaaagtggg ggatcgcaag acctcatgct cgtggagcgg ccgatatctg attagctagt  240
tggtagggta aaagcctacc aaggcatcga tcagtagctg gtctgagagg acgaccagcc  300
acactggaac tgagacacgg tccagactcc tacgggaggc agcagtgggg aattttggac  360
aatgggcgaa agcctgatcc agcaatgccg cgtgagtgaa gaaggccttc gggttgtaaa  420
gctcttttgt cagggaagaa acggtgagag ctaatatctc ttgctaatga cggtacctga  480
agaataagca ccggctaact acgtgccagc agccgcggta atacgtaggg tgcaagcgtt  540
aatcggaatt actgggcgta aagcgtgcgc aggcggtttt gtaagtctga tgtgaaatcc  600
ccgggctcaa cctgggaatt gcattggaga ctgcaaggct agaatctggc agaggggggt  660
agaattccac gtgtagcagt gaaatgcgta gatatgtgga ggaacaccga tggcgaaggc  720
agccccctgg gtcaagattg acgctcatgc acgaaagcgt ggggagcaaa caggattaga  780
taccctggta gtccacgccc taaacgatgt ctactagttg tcgggtctta attgacttgg  840
taacgcagct aacgcgtgaa gtagaccgcc tggggagtac ggtcgcaaga ttaaaactca  900
aaggaattga cggggacccg cacaagcggt ggatgatgtg gattaattcg atgcaacgcg  960
aaaaacctta cctacccttg acatggctgg aatccttgag agatcaggga gtgctcgaaa  1020
gagaaccagt acacaggtgc tgcatggctg tcgtcagctc gtgtcgtgag atgttgggtt  1080
aagtcccgca acgagcgcaa cccttgtcat tagttgctac gaaagggcac tctaatgaga  1140
ctgccggtga caaaccggag gaaggtgggg atgacgtcaa gtcctcatgg cccttatggg  1200
tagggcttca cacgtcatac aatggtacat acagagcgcc gccaacccgc gagggggagc  1260
taatcgcaga aagtgtatcg tagtccggat tgtagtctgc aactcgactg catgaagttg  1320
gaatcgctag taatcgcgga tcagcatgtc gcggtgaata cgttcccggg tcttgtacac  1380
accgcccgtc acaccatggg agcgggtttt accagaagta ggtagcttaa ccgtaaggag  1440
ggcgcttacc acggtaggat tcgtgactgg ggtgaagtcg taacaaggta gccgtatcgg  1500
aaggtgcggc tggatcacct ccttt                                        1525
```

```
SEQ ID NO: 44          moltype = RNA  length = 1497
FEATURE                Location/Qualifiers
source                 1..1497
                       mol_type = rRNA
                       organism = unidentified
                       note = DP44 16S rRNA sequence
SEQUENCE: 44
tggcggcatg ccttacacat gcaagtcgaa cggcagcata ggagcttgct cctgatggcg  60
agtggcgaac gggtgagtaa tatatcggaa cgtgccctag agtgggggat aactagtcga  120
aagactagct aataccgcat acgatctacg gatgaaagtg ggggatcgca agacctcatg  180
ctcctggagc ggccgatatc tgattagcta gttggtgggg taaaagctca ccaaggcgac  240
gatcagtagc tggtctgaga ggacgaccag ccacactggg actgagacac ggcccagact  300
cctacgggag gcagcagtgg ggaattttgg acaatggggg caaccctgat ccagcaatgc  360
cgcgtgagtg aagaaggcct tcgggttgta aagctctttt gtcagggaag aaacggttct  420
ggataatacc taggactaat gacggtacct gaagaataag caccggctaa ctacgtgcca  480
gcagccgcgg taatacgtag ggtgcaagcg ttaatcggaa ttactgggcg taaagcgtgc  540
gcaggcggtt gtgtaagtca gatgtgaaat ccccgggctc aacctgggaa ttgcatttga  600
gactgcacgg ctagagtgtg tcagaggggg gtagaattcc acgtgtagca gtgaaatgcg  660
tagatatgtg gaggaatacc gatggcgaag gcagcccccct gggataacac tgacgctcat  720
gcacgaaagc gtggggagca aacaggatta gataccctgg tagtccacgc cctaaacgat  780
gtctactagt tgtcgggtct taattgactt ggtaacgcag ctaacgcgtg aagtagaccg  840
cctggggagt acggtcgcaa gattaaaact caaaggaatt gacggggacc cgcacaagcg  900
gtggatgatg tggattaatt cgatgcaacg cgaaaaacct tacctaccct tgacatggat  960
ggaatcccga agagatttgg gagtgctcga aagagaacca tcacacaggt gctgcatggc  1020
tgtcgtcagc tcgtgtcgtg agatgttggg ttaagtcccg caacgagcgc aacccttgtc  1080
attagttgct acgaaagggc actctaatga gactgccggt gacaaaccgg aggaaggtgg  1140
ggatgacgtc aagtcctcat ggcccttatg ggtagggctt cacacgtcat acaatggtac  1200
atacagaggg ccgccaaccc gcgaggggga gctaatccca gaaagtgtat cgtagtccgg  1260
attggagtct gcaactcgac tccatgaagt tggaatcgct agtaatcgcg gatcagcatg  1320
tcgcggtgaa tacgttcccg ggtcttgtac acaccgcccg tcacaccatg ggagcgggtt  1380
ttaccagaag tgggtagcct aaccgcaagg agggcgctca ccacggtagg attcgtgact  1440
ggggtgaagt cgtaacaagg tagccgtatc ggaaggtgcg gctggatcac ctccttt     1497

SEQ ID NO: 45          moltype = RNA  length = 1522
FEATURE                Location/Qualifiers
misc_feature           1..1522
                       note = DP45 16S rRNA sequence
source                 1..1522
                       mol_type = rRNA
                       organism = unidentified
SEQUENCE: 45
tacggagagt ttgatcctgg ctcaggacga acgctggcgg cgtgcttaac acatgcaagt  60
cgaacggtga cgctagagct tgctctggtt gatcagtggc gaacgggtga gtaacacgtg  120
agtaacctgc ccttgactct gggataactc cgggaaaccg gggctaatac cggatacgag  180
acgcgaccgc atggtcggcg tctggaaagt ttttcggtca aggatggact cgcggcctat  240
cagcttgttg gtgaggtaat ggctcaccaa ggcgtcgacg ggtagccggc ctgagagggc  300
gaccggccac actgggactg agacacggcc cagactccta cgggaggcag cagtggggaa  360
tattgcacaa tgggcgaaag cctgatgcag cgacgccgcg tgagggatga aggccttcgg  420
gttgtaaacc tctttcagta gggaagaagc gaaagtgacg gtacctgcag aagaagcgcc  480
ggctaactac gtgccagcag ccgcggtaat acgtagggcg caagcgttgt ccggaattat  540
tgggcgtaaa gagctcgtag gcggtttgtc gcgtctggtg tgaaaactca aggctcaacc  600
ttgagcttgc atcgggtacg ggcagactag agtgtggtag ggtgactgg aattcctggt  660
gtagcggtgg aatgcgcaga tatcaggagg aacaccgatg gcgaaggcag gtcactgggc  720
cactactgac gctgaggagc gaaagcatgg ggagcgaaca ggattagata ccctggtagt  780
ccatgccgta aacgttgggc actaggtgtg gggctcattc cacgagttcc gcgccgcagc  840
taacgcatta agtgccccgc ctggggagta cggccgcaag gctaaaactc aaaggaattg  900
acgggggccc gcacaagcgg cggagcatgc ggattaattc gatgcaacgc gaagaacctt  960
accaaggctt gacatacacc ggaatcatgc agagatgtgt gcgtcttcgg actggtgtac  1020
aggtggtgca tggttgtcgt cagctcgtgt cgtgagatgt tgggttaagt cccgcaacga  1080
gcgcaaccct cgtcctatgt tgccagcacg ttatggtggg gactcatagg agactgccgg  1140
ggtcaactcg gaggaaggtg gggatgacgt caaatcatca tgccccttat gtcttgggct  1200
tcacgcatgc tacaatggcc ggtacaaagg gctgcgatac cgcgaggtgg agcgaatccc  1260
aaaaagccgg tctcagttcg gattggggtc tgcaactcga ccccatgaag tcggagtcgc  1320
tagtaatcgc agatcagcaa cgctgcggtg aatacgttcc cgggccttgt acacaccgcc  1380
cgtcaagtca cgaaagtcgg taacacccga agccggtggc ctaacccctt gtgggatgga  1440
gccgtcgaag gtgggattgg cgattgggac taagtcgtaa caaggtagcc gtaccggaag  1500
gtgcggctgg atcacctcct tt                                          1522

SEQ ID NO: 46          moltype = RNA  length = 831
FEATURE                Location/Qualifiers
source                 1..831
                       mol_type = rRNA
                       organism = unidentified
                       note = DP46 16S rRNA sequence
SEQUENCE: 46
ttgaagagtt tgatcatggc tcagattgaa cgctggcggc aggcctaaca catgcaagtc  60
ggacggtagc acagaggagc ttgctccttg ggtgacgagt ggcggacggg tgagtaatgt  120
ctggggatct gcccgataga gggggataac cactggaaac ggtggctaat accgcataac  180
gtcgcaagac caaagagggg gaccttcggg cctctcacta tcggatgaac ccagatggga  240
```

-continued

```
ttagctagta ggcggggtaa tggcccacct aggcgacgat ccctagctgg tctgagagga  300
tgaccagcca cactggaact gagacacggt ccagactcct acgggaggca gcagtgggga  360
atattgcaca atgggcgcaa gcctgatgca gccatgccgc gtgtatgaag aaggccttcg  420
ggttgtaaag tactttcagc ggggaggaag gcgacagggt taataaccct gtcgattgac  480
gttacccgca gaagaagcac cggctaactc cgtgccagca gccgcggtaa tacggagggt  540
gcaagcgtta atcggaatta ctgggcgtaa agcgcacgca ggcggtctgt taagtcagat  600
gtgaaatccc cgggcttaac ctgggaactg catttgaaac tggcaggctt tagtcttgta  660
gagtggggta gaattccagg tgtagcggtg aaatgcgtag agatgtggag gaacaccagt  720
ggcgaaggcg gctttttggt ctgtaactga cgctgaggcg cgaaagcgtg gggagcaaac  780
aggattagat accctggtag tccacgccgt aaacgatgag tgctaagtgt t           831

SEQ ID NO: 47          moltype = RNA  length = 960
FEATURE                Location/Qualifiers
source                 1..960
                       mol_type = rRNA
                       organism = unidentified
                       note = DP47 16S rRNA sequence
SEQUENCE: 47
agggtgcaag cgttaatcgg aattactggg cgtaaagcgc gcgtaggtgg tttgttaagt  60
tgaatgtgaa atccccgggc tcaacctggg aactgcattt gaaactggca agctagagtc  120
tcgtagaggg gggtagaatt ccaggtgtag cggtgaaatg cgtagagatc tggaggaata  180
ccggtggcga aggcggcccc ctggacgaag actgacgctc aggtgcgaaa gcgtggggag  240
caaacaggat tagataccct ggtagtccac gccgtaaacg atgtcaacta gccgttggaa  300
gccttgagct tttagtggcg cagctaacgc attaagttga ccgcctgggg agtacggccg  360
caaggttaaa actcaaatga attgacgggg gcccgcacaa gcggtggagc atgtggttta  420
attcgaagca acgcgaagaa ccttaccagg ccttgacatc caatgaactt tctagagata  480
gattggtgcc ttcgggaaca ttgagacagg tgctgcatgg ctgtcgtcag ctcgtgtcgt  540
gagatgttgg gttaagtccc gcaacgagcg caacccttgt cctgtgttgc cagcgcgtaa  600
tggcggggac tcgcaggaga ctgccggggt caactcggag gaaggtgggg atgacgtcaa  660
atcatcatgc cccttatgtc ttgggcttca cgcatgctac aatggccggt acaaagggct  720
gcaataccgt gaggtggagc gaatcccaaa aagccggtcc cagttcggat tgaggtctgc  780
aactcgacct catgaagtcg gagtcgctag taatcgcaga tcagcaacgc tgcggtgaat  840
acgttcccgg gtcttgtaca caccgcccgt caagtcatga aagtcggtaa cacctgaagc  900
cggtggccca acccttgtgg agggagccgt cgaaggtggg atcggtaatt aggactaagt  960

SEQ ID NO: 48          moltype = RNA  length = 1548
FEATURE                Location/Qualifiers
source                 1..1548
                       mol_type = rRNA
                       organism = unidentified
                       note = DP48 16S rRNA sequence
SEQUENCE: 48
catggagagt ttgatcctgg ctcaggacga acgctggcgg cgtgcctaat acatgcaagt  60
cgagcggaca gatgggagct tgctccctga tgttagcggc ggacgggtga gtaacacgtg  120
ggtaacctgc ctgtaagact gggataactc cgggaaaccg gggctaatac cggatgcttg  180
attgaaccgc atggttcaat tataaaaggt ggcttttagc taccacttac agatggaccc  240
gcggcgcatt agctagttgg tgaggtaacg gctcaccaag gcaacgatgc gtagccgacc  300
tgagagggtg atcggccaca ctgggactga gacacggccc agactcctac gggaggcagc  360
agtagggaat cttccgcaat ggacgaaagt ctgacggagc aacgccgcgt gagtgatgaa  420
ggttttcgga tcgtaaaact ctgttgttag ggaagaacaa gtaccgttcg aatagggcgg  480
taccttgacg gtacctaacc agaaagccac ggctaactac gtgccagcag ccgcggtaat  540
acgtaggtgg caagcgttgt ccggaattat tgggcgtaaa gcgcgcgcag gcggtttctt  600
aagtctgatg tgaaagcccc cggctcaacc ggggagggtc attggaaact ggggaacttg  660
agtgcagaag aggagagtgg aattccacgt gtagcggtga aatgcgtaga gatgtggagg  720
aacaccagtg gcgaaggcga ctctctggtc tgtaactgac gctgaggcgc gaaagcgtgg  780
ggagcgaaca ggattagata ccctggtagt ccacgccgta aacgatgagt gctaagtgtt  840
agagggtttc cgccctttag tgctgcagca aacgcattaa gcactccgcc tggggagtac  900
ggtcgcaaga ctgaaactca aaggaattga cgggggcccg cacaagcggt ggagcatgtg  960
gtttaattcg aagcaacgcg aagaacctta ccaggtcttg acatcctctg acaaccctag  1020
agatagggct tccccttcgg gggcagagtg acaggtggtg catggttgtc gtcagctcgt  1080
gtcgtgagat gttgggttaa gtcccgcaac gagcgcaacc cttgatctta gttgccagca  1140
ttcagttggg cactctaagg tgactgccgg tgacaaaccg gaggaaggtg gggatgacgt  1200
caaatcatca tgccccttat gacctgggct acacacgtgc tacaatgggc agaacaaagg  1260
gcagcgaagc cgcgaggcta agccaatccc acaaatctgt tctcagttcg gatcgcagtc  1320
tgcaactcga ctgcgtgaag ctggaatcgc tagtaatcgc ggatcagcat gccgcggtga  1380
atacgttccc gggccttgta cacaccgccc gtcacaccac gagagtttgt aacacccgaa  1440
gtcggtgagg taaccttttg gagccagccg ccgaaggtgg gacagatgat tggggtgaag  1500
tcgtaacaag gtagccgtat cggaaggtgc ggctggatca cctccttt                1548

SEQ ID NO: 49          moltype = RNA  length = 1551
FEATURE                Location/Qualifiers
source                 1..1551
                       mol_type = rRNA
                       organism = unidentified
                       note = DP49 16S rRNA sequence
SEQUENCE: 49
tatggagagt ttgatcctgg ctcaggacga acgctggcgg cgtgcctaat acatgcaagt  60
cgagcggacg tttttgaagc ttgcttcaaa aacgttagcg gcggacgggt gagtaacacg  120
tgggcaacct gccttatcga ctgggataac tccgggaaac cggggctaat accggataat  180
```

```
atctagcacc tcctggtgca agattaaaag agggccttcg ggctctcacg gtgagatggg  240
cccgcggcgc attagctagt tggagaggta atggctcccc aaggcgacga tgcgtagccg  300
acctgagagg gtgatcggcc acactgggac tgagacacgg cccagactcc tacgggaggc  360
agcagtaggg aatcttccgc aatggacgaa agtctgacgg agcaacgccg cgtgagtgat  420
gaagggtttc ggctcgtaaa gctctgttat gagggaagaa cacgtaccgt tcgaataggg  480
cggtaccttg acggtacctc atcagaaagc cacggctaac tacgtgccag cagccgcggt  540
aatacgtagg tggcaagcgt tgtccggaat tattgggcgt aaagcgcgcg caggcggcct  600
tttaagtctg atgtgaaatc ttgcggctca accgcaagcg gtcattggaa actgggaggc  660
ttgagtacag aagaggagag tggaattcca cgtgtagcgg tgaaatgcgt agatatgtgg  720
aggaacacca gtggcgaagg cgactctctg gtctgtaact gacgctgagg cgcgaaagcg  780
tggggagcaa acaggattag ataccctggt agtccacgcc gtaaacgatg agtgctaggt  840
gttaggggtt tcgatgcccg tagtgccgaa gttaacacat taagcactcc gcctggggag  900
tacggccgca aggctgaaac tcaaaggaat tgacgggggc ccgcacaagc agtggagcat  960
gtggtttaat tcgaagcaac gcgaagaacc ttaccaggtc ttgacatcct ttgaccactc  1020
tggagacaga gcttcccctt cgggggcaaa gtgacaggtg gtgcatggtt gtcgtcagct  1080
cgtgtcgtga gatgttgggt taagtcccgc aacgagcgca acccttgacc ttagttgcca  1140
gcatttagtt gggcactcta aggtgactgc cggtgacaaa ccggaggaag gtggggatga  1200
cgtcaaatca tcatgcccct tatgacctgg gctacacacg tgctacaatg gatggtacaa  1260
agggttgcga agccgcgagg tgaagccaat cccataaagc cattctcagt tcggattgta  1320
ggctgcaact cgcctgcatg aagctggaat tgctagtaat cgcggatcag catgccgcgg  1380
tgaatacgtt cccgggcctt gtacacaccg cccgtcacac cacgagagtt tgtaacaccc  1440
gaagtcggtg aggtaacctt ttggagccag ccgccgaagg tgggacagat gattggggtg  1500
aagtcgtaac aaggtagccg tatcggaagg tgcggctgga tcacctcctt t           1551
```

```
SEQ ID NO: 50           moltype = RNA  length = 1536
FEATURE                 Location/Qualifiers
source                  1..1536
                        mol_type = rRNA
                        organism = unidentified
                        note = DP50 16S rRNA sequence
SEQUENCE: 50
ttgaagagtt tgatcatggc tcagattgaa cgctggcggc aggcctaaca catgcaagtc  60
gaacggtagc acagagagct tgctcttggg tgacgagtgg cggacgggtg agtaatgtct  120
gggaaactgc ccgatggagg gggataacta ctggaaacgg tagctaatac cgcataacgt  180
cgcaagacca aagtggggga ccttcgggcc tcacaccatc ggatgtgccc agatgggatt  240
agctagtagg tggggtaatg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagcga ggaggaaggc attgtggtta ataaccgcag tgattgacgt  480
tactcgcaga agaagcaccg gctaactccg tgccagcagc cgcggtaata cggagggtgc  540
aagcgttaat cggaattact gggcgtaaag cgcacgcagg cggtctgtca agtcggatgt  600
gaaatccccg ggctcaacct gggaactgca ttcgaaactg gcaggctaga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gtgcccttga  840
ggcgtggctt ccggagctaa cgcgttaagt cgaccgcctg gggagtacgg ccgcaaggtt  900
aaaactcaaa tgaattgacg ggggcccgca caagcggtgg agcatgtggt ttaattcgat  960
gcaacgcgaa gaaccttacc tactcttgac atccacggaa tttagcagag atgctttagt  1020
gccttcggga accgtgagac aggtgctgca tggctgtcgt cagctcgtgt tgtgaaatgt  1080
tgggttaagt cccgcaacga gcgcaacccc tatcctttgt tgccagcggt tcggccggga  1140
actcaaagga gactgccagt gataaactgg aggaaggtgg ggatgacgtc aagtcatcat  1200
ggcccttacg agtagggcta cacacgtgct acaatggcat atacaaagag aagcgacctc  1260
gcgagagcaa gcggacctca taaagtatgt cgtagtccgg atcggagtct gcaactcgac  1320
tccgtgaagt cggaatcgct agtaatcgta gatcagaatg ctacggtgaa tacgttcccg  1380
ggccttgtac acaccgcccg tcacaccatg ggagtgggtt gcaaaagaag taggtagctt  1440
aaccttcggg agggcgctta ccactttgtg attcatgact ggggtgaagt cgtaacaagg  1500
taaccgtagg ggaacctgcg gttggatcac ctcctt                           1536
```

```
SEQ ID NO: 51           moltype = RNA  length = 1537
FEATURE                 Location/Qualifiers
source                  1..1537
                        mol_type = rRNA
                        organism = unidentified
                        note = DP51 16S rRNA sequence
SEQUENCE: 51
ttgaagagtt tgatcatggc tcagattgaa cgctggcggc aggcctaaca catgcaagtc  60
gagcggtagc acagggagct tgctcctggg tgacgagcgg cggacgggtg agtaatgtct  120
gggaaactgc ctgatggagg gggataacta ctggaaacgg tagctaatac cgcataacgt  180
cgcaagacca aagaggggga ccttcgggcc tcttgccatc agatgtgccc agatgggatt  240
agctagtagg tgaggtaatg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagcga ggaggaaggc attaaggtta ataaccttgg tgattgacgt  480
tactcgcaga agaagcaccg gctaactccg tgccagcagc cgcggtaata cggggggtgc  540
aagcgttaat cggaattact gggcgtaaag cgcacgcagg cggtttgtca agtcggatgt  600
gaaatccccg ggctcaacct gggaactgca ttcgaaacgg gcaagctaga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gtgcccttga  840
```

-continued

```
ggcgtggctt ccggagctaa cgcgttaagt cgaccgcctg gggagtacgg ccgcaaggtt  900
aaaactcaaa tgaattgacg ggggcccgca caagcggtgg agcatgtggt ttaattcgat  960
gcaacgcgaa gaaccttacc tactcttgac atccagagaa ctttccagag atggattggt  1020
gccttcggga actctgagac aggtgctgca tggctgtcgt cagctcgtgt tgtgaaatgt  1080
tgggttaagt cccgcaacga gcgcaaccct tatcctttgt tgccagcgag taatgtcggg  1140
aactcaaagg agactgccag tgacaaactg gaggaaggtg gggatgacgt caagtcatca  1200
tggcccttac gagtagggct acacacgtgc tacaatggca tatacaaaga gaagcgacct  1260
cgcgagagca agcggacctc acaaagtatg tcgtagtccg gatcggagtc tgcaactcga  1320
ctccgtgaag tcggaatcgc tagtaatcgt agatcagaat gctacggtga atacgttccc  1380
gggccttgta cacaccgccc gtcacaccat gggagtgggt tgcaaaagaa gtaggtagct  1440
taaccttcgg gagggcgctt accactttgt gattcatgac tggggtgaag tcgtaacaag  1500
gtaaccgtag gggaacctgc ggttggatca cctcctt                           1537

SEQ ID NO: 52          moltype = RNA  length = 1517
FEATURE                Location/Qualifiers
source                 1..1517
                       mol_type = rRNA
                       organism = unidentified
                       note = DP52 16S rRNA sequence
SEQUENCE: 52
acggagagtt tgatcctggc tcaggatgaa cgctggcggc gtgcttaaca catgcaagtc  60
gaacgatgat cccagcttgc tgggggatta gtggcgaacg ggtgagtaac acgtgagtaa  120
cctgcccttg actctgggat aagcctggga aactgggtct aataccggat atgactgtct  180
gacgcatgtc aggtggtgga aagcttttgt ggttttggat ggactcgcgg cctatcagct  240
tgttggtggg gtaatggcct accaaggcga cgacgggtag ccggcctgag agggtgaccg  300
gccacactgg gactgagaca cggcccagac tcctacggga ggcagcagtg gggaatattg  360
cacaatgggc gcaagcctga tgcagcgacg ccgcgtgagg gatgacggcc ttcgggttgt  420
aaacctcttt cagtagggaa gaagcgaaag tgacggtacc tgcagaagaa gcgccggcta  480
actacgtgcc agcagccgcg gtaatacgta gggcgcaagc gttatccgga attattgggc  540
gtaaagagct cgtaggcggt ttgtcgcgtc tgctgtgaaa gaccggggct caactccggt  600
tctgcagtgg gtacgggcag actagagtgc agtaggggag actggaattc ctggtgtagc  660
ggtgaaatgc gcagatatca ggaggaacac cgatggcgaa ggcaggtctc tgggctgtaa  720
ctgacgctga ggagcgaaag catggggagc gaacaggatt agataccctg gtagtccatg  780
ccgtaaacgt tgggcactag gtgtggggga cattccacgt tttccgcgcc gtagctaacg  840
cattaagtgc cccgcctggg gagtacggcc gcaaggctaa aactcaaagg aattgacggg  900
ggcccgcaca agcggcggag catgcggatt aattcgatgc aacgcgaaga accttaccaa  960
ggcttgacat gaaccggtaa tacctggaaa caggtgcccc gcttgcggtc ggtttacagg  1020
tggtgcatgg ttgtcgtcag ctcgtgtcgt gagatgttgg gttaagtccc gcaacgagcg  1080
caaccctcgt tctatgttgc cagcgcgtta tggcggggac tcataggaga ctgccggggt  1140
caactcggag gaaggtgggg acgacgtcaa atcatcatgc cccttatgtc ttgggcttca  1200
cgcatgctac aatggccggt acaaagggtt gcgatactgt gaggtggagc taatcccaaa  1260
aagccggtct cagttcggat tggggtctgc aactcgaccc catgaagtcg gagtcgctag  1320
taatcgcaga tcagcaacgc tgcggtgaat acgttcccgg gccttgtaca caccgcccgt  1380
caagtcacga aagttggtaa cacccgaagc cggtggccta acccttgtgg ggggagccgt  1440
cgaaggtggg accggcgatt gggactaagt cgtaacaagg tagccgtacc ggaaggtgcg  1500
gctggatcac ctccttt                                                 1517

SEQ ID NO: 53          moltype = RNA  length = 1406
FEATURE                Location/Qualifiers
source                 1..1406
                       mol_type = rRNA
                       organism = unidentified
                       note = DP53 16S rRNA sequence
SEQUENCE: 53
tgaagagttt gatcatggct cagattgaac gctggcggca ggcctaacac atgcaagtcg  60
agcggtagag agaagcttgc ttctcttgag agcggcggac gggtgagtaa tacctaggaa  120
tctgcctgat agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggctac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggcagtt acctaatacg tgattgtctt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg aatgtgaaat  600
ccccgggctc aacctgggaa ctgcatccaa aactggcaag ctagagtatg gtagagggta  660
gtggaatttc ctgtgtagcg gtgaaatgcg tagatatagg aaggaacacc agtggcgaag  720
gcgactacct ggactgatac tgacactgag gtgcgaaagc gtggggagca aacaggatta  780
gataccctgg tagtccacgc cgtaaacgat gtcaactagc cgttgggagt cttgaactct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc tagagataga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgtaatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgtgaatc agaatgtcac ggtgaatacg ttcccgggcc  1380
ttgtacacac cgcccgtcac accatg                                       1406
```

```
SEQ ID NO: 54          moltype = RNA  length = 1136
FEATURE                Location/Qualifiers
source                 1..1136
                       mol_type = rRNA
                       organism = unidentified
                       note = DP54 16S rRNA sequence
SEQUENCE: 54
cttgagagtt tgatcctggc tcagagcgaa cgctggcggc aggcttaaca catgcaagtc  60
gagcgggcac cttcgggtgt cagcggcaga cgggtgagta acacgtggga acgtaccctt  120
cggttcggaa taacgctggg aaactagcgc taataccgga tacgcccttt tggggaaagg  180
tttactgccg aaggatcggc ccgcgtctga ttagctagtt ggtggggtaa cggcctacca  240
aggcgacgat cagtagctgg tctgagagga tgatcagcca cactgggact gagacacggc  300
ccagactcct acgggaggca gcagtgggga atattggaca atgggcgcaa gcctgatcca  360
gccatgccgc gtgagtgatg aaggccttag ggttgtaaag ctcttttgtc cgggacgata  420
atgacggtac cggaagaata agccccggct aacttcgtgc cagcagccgc ggtaatacga  480
agggggctag cgttgctcgg aatcactggg cgtaaagggc gcgtaggcgg ccattcaagt  540
cgggggtgaa agcctgtggc tcaaccacag aattgccttc gatactgttt ggcttgagtt  600
tggtagaggt tggtggaact gcgagtgtag aggtgaaatt cgtagatatt cgcaagaaca  660
ccagtggcga aggcggccaa ctggaccaat actgacgctg aggcgcgaaa gcgtggggag  720
caaacaggat tagataccct ggtagtccac gccgtaaacg atgaatgcta gctgttgggg  780
tgcttgcacc tcagtagcgc agctaacgct ttaagcattc cgcctgggga gtacggtcgc  840
aagattaaaa ctcaaaggaa ttgacggggg cccgcacaag cggtggagca tgtggtttaa  900
ttcgaagcaa cgcgcagaac cttaccatcc cttgacatgt cgtgccatcc ggagagatcc  960
ggggttccct tcggggacgc gaacacaggt gctgcatggc tgtcgtcagc tcgtgtcgtg  1020
agatgttggg ttaagtcccg caacgagcgc aacccacgtc cttagttgcc atcatttagt  1080
tgggcactct agggagactg ccggtgataa gccgcgagga aggtgtggat gacgtc      1136

SEQ ID NO: 55          moltype = RNA  length = 1374
FEATURE                Location/Qualifiers
source                 1..1374
                       mol_type = rRNA
                       organism = unidentified
                       note = DP55 16S rRNA sequence
SEQUENCE: 55
tcggagagtt tgatcctggc tcaggatgaa cgctggcggc gtgcctaata catgcaagtc  60
gagcgaactg attagaagct tgcttctatg acgttagcgg cggacgggtg agtaacacgt  120
gggcaacctg cctgtaagac tgggataact tcgggaaacc gaagctaata ccggatagga  180
tcttctcctt catgggagat gattgaaaga tggtttcggc tatcacttac agatgggccc  240
gcggtgcatt agctagttgg tgaggtaacg gctcaccaag gcaacgatgc atagccgacc  300
tgagagggtg atcggccaca ctgggactga gacacggccc agactcctac gggaggcagc  360
agtagggaat cttccgcaat ggacgaaagt ctgacggagc aacgccgcgt gagtgatgaa  420
ggctttcggg tcgtaaaact ctgttgttag ggaagaacaa gtacaagagt aactgcttgt  480
accttgacgg tacctaacca gaaagccacg gctaactacg tgccagcagc cgcggtaata  540
cgtaggtggc aagcgttatc cggaattatt gggcgtaaag cgcgcgcagg cggtttctta  600
agtctgatgt gaaagcccac ggctcaaccg tggagggtca ttggaaactg gggaacttga  660
gtgcagaaga gaaaagcgga attccacgtg tagcggtgaa atgcgtagag atgtggagga  720
acaccagtgg cgaaggcggc tttttggtct gtaactgacg ctgaggcgcg aaagcgtggg  780
gagcaaacag gattagatac cctggtagtc cacgccgtaa acgatgagtg ctaagtgtta  840
gagggtttcc gccctttagt gctgcagcta acgcattaag cactccgcct ggggagtacg  900
gtcgcaagac tgaaactcaa aggaattgac gggggcccgc acaagcggtg gagcatgtgg  960
tttaattcga agcaacgcga agaaccttac caggtcttga catcctctga caactctaga  1020
gatagagcgt tccccttcgg gggacagagt gacaggtggt gcatggttgt cgtcagctcg  1080
tgtcgtgaga tgttgggtta agtcccgcaa cgagcgcaac ccttgatctt agttgccagc  1140
atttagttgg gcactctaag gtgactgccg gtgacaaacc ggaggaaggt ggggatgacg  1200
tcaaatcatc atgcccctta tgacctgggc tacacacgtg ctacaatgga tggtacaaag  1260
ggctgcaaga ccgcgaggtc aagccaatcc cataaaacca ttctcagttc ggattgtagg  1320
ctgcaactcg cctacatgaa gctggaatcg ctagtaatcg cggatcagca tgct        1374

SEQ ID NO: 56          moltype = RNA  length = 1554
FEATURE                Location/Qualifiers
source                 1..1554
                       mol_type = rRNA
                       organism = unidentified
                       note = DP56 16S rRNA sequence
SEQUENCE: 56
attggagagt ttgatcctgg ctcaggacga acgctggcgg cgtgcctaat acatgcaagt  60
cgagcggacc tgatggagtg cttgcactcc tgatggttag cggcggacgg gtgagtaaca  120
cgtaggcaac ctgccctcaa gactgggata actaccggaa acggtagcta ataccggata  180
atttatttca cagcattgtg gaataatgaa agacggagca atctgtcact tggggatggg  240
cctgcggcgc attagctagt tggtggggta acggctcacc aaggcgacga tgcgtagccg  300
acctgagagg gtgaacggcc acactgggac tgagacacgg cccagactcc tacgggaggc  360
agcagtaggg aatcttccgc aatgggcgaa agcctgacgg agcaacgccg cgtgagtgat  420
gaaggttttc ggatcgtaaa gctctgttgc caaggaagaa cgtcttctag agtaactgct  480
aggagagtga cggtacttga gaagaaagcc ccggctaact acgtgccagc agccgcggta  540
atacgtaggg ggcaagcgtt gtccggaatt attgggcgta aagcgcgcgc aggcggttct  600
ttaagtctgg tgtttaaacc cgaggctcaa cttcgggtcg cactggaaac tggggaactt  660
gagtgcagaa gaggagagtg gaattccacg tgtagcggtg aaatgcgtag atatgtggag  720
gaacaccagt ggcgaaggcg actctctggg ctgtaactga cgctgaggcg cgaaagcgtg  780
gggagcaaac aggattagat accctggtag tccacgccgt aaacgatgaa tgctaggtgt  840
```

```
taggggtttc gataccettg gtgccgaagt taacacatta agcattccgc ctggggagta  900
cggtcgcaag actgaaactc aaaggaattg acggggaccc gcacaagcag tggagtatgt  960
ggtttaattc gaagcaacgc gaagaacctt accaagtctt gacatccctc tgaatcctct  1020
agagatagag gcggccttcg ggacagaggt gacaggtggt gcatggttgt cgtcagctcg  1080
tgtcgtgaga tgttgggtta agtcccgcaa cgagcgcaac ccttgatttt agttgccagc  1140
acatcatggt gggcactcta gaatgactgc cggtgacaaa ccggaggaag gcggggatga  1200
cgtcaaatca tcatgcccct tatgacttgg gctacacacg tactacaatg gctggtacaa  1260
cgggaagcga agccgcgagg tggagccaat cctataaaag ccagtctcag ttcggattgc  1320
aggctgcaac tcgcctgcat gaagtcggaa ttgctagtaa tcgcggatca gcatgccgcg  1380
gtgaatacgt tcccgggtct tgtacacacc gcccgtcaca ccacgagagt ttacaacacc  1440
cgaagtcggt ggggtaaccc gcaagggagc cagccgccga aggtggggta gatgattggg  1500
gtgaagtcgt aacaaggtag ccgtatcgga aggtgcggct ggatcacctc cttt        1554

SEQ ID NO: 57          moltype = RNA  length = 1550
FEATURE                Location/Qualifiers
source                 1..1550
                       mol_type = rRNA
                       organism = unidentified
                       note = DP57 16S rRNA sequence
SEQUENCE: 57
attggagagt ttgatcctgg ctcaggatga acgctggcgg cgtgcctaat acatgcaagt  60
cgagcgaatg gattaagagc ttgctcttat gaagttagcg gcggacgggt gagtaacacg  120
tgggtaacct gcccataaga ctgggataac tccgggaaac cggggctaat accggataac  180
atttgcacc gcatggtgcg aaattcaaag gcggcttcgg ctgtcactta tggatggacc  240
cgcgtcgcat tagctagttg gtgaggtaac ggctcaccaa ggcaacgatg cgtagccgac  300
ctgagagggt gatcggccac actgggactg agacacggcc cagactccta cgggaggcag  360
cagtagggaa tcttccgcaa tggacgaaag tctgacggag caacgccgcg tgagtgatga  420
aggctttcgg gtcgtaaaac tctgttgtta gggaagaaca agtgctagtt gaataagctg  480
gcaccttgac ggtacctaac cagaaagcca cggctaacta cgtgccagca gccgcggtaa  540
tacgtaggtg gcaagcgtta tccggaatta ttgggcgtaa agcgcgcgca ggtggtttct  600
taagtctgat gtgaaagccc acggctcaac cgtggagggt cattggaaac tgggagactt  660
gagtgcagaa gaggaaagtg gaattccatg tgtagcggtg aaatgcgtag agatatggag  720
gaacaccagt ggcgaaggcg actttctggt ctgtaactga cactgaggcg cgaaagcgtg  780
gggagcaaac aggattagat accctggtag tccacgccgt aaacgatgag tgctaagtgt  840
tagagggttt ccgcccttta gtgctgaagt taacgcatta agcactccgc ctggggagta  900
cggccgcaag gctgaaactc aaaggaattg acgggggccc gcacaagcgg tggagcatgt  960
ggtttaattc gaagcaacgc gaagaacctt accaggtctt gacatcctct gacaacccta  1020
gagatagggc ttccccttcg gggcagagt gacaggtggt gcatggttgt cgtcagctcg  1080
tgtcgtgaga tgttgggtta agtcccgcaa cgagcgcaac ccttgatctt agttgccatc  1140
attaagttgg gcactctaag gtgactgccg gtgacaaacc ggaggaaggt ggggatgacg  1200
tcaaatcatc atgcccctta tgacctgggc tacacacgtg ctacaatgga cggtacaaag  1260
agctgcaaga ccgcgaggtg gagctaatct cataaaaccg ttctcagttc ggattgtagg  1320
ctgcaactcg cctacatgaa gctggaatcg ctagtaatcg cggatcagca tgccgcggtg  1380
aatacgttcc cgggccttgt acacaccgcc cgtcacacca cgagagtttg taacacccga  1440
agtcggtggg gtaacctttt tggagccagc cgcctaaggt gggacagatg attggggtga  1500
agtcgtaaca aggtagccgt atcggaaggt gcggctggat cacctccttt             1550

SEQ ID NO: 58          moltype = RNA  length = 1060
FEATURE                Location/Qualifiers
source                 1..1060
                       mol_type = rRNA
                       organism = unidentified
                       note = DP58 16S rRNA sequence
SEQUENCE: 58
aatgacggta cctgaagaat aagcaccggc taactacgtg ccagcagccg cggtaatacg  60
tagggtgcaa gcgttaatcg gaattactgg gcgtaaagcg tgcgcaggcg gttttgtaag  120
tctgatgtga aatccccggg ctcaacctgg gaattgcatt ggagactgca aggctagaat  180
ctggcagagg ggggtagaat tccacgtgta gcagtgaaat gcgtagatat gtggaggaac  240
accgatggcg aaggcagccc cctgggtcaa gattgacgct catgcacgaa agcgtgggga  300
gcaaacagga ttagataccc tggtagtcca cgccctaaac gatgtctact agttgtcggg  360
tcttaattga cttggtaacg cagctaacgc gtgaagtaga ccgcctgggg agtacggtcg  420
caagattaaa actcaaagga attgacgggg acccgcacaa gcggtggatg atgtggatta  480
attcgatgca acgcgaaaaa ccttacctac ccttgacatg gctggaatcc tcgagagatt  540
ggggagtgct cgaaagagaa ccagtacaca ggtgctgcat ggctgtcgtc agctcgtgtc  600
gtgagatgtt gggttaagtc ccgcaacgag cgcaaccctt gtcattagtt gctacgaaag  660
ggcactctaa tgagactgcc ggtgacaaac cggaggaagg tggggatgac gtcaagtcct  720
catggccctt atgggtaggg cttcacacgt catacaatgg tacatacaga gcgccgccaa  780
cccgcgaggg ggagctaatc gcagaaagtg tatcgtagtc cggattgtag tctgcaactc  840
gactgcatga agttggaatc gctagtaatc gcggatcagc atgtcgcggt gaatacgttc  900
ccgggtcttg tacacaccgc ccgtcacacc atgggagcgg gttttaccag aagtaggtag  960
cttaaccgta aggagggcgc ttaccacggt aggattcgtg actggggtga agtcgtaaca  1020
aggtagccgt atcggaaggt gcggctggat cacctccttt                        1060

SEQ ID NO: 59          moltype = RNA  length = 1538
FEATURE                Location/Qualifiers
source                 1..1538
                       mol_type = rRNA
                       organism = unidentified
                       note = DP59 16S rRNA sequence
```

```
SEQUENCE: 59
ttgaagagtt tgatcatggc tcagattgaa cgctggcggc aggcctaaca catgcaagtc  60
gaacggtaac aggaagcagc ttgctgcttt gctgacgagt ggcggacggg tgagtaatgt  120
ctgggaaact gcctgatgga gggggataac tactggaaac ggtagctaat accgcataac  180
gtcgcaagac caaagagggg gaccttcggg cctcttgcca tcagatgtgc ccagatggga  240
ttagctagta ggtggggtaa cggctcacct aggcgacgat ccctagctgg tctgagagga  300
tgaccagcca cactggaact gagacacggt ccagactcct acgggaggca gcagtgggga  360
atattgcaca atgggcgcaa gcctgatgca gccatgccgc gtgtatgaag aaggccttcg  420
ggttgtaaag tactttcagc ggggaggaag gcgatgcggt taataaccgc gtcgattgac  480
gttacccgca gaagaagcac cggctaactc cgtgccagca gccgcggtaa tacggagggt  540
gcaagcgtta atcggaatta ctgggcgtaa agcgcacgca ggcggtctgt caagtcggat  600
gtgaaatccc cgggctcaac ctgggaactg catccgaaac tggcaggctt gagtctcgta  660
gaggggggta gaattccagg tgtagcggtg aaatgcgtag agatctggag gaataccggt  720
ggcgaaggcg gccccctgga cgaagactga cgctcaggtg cgaaagcgtg gggagcaaac  780
aggattagat accctggtag tccacgccgt aaacgatgtc gacttggagg ttgtgccctt  840
gaggcgtggc ttccggagct aacgcgttaa gtcgaccgcc tggggagtac ggccgcaagg  900
ttaaaactca aatgaattga cgggggcccg cacaagcggt ggagcatgtg gtttaattcg  960
atgcaacgcg aagaacctta cctggtcttg acatccacag aacttggcag agatgccttg  1020
gtgccttcgg gaactgtgag acaggtgctg catggctgtc gtcagctcgt gttgtgaaat  1080
gttgggttaa gtcccgcaac gagcgcaacc cttatccttt gttgccagcg gttaggccgg  1140
gaactcaaag gagactgcca gtgataaact ggaggaaggt ggggatgacg tcaagtcatc  1200
atggccctta cgaccagggc tacacacgtg ctacaatggc gcatacaaag agaagcgatc  1260
tcgcgagagc cagcggacct cataaagtgc gtcgtagtcc ggattggagt ctgcaactcg  1320
actccatgaa gtcggaatcg ctagtaatcg tgaatcagaa tgtcacggtg aatacgttcc  1380
cgggccttgt acacaccgcc cgtcacacca tgggagtggg ttgcaaaaga agtaggtagc  1440
ttaaccttcg ggagggcgct taccactttg tgattcatga ctggggtgaa gtcgtaacaa  1500
ggtaaccgta ggggaacctg cggttggatc acctcctt                          1538

SEQ ID NO: 60          moltype = RNA  length = 1547
FEATURE                Location/Qualifiers
source                 1..1547
                       mol_type = rRNA
                       organism = unidentified
                       note = DP60 16S rRNA sequence
SEQUENCE: 60
tcggagagtt tgatcctggc tcaggacgaa cgctggcggc gtgcctaata catgcaagtc  60
gagcgaatcg atgggagctt gctccctgag attagcggcg gacgggtgag taacacgtgg  120
gcaacctgcc tataagactg ggataacttc gggaaaccgg agctaatacc ggatacgttc  180
ttttctcgca tgagagaaga tggaaagacg gttttgctgt cacttataga tgggcccgcg  240
gcgcattagc tagttggtga ggtaatggct caccaaggcg acgatgcgta gccgacctga  300
gagggtgatc ggccacactg ggactgagac acggcccaga ctcctacggg aggcagcagt  360
agggaatctt ccgcaatgga cgaaagtctg acggagcaac gccgcgtgaa cgaagaaggc  420
cttcgggtcg taaagttctg ttgttaggga agaacaagta ccagagtaac tgctggtacc  480
ttgacggtac ctaaccagaa agccacggct aactacgtgc cagcagccgc ggtaatacgt  540
aggtggcaag cgttgtccgg aattattggg cgtaaagcgc gcgcaggtgg ttccttaagt  600
ctgatgtgaa agcccacggc tcaaccgtgg agggtcattg gaaactgggg aacttgagtg  660
cagaagagga aagtggaatt ccaagtgtag cggtgaaatg cgtagagatt tggaggaaca  720
ccagtggcga aggcgacttt ctggtctgta actgacactg aggcgcgaaa gcgtggggag  780
caaacaggat tagataccct ggtagtccac gccgtaaacg atgagtgcta agtgttagag  840
ggtttccgcc ctttagtgct gcagctaacg cattaagcac tccgcctggg gagtacggcc  900
gcaaggctga aactcaaagg aattgacggg ggcccgcaca agcggtggag catgtggttt  960
aattcgaagc aacgcgaaga accttaccag gtcttgacat cctctgacaa ccctagagat  1020
agggcgttcc ccttcggggg acagagtgac aggtggtgca tggttgtcgt cagctcgtgt  1080
cgtgagatgt tgggttaagt cccgcaacga gcgcaaccct tgatcttagt tgccagcatt  1140
cagttgggca ctctaaggtg actgccggtg acaaaccgga ggaaggtggg gatgacgtca  1200
aatcatcatg ccccttatga cctgggctac acacgtgcta caatggatgg tacaaagggc  1260
tgcaaacctg cgaaggtaag cgaatcccat aaagccattc tcagttcgga ttgtaggctg  1320
caactcgcct acatgaagcc ggaatcgcta gtaatcgcgg atcagcatgc cgcggtgaat  1380
acgttcccgg gccttgtaca caccgcccgt cacaccacga gagtttgtaa cacccgaagt  1440
cggtgaggta acctttatgg agccagccgc ctaaggtggg acagatgatt ggggtgaagt  1500
cgtaacaagg tagccgtatc ggaaggtgcg gctggatcac ctccttt                1547

SEQ ID NO: 61          moltype = RNA  length = 962
FEATURE                Location/Qualifiers
source                 1..962
                       mol_type = rRNA
                       organism = unidentified
                       note = DP61 16S rRNA sequence
SEQUENCE: 61
ggaaggcggt ctgtcaagtc ggatgtgaaa tccccgggct caacctggga actgcattcg  60
aaactggcag gctagagtct tgtagagggg ggtagaattc caggtgtagc ggtgaaatgc  120
gtagagatct ggaggaatac cggtggcgaa ggcggccccc tggacaaaga ctgacgctca  180
ggtgcgaaag cgtggggagc aaacaggatt agataccctg gtagtccacg ccgtaaacga  240
tgtcgacttg gaggttgttc ccttgaggag tggcttccgg agctaacgcg ttaagtcgac  300
cgcctgggga gtacggccgc aaggttaaaa ctcaaatgaa ttgacggggg cccgcacaag  360
cggtggagca tgtggtttaa ttcgatgcaa cgcgaagaac cttacctact cttgacatcc  420
acggaattta gcagagatgc tttagtgcct tcgggaaccg tgagacaggt gctgcatggc  480
tgtcgtcagc tcgtgttgtg aaatgttggg ttaagtcccg caacgagcgc aacccttatc  540
ctttgttgcc agcggtccgg ccgggaactc aaaggagact gccagtgata aactggagga  600
```

```
aggtggggat gacgtcaagt catcatggcc cttacgagta gggctacaca cgtgctacaa  660
tggcgcatac aaagagaagc gacctcgcga gagcaagcgg acctcataaa gtgcgtcgta  720
gtccggatcg gagtctgcaa ctcgactccg tgaagtcgga atcgctagta atcgtagatc  780
agaatgctac ggtgaatacg ttcccgggcc ttgtacacac cgcccgtcac accatgggag  840
tgggttgcaa aagaagtagg tagcttaacc ttcgggaggg cgcttaccac tttgtgattc  900
atgactgggg tgaagtcgta acaaggtaac cgtaggggaa cctgcggttg gatcacctcc  960
tt                                                                 962

SEQ ID NO: 62          moltype = RNA  length = 876
FEATURE                Location/Qualifiers
source                 1..876
                       mol_type = rRNA
                       organism = unidentified
                       note = DP62 16S rRNA sequence
SEQUENCE: 62
tggctcagat tgaacgctgg cggcaggcct aacacatgca agtcgaacgg tagcacagag  60
gagcttgctc cttgggtgac gagtggcgga cgggtgagta atgtctggga aactgcccga  120
tggaggggga taactactgg aaacggtagc taataccgca taacgtcttc ggaccaaagt  180
gggggacctt cgggcctcac accatcggat gtgcccagat gggattagct agtaggtggg  240
gtaatggctc acctaggcga cgatccctag ctggtctgag aggatgacca gccacactgg  300
aactgagaca cggtccagac tcctacggga ggcagcagtg gggaatattg cacaatgggc  360
gcaagcctga tgcagccatg ccgcgtgtat gaagaaggcc ttcgggttgt aaagtacttt  420
cagtggggag gaaggcgtta aggttaataa ccttggcgat tgacgttacc cgcagaagaa  480
gcaccggcta actccgtgcc agcagccgcg gtaatacgga gggtgcaagc gttaatcgga  540
attactgggc gtaaagcgca cgcaggcggt ctgtcaagtc ggatgtgaaa tccccgggct  600
caacctggga actgcattcg aaactggcag gctagagtct tgtagagggg ggtagaattc  660
caggtgtagc ggtgaaatgc gtagagatct ggaggaatac cggtggcgaa ggcggccccc  720
tggacaaaga ctgacgctca ggtgcgaaag cgtggggagc aaacaggatt agataccctg  780
gtagtccacg ccgtaaacga tgtcgacttg gaggttgttc ccttgaggag tggcttccgg  840
agctaacgcg ttaagtcgac cgcctgggga gtacgg                            876

SEQ ID NO: 63          moltype = RNA  length = 1532
FEATURE                Location/Qualifiers
source                 1..1532
                       mol_type = rRNA
                       organism = unidentified
                       note = DP63 16S rRNA sequence
SEQUENCE: 63
tgaagagttt gatcatggct cagattgaac gctggcggca ggcctaacac atgcaagtcg  60
agcggtagag agaagcttgc ttctcttgag agcggcggac gggtgagtaa tgcctaggaa  120
tctgcctggt agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggcgac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggttgta gattaatact ctgcaatttt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg gatgtgaaat  600
ccccgggctc aacctgggaa ctgcattcaa aactgactga ctagagtatg gtagagggtg  660
gtggaatttc ctgtgtagcg gtgaaatgcg tagatatagg aaggaacacc agtggcgaag  720
gcgaccacct ggactaatac tgacactgag gtgcgaaagc gtggggagca aacaggatta  780
gataccctgg tagtccacgc cgtaaacgat gtcaactagc cgttggaagc cttgagcttt  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc tagagataga ttggtgcctt  1020
cgggaacatt gagacaggtg ctgcatggct gtcgtcagct cgtgtcgtga gatgttgggt  1080
taagtcccgt aacgagcgca acccttgttc ttagttacca gcacgttatg gtgggcactc  1140
taaggagact gccggtgaca aaccggagga aggtggggat gacgtcaagt catcatggcc  1200
cttacggcct gggctacaca cgtgctacaa tggtcggtac agagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac accatgggag tgggttgcac cagaagtagc tagtctaacc  1440
ttcgggagga cggttaccac ggtgtgattc atgactgggg tgaagtcgta acaaggtagc  1500
cgtaggggaa cctgcggctg gatcacctcc tt                                1532

SEQ ID NO: 64          moltype = DNA  length = 1649
FEATURE                Location/Qualifiers
source                 1..1649
                       mol_type = genomic DNA
                       organism = unidentified
                       note = DP64 ITS sequence
SEQUENCE: 64
tccgtaggtg aacctgcgga aggatcatta aataatcaat aattttggct tgtccattat  60
tatctattta ctgtgaactg tattattact tgacgcttga gggatgctcc actgctataa  120
ggataggcgg tggggatgtt aaccgagtca tagtcaagct taggcttggt atcctattat  180
tatttaccaa aagaattcag aattaatatt gtaacataga cctaaaaaat ctataaaaca  240
acttttaaca acggatctct tggttctcgc atcgatgaag aacgtagcaa agtgcgataa  300
ctagtgtgaa ttgcatattc agtgaatcat cgagtctttg aacgcaactt gcgctcattg  360
gtattccaat gagcacgcct gtttcagtat caaaacaaac cctctattca atatttttgt  420
```

```
tgaataggaa tactgagagt ctcttgatct tttctgatct cgaacctctt gaaatgtaca  480
aaggcctgat cttgtttgaa tgcctgaact ttttttaat ataaagagaa gctcttgcgg  540
taaactgtgc tggggcctcc caaataatac tctttttaaa tttgatctga aatcaggcgg  600
gattacccgc tgaacttaag catatcaata agcggaggaa aagaaaataa caatgatttc  660
cctagtaacg gcgagtgaag aggaaagagc tcaaagttgg aaactgtttg gcttagctaa  720
accgtattgt aaactgtaga aacattttcc tggcacgccg gattaataag tcctttggaa  780
caaggcatca tggagggtga gaatcccgtc tttgatccga gtagttgtct tttgtgatat  840
gttttcaaag agtcaggttg tttgggaatg cagcctaaat tgggtggtaa atctcaccta  900
aagctaaata tttgcgagag accgatagcg aacaagtacc gtgagggaaa gatgaaaaga  960
actttgaaaa gagagttaaa cagtatgtga aattgttaaa agggaaccgt ttggagccag  1020
actggtttga ctgtaatcaa cctagaattc gttctgggtg cacttgcagt ctatacctgc  1080
caacaacagt ttgatttgga ggaaaaaatt agtaggaatg tagcctctcg aggtgttata  1140
gcctactatc atactctgga ttggactgag gaacgcagcg aatgccatta ggcgagattg  1200
ctgggtgctt tcgctaataa atgttagaat ttctgcttcg ggtggtgcta atgtttaaag  1260
gaggaacaca tctagtatat tttttattcg cttaggttgt tggcttaatg actctaaatg  1320
acccgtcttg aaacacggac caaggagtcc accataagtg caagtatttg agtgacaaac  1380
tcatatgcgt aaggaaactg attgatacga aatcttttga tggcagtatc acccggcgtt  1440
gacgttttat actgaactga ccgaggtaaa gcacttatga tgggacccga aagatggtga  1500
actatgcctg aatagggtga agccagagga aactctggtg gaggctcgta gcgattctga  1560
cgtgcaaatc gatcgtcaaa tttgggtata ggggcgaaag actaatcgaa ccatctagta  1620
gctggttcct gccgaagttt ccctcagga                                    1649

SEQ ID NO: 65          moltype = DNA  length = 1498
FEATURE                Location/Qualifiers
source                 1..1498
                       mol_type = genomic DNA
                       organism = unidentified
                       note = DP65 ITS sequence
SEQUENCE: 65
tccgtaggtg aacctgcgga aggatcatta ttgaaaacaa gggtgtccaa tttaacttgg  60
aacccgaact tctcaattct aactttgtgc atctgtatta tggcgagcag tcttcggatt  120
gtgagccttc acttataaac actagtctat gaatgtaaaa tttttataac aaataaaaac  180
tttcaacaac ggatctcttg gctctcgcat cgatgaagaa cgcagcgaaa tgcgatacgt  240
aatgtgaatt gcagaattca gtgaatcatc gaatctttga acgcatcttg cgctctctgg  300
tattccggag agcatgtctg tttgagtgtc atgaattctt caacccaatc ttttcttgta  360
atcgattggt gtttggattt tgagcgctgc tggcttcggc ctagctcgtt cgtaatacat  420
tagcatccct aatacaagtt tggattgact tggcgtaata gactattcgc taaggattcg  480
gtggaaacat cgagccaact tcattaagga agctcctaat ttaaaagtct accttttgat  540
tagatctcaa atcaggcagg attacccgct gaacttaagc atatcaataa gcggaggaaa  600
agaaactaac aaggattccc ctagtagcgg cgagcgaagc gggaaaagct caaatttgta  660
atctggcgtc ttcgacgtcc gagttgtaat ctcgagaagt gttttccgtg atagaccgca  720
tacaagtctc ttggaacaga gcgtcatagt ggtgagaacc cagtacacga tgcggatgcc  780
tattactttg tgatacactt tcgaagagtc gagttgtttg ggaatgcagc tcaaattggg  840
tggtaaattc catctaaagc taaatattgg cgagagaccg atagcgaaca agtaccgtaa  900
gggaaagatg aaaagcactt tggaaagaga gttaacagta cgtgaaattg ttggaaggga  960
aacacatgca gtgatacttg ctattcgggg caactcgatt ggcaggcccg catcagtttt  1020
tcggggcgga aaagcgtaga gagaaggtag caatttcggt tgtgttatag ctctttactg  1080
gattcgccct gggggactga ggaacgcagc gtgcttttag caattccttc gggaattcca  1140
cgcttaggat gcgggtttat ggctgtatat gacccgtctt gaaacacgga ccaaggagtc  1200
taacatgctt gcgagtattt gggtgtcaaa cccggatgcg caatgaaagt gaatggaggt  1260
gggaagcgca agctgcacca tcgaccgatc tggatttttt aagatggatt tgagtaagag  1320
caagtatgtt gggacccgaa agatggtgaa ctatgcctga atagggcgaa gccagaggaa  1380
actctggtgg aggctcgtag cggttctgac gtgcaaatcg atcgtcaaat ttgggtatag  1440
gggcgaaaga ctaatcgaac catctagtag ctggttcctg ccgaagtttc cctcagga    1498

SEQ ID NO: 66          moltype = DNA  length = 1340
FEATURE                Location/Qualifiers
source                 1..1340
                       mol_type = genomic DNA
                       organism = unidentified
                       note = DP66 ITS sequence
SEQUENCE: 66
tccgtaggtg aacctgcgga aggatcatta ctgtgattta tccaccacac tgcgtgggcg  60
acacgaaaca ccgaaaccga acgcacgccg tcaagcaaga aatccacaaa actttcaaca  120
acggatctct tggttctcgc atcgatgaag agcgcagcga aatgcgatac ctagtgtgaa  180
ttgcagccat cgtgaatcat cgagttcttg aacgcacatt gcgcccgctg gtattccggc  240
gggcatgcct gtctgagcgt cgtttccttc ttggagcgga gcttcagacc tggcgggctg  300
tctttcggga cggcgcgccc aaagcgaggg gccttctgcg cgaactagac tgtgcgcgcg  360
gggcggccgg cgaacttata ccaagctcga cctcagatca ggcaggagta cccgctgaac  420
ttaagcatat caataagcgg aggaaaagaa accaacaggg attgccccag tagcggcgag  480
tgaagcggca aaagctcaga tttggaatcg cttcggcgag ttgtgaattg caggttggcg  540
cctctgcggc ggcggcggtc caagtccctt ggaacagggc gccattgagg gtgagagccc  600
cgtgggaccg tttgcctatg ctctgaggcc cttctgacga gtcgagttgt ttgggaatgc  660
agctctaagc gggtggtaaa ttccatctaa ggctaaatac tggcgagaga ccgatagcga  720
acaagtactg tgaaggaaag atgaaaagca ctttgaaaag agagtgaaac agcacgtgaa  780
attgttgaaa gggaagggta ttgcgcccga catggagcgt gcgcaccgct gcccctcgtg  840
ggcggcgctc tgggcgtgct ctgggccagc atcggttttt gccgcgggag aagggcggcg  900
ggcatgtagc tcttcggagt gttatagcct gccgccggcg ccgcgagcgg ggaccgagga  960
ctgcgacttt tgtctcggat gctggcacaa cggcgcaaca ccgcccgtct tgaaacatgg  1020
```

```
accaaggagt ctaacgtcta tgcgagtgtt tgggtgtgaa accccgggcg cgtaatgaaa  1080
gtgaacgtag gtcggaccgc tcctctcggg gggcgggcac gatcgaccga tcctgatgtc  1140
ttcggatgga tttgagtaag agcatagctg ttgggacccg aaagatggtg aactatgcct  1200
gaatagggtg aagccagagg aaactctggt ggaggctcgt agcggttctg acgtgcaaat  1260
cgatcgtcga atttgggtat aggggcgaaa gactaatcga accatctagt agctggttcc  1320
tgccgaagtt tccctcagga                                               1340

SEQ ID NO: 67          moltype = DNA  length = 1698
FEATURE                Location/Qualifiers
source                 1..1698
                       mol_type = genomic DNA
                       organism = unidentified
                       note = DP53 Glutamine--tRNA ligase sequence
SEQUENCE: 67
atgagcaagc ccactgtcga ccccactctg aatccaaagg ctggccctgc tgtcccggct  60
aacttcctgc gtccaatcgt tcaggcggac ctagactcgg gtaaatacac acagatcgtg  120
acccgctttc cgccggagcc aaacggctat ctgcacatcg gtcatgccaa atccatttgt  180
gtgaactttg ggctggctca agagtttggc ggcgtgacgc atttgcgttt tgacgacacc  240
aacccggcaa aagaagacca ggaatacatc gacgccatcg aaagcgacgt caagtggctg  300
ggcttcgagt gggccggtga agtgcgttac gcgtcgcaat acttcgatca actgcacgag  360
tgggcgattt acctgatcaa agaaggcaag gcctacgtct gcgacctgac gcccgagcaa  420
gccaaggaat accgtggcag cctgaccgag cccggcaaga acagcccgtt ccgcgaccgt  480
agcgttgaag agaacctgga tctgttcgcc cgcatgaccg ccggtgagtt tgaagacggc  540
aagcgtgtgc tgcgcgccaa gatcgacatg acctcgccga acatgaacct gcgcgacccg  600
atcatgtacc gcatccgtca tgcccatcac caccagaccg gtgacaagtg gtgcatctac  660
cccaactatg acttcaccca cggtcagtcg gatgccattg aaggcatcac ccattcgatc  720
tgcaccctgg agttcgaaag ccatcgtccg ctgtacgaat ggttcctgga cagcctgcca  780
gtaccggcgc gcccgcgtca gtacgagttc agccgtctga acctcaacta caccatcacc  840
agcaagcgca agctcaagca gctggtcgat gaaaagcacg tcaacggctg ggatgacccg  900
cgcatgtcga cgctgtcggg tttccgccgt cgcggttaca cgcctaaatc gattcgtaat  960
ttctgtgaca tggtcggcac caaccgttct gacggtgttg ttgacttcgg catgctggaa  1020
ttcagcattc gtgacgattt ggaccacagc gcgccgcgcg ccatgtgcgt gctgcgtcca  1080
ttgaaggtga ttattaccaa ctacccggaa ggtcaggtcg aaaacctcga gctgccttgc  1140
cacccgaaag aagacatggg tgtgcgggtg ttgccgtttg cccgtgaaat ctacatcgac  1200
cgtgaagact tcatggaaga gccgccaaaa ggctacaagc gtcttgagcc tgcgggcgaa  1260
gtgcgtttgc gcggcagcta tgtgatccgt gccgacgaag cgatcaagga tgccgatggc  1320
aacatcgttg aactgcattg ctcgtacgat ccgctgaccc tgggtaaaaa ccctgaaggt  1380
cgcaaggtca agggtgttgt gcactgggtg ccggcggcgg ccagcgtcga atgcgaagtg  1440
cgtttgtatg atcgtctgtt ccgctcgccg aaccctgaaa aggccgaaga cggcgcgggc  1500
ttcctggaaa acatcaaccc tgactcgctg caggtactga ccggttgtcg tgctgaaccc  1560
tcgctgggca atgcacagcc ggaagaccgt ttccagttcg agcgcgaagg ctacttctgc  1620
gcagatatca aggactcgaa acccggtcac ccggtattca accgtaccgt gaccctgcgt  1680
gattcgtggg gccagtga                                                 1698

SEQ ID NO: 68          moltype = DNA  length = 2418
FEATURE                Location/Qualifiers
source                 1..2418
                       mol_type = genomic DNA
                       organism = unidentified
                       note = DP53 DNA gyrase subunit B sequence
SEQUENCE: 68
ttgagcgaag aaaacacgta cgactcaacg agcattaaag tgctgaaagg ccttgatgcc  60
gtacgcaaac gtcccggtat gtacattggt gatactgacg atggcagcgg tctgcaccac  120
atggtgttcg aagtagtcga caactccatc gacgaagcgc tggctggcca ttgcgacgac  180
atcaccatca cgatccaccc ggacgagtcc atcaccgtgc gcgataacgg ccgcggtatt  240
ccggttgacg tgcataaaga agaaggcgta tctgcagccg aggtcatcat gaccgtgctg  300
cacgccggcg gtaagttcga tgacaactcc tacaaagtat ccggcggctt gcacggtgta  360
ggtgtttcgg tggtaaacgc cctgtccgaa ctgctggtct tgactgtacg ccgcagcggc  420
aagatctggg aacagaccta cgtccacggt gttcctcagg cgcctatggc tattgtgggt  480
gaaagcgaaa ccacgggtac gcagatccac ttcaagcctt cggctgaaac cttcaagaat  540
atccacttta gctgggacat cctggccaag cggattcgtg aactgtcctt cctgaactcc  600
ggtgtgggta tcgtcctcaa ggacgagcgc agcggcaagg aggagctgtt caagtacgaa  660
ggtggcctgc gtgcattcgt tgattacctg aacaccaaca agaacgctgt gaaccaggtg  720
ttccacttca atgttcagcg tgaagacggc atcggcgtag aaatcgccct gcagtggaac  780
gacagcttca acgagaacct gttgtgcttc accaacaaca ttccacagcg cgatggtggc  840
acgcacttgg tgggcttccg ctctgccctg acgcgtaacc tcaacacgta catcgaagct  900
gaaggcctgg ccaagaagca caaggtcgcc accaccggtg atgacgcccg tgaaggcttg  960
accgcgatca tctcggtgaa agtgccggat ccaaagttca gctcgcagac taaagacaag  1020
ctggtgtctt ccgaagtgaa gaccgctgtt gaacaggaaa tgggcaagtt cttctccgac  1080
ttcctgctgg aacacccgaa cgaagccaag ttgattgtcg gcaagatgat cgacgcagcc  1140
cgtgctcgtg aagctgcacg taaagcccgt gagatgaccc gtcgtaaagg cgcgttggac  1200
atcgcgggct tgccgggcaa gctggctgac tgccaggaaa aagaccctgc tctgtccgaa  1260
ctgtacctgg tggaaggtga ctctgctggc ggctccgcca agcagggtcg caaccgtcgt  1320
acccaagcca tcctgccgtt gaaaggtaaa atcctcaacg tcgagaaagc ccgttttgac  1380
aagatgatct cttcgcaaga agtcggcacc ttgatcactg cgctgggctg tggcatcggc  1440
cgcgaagagt acaacatcga caaactgcgc tatcacaaca tcatcatcat gaccgatgct  1500
gacgttgacg gttcgcacat ccgtaccctg ctgctgacct tcttcttccg tcagttgccg  1560
gagctgatcg agcgtggcta catctacatc gcccagccac cgttgtacaa agtgaaaaag  1620
ggcaagcaag agcagtacat caaagacgac gaggccatgg aagagtacat gacccagtcg  1680
```

```
gctcttgaag atgccagcct gcacttgaac gaagatgccc ctggcatctc cggtgaggca  1740
ctggagcgtc tggtgtacga cttccgcatg gtgatgaaga ccctcaagcg tttgtcgcgc  1800
ctgtaccctc aggagctgac cgagcacttc atctacctgc cggctgtaag ccttgagcag  1860
ttgggtgacc acgctgccat gcaggactgg atggccaagt ttgaagagcg tctgcgtctg  1920
gttgagaaat cgggcctggt ctacaaagcc agcctgcgtg aagaccgtga gcgtaatgtc  1980
tggttgccag aggtcgaact gatctcccac ggccactcga cgttcatcac cttcaaccgc  2040
gacttcttcg gcagcaacga ttacaaaacc gttgtgaccc tgggcgctca actgagcacc  2100
ctgctggatg aaggcgccta tatccagcgt ggcgaacgtc gcaagcaagt gaccgagttc  2160
aaagaagcac tggactggtt gatggctgaa agcaccaagc gtcacaccat ccagcgctac  2220
aaaggactgg gtgaaatgaa cccggatcag ctctgggaaa ccacgatgga cccaagcgtg  2280
cgtcgcatgc tgaaagtcac catcgaagac gcgatcggcg ccgatcagat cttcaacacc  2340
ttgatgggcg atgctgtaga accacgtcgt gaattcatcg agagcaacgc actggcagtg  2400
tccaacctgg atttctga                                                 2418
```

```
SEQ ID NO: 69          moltype = DNA  length = 2832
FEATURE                Location/Qualifiers
source                 1..2832
                       mol_type = genomic DNA
                       organism = unidentified
                       note = DP53 Isoleucine--tRNA ligase sequence
SEQUENCE: 69
atgaccgact acaaagccac gctaaacctc ccggacaccg ccttcccaat gaaggccggc  60
ctgccacagc gcgaaccgca aattttgcag cgctgggaca gcattggcct gtacgggaag  120
ttgcgcgaga ttggcaagga tcgtccgaag ttcgtacttc acgacggtcc tccgtacgcc  180
aacggcacta tccatatcgg tcatgcgctg aacaagattc tgaaagacat gatcatccgc  240
tccaagaccc tgtcgggttt tgacgcgccg tatgtgccgg gctgggattg ccatggtttg  300
ccgattgaac acaaggtcga agtgacccac ggtaaaaacc tgagcgcgga taaaacccgc  360
gagctgtgcc gtgcctacgc caccgagcag atcgaggggc agaagtccga gttcatccgt  420
ctgggtgtgc tgggtgattt cgccaacccg tacaagacca tggacttcaa aaacgaagcc  480
ggtgaaatcc gtgctttggc tgagatcgtc aagggcggtt ttgtgttcaa gggcctcaag  540
ccggtgaact ggtgcttcga ttgcggttcg gccctggctg aagctgaagt tgaataccag  600
gacaagaagt ctgcggccat cgacgttgcc ttcccggttg ccgacgaggc caagctggcc  660
gaggcctttg gtctggcggc actgagcaaa cctgcttcga tcgtgatctg gaccaccacc  720
ccgtggacca ttccggccaa ccaggcgctt aacgtacacc cggaattcac ctacgcgctg  780
gtcgacgtgg gcgacaagtt gctggtactg gctgaagaac tggtcgaatc gagtctggcg  840
cgttacaacc tgcagggttc ggtcatcgcc accaccactg gctcagcgct tgaactaatc  900
aacttccgtc acccgttcta tgaccgtctg tcgcctgttt atctggccga ctacgttgag  960
ctgggtgctg gcactggtgt ggttcactcg gctccagcct acggcgtaga cgacttcgtg  1020
acctgcaaag cctatggcat ggtcaacgac gacatcatca acccggtgca aagcaatggc  1080
gtttacgtgc cgtcgctgga gttcttcggt ggccagttca tctggaaggc caaccagaac  1140
atcatcgaca agctgatcga agtcggttcg ctgatgttca ccgagaccat cagccacagc  1200
tatatgcact gctggcgcca caagacgccg ctgatctacc gtgccaccgc ccagtggttt  1260
atcggtatgg acaagcagcc gactgatggc gataccttgc gcacccgtgc gctgcaagcg  1320
atcgaagaca cccagttcgt tccggcctgg ggtcaggcgc gcctgcactc gatgatcgcc  1380
aaccgcccgg actggtgcat ctcgcgtcaa cgcaactggg gcgtgccgat cccgtttttc  1440
ctgaacaagg aaagcggcga gctgcacccg cgcaccgtcg aaatgatgga agaagtggcc  1500
aagcgcgttg aagtcgaagg catcgaggcg tggttcaagc tggatgctgc cgagctgctg  1560
ggcgacgaag cgccgctgta cgacaagatc agcgataccc tcgacgtctg gttcgattcg  1620
ggcaccacgc actggcatgt ccttcgcggt tcgcacccga tgggtcatga aaccggccca  1680
cgcgctgatc tctaccttga aggctccgac cagcaccgtg gctggttcca ctcgtcgttg  1740
ctgaccggtt gcgccatcga caaccacgcg ccgtaccgcg agctgctgac ccacggtttt  1800
accgtggacg aagcgggccg caagatgtcc aagtcgctgg gcaacgtgat tgcaccgcaa  1860
aaggtcaacg acaccctggg cgccgacatc atgcgtctgt gggttgcttc gaccgactac  1920
tcgggcgaaa tcgcggtttc cgaccagatc ctgcagcgca gtgcggacgc ctaccgacgt  1980
atccgcaata ccgcacgctt cctgctgtcg aacctgaccg gtttcaatcc agccaccgac  2040
atcctgcctg ccgaagaaat gctggcactg gaccgctggg cggtggatcg tgcgttgctg  2100
ctgcaacgtg agctggagct gcattacggc gaataccgtt tctggaacgt gtactccaag  2160
gtgcacaact tctgcgttca ggagctgggc ggtttctatc tcgacatcat caaggaccgc  2220
cagtacacca ccggcgccaa cagcaaggct cgccgttcgt gccagaccgc gctgttccac  2280
atctctgaag cgctggtgcg ctggatcgct ccgatcctgg cgttcaccgc tgatgagttg  2340
tggcagtacc tgccgggcga gcgcaacgaa tcggtcatgc tcaacacctg gtacgaaggc  2400
ctgactgaac tgccggaagg caccgaactg gatcgcgcct actgggagcg aatcatggcg  2460
gtcaaggttg cggtcaacaa ggaaatggaa aacttgcgcg cagccaaggc cattggcggt  2520
aacttgcaag cagaagtgac cttgttcgcc gaagatcagc tggctgctga tttgtccaag  2580
ttgagcaacg aactgcgttt cgtgttgatc acctccactg ccagcgttgc gccttttgcg  2640
caggctccag cagatgccgt ggttaccgaa gtggctggcc tcaaactcaa ggtggtcaag  2700
tcggcccatg ccaagtgcgc ccgttgctgg cactgccgtg aagacgtcgg cgttaacccc  2760
gagcaccctg aaatctgcgg tcgttgtgta gacaatatca gcggcgctgg tgaggtacgt  2820
cactatgcct aa                                                       2832
```

```
SEQ ID NO: 70          moltype = DNA  length = 1785
FEATURE                Location/Qualifiers
source                 1..1785
                       mol_type = genomic DNA
                       organism = unidentified
                       note = DP53 NADH-quinone oxidoreductase subunit C/D sequence
SEQUENCE: 70
atgactgcag gctccgctct gtacatcccg ccttacaagg ctgacgacca agatgtggtt  60
gtcgaactca atacccgttt tggccctgag gcgttcaccg cccaggccac gcgcaccggc  120
```

-continued

```
atgccggtgc tttgggttag ccgcgcaaaa ctggtcgaag tactgacctt cctgcgcaac  180
ctgccaaaac cctacgtcat gctctatgac ctgcacggtg tggacgaacg tctgcgtacc  240
aagcgtcagg gcctgccatc gggtgcagac ttcaccgtct tctaccacct gatgtcgctg  300
gaacgtaaca gcgacgtcat gatcaaggtg gccctgtctg aaaaagacct gagtgtccct  360
accgtgaccg gtatctggcc gaacgccaac tggtacgagc gtgaagtctg ggacatgttc  420
ggcatcgatt tcaaaggcca cccgcacctg tcgcgcatca tgatgccgcc gacctgggaa  480
ggtcacccgc tgcgcaagga cttcccggcc cgtgccacag agttcgatcc gtacagcctg  540
accctggcca aggtgcagct ggaagaggaa gccgcgcgct tccgcccgga agactggggc  600
atgaaacgct ccggtgaaaa cgaggactac atgttcctca acctgggccc taaccaccct  660
tcggctcacg gtgccttccg catcatcctg cagctggacg gtgaagagat cgtcgactgc  720
gtgcctgacg tcggttacca ccaccgtggc gccgagaaaa tggccgaacg ccagtcctgg  780
cacagtttca tcccgtacac cgaccggatc gattacctcg gcggagtgat gaacaacctg  840
ccgtacgtgc tctcggtcga gaagctggcc ggtatcaaag tgccggatcg ggtcgacacc  900
atccgcatca tgatggccga attcttccgt atcaccagcc acctgctgtt cctgggtacc  960
tatatccagg acgtgggcgc catgaccccg gtgttcttca cgttcaccga ccgtcagcgc  1020
gcttacaagg tgatcgaggc catcaccggt ttccgtctgc acccggcctg gtaccgcatc  1080
ggcggcgttg cccacgacct gccgaacggc tgggatcgcc tggtcaagga attcatcgac  1140
tggatgccca agcgtctgga cgagtaccag aaagccgctc tggacaacag catcctgcgt  1200
ggtcgtacca tcggcgttgc cgcctacaac accaaagagg ccctggaatg gggcgtcacc  1260
ggtgccggcc tgcgctccac cggttgtgac ttcgatatcc gcaaggcgcg cccgtattcc  1320
ggctacgaga acttcgaatt cgaagtcccg ctggcagcca acggcgatgc ctacgatcgt  1380
tgcatcgtgc gcgtcgaaga aatgcgccag agcctgaaaa tcatcgagca gtgcatgcgc  1440
aacatgccgg ccggcccgta caaggcggat cacccgctga ccacgccgcc gcctaaagaa  1500
cgcacgctgc agcatatcga gaccttgatc acgcacttcc tgcaagtttc gtggggcccg  1560
gtgatgccgg ccaacgaatc cttccagatg atcgaagcga ccaagggcat caacagttat  1620
tacctgacga gcgatggcgg caccatgagc taccgcaccc ggattcgcac cccaagcttc  1680
ccgcacctgc aacagatccc ttcggtgatc aaaggtgaaa tggtcgcgga cttgattgcg  1740
tacctgggta gtatcgattt cgttatggcc gacgtggacc gctaa                 1785

SEQ ID NO: 71           moltype = DNA  length = 1119
FEATURE                 Location/Qualifiers
source                  1..1119
                        mol_type = genomic DNA
                        organism = unidentified
                        note = DP53 Protein RecA sequence
SEQUENCE: 71
atggacgaca acaagaagaa agccttggct gcggccctgg gtcagatcga acgtcaattc  60
ggcaagggtg ccgtgatgct gatgggcgac caggagcgtc aggcagtccc ggcgatctcc  120
accggctccc tgggtctgga catcgcactg ggcattggcg gtctgccaaa aggccgtatt  180
gttgaaatct acggccctga gtcgtcgggt aaaaccacac tgaccctgtc cgtgattgcc  240
caggcgcaaa aggccggtgc tacctgcgcc ttcgtcgatg ccgagcacgc ccttgatcct  300
gagtacgctg ccaaactggg cgtaaacgtt gatgacctgc tggtttcaca gcctgacacc  360
ggcgaacagg cactggaaat caccgatatg ctggtgcgtt ccaatgcggt tgacgtgatc  420
atcatcgact ccgttgctgc actgacgcca aaagctgaaa tcgaaggcga catgggcgat  480
acccacgttg gcctgcaagc ccgtctgatg tcgcaagcgc tgcgtaaaat caccggtaac  540
atcaagaacg ccaactgcct ggttatcttc atcaaccaga tccgcatgaa aatcggcgtg  600
atgttcggca gccctgaaac caccaccggt ggtaacgcac tgaagttcta cgcttcggta  660
cgtctggata tccgccgcac cggcgccgta aaagaaggcg atgtggtggt gggtagcgaa  720
acccgcgtga aagtggtcaa gaacaaggtg gcaccaccgt tccgtcaggc tgaattccag  780
atcctgtacg gcaagggtat ctacctgaac ggtgaaatga ttgacctggg cgtactgcat  840
ggctttgttg aaaaagctgg cgcctggtac agctacaacg gcagcaaaat cggtcagggc  900
aaggccaact ccgccaagtt cctggacgat aacccggaca tcaaggatgc gctggagaag  960
cagctgcgtg agaagttgct cgggccaaaa accgatgccg aactggcagc gacggactgc  1020
aatggacctg ctcgcgcgac gcgagcacgg tcgagtcgag ctgacgcgca agttgcgtca  1080
gcgcggcgct tgccccgaca tgatcgacgc tgcccttga                        1119

SEQ ID NO: 72           moltype = DNA  length = 1848
FEATURE                 Location/Qualifiers
source                  1..1848
                        mol_type = genomic DNA
                        organism = unidentified
                        note = DP53 RNA polymerase sigma factor RpoD sequence
SEQUENCE: 72
atgtccggaa aagcgcaaca gcagtctcgt atcaaagagt tgatcaccct cggccgtgag  60
cagaagtatc tgacttacgc agaggtcaac gaccacctgc ccgaagatat ttcagatccg  120
gagcaagtgg aagacatcat ccgcatgatt aatgacatgg ggatccccgt acacgagagt  180
gctccggatg cggacgccct tatgttggcc gatgccgaca ccgacgaagc agcagctgaa  240
gaagcggctg cagcgttggc ggcagtagag accgacattg gtcgtactac cgaccctgtg  300
cgcatgtata tgcgtgaaat gggcacggta gaactgctga cacgtgaagg cgaaatcgaa  360
atcgccaagc gtatcgaaga aggcatccgt gaagtgatgg gcgcaatcgc gcacttccct  420
ggcacggttg accatattct ctccgagtac actcgcgtca ccaccgaagg tggccgcctg  480
tccgacgttc tgagcggtta tatcgacccg gacgacggta ttgcgccgcc cgcagccgaa  540
gtacctcctc ctgtcgacac caaggtgaaa gccgaaggtg atgacgaaga ggacgacaag  600
gaagattccg gcgaagacga ggaagaggtc gaaagcggcc ctgatccgat catcgcggcc  660
cagcgctttg gcgctgtttt cgatcagatg gaaatcgctc gcaaggccct gaaaaagcac  720
ggtcgcggca gcaagcaggc aattgccgag ctggttgcac tggctgagct gttcatgccg  780
atcaaactgg ttccgaagca attcgaaggc ctggttgagc gtgttcgcag cgccctggag  840
cgtctgcgtg cacaagagcg cgcaatcatg cagctgtgtg tacgtgatgc acgcatgccg  900
cgcaccgatt tcctgcgtct gttcccgggc aacgaagtcg acgaaagctg gagcgatgcg  960
```

```
ctggccaaag gcaaaagcaa atatgctgaa gccattggtc gcctgcaacc ggacatcatc  1020
cgttgccagc aaaagctctc tgctctggaa gcagaaaccg gcttgaagat tgccgagatc  1080
aaggacatca accgtcgcat gtcgatcggc gaggccaagg cccgccgcgc gaagaaagaa  1140
atggttgaag ccaacttgcg tctggtgatc tccatcgcca agaagtacac caaccgtggc  1200
ctgcagttcc tcgatctgat ccaggaaggc aacatcggct tgatgaaagc ggtagacaag  1260
tttgaatacc gccgcggcta caaattctcg acttatgcca cctggtggat ccgtcaggcg  1320
atcactcgct cgatcgccga ccaggcccgc accatccgta ttccggtgca catgatcgag  1380
acgatcaaca agctcaaccg tatttcccgt cagatgttgc aggaaatggg ccgtgaaccg  1440
accccggaag agctgggcga acgcatggaa atgcctgagg ataaaatccg caaggtattg  1500
aagatcgcta aagagccgat ctccatggaa accccgatcg gtgatgacga agactcccat  1560
ctgggtgact tcatcgaaga ctcgaccatg cagtcgccaa tcgatgttgc taccgttgag  1620
agccttaaag aagcgacacg cgacgtactc ggcggcctca cagcccgtga agccaaggta  1680
ctgcgcatgc gtttcggtat cgacatgaat accgaccaca cccttgagga ggttggtaaa  1740
cagttcgacg ttacccgtga gcggattcgt cagatcgaag ccaaggcgct gcgcaagctg  1800
cgccacccga cgagaagcga gcatttgcgc tccttcctcg acgagtga              1848
```

```
SEQ ID NO: 73           moltype = DNA  length = 4073
FEATURE                 Location/Qualifiers
source                  1..4073
                        mol_type = genomic DNA
                        organism = unidentified
                        note = DP53 DNA-directed RNA polymerase subunit beta
                         sequence
SEQUENCE: 73
atggcttact catatactga gaaaaaaacgt atccgcaagg actttagcaa gttgccggac  60
gtcatggatg tgccgtatct cttggcaatc cagctggatt cgtatcgtga attcttgcag  120
gcgggagcga ctaaagatca gttccgcgac gtgggcctgc atgcggcctt caaatccgtt  180
ttcccgatca tcagctactc cggcaatgct gcgctggagt acgtcggtta tcgcttgggc  240
gaaccggcat ttgatgtcaa agaatgcgtg ttgcgtggcg taacgtacgc cgtacctttg  300
cgggtaaaag ttcgtttgat cattttcgac aaagaatcgt cgaacaaagc gatcaaggac  360
atcaaagagc aagaagtcta catgggtgaa atccccctga tgactgaaaa cggtaccttc  420
gtaatcaacg gtaccgagcg tgtaattgtt tcccagctgc accgttcccc gggcgtgttc  480
tttgccacga ccgcggcaag acgcacagct ccggtaagct gctttattcc gcgcgtatca  540
ttccttaccg tggttcgtgg ctcgacttcg agttcgaccc gaaagactgc gtgttcgtgc  600
gtattgaccg tcgtcgcaag ctgcctgcat cggtattgct gcgcgcgctg ggttatacca  660
ctgagcaagt gctggacgcg ttctacacca ccaacgtgtt ccacgttcag ggtgagagca  720
tcagcctgga gctggttcca cagcgtctgc gcggtgaaat cgcggccatc gacattaccg  780
atgacaaagg caaggtgatt gttgagcagg gtcgtcgtat cactgctcgt catatcaacc  840
agctggaaaa agccggtgtc aaagagctcg ttatgcctct ggactatgtc ctgggtcgca  900
caacggccaa ggctatcgtg catccggcta ctggcgaaat cattgctgag tgcaacaccg  960
agctgaccac tgaaatcctg gcaaaagttg ccaagggcca ggttgttcgc atcgaaacgt  1020
tgtacaccaa cgatatcgac tgcggtccgt tcgtctccga cacgctgaag atcgactcca  1080
ccagcaacca actggaagcg ctggtcgaaa tctatcgcat gatgcgtcca ggcgagccgc  1140
caaccaaaga cgctgccgag actctgttca acaacctgtt cttcagccct gagcgctatg  1200
acctgtctgc ggtcggccgg atgaagttca accgtcgtat cggtcgtacc gagatcgaag  1260
gttcgggcgt gttgtgcaaa gaagacatcg ttgccgtgct gaagaccctg gtcgacatcc  1320
gtaacggtaa aggcatcgtc gatgacatcg accacctggg taaccgtcgt gttcgctgtg  1380
taggcgaaat ggccgagaac cagttccgcg ttggcctggt acgtgttgag cgtgcggtca  1440
aagagcgtct gtcgatggct gaaagcgaag gcctgatgcc gcaagacctg atcaacgcca  1500
agcctgtggc tgcggcggtg aaagagttct tcggttccag ccagctgtcc cagttcatgg  1560
accagaacaa ccctctgtcc gagatcaccc acaagcgccg tgtttctgca ctgggcccgg  1620
gcggtctgac gcgtgagcgt gcgggctttg aagttcgtga cgtacacccg actcactacg  1680
gccgtgtttg ccctattgag acgccggaag gtccgaacat cggtctgatc aactccctgg  1740
ctgcctatgc gcgcaccaac cagtacggct tcctcgagag cccgtaccgt gtagtgaaag  1800
acgcactggt aactgacgag atcgttttcc tgtccgccat cgaagaagct gatcacgtga  1860
tcgctcaggc ctcggccacg atgaacgaca agaaagtgct gatcgacgag ctggttgctg  1920
ttcgtcactt gaacgaattc accgtcaagg cgccggaaga cgtcaccttg atggacgttt  1980
cgccgaagca ggttgtttcg gttgcagcgt cgctgatccc gttcctggaa cacgatgacg  2040
ccaaccgtgc gttgatgggt tccaacatgc agcgtcaagc tgtaccaacc ctgcgcgctg  2100
acaagccgct ggtaggtacc ggcatggagc gtaacgtagc tcgtgactcc ggcgtttgcg  2160
tcgtggctcg tcgtggcggc gtgatcgact ctgttgatgc cagccgtatc gtggttcgtg  2220
ttgctgatga cgaagttgaa actggcgaag ccggtgtcga catctacaac ctgaccaaat  2280
acacccgttc caaccagaac acttgcatca accagcgtcc gctggtgcgc aagggtgacc  2340
gtgtacagcg tagcgacatc atggctgacg gcccgtccac cgatatgggt gaactggcgc  2400
tgggtcaaaa catgcgcatc gcgttcatgg cctggaacgg ttacaacttc gaagactcca  2460
tctgcttgtc ggaacgagtt gttcaagaag accgctttac cacgatccac attcaggaac  2520
tgacctgtgt ggcacgtgac accaagcttg ggcctgaaga gatcactgca gacatcccta  2580
acgtgggtga agctgcactg aacaaactgg acgaagccgg tatcgtttac gtaggtgctg  2640
aagttggcgc cggcgacatt ctggtaggta aggtcactcc gaaaggcgag acccagctga  2700
ctccggaaga gaagctgttg cgtgccatct tcggtgaaaa agccagcgac gttaaagaca  2760
cctccctgcg cgtacctacc ggtaccaaag gtactgttat cgacgtgcag gtcttcaccc  2820
gtgacggcgt tgagcgtgat gctcgtgcac tgtcgatcga gaagacccag ctggacgaga  2880
tccgcaagga tctgaacgaa gagttccgta tcgttgaagg cgctaccttc gaacgtctgc  2940
gctctgctct ggttggccgc attgccgaag gtggtgccgg tctgaagaaa ggtcaggaaa  3000
tcaccaatga aatcctggac ggtcttgagc atggtcagtg gttcaaactg cgcatggctg  3060
aagatgctct gaacgagcag cttgaaaagg ctcaggctta catcatcgat cgccgtcgtc  3120
tgctggacga caagttcgaa gacaagaagc gcaaactgca gcagggcgat gacctggctc  3180
caggcgtgct gaaaatcgtc aaggtttacc tggcaatccg ccgtcgcatc cagccgggtg  3240
acaagatggc cggtcgtcac ggtaacaagg gtgtggtctc cgtgatcatg ccggttgaag  3300
```

```
acatgccgta cgatgccaat ggcaccccgg ttgatgtggt cctcaacccg ttgggcgtac  3360
cttcgcgtat gaacgttggt cagattctcg aaactcacct gggcctcgcg gccaaaggtc  3420
tgggcgagaa gatcaacctc atgattgaag aacaacgcaa ggtcgctgac ctgcgtaagt  3480
tcctgcatga gatctacaac gaaattggcg gtcgtcaaga aagcctggat gacttctccg  3540
atcaggaaat cctggatctg gcgaagaacc ttcgcggcgg tgtgccaatg gctaccccgg  3600
tgttcgacgg tgccaaggaa agcgaaatca aggcaatgct tcgtttggca gacctgccag  3660
acagcggcca gatggtgctg actgatggtc gtaccggcaa caagttcgag cgtccggtta  3720
ccgttggcta catgtacatg ctgaagctga accacttggt agacgacaag atgcacgctc  3780
gttctaccgg ttcttacagc ctggttaccc agcagccgct gggtggtaag gcgcagttcg  3840
gtggtcagcg tttcggggag atggaggtct gggcgctgga agcctacggc gcggcataca  3900
ctctgcaaga aatgctcaca gtgaagtcgg acgatgtgaa cggccgtacc aagatgtaca  3960
aaaacatcgt ggacggcgat caccgtatgg agccgggcat gcccgagtcc ttcaacgtgt  4020
tgatcaaaga aattcgttcc ctcggcatcg atatcgatct ggaaaccgaa taa         4073
```

```
SEQ ID NO: 74           moltype = DNA  length = 2073
FEATURE                 Location/Qualifiers
source                  1..2073
                        mol_type = genomic DNA
                        organism = unidentified
                        note = DP9 Glycine--tRNA ligase beta subunit sequence
SEQUENCE: 74
atggcacata attatttact agaaattgga ttggaagaaa ttccggccca tgttgtaact  60
ccaagtatca aacagttagt acaaaaagta acagccttct taaaagaaaa tcgcttaaca  120
tacgactcaa ttgatcattt ttcaactcct cgtcgtttgg caattcgaat caatgggtta  180
ggcgaccaac aacctgatat tgaagaagat gctaaaggcc ctgctcgtaa aattgctcaa  240
gatgctgatg gaaattggac taaggctgca attggcttta cacgtggaca aggtcttacg  300
gttgacgata ttacttttaa aacaatcaaa ggtacggact atgtgtacgt ccataagtta  360
atcaaaggaa agatgactaa ggaaatcctt acggggataa aagaagttgt tgaatcaatt  420
aatttcccaa caatgatgaa gtgggctaac tttgatttta aatatgtacg cccaattcgt  480
tggctggttt ctattctaga tgaagaagtc cttcctttta gtatcttaga cgtaactgcg  540
ggacgccgaa cagaaggaca tcgtttctta ggtgaagctg tcgaactggc taatgctgaa  600
gaatatgaag caaaattaca cgatcaattt gtgattgttg atgccgacga gcgtaaacaa  660
ttaatttcaa accaaattaa agcaattgct gaaagcaatc gttggaacgt tacccctaac  720
ccaggtcttt tagaagaggt taacaatttg gttgagtggc caaccgcttt taatgggga  780
tttgatgaaa agtatttagc tattccagaa gaggtattga taacatcaat gcgtgaccac  840
caacgcttct tctttgtccg cgaccaagct ggaaagctat tgccaaactt catctccgta  900
cgaaatggga atgaagaatt tattgaaaat gttgttcgtg gaaatgaaaa agttttaact  960
gcacgtttag aagacgctgc tttcttctac gaagaagatc aaaaacatga tattaattat  1020
tatgttgacc gacttaaaaa ggttagtttc catgataaga ttggttcaat gtacgaaaaa  1080
atgcaacgag ttaattctat tgctaaagtt attggaaaca ccttaaatct taatcaaacg  1140
gaacttgatg atatcgatcg cgctacaatg atttataaat ttgatttggt aactggtatg  1200
gttggtgagt tctcagaatt acaaggagta atgggtgaaa aatatgctca acttaatggt  1260
gaaaaccaag cagtagccca agccattcgc gaacattaca tgccaaatag cgcagaaggt  1320
gatttgcctg aaagtgtaac gggcgcggta gtcgcattag ctgataagtt tgataacatc  1380
tttagttttt tctcagctgg tatgattcca agtggttcaa acgatccata tgcattacgc  1440
cgacatgcat atggaattgt tagaatctta aatagccgtg attggcaatt agatttaaat  1500
caattcaaat cacaatttaa gactgaatta gcggagaatg gcacagcgtt tggtgtggat  1560
gtcgatcaaa actttgacca agtacttaac ttctttaatg accgtattaa acaattgctt  1620
gatcatcaaa agattagtca tgatatcgtt gaaacggtgc ttacaggtaa taatcatgat  1680
gttacggaaa ttatcgaagc tgcccaagta ctagcagatg ctaaagcgag ctctacattt  1740
aaagatgata ttgaagcttt aacacgagtt caaagaattg ctacaaagaa tgaagaaagt  1800
ggagaactta atgtagatcc acaattattt aataatgctt ctgaaggcga actttttgat  1860
caaattatta aaattgaagc tgcaaataat ttgacaatga gccaactatt tgctaaatta  1920
tgcgagttga ctcctgcgat tagcaagtac tttgacgcaa cgatggtcat ggacaaagac  1980
gaaaatatta agtgtaatcg tttgaatatg atgagtcggt tagctaattt aattctaaaa  2040
attggggatc taactaacgt acttgtaaaa taa                              2073
```

```
SEQ ID NO: 75           moltype = DNA  length = 1341
FEATURE                 Location/Qualifiers
source                  1..1341
                        mol_type = genomic DNA
                        organism = unidentified
                        note = DP9 Glutamine synthetase sequence
SEQUENCE: 75
atggcaaaga aaaattattc gcaagcagat attcgtcaga tggcaaagga tgaaaatgta  60
cgttttctcc gattaatgtt tacagatctt tttggaataa ttaagaacgt tgaagtacca  120
attagtcaat tggacaaact attagataat aaattgatgt ttgatggttc ctcaattgac  180
gggtttgttc ggattgaaga aagtgacatg tatttatacc cagatctttc tacttggatg  240
gttttcccat ggggaagcga acatggcaag gtggctcgca ttatttgtga agtatactca  300
aatgatcgta aaccattcgt gggtgatcca cgtaacaatt taattcgagt actccaagag  360
atgaaggatg caggatttac tgattttaat atcggacctg aacctgagtt tttcttgttg  420
aaattagatg aaaatggtaa accaaccact aatttaaatg ataaaggtag ttactttgat  480
ttagctcctg ttgatttagg tgaaaactgc cgtcgtgata ttgttttgga acttgaaaat  540
atgggctttg atgttgaagc ttctcatcat gaagttgctc caggacaaca cgaaattgac  600
tttaaatacg ccgatgcttt gaccgctgcc gataacattc aaacctttaa gttggttgtt  660
aagacagttg cccgtaaata taacctgcat gctacattta tgcctaaacc tatggatgga  720
atcaatggtt cagggatgca tttaaacatg tcacttttca ataaggaagg caatgctttc  780
tatgacgaaa agggtgactt acaactttct caaaatgctt actggttcct tggtggacta  840
ttgaagcatg ctcgtagtta tacggccgta tgtaacccaa ttgttaactc gtacaaacgt  900
```

```
ttagttcctg gatatgaagc tccagtatac gttgcttggt caggttcaaa tcgttcacca  960
cttattcgcg ttccttcaag taagggactc tcaactcgtt ttgaagttcg aagcgtcgat  1020
ccagctgcta acccatactt agcaattgca tcagtattgg aagcaggctt agatggcatt  1080
agaaacaaga ttgaaccaga agattccgtt gatcgtaata tctatcgaat gaacattcaa  1140
gaacgtaatg aagagcatat tacagatcta ccttcaacat tacacaatgc tttgaaggaa  1200
ttccaaaatg atgatgtaat gcgtaaggca ttaggagatc acattttcca aagcttcctc  1260
gaagctaaga agttagaatg ggcttcttac cgtcaagaag tgacacaatg ggaacgtgat  1320
caatatctcg aaatgttcta g                                            1341

SEQ ID NO: 76          moltype = DNA  length = 1947
FEATURE                Location/Qualifiers
source                 1..1947
                       mol_type = genomic DNA
                       organism = unidentified
                       note = DP9 DNA gyrase subunit B sequence
SEQUENCE: 76
ttggcagacg aaaaagaaac gaaagcagaa ttagccagag aatatgatgc gagtcaaatt  60
caggttttag aggggctcga agcagttcgt aaacgcccag gaatgtatat tgggtcgact  120
agttctcaag gactacacca tttggtttgg gaaattattg ataatggtat tgatgaagct  180
cttgcaggat ttgcagacaa aattgatgtg atcgttgaaa aagacaatag tattaccgtc  240
actgataatg gacgtgggat tccggttgat atccaaaaga aaactggaaa accagcttta  300
gaaacagtct ttacggtcct acatgccgga ggtaaattcg gcggtggcgg ttataaagtt  360
tctggaggat tgcatggtgt gggcgcatcc gttgtaaatg cgttatcaac ggaattagat  420
gcgcgcgtca tgaaggacgg taaaatctat tacattgatt ttgcgctagg aaaagtaaaa  480
acaccgatga aaacgattgg tgatactgaa catcctgacg atcatggaac tattgttcat  540
ttcgttccag atccagatat tttccaagaa actaccacat acgacattaa tatcttaaaa  600
acacgaattc gtgaattagc ctttttgaac aaaggtctac ggattacttt gaaggatatg  660
cgtcctgaaa agccaactga agacgacttc ttgtatgaag gtgggattcg ccactacgtt  720
gaatatctaa acgaaggcaa agaagtaatt ttccctgaac ctatctatgt tgaaggggtt  780
acaaaaggta tcactgttga agtagctatg caatatatcg aaggttatca aagtaaattg  840
ttaactttta ctaacaatat tcatacttac gaaggcggta cccacgaaga aggtttcaaa  900
cgtgctttaa cacgagttat taacgattac gctaaaaaca acaatatttt aaaagaaaat  960
gatgataaat tgtctggtga tgatgttcga gaaggtttga cggcagtagt cagcgttaag  1020
catcctgatc ctcaattcga aggacaaacg aaaacaaaat tgggtaactc agatgctcgg  1080
acagctgtta acgaagtgtt tgctgaaact ttcaataaat tcttattgga aaatcctaag  1140
gttgcacgtc aaattgttga taagggaatc ttggcagcaa aagcaagagt cgccgctaaa  1200
cgagctcgtg aagttacgcg taagaagagt ggcctagaac tcaataatct tcctggtaaa  1260
ttagctgata atacttctaa ggatccttca attagtgaat tattcattgt cgagggtgat  1320
tctgccggtg gtagtgctaa gtcgggacgt tcgcgtctca cacaagctat tttgccaatt  1380
cgtgggaaga ttttgaacgt tgaaaaagcc actttggatc gggttttggc caatgaagaa  1440
attcgttcac tctttacagc gctcggaact ggatttggtg aggactttga tgtaagtaaa  1500
gccaactatc ataaattgat tatcatgacc gatgccgatg tcgatggtgc tcatattcgg  1560
acactattat tgacgctgtt ctatcgttac atgcgtccaa tgattgatgc aggatttgtt  1620
tacattgctc aaccaccgct ctaccaagta cgtcaaggta agatgattca atatatcgat  1680
tctgatgaag aattagaaac agtacttgga caattgtcac catcaccaaa acctgtaatt  1740
caacgttata aaggtcttgg tgaaatggat gctgagcaac tttgggaaac aaccatgaat  1800
ccagaaaatc gacgcttgtt acgagtttca gccgaagatg ctgatgctgc aagtggtgat  1860
tttgaaatgt tgatgggtga caaggttgaa ccacgtcgta aattcattga agagaacgct  1920
gtgtttgtta aaaacttgga tatctaa                                      1947

SEQ ID NO: 77          moltype = DNA  length = 2418
FEATURE                Location/Qualifiers
source                 1..2418
                       mol_type = genomic DNA
                       organism = unidentified
                       note = DP9 Leucine--tRNA ligase sequence
SEQUENCE: 77
atggcttata atcataaaga tatcgaacag aagtggcagc aattctggag cgacaatgag  60
acttttaaga cggtcgaaga tgcagacaaa cccaaatatt atgcattaga catgttccct  120
tatccatcag gtcaaggact ccatgtgggc catcctgaag gatatacagc aacagatatt  180
atgtcacgaa tgaaacggat gcaaggttac aaagtacttc atccaatggg atgggatgct  240
tttggtcttc cagcagaaca atatgcgatg aagacgggta acaatccgcg tgattttaca  300
gctaagaata ttcaaaactt taagcgtcaa atccaatcac ttggtttttc ttatgactgg  360
tcgcgagaag ttaatacaac tgatccagct tactacaagt ggactcaatg gatttttgag  420
caactctaca agaagggctt agcttatgaa aaagaaacgc tggtaaactg ggctcctgat  480
ttaatgggtg gaacggtagt tgctaacgaa gaagttgtgg atggtaagac agaacgtggt  540
gggttccccg tttatcgtaa accaatgaaa caatggattc ttaaaattac agcttacgcc  600
gaccgtttga ttgacgattt ggacctggta gattggcccg atagtattaa agaaatgcaa  660
aaaaactgga ttggtcgttc agtgggggct agcgtcttct ttaatgttga agatagcgaa  720
aaacaaattg aagtatttac aacgcgtcca gatacattat ttggcgcaac atacttggta  780
atttcaccag aacatgacct cgttgaccaa attacaactc cagaaagtaa agctgccgtt  840
gaagaataca agaaagctgt tgcaactaaa tcagatcttg aacggacgga tttgagtaaa  900
gataagacgg gagtctttac gggagcatac gcggttaacc ctgttaatgg taagaaaatt  960
ccagtttgga ttagtgatta cgtattggct tcatacggaa ctggagcagt gatggctgtt  1020
cctgctcatg atggccgtga ctacgaattt gctaagaaat tcaagataga tatggtgcca  1080
gtttatgaag gtggcaatct tgaagatgga gtattggaca gcgaaggcgg gctaattaac  1140
tctggattcc tagatgggat ggataagcag acggctattg ataccatgat tagctggttg  1200
gaagaacatg gagttggtca taagaaggtt aactatcgtc ttcgtgactg ggtcttctct  1260
cgccaacgct actggggtga accaatccct gtaattcatt gggaagatgg agaaacaact  1320
```

```
ttgattcctg aagatgaatt gccattgaga ctcccggctg caactgacat tcgtccttcc  1380
ggtaccggag aaagcccatt agctaaccta gatgattggg taaacgtagt tgatgaaaat  1440
ggtcgtaagg gtcgccggga aactaataca atgccacaat gggcgggtag ttcatggtac  1500
ttcctccgtt acgttgatcc taagaatgat caaaagattg ctgacgaaga tttacttaaa  1560
gaatggttac cagtcgactt atatgttggt ggagctgaac atgcggtact tcatttactt  1620
tatgcacgtt tctggcacaa agttttatat gatctaggag ttgtaccaac taaggaacca  1680
ttccaaaaat tggtcaacca agggatgatt ctcggtagca atcatgagaa gatgtctaag  1740
tcaaaaggga acgtggttaa tccagatgat attgttgagc gctttggagc ggatacttta  1800
cgattatacg aaatgttcat gggacctctg acagaatcag tcgcctggag tgaagatggg  1860
cttaacggaa gtcgtaagtg gattgaccgc gtctggcgct tgatgattga cgacgaaaac  1920
caattgcgtg atcatattgt tactgaaaat gatggcagtt tggatatgat ttataaccaa  1980
actgttaaga aggtaactga tgattatgaa aacatgcgct ttaacacggc tatttcacaa  2040
atgatggtct ttgttaatga agcatacaag gctgataaac ttccagcagt atatatggaa  2100
ggattagtta agatgttagc tccaattatt ccgcacgttg ctgaagaact ttggagtttg  2160
ctaggtcacg aaggtggtat ttcatacgct gaatggccaa catatgatga aagtaagtta  2220
gtagaagcta cagttcaagt cattctacaa gttaatggta aagttcggag taaaattacc  2280
gttgacaagg atatcgccaa agaagaactt gaaaaattag cgttagctga tgctaagatt  2340
caacaatgga cggcagataa gactgttcgt aaggtaattg ttattcctaa caagattgtt  2400
aatatcgtag taggctaa                                                 2418

SEQ ID NO: 78          moltype = DNA  length = 1350
FEATURE                Location/Qualifiers
source                 1..1350
                       mol_type = genomic DNA
                       organism = unidentified
                       note = DP9 Glucose-6-phosphate isomerase sequence
SEQUENCE: 78
atggcacata tttcatttga cagttctaat gttgcagatt ttgtacatga aaacgaactt  60
gcagaaatcc aaccacttgt tacagctgct gatcagattt tacgtgatgg ctctggcgct  120
ggtagtgatt tccgtggatg gatcgattta ccatcaaatt atgataagga cgaatttgcc  180
cgtatcaaga aagccgctga taagatccgc aatgactcag aagtattcgt tgctatcggt  240
attggtggtt catatttggg tgctcgtgca gccattgatt tcttgaacaa cactttctac  300
aatcttctta ctaaagaaca acgtaatggt gctcctcaag taatcttcgc tggtaactca  360
attagttcaa cttaccttgc tgacgtattg aacttaatcg ggaccgtgaa cttctcaatt  420
aacgtaattt ctaagtcagg tacaactaca gaaccagcta ttgcattccg tgttcttaaa  480
gaaaaactaa tcaagaagta cggtgaagaa gaagctaaga aacgtatcta tgcaacaact  540
gaccgtgcta aaggcgccct aaagacagaa gctgatgcag aaaactatga agaattcgta  600
gttcctgatg acattggtgg tcgtttctct gttctttcag ctgttggttt attaccaatc  660
gcggttgccg gtggcgatat tgaccaattg atgaagggtg ctgaagatgc aagcaacgaa  720
tacaaggatg ctgatgttac aaagaacgaa gcatacaagt acgctgcttt acgtaacatc  780
ctttatcgta agggctacac aacagaactt cttgaaaact acgaaccaac acttcaatac  840
ttcggcgaat ggtggaagca attgatgggt gaatcagaag gtaaagatca aaagggtatc  900
tacccatctt ctgctaactt ctcaactgac ttacattcac taggacaata catccaagaa  960
ggtcgtcgca atttaatgga aacagttatc aatgttgaaa agcctaacca tgacatcgac  1020
attcctaagg ctgaccaaga ccttgatgga ttacgttatc tcgaaggtcg cacaatggac  1080
gaagttaaca agaaagctta ccaaggtgta actcttgctc ataacgacgg tggtgttcca  1140
gttatgacgg ttaacattcc tgatcaaaca gcttacacat taggctatat gatttacttc  1200
ttcgaagcag ctgttgctgt atctggttac ttgaacggaa ttaatccatt caaccaacca  1260
ggtgttgaag catacaagtc aaatatgttt gcattacttg gtaaaccagg ttatgaagat  1320
aagacagctg aattaaacgc tcgtctataa                                    1350

SEQ ID NO: 79          moltype = DNA  length = 1725
FEATURE                Location/Qualifiers
source                 1..1725
                       mol_type = genomic DNA
                       organism = unidentified
                       note = DP9 Phosphoglucomutase sequence
SEQUENCE: 79
atgagttggg aagattctgt caaagaatgg caagattatg cagatttaga ttttaattta  60
aaaaaagaat tagcaacttt agctgaagat aaagatgctt taaaagaagc cttttatgct  120
ccaatggaat ttggtacagc aggaatgcgt ggcgtaatgg gccctggtat caaccggatg  180
aatatctata cggttcgtca agcaacagaa ggtttagcta attttatgga taccttagat  240
tttactgata agaaacgggg agtggcgatc agttttgatt cccgctatca ctcacaagag  300
tttgctttag cagcagctgg tgttttaggt aagcatggta ttccaagttt tgtttttgat  360
agtatgcgtc ccactccaga attatcatat acagtacgtg agttaaacac ttatgctgga  420
atcatgatta ctgctagtca taatcctaaa caatataatg gatataagat ttatggtcct  480
gatggcggac aaatgccacc aatggaatct gataagatta cagaatatat tcgccaagta  540
actgacatct ttggtgttga agctcttact caaagtgaat taagagctaa gggcttaatg  600
accattattg gtgaagacat tgacctcaag tatcttgagg aagttaagac ggtatcaatt  660
aatcatgaac taatccagcg ctttggtgca gacatgaagt tgatctactc accattacat  720
ggtactggaa aagtagttgg tggacgtgcg ttagaaaatg ctggttttaa ggattacact  780
atggtccctg aacaagcaat tgctgaccca gaatttatta caacgccatt ccctaaccca  840
gaattcccac aaactttga tttggctatt gaattaggta aaaagcaaga tgctgacctt  900
ttgattgcca ctgatccgga tgccgatcgt ttgggagctg ccgttcgttt accaaatggt  960
gactacaaat tattgacagg gaaccaaatt gcagccttga tgttagaata catcttaact  1020
gcgcatgatg cagcaggtga cttgccaggt aacgcagctg ccgttaagtc aattgtttct  1080
agtgaactag caaccagaat tgccgaagcc catcatgtag aaatgattaa cgttctaact  1140
gggtttaagt acattgctga ccaaattaaa cattacgaag aaaatggcga ccataccttt  1200
atgtttggtt tcgaagaaag ttatggctat cttgttcggc catttgttcg cgataaagat  1260
```

-continued

```
gccatccaag gaattgtcct attggctgaa attgctgctt attatcgtag taaggggcaa  1320
accttatatg acggtcttca aaacttattt actacttacg gatatcatga agaaaagacc  1380
atttcaaaag atttccctgg agttgacggt aaagaaaaaa tggctgccat tatggaaaag  1440
gttcgtgaag aacgcccaag tcaatttgat cagtacaagg tattagaaac tgaagacttc  1500
ttagctcaaa ctaagtatga agcagatgga tctacccaag ctatcaaatt accaaaagcg  1560
gatgttttga aatttacatt agatgatggt acttggattg caattcgtcc ttctggaaca  1620
gaaccaaaaa ttaaattcta tattggtaca gttggcgaag atgaaaaaga tgctttgaat  1680
aagattgatg tttttgaaac agctattaat gaacttataa aataa                    1725

SEQ ID NO: 80          moltype = DNA  length = 3426
FEATURE                Location/Qualifiers
source                 1..3426
                       mol_type = genomic DNA
                       organism = unidentified
                       note = DP9 2-oxoglutarate carboxylase small subunit sequence
SEQUENCE: 80
atgcaccgta ttttaattgc caaccgaggc gaaattgcga cccgaattat tcgggcaacg  60
catgaactcg gaaaaacagc tgtagcaatt tatgctaaag cggatgaatt ttctatgcat  120
cgttttaaag cagatgaagc ttaccaagtt ggtgaagata gtgatccaat tggagcatat  180
ttaaatattg atgacattat tcgtattgca aaagaaaata atattgatgc aattcacccc  240
ggctatggat ttttgtcgga aaatgctgta tttgcgcgag cagttgaagc agctgggatt  300
aagttcattg gacctcgacc cgaattacta gaaatgtttg gtgataaatt acaagctaaa  360
aatgcagcca ttaaggccgg tgtaccaact attccgggaa cggaaaaacc agttaaagat  420
gtcgatgacg cgctaaattt tgcagagcaa tttggctatc ctatatttgt taagtcagcg  480
gcaggtggcg gcggaaaagg gatgcggatt gtacatcatc aacaagagat gcgcgaagca  540
tttaagatgg ctcagtcaga agcttcttcg tcttttggtg acgatgaaat ttacttagaa  600
cgttacttag ttgatccaat ccatattgag gttcaagtag ttgcggatga acacggtgag  660
atggttcatt tgtatgaacg aaattcatcg attcagcgac gccatcaaaa aatcattgaa  720
tttgctccag cagtgggaat ttctgccacc gtccgtgatc aaataagaaa agctgcttta  780
aaattattga agtcggtcaa ttatagtaac gctgcaacca ttgagttttt ggtagaaggt  840
aatcaatttt actttatgga agtgaatcca cgaattcagg ttgaacatac agttaccgaa  900
gaagtcacgg gaatcgatat tgtgcaaacc caaattaagg ttgctgaagg tcaaagatta  960
cacgaagaaa tcggtgttcc tcaacaagcc caaattgaag ctgtgggagt ggcaattcaa  1020
gcccgaatta ccactgaaga tccaatgaat aactttattc cagatgtcgg tagaatccag  1080
acgtatcgtt cacctggtgg aacaggtgtg agattggatg ctggaaatgc ctttgctgga  1140
gccattgtaa ctccgcatta tgattcactt ctgaccaagg caattgtcca tgcgccaacc  1200
tttgacgaag ccttggtaaa gatggatcga gtgctcaatg aatttgtaat tgctggggtt  1260
aaaactaata ttccattttt aaagaaatta attcatcatc ctatttttag atcggaatta  1320
gctccgacaa cctttgtgga tgagacacca gaactctttg atttaaaagc tgaaactccg  1380
gtagttactc aacttttgag ttacattgct aatactacta tcaatggtta tccaggctta  1440
gaaaagcaga atccagtagt gttaactcgg ccagtccgtc cacattttga agcacaagta  1500
ccgcatgaaa atgcgaaaca gatcttggat agtaagggac ctgatgccat gatcaattgg  1560
ctgttaaaac aaaagcaggt cttgctaacc gatacgacca tgcgggatgc ccatcaatca  1620
ttatttgcta cgcgaatgcg gaccaaagac atggtagaaa ttgccgatca agtccagaaa  1680
ggtctgccta acctatttc agctgaagtt tggggcggtg cgacctttga tgttgcttat  1740
cggttcctag gtgaggatcc atgggaaaga ctccaacaat tgcgggctaa aatgccaaat  1800
acgatgctcc aaatgctttt acgtgggtca aatgcagtag ggtatcaaaa ttatccagac  1860
aacgccattg acgaatttat tcgattggct gccaaaaatg gaattgatgt tttccgaatc  1920
tttgattctc ttaattgggt gccacagctt gaagaatcta tccaacgggt gcgtgataat  1980
ggaaaagtgg ctgaagcagc catggcatat actggcgata ttttagatac taatcgtact  2040
aaatataatt tgaaatatta tgtggatttg gctcaagaac tccaagcagc aggtgctcat  2100
attattggaa tcaaagatat gtcaggaatt ttaaaaccac aagctgctta tgcattaatt  2160
tcagagttaa aaaatcatct ggatgtgcca attcatttgc atacgcacga tactacaggc  2220
aacggcattt tcttatattc tgaagcaata cgagctggag ttgatgtggt cgacgttgcc  2280
acttctgcgc tagcgggaac gacttctcag ccttcaatgc agtctcttta ctatgcgttg  2340
tctaataacc agcgccaacc agatttagat attcaaaaag cagaaaaact agatgaatat  2400
tggggcggaa ttcgaccata ttacgaagga tttggcaccc aattaaatgg accacaaact  2460
gaaatttatc gaattgaaat gcctggtgga cagtatacca accttcgcca gcaagctaac  2520
gcagtccatt tgggtaagcg ttgggatgag attaaggaaa tgtacgcaac cgtcaatcaa  2580
atgtttggcg atattccaaa ggttacgcct tcttctaaag tagttggcga tatggcacta  2640
ttcatggtcc aaaatgattt gacgcctgaa atggtaatga acgataaggg acaattaagt  2700
tttcccgaat cagtggtaaa ctttttccgt ggtgatttag gacaaccggc gggtggtttt  2760
ccaaaacagc tccaaaaggt gattctaaaa gagcaagccc cattgacagt acgaccagga  2820
gctttagccg atccagttga ttttgatcaa gttcgtaaac aggcaactaa ggttttaggt  2880
caccaagcaa gtgatgaaga agttatgtcg tttattatgt atccagatgt gatgaccgaa  2940
tacattcaac gtcaaaatga atatggtcca gtaccattat tagatactcc aatctttttc  3000
caaggcatgc atattggcca acgcattgat ttacaattgg gacgcggaaa atcggtcatt  3060
attgtccttc gagaaattag tgaagcagat gaggcgggcc aaaggtcact tttctttgat  3120
ataaatggac aaagtgaaga agtgattgtt tatgatgtta atgcgcaggt aacgaaagta  3180
aagaagatta aagctgatcc gactaaagcc gaacagattg gcgctactat ggcgggctcg  3240
gtcattgaag tccaagtaga agcgggccaa aaggtccagc gaggtgataa cttaattgtc  3300
actgaggcga tgaaaatgga gaccgcgtta agagcacctt tcgacgcaac cattaagaag  3360
atttatgcta cccctgaaat gcaaatcgag acgggggatt tattgattga actagaaaag  3420
gagtaa                                                               3426

SEQ ID NO: 81          moltype = DNA  length = 2058
FEATURE                Location/Qualifiers
source                 1..2058
                       mol_type = genomic DNA
```

```
                        organism = unidentified
                        note = DP3 Glycine--tRNA ligase beta subunit sequence
SEQUENCE: 81
atgtcaacat ttttattaga aattggactt gaagaaatac cagctcattt ggtaaccagt  60
tcagagaatc agttaattga aagaactaaa aagttcttat cagagcatcg tttaacagta  120
ggtgatatta aaccatattc aacaccgcga cgtctggctg tcgttttgac agatgttgct  180
gaaacatcag aaagtttaag cgaagaaaag cgtggaccat ctgttgaccg tgcacaagac  240
gaaaacggta attggacaaa ggcagcatta ggttttgcac gtggtcaagg tgctaatcct  300
gaagcatttg aaattaaaga tggatatgtt tggctaacaa aacgtactgc tggtgtagcc  360
gcgaatgaaa ttttagctaa aattggtgat gaagttgtcg cccaaatgaa attttcaact  420
tatatgaagt gggctaatca cagctttttg tatgttcgac ctattcgttg gctcgtagca  480
cttcttgata gtgaagtcat ttctttcaac gtgttagata ttaccacaga tcgtttcaca  540
cgtggtcatc gtttttgtc ttcagaacat gttgaaatat cttctgcaga taattatgta  600
acgactttgc agggtgctaa cgtggttgtt gatgctacag tgcgcaaaaa tgaaattcga  660
tcgcagttga atgcaattgc tgaagctaat ggttgggttc tgcaacttga gaccgatgcg  720
gcgcaagatt tgttggaaga agttaataac attgttgagt ggccaacagc gtttgctggc  780
agtttcgatg agaaatattt agaaatacca gatgaagttt tgattacatc aatgcgcgaa  840
catcagcgtt tcttctttgt gacgaatgaa aaaggacaat tattgccaca ctttttgtca  900
ataagaaatg gtaaccgtga gcatctaaac aacgttattg ctggaaatga aaaagtattg  960
gtagcaaggt tagaagatgc cgaattcttc tatcatgaag accaaaccaa atcaatttct  1020
gattacatga ctaaagttaa aaagttagtc ttccatgaaa aaattggtac ggtgtatgaa  1080
cacatgcaac gcactggtgc tttggcttca gcaatggcgg tggttttgaa gtttgatgaa  1140
gtacaacagg ctgatttgac ccgtgcatca gaaatttata aatttgattt gatgaccggt  1200
atggttggtg aatttgatga acttcaaggc attatgggtg agcattatgc caagcttttt  1260
ggcgaagatg atgcggttgc aacagccatt cgagagcatt atatgccaac ttcagctaat  1320
ggtgaggttg cgcaatctga aattggtgct ttgttggccg ttgcggataa acttgatagc  1380
attgtgacgt tttttgctgc tggattaata ccaagtggtt ctaatgatcc ttatggctta  1440
cgacgtgcag ctactggcat cgtgcgtaca ttggtggata aaaaatggca tattgatttg  1500
cggcctttgc tagctgattt tgtgcaacag caaggtaagg taactgacac cgatttaacg  1560
acatttgttg atttcatgtt ggatcgtgtt cgtaaattat cgttggatgc tggaatacgt  1620
caagatattg tcattgctgg attaggcaac gttgatagag ctgatatcgt atatattagt  1680
cagcgagtcg aagttttgtc ccaacatagt ggtgatggca atttccgaga tgtaattgag  1740
gcactgactc gtgtggatcg cttagccgta aagcaagtaa ctaatgcaac ggttgatcct  1800
gctaagtttg aaaatcaatc tgaaaaggac ctatatcaag caacgttaac gcttgattta  1860
aatactttga tgcatgacgg tgcagaaaat ctctacatgg ccttagcaaa tttgcaaaaa  1920
ccaattgcgg cttattttga tgaaaccatg gttaacgctg aagatgaatc tgttaaagat  1980
aatcgatatg cgcagctgaa cgtcatacaa cgactaacca acggattagg agatttgacg  2040
caaatcgtca ttaagtaa                                               2058

SEQ ID NO: 82           moltype = DNA  length = 1347
FEATURE                 Location/Qualifiers
source                  1..1347
                        mol_type = genomic DNA
                        organism = unidentified
                        note = DP3 Glutamine synthetase sequence
SEQUENCE: 82
atggctcgta aaacatttac caaagaagaa attaaacaaa ttgttgttga tgaaaatgta  60
gaattcattc gtgtaacatt cactgatgtc ttaggtgcga ttaaaaacgt tgaagtacca  120
acttctcaat tagataaggt gcttgacaac aatttaatgt ttgacggttc atcaatcgag  180
ggatttgttc gtatcaatga atcagatatg tatctttacc ccgatttatc aacatttatg  240
attttcccat gggcaacgga tggtcatggt ggtaaagtgg cccgcttgat tgccgacatt  300
tatactgctg atcgtgagcc atttgctgga gaccccccgtc atgcgttacg ttcggtactc  360
gctgacgcgc gtgaagctgg gtttacggcg tttaatgtcg ggacagaacc tgaatttttc  420
ttgtttaaac ttgatgaaaa aggcaaccca accacagagt taaacgacaa aggtggttat  480
tttgacctag caccattgga tatgggtgaa aatgttcgtc gtgaaattgt tttgactttg  540
gaaaaaatgg gctttgaaat tgaagctgct caccacgaag ttgccgaagg acagcatgaa  600
gtagacttta aatacgcttc agctcttgaa gccgctgaca acattcagac gtttaagttg  660
gttgttaaaa ccatcgcacg caagaatggt tactatgcta cctttatgcc aaagcctgtt  720
gcaggtatta acggatccgg tatgcacaca aacatgtcat tatttacaaa agatggtaac  780
gcatttgttg atacatcgga tgaaatgggc ttgtcaaaaa cagcatataa cttcttgggt  840
ggtattttag aacatgcgac tgcgtttaca gcgcttgcaa acccaacagt taactcatac  900
aagcgcttga caccaggatt cgaagcacct gtttatgttg catggtcagc atcaaatcgt  960
tcaccaatgg ttcgagttcc ggcctcacgt ggtaattcaa cacgtttgga acttcgttca  1020
gttgacccaa cagctaatcc ttatactgca ttggcagcca ttttggcttc aggactggat  1080
gggatcaagc gtgaattaga gcctttggcc tcagttgata aaaatattta tttgatggat  1140
gaggtcgaac gggaaaaggc aggcattaca gacttaccag atactctgtt ggctgcagtt  1200
cgtgagttgg cggctgatga tgttgttcgt tcagctattg gagaacatat tgctgataag  1260
tttattgaag caaagaagat tgaatacaca tcatatcgtc agtttgtttc tgaatgggaa  1320
acagattctt atcttgaaaa ttactaa                                     1347

SEQ ID NO: 83           moltype = DNA  length = 2049
FEATURE                 Location/Qualifiers
source                  1..2049
                        mol_type = genomic DNA
                        organism = unidentified
                        note = DP3 DNA gyrase subunit B sequence
SEQUENCE: 83
gtgttcgcag attatatctg ttcacacgct aataatatgg cagagaatat cgaaaatgaa  60
gcattggaga acattgatgg catcgtaacc gatgataccg aaatccgtca agcaagcacc  120
```

-continued

```
gttcatgcag cagcaggcgc ttacaatgct gatcagattc aagttttgga aggattggaa  180
gctgtccgca aacgccctgg catgtacatt ggtacgacca cagcgcaagg cttgcaccat  240
ttggtatggg aaattgttga taacgggatt gatgaggcat tagcagggtt tgcgtcacat  300
attacggtca caatcgaaaa ggataactca atcacggtaa ccgatgacgg ccgtggtatt  360
cctgtcgaca ttcaaactaa aacgggtaag ccagctcttg aaactgtctt tacggtatta  420
cacgccggtg gtaaatttgg cggtggcggt tataaagtat ctggtggatt acacggtgtt  480
ggagcttctg ttgtcaatgc cttgtcaacg gatttggacg ttagagttgt tcgtgataat  540
actgtttatt acatggactt caaagtggga cgcgtcaaca caccgatgaa acaattgacg  600
gaaaagccca ctattgagcg tggtacaatt gttcatttta agcccgatgc agatattttc  660
cgtgaaacaa cagtttataa ctacaacaca ttactaacac gtgtgcgcga attggccttt  720
ttgaataaag gtttgcgcat ttcgattaca gataatcgac ctgaagaagc tgtttctgaa  780
agctttcatt ttgaaggtgg gattaaagaa tacgtcagct atttgaataa ggacaagact  840
gctattttcc ctgaacctgt ttacgttgag ggtgaagaaa atggcattgt agtggaagct  900
gccttacagt acactaccga tattaaagac aatctgcgga cgtttactaa caatatcaat  960
acctatgaag gtgggacgca cgaaactggc tttaaaacag ccttaacacg tgtaatcaat  1020
gattacgctc gtaaaaatgg tcagctcaaa gataatgcag aaagtttgac aggggaagat  1080
gtgcgcgaag gcatgactgc tatcgtgtca atcaagcacc cagatccaca atttgaagga  1140
caaaccaaaa ctaaattagg taactccgat gcacgtcaag caacggatcg gatgttctca  1200
gaaacgttca gtcgtttcat gatggaaaat ccagcagttg ccaagcaaat tgttgaaaaa  1260
ggtgtcttag cccaaaaagc acgattggct gccaagcgtg cacgcgaaat gacacgcaaa  1320
caatctggtt tggaaattgg taatttgcca ggtaaattag ctgataatac ctcaaatgat  1380
cctgaaattt cagaattatt tattgttgag ggtgattcag ccggtggttc agctaagcaa  1440
ggacgtaacc gtttgacgca agctattttg ccaattcgag gcaaaatttt aaatgttggg  1500
aaagcctcat tggatcgggt gttagccaac gaagaaattc gatcattgtt tacagcaatg  1560
ggaactggat ttggtgagga ctttaatgtt gaaaaagcca attatcacaa agtcattatt  1620
atgacagatg ccgatgtcga tggcgcccat attcgaacac tattgttaac gctattttat  1680
cgttatatgc gaccacttgt tgacgcaggc tatatttata ttgcgcagcc accgctttac  1740
ggtgttgcct taggcaataa taaatcaatg acgtacattg attctgatga agaacttgaa  1800
gactatttgt cacaattgcc atctaatatt aaaccaaaag ttcaacgtta taagggacta  1860
ggggaaatgg attacgatca actagcagat acaaccatgg atccgcagaa tcgtcgtttg  1920
ctacgtgttg acccaactga tgctgaagaa gccgaagcag ttattgatat gttaatgggt  1980
ggggatgtac caccacgtcg taagtttatt gaagacaatg ctgtctttgt tgagaacttg  2040
gatatttaa                                                          2049

SEQ ID NO: 84          moltype = DNA  length = 375
FEATURE                Location/Qualifiers
source                 1..375
                       mol_type = genomic DNA
                       organism = unidentified
                       note = DP3 Leucine--tRNA ligase sequence
SEQUENCE: 84
atgattttcg tcaacgaagc ttacaaaacc gatgctgtgc cgaaagcggc ggcggaaaac  60
ttcgtacaga tgctgtcccc actggcaccg catttggcag aagaactgtg ggaacgactt  120
ggtcataccg atacgattac gtatgaacca tggccaacgt acgatgaggc ttggaccata  180
gaatccgaag tggaaatcgt cgtgcaagtg aacggcaaaa tcgtagaacg cacgaaaatt  240
tccaaagacc tggatcaagc agcgatgcaa gaacacagct taagcctgcc gaatgttcag  300
caggctgtgg ctgggaagac gatccgcaaa gtgattgcgg tgccaggcaa gctggtgaat  360
atcgtcgttg gataa                                                   375

SEQ ID NO: 85          moltype = DNA  length = 1353
FEATURE                Location/Qualifiers
source                 1..1353
                       mol_type = genomic DNA
                       organism = unidentified
                       note = DP3 Glucose-6-phosphate isomerase sequence
SEQUENCE: 85
atggcacaca ttacatttga cacaaagaac attgagaatt ttgttgcacc atacgaattg  60
gacgaaatgc aaccattaat tacgatggct gaccaacaat tgcgcaatcg tacgggcgct  120
ggtgcagaat attctgattg gttgactcta cctactgatt acgacaagga agaatttgca  180
cgtattcaaa aggcggcgca acaaattcaa tctgattcaa agattttggt tgtcattggt  240
attggtggtt catatttggg cgcgaagatg gcggttgatt tcttgaatcc aatgtttaat  300
aatgaattgt cggatgacca acgtcaaggt gttaaaattt attttgctgg taactcaact  360
tctgcagctt acttaaatga tttagttcgt gtcattggtg atcaagactt ttctgtcaac  420
gttatctcaa agtctggcac aacaacggaa ccatcaatcg ctttccgtgt gtttaaacaa  480
ttgttagaga aaaagtatgg ttctgatgct gctaagaagc gtatctatgc cacaacagat  540
gccaatcgtg gtgctttgca cgatgaagca gcggcttcag gttatgaaac attcacaatt  600
cctgatggtg tcggtggtcg cttctctgtt ttgacagctg ttggcttgtt gccaattgct  660
gcttcaggcg ctgatatcca aaaattgatg gacggcgctc gtgatgcgca aaacgaatat  720
actgattctg atttgaaaaa gaacgaggca tataaatatg cagccgttcg tcgtattttg  780
tatgataagg gttatacaac agaattgttg attaactggg aaccttcaat gcaatatttg  840
tcagagtggt ggaagcaatt gatgggcgag tctgaaggta aaaatcaaaa gggtatctat  900
ccatcttcag ctaacttctc aaccgacttg cactcacttg gacaatatat tcaagaagga  960
cgccgtgatt tgtttgagac ggtggttaag ttagacaatc ctgtatctaa tttggaccta  1020
ccacatgaag aaggcaacaa tgatggtttg caatatttgg aaggtatcac gatcgatgaa  1080
gtgaacacca aagcatctca aggggttact ttggctcacg ttgatggtgg tgtgcctaac  1140
ttggctgttc acttgccagc acaagatgct tattcactcg gttacatgat ttacttcttt  1200
gaaatggctg ttggggcgtc tggttatacg tttggtatta acccattcaa ccaaccgggt  1260
gtcgaagcct ataagacagc tatgtttgca ctattaggta agcctggcta tgaggaagcg  1320
acaaaagcat tccgtgcccg cttagacaaa taa                               1353
```

```
SEQ ID NO: 86          moltype = DNA  length = 672
FEATURE                Location/Qualifiers
source                 1..672
                       mol_type = genomic DNA
                       organism = unidentified
                       note = DP3 Beta-phosphoglucomutase sequence
SEQUENCE: 86
atgactaaat tttcagatat taaaggtttt gcctttgatt tagatggggt tattgctgat  60
acggcgcgtt tccatggtga agcttggcat caaacagctg atgaggttgg cacaacttgg  120
acaccagaat tggctgaagg tttgaagggc attagtcgta tggcttcctt gcaaatgatt  180
ttggatgctg gggatcatgc cgatgatttt tcgcaagcag ataaagaagc attagcagaa  240
aagaaaaatc ataattatca acaacttatt tcaacattga cggaagatga tattttgcct  300
ggcatgaaag attttattca atcagccaag gcagccggct atacaatgtc ggtggcatca  360
gcttctaaaa acgcaccaat gattctagat catttgggat tgaccaagta ttttgtcggc  420
attgttgatc ccgccacttt gacaaaggga aaacctgatc ctgaaatctt cgttcgtgct  480
gcggaagtct tacatttaaa tccagaaaat gttattggat tggaagattc agctgctggt  540
attgtgtcaa tcaatggcgc aggtgagaca tcactagcca ttggtaacgc agatgttttg  600
tcaggagcgg acttgaattt tgcgtctact tcagaagtga ccttagcaaa tattgaagct  660
aaaatgcaat ag                                                     672

SEQ ID NO: 87          moltype = DNA  length = 1377
FEATURE                Location/Qualifiers
source                 1..1377
                       mol_type = genomic DNA
                       organism = unidentified
                       note = DP3 2-oxoglutarate carboxylase small subunit sequence
SEQUENCE: 87
atgtttaaaa aagtgcttgt tgctaatcgt ggtgaaattg cggttcgcat cattcgaacg  60
ctcaaagaaa tggggattgc ttcagtcgct atttactcga cagccgataa agatagttta  120
cacgtacaaa tcgctgacga agcgattgct gtggggggac cgaaacctaa agattcatac  180
ttaaatatga aaaatatttt aagtgcagcc ctgctgtcgg gagcagaggc aattcatcca  240
ggatatggct ttttagctga aaatacattg tttgctgaaa tggttggcga agttggtatt  300
aaatggattg ggcctaggcc agaaacaatt gagttaatgg gtaacaaagc taacgcacgt  360
gaagaaatgc ggcgtgccgg cgtaccagta attccaggtt cagagggatt tatccgtgat  420
tttcatgaag caaaaacggt tgctgataaa attggctatc ctttgttgct aaaagctgcc  480
gctggtggtg gtggtaaagg catgcgtttt gtttacggtg aggatgagtt atcagataaa  540
tttgatgatg ctcaaaacga agcgcgtgct tcgtttggcg atgatcacat gtatattgaa  600
aaagttatgt cacgtgttcg ccacattgaa atgcaagtgt ttcgtgatga gaatggtcat  660
gttgtttact tgccagaacg aaattgctca ttgcaacgca ataatcaaaa ggtgattgaa  720
gaatcaccag ctacgggtgt aacgcctgaa atgcgtgcgc atcttggcga aattgttact  780
aaagccgcaa aagcattggc gtatgaaaat actggaacca ttgaattttt gcaagatcgc  840
gatggtcatt tctactttat ggaaatgaac acacgtattc aagtagaaca tccagtttct  900
gaaatggtaa cgggattaga tttaattaag ttacaaattc aagttgctgc aggcttagat  960
ttaccggtgg ttcaagatga cgtgatcgtt caaggccact ctatcgaagt acgtttgacg  1020
gctgagcagc cagaaaaaca ctttgcacct agtgctggaa cgattgattt tgttttttg  1080
ccaactggtg gaccgggtgt tcgtattgat tcagccttat ttaatggcga taaaattcaa  1140
ccattttacg attctatgat tggcaaatta attgttaagg ccgatgatcg tgaaacagcc  1200
atgagaaaga ttcaacgtgt ggttgatgaa actgttgtac gtggtgtagc aacgagccgt  1260
aattttcaaa aagctctgtt agctgatcca caggttcaac gtggcgaatt tgacacacgt  1320
tatttggaaa ctgaattttt accgagatgg acacaaacat tgccagataa tcaataa     1377

SEQ ID NO: 88          moltype = DNA  length = 1701
FEATURE                Location/Qualifiers
source                 1..1701
                       mol_type = genomic DNA
                       organism = unidentified
                       note = DP1 Glutamine--tRNA ligase sequence
SEQUENCE: 88
atgagcaagc ccactgtcga ccctacctcg aattccaagg ccggacctgc cgtcccggtc  60
aatttcctgc gcccgatcat ccaggcggac ctggattcgg gcaagcatac gcagatcgtc  120
acccgcttcc cgccagagcc caacggctac ctgcacatcg gtcatgccaa gtcgatttgt  180
gtgaacttcg gcctggctca ggagttcggt ggcgttacgc acctgcgttt cgacgacacc  240
aacccggcca aggaagacca ggaatacatc gacgccatcg aaagcgacat caagtggctg  300
ggcttcgaat ggtccggtga agtgcgctat gcatccaagt atttcgacca gctgttcgac  360
tgggccgtcg agttgatcaa ggccggcaag gcctacgttg acgacctgac cccgagcaa   420
gccaaggaat accgtggcag cctgaccgag ccgggcaaga acagcccgtt ccgcgaccgt  480
tcggtcgaag agaacctcga ctggttcaac cgcatgcgcg ccggtgagtt cccggacggc  540
gcccgcgtgc tgcgcgccaa gatcgacatg gcctcgccga acatgaacct gcgcgacccg  600
atcatgtacc gcattcgcca tgcccatcac caccagaccg gtgacaagtg gtgcatctac  660
cccaactacg acttcaccca cggtcagtcg gacgccatcg aaggcatcac ccactccatc  720
tgcaccctgg agttcgaaag ccatcgccct ctgtacgaat ggttcctgga cagcctgccg  780
gtgccggcgc acccgcgtca gtacgaattc agccgcctga acctgaacta caccatcacc  840
agcaagcgca agctcaagca actggtcgat gaaaagcacg tgcatggctg ggacgacccg  900
cgcatgtcga cgctctcggg tttccgtcgt cgtggctaca ccccggcgtc gatccgcaat  960
ttctgcgaca tggtcggcac caaccgttct gacggtgtgg tcgattacgg catgcttgag  1020
ttcagcatcc gtcaggatct ggacgcgaac gcgccgcgcg ccatgtgcgt gctgcgtccg  1080
ttgaaagtcg tgatcaccaa ctacccggaa gacaaggtcg accaccttga gctgccgcgt  1140
cacccgcaga aagaagagct gggcgtgcgc aagctgccgt tcgcgcgcga aatctacatc  1200
```

```
gaccgtgacg acttcatgga agagccgccg aagggttaca agcgcctgga gccgaacggc  1260
gaagtgcgcc tgcgtggcag ctacgtgatc cgcgccgacg aagcaatcaa ggacgccgaa  1320
ggcaacatcg tcgaactgcg ctgctcgtac gatccggaaa cactcggcaa gaaccctgaa  1380
ggccgtaagg tcaagggcgt gatccactgg gtgccggccg ctgccagcat cgagtgcgaa  1440
gtgcgtctgt acgatcgtct gttccgatcg ccgaacccgg agaaggccga agacagcgcc  1500
agcttcctgg acaacatcaa ccctgactcg ctgcaagtgc ttacaggttg tcgtgctgag  1560
ccatcgcttg gcgacgcaca gccggaagac cgtttccagt tcgagcgcga aggttacttc  1620
tgcgcggata tcaaggactc gaaacccggt gctccggtat tcaaccgtac cgtgaccttg  1680
cgtgattcgt ggggccagtg a                                             1701
```

```
SEQ ID NO: 89          moltype = DNA  length = 2418
FEATURE                Location/Qualifiers
source                 1..2418
                       mol_type = genomic DNA
                       organism = unidentified
                       note = DP1 DNA gyrase subunit B sequence
SEQUENCE: 89
atgagcgaag aaaacacgta cgactcgacc agcattaaag tgctgaaagg tttggatgcc  60
gtacgcaaac gtcccggtat gtacatcggc gacaccgatg atggtagcgg tctgcaccac  120
atggtgttcg aggtggtcga caactccatc gacgaagctt tggccggtca ctgcgacgac  180
atcagcatta tcatccaccc ggatgagtcc atcacggtgc gcgacaacgg tcgcggcatt  240
ccggtcgatg tgcacaaaga agaaggcgtt tcggcggctg aggtcatcat gaccgtgctg  300
cacgccggcg gtaagttcga tgacaactct tataaagtct ccggcggtct gcacggtgta  360
ggtgtgtcgg tagtgaacgc actgtccgaa gagctgatcc tgaccgttcg ccgtagcggc  420
aagatttggg agcagacgta cgtccatggt gtgccacaag agccgatgaa aatcgttggc  480
gacagtgaat ccacgggtac gcagatccac ttcaagccat cggctgaaac cttcaagaac  540
atccacttta gctgggacat cctggccaag cggattcgcg aactgtcctt cctcaactcc  600
ggtgtgggta tcgtcctcaa ggacgagcgc agcggcaagg aagaactgtt caagtacgaa  660
ggcggtctgc gcgcgttcgt tgaatacctg aacaccaata agaccgcggt caaccaggtg  720
ttccacttca acattcagcg tgaagacggc atcggcgtgg aaatcgccct gcagtggaac  780
gacagcttca acgagaactt gttgtgcttc accaacaaca ttccacagcg cgatggcggt  840
actcacttgg tgggtttccg ttccgcactg acgcgtaacc tgaacactta catcgaagcc  900
gaaggcttgg ccaagaagca caaagtcgcc accaccggtg acgatgcgcg tgaaggcctg  960
accgcgatta tctcggtgaa agtgccggat cccaagttca gctcccagac caaagacaag  1020
ctggtttctt ccgaggtgaa gaccgccgtg gaacaggaga tggcaagta cttctccgac  1080
ttcctgctgg agaacccgaa cgaagccaag ctggtcgtcg gcaagatgat cgacgctgca  1140
cgtgctcgcg aagcggcgcg taaagcccgt gagatgaccc gtcgtaaagg cgcgctggat  1200
attgctggct tgcctggcaa gttggctgac tgccaggaga aggacccagc gctctccgag  1260
ctatatcttg tggaaggtga ctctgctggc ggttccgcca agcagggtcg taaccgtcgc  1320
acccaggcga tcctgccgtt gaaaggcaag attctcaacg tagagaaggc ccgcttcgac  1380
aagatgattt cctcccagga agtcggcacc ttgattacgg cgttgggttg cggcattggc  1440
cgcgatgagt acaacatcga caagctgcgc taccacaaca tcatcatcat gaccgatgct  1500
gacgtcgacg gttcgcacat ccgtaccttg ctgctgacct tcttcttccg tcagttgcct  1560
gagctgattg agcgtggcta catctatatc gcgcagccgc cgttgtacaa agtgaaaaag  1620
ggcaagcaag agcagtacat caaagacgac gacgccatgg aagagtacat gacgcagtcg  1680
gccctggaag atgcaagcct gcacttgaac gacgaagcac cgggtatctc cggtgaggcg  1740
ttggagcgtc tggttaacga cttccgtatg gtgatgaaga ccctcaagcg tctatcgcgt  1800
ctgtaccctc aggaactgac cgagcacttc atctacctgc cggccgtcag tctggagcag  1860
ttgggtgatc atgcagcgat gcaagagtgg ctggctcagt acgaagtacg cctgcgcact  1920
gttgagaagt ctggcctggt gtacaaagcc agtctgcgtg aagaccgtga acgtaacgtg  1980
tggctgccgg aggttgagtt gatctcccac ggcctgtcga attacgtcac cttcaaccgc  2040
gacttcttcg gcagtaatga ctacaagacg gtcgtgaccc tcggcgcgca gttgagcacc  2100
ttgctggatg atggtgctta cattcaacgt ggcgagcgta agaaagcggt caaggagttc  2160
aaggaagcct tggactggct gatggcggaa agcaccaagc gtcataccat tcagcgatac  2220
aaaggtctgg gcgagatgaa ccctgatcag ttgtgggaaa ccaccatgga tccagcacag  2280
cgtcgcatgc tgcgcgtgac catcgaagac gccattggcg cagatcagat cttcaacacc  2340
ctgatgggtg atgcggtcga acctcgccgt gacttcatcg agagcaatgc cttggcggtg  2400
tccaacctgg acttctga                                                 2418
```

```
SEQ ID NO: 90          moltype = DNA  length = 1632
FEATURE                Location/Qualifiers
source                 1..1632
                       mol_type = genomic DNA
                       organism = unidentified
                       note = DP1 Isoleucine--tRNA ligase sequence
SEQUENCE: 90
atgaccgact ataaagccac gctaaacctt ccggacaccg ccttcccaat gaaggccggc  60
ctgccacagc gcgaaccgca gatcctgcag cgctgggaca gtattggcct gtacggaaag  120
ttgcgcgaaa ttggcaagga tcgtccgaag ttcgtcctgc acgacggccc tccttatgcc  180
aacggcacga ttcacatcgg tcatgcgctg aacaaaattc tcaaggacat gatcctgcgc  240
tcgaaaaccc tgtcgggttt tgacgcgccg tatgtcccgg gctgggactg ccatggcctg  300
ccgatcgaac acaaagtcga agtgacctac ggcaaaaacc tgggcgcgga taaaacccgc  360
gaactgtgcc gtgcctacgc cactgagcag atcgaagggc agaagtccga attcatccgc  420
ctgggcgtgc tgggcgagtg ggacaacccg tacaagacca tgaacttcaa gaacgaggcc  480
ggtgaaatcc gtgccttggc tgaaatcgtc aaaggcggtt ttgtgttcaa gggcctcaag  540
cccgtgaact ggtgcttcga ctgcggttcg gccctggctg aggcggaagt cgaatacgaa  600
gacaagaagt cctcgaccat cgacgtggcc ttcccgatcg ccgacgacgc caagttggcc  660
caggctttcg gcctggcaag cctgagcaag ccggcggcca tcgtgatctg gaccaccacc  720
ccgtggacca tcccggccaa ccaggcgctg aacgtgcacc cggaattcac ctacgccctg  780
```

-continued

```
gtggacgtcg gtgatcgcct gctggtgctg gccgaggaaa tggtcgaggc ctgtctggcg  840
cgctacgaac tgcaaggttc ggtgatcgcc accaccaccg gctccgcgct ggaactgatc  900
aacttccgtc acccgttcta tgaccgcctg tcgccggttt acctggctga ctacgtcgaa  960
ctgggttcgg gtacgggtgt ggttcactcc gcaccggcct acggcgttga cgacttcgtg  1020
acctgcaaag cctacggtat ggtcaacgat gacatcctca acccggtgca gagcaatggt  1080
gtgtacgcgc catcgctgga gttcttcggc ggccagttca tcttcaaggc taacgagccg  1140
atcatcgaca aactgcgtga agtcggtgcg ctgctgcaca ccgaaaccat caagcacagc  1200
tacatgcact gctggcgcca caaaaccccg ctgatctacc gcgccaccgc gcagtggttt  1260
atcggcatgg acaaagagcc gaccagcggc gacaccctgc gtgtgcgctc gctcaaagcc  1320
atcgaagaca ccaagttcgt cccggcctgg ggccaggcgc gcctgcactc gatgatcgcc  1380
aatcgtccgg actggtgcat ctcccgccag cgtaactggg gcgtaccgat cccgttcttc  1440
ctgaacaagg aaagcggcga gctgcaccca cgcaccgtcg agctgatgga agccgtggcc  1500
ttgcgcgttg aacaggaagg catcgaagcc tggttcaagc tggacgccgc cgagctgctg  1560
ggcgacgaag cgccgctgta cgacaagaag gctcggacca acaccgtggc tggttccact  1620
cgtcgctgct ga                                                    1632

SEQ ID NO: 91          moltype = DNA  length = 1784
FEATURE                Location/Qualifiers
source                 1..1784
                       mol_type = genomic DNA
                       organism = unidentified
                       note = DP1 NADH-quinone oxidoreductase subunit C/D sequence
SEQUENCE: 91
atgactacag gcagtgctct gtacatcccg ccttataagg cagacgacca ggatgtggtt  60
gtcgaactca ataaccgttt tggccctgac gcctttaccg cccaggccac acgtaccggc  120
atgccggtgc tgtgggtggc gcgcgccagg ctcgtcgaag tcctgacctt cctgcgcaac  180
ctgcccaagc cgtacgtcat gctctatgac ctgcatggcg tggacgagcg tctgcggacc  240
aagcgccagg gcctgccgag cggcgccgat ttcaccgtgt tctatcacct gctgtcgatc  300
gaacgtaaca gcgacgtgat gatcaaggtc gccctctccg aaagcgacct gagcgtcccg  360
accgtgaccg gcatctggcc caacgccagt tggtacgagc gtgaagtctg ggacatgttc  420
ggtatcgact tccctggcca cccgcacctg acgcgcatca tgatgccgcc gacctgggaa  480
ggtcacccgc tgcgcaagga cttccctgcg cgcgccaccg aattcgaccc gttcagcctg  540
aacctcgcca agcaacagct tgaagaagag gctgcacgct tccggccgga agactggggc  600
atgaaacgct ccggcaccaa cgaggactac atgttcctca acctgggccc gaaccaccct  660
tcggcgcacg gtgccttccg tatcatcctg caactggacg gcgaagaaat cgtcgactgc  720
gtgccggaca tcggttacca ccaccgtggt gccgagaaga tggccgagcg ccagtcgtgg  780
cacagcttca tcccgtacac cgaccgtatc gactacctcg gcggcgtgat gaacaatctg  840
ccgtacgtgc tctcggtcga gaagctggcc ggtatcaagg tgccggaccg cgtcgacacc  900
atccgcatca tgatggccga gttcttccgg atcaccagcc acctgctgtt cctgggtacc  960
tacatccagg acgtcggcgc catgaccccg gtgttcttca ccttcaccga ccgtcagcgc  1020
gcctacaagg tcatcgaagc catcaccggc ttccgcctgc acccggcctg gtaccgcatc  1080
ggcggtgtcg cgcacgacct gccaaatggc tgggaacgcc tggtcaagga attcatcgac  1140
tggatgccca agcgtctgga cgagtaccag aaagccgccc tggacaacag catcctcaag  1200
ggccggacca ttggggtcgc ggcctacaac accaaagagg ccctggaatg gggcgtcacc  1260
ggtgctggcc tgcgttccac cggttgcgat ttcgacctgc gtaaagcgcg cccgtactcc  1320
ggctacgaga acttcgaatt cgaagtgccg ttggcggcca atggcgatgc ctacgaccgt  1380
tgcatcgtgc gcgtcgaaga aatgcgccag agcctgaaga tcatcgagca atgcatgcgc  1440
aacatccggc aggcccgtac aaggcggacc acccgctgac cacgccgccg ccgaaagagc  1500
gcacgctgca acacatcgaa accctgatca cgcacttcct gcaggtttcg tggggcccgg  1560
tgatgccggc caacgaatcc ttccagatga tcgaagcgac caagggtatc aacagttatt  1620
acctgacgag cgatggcggc accatgagct accgcacccg gattcgcact ccaagcttcc  1680
cgcacctgca gcagatccct tcggtgatca aggtgaaat ggtcgcggac ttgattgcgt  1740
acctgggtag tatcgatttc gttatggccg acgtggaccg ctaa                 1784

SEQ ID NO: 92          moltype = DNA  length = 1059
FEATURE                Location/Qualifiers
source                 1..1059
                       mol_type = genomic DNA
                       organism = unidentified
                       note = DP1 Protein RecA sequence
SEQUENCE: 92
atggacgaca acaagaagaa agccttggct gcggccctgg gtcagatcga acgtcaattc  60
ggcaagggtg ccgtaatgcg tatgggcgat cacgaccgtc aggcgatccc ggctatttcc  120
actggctctc tgggtctgga catcgcactc ggcattggcg gcctgccaaa aggccgtatc  180
gttgaaatct acggccctga atcttccggt aaaaccaccc tgaccctgtc ggtgattgcc  240
caggcgcaaa aaatgggcgc cacttgtgcg ttcgtcgatg ccgagcacgc tcttgaccct  300
gaatacgccg gcaagctggg cgtcaacgtt gacgacctgc tggtttccca accggacacc  360
ggtgagcaag ccttggaaat caccgacatg ctggtgcgct ccaacgccat cgacgtgatc  420
gtggtcgact ccgtggctgc cctggtgccg aaagctgaaa tcgaaggcga aatgggcgac  480
atgcacgtgg gcctgcaagc ccgtctgatg tcccaggcgc tgcgtaaaat caccggtaac  540
atcaagaacg ccaactgcct ggtgatcttc atcaaccaga tccgtatgaa gattggcgtg  600
atgttcggca gcccggaaac caccaccggt ggtaacgcgt tgaagttcta cgcttcggtc  660
cgtctggata tccgccgtac tggcgcggtg aaggaaggcg acgaggtggt gggtagcgaa  720
acccgcgtta aagttgtgaa gaacaaggtg gccccgccat tccgtcaggc tgagttccag  780
attctctacg gcaagggtat ctacctgaac ggcgagatga tcgacctggg cgtactgcac  840
ggtttcgtcg agaagtccgg tgcctggtat gcctacaacg gcagcaagat cggtcagggc  900
aaggccaact cggccaagtt cctggcggac aacccggata tcgctgccac gcttgagaag  960
cagattcgcg acaagctgct gaccccggca ccagacgtga aagctgctgc caaccgcgag  1020
ccggttgaag aagtagaaga agtcgacact gacatctga                        1059
```

```
SEQ ID NO: 93          moltype = DNA  length = 1161
FEATURE                Location/Qualifiers
source                 1..1161
                       mol_type = genomic DNA
                       organism = unidentified
                       note = DP1 RNA polymerase sigma factor RpoD sequence
SEQUENCE: 93
atggaaatca cccgcaaggc tctgaaaaag cacggtcgcg gcaacaagct ggcaattgcc  60
gagctggtgg ccctggctga gctgttcatg ccaatcaagc tggtgccgaa gcaatttgaa  120
ggcctggttg agcgtgtgcg cagtgctctt gagcgtctgc gtgcccaaga gcgcgcaatc  180
atgcagctct gcgtacgtga tgcacgcatg ccgcgtgccg acttcctgcg ccagttcccg  240
ggcaacgaag tggatgaaag ctggaccgac gcactggcca aaggcaaggc gaagtacgcc  300
gaagccattg gtcgcctgca gccggacatc atccgttgcc agcagaagct gaccgcgctt  360
caaaccgaaa ccggtctgac gattgctgag atcaaggaca tcaaccgtcg catgtcgatc  420
ggtgaggcca aggcccgccg cgcgaagaaa gagatggttg aagcgaactt gcgtctggtg  480
atctccatcg ccaagaagta caccaaccgt ggcctgcaat tcctcgatct gatccaggaa  540
ggcaacatcg gcttgatgaa ggctgtggac aagttcgaat accgtcgcgg ctacaagttc  600
tcgacttatg ccacctggtg gatccgtcag gcgatcactc gctcgatcgc agaccaggcc  660
cgcaccatcc gtattccggt gcacatgatc gagaccatca acaagctcaa ccgtatttcc  720
cggcagatgt tgcaggaaat gggtcgcgaa ccgacgccgg aagagctggg cgaacgcatg  780
gaaatgcctg aggataaaat ccgtaaggta ttgaagatcg ctaaagagcc gatctccatg  840
gaaacgccga ttggtgatga cgaagactcc catctgggtg acttcatcga agactcgacc  900
atgcagtcgc ccatcgatgt ggctaccgtt gagagcctta aagaagcgac tcgcgacgta  960
ctgtccggcc tcactgcccg tgaagccaag gtactgcgca tgcgtttcgg catcgacatg  1020
aataccgacc acacccttga ggaagtcggt aagcagtttg acgtgacccg tgaacggatc  1080
cgtcagatcg aagccaaggc actgcgcaag ttgcgccacc cgacgcgaag cgagcatcta  1140
cgctccttcc tcgacgagtg a                                            1161

SEQ ID NO: 94          moltype = DNA  length = 4074
FEATURE                Location/Qualifiers
source                 1..4074
                       mol_type = genomic DNA
                       organism = unidentified
                       note = DP1 DNA-directed RNA polymerase subunit beta sequence
SEQUENCE: 94
atggcttact catatactga gaaaaaacgt atccgcaagg actttagcaa gttgccggac  60
gtcatggatg tcccgtacct tctggctatc cagctggatt cgtatcgtga attcttgcaa  120
gcgggagcga ctaaagatca gttccgcgac gtgggcctgc atgcggcctt caaatccgtt  180
ttcccgatca tcagctactc cggcaatgct gcgctggagt acgtgggtta tcgcctgggc  240
gaaccggcat ttgatgtcaa agaatgcgtg ttgcgcggtg ttacgtacgc cgtacctttg  300
cgggtaaaag tccgtctgat cattttcgac aaagaatcgt cgaacaaagc gatcaaggac  360
atcaaagagc aagaagtcta catgggcgaa atcccattga tgactgaaaa cggtaccttc  420
gttatcaacg gtaccgagcg cgttatcgtt tcccagctgc accgttcccc gggcgtgttc  480
ttcgaccacg accgcggcaa gacgcacagc tccggtaagc tcctgtactc cgcgcggatc  540
attccgtacc gcggctcgtg gttggacttc gagttcgacc cgaaagactg cgtgttcgtg  600
cgtatcgacc gtcgtcgtaa gctgccggcc tcggtactgc tgcgcgcgct cggctatacc  660
actgagcaag tgcttgatgc tttctacacc accaacgtat tcagcctgaa ggatgaaacc  720
ctcagcctgg aactgattgc ttcgcgtctg cgtggtgaaa ttgccgtcct ggatatccag  780
gatgaaaacg gcaaggtcat cgttgaagct ggccgccgta ttaccgcgcg ccacatcaac  840
cagatcgaaa aagccggtat caagtcgctg gacgtgccgc tggactacgt cctgggtcgc  900
accactgcca aggtcatcgt tcacccggct acaggcgaaa tcctggctga gtgcaacacc  960
gagctgaaca ccgagatcct ggcaaaaatc gccaaggccc aggttgttcg catcgagacc  1020
ctgtacacca acgacatcga ctgcggtccg ttcatctccg acacgctgaa gatcgactcc  1080
accagcaacc aattggaagc gctggtcgag atctatcgca tgatgcgtcc tggtgagcca  1140
ccgaccaaag acgctgccga gaccctgttc aacaacctgt tcttcagccc tgagcgctat  1200
gacctgtctg cggtcggccg gatgaagttc aaccgtcgta tcggtcgtac cgagatcgaa  1260
ggttcgggcg tgctgtgcaa ggaagacatc gtcgcggtac tgaagacctt ggtcgacatc  1320
cgtaacggta aaggcatcgt cgatgacatc gaccacttgg gtaaccgtcg tgttcgctgc  1380
gtaggcgaaa tggccgagaa ccagttccgc gttggcctgg tacgtgttga gcgtgcggtc  1440
aaagagcgtc tgtcgatggc tgaaagcgaa ggcctgatgc cgcaagatct gatcaacgcc  1500
aagccagtgg ctgcggcggt gaaagagttc ttcggttcca gccagctctc gcagttcatg  1560
gaccagaaca acccgctctc cgagatcacc cacaagcgcc gtgtttccgc actgggcccg  1620
ggcggtctga cccgtgagcg tgcaggcttt gaagttcgtg acgtacaccc aacgcactac  1680
ggtcgtgttt gcccgatcga aacgccggaa ggtccgaaca tcggtctgat caactccctt  1740
gccgcttatg cacgcactaa ccagtacggc ttcctcgaga gcccgtaccg tgtagtgaaa  1800
gatgcactgg tcaccgacga gatcgtgttc ctgtccgcca tcgaagaagc cgatcacgtg  1860
atcgctcagg cttcggccac gatgaacgac aagaaagtcc tgatcgacga gctggtagct  1920
gttcgtcact tgaacgagtt caccgttaag gcgccggaag acgtcacctt gatggacgtt  1980
tcgccgaagc aggtagtttc ggttgcagcg tcgctgatcc cgttcctgga gcacgatgac  2040
gccaaccgtg cgttgatggg ttccaacatg cagcgtcaag ctgtacccac cctgcgtgcc  2100
gacaagccgc tggtaggtac cggcatggag cgtaacgtag cccgtgactc cggcgtttgc  2160
gtcgtggctc gtcgtggcgg cgtgatcgac tctgttgatg ccagccgtat cgtggttcgt  2220
gttgccgatg acgaagttga gactggcgaa gccggtgtcg acatctacaa cctgaccaaa  2280
tacacccgct cgaaccagaa cacctgcatc aaccagcgcc cgctggtgag caagggtgat  2340
cgcgttcagc gtagcgacat catggccgac ggcccgtcca ccgatatggg tgagctggca  2400
ctgggtcaga acatgcgcat cgcgttcatg gcatggaacg gcttcaactt cgaagactcc  2460
atctgcctgt ccgagcgtgt tgttcaagaa gaccgcttca ccacgatcca cattcaggag  2520
ctgacctgtg tggcgcgtga caccaagctt gggccagagg aaatcactgc agacatcccg  2580
```

-continued

```
aacgtgggtg aagctgcact gaacaaactg gacgaagccg gtatcgttta cgtaggtgct  2640
gaagttggcg caggcgacat cctggttggt aaggtcactc cgaaaggcga gacccaactg  2700
actccggaag agaagctgtt gcgtgccatc ttcggtgaaa aagccagcga cgttaaagac  2760
acttccctgc gcgtacctac cggtaccaag ggtactgtca tcgacgtaca ggtcttcacc  2820
cgtgacggcg ttgagcgtga tgctcgtgca ctgtccatcg agaagactca actcgacgag  2880
atccgcaagg acctgaacga agagttccgt atcgttgaag gcgcgacctt cgaacgtctg  2940
cgttccgctc tggtaggcca caaggctgaa ggcggcgcag gtctgaagaa aggtcaggac  3000
atcaccgacg aaatcctcga cggtcttgag cacggccagt ggttcaaact gcgcatggct  3060
gaagacgctc tgaacgagca gctcgagaag gcccaggcct atatcgttga tcgccgccgt  3120
ctgctggacg acaagttcga agacaagaag cgcaaactgc agcagggcga tgacctggct  3180
ccaggcgtgc tgaaaatcgt caaggtttac ctggcaatcc gtcgccgcat tcagccgggc  3240
gacaagatgg ccggtcgtca cggtaacaag ggtgtggtct ccgtgatcat gccggttgaa  3300
gacatgccgc acgatgccaa tggcaccccg gtcgacgtcg tcctcaaccc gttgggcgta  3360
ccttcgcgta tgaacgttgg tcagatcctt gaaacccacc tgggcctcgc ggccaaaggt  3420
ctgggcgaga agatcaaccg tatgatcgaa gagcagcgca aggtcgcaga cctgcgtaag  3480
ttcctgcacg agatctacaa cgagatcggc ggtcgcaacg aagagctgga caccttctcc  3540
gaccaggaaa tcctggatct ggcgaagaac ctgcgcggcg gcgttccaat ggctaccccg  3600
gtattcgacg gtgccaagga aagcgaaatc aaggccatgc tgaaactggc agacctgccg  3660
gaaagtggcc agatgcagct gttcgacggc cgtaccggca acaagtttga gcgcccggtt  3720
actgttggct acatgtacat gctgaagctg aaccacttgg tagacgacaa gatgcacgct  3780
cgttctaccg gttcgtacag cctggttacc cagcagccgc tgggtggtaa ggctcagttc  3840
ggtggtcagc gtttcgggga gatggaggtc tgggcactgg aagcatacgg tgctgcttac  3900
actctgcaag aaatgctcac agtgaagtcg gacgatgtga acggtcggac caagatgtac  3960
aaaaacatcg tggacggcga tcaccgtatg gagccgggca tgcccgagtc cttcaacgtg  4020
ttgatcaaag aaattcgttc cctcggcatc gatatcgatc tggaaaccga ataa        4074
```

```
SEQ ID NO: 95            moltype = DNA  length = 1671
FEATURE                  Location/Qualifiers
source                   1..1671
                         mol_type = genomic DNA
                         organism = unidentified
                         note = DP22 Glutamine--tRNA ligase sequence
SEQUENCE: 95
atgagtgagg ctgaagcccg cccaacaaat tttatccgtc agattattga tgaagatctg  60
gcgaccggga aacacaatac cgttcatacc cgtttcccgc ctgagccaaa tggctatctg  120
catatcggtc atgcgaaatc tatctgcctg aacttcggca ttgcgcaaga ctatcagggg  180
cagtgcaacc tgcgttttga cgataccaac ccggcaaaag aagacatcga attcgttgag  240
tcgatcaaac acgacgtcca gtggttaggt ttcgactgga gcggtgatat tcactactct  300
tcagactatt ttgatcaact gcacgcttat gcgctggaac tgatcaacaa aggtctggcg  360
tacgttgacg aactgtcacc ggatcagatc cgtgaatacc gcggctcgct gacgtctccg  420
ggcaaaaaca gcccgtaccg tgaccgttca gtggaagaga acatcgcgct gtttgagaaa  480
atgcgtaacg gtgaatttgc cgaaggcgct gcctgtctgc gtgcaaaaat cgatatggcg  540
tcgccctttct tcgtgatgcg cgatccggtt ctgtaccgta ttaagtttgc agaacaccac  600
cagaccggca aaaaatggtg catctatccg atgtacgatt tcacccactg catttccgat  660
gcgctggaag ggatcaccca ttcgctgtgt acgctggaat tccaggacaa ccgccgtctg  720
tacgactggg ttctggataa catctccatt ccatgccacc cgcgtcagta cgagttctcc  780
cgtctgaatc tcgagtactc catcatgtct aagcgtaagc tgaaccagct ggtgaccgag  840
aagattgtgg aaggctggga cgacccgcgt atgccgactg tttcaggtct gcgtcgtcgt  900
ggttacaccg ccgcgtctat ccgtgaattc tgccgtcgta tcggcgtcac caagcaagac  960
aacaacgtcg aaatgatggc gctggaatcc tgtatccgtg acgatctgaa cgaaaatgca  1020
ccgcgcgcca tggcggtgat caacccggtt aaagtgatca ttgaaaactt taccggtgat  1080
gacgtgcaga gggtgaaaat gccgaaccac ccgagcaaac cggaaatggg cacccgcgaa  1140
gtgccattta cccgtgagat ttatatcgat caggcagatt tccgcgaaga agcgaacaag  1200
caatacaagc gtctggtgct cggcaaagaa gtgcgtctgc gcaatgcgta tgtgatcaaa  1260
gcagaacgta tcgagaaaga tgcagaaggc aatatcacca cgatcttctg ttcttacgat  1320
atcgatacac tgagcaaaga tcctgccgat ggccgcaagg tgaaaggcgt gatccactgg  1380
gtttcggcgt cagaaggcaa accggcggag ttccgcctgt atgaccgtct gttcagcgtc  1440
gccaacccgg gtcaggcaga agatttcctg accaccatca acccggaatc tctggtgatt  1500
tcccacggtt tcgtggagcc atcactggtg gctgcacagg ctgaaatcag cctgcagttc  1560
gagcgtgaag gttacttctg cgccgacagc cgctactcaa gcgctgaaca tctggtgttt  1620
aaccgtaccg ttggcctgcg cgatacctgg gaaagcaaac ccgtcgtgta a           1671
```

```
SEQ ID NO: 96            moltype = DNA  length = 2415
FEATURE                  Location/Qualifiers
source                   1..2415
                         mol_type = genomic DNA
                         organism = unidentified
                         note = DP22 DNA gyrase subunit B sequence
SEQUENCE: 96
atgtcgaatt cttatgactc ctcaagtatc aaggtattaa aagggctgga cgcggtgcgt  60
aagcgccccg gcatgtatat cggcgatacc gatgacggca ctggtctgca ccacatggta  120
ttcgaggttg tggacaacgc tatcgacgaa gccctcgcgg gccactgtaa agagattcag  180
gtcacgatcc atgcggataa ctctgtgtcc gtacaggatg atggtcgtgg cattccgacc  240
ggtattcatg aagaagaggg cgtttctgct gctcaggtca tcatgaccgt tcttcacgcc  300
ggcggtaaat ttgacgataa ctcgtataaa gtctccggcg gtctgcatgg cgtgggtgtt  360
tccgtcgtta acgccctgtc agaaaaactg gaactggtta tccgccgcga aggcaaagtg  420
cacacccaga cttacgtgca tggcgaacct caggatccgc tgaaagtgat tggcgatact  480
gacgtgaccg gtaccacggt acgtttctgg ccaagcttca acaccttcac caatcacact  540
gaattcgagt atgacattct ggcgaaacgc ctgcgtgaac tgtcattcct gaactccggc  600
```

```
gtggcgatcc gcctgctgga taaacgtgat ggtaaaaacg atcacttcca ttatgaaggc  660
ggtatcaaag ctttcgtgga atatctgaac aaaaacaaaa ccccaatcca tccgaccgta  720
ttctatttct ccacggtcaa agatgacatt ggcgttgaag tggcgttgca gtggaacgac  780
ggtttccagg aaaacattta ctgcttcacc aacaacattc cacagcgcga tggcgggact  840
cacttagccg gtttccgttc ggcaatgacc cgtaccctga acgcgtacat ggataaagaa  900
ggctacagca agaaatccaa aatcagcgcc accggtgatg atgcccgtga aggcctgatt  960
gctgtggtgt cggtgaaggt gccggatcct aagttctctt ctcagaccaa agacaaactg  1020
gtgtcttctg aagtgaaaac agcggttgaa acgctgatga acgagaagct ggtggattac  1080
ctgatggaaa acccgtcaga cgccaaaatc gttgtcggta aaatcatcga cgcagcgcgt  1140
gcccgtgaag cagcacgtaa agcgcgtgaa atgacccgcc gtaaaggcgc gctggatctg  1200
gctggcttgc caggcaaact ggcggactgt caggaacgcg atccggcaca ttccgaactg  1260
tacttagtgg aaggggactc agcgggcggc tctgcaaaac aaggccgtaa ccgtaagaac  1320
caggcgattc tgccgttgaa aggtaaaatc ctcaacgtgg agaaagcgcg cttcgacaaa  1380
atgctctctt ctcaggaagt ggcaacgctg attacagcac tcggttgcgg cattggccgt  1440
gacgaataca acccggacaa actgcgctat cacagcatca tcatcatgac cgatgccgac  1500
gtcgatggtt cgcacatccg taccctgttg ctgacattct tctaccgtca gatgcctgaa  1560
attgtagaac gtggccacgt gtttatcgcc cagccgccgt tgtacaaagt gaaaaaaggc  1620
aagcaggaac agtacattaa agatgacgaa gcgatggatc agtatcagat ttccattgcg  1680
atggacgggg caacgttaca cgccaacgct catgcgccag ccctggcggg tgaaccgctg  1740
gagaaactgg tcgctgaaca tcacagcgtg cagaaaatga ttggccgcat ggaacgtcgt  1800
tatccgcgtg cgctgctgaa taacctgatc tatcagccga ccctgccggg tgcagatctg  1860
gccgatcagg cgaaagtgca ggcctggatg gaatcgctgg tggcgcgtct caacgagaaa  1920
gagcagcacg gcagttctta cagcgcgatc gtgcgtgaaa accgcgaaca tcagctgttc  1980
gaaccggttc tgcgtatccg cacccacggt gttgataccg attacgatct ggatgccgac  2040
ttcatcaaag gcggcgaata ccgcaaaatc tgtgcgctgg gtgaacagct gcgcggcctg  2100
atcgaagaag atgccttcat cgaacgtggc gaacgccgtc agcccgtcac cagcttcgaa  2160
caggcgctgg aatggctggt gaaagagtcc cgtcgtggtc tgtcgattca gcgatacaaa  2220
ggtctgggtg aaatgaaccc tgaacagctg tgggaaacca ccatggatcc tgagcaacgt  2280
cgcatgttac gtgtgaccgt gaaggatgcc atcgccgctg accagttgtt cacgacgctg  2340
atgggcgatg cggttgaacc gcgccgcgcc tttatcgaag agaacgccct gaaagccgcc  2400
aatatcgata tctga                                                   2415
```

```
SEQ ID NO: 97          moltype = DNA  length = 2733
FEATURE                Location/Qualifiers
source                 1..2733
                       mol_type = genomic DNA
                       organism = unidentified
                       note = DP22 Isoleucine--tRNA ligase sequence
SEQUENCE: 97
atgagtgact acaagaacac cctgaatttg ccggaaacag ggttcccgat gcgtggcgat  60
ctggccaagc gtgaacctga catgctgaaa aattggtatg accaggatct gtacgggatt  120
attcgtgctg ccaagaaagg caaaaaaacc tttattttgc atgacggccc tccgtatgcg  180
aacggcagca ttcatattgg tcactcagta aacaaaattc ttaaagacat gattatcaag  240
tccaaaggac ttgcgggctt tgatgcgccg tatgtgccgg gctgggattg tcatggtctg  300
ccgatcgagc tgaaagtcga acaactgatc ggtaagccgg gcgagaaagt tacggcggcg  360
gaattccgtg aagcctgccg taaatatgcc gcagaacagg ttgaaggcca gaagaaagac  420
ttcatccgtc tgggcgtgct gggcgactgg gatcatccgt acctgacgat ggatttcaaa  480
accgaagcca acatcatccg tgcgctgggc aaaatcatcg gtaacggcca cctgcataaa  540
ggcgccaagc cggtgcactg gtgtacagat tgcggttcgt cgctggccga agccgaagtc  600
gaatattacg acaaagcctc gccttctatt gatgtggcgt tcaacgcgac ggatgccgca  660
gccgtggcag cgaaatttgg cgttactgcc tttaatggcc cgatctcgct ggttatctgg  720
accacaacac cgtggactat gcccgctaac cgcgccattt cactgaatcc tgagtttgct  780
tatcagctgg ttcaggtcga aggtcagtgt ctgatcctgg caaccgatct ggttgaaagc  840
gtcatgaaac gtgccggtat tgccggatgg accgttctgg gcgagtgcaa aggcgcagac  900
ctcgaactgc tgcgcttcaa acacccgttc ctcggtttcg acgttccggc gatcctgggc  960
gatcacgtga cgctcgatgc gggtaccggt gccgtgcata ccgcaccagg ccacggccct  1020
gacgactttg ttatcggcca gaaatacggt ctggaagtgg cgaatccggt agggccgaac  1080
ggttgctacc tgccgggcac ttacccgacg ctggacggta aatttgtctt taaagccaac  1140
gacctgatcg ttgagttgct gcgtgaaaaa ggcgcattgc tgcacgttga gaaaatcacg  1200
cacagctatc cttgctgctg gcgccacaaa acgccaatca tcttccgcgc gacgccgcaa  1260
tggttcatca gcatggatca gaagggcctg cgtcagcagt cgctggaaga gatcaaaggc  1320
gtgcagtgga tcccggactg ggtcaggcca cgtatcgaaa acatggtcgc taaccgtcct  1380
gactggtgta tctcccgtca gcgtacctgg ggcgtgccga tgtctctgtt cgttcacaaa  1440
gacactgagc agctgcatcc gcgcagcctt gagctgatgg aagaagtggc gaaacgtgtt  1500
gaggtggatg gcattcaggc gtggtgggat ctgaatccgg aagacattct gggtgcagac  1560
gccgcagatt acgtcaaagt accggacacg ctggacgtct ggtttgactc cggttcaacg  1620
cattcttccg ttgtggatgt gcgtcctgag ttcaacgggc attctcctga tctgtatctg  1680
gaaggttctg accagcatcg cggctggttc atgtcttccc tgatgatttc gacggcaatg  1740
aaaggcaaag cgccttacaa acaagtgctg actcacggtt tcaccgtgga tggtcagggc  1800
cgcaaaatgt ctaaatccat cggcaatacc atcgcgccgc aagacgtgat gaacaagctg  1860
ggtggcgaca ttctgcgtct gtgggtcgcg tcgacggatt acaccggcga aatcgccgtg  1920
tccgacgaaa tcctcaaacg tgctgctgat tcttaccgcc gtatccgtaa caccgcgcgc  1980
ttcctgctgg cgaaccttaa cggtttcgat ccggcgctgc acagcgtggc tccggaagac  2040
atggtggtgc tggaccgctg ggcggttggc cgtgcgaaag ccgctcagga agaaatcatt  2100
gctgcgtatg aagcctatga tttccatggc gttgttcagc gtctgatgca gttctgctcg  2160
atcgaaatgg gttccttcta tctggatatc attaaagatc gtcagtacac cgcgaaaagc  2220
gacagcgttg cacgtcgcag ctgtcagacc gcgctgtatc acatcagtga agcgctggtt  2280
cgctggatgg caccgatcat gtcgttcaca gccgatgaaa tctgggcgga actgccggga  2340
agccgtgaga aattcgtctt caccgaagag tggtacgacg gtctgttcgg tctcgcaggc  2400
```

-continued

```
aacgaatcca tgaacgatgc gttctgggat gaactgctga aagtgcgtgg cgaagtgaac  2460
aaagtgatcg aacaggcgcg tgcggataaa cgtctgggcg gttctctgga agcagcggtt  2520
acgctgtttg ctgatgatgc gctggcaaca gacctgcgtt ctctgggcaa tgaactgcgc  2580
tttgtgctgc tgacgtcagg ggcgaaagtt gccgcactga gtgatgcaga tgacgcggct  2640
cagtcgagtg aattgctgaa aggcctgaag attggtctgg cgaaagcaga aggcgacaag  2700
tgcccgcgct gctggcatta cactaccgat taa                              2733

SEQ ID NO: 98          moltype = DNA  length = 1800
FEATURE                Location/Qualifiers
source                 1..1800
                       mol_type = genomic DNA
                       organism = unidentified
                       note = DP22 NADH-quinone oxidoreductase subunit C/D sequence
SEQUENCE: 98
atgacagatt tgacgacgca agattccgcc ctgccagcat ggcataccccg tgatcatctc  60
gatgatccgg ttatcggcga attgcgtaac cgttttgggc cagaggcctt tactgtccag  120
gcaacccgca ccggaattcc cgtggtgtgg ttcaagcgtg aacagttact ggaagcgatt  180
accttttac gaaaacagcc aaaaccttac gtcatgcttt tcgatttgca tggctttgat  240
gagcgtttac gtacacaccg cgacggttta ccggctgcgg atttttccgt tttctaccac  300
ctgatctccg tcgagcgtaa ccgcgacatc atgatcaaag tggcgttgtc agaaaacgat  360
cttcatgttc cgacgatcac caaagtgttc ccgaacgcta actggtacga acgcgaaaca  420
tgggaaatgt tcggtattac cttcgacggc catccgcacc tgacgcgcat catgatgccg  480
cagacctggg aagggcatcc gctgcgtaaa gactatccgg cgcgcgccac cgagttcgat  540
ccttatgagc tgactaagca aaaagaagaa ctcgagatgg aatcgctgac cttcaagccg  600
gaagactggg gcatgaagcg cggtaccgat aacgaggact ttatgttcct caacctcggt  660
cctaaccacc cgtcagcgca tggtgcattc cgtattatcc tgcagctgga tggcgaagag  720
attgtcgact gcgtgcctga cgtcggttac caccaccgtg gtgcggagaa aatgggcgaa  780
cgccagtcat ggcacagcta cattccgtat actgaccgta tcgaatatct cggcggttgt  840
gttaacgaaa tgccttacgt gctggctgtt gaaaaactcg ccggtatcgt gacgccggat  900
cgcgttaaca ccatccgtgt gatgctgtct gaactgttcc gtatcaacag ccatctgctg  960
tacatctcta cgtttattca ggacgtgggt gcgatgacgc cggtattctt cgcctttacc  1020
gatcgtcaga aaatttacga tctggtggaa gcgatcaccg gtttccgtat gcacccggcc  1080
tggttccgta tcggtggcgt agcgcatgac ctgccgaaag gctgggaccg cctgctgcgt  1140
gaattccttg actggatgcc agcccgtttg gattcctacg tcaaagcggc gctgagaaac  1200
accattctga ttggccgttc caaaggcgtg gccgcgtata acgccgacga cgcactggcc  1260
tggggcacca ccggtgctgg cctgcgcgca acgggtatcc cgttcgatgt gcgtaaatgg  1320
cgtccgtatt caggttatga aaactttgac tttgaagtgc cgaccggtga tggcgtcagt  1380
gactgctatt cccgcgtgat gctgaaagtg gaagaacttc gtcagagcct gcgcattctg  1440
gaacagtgct acaaaaacat gccggaaggc ccgttcaagg cggatcaccc gctgaccacg  1500
ccgccaccga aagagcgcac gctgcaacac atcgagaccc tgatcacgca cttcctgcaa  1560
gtgtcgtggg ggccggtcat gcctgcacaa gaatctttcc agatggttga agcaaccaaa  1620
gggatcaaca gctactacct gaccagtgac ggcagcacca tgagctaccg cacccgtgtc  1680
cgtacgccga gcttcccgca tttgcagcag atcccgtccg taatccgtgg cagcctggta  1740
tccgacctga tcgtgtatct gggcagtatc gattttgtaa tgtcagatgt ggaccgctaa  1800

SEQ ID NO: 99          moltype = DNA  length = 1065
FEATURE                Location/Qualifiers
source                 1..1065
                       mol_type = genomic DNA
                       organism = unidentified
                       note = DP22 Protein RecA sequence
SEQUENCE: 99
atggctattg atgagaacaa gcaaaaagcg ttagctgcag cactgggcca gattgaaaag  60
caattcggta aaggctccat catgcgtctg ggtgaagatc gctccatgga cgttgaaacg  120
atctctaccg gctctttgtc tctggatatc gcgttaggtg ccggcggttt gccaatgggc  180
cgtatcgttg agatctatgg cccggaatct tccggtaaaa caacgctgac cttgcaagtt  240
atcgcggctg cacagcgtga aggcaaaacc tgtgcgttca tcgatgcaga acacgccctg  300
gacccgatct acgctaaaaa actgggcgtg gatatcgata acctgctgtg ttctcagcca  360
gataccggcg aacaggctct ggaaatctgt gacgcgctga cccgttcagg cgctgttgac  420
gtgatcatcg ttgactccgt tgccgcactg acaccgaaag cggaaatcga aggcgaaatt  480
ggtgactctc acatgggcct cgcggcacgt atgatgagcc aggcgatgcg taagctggcc  540
ggtaacctga aaaacgccaa caccttgctg atcttcatca accagatccg tatgaaaatt  600
ggtgtgatgt tcggtaaccc ggaaaccacc accggcggta acgccctgaa attctacgct  660
tctgtgcgtc tggatatccg ccgtatcggc gcgatcaaag aaggcgatgt ggttgtcggt  720
agcgaaacgc gtgtgaaagt ggtgaagaac aaaatcgctg cgccatttaa acaagctgaa  780
ttccagatca tgtacggcga aggcatcaat atcaacggcg agctgattga tctcggcgtg  840
aagcacaagc tgatcgaaaa agccggtgca tggtatagct acaacggtga gaagattggt  900
cagggtaaag cgaactcctg caacttcctg aaagaaaacc cgaaagtggc tgccgagctg  960
gataaaaaac tgcgtgatat gctgttgagc ggtaccggtg aactgagtgc tgcgaccacg  1020
gctgaagatg ctgacgacaa catggaaacc agcgaagagt tttaa                  1065

SEQ ID NO: 100         moltype = DNA  length = 1839
FEATURE                Location/Qualifiers
source                 1..1839
                       mol_type = genomic DNA
                       organism = unidentified
                       note = DP22 RNA polymerase sigma factor RpoD sequence
SEQUENCE: 100
atggagcaaa acccgcagtc acagcttaag ctacttgtca cccgtggtaa ggagcaaggc  60
```

```
tatctgacct atgctgaggt caatgaccat ctgccggaag atatcgtcga ttccgaccag  120
atcgaagaca tcatccagat gattaacgac atgggcatcc aggtacttga agaagcaccg  180
gacgccgatg atttgatgct ggccgaaaac cgccctgata ccgatgaaga cgctgcagaa  240
gccgcggcgc aggtgctttc cagcgttgaa tccgaaattg gccgtaccac cgaccctgtg  300
cgtatgtata tgcgcgagat gggtaccgtt gagttgctga cccgtgaagg cgaaatcgac  360
atcgccaaac gtatcgaaga cggtatcaat caggtccagt gctccgttgc tgaatatcct  420
gaagctatca cttatttgtt agagcaatat gaccgtgtgg aagcaggcga agtacgtctg  480
tctgacctga tcaccggttt tgttgacccg aacgccgaag aagaaatcgc accaactgcg  540
actcacgtgg gttctgaact gaccactgaa gagcagaatg atgacgacga agacgaagat  600
gaagacgacg acgctgaaga cgacaacagc atcgatccgg aactggctcg ccagaagttc  660
accgaactgc gtgaacagca tgaagcgacg cgtctggtca tcaagaaaaa cggccgtagt  720
cacaagagcg cagcagaaga aatcctgaag ctgtccgatg tgttcaaaca gttccgtctg  780
gtgccaaaac agttcgattt cctggttaac agcatgcgtt ccatgatgga tcgcgttcgt  840
gctcaggaac gtctgatcat gaaagtgtgc gttgaacagt gcaaaatgcc gaagaaaaac  900
ttcgtcaatc tgttcgccgg taacgaaacc agcgatacct ggtttgatgc cgctctggca  960
atgggtaaac catggtccga gaagctgaaa gaagtcaccg aagacgtgca acgcggcctg  1020
atgaaactgc gtcagatcga agaagaaacc ggcctgacta tcgaacaggt taaagacatc  1080
aaccgtcgca tgtcgatcgg cgaagcgaaa gcccgtcgcg cgaagaaaga gatggttgaa  1140
gcaaacttac gtctggttat ttctatcgcc aagaaataca ccaaccgtgg tctgcagttc  1200
cttgacctga tccaggaagg taacatcggc ctgatgaaag ccgttgataa gtttgaatat  1260
cgccgtggtt ataagttctc aacttatgcg acctggtgga tccgtcaggc tatcacccgc  1320
tccatcgccg accaggcgcg taccatccgt atcccggtac atatgattga gacgatcaac  1380
aaactcaacc gtatctcccg tcagatgctg caagagatgg gccgcgaacc gacaccggaa  1440
gagctggctg agcgtatgtt gatgccggaa gacaaaatcc gcaaagtgct gaaaattgcc  1500
aaagagccaa tctccatgga aacgccaatc ggcgacgatg aagattcgca tctgggcgat  1560
ttcatcgagg ataccaccct cgagctgcca ctggattctg cgacgtctga aagcctgcgt  1620
tctgcaacgc atgacgttct ggctggcctg actgcacgtg aagcgaaagt tctgcgtatg  1680
cgtttcggta tcgatatgaa cactgaccac acgctggaag aagtgggcaa acagttcgac  1740
gtgacccgtg agcgtatccg tcagatcgaa gcgaaagcgt tgcgtaaact gcgccacccg  1800
agccgctccg aagtactgcg cagcttcctg gacgattaa                          1839
```

```
SEQ ID NO: 101          moltype = DNA  length = 4221
FEATURE                 Location/Qualifiers
source                  1..4221
                        mol_type = genomic DNA
                        organism = unidentified
                        note = DP22 DNA-directed RNA polymerase subunit beta'
                         sequence
SEQUENCE: 101
gtgaaagact tactaaagtt tctgaaagcg caaactaaga ccgaagagtt tgatgcgatc  60
aaaattgctc tggcatcgcc agacatgatc cgttcttggt cttttggtga agttaagaag  120
ccagaaacca ttaactaccg tacgttcaaa ccagaacgtg acggcctttt ctgtgcccgt  180
attttcggac cagtaaaaga ctacgaatgc ctgtgcggta agtacaagcg tttaaaacat  240
cgcggcgtga tctgcgagaa gtgcggcgtt gaagtgaccc agactaaagt acgccgtgag  300
cgtatgggcc acatcgaact ggcttccccg actgcacaca tctggttcct gaaatcgctg  360
ccatcgcgca tcggtttgct gctggatatg ccactgcgtg acatcgaacg tgttctgtac  420
ttcgaatcct atgtggttat cgaaggcggc atgactaacc tcgaaaaacg ccagatcctg  480
actgaagagc agtatctgga tgcgttggaa gagtttggtg atgagttcga cgcgaagatg  540
ggtgcggaag ctattcaggc cctgttgaaa aacatggatc tggaagcaga gtgcgagcaa  600
ctgcgtgaag agttgaacga aaccaactcc gaaaccaaac gtaagaagct gaccaagcgt  660
atcaagctgc tggaagcgtt cgttcagtct ggtaacaaac cagagtggat gatcctgact  720
gtgctgccgg tactgccacc agacttgcgt ccattggttc cgttggacgg cggccgtttc  780
gcaacgtcgg atctgaacga tctgtatcgt cgcgtgatca accgtaacaa ccgtctgaaa  840
cgcctgctgg atctggctgc gccagacatc atcgtacgta acgaaaaacg tatgctgcaa  900
gaagcggtag atgctttgct ggataacggc cgtcgcggtc gtgctatcac cggctctaac  960
aagcgtccgc tgaaatctct ggcagacatg attaaaggta aacagggtcg tttccgtcag  1020
aacttgctgg gtaaacgtgt cgactactct ggtcgttccg ttatcaccgt aggtccatac  1080
ctgcgtctgc accagtgtgg tctgccgaag aaaatggcac tggaactgtt caaaccgttc  1140
atctacggca agctggaact gcgtggcctg gccaccacca tcaaagccgc gaagaaaatg  1200
gttgagcgcg aagaagctgt cgtttgggac atcctggacg aagttatccg cgaacacccg  1260
gtactgctga accgtgcacc aaccctgcac cgtttgggta tccaggcgtt tgaaccggtt  1320
ctgatcgaag gtaaagcaat ccagctgcac ccgctggttt gtgcggcata taacgccgac  1380
ttcgatggtg accagatggc tgttcacgta ccgttgacgc tggaagccca gctggaagcg  1440
cgtgcgttga tgatgtctac caacaacatc ctgtcacctg cgaacggcga gccaatcatc  1500
gttccttctc aggacgttgt attgggtctg tactacatga cccgtgactg tgttaacgcc  1560
aaaggcgaag gcatggttct gaccggtcct aaagaagctg agcgtattta ccgcgccggt  1620
ttggcctctc tgcatgcgcg tgtcaaagtg cgtattacag aagagatcaa aaataccgaa  1680
ggcgaagtta cgcacaagac gtcgattatc gacacgacag ttggtcgcgc catcctttgg  1740
atgatcgtac ctaaaggtct gccgttctct atcgtcaacc agcctctggg caaaaaagct  1800
atctccaaaa tgctgaacac ctgttaccgc attttgggcc tgaagccgac cgttattttt  1860
gctgaccaga tcatgtacac cggttttgct tacgctgccc gttcaggcgc gtcagtaggt  1920
atcgatgaca tggtaatccc tgcgaagaaa gcagagatca tcgaagaagc agaaaccgaa  1980
gttgctgaaa tccaggaaca gttccagtct ggtctggtca ctgctggcga acgctataac  2040
aaagtgatcg acatctgggc tgcggccaac gaacgtgttg ctaaggcaat gatggaaaac  2100
ttgtctgttg aagacgtcgt caaccgtgac ggtgttgttg aacagcaggt ttccttcaac  2160
agtatcttta tgatggccga ctccggtgcg cgtggttctg ctgcacagat tcgtcagctg  2220
gccggtatgc gtggcctgat ggcgaaacca gatggttcca tcattgaaac gccaatcacc  2280
gcgaacttcc gtgaaggtct gaacgtactc cagtacttca tctctactca cggtgctcgt  2340
aaaggtttgg cggataccgc acttaaaacg gctaactccg gttatctgac ccgtcgtctg  2400
```

```
gttgacgtcg cgcaggatct ggttgtgacc gaagacgact gtgggactca cgaaggcatc  2460
atgatgactc cggtcatcga aggtggcgac gttaaagaac cactgcgtga gcgtgtactg  2520
ggtcgtgtga ctgcagaaga tatcctcaag ccgggtacgg cggatatcct ggttccacgt  2580
aacaccctgc ttcacgagaa gacgtgtgat ctgttagaag agaactcagt cgacagcgtg  2640
aaagtacgtt cagtcgtaag ttgcgaaacc gactttggtg tgtgtgcaaa ctgctacggt  2700
cgcgacctgg cacgtggtca catcatcaac aaaggtgaag cgatcggtgt tattgcagca  2760
cagtccatcg gtgagccggg tacccagctg acgatgcgta cgttccacat cggtggtgcg  2820
gcatctcgtg cggcagcgga atccagcatc caggttaaga acactggtac cattaaactg  2880
agcaaccaca agcacgttag caactctaac ggcaaactgg tgatcacttc ccgtaacact  2940
gagctgaaat tgatcgacga attcggtcgt accaaagaaa gctataaagt gccttacggt  3000
tccgtgatgg gcaaaggcga tggcgcatca gttaacggcg gcgaaaccgt tgctaactgg  3060
gatccgcaca ccatgccagt tatcagtgaa gtgagtggtt tcattcgctt tgccgatatg  3120
gtggatactc agaccatcac acgccagacc gacgacctga ccggtttgtc ttctctggtt  3180
gttctggact ctgcagagcg taccggtagc ggtaaagacc tgcgtccggc actgaaaatc  3240
gttgacgcta aaggcgacga cgtattgatt ccaggtactg atatgcctgc tcaatacttc  3300
ctgccaggta aagcgattgt tcagctggaa gatggtactc agatccactc tggtgacacc  3360
ctggcgcgta ttcctcagga atccggcggt accaaggaca tcaccggtgg tctgccacgc  3420
gttgctgacc tgttcgaagc acgtcgtccg aaagagcctg caatccttgc tgaaatcagc  3480
gggatcatct ccttcggtaa agaaaccaaa ggcaaacgtc gtctggtaat ttctccgtta  3540
gatggcagcg atgcttacga agaaatgatc cctaaatggc gtcagctgaa cgtgttcgaa  3600
ggcgaagttg tggaacgtgg tgacgtcgta tccgacggcc ctgagtctcc gcacgacatc  3660
ttgcgtttac gtggtgttca cgcggttacc cgctacatca ccaacgaagt gcaggaagtt  3720
taccgtctgc aaggcgttaa gattaacgat aagcacatcg aagttatcgt tcgtcagatg  3780
ttgcgtaaag gcaccatcgt tagcgctggt ggcactgact tcctggaagg cgagcaggca  3840
gaaatgtctc gcgttaaaat cgctaaccgt aagctggaag ctgaaggcaa aatcacggca  3900
acattcagcc gtgacctgct cggtatcacc aaggcatccc tggcgaccga atccttcatc  3960
tctgcagcgt cgttccagga aaccacgcgt gttcttaccg aagcggctgt tgccggtaaa  4020
cgtgatgaac tgcgtggcct gaaagagaac gttatcgttg gccgtctgat cccagccggt  4080
accggttacg cttatcatca ggatcgtgca cgccgtaaag cacaaggcga agtgccagtt  4140
gtaccgcaag tcagcgcgga tgaagcaacg gctaacctgg ctgaactgct gaacgcaggt  4200
ttcggtaaca gcgacgatta a                                            4221

SEQ ID NO: 102          moltype = DNA  length = 1668
FEATURE                 Location/Qualifiers
source                  1..1668
                        mol_type = genomic DNA
                        organism = unidentified
                        note = DP67 Glutamine--tRNA ligase sequence
SEQUENCE: 102
atgagtgagg ctgaagcccg cccaactaac tttattcgtc agattatcga cgaagatctg  60
gcgaacggta agcacagttc agtgcacacc cgcttcccgc ctgagccgaa tggctatctg  120
catattggcc atgcgaaatc aatctgcctg aactttggta tcgctcagga ttatcagggg  180
cagtgtaacc tgcgctttga tgacactaac ccggtgaaag aagatctgga gtttgttgaa  240
tcaatcaagc gtgatgtgca gtggctgggc tttaagtgga gtggtgacgt acgctactca  300
tctgactatt tcgagcaact gcacaattat gccgttgagc tgattagtaa agggctggcg  360
tacgttgatg aactgtcacc ggagcagatc cgtgaatacc gtggcagcct gacctcagcg  420
ggtaaaaaca gccccttccg cgatcgcagc gtggacgaaa accttgcgct ctttgcaaaa  480
atgcgcgcgg gcggctttgc cgagggcacc gcgtgtttac gagccaaaat tgatatggct  540
tccaacttta tcgttctgcg cgatccggtg atctaccgca tcaaatttgc cgaacatcat  600
cagaccggca ataagtggtg catctatccg atgtatgact ttacccactg catctctgat  660
gcgctggaag gcattactca ctcactgtgt acgctggaat tccaggataa ccgtcgcctg  720
tacgactggg tgctggataa catcaccatt ccggttcatc cgcgtcagta tgaattctct  780
cgcctgaatc ttgaatatgc catcatgtcc aagcgtaagt tgagtcagtt ggtgaccgag  840
aacgtggtgg aaggttggga tgatccccgt atgctgactg tttcgggttt gcgccgccgt  900
ggctacactg cggaatccat ccgtgaattc tgccgccgca ttggggtgac caagcaggac  960
aatattgttg aaatggccgc tctggaatcc tgtatccgtg acgacctcaa tgagaatgcc  1020
ccgcgtgcca tggcagtgat ggatccggta aaagtggtga tagaaaatct gcctgcgcat  1080
cacgatgagg tgatcaccat gccgaatcat ccgagcaagc cggaaatggg tacccgcgaa  1140
gtcccgttca gtcgtgagat ctacatcgat cgtgctgact tccgtgagga agcaaacaag  1200
cagtacaagc ggctggtgct gggcaaagaa gtgcgtctgc gtaacgctta tgtgatcaaa  1260
gccgagcgcg tggcaaagga cgatgaaggc aacattacct gcctgttctg tacctgtgat  1320
gtggatactc tgagcaagga tccggccgac gggcgtaaag tgaagggcgt tatccactgg  1380
gtgtcagctg ttcatgccct tccggcagag ttccgtctgt acgatcggct gttcagcgta  1440
ccgaatccgg gggcggcaga agacttcctg gccagcatca acccggaatc tctggtgatc  1500
cgtcagggct tcgtggagcc cgggatgcag caggcggagg cgtcagcccc gtatcagttt  1560
gagcgtgaag gctacttctg cgctgacagt gtctactcca gtgccagcaa tctggtgttc  1620
aaccgcaccg ttggcctgcg tgacacctgg gcgaaagtcg gcgagtaa               1668

SEQ ID NO: 103          moltype = DNA  length = 2409
FEATURE                 Location/Qualifiers
source                  1..2409
                        mol_type = genomic DNA
                        organism = unidentified
                        note = DP67 DNA gyrase subunit B sequence
SEQUENCE: 103
atgtcgaatt cttatgactc ctccagtatc aaagttctga aagggctcga tgctgtacgc  60
aaacgcccgg gtatgtatat cggcgatacg gatgacggta ccggtctgca tcacatggta  120
tttgaggtcg tggataacgc cattgacgaa gcgctcgccg gtcactgttc cgatattctt  180
gtcactattc atgccgataa ctctgtttcc gttgtggatg atggccgtgg tattccgacc  240
```

```
ggtattcacg aagaagaagg catctcagcc gctgaagtga tcatgaccgt gctgcacgcc  300
ggcggtaagt tcgacgataa ctcttataaa gtctccggcg gcctgcacgg cgtgggcgtg  360
tcagtggtga acgccctgtc ggaaaaactg gagctgacca ttcgtcgcga agggaaagtt  420
caccagcaga cttacgtcca cggcgtgcca caggccccgt tgagtgtgag cggtgaaact  480
gacctgacgg gaacgcgcgt gcgtttctgg cccagccatc agacgttcac taacgtcgtg  540
gagttcgagt acgaaatttt ggcaaagcgc ctgcgtgagc tgtcgttcct gaactccggt  600
gtatcaatca agctggaaga taagcgcgac ggtaaaagcg accattacca ctatgaaggt  660
ggtatcaagg cgtttgttga gtacctcaac aagaacaaaa ccccgatcca cccgaatgtg  720
ttctatttct caaccgagaa agacggcatt ggtgtggaag tggcgctgca gtggaacgat  780
ggtttccagg aaaatatcta ctgctttacc aacaacatcc cacagcggga tgggggcacg  840
cacctcgttg gtttccgtac cgcgatgacc cgtaccctga atgcctacat ggataaagaa  900
ggctacagca agaaagccaa agtcagcgcc accggtgacg acgcgcgtga aggcctgatt  960
gctgtggtgt cggtgaaagt gccggatccg aaattctctt cacagaccaa agataaactg  1020
gtctcttctg aagtgaaaac cgccgttgag cagcagatga acgagctgct ggcagaatac  1080
ctgctggaaa acccgaccga tgccaaaatc gtcgtcggta aaatcattga tgcggcccgc  1140
gcccgtgaag cggcccgtcg tgcacgtgaa atgacccgcc gtaaaggcgc gctggatctg  1200
gcaggcctgc cgggcaaact ggcggactgc caggagcgtg atccggctct gtccgaaatt  1260
tacctggtgg aaggggactc tgcgggcggc tctgccaagc agggacgtaa ccgtaaaaac  1320
caggccatcc tgccgctgaa gggtaaaatc ctcaacgtcg agaaggcgcg ctttgacaag  1380
atgctcgcgt cgcaggaagt cgctacgctg atcaccgcgc tgggctgtgg tatcggtcgt  1440
gatgagtaca accccgacaa actgcgctat cacagcatca ttatcatgac cgatgccgac  1500
gtggatggct cgcatatccg taccctgctg ctgaccttct tctaccgtca gatgccagaa  1560
atcattgagc gtggtcatgt ctatattgcc cagccaccgc tgtacaaggt gaaaaaaggc  1620
aagcaggagc agtatattaa agacgacgat gcgatggatc agtaccagat cgccatcgcg  1680
ctggacggtg ccacgctgca tgcgaacgcc agcgccccgg cccttggcgg taagccactg  1740
gaagatctgg tgtctgagtt caacagcacg cgcaagatga tcaagcgcat ggagcgccgt  1800
tacccggtgg ccttgctgaa tgcgctggtc tacaacccga ccctgagcga tttgaccgcc  1860
gaagcgccgg tacagagctg gatggatgtg ctggtgaagt atctgaacga caacgaccag  1920
cacggcagca cctacagcgg tctggtacgc gaaaatctgg agctgcatat ctttgagccg  1980
gtactgcgta tcaaaaccca cggcgtggat accgattatc cgctcgacag cgagtttatg  2040
ctcggcggcg aataccgtaa gctctgcgcg ctgggtgaga agctgcgtgg cctgatcgaa  2100
gaagacgcgt tcatcgaacg tggtgagcgg cgtcagccga ttgccagctt tgagcaggcg  2160
atggagtggc tggttaaaga gtcacgccgt ggcctgacgg ttcagcgtta taaaggtctg  2220
ggcgagatga acccggatca gctgtgggaa accaccatgg atccggacag ccgccgtatg  2280
ctgcgcgtga ccatcaaaga tgccgtggcc gccgaccagc tgttcaccac cctgatgggg  2340
gatgcggtag agccccgtcg tgcctttatt gaagagaacg ccctgcgcgc ggcaaacatc  2400
gatatctga                                                          2409

SEQ ID NO: 104          moltype = DNA  length = 2817
FEATURE                 Location/Qualifiers
source                  1..2817
                        mol_type = genomic DNA
                        organism = unidentified
                        note = DP67 Isoleucine--tRNA ligase sequence
SEQUENCE: 104
atgagtgact ataaatctac cctgaatttg ccggaaacgg ggttcccgat gcgtggcgat  60
ctggccaaac gcgaaccggg tatgctgcaa cgttggtatg atgacaagct gtacggcatc  120
attcgcgaag ccaagaaagg gaaaaaaacc tttatcctgc acgatggccc tccttacgcc  180
aacggcagca ttcatattgg tcactccgtt aacaagattc tgaaagacat tatcgttaag  240
tcgaaaggca tggcgggcta tgactcgcct tatgtaccgg gttgggactg ccacggtctg  300
cctatcgagc ataaagttga gcagatgatc ggtaagccgg gagagaaagt cagcgccgct  360
gagttccgtg ctgcctgccg caaatacgct gccgagcagg tggaagggca gaaagccgac  420
tttatccgtc tgggtgtgtt gggtgactgg gatcgtccgt atctgacaat gaacttccag  480
accgaagcca atattatccg tgcgctgggt aaaatcatcg gtaacgggca cctgcacaaa  540
ggggccaagc cggtacactg gtgcctggac tgccgttctg ccctggctga ggcggaagtg  600
gagtactacg ataaaacctc tccgtctatc gatgtcatgt tcaatgcgac tgataaagag  660
ggggtacagg ccaaatttgc ggcaacgaat gttgacggcc cgatctcgct ggtgatctgg  720
actaccacgc cgtggaccat gccggctaac cgcgctatct cactgcatcc tgaattcgac  780
taccagctgg tacagattga aggccgtgct ctgatcctcg ccaaagagat ggttgagagc  840
gtgatgcagc gcgttggtgt tgccgcctgg accgtgctgg gcgaagcgaa aggggcagac  900
ctggagctga tgggcttcca gcatccgttc ctcgaccata cctctccggt tgtgctgggt  960
gagcatgtca cgctggaagc cggtaccggt gcggtccata ccgcaccagg ccatggcccg  1020
gacgactatg ttatcggtca gaaatacggt atcgaagtgg ctaacccggt cggcccggat  1080
ggctgctacc tgccgggaac ctacccgacg ctggatggtg tgaacgtctt taaagccaac  1140
gatatgatcg ttgaactgct gcgtgaaaag ggtgctctgc tgcacgttga gaaactgttc  1200
cacagctatc cacactgctg gcgtcataaa acgcccatca tcttccgcgc tacgccacag  1260
tggtttatca gcatggatca gaagggcctg cgtgcgcagt cgctgaaaga gatcaagggc  1320
gtgcagtgga tcccggactg gggtcaggca cgtattgaat cgatggtcgc gaaccgtcct  1380
gactggtgta tttcccgtca gcgtacctgg ggcgtgccga tggcgctgtt cgtccataaa  1440
gacaccgaac agctgcaccc ggattcgctg gagctgatgg agaaagtggc gaagcgggtt  1500
gagcaggacg gcattcaggc atggtgggat cttgatgccc gcgacctgat gggcgccgat  1560
gctgacaact acgttaaagt cccggatacc ctggacgtct ggtttgactc cggttcaacc  1620
agctactcgg tcgtcgatgc ccgccctgaa tttgacggca atgcccctga cctgtatctg  1680
gaaggatcgg atcagcaccg cggctggttt atgtcctcac tgatgatctc gaccgcgatg  1740
aaaggcaaag cgccttaccg tcaggtactg acgcacggct tcaccgtcga tggtcagggc  1800
cgtaagatgt ccaagtcact gggcaatact gtcagcccgc aggatgtgat gaacaaactg  1860
ggcgccgata ttctgcgcct gtgggtcgcc tctacggact actccggtga gatcgccgta  1920
tccgacgaga tccttaaacg ctctgccgac agctatcgcc gcatccgtaa caccgcacgt  1980
ttcctgctgg caaaccttgc cggttttaat ccggaaaccg atagggtgaa accggaagag  2040
```

-continued

```
atggtggtgg tggatcgctg ggccgttggc cgtgcgctgg cggcacagaa tgatatcgta  2100
gcctcgtatg aagcttatga cttccatgaa gtcgtgcagc gtctgatgca gttctgttcg  2160
gttgagatgg gctccttcta cctggatatc atcaaggatc gtcagtacac cgcgaaggcc  2220
gatggcctgg cgcgtcgcag ctgtcagacg gcgctgtggt atatcgtgga agcgctggtg  2280
cgctggatgg caccgattat gtccttcact gccgatgaaa tctggggtta cctgccgggt  2340
aaacgcagcc agtatgtctt taccgaagag tggtttgacg ggctgttcag cctggaggac  2400
aatcagccga tgaacgacag ttactgggca gaactgctga aagtacgcgg tgaagtcaac  2460
aaggtgatcg agcaggcccg cgctgataag cggattggcg ggtctctgga agccagcgtg  2520
acgctgtatg ctgacgcaga cctggccgcg aagctgacca gcctgggtga ggagctgcgc  2580
tttgtgttgc tgacttccgg ggcgcaggtt gcggattatg cgcaggccac cgctgatgca  2640
cagcaaagcg aaggggtaaa aggtctgaaa attgccctga gcaaagcgga aggcgagaag  2700
tgcccgcgct gctggcatta cactaacgat atcggccaga atgctgaaca cgctgacgtg  2760
tgcggccgtt gtgtcactaa cgtcgcgggc agcggcgaac agcgtaagtt tgcatga     2817

SEQ ID NO: 105         moltype = DNA  length = 1731
FEATURE                Location/Qualifiers
source                 1..1731
                       mol_type = genomic DNA
                       organism = unidentified
                       note = DP67 NADH-quinone oxidoreductase subunit C/D sequence
SEQUENCE: 105
gtgatcggcg agctgcgtaa tcgttttggg cctgatgcct ttacagtaca agcgacccgt  60
accggcgtgc cggtggtctg ggtaaaacgt gagcagttgc ttgagattat tgagttcctg  120
cgcaagctgc ctaaacccta tgtgatgctg tatgacctgc atggcatgga tgagcgcctg  180
cgtactcacc gtgccggttt accggcggcg gatttttccg ttttctatca cttcatctcc  240
attgaacgta accgcgacat catgctcaag gtggcgttgt ctgaaaacga tttgaatgtg  300
cccaccatca ccaaaatttt cccgaatgcc aactggtatg agcgtgaaac ctgggagatg  360
tttggtatca atgttgaagg ccacccgcac ctgacgcgca ttatgatgcc gcagagctgg  420
gaagggcatc cgctgcgcaa agattaccct gcgcgtgcga ccgagttcga tccgtttgaa  480
ctgaccaagc agaaagaaga tctggagatg gaatctctga ccttcaagcc tgaagactgg  540
ggcatgaagc gttcgaccaa caatgaggac ttcatgttcc tcaacctggg cccgaaccac  600
ccttctgcgc acggcgcgtt ccgtatcatc ctgcaactgg acggtgaaga gatcgtcgac  660
tgcgtgccgg atatcggata ccaccatcgt ggtgccgaaa aaatgggtga acgccagtcc  720
tggcacagct acattccgta taccgaccgt attgagtatc tcggcggctg cgtaaacgaa  780
atgccgtacg tgctggcggt agaaaagctg gctggtatca aagtccctga gcgcgtggaa  840
gtcattcgcg tgatgctatc agagctgttc cgtataaaca gccacctgct gtacatctct  900
acgtttatcc aggacgtcgg tgctatgtcc ccggtgttct ttgcctttac tgaccgccag  960
aaaatttacg acgtggtaga agccattacc ggcttccgta tgcatccggc ctggttccgc  1020
attggtggcg tggcgcatga tctgcctaaa ggctgggagc gcctgctgcg tgagttcctg  1080
gattggatgc ctaagcgtct gaaagcctat gagcagaccg cactgaaaaa ctccgtgctt  1140
attgcccgtt ccaaaggggt ttctgcctat aacatggaag aagcactggc ctggggcacg  1200
acgggggctg gcctgcgtgg taccggtctg gactttgatg tgcgtaaatg gcgtccatat  1260
tccggttatg aaaacttcga tttcgaagtg ccaatcggag atggcgtaag ctgtgcttac  1320
acccgtgtca tgctgaagat ggaagagatg cgccagagta tgcgcatcct ggaacagtgc  1380
ctgaagaaca tgccagcagg cccgttcaag gctgaccatc cgctgaccac gccgccgccg  1440
aaagagcgca cgctgcagca tatcgaaacc ctgatcactc acttcctgca ggtttcgtgg  1500
ggcccggtaa tgccggcaaa cgaatccttc cagatgattg aagcgaccaa agggatcaac  1560
agttactacc tgaccagtga tggcagcacg atgagctacc gcacccgcgt gcgtacgccg  1620
agcttcccgc atttgcaaca gatcccatcg gtgatcaacg gcagcctggt atccgatctg  1680
atcgtatacc tcggtagtat cgattttgtt atgtcagacg tggaccgcta a           1731

SEQ ID NO: 106         moltype = DNA  length = 1062
FEATURE                Location/Qualifiers
source                 1..1062
                       mol_type = genomic DNA
                       organism = unidentified
                       note = DP67 Protein RecA sequence
SEQUENCE: 106
atggctatcg acgaaaacaa gcaaaaagca ctggcagcag cgctgggcca gattgaaaag  60
cagtttggta aaggctccat catgcgcctg ggtgaagacc gcaccatgga tgtggaaacc  120
atctcaaccg gttctttatc actggatatc gcgctgggtg ccggtggttt accaatgggc  180
cgtatcgttg aaatctatgg cccggagtct tccggtaaaa ccaccctgac gctgcaggtt  240
atcgcttctg cacagcgtaa agggaaaacc tgtgcattta tcgatgccga gcatgctctg  300
gacccggtct acgctaaaaa actgggcgtg gatatcgata acttgctgtg ttctcagccg  360
gataccggtg agcaggcgct ggaaatctgt gatgcgctgg cccgttccgg tgcggttgac  420
gtcatcatcg tcgactccgt agcggcgttg acaccaaaag cagaaatcga aggtgaaatc  480
ggtgactctc atatgggcct tgcggcacgt atgatgagcc aggcgatgcg taagctggcc  540
ggtaacctga agaactccgg tacgctgctg atctttatca accagatccg tatgaaaatt  600
ggcgtgatgt tcggtaaccc ggaaaccact accggtggta acgctctgaa attctacgct  660
tctgtccgtc tggatattcg ccgcatcggc gcgatcaaag agggtgatga agtggtgggt  720
agcgaaaccc gcgttaaagt ggtgaaaaac aaaatcgcag caccgtttaa acaggctgag  780
ttccagatca tgtacggcga aggtatcaac gtttacggtg agctggtcga cctgggcgtg  840
aagcacaagc tgatcgaaaa agccggtgcc tggtacagct ataacggtga caagattggt  900
cagggtaaag ccaactcagg taacttcctg aaagagaacc cggctatcgc taacgaaatc  960
gaagcaaaac tgcgtgaaat gctgttgaac agcccggacg ataagcctga ttttgttccg  1020
gctccgcatg aagccgatag tgaagttaac gaagatatct aa                     1062

SEQ ID NO: 107         moltype = DNA  length = 1842
FEATURE                Location/Qualifiers
```

```
source                  1..1842
                        mol_type = genomic DNA
                        organism = unidentified
                        note = RNA polymerase sigma factor RpoD sequence
SEQUENCE: 107
atggagcaaa acccgcagtc acagcttaag ctacttgtca cccgtggtaa ggagcaaggc  60
tatctgacct atgccgaggt caatgaccat ctgccggaag atatcgtcga ctccgatcag  120
attgaagaca tcattcagat gatcaacgac atgggcattc aggttgtaga agaagcgcct  180
gatgccgatg atttgatgct gaatgagaac aacaacgaca cggacgaaga cgctgccgaa  240
gcggctgctc aggtattatc cagcgtagaa tctgaaatcg gacgtaccac cgacccggtg  300
cgcatgtaca tgcgcgaaat ggggacggtt gaactgctga cgcgtgaagg cgagatcgat  360
atcgccaaac gcatcgaaga gggtatcaac caggtacagt gttccgttgc tgaatatcct  420
gaagcgatta cttacctgct tgagcaatat gaccgtgttg aagcgggcga agcgcgcctg  480
tcggatctga tcaccggttt tgtcgacccg aatgccgaag cagagatcgc ccctactgcg  540
actcacgtgg gttcagaact ttccgctgaa gagcgtgatg acgaagaaga agacgaagag  600
tctgacgacg acagctcgga tgatgacaac agcatcgatc cggaactggc gcgggaaaaa  660
ttcaacgacc tgcgcgttca gtacgaaacc acccgtaccg ttatcaaagc gaaaagccgc  720
agccacgctg atgccatcgc tgagatccag aatctgtccg acgtgttcaa gcagttccgc  780
ctggtgccga agcagttcga cttcctggtg aacagcatgc gcaccatgat ggatcgcgtc  840
cgtactcagg aacgcctgat cctcaagctg tgcgtagaaa tctgtaagat gccgaagaag  900
aacttcatta ccctgttcac cggtaatgaa accagcgaaa cctggttcaa agcggcactg  960
gcaatgaata agccgtggtc agagaagctg aacgatgtgt cagatgacgt acaccgtagc  1020
ctgatgaagc tgcagcagat cgaaacggaa actggcctga cgattgaaca ggtaaaagac  1080
atcaaccgtc gtatgtcgat cggcgaagcg aaagcgcgcc gtgcgaagaa agagatggtt  1140
gaggctaacc tgcgtctggt tatctctatc gccaagaagt acaccaaccg tggcctgcag  1200
ttcctggatc tgattcagga aggtaacatc ggtctgatga aagcggtgga taagtttgaa  1260
tatcgccgtg gttataagtt ctcgacttat gccacctggt ggatccgtca ggcgatcacc  1320
cgttcaatcg ctgaccaggc gcgtaccatc cgtattccgg tgcacatgat tgagacgatt  1380
aacaagctca accgtatttc ccgccagatg ctgcaagaga tgggccgtga gccgacgccg  1440
gaagagctgg ccgagcgtat gctgatgccg gaagataaga tccgtaaggt gctgaaaatt  1500
gccaaagagc cgatctctat ggagacgccg attggtgatg atgaagattc acatctgggt  1560
gattttatcg aagacaccac gctggagctg ccgctggact ccgcgacgtc agagagcctg  1620
cgttctgcca cgcacgacgt gctggccggt ctgaccgcgc gtgaagccaa agtactgcgt  1680
atgcgtttcg gtatcgatat gaataccgac cacacgctgg aagaagtggg caaacagttc  1740
gacgtaacgc gtgagcgtat tcgtcagatt gaggcgaaag cgctgcgtaa gctgcgtcac  1800
ccaagccgct ctgaagtgct gcgcagcttc ctcgacgatt aa                      1842

SEQ ID NO: 108          moltype = DNA  length = 4029
FEATURE                 Location/Qualifiers
source                  1..4029
                        mol_type = genomic DNA
                        organism = unidentified
                        note = DNA-directed RNA polymerase subunit beta sequence
SEQUENCE: 108
atggtttact cctataccga gaaaaaacgt attcgtaagg attttggaaa gcgtccacaa  60
gttctggaca ttccatatct cctttctatc cagcttgact cgttccagaa gttcatcgag  120
caagatccgg aaggtcaata tggtctggaa gcagcattcc gctccgtatt tccaatccaa  180
agctatagcg gtaattctga gctgcagtac gtcagctacc gtttaggcga acccgtcttt  240
gatgtgaaag agtgtcagat tcgtggcgtc acgtattctg ctcctctgcg cgtaaaactg  300
cgcctggtga tctacgagcg cgaagcgccg gaaggcaccg ttaaagacat caaagaacaa  360
gaagtttaca tgggcgaaat tccgctcatg acggataacg gtacctttgt tatcaacggt  420
actgagcgcg ttatcgtttc tcagctccac cgtagtcctg gtgtcttctt cgacagcgat  480
aagggtaaaa cccactcgtc cggtaaagtg ctgtataacg cacgtatcat cccttaccgt  540
ggttcatggc tggacttcga gttcgacccg aaagacaacc tgttcgtccg tattgaccgt  600
cgccgtaaac tgccagcgac catcattctg cgcgcgttga attacaccac tgaacagatc  660
ctcgacctgt tcttcgataa agtggtttac caaattcgcg acaacaagct gcagatggag  720
cttattcctg agcgcctgcg tggtgagacc gcttcatttg atattgaagc gaacggcacc  780
gtttacgtcg aaaaaggccg ccgtattact gcgcgccata ttcgccagct tgagaaagat  840
gctgttgccc acatcgaagt gccggttgag tatattgccg gtaaagtggt cgctaaagac  900
tacgttgatg agagcaccgg tgaactgctg atcgcagcga acatggaact gtcactggat  960
ctgctggcta aactcagcca gtccggtcac aagcgcattg aaaccctgtt caccaacgat  1020
ctggatcacg gtgcgtacat gtctgagacg gtacgtgtcg acccaaccag cgatcgcctg  1080
agcgctctgg ttgagatcta ccgcatgatg cgtcctggtg agccaccaac gcgtgaagcg  1140
gctgaaaacc tgtttgagaa cctgttcttc tctgaagacc gctatgatct gtctgcggtt  1200
ggtcgtatga agttcaaccg ttctctgctg cgcgacgaga tcgaaggttc cggtatcctg  1260
agcaaagacg acatcattca ggtgatgaag aagctcatcg gtatccgtaa cggtattggc  1320
gaagtggatg atatcgacca cctcggcaac cgtcgtatcc gttccgttgg cgaaatggct  1380
gaaaaccagt tccgtgttgg ccttgtgcgc gtagagcgtg cggtgaaaga gcgtctgtcc  1440
ctgggcgatc tggataccct gatgccacag gacatgatca acgccaagcc aatttctgcg  1500
gcagtgaaag agttcttcgg ctccagccag ctgtcacagt ttatggacca gaacaacccg  1560
ttgtctgaga tcacgcataa gcgtcgtatc tctgcactgg gtccgggcgg tctgacgcgt  1620
gagcgtgcag gcttcgaagt tcgagacgta cacccgacgc actacggtcg cgtatgtcca  1680
atcgaaacgc cggaaggtcc aaacatcggt ctgatcaact ccttgtctgt gtatgcacag  1740
accaatgagt acggtttcct ggaaacccca taccgtcgcg ttcgcgaagg cgtggtgacc  1800
gacgaaattc attacctctc tgctattgaa gagggtaact acgttatcgc tcaggcaaac  1860
accaatctcg acgacgaagg tcacttcgta gacgacctgg tcacctgccg tagcaaaggc  1920
gaatcgagtc tcttcaaccg cgatcaagtt gactacatgg acgtttccac ccagcaggtg  1980
gtttccgtcg gtgcgtcact gatcccgttc ctggagcacg atgacgccaa ccgcgcattg  2040
atgggtgcaa acatgcaacg tcaggcggtt cctactctgc gtgctgataa gccgctggta  2100
```

```
ggtaccggta tggagcgtgc ggttgcggtt gactccggtg ttactgccgt agcgaaacgt  2160
ggtggtaccg tgcagtacgt ggatgcatcc cgtatcgtta ttaaagttaa cgaagacgaa  2220
atgtatccgg gcgaagccgg tatcgacatt tacaacctga ccaaatatac ccgttctaac  2280
cagaacacct gcatcaacca gatgccttgc gtgaacctgg gtgagccaat cgaacgtggt  2340
gatgtgctgg ctgatggccc ttcaaccgat ctcggcgaac tggcactcgg tcagaacatg  2400
cgcgtcgcgt tcatgccgtg gaacggctac aacttcgaag actccattct ggtctcggag  2460
cgcgttgttc aggaagatcg cttcaccact atccacattc aggaactggc gtgtgtgtct  2520
cgtgacacca agctggggcc agaagagatc accgctgaca tccctaacgt gggtgaagct  2580
gcgctctcta aactggatga gtccggtatc gtgtatatcg gtgcggaagt gaccggtggg  2640
gacattctgg ttggtaaggt aacacctaaa ggtgaaaccc agctgacgcc agaagagaaa  2700
ctgctgcgtg cgatcttcgg tgaaaaagcg tctgacgtta aagactcttc tctgcgcgta  2760
ccaaacggtg tgtcagggac aatcatcgac gttcaggtct ttacccgcga tggcgtggaa  2820
aaagacaagc gtgcgctgga aatcgaagag atgcagctga agcaggcgaa gaaagacctg  2880
tctgaagaat tgcagatcct cgaagccggc ttgttcagcc gtattaacta cctgctggtt  2940
gccggcggtg ttgaagcgga aaaactggag aagctgccac gtgagcgctg gctcgaactg  3000
ggcctgaccg acgaagagaa gcaaaatcag ctggaacagc tggccgagca gtacgacgag  3060
ctgaagcacg agtttgagaa aaaacttgaa gccaagcgcc gtaaaatcac tcagggcgat  3120
gacctggcac ctggcgtgct gaaaatcgtg aaagtgtatc tggccgttaa acgtcagatc  3180
cagcctggtg acaaaatggc aggtcgtcac gggaacaaag gtgttatctc caagatcaac  3240
ccgatcgaag atatgccata cgatgagttc ggtacgccgg tcgacatcgt actgaacccg  3300
ctgggcgttc catcacgtat gaacattggt cagattcttg aaacccacct gggtatggct  3360
gcgaaaggca ttggcgagaa aattaacgct atgcttaaga agcaggaaga agtgtccaag  3420
ctgcgtgaat tcattcagcg tgcttacgat ctgggcagcg atctgcgtca gaaagttgac  3480
ctgaacacct tcaccgatga cgaagtgctg cgcctggcag agaatctgaa aaaaggtatg  3540
ccaattgcaa caccagtgtt tgacggcgcg aaagagagcg aaatcaaaga gctgttacag  3600
ctcggcggcc tgccttcttc tggccagatc acgctgtttg atggtcgtac cggtgagcag  3660
ttcgaacgtc aggttaccgt tggctacatg tacatgctga agctgaacca cctggttgat  3720
gacaaaatgc atgcgcgttc taccggttct tacagcctcg ttactcagca gccgctgggt  3780
ggtaaggcgc agttcggtgg tcagcgcttc ggtgagatgg aagtgtgggc actggaagca  3840
tacggtgccg cgtataccct gcaggaaatg ctgaccgtga agtctgatga cgttaacggc  3900
cgtaccaaga tgtataaaaa catcgttgac ggcaaccatc agatggaacc gggcatgccg  3960
gaatctttca acgtactgtt gaaagagatc cgctcgctgg gtatcaacat cgagctggaa  4020
gacgagtaa                                                          4029
```

```
SEQ ID NO: 109          moltype = DNA  length = 1700
FEATURE                 Location/Qualifiers
source                  1..1700
                        mol_type = genomic DNA
                        organism = unidentified
                        note = DP68 Glutamine--tRNA ligase sequence
SEQUENCE: 109
atgagcaagc ccactgtcga ccctacctcg aattccaagg ccggacctgc cgtcccggtc  60
aatttcctgc gcccgatcat ccaggcggac ctggattcgg gcaagcacac gcagatcgtc  120
acccgcttcc cgccagagcc caacggctac ctgcacatcg gtcacgccaa gtcgatctgt  180
gtgaacttcg gcctggccca ggagttcggt ggcgtcacgc acctgcgttt cgacgacacc  240
aacccggcca aggaagacca ggaatacatc gacgccatcg aaagcgacat caagtggctg  300
ggcttcgaat ggtccggtga agtgcgctat gcgtccaagt atttcgacca gttgttcgac  360
tgggccgtcg agctgatcaa ggccggcaag gcctacgtcg acgacctgac cccggagcag  420
gccaaggaat accgtggcac gctgaccgag ccgggcaaga acagcccgtt ccgtgaccgt  480
tcggtagaag agaacctcga ctggttcaac cgcatgcgcg ccggtgagtt cccggacggc  540
gcccgcgtgc tgcgcgccaa gatcgacatg gcctcgccga acatgaacct gcgcgacccg  600
atcatgtacc gcatccgcca cgcccatcac caccagaccg gtgacaagtg gtgcatctac  660
ccgaactatg acttcaccca cggtcagtcg gacgccatcg aaggcatcac ccactccatc  720
tgcaccctgg agttcgaaag ccatcgcccg ctgtatgagt ggttcctcga cagcctgccg  780
gttccggcgc acccgcgtca gtacgagttc agccgcctga acctgaacta caccatcacc  840
agcaagcgca agctcaagca gttggtggac gaaaagcacg tgcatggctg ggatgacccg  900
cgcatgtcca ccctgtcggg tttccgccgt cgcggctaca ccccggcgtc gatccgcagc  960
ttctgcgaca tggtcggcac caaccgctcc gacggcgtgg tcgattacgg catgctcgag  1020
ttcagcatcc gtcaggacct ggacgccaac gcgccgcgtg ccatgtgcgt attgcgcccg  1080
ttgaaagtcg tgatcaccaa ctatccggaa gacaaggtcg accacctcga actgccgcgt  1140
cacccgcaga aagaagaact tggcgtgcgc aagctgccgt tcgcgcgtga aatctacatc  1200
gaccgtgatg acttcatgga agagccgccg aaaggctaca agcgcctgga gcctaacggc  1260
gaagtgcgcc tgcgcggcag ctacgtgatc cgtgccgatg aagcgatcaa ggacgccgat  1320
ggcaacatcg tcgaactgcg atgctcctac gacccggaaa ccctgggcaa gaaccctgaa  1380
ggccgcaagg tcaaaggcgt cgttcactgg gtgccggctg ctgccagcat cgagtgcgaa  1440
gtgcgcctgt acgatcgtct gttccgttcg ccgaaccctg agaaggctga agacagcgcc  1500
agcttcctgg acaacatcaa ccctgactcc ctgcaagttc tcacgggttg tcgtgccgag  1560
ccatcgcttg gcgacgcaca gccggaagac cgtttccagt tcgagcgcga aggttacttc  1620
tgcgcggata tcaaggactc caaacctggt catccggtct tcaaccgtac cgtgaccttg  1680
cgtgattcgt ggggccagtg                                              1700
```

```
SEQ ID NO: 110          moltype = DNA  length = 2418
FEATURE                 Location/Qualifiers
source                  1..2418
                        mol_type = genomic DNA
                        organism = unidentified
                        note = DP68 DNA gyrase subunit B sequence
SEQUENCE: 110
atgagcgaag aaaacacgta cgactcgacc agcattaaag tgctgaaagg tttggatgcc  60
```

```
gtacgcaaac gtcccggtat gtacatcggc gacaccgatg atggtagcgg tctgcaccac  120
atggtgttcg aggtggtcga caactccatc gacgaagctt tggccggtca ctgcgacgac  180
atcagcatta tcatccaccc ggatgagtcc atcaccgtgc gcgacaacgg tcgcggtatt  240
ccggtcgatg tgcacaaaga agaaggcgta tcggcggcag aggtcatcat gaccgtgctt  300
cacgccggcg gtaagttcga cgacaactcc tataaagttt ccggcggttt gcacggtgta  360
ggtgtgtcgg tggtgaacgc tctgtccgaa gagcttatcc tgactgttcg ccgtagcggc  420
aagatctggg aacagaccta cgtgcatggt gttccacaag aaccgatgaa aatcgttggc  480
gacagtgaat ccaccggtac gcagatccac ttcaagcctt cggcagaaac cttcaagaat  540
atccacttca gttgggacat cctggccaag cgtattcgtg aactgtcgtt ccttaactcc  600
ggtgtgggta tcgtcctcaa ggacgagcgc agcggcaagg aagagttgtt caagtacgaa  660
ggcggcttgc gtgcgttcgt tgagtacctg aacaccaaca agactgcggt caaccaggtg  720
ttccacttca acatccagcg tgaagacggt atcggcgttg aaatcgccct gcagtggaac  780
gacagcttca acgagaacct gttgtgcttc accaacaaca ttccacagcg cgacggcggt  840
actcacttgg tgggtttccg ttccgcactg acgcgtaacc tgaacaccta catcgaagcg  900
gaaggcttgg ccaagaagca caaagtggcc actaccggtg acgatgcgcg tgaaggcctg  960
acggcgatta tctcggtgaa agtgccggat ccaaagttca gctcccagac caaagacaag  1020
ctggtgtctt ccgaagtgaa gaccgcagtg gaacaggaga tgggcaagta cttctccgac  1080
ttcctgctgg aaaacccgaa cgaagccaag ttggttgtcg gcaagatgat cgacgcggcg  1140
cgtgcccgtg aagcggcgcg taaagcccgt gagatgaccc gccgtaaagg cgcgttggat  1200
atcgccggcc tgccgggcaa actggctgac tgccaggaga aggaccctgc cctctccgaa  1260
ctgtacctgg tggaaggtga ctctgctggc ggttccgcca agcagggtcg taaccgtcgc  1320
acccaggcta tcctgccgtt gaagggtaag atcctcaacg tcgagaaggc ccgcttcgac  1380
aagatgattt cctctcagga agtcggcacc ttgatcacgg cgttgggctg cggtattggc  1440
cgcgatgagt acaacatcga caaactgcgt taccacaaca tcatcatcat gaccgatgct  1500
gacgtcgacg gttcgcacat ccgtaccctg ctgctgacct tcttcttccg tcagttgccg  1560
gagctgatcg agcgtggcta catctacatc gctcagccgc cgttgtacaa agtgaaaaag  1620
ggcaagcaag agcagtacat caaagacgac gacgccatgg aagagtacat gacgcagtcg  1680
gccctggaag atgccagcct gcacttgaac gacgaagccc cgggcatttc cggtgaggcg  1740
ctggagcgtt tggttaacga cttccgcatg gtaatgaaga ccctcaagcg tctgtcgcgc  1800
ctgtaccctc aggagctgac cgagcacttc atctacctgc cttccgtgag cctggagcag  1860
ttgggcgatc acgcccacat gcagaattgg ctggctcagt acgaagtacg tctgcgcacc  1920
gtcgagaagt ctggcctggt ttacaaagcc agcttgcgtg aagaccgtga acgtaacgtg  1980
tggctgccgg aggttgaact gatctcccac ggcctgtcga actacgtcac cttcaaccgc  2040
gacttcttcg gcagcaacga ctacaagacc gtggttaccc tcggcgcgca attgagcacc  2100
ctgttggacg acggtgctta catccagcgt ggcgagcgta agaaagcggt caaggagttc  2160
aaggaagccc tggactggtt gatggctgaa agcaccaagc gccacaccat ccagcgatac  2220
aaaggtctgg gcgagatgaa cccggatcaa ctgtgggaaa ccaccatgga tcctgctcag  2280
cgtcgcatgc tacgcgtgac catcgaagac gccattggcg cagaccagat cttcaacacc  2340
ctgatgggtg atgcggtcga gcctcgccgt gacttcatcg agagcaacgc cttggcggtg  2400
tctaacctgg atttctga                                                2418

SEQ ID NO: 111         moltype = DNA  length = 2832
FEATURE                Location/Qualifiers
source                 1..2832
                       mol_type = genomic DNA
                       organism = unidentified
                       note = DP68 Isoleucine--tRNA ligase sequence
SEQUENCE: 111
atgaccgact ataaagccac gctaaacctt ccggacaccg ccttcccaat gaaggccggc  60
ctgccacagc gcgaaccgca gatcctgcag cgctgggaca gtattggcct gtacggaaag  120
ttgcgcgaaa ttggcaagga tcgtccgaag ttcgtcctgc acgacggccc tccttatgcc  180
aacggcacga ttcacatcgg tcatgcgctg aacaaaattc tcaaggacat gatcctgcgt  240
tcgaaaaccc tgtcgggctt cgacgcgcct tatgttccgg gctgggactg ccacggcctg  300
ccgatcgaac acaaagtcga agtgacctac ggcaagaacc tgggcgcgga taaaacccgc  360
gaactgtgcc gtgcctacgc caccgagcag atcgaagggc agaagtccga attcatccgc  420
ctgggcgtgc tgggcgagtg ggacaacccg tacaagacca tgaacttcaa gaacgaggcc  480
ggtgaaatcc gtgccttggc tgaaatcgtc aaaggcggtt tcgtgttcaa gggcctcaag  540
cccgtgaact ggtgcttcga ctgcggttcg gccctggctg aagcggaagt cgagtacgaa  600
gacaagaagt cctcgaccat cgacgtggcc ttcccgatcg ccgacgacga caagctggct  660
caagcctttg gcctgtccag cctgccaaag cctgcagcca tcgtgatctg gaccaccacc  720
ccgtggacca tcccggccaa ccaggcgctg aacgtgcacc cggaattcac ctacgccctg  780
gtggacgtcg gtgatcgcct gctggtgctg gctgaagaaa tggtcgaggc ctgcctggcg  840
cgctacgagc tgcaaggttc ggtcatcgcc accaccaccg gcactgcgct ggagctgatc  900
aatttccgtc acccgttcta tgaccgtctg tcgccggtgt acctggctga ctacgtagag  960
ctgggttcgg gtactggtgt ggttcactcc gcgccggcct acggcgttga tgactttgtg  1020
acctgcaaag cctacggcat ggtcaacgat gacatcctca acccggtgca gagcaatggc  1080
gtgtacgcgc cgtcgctgga gttctttggc ggccagttca tcttcaaggc caacgagccg  1140
atcatcgaca aactgcgtga agtcggttcg ctgctgcaca ccgaaaccat caagcacagc  1200
tacatgcact gctggcgtca caagaccccg ctgatctacc gcgctaccgc gcagtggttt  1260
atcggcatgg acaaagagcc gaccagcggc gacaccctgc gtgtgcgctc gctcaaagcg  1320
atcgaagaga ccaagtttgt cccggcctgg ggccaggcgc gcctgcactc gatgatcgcc  1380
aaccgcccgg actggtgcat ctcccgccag cgcaactggg gcgtgccgat tccgttcttc  1440
ctgaacaagg aaagcggcga gctgcaccca cgtaccgttg aactgatgga agcagtggcg  1500
ctgcgcgttg agcaggaagg catcgaagcc tggttcaagc tggacgccgc cgaactgctg  1560
ggcgacgaag cgccgctgta cgacaagatc agcgacaccc tcgacgtgtg gttcgactcg  1620
ggtaccaccc actggcacgt gctgcgcggt tcgcacccga tgggtcacgc caccggcccg  1680
cgtgccgacc tgtacctgga aggctcggac caacaccgtg gctggttcca ctcgtcgttg  1740
ctgaccggct gcgccatcga caaccacgcg ccgtaccgcg aactgctgac ccacggcttc  1800
accgtcgacg agacgggccg caagatgtcc aagtcgctga aaaacgtgat cgagccgaaa  1860
```

-continued

```
aagatcaacg acaccctggg cgccgatatc atgcgtctgt gggtcgcctc gaccgattac  1920
tcgggcgaaa tcgccgtgtc ggaccagatc ctggcccgta gcgccgatgc ctaccgccgt  1980
atccgtaata ccgcacgctt cctgctgtcg aacctgaccg gtttcaaccc ggccaccgac  2040
atcctgccgg ccgaggacat gctcgccctg gaccgttggg ccgtggaccg tacgctgttg  2100
ctgcagcgcg agttgcagga acactacggc gaataccgtt tctggaacgt gtactccaag  2160
atccacaact tctgcgtgca ggagctgggt ggtttctacc tcgatatcat caaggaccgc  2220
cagtacacca ccggcgccaa cagcaaggcg cgccgctcgg cgcagaccgc gctgtaccac  2280
atctctgaag cgctggtgcg ctggatcgca ccgatcctgg ccttcaccgc tgacgaactg  2340
tgggaatacc tgccgggcga gcgtaacgaa tcggtgatgc tcaacacctg gtacgaaggc  2400
ctgaccgaat tgccggccaa cttcgaactg ggccgcgagt actgggaagg cgtgatggcc  2460
gtcaaggttg cggtgaacaa ggagctggaa gttcagcgcg cggccaaggc cgtcggtggc  2520
aacctgcaag ccgaagtcac cctgtttgcc gaggaaggcc tgaccgccga cctggccaag  2580
ctgagcaacg aactgcgctt cgtactgatc acctcgaccg cgagcctggc accgtttgcc  2640
caggcacctg cggacgcagt ggccaccgaa gtgccgggcc tcaagctcaa agtggtcaag  2700
tcggcctttc ctaagtgcgc ccgttgctgg cactgccgtg aagacgtcgg cgtgaaccca  2760
gagcatccgg aaatctgcgg tcgttgcgtc gacaacatca gcggtgctgg cgaggttcgc  2820
cactatgcct aa                                                   2832

SEQ ID NO: 112         moltype = DNA  length = 1785
FEATURE                Location/Qualifiers
source                 1..1785
                       mol_type = genomic DNA
                       organism = unidentified
                       note = DP68 NADH-quinone oxidoreductase subunit C/D sequence
SEQUENCE: 112
atgactacag gcagtgctct gtacatcccg ccttacaagg cagacgacca ggatgtggtt  60
gtcgaactca ataaccgttt tggccctgac gccttcaccg cccaggccac acgcaccggt  120
atgccggtgc tgtgggtggc gcgcgccaag ctcgtcgaag tcctgagctt cctgcgcaac  180
ctgcccaagc cgtacgtcat gctttatgac ctgcatggcg tggacgagcg tctgcgcacc  240
aagcgtcaag gtttgccgag cggtgccgat ttcaccgtgt tctaccactt gatgtcgctg  300
gaacgtaaca gcgacgtgat gatcaaggtc gcgctgtccg aaagcgactt gagcatcccg  360
accgtcaccg gtatctggcc gaatgccagc tggtacgagc gcgaagtttg ggacatgttc  420
ggtatcgact tcccgggcca cccgcacctg acgcgcatca tgatgccgcc gacctgggaa  480
ggtcacccgc tgcgcaagga ctttcctgcc cgcgcaaccg aattcgaccc gttcagcctc  540
aacctcgcca agcagcagct tgaagaagaa gctgcacgct tccgtccgga agactggggc  600
atgaaacgct ccggcaccaa cgaggactac atgttcctca acctgggccc gaaccaccct  660
tcggctcacg gtgccttccg tatcatcctg caactggacg gcgaagaaat cgtcgactgt  720
gtgccggaca tcggttacca ccaccgtggt gccgagaaga tggccgagcg ccagtcctgg  780
cacagcttca tcccgtacac cgaccgtatc gactacctcg gcggcgtgat gaacaacctg  840
ccgtacgtgc tgtcggtcga gaagctggcc ggtatcaagg tgccggaccg cgtcgacacc  900
atccgcatca tgatggccga gttcttccgc atcaccagcc acctgctgtt cctgggtacc  960
tatatccagg acgttggcgc catgaccccg gtgttcttca ccttcaccga ccgtcaacgc  1020
gcctacaagg tgatcgaagc catcaccggt ttccgcctgc acccggcctg gtatcgcatc  1080
ggcggcgtgg cgcacgacct gccgaacggc tgggagcgcc tggtcaagga attcatcgac  1140
tggatgccca agcgtctgga cgagtaccaa aaggctgcgc tggacaacag catcctcaag  1200
ggtcgtacca tcggcgtcgc gcagtacaac accaaagaag ccctggaatg gggcgtcact  1260
ggtgccggcc tgcgttcgac cggctgcgac ttcgacctgc gtaaagcacg gccgtactcg  1320
ggctacgaga acttcgagtt cgaagtgccg ctggccgcca atggcgatgc ctacgaccgg  1380
tgcatcgtgc gcgttgaaga aatgcgccag agcctgaaga tcatcgagca gtgcatgcgc  1440
aacatgccgg ctggcccgta caaggcggat catccgctga ccacaccgcc gccgaaagag  1500
cgcacgctgc agcacatcga aaccctgatc acgcacttcc tgcaagtttc gtggggcccg  1560
gtgatgccgg ccaacgaatc cttccagatg atcgaagcga ccaagggtat caacagttat  1620
tacctgacga gcgatggcgg caccatgagc taccgcaccc ggattcgtac cccaagcttt  1680
gcccacttgc agcagatccc ttcggtgatc aaaggcgaga tggtcgcgga cttgattgcg  1740
tacctgggta gtatcgattt cgttatggcc gacgtggacc gctaa                1785

SEQ ID NO: 113         moltype = DNA  length = 1059
FEATURE                Location/Qualifiers
source                 1..1059
                       mol_type = genomic DNA
                       organism = unidentified
                       note = DP68 Protein RecA sequence
SEQUENCE: 113
atggacgaca acaagaagaa agccttggct gcggccctgg gtcagatcga acgtcaattc  60
ggcaagggtg ccgtaatgcg tatgggcgat cacgaccgtc aggcgatccc ggctatttcc  120
actggctctc tgggtctgga catcgcactc ggcattggcg gcctgccaaa aggccgtatc  180
gttgaaatct acggtcctga atcttccggt aaaaccaccc tgaccctgtc ggtgattgcc  240
caggcgcaaa aaatgggcgc cacctgtgcg ttcgtcgacg ccgagcacgc cctggacccg  300
gaatacgccg gtaagctggg cgtcaacgtt gacgacctgc tggtttccca gccggacacc  360
ggtgagcaag ccctggaaat caccgacatg ctggtgcgct ccaacgccat cgacgtgatc  420
gtggtcgact ccgtggctgc cctggtaccg aaagctgaaa tcgaaggcga aatgggcgac  480
atgcacgtgg gcctgcaagc ccgcctgatg tcccaggcgc tgcgtaaaat taccggtaac  540
atcaagaacg ccaactgcct ggtgatcttc atcaaccaga tccgtatgaa gatcggcgta  600
atgttcggca gcccggaaac cactaccggt ggtaacgcgc tgaagttcta cgcttcggtc  660
cgtctggaca tccgccgtac cggcgcggtg aaggaaggtg acgaagttgt tggtagcgaa  720
actcgcgtta aagtcgtgaa gaacaaggtc gctccgcctt tccgtcaggc agagttccag  780
attctctacg gcaagggtat ctacctgaac ggcgagatga ttgacctggg cgtactgcac  840
ggtttcgtcg agaagtccgg tgcctggtat gcctacaacg gcagcaagat cggtcagggc  900
aaggccaact cggccaagtt cctggcagac aacccggata tcgctgccac gcttgagaag  960
```

-continued

```
cagattcgcg acaagctgct gaccccagcg ccagacgtga aagctgccgc caaccgcgag  1020
ccggttgaag aagtggaaga agctgacact gatatctga                         1059

SEQ ID NO: 114          moltype = DNA  length = 1851
FEATURE                 Location/Qualifiers
source                  1..1851
                        mol_type = genomic DNA
                        organism = unidentified
                        note = DP68 RNA polymerase sigma factor RpoD sequence
SEQUENCE: 114
atgtccggaa aagcgcaaca acagtctcgt attaaagagt tgatcaccct tggtcgtgag  60
cagaaatatc tgacttacgc agaggtcaac gatcacctgc ctgaggatat ttcagatcct  120
gagcaggtgg aagacatcat ccgcatgatt aatgacatgg ggatccccgt acacgagagt  180
gctccggatg cggacgccct tatgttggcc gactccgata ccgacgaggc agctgctgaa  240
gaagcggctg ctgcgctggc agcggtggag accgacatcg gtcgtacgac tgaccctgtg  300
cgcatgtata tgcgtgaaat gggtaccgtc gagctgctga cacgtgaagg cgaaatcgaa  360
atcgccaaac gtattgaaga gggtatccgt gaagtgatgg gcgcaatcgc gcacttccct  420
ggcacggttg accacattct ctccgagtac actcgcgtca ccaccgaagg tggccgcctg  480
tctgacgttc tgagcggcta catcgacccg gacgacggca ttgcgccgcc tgccgccgaa  540
gtaccgccgc ccgtcgatgc gaaagccgcg aaggctgacg acgacaccga agacgacgat  600
gctgaagcca gcagcgacga cgaagatgaa gttgaaagcg gcccggaccc gatcatcgca  660
gcccagcgtt tcggtgcggt ttccgatcaa atggaaatca cccgcaaggc cctgaaaaag  720
cacggtcgct ccaacaagct ggcgattgcc gagctggtgg ccctggctga gctgttcatg  780
ccgatcaagc tggtaccgaa gcaattcgaa ggcttggttg agcgtgttcg cagtgccctt  840
gaacgtctgc gtgcgcaaga acgcgcaatc atgcagctgt gtgtacgtga tgcacgtatg  900
ccgcgggctg acttcctgcg ccagttcccg ggcaacgaag tagacgaaag ctggaccgac  960
gcactggcca aaggcaaggc gaaatacgcc gaagccattg gtcgcctgca gccggacatc  1020
atccgttgcc agcagaagct gaccgcgctt gagaccgaaa ccggtctgac gattgctgaa  1080
atcaaagaca tcaaccgtcg catgtcgatc ggtgaggcca aggcccgccg cgcgaagaaa  1140
gagatggttg aagcgaactt gcgtctggtg atctcgatcg ccaagaagta caccaaccgt  1200
ggtctgcaat tcctcgatct gatccaggaa ggcaacatcg gcttgatgaa ggcggtggac  1260
aagttcgaat accgtcgcgg ctacaagttc tcgacttatg ccacctggtg gatccgtcag  1320
gcgatcactc gctcgatcgc cgaccaggct cgcaccatcc gtattccggt gcacatgatc  1380
gagacgatca acaagctcaa ccgtatttcc cggcagatgt tgcaggaaat gggtcgcgaa  1440
ccgacccccgg aagagctggg cgaacgcatg gaaatgcctg aggataaaat ccgcaaggta  1500
ttgaagatcg ctaaagagcc gatctccatg gaaacgccga ttggtgatga cgaagactcc  1560
cacctgggtg acttcatcga agactcgacc atgcagtcgc caatcgatgt cgccactgtt  1620
gagagcctta aagaagcgac tcgcgacgta ctgtccggcc tcactgcccg tgaagccaag  1680
gtactgcgca tgcgtttcgg catcgacatg aataccgacc acacccttga ggaagtcggt  1740
aagcagtttg acgtgacccg cgagcggatc cgtcagatcg aagccaaggc gctgcgcaag  1800
ttgcgccacc cgacgcgaag cgagcatctg cgctccttcc tcgacgagtg a           1851

SEQ ID NO: 115          moltype = DNA  length = 4074
FEATURE                 Location/Qualifiers
source                  1..4074
                        mol_type = genomic DNA
                        organism = unidentified
                        note = DP68 DNA-directed RNA polymerase subunit beta
                         sequence
SEQUENCE: 115
atggcttact catatactga gaaaaaacgt atccgcaagg actttagcaa gttgccggac  60
gtcatggatg tcccgtacct tctggctatc cagctggatt cgtatcgtga attcttgcag  120
gcgggagcga ccaaagatca gttccgcgac gtgggcctgc atgcggcctt caaatccgtt  180
ttcccgatca tcagctactc cggcaatgct gcgctggagt acgtgggtta tcgcctgggc  240
gaaccggcat ttgatgtcaa agaatgcgtg ttgcgcggtg ttacgtacgc cgtacctttg  300
cgggtaaaag tccgcctgat cattttcgac aaagaatcgt cgaacaaagc gatcaaggac  360
atcaaagagc aagaagtcta catgggcgaa atcccactga tgactgaaaa cggtaccttc  420
gtaatcaacg gtaccgagcg tgttattgtt tcccagctgc accgttcccc gggcgtgttc  480
ttcgaccacg accgcggcaa gacgcacagc tccggtaaac tcctgtactc cgcgcggatc  540
attccgtacc gcggttcgtg gttggacttc gagttcgacc cgaaagactg cgtgttcgtg  600
cgtatcgacc gtcgtcgcaa gctgccggcc tcggtactgc tgcgcgcgct cggttacacc  660
actgagcagg tgctggacgc tttctacacc accaacgtat tcagcctgaa ggatgaaacc  720
ctcagcctgg agctgattgc ttcgcgtctg cgtggtgaaa ttgccgttct ggacattcag  780
gacgaaaacg gcaaagtgat cgttgaagcg ggtcgtcgta ttactgcgcg ccacatcaac  840
cagatcgaaa aagccggcat caagtcgctg gaagtgcctc tggactacgt cctgggtcgc  900
accaccgcca aggttatcgt tcacccggct acaggcgaaa tcctggctga gtgcaacacc  960
gagctgaaca ccgaaatcct ggcaaaaatc gccaaggccc aggttgttcg catcgagacc  1020
ctgtacacca acgacatcga ctgcggtccg ttcatctccg acacactgaa gatcgactcc  1080
accagcaacc aattggaagc gctggtcgag atctatcgca tgatgcgtcc tggtgagcca  1140
ccgaccaaag acgctgccga gaccctgttc aacaacctgt tcttcagccc tgagcgttat  1200
gacctgtctg cggtcggccg gatgaagttc aaccgtcgta tcggtcgtac cgagatcgaa  1260
ggttcgggcg tgctgtgcaa ggaagatatc gtcgcggtac tgaagactct ggtcgacatc  1320
cgtaacggta aaggcatcgt cgatgacatc gaccacctgg gtaaccgtcg tgttcgctgc  1380
gtaggcgaaa tggccgaaaa ccagttccgc gttggccttg tgcgtgttga acgtgcggtc  1440
aaagagcgtc tgtcgatggc tgaaagcgaa ggcctgatgc cgcaagacct gatcaacgcc  1500
aagccagtgg ctgcggcagt gaaagagttc ttcggttcca gccagctttc ccagttcatg  1560
gaccagaaca acccgctctc cgagatcacc cacaagcgcc gtgtttctgc actgggcccg  1620
ggcggtctga cccgtgagcg tgctggcttt gaagttcgtg acgtacaccc gacgcactac  1680
ggtcgtgttt gcccgatcga aacgccggaa ggtccgaaca tcggtctgat caactccctg  1740
```

```
gccgcttatg cgcgcaccaa ccagtacggc ttcctcgaga gcccgtaccg cgtggtgaaa  1800
gacgctctgg tcaccgacga gatcgtattc ctgtccgcca tcgaagaagc tgatcacgtg  1860
atcgctcagg cttcggccac gatgaacgac aagaaagtcc tgatcgacga gctggtagct  1920
gttcgtcact tgaacgagtt caccgtcaag gcgccggaag acgtcacctt gatggacgtt  1980
tcgccgaagc aggtagtttc ggttgcagcg tcgctgatcc cgttcctgga acacgatgac  2040
gccaaccgtg cgttgatggg ttccaacatg cagcgtcaag ctgtaccaac cctgcgcgct  2100
gacaagccgc tggtaggtac cggcatggag cgtaacgtag cccgtgactc cggcgtttgc  2160
gtcgtagccc gtcgtggcgg cgtgatcgac tccgttgatg ccagccgtat cgtggttcgt  2220
gttgccgatg atgaagttga aactggcgaa gccggtgtcg acatctacaa cctgaccaaa  2280
tacacccgct cgaaccagaa cacctgcatc aaccagcgtc cgctggtgag caagggtgac  2340
cgcgttcagc gtagcgacat catggccgac ggcccgtcca ctgacatggg tgaactggct  2400
ctgggtcaga acatgcgcat cgcgttcatg gcatggaacg gcttcaactt cgaagactcc  2460
atctgcctgt ccgagcgtgt tgttcaagaa gaccgtttca ccacgatcca cattcaggaa  2520
ctgacctgtg tggcacgtga taccaagctt gggccagagg aaatcactgc agacatcccg  2580
aacgtgggtg aagctgcact gaacaagctg gacgaagccg gtatcgttta cgtaggtgct  2640
gaagttggcg caggcgacat cctggtaggt aaggtcactc cgaaaggcga gacccaactg  2700
actccggaag agaagctgct gcgtgccatc ttcggtgaaa aagccagcga cgttaaagac  2760
acctccctgc gtgtacctac cggtaccaag ggtactgtta tcgacgtaca ggtcttcacc  2820
cgtgacggcg ttgagcgtga tgctcgtgca ctgtccatcg agaagactca actcgacgag  2880
atccgcaagg acctgaacga agagttccgt atcgttgaag gcgcgacctt cgaacgtctg  2940
cgttccgctc tggtaggcca caaggctgaa ggcggcgcag gtctgaagaa aggtcaggac  3000
atcaccgacg aagtactcga cggtcttgag cacggccagt ggttcaaact gcgcatggct  3060
gaagatgctc tgaacgagca gctcgagaag gcccaggcct acatcgttga tcgccgtcgt  3120
ctgctggacg acaagttcga agacaagaag cgcaaactgc agcagggcga tgacctggct  3180
ccaggcgtgc tgaaaatcgt caaggtttac ctggcaatcc gtcgccgcat ccagccgggc  3240
gacaagatgg ccggtcgtca cggtaacaaa ggtgtggtct ccgtgatcat gccggttgaa  3300
gacatgccgc acgatgccaa tggcaccccg gtcgacgtcg tcctcaaccc gttgggcgta  3360
ccttcgcgta tgaacgttgg tcagatcctc gaaacccacc tgggcctcgc ggccaaaggt  3420
ctgggcgaga agatcaaccg tatgatcgaa gagcagcgca aggttgctga cctgcgtaag  3480
ttcctgcacg agatctacaa cgagatcggc ggtcgcaacg aagagctgga caccttctcc  3540
gaccaggaaa tcctggactt ggcgaagaac ctgcgcggcg gcgttccaat ggctaccccg  3600
gtgttcgacg gtgccaagga aagcgaaatc aaggccatgc tgaaactggc agacctgccg  3660
gaaagcggcc agatgcagct gttcgacggc cgtaccggca acaagtttga gcgcccggtt  3720
actgttggct acatgtacat gctgaagctg aaccacttgg tagacgacaa gatgcacgct  3780
cgttctaccg gttcgtacag cctggttacc cagcagccgc tgggtggtaa ggctcagttc  3840
ggtggtcagc gtttcgggga gatggaggtc tgggcactgg aagcatacgg tgctgcatac  3900
actctgcaag aaatgctcac agtgaagtcg gacgatgtga acggtcggac caagatgtac  3960
aaaaacatcg tggacggcga tcaccgtatg gagccgggca tgcccgagtc cttcaacgtg  4020
ttgatcaaag aaattcgttc cctcggcatc gatatcgatc tggaaaccga ataa        4074
```

```
SEQ ID NO: 116          moltype = DNA  length = 1674
FEATURE                 Location/Qualifiers
source                  1..1674
                        mol_type = genomic DNA
                        organism = unidentified
                        note = DP69 Glutamine--tRNA ligase sequence
SEQUENCE: 116
gtgcgcgagg acctggccag cggaaagcac caggcgatca agacccgctt cccgccggag  60
ccgaacggct acctgcacat cggccacgcc aagtcgatct gcctgaactt cggcatcgcc  120
ggtgagttca gcggcgtctg caacctgcgt ttcgacgaca ccaatccggc caaggaagac  180
ccggagtacg tggccgcgat ccaggacgac gtgcgctggc tgggctttga atggaacgag  240
ctgcgccacg cctcggacta cttccagacc tattacctgg ccgccgagaa gctgatcgaa  300
cagggcaagg cctacgtctg cgacctgtcg gccgaggaag tgcgcgccta ccgcggcacc  360
ctgaccgagc cgggccgccc gtcgccgtgg cgtgaccgca gcgtcgagga gaacctcgac  420
ctgttccgcc gcatgcgtgc cggtgaattc cccgatggcg cgcgcaccgt gcgcgccaag  480
atcgacatgg ccagcggcaa catcaacctg cgtgatccgg cgctgtaccg catcaagcac  540
gtcgagcacc agaacaccgg caacgcgtgg ccgatctacc cgatgtacga cttcgcccat  600
gcgctgggcg attcgatcga gggcatcacc cactcgctgt gcacgctgga attcgaagac  660
caccgcccgc tgtacgactg gtgcgtggac aacgtcgact tcgcccacga tgacgcgctg  720
acccagccgc tggtcgacgc cggcctgccg cgcgaagcgg ccaaaccgcg ccagatcgag  780
ttctcgcgcc tgaacatcaa ctacacggtg atgagcaagc gcaagctgat ggcgctggtc  840
accgaacagc tggtggacgg ctgggaagac ccgcgcatgc cgaccctgca gggcctgcgt  900
cgccgtggct acacccggc agcgatgcgc ctgttcgccg agcgcgtggg catcagcaag  960
cagaattcgc tgatcgattt cagcgtgctg gaaggcgcgc tgcgcgaaga cctggacagc  1020
gccgcaccgc gccgcatggc cgtggtcgac ccggtcaagc tggtgctgac caacctggcc  1080
gaaggccacg aagagcagct gaccttcagc aaccacccga aggacgagag cttcggtacc  1140
cgcgaagtgc cgttcgcacg tgaagtgtgg atcgaccgcg aggacttcgc cgaagtgccg  1200
ccgaagggct ggaagcgcct ggttcccggt ggtgaagtgc gcctgcgcgg cgccggcatc  1260
atccgctgcg acgacgtgat caaggatgcc gacggcacca tcaccgagct gcgcggctgg  1320
ctggatccgg aatcgcgccc gggcatggaa ggcgccaacc gcaaggtcaa gggcaccatc  1380
cactgggtca gcgcggtgca cggtgtgccg gccgagatcc gcctgtatga ccgcctgttc  1440
tcggtgccga acccggacga tgaatcggaa ggcaagacct accgcgacta cctcaatccg  1500
gactcgcgcc gcaccgtcac cggctatgtc gagccggcgg ctgccagcgc tgcgccggaa  1560
cagtcgttcc agttcgagcg caccggctac ttcgttgccg accgccgcga ccacaccgaa  1620
gccaagccgg tgttcaaccg cagcgtgacc ctgcgcgaca cctggtcggc ctga        1674
```

```
SEQ ID NO: 117          moltype = DNA  length = 2460
FEATURE                 Location/Qualifiers
source                  1..2460
```

```
                        mol_type = genomic DNA
                        organism = unidentified
                        note = DP69 DNA gyrase subunit B sequence
SEQUENCE: 117
atgaccgacg aacagaacac cccggcaaac aacggcaact acgacgccaa cagcattacg  60
gccctggaag gcctggaggc tgtccgcaag cgcccaggca tgtacatcgg cgacgtccat  120
gacggcaccg gcctgcatca catggtgttc gaggtcgtcg acaactcaat cgacgaagcc  180
ctcgccggcc atgccgacca cgtctcggtg acgatccatg ccgatggctc ggtaggcgtg  240
tccgacaacg gtcgcggcat cccgacgggc aagcacgagc agatgagcaa gaagctcgac  300
cgcgatgtgt ctgcagccga agtggtgatg acggtcctgc acgcaggcgg caagttcgac  360
gacaacagct acaaggtttc cggcggcctg cacggcgtgg gcgtcagcgt ggtcaacgcg  420
ctgtcgcaga agctggtcct ggatatctac cagggtggct tccactacca gcaggagtac  480
gccgacggcg cagcactgca tccgctgaag cagatcggcc ccagcaccaa gcgcgggacc  540
accctgcgct tctggccctc ggtaaaggct ttccacgaca acgtggaatt ccactacgac  600
atcctggccc ggcgcctgcg cgaactgtcc ttcctcaatt ccggcgtcaa gatcgtgctg  660
gtggacgagc gtggtgatgg ccgccgcgac gacttccatt acgagggcgg catccgcagc  720
ttcgtggagc atctggcgca gttgaagacg ccgttgcacc cgaacgtgat ctcggtgacc  780
ggcgaatcca atggcatcac cgtggaagtg gcgctgcagt ggaccgactc ctaccaggag  840
acgatgtact gcttcaccaa caacattccg cagaaggacg gcggtaccca cctggccggc  900
ttccgtggcg cattgacccg cgtgctcaac aactacatcg agcagaacgg catcgccaag  960
caggccaaga tcaacctgac cggcgatgac atgcgcgaag gcatgatcgc ggtgctgtcg  1020
gtgaaggtgc cggatcccag cttctccagc cagaccaagg aaaagctggt cagctcggat  1080
gtgcgcccgg ccgtggaaag cgcgttcggc cagcgcctgg aagagttcct gcaggaaaac  1140
ccgaacgaag ccaaggccat cgccggcaag atcgtcgacg ctgcccgtgc ccgcgaagcg  1200
gcgcgcaagg cccgcgacct gacccgccgc aagggtgcgc tggatatcgc cggcctgccg  1260
ggcaagctgg ccgactgcca ggaaaaggat ccggcgctgt ccgaactgtt catcgtcgag  1320
ggtgactcgg caggtggttc ggccaagcag ggtcgcaacc gcaagaacca ggcggtgctg  1380
ccgctgcgcg gcaagatcct caacgtggaa cgtgcgcgct tcgaccgcat gctggcgtcc  1440
gaccaggtgg gtacgctgat caccgcgctg ggtaccggca tcggtcgtga cgagtacaac  1500
ccggacaagc tgcggtacca caagatcatc atcatgaccg acgccgacgt cgacggcgcg  1560
cacatccgca ccctgctgct gacgttcttc taccgtcaga tgccggagct gatcgagcgc  1620
ggttatgtct atatcggcct gccgccgttg tacaagatca agcagggcaa gcaggagctg  1680
tacctgaagg acgacccggc gctggacagc tatctggcca gcagcgcggt ggagaacgct  1740
gggctggtgc cggccagcgg cgagccgccg atcgacggcg tggcactgga aaagctgctg  1800
ctcgcctacg ctgccgcgca ggacacgatc aaccgcaata cccaccgcta cgaccgcaac  1860
ctgctcgaag cgctggtcga cttcatgccg ctggagctgg aaaacctgcg cactgcaggt  1920
cctggcgaag gtctggacgc gttggccaag cacctcaacc agggcaacct cggcagcgcc  1980
cgcttcaccc tggaactgca ggaacccaac gagcagcgtc cggcggccgt actggtgacc  2040
cgcagccaca tgggcgaaca gcacatccag gtgctgccgc tgtccgcgct ggaaagcggc  2100
gaactgcgcg gcatccatca ggcagcgcag ctgctgcacg gtctggtccg cgaaggcgcg  2160
gtcatcaccc gtggcgccaa gtcgatcgag atcgactcgt tcgcacaggc ccgcaactgg  2220
ctgttggacg aagccaagcg cggccggcag atccagcgat tcaagggtct gggcgaaatg  2280
aatccggaac agctgtggga taccaccgtc aatcccgata cccgtcgcct gctgcaggtg  2340
cgcatcgaag acgcggtggc cgctgaccag atcttcagca ccctgatggg tgatgtggtc  2400
gaaccgcgtc gtgacttcat cgaagacaac gcgttgaagg tcgccaacct ggatatctga  2460

SEQ ID NO: 118          moltype = DNA  length = 2835
FEATURE                 Location/Qualifiers
source                  1..2835
                        mol_type = genomic DNA
                        organism = unidentified
                        note = DP69 Isoleucine--tRNA ligase sequence
SEQUENCE: 118
gtgagccagg actacaagac caccctcaac ctgccggcca ccgaattccc gatgcgcggc  60
gacctgccca agcgcgagcc gggcattctg gcgcgctggg aagagcaggg gctctaccag  120
cagctgcgcg acaacgccgc cggccgcccg ctgttcgtgc tgcatgacgg cccgccgtac  180
gccaatgcgc gcatccacct gggccatgcg gtcaacaaga tcctcaagga catcatcgtc  240
aagtcgcgct acctggccgg cttcgatgcg ccctacgtgc cgggctggga ctgccatggc  300
ctgccgatcg aaatcgcggt ggaaaaagag tggggcaagg tcggggtgaa gctcgatgcg  360
gtcgagttcc ggcagaagtg ccgcgagttc gccgaagaac agatcgacat ccagcgtgcc  420
gacttcaagc gcctgggcgt caccggcgac tgggacaacc cgtacaagac cctaagcttc  480
gatttcgagg ccaacgagat ccgtgcgctg tccaagatcg tggccaacgg ccatctgctg  540
cgtggcgcca agccggtcta ctggtgcttc gactgcggct cggcactggc cgaggccgag  600
atcgagtacc acgagaagac ctcgccggcg atcgacgtgg cctacaccgc gcgtgatccg  660
caggcggtgg cgcaggcgtt cggcgtcagc ctgccggccg atgtcgaagt ggcggtgccg  720
atctggacca ccactccgtg gacgctgccg gcttcgctgg cggtgtcgct gggcgcggac  780
atccgctacg tgctggccga aggcccggcg cacaacggca agcgccgttg gctggtgctg  840
gctgctgcgc tggccgaacg gtcgctgcag cgctacggcg tggacgcggt ggtgctgcac  900
ggtgaagccg aaggttcggc gctggaaaac cagctgctgg cgcacccgtt ctacccggag  960
cgcgagatcc ccgtgctcaa cggcgaacac gtgtccgacg aggacggtac cggtgcggtg  1020
cacactgccc ccggccacgg ccaggaagac tacgtggtca gccagaagta cggcctgctg  1080
gagaagtaca acgccggcca gatcaatccg gtcgacggtg cgggcgtgta cctggcgtcc  1140
accccgcccg ccggtgacct ggtgctggcc ggtacccaca tctggaaggc gcagcagccg  1200
atcatcgaag tgctggccgc cagcggcgcg ctgctcaagg ccgtggagat cgtgcacagt  1260
tatccgcatt gttggcgcca caagaagacc ccgctggtgt tccgcgccac cccgcagtgg  1320
ttcatttcga tggacaaggc caacctgcgc aacgatgcgc tggccgcgat cgataccgtc  1380
ggctggttcc cgagctgggg caaggcgcgc atccaaagca tgatcgacgg ccgcccggac  1440
tggaccatct cgcgccagcg cacctggggc gtgccgatcg cgctgttcac ccaccgccag  1500
accggcgaga tccacccgcg ttcggtggag ctgatgcagc aggtggccga ccgcgttgaa  1560
```

```
gccgaaggca tcgacgtgtg gtactcgctg gatgcggctg aactgctggg cgctgaagcg  1620
gccgactacg agaaggtcac cgacatcctc gatgtctggt tcgattccgg cgtgacccac  1680
gaagccgtgc tggctgcccg tggcttcggc aagccggccg atctgtacct ggaaggttcg  1740
gaccagcatc gcggctggtt ccagtcctcg ctgctgaccg gcgtggccat cgacaagcgc  1800
gcgccgtaca agcagtgcct cacccacggt ttcaccgtgg acgagcacgg ccgcaagatg  1860
tccaagtcgc tgggcaacgg catcgaaccg caggaaatca tgaacaagct gggcgcggac  1920
atcctgcgcc tgtggatcgc ctcggccgac tacagcaacg agatgtcgct gtcgcaggaa  1980
atcctcaagc gcaccgccga cgcctaccgc cgcctgcgca acaccgcccg cttcctgctg  2040
ggcaacctgg acggtttcga tccggcccag cacctgcgcc cgctcaacga gatggtcgcg  2100
ctggaccgct ggatcgtgca tcgcgcctgg gagctgcagg agaagatcaa ggcggcgtat  2160
gacaactacg acatggccga gatcgtgcag ttgctgctga acttctgcag cgtggacctg  2220
ggctcgctgt acctggacgt gaccaaggat cgcctgtata cgatgccgac cgattcggat  2280
ggtcgtcgtt cggcgcagag cgcgatgtac cacatcgccg aagcgttcac ccgctgggtg  2340
gcgccgatcc tgaccttcac cgccgacgag ctgtggggct acctgccggg cgatcgtgcc  2400
ggccacgtgc tgttcactac ctggtacgag ggcctggcac cgctgccgac cgatgcacag  2460
ctcaacgctg ccgacttcga tcagctgctg gccgtgcgcg agcaggtggc caaggtgctg  2520
gagccgatgc gcgccaatgg tgcgatcggt gccgcgctgg aagcggagat caccatcgcc  2580
gccagcgaag agcaggccgc gcgctggcag ccgctggccg atgaactgcg tttcctgttc  2640
atcagtggtg acgtgcaggt gcgtccggcg accaccgacg aggtgttcgt cagcgcgcag  2700
ccgacgcaga agtccaagtg cgtgcgctgc tggcaccacc gtgccgacgt tggcagcaat  2760
gccgaccacc cggaactgtg cggccgctgc gtgaccaaca tcgccggtgc cggcgaagcg  2820
cggagctggt tctga                                                   2835
```

```
SEQ ID NO: 119         moltype = DNA  length = 2076
FEATURE                Location/Qualifiers
source                 1..2076
                       mol_type = genomic DNA
                       organism = unidentified
                       note = DP69 Glycine--tRNA ligase beta subunit sequence
SEQUENCE: 119
atgagccact tgtctcccct gctgattgaa ctgggcaccg aagagttgcc ggtcaaggcg  60
ctgccgggcc tggcccaggc cttcttcgac ggtgttgtcg atggcctgcg caagcgcggc  120
gtcgaactgg agctgggcga tgcccgcccg ctgtcgaccc cgcgccgcct ggccgtgctg  180
ctgccgggcg ttggcctgga acagccggaa caacacagcg aagtgctggg cccgtacctg  240
aacatcgcgc tggacgccga aggccagccg accaaggcgc tgcagggttt cgcggccaag  300
gccgggatcg actggaccgc gctggagaag accaccgaca acaagggtga gcgcttcgtg  360
caccgtgcgg tgactccggg cgcgcgcacc gctgcgctgc tgccggagat cctgcgcgag  420
gccatcgccg gcatgccgat tcccaagccg atgcgctggg gcgaccacag ctggggcttc  480
gcccgcccgg tgcactggct ggtgctgctg catggcggcg acgtggtcga ggccgaactg  540
tttggcctga aggccgaccg catgagccgc ggccaccgct tcctgcacga caagaccgtg  600
tggctgaccc agccgcagga ctatgtcgaa tcgctgcgcg ccgccttcgt gctggtcgat  660
ccggccgagc gccgccggcg catcgttgcc gaagtggaag ccgctgccgc caccgccggt  720
ggcagcgcac gcatcaccga ggacaacctg gagcaggtgg tgaacctggt cgagtggccg  780
gcggcagtgt tgtgcagctt cgagcgcgcg ttcctggcgg taccgcagga agcgctgatc  840
gagacgatgg agatcaacca gaagttcttc ccggtgctgg atgacggcgg caagctgacc  900
gagaagttca tcggcatcgc caacatcgag tccaaggacg tggccgaagt ggccaagggc  960
tacgagcgcg tgatccgccc gcgcttcgcc gatgccaagt tcttcttcga cgaagacctg  1020
aagcagggcc tgcaggcgat gggcgagggc ctgaagacgg tgacctacca ggccaagctg  1080
ggcagcgtgg ccgacaaggt cgcgcgcgtg gcggcgctgg ccgaggtgat cgctgcgcag  1140
gtgggggccg acccggtgct ggccaagcgt gccgcgcagc tggccaagaa cgacctgcag  1200
tcgcgcatgg tcaatgagtt cccggaactg cagggcatcg ctggccgcca ctacgcggtg  1260
gccggtggcg agtcgccgga ggtggcgctg gccatcgacg aggcctacca gccgcgcttc  1320
ggtggcgatg acatcgcgct gtcgccgctg ggcaaggtgc tggcgatcgc cgagcgtgtg  1380
gacacgctgg ccggcggttt cgccgcgggc ctgaagccga ccggcaacaa ggacccgttc  1440
gccctgcgcc gcaacgcgct gggcctggcc cgcacgatta tcgaaagtgg cttcgagctg  1500
gacctgcgcg cgctgctggc cagcgccaat gccgggctga ccgtgcgcaa cgtgcaggcc  1560
gacgtggctg agctgtacga cttcatcctc gaccgcctga agggctacta cagcgacaag  1620
ggcgtgccgg ccagccactt caatgcggtg gctgagctga agccggtctc gctgtacgat  1680
ttcgaccgtc gcctggacgc catcggtatc ttcgcggcgc tgccggaggc cgaggcgctg  1740
gcagcggcca acaagcgcat ccgcaacatc ctgcgcaagg ccgaaggcga tattccgggc  1800
cagatcgatg cggccctgtt gcaggaagat gccgagcgcg cgctggcgga agccgtgact  1860
gcagccatcg acgacaccgg cgccagcctg caccagaagg actacgtggc cgtgctggcg  1920
cgcctggccc gcctgcgtcc gcaggtcgat gcgttcttcg atggggtgat ggtcaatgcc  1980
gaggatccgg cactgcgcgg caaccgcctg gcgctgctga cgatgctggg cgagcgcttg  2040
ggcaaggtcg cggcgatcga gcatctgtcg agctga                             2076
```

```
SEQ ID NO: 120         moltype = DNA  length = 1410
FEATURE                Location/Qualifiers
source                 1..1410
                       mol_type = genomic DNA
                       organism = unidentified
                       note = DP69 Glutamine synthetase sequence
SEQUENCE: 120
atgtccgtgg aaaccgtaga gaagctgatc aaggacaacc agatcgagtt cgtcgatctg  60
cgcttcgtcg acatgcgtgg tgtcgaacag catgtgacct tcccggtcag catcgtcgag  120
ccgtcgctgt ttgaagaagg caagatgttc gatggcagct cgatcgccgg ctggaagggc  180
atcaacgagt cggacatggt gctgctgccg gacaccgcca gcgcctacgt cgacccgttc  240
tacgccgatc cgaccatcgt gatcagctgc gacatcctcg acccggccac catgcagccg  300
tatggccgtt gcccgcgcgg catcgccaag cgcgccgagt cctacctgaa gtcctcgggc  360
```

```
atcgccgaaa ccgcgttctt cggcccggag ccggagttct tcatcttcga ctcggtgcgt  420
ttcgccaatg aaatgggcaa caccttcttc aaggtcgact cggaagaagc ggcgtggaac  480
agcggcgcca agtacgacgg cgccaacagc ggctaccgtc cgggcgtgaa gggcggttat  540
ttccccgttc cgccgaccga caccctgcac gacctgcgtg cggagatgtg caagaccctg  600
gaacaggtcg gcatcgaagt ggaagtgcag caccacgaag tggccaccgc cggccagtgc  660
gagatcggca ccaagttcag caccctggtg cagaaggccg acgaactgct gcggatgaag  720
tacgtcatca agaacgtcgc ccaccgcaac ggcaagaccg tcaccttcat gcccaagccg  780
atcgtcggcg acaacggcag cggcatgcac gtgcaccagt cgctgtccaa gggcggcacc  840
aacctgttct ccggtgacgg ctacggtggc ctgagccaga tggcgctgtg gtacatcggc  900
ggcatcttca agcatgccaa ggcgatcaac gcctttgcca actcgggtac caacagctac  960
aagcgcctgg tgccgggctt cgaagccccg gtgatgctgg cctactcggc gcgcaaccgt  1020
tcggcctcgt gccgcattcc gtgggtgtcc aacccgaagg cgcgtcgcat tgaaatgcgc  1080
ttccccgatc cgatccagtc gggctacctg accttcaccg cgctgatgat ggccggcctg  1140
gacggcatca agaaccagat cgacccgggc gcaccgagcg acaaggatct gtacgacctg  1200
ccgccggaag aagagaagct gattccgcag gtctgctcct cgctggacca ggccctggaa  1260
gcgctggaca aggaccgtga gttcctcaag gccggtggcg tgatgagcga tgacttcatc  1320
gacggctaca tcgcgctgaa gatgcaggaa gtgaccaagt tccgcgcggc gacccacccg  1380
ctggaatacc agttgtacta cgccagctga                                  1410

SEQ ID NO: 121         moltype = DNA  length = 1515
FEATURE                Location/Qualifiers
source                 1..1515
                       mol_type = genomic DNA
                       organism = unidentified
                       note = DP69 Glucose-6-phosphate isomerase sequence
SEQUENCE: 121
atgacaacga acaacggatt cgactcgctg cattcccacg cccagcgcct gaagggcgca  60
agcatcccca gcctgctcgc cgccgaaccc ggccgcgtac aggacctggc gctgcgggtc  120
ggtccgttgt atgtcaactt cgcccggcag aaatacgatg ccgcggcgtt gcaggcgctg  180
ttggcgctgg ctgccgaacg tgatgtcggc ggcgccatca cgcgcctgtt ccgtggcgag  240
caggtcaatc tgaccgaagg ccgcgccgca ctgcacaccg cactgcgcgg cgacgtggtc  300
gatgcgccgg ttgccgccga ggcctatgcc acggcccgcg aaatccgcca gcgcatgggc  360
gtgctggtgc gcgcactgga agacagtggc gtgaccgatg tggtcagtgt cggcatcggc  420
ggttccgatc tcggtccgcg tctggtcgcc gacgcactgc gtccagtcac tggcgctcgc  480
ctgcgcgtgc atttcgtgtc taacgtggac ggcgctgcca tgcagcgcac gctggccacg  540
ctggatccgg cgaagaccgc cggcatcctc atttccaaga ccttcggtac ccaggaaacc  600
ctgctcaacg gccagatcct gcacgattgg ctgggtggca gcgagcgcct gtacgcggtc  660
agcgccaatc cggaacgcgc cgccaaggcc ttcgccatcg ccgccgagcg cgtgctgccg  720
atgtgggact gggtaggggg gcgctattcg ctgtggtcgg ccgtcggttt cccgatcgca  780
ctggccatcg gcttcgagcg tttcgagcag ttgctggaag gcgccgcgca gatggatgcg  840
catgcgctgg acgcgccgct ggagcgcaac ctgccggtgc tgcacggcct gaccgacatc  900
tggaaccgca atctgctggg ctctgccacg catgcggtga tgacctacga ccagcgcttg  960
gcgctgctgc cggcctacct gcagcagctg gtgatggaaa gcctgggcaa gcgcgtgcag  1020
cgcgatggcc agccggtcac caccgacacc gtgccggtgt ggtggggcgg tgccggcacc  1080
gatgtgcagc acagcttctt ccaggccctg caccagggca ccagcatcat tccggccgat  1140
ttcatcggct gcgtgcacaa cgacgatccg tatacggtca accaccaggc gttgatggcc  1200
aacctgctgg cgcagaccga agcgctggcc aacggccagg gcagtgacga tccgcaccgc  1260
gattatccgg gtggccgccc gagcacgatg atcctgctcg acgcgctcac cccgcaggcg  1320
ctgggcgcct tgatcgcgat gtacgaacac gccgtgtacg tgcagtcggt gatctggaac  1380
atcaacgcct tcgaccagtt cggtgtcgag ctgggcaagc agctggccag tggcctgctg  1440
cccgctctgc agggtgagga tgtcgaggtc aacgacccgc tgacccgtga gctgctggcc  1500
cagctgaagg gctga                                                  1515

SEQ ID NO: 122         moltype = DNA  length = 2640
FEATURE                Location/Qualifiers
source                 1..2640
                       mol_type = genomic DNA
                       organism = unidentified
                       note = DP69 Leucine--tRNA ligase sequence
SEQUENCE: 122
atgaccagcg tcgaacccaa cgtttacgat ccgcagcagg ttgaatccgc cgcccagaag  60
tactgggacg ctacccgtgc cttcgaggtc gatgaagcct cggacaagcc gaagtactac  120
tgcctgtcga tgcttccgta tccgtccggt gcgctgcaca tgggccacgt gcgcaattac  180
acgatcggcg acgtgatcag ccgctacaag cgcatgaccg gccacaacgt gctgcagccg  240
atgggctggg acgcgtttgg cctgccggcg gaaaacgctg cgatcaagaa caagaccgcg  300
ccggccgcct ggacctacaa gaacatcgac cacatgcgca gccagctgca gtcgctgggc  360
tatgccatcg actggtcgcg cgagttcgcc acctgccgcc cggactatta cgtccacgag  420
cagcgcatgt tcacccgcct gatgcgcaag ggcctggcct accgccgcaa cgcggtggtg  480
aactgggacc cggtcgacca gaccgtgctg gccaacgagc aggtcatcga cggccgtggc  540
tggcgctccg gcgcgcttgt ggaaaagcgc gagatcccgc agtggttcct gcgcatcacc  600
gactacgccc aggaactgct ggacggcctg gatgagctgg acggctggcc ggagtcggtc  660
aagaccatgc agcgcaactg gatcggccgc tccgaagggc tggaaatcca gttcgacgtg  720
cgcgacgtcg atggtgccgc actggatccg ctgcgcgtgt tcaccacccg cccggacacc  780
gtgatgggcg tgactttcgt gtcgatcgcg gccgaacatc cgctggcgct gcatgccgcg  840
aagaacaacc cggaactggc tgcgctgctg tcggaaatga agcagggcgg cgtgtccgag  900
gccgagctgg agacccagga aaagcgcggc atggataccg gcctgcgcgc cgtgcatccg  960
gttaccggtg cccaggtgcc ggtgtgggtc gccaacttcg tgctgatggg ctacggcact  1020
ggcgcggtga tggccgtacc gggccacgac cagcgcgaca atgaattcgc caacaagtac  1080
aacctgccga tccgccaggt catcgcgctg aagtcgctgc gcaaggacga aggcgcctac  1140
```

-continued

```
gacgcgacgc gctggcagga ctggtacggc gacaagaccc gcgagaccga actggtcaac  1200
tccgaagagt tcgacggcct ggacttccag ggcgctttcg aggcgctggc cgaacggttc  1260
gagcgcaagg cccagggaca gcgccgggtg aactaccgcc tgcgcgactg ggcgtgagc  1320
cgccagcgct actggggctg cccgattccg gtgatctact gcgacaagtg tggcgcggta  1380
ccggtgccgg aagaccagct gccggtggtg ctgccggaag acgtggcgtt cgccggtacc  1440
ggttcgccga tcaagaccga tccggaatgg cgcaagacca cctgcccgga ctgcggcggt  1500
gcggccgagc gtgagaccga caccttcgac accttcatgg agtcgagctg gtactacgcc  1560
cgctacacct cgccgggcgc ccgcgatgcg gtcgacaagc gcggcaacta ctggctgccg  1620
gtggaccagt acatcggtgg catcgaacac gcgatcctgc acctgatgta tttccgcttc  1680
taccacaagc tgctgcgcga cgcgcggatg gtggacagca acgaacccgc gcggaacctg  1740
ctgtgccagg gcatggtgat cgctgagacc tactaccgcc cgaacccgga cggctcgaag  1800
gactggatca acccggccga tgtggaagtg cagcgcgacg agcgcggccg catcaccggc  1860
gccaccctga tcgccgacgg tcagccggtg gtggtcggtg gtaccgagaa gatgtccaag  1920
tcgaagaaca acggcgtgga cccgcaggcg atggtcggca agtacggcgc cgataccgtg  1980
cgcctgttct cgatgttcgc tgcaccgccg gaacagtcgc tggaatggaa cgaagccggc  2040
gtggacggca tggcccgctt cctgcgccgc ctgtgggcac aggtgcagaa gcacgctgcc  2100
gagggtgccg caccggcgct cgacgcggcc gcgctggatg ccggccagaa ggccctgcgc  2160
cgcaagaccc acgagaccat cggcaaggtc ggcgacgact acggccgccg ccacagcttc  2220
aacaccgcca ttgccgcggt gatggagctg atgaacgcgc tggccaagtt cgaggacggc  2280
agtgaacagg ggcgcgccgt gcgccaggaa gcactgcagg ccatcgtgct gctgctcaac  2340
ccgatcaccc cgcatgccag ccacgccctg tggcaggtac tgggccatgg cgaaacgctg  2400
ctggaagatc agccgttccc gcaggccgac agcagtgcgc tggtgcgcga tgcgctgact  2460
ttggccgtgc aggtcaatgg caagctgcgt ggcaccatcg aggtcgccgc cgatgccgcg  2520
cgcgagcaga tcgaagcgct ggccctggcc gagccgaacg cggccaagtt cctggaaggc  2580
ctgacggtgc gcaagatcat catcgttccc ggcaagatcg tgaacatcgt cgctgcctga  2640
```

```
SEQ ID NO: 123          moltype = DNA  length = 2070
FEATURE                 Location/Qualifiers
source                  1..2070
                        mol_type = genomic DNA
                        organism = unidentified
                        note = DP70 Glycine--tRNA ligase beta subunit sequence
SEQUENCE: 123
atgtctaaac atacagtatt gttcgaattg ggctgtgaag aacttccacc taaaagcctc  60
aaaaaattac gtgatgcact gcatgctgaa acggtaaaag gcttaaaaga tgcaggctta  120
gcattcgact caatcgaagc ttatgcagca ccgcgtcgtt tggcacttaa aattgtgaat  180
atcgatggcg ctcagcctga tacacaaaaa cgctttgacg gccctgcaaa agaagcggct  240
tatgatgctg aaggcaaacc aagcaaagca ttagaaggct ttatgcgtgg tcaaggcatc  300
actgcggatc aagtcaccac gttccaagcg ggtaaagttg aaaaggtttg ctatttaaaa  360
gatgttaaag gtcaaagcct tgaggtttta ctgccacaaa ttctacaagc agctttggac  420
aatcttccaa ttgcaaaacg tatgcgttca gcggcaagcc gtactgaatt cgtgcgtcct  480
gtaaaatggg tggtgttgct caaagacaat gatgtgattg cagccactat tcaagatcac  540
aaagcaggca atgtgactta tggtcatcgt ttccatgccc ctgaagcgat tactttggct  600
catgcagatg aatatcttgc caagttaaaa gcggcttatg tggttgctga ctttgcagaa  660
cgccaagcca tcattgacca acaagtcaaa gcgttggctg atgaagttaa tgcgattgcg  720
attgtaccaa gcgacctgcg tgatgaagtg accgcattgg tggaatggcc tgttgcgcta  780
cgtgccagct ttgaggagcg tttccttgct gtaccgcaag aagctttgat taccacgatg  840
caagacaacc aaaaatactt ctgtttggtg aatagtgata acaagctaca gccttatttc  900
attactgttt caaatattga gtctaaagat ccgattcaaa ttattgaagg caatgaaaaa  960
gtggttcgtc cacgtttgtc ggatgctgaa ttcttcttct tgcaagatca aaagcaacca  1020
ctagcttctc gtaaagaaaa actggctaac atggtgttcc aagcacaatt gggtacgctg  1080
tgggataagt cacaacgtat tgcaaaattg gctgtggctt tatcgaacat cacgggtgca  1140
actgcggctg atgctgaaaa agcagcattg ctggcaaaat gtgacttaac ctctgaattg  1200
gtgggtgaat tccctgaact tcaaggcatt gcgggaacct attacgcacg cattgaaggt  1260
gaaaaccatg aagtggctga agctttaggc gaacagtatt tacctaaatt tgcaggcgat  1320
gttttaccgc aaacaaaaac aggcacaacc attgcccttg ccgaccgttt agacacgctc  1380
acgggtattt ttggtattgg tcaagcacct acaggttcta aagatccgtt tgcattacgt  1440
cgttctgcaa tcggtatttt acgtttggtg actgaaaaca atcttgatgt gtcgattgaa  1500
gatttaatcc agctggcatt aaacgcttat ggcgatgttg tagcggatca tgcgaagact  1560
ttagcggatg ctgttgcatt ccttgaaggt cgttaccgtg ccaagtatga agaccaaggc  1620
gttgcagttg atgtgattca agcggttcaa gcattatcac caaaatcacc tttagatttt  1680
gataagcgtg tgactgcggt aaatcatttc cgtgcattgc ctgaagctgc tgcactggct  1740
gctgcaaata agcgtgttgc caacattctt gccaaagaag cagaactaac aggcgcagtg  1800
gttgaagcaa acttggttga agaggctgaa aaagcattat tcgctgtact tgctaaaatt  1860
acgcctgaag ttgaaccatt atttgctgcc aaagattaca ccactgcatt gtctaagctt  1920
gctgctttac gtgcgcctgt ggatgcattc tttgaaggcg tcatggtcat ggcagatgat  1980
gcagaattga aagccaaccg tttacgttta ttggctcaat tacgtggttt gtttacaagt  2040
gttgcggata tttcggtgtt gcagcactaa                                  2070
```

```
SEQ ID NO: 124          moltype = DNA  length = 2472
FEATURE                 Location/Qualifiers
source                  1..2472
                        mol_type = genomic DNA
                        organism = unidentified
                        note = DP70 DNA gyrase subunit B sequence
SEQUENCE: 124
atgagttcag aagatcaagc tgcttctcaa acagaacaaa ccaatgaaaa ggcttatgat  60
tcctctagta tcaaagtatt acgtggccta gatgctgttc gtaagcgtcc gggtatgtat  120
attggtgata cggacgatgg ttcaggttta catcacatgg tgtttgaggt ggtcgataat  180
```

```
gcgattgatg aagccttagc gggtcactgt gatgaaatct tagtcaccat ccatgaagat  240
gagtctgtaa gtgttgcaga taacggtcgt gggattccaa cggatattca ccctgaagaa  300
ggggtatctg ccgctgaagt gattttaacc attttgcatg ctggcggtaa gtttgatgat  360
aatagctata aagtttccgg tggtttacac ggggtaggtg tttctgttgt aaatgccttg  420
tcgagtaaat tattactaaa tattcgtcgt gcaggaaaag tatatgaaca ggaatatcac  480
catggtgatc ctgtctatcc attacgcgcg attggtgata ctgaagaaac cggtaccacc  540
gttcgtttct atccgagtga attaaccttc tctcaaacga tttttaatgt tgatatttta  600
gcgcgtcgtt tgcgcgaact ttcattctta aatgcagggg ttcgtattgt attacgtgat  660
gaacgtatca atgctgaaca tgtatttgat tatgaaggtg gtttgtctga atttgtaaaa  720
tatatcaatc aaggtaaaac ccacttgaat gagattttc attttaccag tgaagttgtg  780
gaaacaggaa ttactgttga agtagcatta cagtggaatg atacttatca agaaaatgtc  840
cgttgcttta ccaataacat cccacaaaaa gatggtggta cgcatttagc cggtttccgt  900
gccgcgttaa cacggggttt aaaccagtat cttgatagtg aaaatattct taagaaagaa  960
aaagttgctg tcacaggtga tgatgcccgt gaaggtttaa cggcgattgt ttcagtgaaa  1020
gtgcctgatc caaaattctc atcacaaacc aaagaaaaat tggtttccag tgaagtgaaa  1080
actgctgtag agcaggcgat gaacaagtct ttttctgaat atcttttaga aaatccacaa  1140
gcggctaaat cgattgccgg caaaattatt gatgctgcac gtgcacgtga tgctgcgcgt  1200
aaagcacgtg aaatgacacg tcgtaagagt gcattagata ttgctggtct gcctggtaaa  1260
ctggcggatt gccaagaaaa agatccagca ttgtctgaac tttacttggt cgaaggtgac  1320
tcggcgggcg gttctgcaaa acagggtcgt aaccgtaaga tgcaagctat tctgccgctt  1380
aaaggtaaaa tcttaaacgt agaacgtgca cgttttgaca aaatgatttc atcgcaagaa  1440
gtgggcacgc tgattactgc actgggctgt ggtattggtc gtgaggaata caatcctgat  1500
aaattgcgtt atcacaaaat cattatcatg accgatgccg acgtcgatgg ttcgcacatt  1560
cgtacgctcc tgttgacctt cttcttccgt caaatgccag aacttgtgga acgtggttat  1620
atttatattg cacagccacc gttgtataag ttgaaaaaag gtaagcaaga gcaatatctt  1680
aaagataatg atgctttaga aacctatctt atttcgaatg ccattgatga gcttgaactg  1740
catattagtg ctgaggcacc tgcgattcgt ggtgaatctt tggctaaagt gattgctgat  1800
tatcaaacct cacaaaaaag tttaaatcgt ttaacgctac gttatcctgc aagcttgctg  1860
gatggtttac ttggtttgga tgcatttaaa cttgatcaaa atcatgatga agattatgta  1920
aaacaatggt ctgaacaatt gcgtgcagca attgaacaac accaaccaag tttgcgtcct  1980
gaaatcacct tagaagcttt tgaaaaagag catgcagatg gtgagaaagt gacgcattat  2040
tggccacgtg taacggtcta tgtacataac ttgccgcatc attatttact tgattctgga  2100
ttattggctt caagtgaata caagcgttta ctgcaaaatt cgaagagttg gttcacattg  2160
cttgaagatg gcgcttattt gcaaaaaggt gagcgtaaaa ttcatgtcgc cactttccat  2220
caagtttggc aacatatttt atccgactcg cgtcgtggca tgatgatcca gcgctataaa  2280
ggtttgggtg agatgaacgc ggaacagctt tgggaaacca ccatggatcc tgaaaaccgt  2340
aacatgttgc aagtcaccat taatgatgcg attgaagcgg atcgtatgtt ctcttgtttg  2400
atgggagatg atgtggaacc acgtcgtgcc ttcattgaag aaaatgcttt aaatgcggat  2460
attgacgctt aa                                                     2472

SEQ ID NO: 125          moltype = DNA  length = 2625
FEATURE                 Location/Qualifiers
source                  1..2625
                        mol_type = genomic DNA
                        organism = unidentified
                        note = DP70 Leucine--tRNA ligase sequence
SEQUENCE: 125
atgactactt ctcacattga ccctgaatat caagcgagcg cgattgaatc cactgtccaa  60
caagactggg aaactcgcaa agcctttaaa gttgccgaca ctgtagaagg taaacatcgt  120
tatatcctct cgatgttccc ttatccaagt ggcaagctgc atatgggtca tgtgcgtaac  180
tacaccattg gcgacgtgat tagccgtttc caccgtctca aggtgaaac tgtcctacaa  240
ccgatgggtt gggatgcttt tggtctgcct gcggaaaatg cagcgattgc acaccaagtt  300
gcccctgcaa aatggacctt tgaaaacatc gcgtacatgc gtgaccagtt aaaaaaattg  360
ggtctgtcag tcgattggga tcgtgaattt gcgacctgta cgccagagta ttatcactgg  420
gaacaatggt tatttgtaca gctgtataaa aaagggctga tttatcgcaa actttcaacg  480
gtaaactggg atcctgtcga tcagactgta cttgctaatg aacaagttga aaatggtcgt  540
ggttggcgtt cgggtgcatt ggttgaaaaa cgtgatattc caatgtatta cttccgtatt  600
accgattatg cacaagaatt attagacgat ttagattcgc ttaaagatgg ttggccgcaa  660
caagtcttga ccatgcaacg caactggatt ggtcgttcac aaggcatgga aatcaccttt  720
ccatctgcga accctgaaat ctatgcagat gatttaacgg tttataccac acgtggtgac  780
accttgatgg gcgtgacgta tgttgcggtt gccgctgaac atccaatggc gcttaaagcg  840
gctgaaacaa atcccgaatt ggctgcattt attgaagaat gccgtatggg ttcagtggct  900
gaagcagatc ttgccactgc cgagaaaaaa ggcatggcca ctggtttgtc tgtgaagcat  960
cctgtaacgg gtgaagtggt tccagtgtgg attgcgaact atgtattgat gtcatacggt  1020
tcaggtgcgg tgatggcagt tccagcacac gacgaacgtg atttcgaatt tgccaacaaa  1080
tatggtttaa ccctccagca agtgattgat gccaaaggtg cagacgatgc tgaattttct  1140
gcaactgaat ggcaggaatg gtatggctcg aaagaaggca aactggttaa ttctggcgaa  1200
tttgacggtt tagacttcca agctgcattt gatgcattca ttgcaaaatt agaaccacaa  1260
aaactggcaa atacgaaagt tcagttccgt ctacgtgact ggggtgtttc gcgtcagcgt  1320
tattggggtt gtccaattcc aatgatcaac tgtgaaactt gtggtcaagt acctgtacct  1380
gaagaacaac ttccagtaat tttaccaact gacgtggtgc cagatggttc aggcaatccg  1440
ttaaataaaa tgcctgaatt ttatgaaacc caatgtccat gttgtggtgc aggtgcacgc  1500
cgtgaaaccg atactttgga tacgttcgta gagtcatctt ggtactatgc acgttatgca  1560
tctccagatt tcactggcgg tttagttaaa cctgaagctg caaaatcatg gctaccagtc  1620
aaccaatata ttggcggtgt ggaacatgca attttgcatt tattgtatgc ccgtttcttc  1680
cataaattga tgcgtgatga aggcgtcgtt gaaggcaatg aaccctttcgc taacttactg  1740
actcaaggta tggttttagc tgataccttc taccgtgaag ccgaatcagg taagaaaaca  1800
tggtttaatc ctgcggatat tgaattagaa aaagacgaaa aaggtcgtgt tctttctgct  1860
aaatacacag gtgatggcca agaagttgtg gttggcggtc aagaaaaaat gtcgaaatcg  1920
```

-continued

```
aaaaataatg gcatcgaccc gcaatcgatt attgatcaat acggcgcaga tactgcacgt  1980
gtatttatga tgtttgcggc cccacccgat caatcgcttg aatggtctga tgccggtgtg  2040
gaaggtgcaa accgtttctt gaaacgtgta tggcgtttaa ccacaggttt cttagaaaaa  2100
ggcaaccatg ctgctgtaat tgatgttgcg aatttgtcat cagcggcaca agacttacgt  2160
cgtaaaaccc acgaaaccat tcaaaaagtc ggtgatgaca ttgaacgtcg tcatgccttc  2220
aatactgcca ttgcagcgca aatggaatta ttgaatgctt gcaataaatt tgaagccaaa  2280
gatgataatg acgttgcggt tgaacgcgat gctattgtta gcttactcac tttacttgca  2340
ccatttgcac cacatttaag tcagacccta ttggctcaat tcggtattga gttaactgaa  2400
accttgttcc ctactgtgga tgagtctgcg ctaacccgca acacacaaac tattgtggta  2460
caggtcaatg gtaaacttcg tggcaagttg gaagtgtctg ttgatctctc taaagaagat  2520
attttggatc aagccaaagc attgcctgaa gtacaacaat tcttaaccgg tccaaccaag  2580
aaagaaattg tggtgccgaa taaattggtc aatttggtgg tttaa                 2625

SEQ ID NO: 126          moltype = DNA  length = 1671
FEATURE                 Location/Qualifiers
source                  1..1671
                        mol_type = genomic DNA
                        organism = unidentified
                        note = DP70 Glucose-6-phosphate isomerase sequence
SEQUENCE: 126
atgaatagta ttgaaaaatt tcccttgcat gatacggatc tgattcagga aaaactaaaa  60
agttttgccc aacaagagca agagattaat ttaaattatt tatttaaaaa aaataaaaaa  120
cgttttgatg aatattccgt tcatgcgggt cagttatgtt ttgattatag taagcaccgt  180
gttgatgagc gtattattaa cgagcttatt tgttatgcgg aatcacaaca tttgggtaac  240
tggattcagc gcttattttc tttagaaaaa attaattaca ctgaaaatcg cgcagcgatg  300
cattgggctt tgcgtttgcc gaagcaagat agtacacatg cagatttggc agcgcaggta  360
catagtcagc ttgatcgtat gtatcaattg gtcgagaaaa ttcatcaggg gcagtatcga  420
ggagctacag gtgaggtcat ccatgatgtg gtcaatattg gtgtcggtgg atcagatctt  480
ggtcctttaa tggtgtctca agcgctgact gattttaaag ttcaaacggc tcaaaaatta  540
aaagtccatt ttgtttcgac gatggatggc agccaacttt cagatctttt acatcagttt  600
cgcccagaaa ccaccttgtt tattatttca tccaagtctt ttggcaccat tgatacgctt  660
tccaatgcac aaacggcaaa atgctggctt gagcaatctt taggaacgtc gaaatcagtt  720
ctaagatgtc actttgttgg tgtttcaacc aagcccgata agatgaccga gtggggaatc  780
agcactgaaa atcaattctt attgtgggat tgggtcggtg ggcgctattc actatggtcg  840
tgtattggtt tgcctattgc attaagtatt ggggtcgagg gctttaaaca gttgcttgct  900
ggtgcttatg aaatggatca gcattttcag aacacaccac ttgaacaaaa tattcctgtg  960
ttgatgggtt tactgggaat atggaataac aacttcctga atattcaaac tcatgcggta  1020
cttccttatg atggtcggct gaaatatttt gcggcttatt tacagcaatt ggaaatggag  1080
tcgaatggta agtcgattca gcgttctggt gaaaaagtcg tattagatac ctgcccaatt  1140
ttatggggtg aagttggacc aaatgcacaa catgcttttt atcagctgct gcatcaaggt  1200
acacatgctg tgagttgtga ctttattgca cctgtgaaac gctataatgc caatcaattt  1260
acctatgttg aaaatgcaga ggctttagtt gaacaacacc atttagcctt atcgaattgt  1320
ttggcacaat cacgtctatt ggcctttggt aatcatgttc tagatccgaa agaagtagaa  1380
agttcaccga aatataaaca atatgcaggc aaccaaccga ccacaacaat tttgttaaaa  1440
gagttgaatc cgcgcagttt aggtatgctc attgcgatgt atgagcacaa ggtatttgtg  1500
caatccgtga tgtggaatat taatccattt gaccaatggg gcgtagaaaa aggtaaagaa  1560
attgccaatc aactgttacc gattctcaat caagagcaag ctgatgtttc tgatcttgat  1620
tcttcaacgc aaggtctatt aagaatttta ctgggaaaag ctgatggcta a          1671

SEQ ID NO: 127          moltype = DNA  length = 1788
FEATURE                 Location/Qualifiers
source                  1..1788
                        mol_type = genomic DNA
                        organism = unidentified
                        note = DP70 NADH-quinone oxidoreductase subunit C/D sequence
SEQUENCE: 127
atggctgaaa ctgacattgc tatgccagaa tcaacgcctg ttgattcacg cccagcattt  60
gcaattgtag aagagctcaa agccaaattt ggtgagaact tctatgtgca agcgactttt  120
gaagattttc caacggtctg ggttgagcgc gcgcgcgtac aagatgtttt aatgttcttg  180
cgtaaagtat cacgtccata cgtgatgctg ttcgacttgt ctgcggtaga tgagcgttta  240
cgtacccacc gtgacggttt acctgcatca gacttcactg tgttttatca tttgttgtcg  300
ctagagcgca acagtgatat tcgtattaaa gttgcgttga gtgagagtga tctcaatctt  360
ccaaccgcaa ccaacatttg gccaaatgcc aactggtacg aacgtgaagc ttacgatatg  420
ttcgggatca atttcgaagg gcatccaatg ctccgtcgta ttttgttgcc aacctattgg  480
gaaggtcacc cactgcgtaa agaatattct gcacgtgcga ctgaatatac accgtatatg  540
cagaaccaag cgaagcagga tttcgagcaa gaacatttac gttttgttcc tgaagattgg  600
ggtctatcac gcggtaatgc cgatgaagat ttcatgttct tgaacttagg tccaaaccat  660
ccatctgcgc acggtgcatt ccgtatcatt ttgcagttgg acggtgaaga agtgaaagac  720
tgtgtgcctg atattggcta tcaccaccgt ggtgtggaaa agatggctga acgtcaaact  780
tggcattcat tcattccata taccgaccgt gttgactact tgggtggttg tgcgcaaaac  840
atgccttatg tgatgggtgt ggagcaaatg gcaggaatta ctgttcctga ccgtgcacaa  900
tgtatccgtg tcatgatgtc tgaattattc cgtatcaata accatttatt gtttattggt  960
actgcaattc aagatgccgg cggtatgacg ccagtcttct atatgtttgc cgatcgtcaa  1020
aagatctatg atgcgattga agcgattaca ggctaccgta tgcatccagc atggttccgt  1080
attggcggga ctgcgcacga ccttccaaac aattggcaac atctgattcg tgaaattctc  1140
gaatggatgc cgaagcgtat gaatgaatac tatacagctg cactacgcaa ctcagtattt  1200
attggtcgta cccgtaatgt tgcacaatac gatgcaaaat ctgcattggc ttggggtgta  1260
acaggtacag gtctacgcgc gacagggatt gatttcgacg tgcgtaaata ccgtccgtat  1320
agcggttatg aaaactacga cttcgacgtg cctttagaat acgaaggcga tgcttacgct  1380
```

```
cgtgtgatgg ttcacttccg tgaaattgaa gaatcactga aaattgtgaa gcagtgcttg  1440
gataacatgc catctggtcc atataaagcg gatcatcctt tggctgttcc accaccaaaa  1500
gacaagacat tacaagatat tgaaactttg attacgcact tcttgagcgt gtcatggggt  1560
cctgtgatgc ctgcgggtga agcgtctgta atggctgaag tggtaaaagg tgcatcgaac  1620
tactacttga cttcagacaa gtcaaccatg agttatcgta cccgtattcg tacaccaact  1680
ttcacgcact tacagcaaat gccttctgtg attaatggca gtcttgtatc tgacttgatc  1740
atttatttag cgaccattga cgtcgtaatg gctgacgtgg atcgctag              1788

SEQ ID NO: 128          moltype = DNA  length = 1044
FEATURE                 Location/Qualifiers
source                  1..1044
                        mol_type = genomic DNA
                        organism = unidentified
                        note = DP70 Protein RecA sequence
SEQUENCE: 128
atggatgata ataaaagtaa ggcgcttaat gctgccctaa gccagattga aaaacaattt  60
ggtaaaaata ccgtaatgcg tcttggtgat aataccgtat tggccgttga agcggtctct  120
acaggttctt taacactaga cattgcactt ggtattggtg gcttaccaaa aggtcgtatc  180
gttgaaattt acggtcctga atcttctggt aaaaccacaa tgacattgca agcgattgca  240
caatgtcaaa aagccggtgg tacttgtgct tttatcgatg cagaacatgc actcgatcct  300
cagtatgcac gtaagcttgg tgtcgacctt gacaacctgt tggtttctca accagaccac  360
ggtgaacaag cccttgaaat tgcagacatg ttagtccgct ctggtgctat tgacatgatc  420
gttgtcgatt ccgtggctgc actgacacct cgcgctgaaa ttgaaggtga aatgggcgac  480
tcacatatgg gcttacaagc acgtttgatg agtcaggcat tacgtaaaat tactggtaat  540
gcaaaacgct caaactgtat ggtgatcttc attaaccaaa tccgtatgaa gattggtgta  600
atgtttggta gccctgaaac cacaacaggt ggtaatgcac tcaaattcta cgcttctgta  660
cgtttggata tccgtcgtat tggtcaagtg aaagaaggcg atgaaattgt cggttcagaa  720
acccgcgtta aagtcgtaaa aaataaaatg gcacctcctt ttaaggaagc gttattccaa  780
attttatatg gcaaaggtgt caatcaactg ggtgaactgg ttgatcttgc tgttgcgcaa  840
gaactggtac aaaaagcagg tgcttggtat tcatatcaag gcaataaaat tggtcaaggt  900
aaaaacaacg tgatccgcca tttagaggaa aatcctcaaa ttgcacaaga acttgatcgc  960
ctgattcgtg aaaaattgtt gacaccaacg accacgccta ttgaagaaaa agatgaagta  1020
gaaccagact ttctagatgc ttaa                                        1044

SEQ ID NO: 129          moltype = DNA  length = 1887
FEATURE                 Location/Qualifiers
source                  1..1887
                        mol_type = genomic DNA
                        organism = unidentified
                        note = DP70 RNA polymerase sigma factor RpoD sequence
SEQUENCE: 129
atgagcgata tgacttcccc tacttcgcaa gtagcggctc tgattagccg aggcaaagag  60
caaggttact taacttacgc tgaggttaac gatcatctcc cagactcgat cacggaaagc  120
gaacagattg aagacattat tcaaatgctt caagatgtcg gcattccagt gcatgaacgt  180
gcgcctgaat ctgatgacac catgttcgac ggtaacaatg cagaagcaac cgatgaagtc  240
gctgaagaag aagcggcagc tgttcttgct tcagttgaaa gcgaacctgg tcgtaccacc  300
gatccagtac gtatgtacat gcgtgaaatg ggaacggttg aactattaac gcgtgaaggc  360
gaaattagca ttgcaaaacg cattgaagaa ggtattcgtg acgttcttca ttcgattgcg  420
tactggccaa atgcagttga agttgtatta aaagaatata gcgatgttgc tgaaggcgaa  480
cgtcgtcttg ctgatatttt atctggttat ttagacccag aatctgacga agaaattcca  540
gaagttttag aagaagaagc tgaaattgtt gaagatgatg aagcgacgac taaaaccact  600
aaagatgtaa aattggacga tgacgaagaa gaagaatctg aaagtgatga tgattctgaa  660
ggtgagtctg gtccagatcc agaaattgca cgtgttcgtt tcactgaatt agaagatgcg  720
tggaaagtaa ccaaagccac cattgaaaag catggccgta acagcaaaca agcagatgaa  780
gcgcttgaag ctcttgcaac tgtgtttatg atgttcaaat ttacaccacg tttatttgaa  840
atcatttcag aaatgattcg tggcacgcat gaacaaattc gtacagcaga acgtgaagtg  900
atgcgttacg cagttcgtcg tggtcgtatg gaccgtaccc aattccgtac atcgttccca  960
ggccaagagt caaatccagc ttggttagat gaacaaattg ctaaagcacc tgcggatcaa  1020
aaaggttatt tagaaaaagt acgtccagat gttgttgcat tccagcaaaa gattgccgat  1080
atcgaaaaag aattgggctt agatgttaaa gacatcaaag acatttctaa acgtatggct  1140
gtgggtgaag cgaaagcacg tcgcgcgaaa aaagaaatgg ttgaagcaaa cttacgtttg  1200
gtgatttcga ttgcgaaaaa atataccaac cgtggtttac aattccttga cttgattcaa  1260
gaaggtaaca tcggtttgat gaaagccgta gacaagtttg aataccgtcg tggttataaa  1320
ttctcgactt atgcaacttg gtggattcgt caggcgatta cccgttcgat tgccgatcaa  1380
gcacgtacca tccgtattcc agtacacatg atcgaaacca ttaacaagat caaccgtgta  1440
tctcgtcaac ttcttcaaga aatgggccgt gagcctaccc ctgaagaatt aggcgaacgt  1500
ctggaaatgg acgaagttaa agtacgtaaa gtgctgaaaa ttgccaaaga accgatttcg  1560
atggaaacac cgattggtga tgacgaagat tcgcatcttg gtgacttcat tgaagatggt  1620
aacattacct ctccaattga tgccgcgact tctgaaggct taaaagaagc aacacgtgaa  1680
gtgctggaaa acttgaccga acgtgaagcg aaagtcttaa aaatgcgttt tggtattgat  1740
atgccaaccg accatacttt agaagaagtg ggtaaacaat ttgatgtaac acgtgaacgt  1800
attcgtcaga ttgaagccaa agctttacgt aaattacgtc acccttctcg ttctgaacac  1860
ttacgttcat tcctagaaaa tgactaa                                     1887

SEQ ID NO: 130          moltype = DNA  length = 1671
FEATURE                 Location/Qualifiers
source                  1..1671
                        mol_type = genomic DNA
                        organism = unidentified
```

note = DP71 Glutamine--tRNA ligase sequence
SEQUENCE: 130
```
atgagtgagg ctgaagcccg cccaacaaat tttatccgtc agattattga tgaagatctg  60
gcgaccggga aacacaatac cgttcacacc cgtttcccgc ctgagcctaa tggctatttg  120
catatcggcc atgcgaagtc tatctgcctg aatttcggca ttgcgcaaga ctaccagggt  180
cagtgcaatc tgcgttttga cgatactaac ccggcaaaag aagacatcga attcgttgag  240
tcgatcaaat acgacgtcca gtggctgggc ttcgactgga gcggtgatat tcactactcc  300
tcagactatt tcgatcaact gcacgcatac gcgctggagc taatcaacaa aggtctggcg  360
tacgttgacg aactgtctcc cgatcaaatt cgcgaatacc gtggttcgct gaccgcaccg  420
ggcaaaaaca gcccgtatcg cgatcgcagc gtggaagaaa atatcgcgct gtttgaaaaa  480
atgcgtaacg gtgaattcgc cgaaggtgcc gcttgcctgc gtgccaaaat cgatatggcg  540
tcgccattct tcgtgatgcg cgatccggtc atctaccgta ttaagtttgc cgaacatcat  600
cagactggca caaaatggtg catctacccg atgtacgatt tcactcactg catttccgat  660
gcgctggaag ggatcaccca ttcactgtgt acgctggaat tccaggacaa ccgccgtctg  720
tacgactggg tactggataa catcactatt ccatgccatc cgcgtcagta tgagttctcc  780
cgtctgaatc ttgaatactc catcatgtcc aagcgtaagc tgaacctgct ggtgacggat  840
aagattgtag aaggttggga cgatccgcgt atgccgacgg tttccggtct gcgtcgccgt  900
ggttataccg ccgcgtctat ccgcgaattc tgccgtcgta tcggcgtgac caagcaggac  960
aacaacgttg aaatgatggc gctggaatcc tgtattcgtg acgatctgaa cgaaaacgca  1020
ccgcgcgcca tggccgttat taacccggtt aaagttgtca ttgagaactt caccggtgat  1080
gacgtgcaaa tggtgaaaat gccgaatcat ccgagcaaac cggaaatggg cacccgcgaa  1140
gtgccgttca cccgtgagat ttacatcgat caggctgatt tccgcgaaga agcgaacaaa  1200
cagtacaaac gtctggtgct gggcaaagaa gttcgcctgc gcaatgcgta tgtgatcaaa  1260
gcggaacaca tcgagaaaga cgcggaaggg aatatcacca ccatcttctg ttcttacgat  1320
atcgatacgc tgagcaaaga tcccgctgat ggccgtaagg tgaaaggcgt gattcactgg  1380
gtttctgctt ctgaaggtaa accggcagaa tttcgcctgt atgaccgtct gttcagtgtt  1440
gcgaaccctg gccaggctga agatttcctg accaccatca acccggaatc tctggtgatt  1500
gctcagggct tcgttgagcc gtctctggtc gctgctcagg cagaagtcag tgtgcagttc  1560
gaacgtgaag gttacttctg tgccgacagc cgctattcaa gtgctgagca tctggtgttc  1620
aaccgcaccg tcggccttcg cgacacctgg gaaagcaaac ccgtcgcctg a           1671
```

SEQ ID NO: 131 moltype = DNA length = 2415
FEATURE Location/Qualifiers
source 1..2415
mol_type = genomic DNA
organism = unidentified
note = DP71 DNA gyrase subunit B sequence
SEQUENCE: 131
```
atgtcgaatt cttatgactc ctcaagtatc aaggtattaa aagggctgga cgcggtgcgt  60
aagcgccccg gcatgtatat cggcgatacc gatgacggca ctggtctgca ccacatggta  120
ttcgaggttg tggacaacgc tatcgacgaa gccctcgcgg gccactgtaa agagattcag  180
gtcacgatcc atgcggataa ctctgtttcc gtacaggatg atggtcgtgg tattcctacc  240
ggcattcacg aagaagaggg cgtttctgct gctcaggtca tcatgaccgt acttcatgcc  300
ggcggtaaat ttgacgataa ctcgtacaaa gtctccggcg gtctgcatgg cgtgggtgtt  360
tccgtcgtta acgccctgtc ggaaaaactg gagctggtta tccgccgtga aggcaaagtg  420
cacacccaga cttacgtcca cggtgagccg caggatccgc tgaaagtggt tggcgatacc  480
gaggcgaccg gtacgaccgt gcgcttctgg ccaagctacg ccaccttcac caatcaaaca  540
gaattcgagt atgacattct ggcgaaacgc ctccgtgagc tgtcattcct gaactctggt  600
gtggcgatcc gcctgctcga caaacgcgat ggcaagaacg atcacttcca ttatgaaggc  660
ggtatcaaag ctttcgtgga atacctgaac aaaaacaaaa ccccaatcca cccaaccgtg  720
ttctatttct ccaccgtgaa agacgatatc ggtgtggaag tggcgttgca gtggaatgat  780
ggtttccagg aaaatattta ctgctttacc aacaatatcc ctcagcgcga cggcggcacc  840
catctggtag gcttccgttc tgcgatgacc cgtacgctta acgcgtatat ggataaagaa  900
ggctacagca agaaatccaa aatcagcgcc accggtgatg atgcccgtga aggcctgatc  960
gccgtggttt cggtaaaagt gccggatcct aagttctcct ctcagaccaa agacaaactg  1020
gtttcttccg aagtgaagac cgccgttgag tctctgatga acgagaagct ggttgattat  1080
ctgatggaaa acccggccga cgcgaaaatc gttgtcggta aaatcatcga tgcagcccgt  1140
gcgcgtgaag ccgcgcgtaa agcacgtgaa atgacccgtc gtaaaggcgc gctcgatctg  1200
gccggtctgc caggcaaact ggctgactgt caggaacgcg acccggcaca ttccgaactg  1260
tacttagtgg aaggggactc agcgggcggc tctgcaaaac aaggccgtaa ccgtaagaac  1320
caggcgattc tgccgttgaa agggaaaatc ctcaacgttg agaaagcgcg cttcgacaaa  1380
atgctctctt ctcaggaagt ggcgacgctg attaccgcgc tcggttgcgg tatcggccgt  1440
gacgaataca acccggataa actgcgttat cacagcatca tcatcatgac cgatgccgac  1500
gtcgatggtt cgcacatccg taccctgtta ctgacattct tctaccgtca gatgcctgaa  1560
attgtagagc gtggccacgt gtttatcgcg cagcctccgc tgtacaaagt gaaaaaaggc  1620
aaacaggaac agtacattaa agatgatgaa gcgatggatc agtatcaaat ctctatcgcg  1680
atggacgggg caacgttaca cgccaacgcc catgcaccag cactggcggg cgaaccgctg  1740
gagaaactgg tggctgaaca tcacagcgtg cagaaaatga ttggccgtat ggaacgtcgt  1800
tatccgcgtg cgctgctgaa taatctggtc tatcagccaa cgctggcggg tgctgaactt  1860
gccgacgaag cgaaagtgaa ggaatggatt gaaacgctgg tgtctcgtct gaacgagaaa  1920
gagcagcacg gcagcagcta cagtgcgatc gtgcgcgaaa atcttgaaca ccagctgttc  1980
gagccaatcc tgcgcattcg tactcacggt gtggataccg actacgatct cgatgcagac  2040
ttcattcagg gcggcgaata ccgcaaaatc tgtaccctgg gtgaaaaact gcgcggcctg  2100
atcgaagaag atgcttacat cgaacgtggc gaacgccgtc agccagtgac cagcttcgag  2160
caggcgctgg aatggctggt gaaagagtcg cgtcgcggtc tgtcgattca gcgttataaa  2220
ggtctgggtg aaatgaaccc tgagcaattg tgggaaacca cgatggatcc gacacaacgc  2280
cgcatgctgc gcgtgacggt gaaagatgct atcgcggcgg accagctgtt caccacgctg  2340
atgggcgatg cggttgaacc gcgccgcgcc ttcatcgaag agaacgccct taaagctgcc  2400
aatatcgata tctga                                                   2415
```

```
SEQ ID NO: 132          moltype = DNA  length = 2817
FEATURE                 Location/Qualifiers
source                  1..2817
                        mol_type = genomic DNA
                        organism = unidentified
                        note = DP71 Isoleucine--tRNA ligase sequence
SEQUENCE: 132
atgagtgact acaagaacac cctgaatttg ccggaaacag ggttcccgat gcgtggcgat  60
ctggccaagc gtgaacctga catgctgaag aattggtatg accaggatct gtacgggatt  120
attcgtgctg ccaagaaagg caagaaaacc tttatcttgc atgacggccc tccgtatgcg  180
aacggcagca ttcatattgg tcactcagta aacaaaattc ttaaagacat gatcgttaag  240
tccaaaggac tggcgggctt tgatgcgccg tatgttccgg gctgggattg tcatggtctg  300
ccgattgaac tgaaagttga acagctgatc ggtaagccgg gcgaaaaagt cacggcggcg  360
gaattccgtg aagcctgccg caagtacgct gctgaacagg ttgaaggtca gaagaaagac  420
ttcatccgtc tgggcgtgct cggtgactgg gatcatccgt acctgaccat ggacttcaaa  480
acagaagcca acatcattcg tgccctgggt aaaatcatcg gcaacggtca cctgcataaa  540
ggtgcgaaac ctgttcactg gtgtaccgat tgcggatctt cactggctga agccgaagtc  600
gaatattacg acaaagtgtc tccgtctatc gacgtgacgt ttaatgcgac ggatgccgcc  660
gctgttgctg cgaaattcgg tgccactgct ttcaatggcc cggtttctct ggtcatctgg  720
accaccaccc cgtggaccat gccagctaac cgcgcgattt cactcaacgc tgagttctct  780
tatcagctgg tgcagattga aggtcagtgc ctgatcctgg ctaccgatct ggtagaaagc  840
gtgatgaatc gcgccggtat cgctgagtgg actgtgctgg gcgaatgtaa aggtgcggat  900
cttgaattgc ttcgattcca gcatccgttc ctcggtttcg atgttccggc gatcctcggc  960
gatcacgtta ctctcgatgc cggtaccggt gctgtacata ccgcacctgg ccacggtcct  1020
gatgactttg tcattggcca gaaatacggt ctggaagtcg caaacccggt tggaccgaac  1080
ggctgctacc tgccgggcac ttatccgacg ctggatggca aattcgtctt taaagcgaat  1140
gatctgatcg ttgaattgct gcgtgagaag ggcgcactgc tgcacgttga gaaaatgaac  1200
cacagctatc cgtgctgctg gcgtcacaaa acgccgatca tcttccgcgc tacgccacaa  1260
tggttcatca gcatggatca gaaaggtttg cgtcagaagt ctctggaaga gatcaaaggc  1320
gtgcagtgga tccctgactg gggtcaggcg cgtatcgaaa acatggtcgc taaccgtcct  1380
gactggtgta tctcccgcca gcgtacgtgg ggcgtaccga tgtctctgtt cgtgcataaa  1440
gataccgaac agcttcatcc gcgcagcctt gagctgatgg aagaagtggc aaaacgcgtg  1500
gaagccgatg gcattcaggc atggtgggat ctgaaccctg aagagatttt gggtgcagac  1560
gctgccgatt acgtcaaagt gccggatacg ctggacgtct ggtttgactc cggttccacg  1620
cactcctccg ttgtggatgt gcgccctgag ttcaacggtc attcaccgga tctgtatctg  1680
gaaggttctg accagcatcg cggctggttc atgtcttctc tgatgatttc tacggcgatg  1740
aaaggcaaag cgccttacaa acaagtactg actcacggtt tcaccgtcga tggtcagggc  1800
cgtaaaatgt ctaaatccat cggtaacacc atcgcgcctc aggatgtgat gaataagctg  1860
ggtggcgaca tcctgcgttt gtgggtggca tctacggatt acaccggcga aatcgccgtg  1920
tccgacgaaa tcctcaaacg tgctgccgat tcttatcgcc gtatccgtaa caccgcgcgc  1980
ttcctgctgg cgaaccttaa cggtttcgat ccggcgctgc acagcgtggc accggaagag  2040
atggttgtgc tggatcgctg ggcggttggc cgcgcgaaag ctgcacaaga cgagatcatt  2100
gctgcgtacg aagcctatga tttccacggc gttgttcagc gtctgatgca gttctgctcg  2160
atcgaaatgg gttcgttcta tctggatatc attaaagatc gccagtacac cgcgaagagc  2220
gacagcgttg cgcgccgcag ctgccagacc gcgctgtatc acatctgcga agcactggtt  2280
cgctggatgg cgccaatcat gtccttcact gccgatgaaa tctgggctga actgccaggt  2340
catcgcgaga agttcgtctt tactgaagaa tggtacgacg gtctgtttgg cctgatcggt  2400
aacgaatcca tgaacgatgc gttctgggat gagctgctga aagtgcgtgg tgaagtgaac  2460
aaagtgatcg aacaggcgcg tgctgataaa cgtctgggcg gttctctgga agcagccgtg  2520
accttatatg cagacgacgc gctggcaaca gacctgcgtt ctctgggtaa cgaactgcgc  2580
tttgtgctcc tgacttccgg tgcgaaagtc gccgcgctgt ctgaagctga tgactcagcg  2640
caggccagcg aattgttgaa aggactgaaa attggtctgg cgaaagcaga aggcgagaag  2700
tgcccgcgct gctggcattt caccactgat atcggccaga atgcggaaca cagtgacatc  2760
tgtggccgtt gtgtgactaa cattgccggt gacggcgaag agcgtaagtt tgcataa     2817

SEQ ID NO: 133          moltype = DNA  length = 1560
FEATURE                 Location/Qualifiers
source                  1..1560
                        mol_type = genomic DNA
                        organism = unidentified
                        note = DP71 NADH-quinone oxidoreductase subunit C/D sequence
SEQUENCE: 133
atgtcagaac ttactcatat taatgcttcc ggcgacgccc acatggtgga tgtctccggt  60
aaagacgaca ccgttcgtga agcccgtgcc gaagcctttg ttgaaatggc cgaaagcacg  120
ctggcgatga tcatcggcgg taatcaccat aagggtgacg tgttcgcgac cgcgcggatt  180
gccggtattc aggcagcgaa gaaaacctgg gatctgatcc cgctgtgtca tccgctgttg  240
ctgaccaagg tggaagtgaa tcttgaagcg cagccagaat ttaatcgtgt acgtattgaa  300
tcccgctgcc gcctgagcgg taaaaccggc gtcgagatgg aagcgctgac cttcaagcct  360
gaagactggg gaatgaagcg cggcaccgaa aacgaggact tcatgttcct caacctcgga  420
cctaaccatc cgtctgcgca cggtgcgttc cgcatcatcc tgcagcttga tggcgaagaa  480
attgtcgact gtgtaccgga cgtcggttac caccaccgtg gtgctgagaa gatgggcgag  540
cgccagtcat ggcacagcta cattccatac acggaccgta tcgaatacct cggcggttgc  600
gttaacgaga tgccatacgt actggctgtt gaaaaactgg cgggtatcgt cgtgccggat  660
cgcgttaaca ccatccgcgt gatgctgtct gaactgttcc gtatcaacag ccacctgctg  720
tacatctcta cgtttattca ggacgtgggc gcgatgacgc cagtgttctt cgcctttacc  780
gatcgtcaga aaatttacga tctggtggaa gcgatcaccg gtttccgtat gcacccggcc  840
tggttccgta ttggtggcgt tgcacacgac ctgccgaaag gctgggagcg tctgctgcgt  900
gaattccttg actggatgcc agcccgtctg gattcctacg tcaaggcagc gctgaaaaac  960
```

```
accattctga ttggacgttc caaaggcgta gcagcataca acgccgatga tgcgctggcg  1020
tggggcacca ccggtgctgg cctgcgtgcg accgggatcg acttcgatgt ccgcaaatgg  1080
cgtccatatt caggttacga aaacttcgat tttgaagtgc cggtcggcga tggcgtcagt  1140
gattgctatt cccgcgtgat gctaaaagtg gaagagcttc gtcagagcct gcgcattctg  1200
gaacagtgct acaaaaacat gccggaaggc ccgttcaagg cggatcaccc gctgaccacg  1260
ccgccaccga aagagcgtac gctgcaacac atcgaaaccc tgatcactca cttcctgcaa  1320
gtgtcgtggg gtccgatcat gcctgcgcaa gaatctttcc agatggttga agccaccaaa  1380
gggatcaaca gctactacct gaccagtgac ggcagcacca tgagctaccg cacgcgcgtc  1440
cgtacgccaa gcttcccgca tttgcagcag atcccgtccg taatccgtgg cagcctggta  1500
tccgacctga tcgtgtatct gggcagtatc gattttgtaa tgtcagatgt ggaccgctaa  1560

SEQ ID NO: 134         moltype = DNA  length = 1065
FEATURE                Location/Qualifiers
source                 1..1065
                       mol_type = genomic DNA
                       organism = unidentified
                       note = DP71 Protein RecA sequence
SEQUENCE: 134
atggctattg atgagaacaa gcaaaaagcg ttagctgcag cactgggcca gattgaaaag  60
caattcggta aaggctccat catgcgtctg ggtgaagatc gctctatgga cgtggaaacg  120
atctctaccg gctctttgtc tctggatatc gcgttaggcg ccggtggttt gccgatgggc  180
cgtatcgttg agatttatgg cccggaatcc tccggtaaaa ctacgctgac ccttcaggtt  240
attgctgccg cacagcgcga aggcaaaacc tgtgcgttca tcgatgcgga acatgcactt  300
gaccctatct acgcgaagaa attgggcgta gatatcgaca acctgttgtg ttctcagccg  360
gataccggcg aacaggctct ggaaatctgt gacgcgctga cccgttcagg cgcggtcgac  420
gttatcatcg tcgactccgt tgctgcactg acgccaaaag cagaaatcga aggcgaaatc  480
ggtgactctc acatgggcct tgcggcacgt atgatgagcc aggcaatgcg taagcttgcc  540
ggtaacctga aaaacgccaa caccttgctg atcttcatca accagatccg tatgaaaatc  600
ggtgtgatgt tcggtaaccc ggaaaccacc accggtggta acgccctgaa attctacgcc  660
tctgtgcgtc tggatatccg ccgcatcggc gctatcaaag aaggcgacgt ggtgatcggc  720
agtgaaacgc gcgtgaaagt tgtgaagaac aaaatcgctg cgcctttcaa acaggctgaa  780
ttccagatcc tatacggcga aggcatcaac attaacggcg agctgatcga tttgggcgtt  840
aagcacaaac tggtcgaaaa agccggtgca tggtacagct acaacggcga gaagattggt  900
cagggtaaat ctaactcctg caactatctg aaagaaaacc cgaaaatcgc tgctgaactg  960
gataaaaaac tgcgtgatat gttgttgagt ggcactggtg aactggccgc tgcaaccaca  1020
gcagaacttg cagacgacga tatggaaacc agcgaagagt tttaa                 1065

SEQ ID NO: 135         moltype = DNA  length = 1794
FEATURE                Location/Qualifiers
source                 1..1794
                       mol_type = genomic DNA
                       organism = unidentified
                       note = DP71 RNA polymerase sigma factor RpoD sequence
SEQUENCE: 135
ggtaaggagc aaggctatct gacctttgct gaggtcaatg accatctgcc ggaagatatc  60
gtcgactccg accagatcga agacatcatc cagatgatta acgacatggg catccaggtt  120
cttgaagaag cgccggacgc cgatgatttg atgctggccg aaaaccgccc tgataccgat  180
gaagatgctg cagaagcagc ggctcaggtg ctttccagcg ttgaatctga aattggccgt  240
accaccgacc ctgtgcgtat gtatatgcgc gaaatgggta ccgttgagct cctgacccgt  300
gaaggcgaaa tcgacatcgc caaacgtatc gaagacggta tcaatcaggt ccagtgctcc  360
gttgctgaat atcctgaagc tatcacctat ttgttagagc aatatgaccg tgttgaagca  420
ggcgaagcac gtctgtctga tttgatcacc ggttttgttg atccgaacgc cgaagaagaa  480
atcgcgccga ctgcgactca cgtgggttct gaactgacca ctgaagagca aaatgatacc  540
gacgacgatg aagaagacga cgacgatgct gaagacgaca acagcatcga cccggaactg  600
gcgcgtcaga agttcaccga tctgcgtgag caacatgaag cgacccgtgc cgtcatcaag  660
aaaaatggcc gtagccacaa aagcgccgca gaagaaattc tgaagctgtc cgatgtgttt  720
aaacagttcc gtctggtacc aaaacagttc gatttcctgg tgaacagcat gcgctccatg  780
atggatcgcg tccgtactca ggaacgtctg atcatgaaag tgtgcgttga acagtgcaaa  840
atgccgaaga aaaacttcgt caatctgttc gccggtaacg aaaccagcag tacctggttt  900
gatgctgctc tggcaatggg taaaccatgg tctgagaagc tgaaagaagt gaccgaagac  960
gtgcagcgcg gcctgatgaa actgcgccaa atcgaagaag aaactggcct gactatcgaa  1020
caggtaaaag acattaaccg tcgcatgtcg atcggcgaag cgaaagcacg ccgcgcgaag  1080
aaagagatgg ttgaagcgaa cttacgtctg gttatctcta tcgcgaagaa atacaccaac  1140
cgtggcttgc agttccttga cctgattcag gaaggtaaca tcggcctgat gaaagccgtt  1200
gataagtttg aatatcgccg tggttataag ttctctactt atgcgacctg gtggatccgt  1260
caggctatca cccgctccat cgccgaccag gcacgtacca tccgtattcc ggtgcatatg  1320
attgagacca tcaacaaact caaccgtatt tcgcgccaga tgttgcagga gatgggccgt  1380
gagccgacgc cggaagagct ggctgaacgc atgctgatgc cggaagacaa gatccgtaaa  1440
gtgctgaaaa ttgctaaaga gccaatctcc atggaaacgc caatcggcga cgatgaagat  1500
tcgcatctgg gtgatttcat cgaggatact accctcgagc tgccgctgga ttctgcgacc  1560
tctgaaagcc tgcgttctgc aacgcacgac gttctggctg gcctgaccgc acgtgaagcg  1620
aaagttctgc gtatgcgttt cggtatcgat atgaacactg accacactct ggaagaagtg  1680
ggcaaacagt tcgacgtaac ccgtgaacgt atccgtcaga tcgaagccaa agcgttgcgt  1740
aaactacgcc acccaagccg ctccgaagtg ctgcgcagct tcctcgacga ctag        1794

SEQ ID NO: 136         moltype = DNA  length = 2487
FEATURE                Location/Qualifiers
source                 1..2487
                       mol_type = genomic DNA
```

```
                         organism = unidentified
                         note = DP71 DNA-directed RNA polymerase subunit beta
                          sequence
SEQUENCE: 136
atggaccaga acaacccgtt gtctgagatc acgcacaaac gtcgtatctc tgcactgggc  60
ccgggcggtt tgacccgtga acgtgctggc tttgaagttc gagacgtaca cccgacgcac  120
tacggtcgcg tatgtccaat cgaaacgcca gaaggtccaa acatcggtct gatcaactca  180
ttatctgtct atgcacagac aaatgagtat ggtttcctgg aaacccctta ccgccgtgtg  240
cgtgaaggta tggttaccga tgaaattaac tacctgtctg ccatcgaaga aggcaacttt  300
gttatcgctc aggcgaactc caacctggat gacgaaggcc acttcctgga agatttagtc  360
acttgtcgta gcaaaggcga atcaagcctg ttcagccgcg accaggttga ctacatggac  420
gtttctaccc agcagatcgt atccgttggt gcttcactga ttccattcct ggaacacgat  480
gacgccaacc gtgcattgat gggtgcgaac atgcaacgtc aggcagttcc tactctgcgt  540
gctgataagc cgctggtagg tactggtatg gaacgtgctg ttgcggttga ctccggtgtt  600
actgccgttg ccaaacgtgg tggtactgtt cagtacgtag atgcatcccg tatcgttatt  660
cgtgttaacg aagaagagat gaatccaggc gaagcaggta tcgacattta taacctgact  720
aagtacaccc gttctaacca gaacacctgc atcaaccaga tgccgtgtgt gaatctgggc  780
gagccaatcg agcgcggcga cgtgctggca gatggtccgt caacagatct gggcgaactg  840
gcactgggtc agaacatgcg tgtcgcgttc atgccttgga acggttacaa cttcgaagac  900
tccatcttgg tctccgaacg tgttgtgcag gaagatcgct tcacgaccat ccatatccag  960
gaactggcat gtgtgtcccg tgacacaaag ttagggcctg aagagatcac tgctgatatc  1020
cctaacgtgg gtgaagctgc gctctccaaa ctggatgagt ccggtattgt gtatatcggt  1080
gctgaagtga ccggtggtga cattctggtc ggtaaagtta cgcctaaagg cgaaacccag  1140
ctgactccag aagagaaact gctgcgtgcg atcttcggtg agaaagcgtc tgacgttaaa  1200
gattcttctc tgcgtgtacc aaacggcgtt tccggtacga ttattgacgt gcaagtcttt  1260
acccgcgatg gcgtggaaaa agataagcgt gcgttagaaa tcgaagaaat gcagctgaaa  1320
caggctaaga aagacctgac tgaagagctg caaattctgg aagctggtct gtttgcacgt  1380
atccagtccg cgctggttgc tggcggtgtt gaagccgata agctgggcaa attgccacgc  1440
gatcgttggc ttgaactgtc actgactgac gaagacaaac agaatcagtt ggaacagctt  1500
gctgaacagt acgacgaact gaaatccgag tttgagaaaa aactcgaagc taaacgtcgt  1560
aaaatcactc agggcgatga cctagcacca ggtgtgctga aaatcgttaa agtgtacctg  1620
gccgttaaac gtcagatcca acctggtgac aaaatggcag gccgccacgg taacaaaggt  1680
gttatctcca agatcaaccc gatcgaagat atgccttacg atgaaaacgg gactcctgtt  1740
gacatcgtac tgaacccgct gggcgttcca tcacgtatga acattggtca gattttagaa  1800
acccacctgg gtatggccgc gaaaggtatt ggtgaaaaaa tcaatgccat gcttaagaaa  1860
catgaagaag tttctaagct gcgcgagttc atccagcgtg cctatgatct gggcgacgac  1920
gtacgtcaga aagttgatct gaccaccttc accgatgatg aagtattgcg tttggctgaa  1980
aacctgaaaa agggtatgcc aattgcaaca ccagtcttcg acggtgcgaa agagacagag  2040
atcaagcaac tgcttgaaat gggcggcgtc ccaacctctg gccagatcac actgtttgac  2100
ggccgtaccg gcgagcaatt cgagcgccag gttaccgtcg gctacatgta catgctgaaa  2160
ctgaaccacc tggttgacga taagatgcat gcgcgttcta ccggttctta cagccttgtt  2220
actcagcagc cgctgggtgg taaagctcag ttcggtggtc agcgcttcgg tgagatggaa  2280
gtgtgggcac tggaagcata cggtgccgct tataccctgc aggaaatgct gactgttaag  2340
tccgatgacg tgaacggccg tactaagatg tataaaaaca tcgtagatgg cgatcaccgg  2400
atggaaccag gcatgccgga atcattcaac gtactgttga aagaaatccg ctctctgggt  2460
atcaacatcg agctggaaga cgagtaa                                  2487

SEQ ID NO: 137           moltype = RNA  length = 1547
FEATURE                  Location/Qualifiers
source                   1..1547
                         mol_type = rRNA
                         organism = unidentified
                         note = DP72 16S rRNA sequence
SEQUENCE: 137
ttcggagagt ttgatcctgg ctcaggacga acgctggcgg cgtgcctaat acatgcaagt  60
cgagcggaca gaagggagct tgctcccgga tgttagcggc ggacgggtga gtaacacgtg  120
ggtaacctgc ctgtaagact gggataactc cgggaaaccg gagctaatac cggatagttc  180
cttgaaccgc atggttcaag gatgaaagac ggtttcggct gtcacttaca gatggacccg  240
cggcgcatta gctagttggt ggggtaatgg ctcaccaagg cgacgatgcg tagccgacct  300
gagagggtga tcggccacac tgggactgag acacggccca gactcctacg ggaggcagca  360
gtagggaatc ttccgcaatg gacgaaagtc tgacggagca acgccgcgtg agtgatgaag  420
gttttcggat cgtaaagctc tgttgttagg gaagaacaag tgcgagagta actgctcgca  480
ccttgacggt acctaaccag aaagccacgg ctaactacgt gccagcagcc gcggtaatac  540
gtaggtggca agcgttgtcc ggaattattg ggcgtaaagg gctcgcaggc ggtttcttaa  600
gtctgatgtg aaagcccccg gctcaaccgg ggagggtcat tggaaactgg gaaacttgag  660
tgcagaagag gagagtggaa ttccacgtgt agcggtgaaa tgcgtagaga tgtggaggaa  720
caccagtggc gaaggcgact ctctggtctg taactgacgc tgaggagcga aagcgtgggg  780
agcgaacagg attagatacc ctggtagtcc acgccgtaaa cgatgagtgc taagtgttag  840
ggggtttccg ccccttagtg ctgcagctaa cgcattaagc actccgcctg gggagtacgg  900
tcgcaagact gaaactcaaa ggaattgacg ggggcccgca caagcggtgg agcatgtggt  960
ttaattcgaa gcaacgcgaa gaaccttacc aggtcttgac atcctctgac aaccctagag  1020
atagggcttt ccccttcggg acagagtgac aggtggtgca tggttgtcgt cagctcgtgt  1080
cgtgagatgt tgggttaagt cccgcaacga gcgcaaccct tgatcttagt tgccagcatt  1140
tagttgggca ctctaaggtg actgccggtg acaaaccgga ggaaggtggg gatgacgtca  1200
aatcatcatg ccccttatga cctgggctac acacgtgcta caatggacag aacaaagggc  1260
tgcgagaccg caaggtttag ccaatcccat aaatctgttc tcagttcgga tcgcagtctg  1320
caactcgact gcgtgaagct ggaatcgcta gtaatcgcgg atcagcatgc cgcggtgaat  1380
acgttcccgg gccttgtaca caccgcccgt cacaccacga gagtttgcaa cacccgaagt  1440
cggtgaggta acctttatgg agccagccgc cgaaggtggg gcagatgatt ggggtgaagt  1500
```

-continued

```
cgtaacaagg tagccgtatc ggaaggtgcg gctggatcac ctccttt              1547

SEQ ID NO: 138         moltype = RNA  length = 841
FEATURE                Location/Qualifiers
source                 1..841
                       mol_type = rRNA
                       organism = unidentified
                       note = DP73 16S rRNA sequence
SEQUENCE: 138
aacggagagt ttgatcctgg ctcaggacga acgctggcgg cgtgcctaat acatgcaagt  60
cgagcggaca gaagggagct tgctcccgga cgttagcggc ggacgggtga gtaacacgtg  120
ggcaacctgc cccttagact gggataactc cgggaaaccg gagctaatac cggataatcc  180
ctttctccac ctggagagag ggtgaaagat ggcttcggct atcactaagg gatgggcccg  240
cggcgcatta gctagttggt aaggtaacgg cttaccaagg cgacgatgcg tagccgacct  300
gagagggtga tcggccacac tgggactgag acacggccca gactcctacg ggaggcagca  360
gtagggaatc ttccgcaatg gacgaaagtc tgacggagca acgccgcgtg agtgaggaag  420
gccttcgggt cgtaaagctc tgttgtgagg gaagaagcgg tgccgttcga atagggcggt  480
accttgacgg tacctcacca gaaagccacg gctaactacg tgccagcagc cgcggtaata  540
cgtaggtggc aagcgttgtc cggaattatt gggcgtaaag cgcgcgcagg cggcttctta  600
agtctgatgt gaaatctcgg ggctcaaccc cgagcggcca ttggaaactg gggagcttga  660
gtgcagaaga ggagagtgga attccacgtg tagcggtgaa atgcgtagag atgtggagga  720
acaccagtgg cgaaggcgac tctctggtct gtaactgacg ctgaggcgcg aaagcgtggg  780
gagcaaacag gattagatac cctggtagtc cacgccgtaa acgatgagtg ctaggtgtta  840
g                                                                 841

SEQ ID NO: 139         moltype = RNA  length = 1105
FEATURE                Location/Qualifiers
source                 1..1105
                       mol_type = rRNA
                       organism = unidentified
                       note = DP74 16S rRNA sequence
SEQUENCE: 139
gcctaataca tgcaagtcgt gcggaccttt taaaagcttg cttttaaaag gttagcggcg  60
aacgggtgag taacacgtgg gcaacctgcc tgtaagatcg ggataatgcc gggaaaccgg  120
ggctaatacc ggatagtttt ttcctccgca tggaggaaaa aggaaagacg gcttcggctg  180
tcacttacag atgggcccgc ggcgcattag cttgttggtg gggtaacggc tcaccaaggc  240
aacgatgcgt agccgacctg agagggtgat cggccacatt gggactgaga cacggcccaa  300
actcctacgg gaggcagcag tagggaatct tccgcaatgg acgaaagtct gacggagcaa  360
cgccgcgtga gtgaagaagg ccttcgggtc gtaaaactct gttgccgggg aagaacaagt  420
gccgttcgaa cagggcggcg ccttgacggt acccggccag aaagccacgg ctaactacgt  480
gccagcagcc gcggtaatac gtaggtggca agcgttgtcc ggaattattg ggcgtaaagc  540
gcgcgcaggc ggcttcttaa gtctgatgtg aaatcttgcg gctcaaccgc aagcggtcat  600
tggaaactgg gaggcttgag tgcagaagag gagagtggaa ttccacgtgt agcggtgaaa  660
tgcgtagaga tgtggaggaa caccagtggc gaaggcggct ctctggtctg taactgacgc  720
tgaggcgcga aagcgtgggg agcaaacagg attagatacc ctggtagtcc acgccgtaaa  780
cgatgagtgc taagtgttag agggtttccg ccctttagtg ctgcagctaa cgcattaagc  840
actccgcctg gggagtacgg ccgcaaggct gaaactcaaa ggaattgacg gggcccgca  900
caagcggtgg agcatgtggt ttaattcgaa gcaacgcgaa gaaccttacc aggtcttgac  960
atcctctgac ctccctggag acagggcctt ccccttcggg ggacagagtg acaggtggtg  1020
catggttgtc gtcagctcgt gtcgtgagat gttgggttaa gtcccgcaac gagcgcaacc  1080
cttgacctta gttgccagca ttcag                                      1105

SEQ ID NO: 140         moltype = RNA  length = 1515
FEATURE                Location/Qualifiers
source                 1..1515
                       mol_type = rRNA
                       organism = unidentified
                       note = DP75 16S rRNA sequence
SEQUENCE: 140
tgaagagttt gatcatggct cagattgaac gctggcggca ggcctaacac atgcaagtcg  60
agcggtagag agaagcttgc ttctcttgag agcggcggac gggtgagtaa tgcctaggaa  120
tctgcctggt agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggcgac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggttgta gattaatact ctgcaatttt gacgttaccg  480
acagaataag caccggctaa ctctgtgcca gcagccgcgg taatacagag ggtgcaagcg  540
ttaatcggaa ttactgggcg taaagcgcgc gtaggtggtt cgttaagttg gatgtgaaag  600
ccccgggctc aacctgggaa ctgcattcaa aactgacgag ctagagtatg gtagagggtg  660
gtggaatttc ctgtgtagcg gtgaaatgcg tagatatagg aaggaacacc agtggcgaag  720
gcgaccacct ggactgatac tgacactgag gtgcgaaagc gtggggagca aacaggatta  780
gataccctgg tagtccacgc cgtaaacgat gtcaactagc cgttggaatc cttgagattt  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc cagagatgga tgggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgttatg gtgggcactc  1140
taaggagact gccggtgaca aaccggagga aggtggggat gacgtcaagt catcatggcc  1200
```

-continued

```
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgcgaatc agaatgtcgc ggtgaatacg ttcccgggcc  1380
ttgtacacac cgcccgtcac accatgggag tgggttgcac cagaacggga ggacggttac  1440
cacggtgtga ttcatgactg gggtgaagtc gtaacaaggt agccgtaggg gaacctgcgg  1500
ctggatcacc tcctt                                                   1515

SEQ ID NO: 141          moltype = RNA  length = 1479
FEATURE                 Location/Qualifiers
source                  1..1479
                        mol_type = rRNA
                        organism = unidentified
                        note = DP76 16S rRNA sequence
SEQUENCE: 141
cttgagagtt tgatcctggc tcagaacgaa cgctggcggc aggcttaaca catgcaagtc  60
gagcgccccg caaggggagc ggcagacggg tgagtaacgc gtgggaatct accttttgct  120
acggaacaac agttggaaac gactgctaat accgtatgtg cccttcgggg gaaagattta  180
tcggcaaagg atgagcccgc gttggattag ctagttggtg aggtaaaggc tcaccaaggc  240
gacgatccat agctggtctg agaggatgat cagccacact gggactgaga cacggcccag  300
actcctacgg gaggcagcag tggggaatat tggacaatgg gcgcaagcct gatccagcca  360
tgccgcgtga gtgatgaagg ccctagggtt gtaaagctct ttcaccggtg aagataatga  420
cggtaaccgg agaagaagcc ccggctaact tcgtgccagc agccgcggta atacgaaggg  480
ggctagcgtt gttcggattt actgggcgta aagcgcacgt aggcggattt ttaagtcagg  540
ggtgaaatcc cggggctcaa ccccggaact gcctttgata ctggaagtct tgagtatggt  600
agaggtgagt ggaattccga gtgtagaggt gaaattcgta gatattcgga ggaacaccag  660
tggcgaaggc ggctcactgg accattactg acgctgaggt gcgaaagcgt ggggagcaaa  720
caggattaga taccctggta gtccacgccg taaacgatga atgttagccg tcggggggtt  780
tacctttcgg tggcgcagct aacgcattaa acattccgcc tggggagtac ggtcgcaaga  840
ttaaaactca aaggaattga cgggggcccg cacaagcggt ggagcatgtg gtttaattcg  900
aagcaacgcg cagaacctta ccagcccttg acataccggt cgcggacaca gagatgtgtc  960
tttcagttcg gctggaccgg atacaggtgc tgcatggctg tcgtcagctc gtgtcgtgag  1020
atgttgggtt aagtcccgca acgagcgcaa ccctcgcctt tagttgccag catttagttg  1080
ggcactctaa agggactgcc agtgataagc tggaggaagg tggggatgac gtcaagtcct  1140
catggccctt acgggctggg ctacacacgt gctacaatgg tggtgacagt gggcagcaag  1200
cacgcgagtg tgagctaatc tccaaaagcc atctcagttc ggattgcact ctgcaactcg  1260
agtgcatgaa gttggaatcg ctagtaatcg cggatcagca tgccgcggtg aatacgttcc  1320
cgggccttgt acacaccgcc cgtcacacca tgggagttgg ttttacccga aggcactgtg  1380
ctaaccgcaa ggaggcaggt gaccacggta gggtcagcga ctggggtgaa gtcgtaacaa  1440
ggtagccgta ggggaacctg cggctggatc acctcctttt                        1479

SEQ ID NO: 142          moltype = RNA  length = 1549
FEATURE                 Location/Qualifiers
source                  1..1549
                        mol_type = rRNA
                        organism = unidentified
                        note = DP77 16S rRNA sequence
SEQUENCE: 142
tcggagagtt tgatcctggc tcaggatgaa cgctggcggc gtgcctaata catgcaagtc  60
gagcgaactg attagaagct tgcttctatg acgttagcgg cggacgggtg agtaacacgt  120
gggcaacctg cctgtaagac tgggataact tcgggaaacc gaagctaata ccggatagga  180
tcttctcctt catgggagat gattgaaaga tggtttcggc tatcacttac agatgggccc  240
gcggtgcatt agctagttgg tgaggtaacg gctcaccaag gcaacgatgc atagccgacc  300
tgagagggtg atcggccaca ctgggactga gacacggccc agactcctac gggaggcagc  360
agtagggaat cttccgcaat ggacgaaagt ctgacggagc aacgccgcgt gagtgatgaa  420
ggctttcggg tcgtaaaact ctgttgttag ggaagaacaa gtacaagagt aactgcttgt  480
accttgacgg tacctaacca gaaagccacg gctaactacg tgccagcagc cgcggtaata  540
cgtaggtggc aagcgttatc cggaattatt gggcgtaaag cgcgcgcagg cggtttctta  600
agtctgatgt gaaagcccac ggctcaaccg tggagggtca ttggaaactg gggaacttga  660
gtgcagaaga gaaaagcgga attccacgtg tagcggtgaa atgcgtagag atgtggagga  720
acaccagtgg cgaaggcggc tttttggtct gtaactgacg ctgaggcgcg aaagcgtggg  780
gagcaaacag gattagatac cctggtagtc cacgccgtaa acgatgagtg ctaagtgtta  840
gagggtttcc gccctttagt gctgcagcta acgcattaag cactccgcct ggggagtacg  900
gtcgcaagac tgaaactcaa aggaattgac gggggcccgc acaagcggtg gagcatgtgg  960
tttaattcga agcaacgcga agaaccttac caggtcttga catcctctga caactctaga  1020
gatagagcgt tccccttcgg gggacagagt gacaggtggt gcatggttgt cgtcagctcg  1080
tgtcgtgaga tgttgggtta agtcccgcaa cgagcgcaac ccttgatctt agttgccagc  1140
attcagttgg gcactctaag gtgactgccg gtgacaaacc ggaggaaggt ggggatgacg  1200
tcaaatcatc atgcccctta tgacctgggc tacacacgtg ctacaatgga tggtacaaag  1260
ggctgcaaga ccgcgaggtc aagccaatcc cataaaacca ttctcagttc ggattgtagg  1320
ctgcaactcg cctacatgaa gctggaatcg ctagtaatcg cggatcagca tgccgcggtg  1380
aatacgttcc cgggccttgt acacaccgcc cgtcacacca cgagagtttg taacacccga  1440
agtcggtgga gtaaccgtaa ggagctagcc gcctaaggtg ggacagatga ttggggtgaa  1500
gtcgtaacaa ggtagccgta tcggaaggtg cggctggatc acctcctttt              1549

SEQ ID NO: 143          moltype = RNA  length = 1536
FEATURE                 Location/Qualifiers
source                  1..1536
                        mol_type = rRNA
                        organism = unidentified
```

```
                        note = DP78 16S rRNA sequence
SEQUENCE: 143
ttgaagagtt tgatcatggc tcagattgaa cgctggcggc aggcctaaca catgcaagtc  60
ggacggtagc acagagagct tgctcttggg tgacgagtgg cggacgggtg agtaatgtct  120
ggggatctgc ccgatagagg gggataacca ctggaaacgg tggctaatac cgcataacgt  180
cgcaagacca aagagggggga ccttcgggcc tctcactatc ggatgaaccc agatgggatt  240
agctagtagg cggggtaatg gcccacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtatgaagaa ggccttcggg  420
ttgtaaagta ctttcagcgg ggaggaaggc gacggggtta ataaccctgt cgattgacgt  480
tacccgcaga agaagcaccg gctaactccg tgccagcagc cgcggtaata cggagggtgc  540
aagcgttaat cggaattact gggcgtaaag cgcacgcagg cggtctgtta agtcagatgt  600
gaaatccccg ggcttaacct gggaactgca tttgaaactg gcaggcttga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgccgtaa acgatgtcga cttggaggtt gttcccttga  840
ggagtggctt ccggagctaa cgcgttaagt cgaccgcctg gggagtacgg ccgcaaggtt  900
aaaactcaaa tgaattgacg ggggcccgca caagcggtgg agcatgtggt ttaattcgat  960
gcaacgcgaa gaaccttacc tactcttgac atccagcgaa cttagcagag atgctttggt  1020
gccttcggga acgctgagac aggtgctgca tggctgtcgt cagctcgtgt tgtgaaatgt  1080
tgggttaagt cccgcaacga gcgcaaccct tatcctttgt tgccagcgat tcggtcggga  1140
actcaaagga gactgccggt gataaaccgg aggaaggtgg ggatgacgtc aagtcatcat  1200
ggcccttacg agtagggcta cacacgtgct acaatggcgc atacaaagag aagcgacctc  1260
gcgagagcaa gcggacctca caaagtgcgt cgtagtccgg atcggagtct gcaactcgac  1320
tccgtgaagt cggaatcgct agtaatcgtg gatcagaatg ccacggtgaa tacgttcccg  1380
ggccttgtac acaccgcccg tcacaccatg ggagtgggtt gcaaaagaag taggtagctt  1440
aaccttcggg agggcgctta ccactttgtg attcatgact ggggtgaagt cgtaacaagg  1500
taaccgtagg ggaacctgcg gttggatcac ctcctt                          1536

SEQ ID NO: 144          moltype = RNA  length = 1532
FEATURE                 Location/Qualifiers
source                  1..1532
                        mol_type = rRNA
                        organism = unidentified
                        note = DP79 16S rRNA sequence
SEQUENCE: 144
tgaagagttt gatcatggct cagattgaac gctggcggca ggcctaacac atgcaagtcg  60
agcggtagag agaagcttgc ttctcttgag agcggcggac gggtgagtaa tacctaggaa  120
tctgcctgat agtgggggat aacgttcgga aacggacgct aataccgcat acgtcctacg  180
ggagaaagca ggggaccttc gggccttgcg ctatcagatg agcctaggtc ggattagcta  240
gttggtgagg taatggctca ccaaggctac gatccgtaac tggtctgaga ggatgatcag  300
tcacactgga actgagacac ggtccagact cctacgggag gcagcagtgg ggaatattgg  360
acaatgggcg aaagcctgat ccagccatgc cgcgtgtgtg aagaaggtct tcggattgta  420
aagcacttta agttgggagg aagggcagtt acctaatacg tgactgtctt gacgttaccg  480
acagaataag caccggctaa ctctgtgcca gcagccgcgg taatacagag ggtgcaagcg  540
ttaatcggaa ttactgggcg taaagcgcgc gtaggtggtt tgttaagttg aatgtgaaat  600
ccccgggctc aacctgggaa ctgcatccaa aactggcaag ctagagtatg gtagagggta  660
gtggaatttc ctgtgtagcg gtgaaatgcg tagatatagg aaggaacacc agtggcgaag  720
gcgactacct ggactgatac tgacactgag gtgcgaaagc gtggggagca aacaggatta  780
gataccctgg tagtccacgc cgtaaacgat gtcaactagc cgttgggagt cttgaactct  840
tagtggcgca gctaacgcat taagttgacc gcctggggag tacggccgca aggttaaaac  900
tcaaatgaat tgacgggggc ccgcacaagc ggtggagcat gtggtttaat tcgaagcaac  960
gcgaagaacc ttaccaggcc ttgacatcca atgaactttc tagagataga ttggtgcctt  1020
cgggaacatt gagacaggtg ctgcatggct gtcgtcagct cgtgtcgtga gatgttgggt  1080
taagtcccgt aacgagcgca acccttgtcc ttagttacca gcacgtaatg gtgggcactc  1140
taaggagact gccggtgaca aaccggagga aggtggggat gacgtcaagt catcatggcc  1200
cttacggcct gggctacaca cgtgctacaa tggtcggtac aaagggttgc caagccgcga  1260
ggtggagcta atcccataaa accgatcgta gtccggatcg cagtctgcaa ctcgactgcg  1320
tgaagtcgga atcgctagta atcgtgaatc agaatgtcac ggtgaatacg ttcccgggcc  1380
ttgtacacac cgcccgtcac accatgggag tgggttgcac cagaagtagc tagtctaacc  1440
ttcgggagga cggttaccac ggtgtgattc atgactgggg tgaagtcgta acaaggtagc  1500
cgtaggggaa cctgcggctg gatcacctcc tt                              1532

SEQ ID NO: 145          moltype = RNA  length = 1136
FEATURE                 Location/Qualifiers
source                  1..1136
                        mol_type = rRNA
                        organism = unidentified
                        note = DP80 16S rRNA sequence
SEQUENCE: 145
cttgagagtt tgatcctggc tcagagcgaa cgctggcggc aggcttaaca catgcaagtc  60
gagcgggcac cttcgggtgt cagcggcaga cgggtgagta acacgtggga acgtaccctt  120
cggttcggaa taacgctggg aaactagcgc taataccgga tacgcccttt tggggaaagg  180
tttactgccg aaggatcggc ccgcgtctga ttagctagtt ggtggggtaa cggcctacca  240
aggcgacgat cagtagctgg tctgagagga tgatcagcca cactgggact gagacacggc  300
ccagactcct acgggaggca gcagtgggga atattggaca atgggcgcaa gcctgatcca  360
gccatgccgc gtgagtgatg aaggccttag ggttgtaaag ctcttttgtc cgggacgata  420
atgacggtac cggaagaata agccccggct aacttcgtgc cagcagccgc ggtaatacga  480
agggggctag cgttgctcgg aatcactggg cgtaaagggc gcgtaggcgg ccattcaagt  540
```

```
cgggggtgaa agcctgtggc tcaaccacag aattgccttc gatactgttt ggcttgagtt  600
tggtagaggt tggtggaact gcgagtgtag aggtgaaatt cgtagatatt cgcaagaaca  660
ccagtggcga aggcggccaa ctggaccaat actgacgctg aggcgcgaaa gcgtggggag  720
caaacaggat tagataccct ggtagtccac gccgtaaacg atgaatgcta gctgttgggg  780
tgcttgcacc tcagtagcgc agctaacgct ttaagcattc cgcctgggga gtacggtcgc  840
aagattaaaa ctcaaaggaa ttgacggggg cccgcacaag cggtggagca tgtggtttaa  900
ttcgaagcaa cgcgcagaac cttaccatcc cttgacatgt cgtgccatcc ggagagatcc  960
ggggttccct tcggggacgc gaacacaggt gctgcatggc tgtcgtcagc tcgtgtcgtg  1020
agatgttggg ttaagtcccg caacgagcgc aacccacgtc cttagttgcc atcatttagt  1080
tgggcactct agggagactg ccggtgataa gccgcgagga aggtgtggat gacgtc      1136

SEQ ID NO: 146          moltype = RNA  length = 1547
FEATURE                 Location/Qualifiers
source                  1..1547
                        mol_type = rRNA
                        organism = unidentified
                        note = DP81 16S rRNA sequence
SEQUENCE: 146
aacggagagt ttgatcctgg ctcaggacga acgctggcgg cgtgcctaat acatgcaagt  60
cgagcggaca gaagggagct tgctcccgga cgttagcggc ggacgggtga gtaacacgtg  120
ggcaacctgc ccttagact gggataactc cgggaaaccg gagctaatac cggataatcc  180
ctttctccac ctggagagag ggtgaaagat ggcttcggct atcactaggg gatgggcccg  240
cggcgcatta gctagttggt aaggtaacgg cttaccaagg cgacgatgcg tagccgacct  300
gagagggtga tcggccacac tggactgag acacggccca gactcctacg ggaggcagca  360
gtagggaatc ttccgcaatg gacgaaagtc tgacggagca acgccgcgtg agtgaggaag  420
gctttcgggt cgtaaagctc tgttgtgagg gaagaagcgg taccgttcga atagggcggt  480
accttgacgg tacctcacca gaaagccacg gctaactacg tgccagcagc cgcggtaata  540
cgtaggtggc aagcgttgtc cggaattatt gggcgtaaag cgcgcgcagg cggcttctta  600
agtctgatgt gaaatctcgg ggctcaaccc cgagcggcca ttggaaactg gggagcttga  660
gtgcagaaga ggagagtgga attccacgtg tagcggtgaa atgcgtagag atgtggagga  720
acaccagtgg cgaaggcgac tctctggtct gtaactgacg ctgaggcgcg aaagcgtggg  780
gagcaaacag gattagatac cctggtagtc cacgccgtaa acgatgagtg ctaggtgtta  840
ggggtttcga tgcccgtagt gccgaagtta acacattaag cactccgcct ggggagtacg  900
gccgcaaggc tgaaactcaa aggaattgac ggggacccgc acaagcagtg gagcatgtgg  960
tttaattcga agcaacgcga agaaccttac caggtcttga catcctttga ccacccaaga  1020
gattgggctt ccccttcggg ggcaaagtga caggtggtgc atggttgtcg tcagctcgtg  1080
tcgtgagatg ttgggttaag tcccgcaacg agcgcaaccc ttgatcttag ttgccagcat  1140
tgagttgggc actctaaggt gactgccggt gacaaaccgg aggaaggtgg ggatgacgtc  1200
aaatcatcat gccccttatg acctgggcta cacacgtgct acaatggatg gtacaaaggg  1260
cagcgaaacc gcgaggtgaa gccaatccca taaagccatt ctcagttcgg attgcaggct  1320
gcaactcgcc tgcatgaagc cggaattgct agtaatcgcg gatcagcatg ccgcggtgaa  1380
tacgttcccg ggtcttgtac acaccgcccg tcacaccacg agagtttgta acacccgaag  1440
tcggtgaggc aacctttgg agccagccgc ctaaggtggg acaaatgatt ggggtgaagt  1500
cgtaacaagg tagccgtatc ggaaggtgcg gctggatcac ctccttt                1547

SEQ ID NO: 147          moltype = RNA  length = 1547
FEATURE                 Location/Qualifiers
source                  1..1547
                        mol_type = rRNA
                        organism = unidentified
                        note = DP82 16S rRNA sequence
SEQUENCE: 147
aacggagagt ttgatcctgg ctcaggacga acgctggcgg cgtgcctaat acatgcaagt  60
cgagcggaca gaagggagct tgctcccgga cgttagcggc ggacgggtga gtaacacgtg  120
ggcaacctgc ccttagact gggataactc cgggaaaccg gagctaatac cggataatcc  180
ctttctccac ctggagagag ggtgaaagat ggcttcggct atcactaagg gatgggcccg  240
cggcgcatta gctagttggt aaggtaacgg cttaccaagg caacgatgcg tagccgacct  300
gagagggtga tcggccacac tggactgag acacggccca gactcctacg ggaggcagca  360
gtagggaatc ttccgcaatg gacgaaagtc tgacggagca acgccgcgtg agtgaggaag  420
gccttcgggt cgtaaagctc tgttgtgagg gaagaagcgg taccgttcga atagggcggt  480
accttgacgg tacctcacca gaaagccacg gctaactacg tgccagcagc cgcggtaata  540
cgtaggtggc aagcgttgtc cggaattatt gggcgtaaag cgcgcgcagg cggcttctta  600
agtctgatgt gaaatctcgg ggctcaaccc cgagcggcca ttggaaactg gggagcttga  660
gtgcagaaga ggagagtgga attccacgtg tagcggtgaa atgcgtagag atgtggagga  720
acaccagtgg cgaaggcgac tctctggtct gtaactgacg ctgaggcgcg aaagcgtggg  780
gagcaaacag gattagatac cctggtagtc cacgccgtaa acgatgagtg ctaggtgtta  840
ggggtttcga tgcccgtagt gccgaagtta acacattaag cactccgcct ggggagtacg  900
gccgcaaggc tgaaactcaa aggaattgac ggggacccgc acaagcagtg gagcatgtgg  960
tttaattcga agcaacgcga agaaccttac caggtcttga catcctttga ccacccaaga  1020
gattgggctt ccccttcggg ggcaaagtga caggtggtgc atggttgtcg tcagctcgtg  1080
tcgtgagatg ttgggttaag tcccgcaacg agcgcaaccc ttgatcttag ttgccagcat  1140
tcagttgggc actctaaggt gactgccggt gacaaaccgg aggaaggtgg ggatgacgtc  1200
aaatcatcat gccccttatg acctgggcta cacacgtgct acaatggatg gtacaaaggg  1260
cagcgaaacc gcgaggtgaa gccaatccca taaagccatt ctcagttcgg attgcaggct  1320
gcaactcgcc tgcatgaagc cggaattgct agtaatcgcg gatcagcatg ccgcggtgaa  1380
tacgttcccg ggtcttgtac acaccgcccg tcacaccacg agagtttgta acacccgaag  1440
tcggtgaggc aacctttgg agccagccgc ctaaggtggg acaaatgatt ggggtgaagt  1500
cgtaacaagg tagccgtatc ggaaggtgcg gctggatcac ctccttt                1547
```

```
SEQ ID NO: 148          moltype = RNA  length = 1548
FEATURE                 Location/Qualifiers
source                  1..1548
                        mol_type = rRNA
                        organism = unidentified
                        note = DP83 16S rRNA sequence
SEQUENCE: 148
acggagagtt tgatcctggc tcaggacgaa cgctggcggc gtgcctaata catgcaagtc  60
gagcggagtt tcaagaagct tgctttttga aacttagcgg cggacgggtg agtaacacgt  120
gggcaacctg ccccttagac tggataact  ccgggaaacc ggagctaata ccggataatc  180
cctttctcca cctggagaga gggtgaaaga tggcttcggc tatcactaag ggatgggccc  240
gcggcgcatt agctagttgg taaggtaacg gcttaccaag gcaacgatgc gtagccgacc  300
tgagagggtg atcggccaca ctgggactga gacacggccc agactcctac gggaggcagc  360
agtagggaat cttccgcaat ggacgaaagt ctgacggagc aacgccgcgt gagtgaggaa  420
ggccttcggg tcgtaaagct ctgttgtgag ggaagaagcg gtaccgttcg aatagggcgg  480
taccttgacg gtacctcacc agaaagccac ggctaactac gtgccagcag ccgcggtaat  540
acgtaggtgg caagcgttgt ccggaattat tgggcgtaaa gcgcgcgcag gcggcttctt  600
aagtctgatg tgaaatctcg ggctcaacc  ccgagcggcc attggaaact ggggagcttg  660
agtgcagaag aggagagtgg aattccacgt gtagcggtga aatgcgtaga gatgtggagg  720
aacaccagtg gcgaaggcga ctctctggtc tgtaactgac gctgaggcgc gaaagcgtgg  780
ggagcaaaca ggattagata ccctggtagt ccacgccgta aacgatgagt gctaggtgtt  840
aggggtttcg atgcccgtag tgccgaagtt aacacattaa gcactccgcc tggggagtac  900
ggccgcaagg ctgaaactca aaggaattga cggggacccg cacaagcagt ggagcatgtg  960
gtttaattcg aagcaacgcg aagaacctta ccaggtcttg acatcctttg accacccaag  1020
agattgggct tccccttcgg gggcaaagtg acaggtggtg catggttgtc gtcagctcgt  1080
gtcgtgagat gttgggttaa gtcccgcaac gagcgcaacc cttgatctta gttgccagca  1140
ttcagttggg cactctaagg tgactgccgg tgacaaaccg gaggaaggtg gggatgacgt  1200
caaatcatca tgccccttat gacctgggct acacacgtgc tacaatggat ggtacaaagg  1260
gcagcgaagc cgcgaggtga agccaatccc ataaagccat tctcagttcg gattgcaggc  1320
tgcaactcgc ctgcatgaag ccggaattgc tagtaatcgc ggatcagcat gccgcggtga  1380
atacgttccc gggtcttgta cacaccgccc gtcacaccac gagagtttgt aacacccgaa  1440
gtcggtgagg caacctttg  gagccagccg cctaaggtgg gacaaatgat tggggtgaag  1500
tcgtaacaag gtagccgtat cggaaggtgc ggctggatca cctccttt              1548

SEQ ID NO: 149          moltype = RNA  length = 1480
FEATURE                 Location/Qualifiers
source                  1..1480
                        mol_type = rRNA
                        organism = unidentified
                        note = DP84 16S rRNA sequence
SEQUENCE: 149
tacggagagt ttgatcctgg ctcaggatga acgctggcgg cgtgcttaac acatgcaagt  60
cgaacggtga agccaagctt gcttggtgga tcagtggcga acgggtgagt aacacgtgag  120
caacctgccc tggactctgg gataagcgct ggaaacggcg tctaatactg gatatgagct  180
ctcatcgcat ggtgggggtt ggaaagattt tttggtctgg gatgggctcg cggcctatca  240
gcttgttggt gaggtaatgg ctcaccaagg cgtcgacggg tagccggcct gagagggtga  300
ccggccacac tgggactgag acacggccca gactcctacg ggaggcagca gtggggaata  360
ttgcacaatg ggcgaaagcc tgatgcagca acgccgcgtg agggatgacg gccttcgggt  420
tgtaaacctc ttttagcagg gaagaagcga aagtgacggt acctgcagaa aaagcgccgg  480
ctaactacgt gccagcagcc gcggtaatac gtagggcgca agcgttatcc ggaattattg  540
ggcgtaaaga gctcgtaggc ggtttgtcgc gtctgctgtg aaatcccgag gctcaacctc  600
gggcctgcag tgggtacggg cagactagag tgcggtaggg gagattggaa ttcctggtgt  660
agcggtggaa tgcgcagata tcaggaggaa caccgatggc gaaggcagat ctctgggccg  720
taactgacgc tgaggagcga aagggtgggg agcaaacagg cttagatacc ctggtagtcc  780
accccgtaaa cgttgggaac tagttgtggg gaccattcca cggtttccgt gacgcagcta  840
acgcattaag ttccccgcct ggggagtacg gccgcaaggc taaaactcaa aggaattgac  900
ggggacccgc acaagcggcg gagcatgcgg attaattcga tgcaacgcga agaaccttac  960
caaggcttga catacaccag aacgggccag aaatggtcaa ctctttggac actggtgaac  1020
aggtggtgca tggttgtcgt cagctcgtgt cgtgagatgt tgggttaagt cccgcaacga  1080
gcgcaaccct cgttctatgt tgccagcacg taatggtggg aactcatggg atactgccgg  1140
ggtcaactcg gaggaaggtg gggatgacgt caaatcatca tgccccttat gtcttgggct  1200
tcacgcatgc tacaatggcc ggtacaaagg gctgcaatac cgtgaggtgg agcgaatccc  1260
aaaaagccgg tcccagttcg gattgaggtc tgcaactcga cctcatgaag tcggagtcgc  1320
tagtaatcgc agatcagcaa cgctgcggtg aatacgttcc cgggtcttgt acacaccgcc  1380
cgtcaagtca tgaaaggagc cgtcgaaggt gggatcggta attaggacta agtcgtaaca  1440
aggtagccgt accggaaggt gcggctggat cacctccttt                        1480

SEQ ID NO: 150          moltype = RNA  length = 924
FEATURE                 Location/Qualifiers
source                  1..924
                        mol_type = rRNA
                        organism = unidentified
                        note = DP85 16S rRNA sequence
SEQUENCE: 150
acggtcgggg gcatcagtat tcagtcgtca gaggtgaaat tcttggattg actgaagact  60
aactactgcg aaagcatttg ccaaggacgt tttcattaat caagaacgaa agttagggga  120
tcgaagatga tcagataccg tcgtagtctt aaccataaac tatgccgact agagatcggg  180
tggtgctttt tgcgcactcg gcatcttacg agaaatcaaa gtctttgggt tctgggggga  240
gtatggtcgc aaggctgaaa cttaaaggaa ttgacggagg ggcaccacca ggagtggagc  300
```

```
ctgcggctta atttgactca acacggggaa actcaccagg tccagacgta ataaggattg  360
acaagttaga gacttctctt gatcttacgg gtggtggtgc atggccgttt ttagtccttg  420
gagtgatttg tctgcttaat tgcgataacg gacgagacct taacctgcta aatagggctg  480
cgagcatctg ctcgtgggct cttcttagag ggactatggg tatcaaaccc atggaagttt  540
gaggcaacaa caggtctgtg atgcccttag acgttctggg ccgcacgcgc gctacactga  600
cggagccagc aagcataacc ttggtcgaga ggcctgggta atctcgtgaa actccgtcgt  660
gctggggata gagcattgta atttttgctc ttcaacgagg aattcctagt aagcgcaagt  720
catcagcttg cgttgattac gtccctgccc cttgtacaca ccgcccgtcg ctactaccga  780
ttgaatggct tagtgaggct tcaagaccgg cgcggcctgc ggggcaactc gcgcgctgcg  840
ctgggaattt agtcaaactt ggtcatttag aggtcgtaaa agtcgtaaca aggtttccgt  900
aggtgaacct gcggaaggat catt                                         924

SEQ ID NO: 151          moltype = RNA  length = 881
FEATURE                 Location/Qualifiers
source                  1..881
                        mol_type = rRNA
                        organism = unidentified
                        note = DP86 16S rRNA sequence
SEQUENCE: 151
cgatgcgtag ccgacctgag agggtgatcg gccacactgg gactgagaca cggcccagac  60
tcctacggga ggcagcagta gggaatcttc cgcaatggac gaaagtctga cggagcaacg  120
ccgcgtgagt gatgaaggtt ttcggatcgt aaagctctgt tgttagggaa gaacaagtgc  180
cgttcaaata gggcggcacc ttgacggtac ctaaccagaa agccacggct aactacgtgc  240
cagcagccgc ggtaatacgt aggtggcaag cgttgtccgg aattattggg cgtaaagggc  300
tcgcaggcgg tttcttaagt ctgatgtgaa agcccccggc tcaaccgggg agggtcattg  360
gaaactgggg aacttgagtg cagaagagga gagtggaatt ccacgtgtag cggtgaaatg  420
cgtagagatg tggaggaaca ccagtggcga aggcgactct ctggtctgta actgacgctg  480
aggagcgaaa gcgtggggag cgaacaggat tagataccct ggtagtccac gccgtaaacg  540
atgagtgcta agtgttaggg ggtttccgcc ccttagtgct gcagctaacg cattaagcac  600
tccgcctggg gagtacggtc gcaagactga aactcaaagg aattgacggg ggcccgcaca  660
agcggtggag catgtggttt aattcgaagc aacgcgaaga accttaccag gtcttgacat  720
cctctgacaa tcctagagat aggacgtccc cttcgggggc agagtgacag gtggtgcatg  780
gttgtcgtca gctcgtgtcg tgagatgttg ggttaagtcc cgcaacgagc gcaacccttg  840
atcttagttg ccagcattca gttgggtgtt ctttgaaaac t                      881

SEQ ID NO: 152          moltype = RNA  length = 1563
FEATURE                 Location/Qualifiers
source                  1..1563
                        mol_type = rRNA
                        organism = unidentified
                        note = DP87 16S rRNA sequence
SEQUENCE: 152
tttgagagtt tgatcctggc tcaggacgaa cgctggcggc gtgcctaata catgcaagtc  60
gaacgaactc tggtattgat tggtgcttgc atcatgattt acatttgagt gagtggcgaa  120
ctggtgagta acacgtggga aacctgccca gaagcggggg ataacacctg gaaacagatg  180
ctaataccgc ataacaactt ggaccgcatg gtccgagctt gaaagatggc ttcggctatc  240
acttttggat ggtcccgcgg cgtattagct agatggtggg gtaacggctc accatggcaa  300
tgatacgtag ccgacctgag agggtaatcg gccacattgg gactgagaca cggcccaaac  360
tcctacggga ggcagcagta gggaatcttc cacaatggac gaaagtctga tggagcaacg  420
ccgcgtgagt gaagaagggt ttcggctcgt aaaactctgt tgttaaagaa gaacatatct  480
gagagtaact gttcaggtat tgacggtatt taaccagaaa gccacggcta actacgtgcc  540
agcagccgcg gtaatacgta ggtggcaagc gttgtccgga tttattgggc gtaaagcgag  600
cgcaggcggt tttttaagtc tgatgtgaaa gccttcggct caaccgaaga agtgcatcgg  660
aaactgggaa acttgagtgc agaagaggac agtggaactc catgtgtagc ggtgaaatgc  720
gtagatatat ggaagaacac cagtggcgaa ggcggctgtc tggtctgtaa ctgacgctga  780
ggctcgaaag tatgggtagc aaacaggatt agataccctg gtagtccata ccgtaaacga  840
tgaatgctaa gtgttggagg gtttccgccc ttcagtgctg cagctaacgc attaagcatt  900
ccgcctgggg agtacggccg caaggctgaa actcaaagga attgacgggg gcccgcacaa  960
gcggtggagc atgtggttta attcgaagct acgcgaagaa ccttaccagg tcttgacata  1020
ctatgcaaat ctaagagatt agacgttccc ttcggggaca tggatacagg tggtgcatgg  1080
ttgtcgtcag ctcgtgtcgt gagatgttgg gttaagtccc gcaacgagcg caacccttat  1140
tatcagttgc cagcattaag ttgggcactc tggtgagact gccggtgaca aaccggagga  1200
aggtggggat gacgtcaaat catcatgccc cttatgacct gggctacaca cgtgctacaa  1260
tggatggtac aacgagttgc gaactcgcga gagtaagcta atctcttaaa gccattctca  1320
gttcggattg taggctgcaa ctcgcctaca tgaagtcgga atcgctagta atcgcggatc  1380
agcatgccgc ggtgaatacg ttcccgggcc ttgtacacac cgcccgtcac accatgagag  1440
tttgtaacac ccaaagtcgg tggggtaacc ttttaggaac cagccgccta aggtgggaca  1500
gatgattagg gtgaagtcgt aacaaggtag ccgtaggaga acctgcggct ggatcacctc  1560
ctt                                                                1563

SEQ ID NO: 153          moltype = RNA  length = 1546
FEATURE                 Location/Qualifiers
source                  1..1546
                        mol_type = rRNA
                        organism = unidentified
                        note = DP88 16S rRNA sequence
SEQUENCE: 153
tagtgggttt gatcctggct caggacgaac gctggcggcg tgcctaatac atgcaagtcg  60
agcggacaga tgggagcttg ctccctgatg ttagcggcgg acgggtgagt aacacgtggg  120
```

```
taacctgcct gtaagactgg gataactccg ggaaaccggg gctaataccg gatggttgtc  180
tgaaccgcat ggttcagaca taaaaggtgg cttcggctac cacttacaga tggacccgcg  240
gcgcattagc tagttggtga ggtaacggct caccaaggcg acgatgcgta gccgacctga  300
gagggtgatc ggccacactg ggactgagac acggcccaga ctcctacggg aggcagcagt  360
agggaatctt ccgcaatgga cgaaagtctg acggagcaac gccgcgtgag tgatgaaggt  420
tttcggatcg taaagctctg ttgttaggga agaacaagtg ccgttcaaat agggcggcac  480
cttgacggta cctaaccaga aagccacggc taactacgtg ccagcagccg cggtaatacg  540
taggtggcaa gcgttgtccg gaattattgg gcgtaaaggg ctcgcaggcg gtttcttaag  600
tctgatgtga aagcccccgg ctcaaccggg gagggtcatt ggaaactggg gaacttgagt  660
gcagaagagg agagtggaat tccacgtgta gcggtgaaat gcgtagagat gtggaggaac  720
accagtggcg aaggcgactc tctggtctgt aactgacgct gaggagcgaa agcgtgggga  780
gcgaacagga ttagataccc tggtagtcca cgccgtaaac gatgagtgct aagtgttagg  840
gggtttccgc cccttagtgc tgcagctaac gcattaagca ctccgcctgg ggagtacggt  900
cgcaagactg aaactcaaag gaattgacgg gggcccgcac aagcggtgga gcatgtggtt  960
taattcgaag caacgcgaag aaccttacca ggtcttgaca tcctctgaca atcctagaga  1020
taggacgtcc ccttcggggg cagagtgaca ggtggtgcat ggttgtcgtc agctcgtgtc  1080
gtgagatgtt gggttaagtc ccgcaacgag cgcaaccctt gatcttagtt gccagcattc  1140
agttgggcac tctaaggtga ctgccggtga caaaccggag gaaggtgggg atgacgtcaa  1200
atcatcatgc cccttatgac ctgggctaca cacgtgctac aatggacaga acaaagggca  1260
gcgaaaccgc gaggttaagc caatcccaca aatctgttct cagttcggat cgcagtctgc  1320
aactcgactg cgtgaagctg gaatcgctag taatcgcgga tcagcatgcc gcggtgaata  1380
cgttcccggg ccttgtacac accgcccgtc acaccacgag agtttgtaac acccgaagtc  1440
ggtgaggtaa cctttatgga gccagccgcc gaaggtggga cagatgattg gggtgaagtc  1500
gtaacaaggt agccgtatcg gaaggtgcgg ctggatcacc tccttt                1546

SEQ ID NO: 154          moltype = RNA  length = 1285
FEATURE                 Location/Qualifiers
source                  1..1285
                        mol_type = rRNA
                        organism = unidentified
                        note = DP89 16S rRNA sequence
SEQUENCE: 154
gtaacggctc accaaggcaa cgatgcgtag ccgacctgag agggtgatcg gccacactgg  60
gactgagaca cggcccagac tcctacggga ggcagcagta gggaatcttc cgcaatggac  120
gaaagtctga cggagcaacg ccgcgtgagt gatgaaggtt ttcggatcgt aaagctctgt  180
tgttagggaa gaacaagtac cgttcgaata gggcggtacc ttgacggtac ctaaccagaa  240
agccacggct aactacgtgc cagcagccgc ggtaatacgt aggtggcaag cgttgtccgg  300
aattattggg cgtaaagggc tcgcaggcgg tttcttaagt ctgatgtgaa agcccccggc  360
tcaaccgggg agggtcattg gaaactgggg aacttgagtg cagaagagga gagtggaatt  420
ccacgtgtag cggtgaaatg cgtagagatg tggaggaaca ccagtggcga aggcgactct  480
ctggtctgta actgacgctg aggagcgaaa gcgtggggag cgaacaggat tagataccct  540
ggtagtccac gccgtaaacg atgagtgcta agtgttaggg ggtttccgcc ccttagtgct  600
gcagctaacg cattaagcac tccgcctggg gagtacggtc gcaagactga aactcaaagg  660
aattgacggg ggcccgcaca agcggtggag catgtggttt aattcgaagc aacgcgaaga  720
accttaccag gtcttgacat cctctgacaa tcctagagat aggacgtccc cttcgggggc  780
agagtgacag gtggtgcatg gttgtcgtca gctcgtgtcg tgagatgttg ggttaagtcc  840
cgcaacgagc gcaacccttg atcttagttg ccagcattca gttgggcact ctaaggtgac  900
tgccggtgac aaaccggagg aaggtgggga tgacgtcaaa tcatcatgcc ccttatgacc  960
tgggctacac acgtgctaca atggacagaa caaagggcag cgaaaccgcg aggttaagcc  1020
aatcccacaa atctgttctc agttcggatc gcagtctgca actcgactgc gtgaagctgg  1080
aatcgctagt aatcgcggat cagcatgccg cggtgaatac gttcccgggc cttgtacaca  1140
ccgcccgtca caccacgaga gtttgtaaca cccgaagtcg gtgaggtaac cttttaggag  1200
ccagccgccg aaggtgggac agatgattgg ggtgaagtcg taacaaggta gccgtatcgg  1260
aaggtgcggc tggatcacct ccttt                                       1285

SEQ ID NO: 155          moltype = RNA  length = 1563
FEATURE                 Location/Qualifiers
source                  1..1563
                        mol_type = rRNA
                        organism = unidentified
                        note = DP90 16S rRNA sequence
SEQUENCE: 155
tttgagagtt tgatcctggc tcaggacgaa cgctggcggc gtgcctaata catgcaagtc  60
gaacgaactc tggtattgat tggtgcttgc atcatgattt acatttgagt gagtggcgaa  120
ctggtgagta acacgtggga aacctgccca gaagcggggg ataacacctg gaaacagatg  180
ctaataccgc ataacaactt ggaccgcatg gtccgagctt gaaagatggc ttcggctatc  240
acttttggat ggtcccgcgg cgtattagct agatggtggg gtaacggctc accatggcaa  300
tgatacgtag ccgacctgag agggtaatcg gccacattgg gactgagaca cggcccaaac  360
tcctacggga ggcagcagta gggaatcttc cacaatggac gaaagtctga tggagcaacg  420
ccgcgtgagt gaagaagggt ttcggctcgt aaaactctgt tgttaaagaa gaacatatct  480
gagagtaact gttcaggtat tgacggtatt taaccagaaa gccacggcta actacgtgcc  540
agcagccgcg gtaatacgta ggtggcaagc gttgtccgga tttattgggc gtaaagcgag  600
cgcaggcggt tttttaagtc tgatgtgaaa gccttcggct caaccgaaga agtgcatcgg  660
aaactgggaa acttgagtgc agaagaggac agtggaactc catgtgtagc ggtgaaatgc  720
gtagatatat ggaagaacac cagtggcgaa ggcggctgtc tggtctgtaa ctgacgctga  780
ggctcgaaag tatgggtagc aaacaggatt agataccctg gtagtccata ccgtaaacga  840
tgaatgctaa gtgttggagg gtttccgccc ttcagtgctg cagctaacgc attaagcatt  900
ccgcctgggg agtacggccg caaggctgaa actcaaagga attgacgggg gcccgcacaa  960
gcggtggagc atgtggttta attcgaagct acgcgaagaa ccttaccagg tcttgacata  1020
```

-continued

```
ctatgcaaat ctaagagatt agacgttccc ttcggggaca tggatacagg tggtgcatgg  1080
ttgtcgtcag ctcgtgtcgt gagatgttgg gttaagtccc gcaacgagcg caacccttat  1140
tatcagttgc cagcattaag ttgggcactc tggtgagact gccggtgaca aaccggagga  1200
aggtggggat gacgtcaaat catcatgccc cttatgacct gggctacaca cgtgctacaa  1260
tggatggtac aacgagttgc gaactcgcga gagtaagcta atctcttaaa gccattctca  1320
gttcggattg taggctgcaa ctcgcctaca tgaagtcgga atcgctagta atcgcggatc  1380
agcatgccgc ggtgaatacg ttcccgggcc ttgtacacac cgcccgtcac accatgagag  1440
tttgtaacac ccaaagtcgg tggggtaacc ttttaggaac cagccgccta aggtgggaca  1500
gatgattagg gtgaagtcgt aacaaggtag ccgtaggaga acctgcggct ggatcacctc  1560
ctt                                                                1563

SEQ ID NO: 156         moltype = RNA  length = 1265
FEATURE                Location/Qualifiers
source                 1..1265
                       mol_type = rRNA
                       organism = unidentified
                       note = DP92 16S rRNA sequence
SEQUENCE: 156
cgatgcgtag ccgacctgag agggtgatcg gccacactgg gactgagaca cggcccagac  60
tcctacggga ggcagcagta gggaatcttc cgcaatggac gaaagtctga cggagcaacg  120
ccgcgtgagt gatgaaggtt ttcggatcgt aaagctctgt tgttagggaa gaacaagtac  180
cgttcgaata gggcggtacc ttgacggtac ctaaccagaa agccacggct aactacgtgc  240
cagcagccgc ggtaatacgt aggtggcaag cgttgtccgg aattattggg cgtaaagggc  300
tcgcaggcgg tttcttaagt ctgatgtgaa agcccccggc tcaaccgggg agggtcattg  360
gaaactgggg aacttgagtg cagaagagga gagtggaatt ccacgtgtag cggtgaaatg  420
cgtagagatg tggaggaaca ccagtggcga aggcgactct ctggtctgta actgacgctg  480
aggagcgaaa gcgtggggag cgaacaggat tagataccct ggtagtccac gccgtaaacg  540
atgagtgcta agtgttaggg ggtttccgcc ccttagtgct gcagctaacg cattaagcac  600
tccgcctggg gagtacggtc gcaagactga aactcaaagg aattgacggg ggcccgcaca  660
agcggtggag catgtggttt aattcgaagc aacgcgaaga accttaccag gtcttgacat  720
cctctgacaa tcctagagat aggacgtccc cttcgggggc agagtgacag gtggtgcatg  780
gttgtcgtca gctcgtgtcg tgagatgttg ggttaagtcc cgcaacgagc gcaacccttg  840
atcttagttg ccagcattca gttgggcact ctaaggtgac tgccggtgac aaaccggagg  900
aaggtgggga tgacgtcaaa tcatcatgcc ccttatgacc tgggctacac acgtgctaca  960
atggacagaa caaagggcag cgaaaccgcg aggttaagcc aatcccacaa atctgttctc  1020
agttcggatc gcagtctgca actcgactgc gtgaagctgg aatcgctagt aatcgcggat  1080
cagcatgccg cggtgaatac gttcccgggc cttgtacaca ccgcccgtca caccacgaga  1140
gtttgtaaca cccgaagtcg gtgaggtaac cttttaggag ccagccgccg aaggtgggac  1200
agatgattgg ggtgaagtcg taacaaggta gccgtatcgg aaggtgcggc tggatcacct  1260
ccttt                                                              1265

SEQ ID NO: 157         moltype = RNA  length = 1548
FEATURE                Location/Qualifiers
source                 1..1548
                       mol_type = rRNA
                       organism = unidentified
                       note = DP93 16S rRNA sequence
SEQUENCE: 157
attgagagtt tgatcctggc tcaggatgaa cgctggcggc gtgcctaata catgcaagtc  60
gaacgcacag cgaaaggtgc ttgcaccttt caagtgagtg gcgaacgggt gagtaacacg  120
tggacaacct gcctcaaggc tggggataac atttggaaac agatgctaat accgaataaa  180
acttagtgtc gcatgacaaa aagttaaaag gcgcttcggc gtcacctaga gatggatccg  240
cggtgcatta gttagttggt ggggtaaagg cctaccaaga caatgatgca tagccgagtt  300
gagagactga tcggccacat tgggactgag acacggccca aactcctacg ggaggctgca  360
gtagggaatc ttccacaatg ggcgaaagcc tgatggagca acgccgcgtg tgtgatgaag  420
gctttcgggt cgtaaagcac tgttgtatgg gaagaacagc tagaatagga aatgatttta  480
gtttgacggt accataccag aaagggacgg ctaaatacgt gccagcagcc gcggtaatac  540
gtatgtcccg agcgttatcc ggatttattg ggcgtaaagc gagcgcagac ggtttattaa  600
gtctgatgtg aaagcccgga gctcaactcc ggaatggcat tggaaactgg ttaacttgag  660
tgcagtagag gtaagtggaa ctccatgtgt agcggtggaa tgcgtagata tatggaagaa  720
caccagtggc gaaggcggct tactggactg caactgacgt tgaggctcga aagtgtgggt  780
agcaaacagg attagatacc ctggtagtcc acaccgtaaa cgatgaacac taggtgttag  840
gaggtttccg cctcttagtg ccgaagctaa cgcattaagt gttccgcctg gggagtacga  900
ccgcaaggtt gaaactcaaa ggaattgacg ggacccgca caagcggtgg agcatgtggt  960
ttaattcgaa gcaacgcgaa gaaccttacc aggtcttgac atcctttgaa gcttttagag  1020
atagaagtgt tctcttcgga gacaaagtga caggtggtgc atggtcgtcg tcagctcgtg  1080
tcgtgagatg ttgggttaag tcccgcaacg agcgcaaccc ttattgttag ttgccagcat  1140
tcagatgggc actctagcga gactgccggt gacaaaccgg aggaaggcgg ggacgacgtc  1200
agatcatcat gccccttatg acctgggcta cacacgtgct acaatggcgt atacaacgag  1260
ttgccaaccc gcgagggtga gctaatctct taaagtacgt ctcagttcgg attgtagtct  1320
gcaactcgac tacatgaagt cggaatcgct agtaatcgcg gatcagcacg ccgcggtgaa  1380
tacgttcccg ggtcttgtac acaccgcccg tcacaccatg ggagtttgta atgcccaaag  1440
ccggtggcct aacctttag gaaggagccg tctaaggcag gacagatgac tggggtgaag  1500
tcgtaacaag gtagccgtag gagaacctgc ggctggatca cctccttt           1548

SEQ ID NO: 158         moltype = RNA  length = 1421
FEATURE                Location/Qualifiers
source                 1..1421
                       mol_type = rRNA
```

```
                         organism = unidentified
                         note = DP94 16S rRNA sequence
SEQUENCE: 158
atctgcccag aagcagggga taacacttgg aaacaggtgc taataccgta taacaacaaa  60
atccgcatgg attttgtttg aaaggtggct tcggctatca cttctggatg atcccgcggc  120
gtattagtta gttggtgagg taaaggccca ccaagacgat gatacgtagc cgacctgaga  180
gggtaatcgg ccacattggg actgagacac ggcccaaact cctacgggag gcagcagtag  240
ggaatcttcc acaatggacg aaagtctgat ggagcaatgc cgcgtgagtg aagaagggtt  300
tcggctcgta aaactctgtt gttaaagaag aacacctttg agagtaactg ttcaagggtt  360
gacggtattt aaccagaaag ccacggctaa ctacgtgcca gcagccgcgg taatacgtag  420
gtggcaagcg ttgtccggat ttattgggcg taaagcgagc gcaggcggtt ttttaagtct  480
gatgtgaaag ccttcggctt aaccggagaa gtgcatcgga aactgggaga cttgagtgca  540
gaagaggaca gtggaactcc atgtgtagcg gtggaatgcg tagatatatg gaagaacacc  600
agtggcgaag gcggctgtct agtctgtaac tgacgctgag gctcgaaagc atgggtagcg  660
aacaggatta gataccctgg tagtccatgc cgtaaacgat gagtgctaag tgttggaggg  720
tttccgccct tcagtgctgc agctaacgca ttaagcactc cgcctgggga gtacgaccgc  780
aaggttgaaa ctcaaaggaa ttgacggggg cccgcacaag cggtggagca tgtggtttaa  840
ttcgaagcta cgcgaagaac cttaccaggt cttgacatct tctgccaatc ttagagataa  900
gacgttccct tcggggacag aatgacaggt ggtgcatggt tgtcgtcagc tcgtgtcgtg  960
agatgttggg ttaagtcccg caacgagcgc aacccttatt atcagttgcc agcattcagt  1020
tgggcactct ggtgagactg ccggtgacaa accggaggaa ggtggggatg acgtcaaatc  1080
atcatgcccc ttatgacctg ggctacacac gtgctacaat ggacggtaca acgagttgcg  1140
aagtcgtgag gctaagctaa tctcttaaag ccgttctcag ttcggattgt aggctgcaac  1200
tcgcctacat gaagttggaa tcgctagtaa tcgcggatca gcatgccgcg gtgaatacgt  1260
tcccgggcct tgtacacacc gcccgtcaca ccatgagagt ttgtaacacc caaagccggt  1320
gagataacct tcgggagtca gccgtctaag gtgggacaga tgattagggt gaagtcgtaa  1380
caaggtagcc gtaggagaac ctgcggctgg atcacctcct t                     1421

SEQ ID NO: 159           moltype = RNA  length = 1388
FEATURE                  Location/Qualifiers
source                   1..1388
                         mol_type = rRNA
                         organism = unidentified
                         note = DP95 16S rRNA sequence
SEQUENCE: 159
tgctaatacc gcatagatcc aagaaccgca tggttcttgg ctgaaagatg gcgtaagcta  60
tcgcttttgg atggacccgc ggcgtattag ctagttggtg aggtaatggc tcaccaaggc  120
gatgatacgt agccgaactg agaggttgat cggccacatt gggactgaga cacggcccaa  180
actcctacgg gaggcagcag tagggaatct tccacaatgg acgcaagtct gatggagcaa  240
cgccgcgtga gtgaagaagg ctttcgggtc gtaaaactct gttgttggag aagaatggtc  300
ggcagagtaa ctgttgtcgg cgtgacggta tccaaccaga aagccacggc taactacgtg  360
ccagcagccg cggtaatacg taggtggcaa gcgttatccg gatttattgg gcgtaaagcg  420
agcgcaggcg gtttttttaag tctgatgtga aagccctcgg cttaaccgag gaagcgcatc  480
ggaaactggg aaacttgagt gcagaagagg acagtggaac tccatgtgta gcggtgaaat  540
gcgtagatat atggaagaac accagtggcg aaggcggctg tctggtctgt aactgacgct  600
gaggctcgaa agcatgggta gcgaacagga ttagataccc tggtagtcca tgccgtaaac  660
gatgaatgct aggtgttgga gggtttccgc ccttcagtgc cgcagctaac gcattaagca  720
ttccgcctgg ggagtacgac cgcaaggttg aaactcaaag gaattgacgg gggcccgcac  780
aagcggtgga gcatgtggtt taattcgaag caacgcgaag aaccttacca ggtcttgaca  840
tcttttgatc acctgagaga tcaggtttcc ccttcggggg caaaatgaca ggtggtgcat  900
ggttgtcgtc agctcgtgtc gtgagatgtt gggttaagtc ccgcaacgag cgcaaccctt  960
atgactagtt gccagcattt agttgggcac tctagtaaga ctgccggtga caaaccggag  1020
gaaggtgggg atgacgtcaa atcatcatgc cccttatgac ctgggctaca cacgtgctac  1080
aatggatggt acaacgagtt gcgagaccgc gaggtcaagc taatctctta aagccattct  1140
cagttcggac tgtaggctgc aactcgccta cacgaagtcg gaatcgctag taatcgcgga  1200
tcagcacgcc gcggtgaata cgttcccggg ccttgtacac accgcccgtc acaccatgag  1260
agtttgtaac acccgaagcc ggtggcgtaa ccctttttagg gagcgagccg tctaaggtgg  1320
gacaaatgat tagggtgaag tcgtaacaag gtagccgtag gagaacctgc ggctggatca  1380
cctccttt                                                          1388

SEQ ID NO: 160           moltype = RNA  length = 1219
FEATURE                  Location/Qualifiers
source                   1..1219
                         mol_type = rRNA
                         organism = unidentified
                         note = DP96 16S rRNA sequence
SEQUENCE: 160
acacggccca aactcctacg ggaggcagca gtagggaatc ttccacaatg gacgcaagtc  60
tgatggagca acgccgcgtg agtgaagaag gctttcgggt cgtaaaactc tgttgttgga  120
gaagaatggt cggcagagta actgttgtcg gcgtgacggt atccaaccag aaagccacgg  180
ctaactacgt gccagcagcc gcggtaatac gtaggtggca agcgttatcc ggatttattg  240
ggcgtaaagc gagcgcaggc ggtttttttaa gtctgatgtg aaagccctcg gcttaaccga  300
ggaagcgcat cggaaactgg gaaacttgag tgcagaagag gacagtggaa ctccatgtgt  360
agcggtgaaa tgcgtagata tatggaagaa caccagtggc gaaggcggct gtctggtctg  420
taactgacgc tgaggctcga aagcatgggt agcgaacagg attagatacc ctggtagtcc  480
atgccgtaaa cgatgaatgc taggtgttgg agggtttccg cccttcagtg ccgcagctaa  540
cgcattaagc attccgcctg gggagtacga ccgcaaggtt gaaactcaaa ggaattgacg  600
ggggcccgca caagcggtgg agcatgtggt ttaattcgaa gcaacgcgaa gaaccttacc  660
aggtcttgac atcttttgat cacctgagag atcaggtttc cccttcgggg gcaaaatgac  720
```

```
aggtggtgca tggttgtcgt cagctcgtgt cgtgagatgt tgggttaagt cccgcaacga  780
gcgcaaccct tatgactagt tgccagcatt tagttgggca ctctagtaag actgccggtg  840
acaaaccgga ggaaggtggg gatgacgtca aatcatcatg ccccttatga cctgggctac  900
acacgtgcta caatggatgg tacaacgagt tgcgagaccg cgaggtcaag ctaatctctt  960
aaagccattc tcagttcgga ctgtaggctg caactcgcct acacgaagtc ggaatcgcta  1020
gtaatcgcgg atcagcacgc cgcggtgaat acgttcccgg gccttgtaca caccgcccgt  1080
cacaccatga gagtttgtaa cacccgaagc cggtggcgta accctttag ggagcgagcc  1140
gtctaaggtg ggacaaatga ttagggtgaa gtcgtaacaa ggtagccgta ggagaacctg  1200
cggctggatc acctcctt                                               1219

SEQ ID NO: 161         moltype = RNA  length = 1546
FEATURE                Location/Qualifiers
source                 1..1546
                       mol_type = rRNA
                       organism = unidentified
                       note = DP97 16S rRNA sequence
SEQUENCE: 161
aatgagagtt tgatcctggc tcaggacgaa cgctggcggc gtgcctaata catgcaagtc  60
gagcgatgat taaagatagc ttgctatttt tatgaagagc ggcgaacggg tgagtaacgc  120
gtgggaaatc tgccgagtag cgggggacaa cgtttggaaa cgaacgctaa taccgcataa  180
caatgagaat cgcatgattc ttatttaaaa gaagcaattg cttcactact tgatgatccc  240
gcgttgtatt agctagttgg tagtgtaaag gactaccaag gcgatgatac atagccgacc  300
tgagagggtg atcggccaca ctgggactga gacacggccc agactcctac gggaggcagc  360
agtagggaat cttcggcaat gggggcaacc ctgaccgagc aacgccgcgt gagtgaagaa  420
ggttttcgga tcgtaaaact ctgttgttag agaagaacgt taagtagagt ggaaaattac  480
ttaagtgacg gtatctaacc agaaagggac ggctaactac gtgccagcag ccgcggtaat  540
acgtaggtcc caagcgttgt ccggatttat tgggcgtaaa gcgagcgcag gtggtttctt  600
aagtctgatg taaaaggcag tggctcaacc attgtgtgca ttggaaactg ggagacttga  660
gtgcaggaga ggagagtgga attccatgtg tagcggtgaa atgcgtagat atatggagga  720
acaccggagg cgaaagcggc tctctggcct gtaactgaca ctgaggctcg aaagcgtggg  780
gagcaaacag gattagatac cctggtagtc cacgccgtaa acgatgagtg ctagctgtag  840
ggagctataa gttctctgta gcgcagctaa cgcattaagc actccgcctg gggagtacga  900
ccgcaaggtt gaaactcaaa ggaattgacg ggggcccgca caagcggtgg agcatgtggt  960
ttaattcgaa gcaacgcgaa gaaccttacc aggtcttgac atactcgtga tatccttaga  1020
gataaggagt tccttcggga cacgggatac aggtggtgca tggttgtcgt cagctcgtgt  1080
cgtgagatgt tgggttaagt cccgcaacga gcgcaaccct tattactagt tgccatcatt  1140
aagttgggca ctctagtgag actgccggtg ataaaccgga ggaaggtggg gatgacgtca  1200
aatcatcatg ccccttatga cctgggctac acacgtgcta caatggatgg tacaacgagt  1260
cgccaacccg cgagggtgcg ctaatctctt aaaaccattc tcagttcgga ttgcaggctg  1320
caactcgcct gcatgaagtc ggaatcgcta gtaatcgcgg atcagcacgc cgcggtgaat  1380
acgttcccgg gccttgtaca caccgcccgt cacaccacgg aagttgggag tacccaaagt  1440
aggttgccta accgcaagga gggcgcttcc taaggtaaga ccgatgactg gggtgaagtc  1500
gtaacaaggt agccgtatcg gaaggtgcgg ctggatcacc tccttt                1546

SEQ ID NO: 162         moltype = RNA  length = 1546
FEATURE                Location/Qualifiers
source                 1..1546
                       mol_type = rRNA
                       organism = unidentified
                       note = DP98 16S rRNA sequence
SEQUENCE: 162
aatgagagtt tgatcctggc tcaggacgaa cgctggcggc gtgcctaata catgcaagtc  60
gagcgatgat taaagatagc ttgctatttt tatgaagagc ggcgaacggg tgagtaacgc  120
gtgggaaatc tgccgagtag cgggggacaa cgtttggaaa cgaacgctaa taccgcataa  180
caatgagaat cgcatgattc ttatttaaaa gaagcaattg cttcactact tgatgatccc  240
gcgttgtatt agctagttgg tagtgtaaag gactaccaag gcgatgatac atagccgacc  300
tgagagggtg atcggccaca ctgggactga gacacggccc agactcctac gggaggcagc  360
agtagggaat cttcggcaat gggggcaacc ctgaccgagc aacgccgcgt gagtgaagaa  420
ggttttcgga tcgtaaaact ctgttgttag agaagaacgt taagtagagt ggaaaattac  480
ttaagtgacg gtatctaacc agaaagggac ggctaactac gtgccagcag ccgcggtaat  540
acgtaggtcc caagcgttgt ccggatttat tgggcgtaaa gcgagcgcag gtggtttctt  600
aagtctgatg taaaaggcag tggctcaacc attgtgtgca ttggaaactg ggagacttga  660
gtgcaggaga ggagagtgga attccatgtg tagcggtgaa atgcgtagat atatggagga  720
acaccggagg cgaaagcggc tctctggcct gtaactgaca ctgaggctcg aaagcgtggg  780
gagcaaacag gattagatac cctggtagtc cacgccgtaa acgatgagtg ctagctgtag  840
ggagctataa gttctctgta gcgcagctaa cgcattaagc actccgcctg gggagtacga  900
ccgcaaggtt gaaactcaaa ggaattgacg ggggcccgca caagcggtgg agcatgtggt  960
ttaattcgaa gcaacgcgaa gaaccttacc aggtcttgac atactcgtga tatccttaga  1020
gataaggagt tccttcggga cacgggatac aggtggtgca tggttgtcgt cagctcgtgt  1080
cgtgagatgt tgggttaagt cccgcaacga gcgcaaccct tattactagt tgccatcatt  1140
aagttgggca ctctagtgag actgccggtg ataaaccgga ggaaggtggg gatgacgtca  1200
aatcatcatg ccccttatga cctgggctac acacgtgcta caatggatgg tacaacgagt  1260
cgccaacccg cgagggtgcg ctaatctctt aaaaccattc tcagttcgga ttgcaggctg  1320
caactcgcct gcatgaagtc ggaatcgcta gtaatcgcgg atcagcacgc cgcggtgaat  1380
acgttcccgg gccttgtaca caccgcccgt cacaccacgg aagttgggag tacccaaagt  1440
aggttgccta accgcaagga gggcgcttcc taaggtaaga ccgatgactg gggtgaagtc  1500
gtaacaaggt agccgtatcg gaaggtgcgg ctggatcacc tccttt                1546

SEQ ID NO: 163         moltype = RNA  length = 1263
```

```
FEATURE                Location/Qualifiers
source                 1..1263
                       mol_type = rRNA
                       organism = unidentified
                       note = DP100 16S rRNA sequence
SEQUENCE: 163
tttgagagtt tgatcctggc tcaggacgaa cgctggcggc gtgcctaata catgcaagtc  60
gaacgaactc tggtattgat tggtgcttgc atcatgattt acatttgagt gagtggcgaa  120
ctggtgagta acacgtggga aacctgccca gaagcggggg ataacacctg gaaacagatg  180
ctaataccgc ataacaactt ggaccgcatg gtccgagctt gaaagatggc ttcggctatc  240
acttttggat ggtcccgcgg cgtattagct agatggtggg gtaacggctc accatggcaa  300
tgatacgtag ccgacctgag agggtaatcg gccacattgg gactgagaca cggcccaaac  360
tcctacggga ggcagcagta gggaatcttc cacaatggac gaaagtctga tggagcaacg  420
ccgcgtgagt gaagaagggt ttcggctcgt aaaactctgt tgttaaagaa gaacatatct  480
gagagtaact gttcaggtat tgacggtatt taaccagaaa gccacggcta actacgtgcc  540
agcagccgcg gtaatacgta ggtggcaagc gttgtccgga tttattgggc gtaaagcgag  600
cgcaggcggt tttttaagtc tgatgtgaaa gccttcggct caaccgaaga agtgcatcgg  660
aaactgggaa acttgagtgc agaagaggac agtggaactc catgtgtagc ggtgaaatgc  720
gtagatatat ggaagaacac cagtggcgaa ggcggctgtc tggtctgtaa ctgacgctga  780
ggctcgaaag tatgggtagc aaacaggatt agataccctg gtagtccata ccgtaaacga  840
tgaatgctaa gtgttggagg gtttccgccc ttcagtgctg cagctaacgc attaagcatt  900
ccgcctgggg agtacggccg caaggctgaa actcaaagga attgacgggg gcccgcacaa  960
gcggtggagc atgtggttta attcgaagct acgcgaagaa ccttaccagg tcttgacata  1020
ctatgcaaat ctaagagatt agacgttccc ttcggggaca tggatacagg tggtgcatgg  1080
ttgtcgtcag ctcgtgtcgt gagatgttgg gttaagtccc gcaacgagcg caacccttat  1140
tatcagttgc cagcattaag ttgggcactc tggtgagact gccggtgaca aaccggagga  1200
aggtggggat gacgtcaaat catcatgccc cttatgacct gggctacaca cgtgctacaa  1260
tgg                                                                1263

SEQ ID NO: 164         moltype = RNA  length = 1457
FEATURE                Location/Qualifiers
source                 1..1457
                       mol_type = rRNA
                       organism = unidentified
                       note = DP101 16S rRNA sequence
SEQUENCE: 164
atgagagttt gatcttggct caggatgaac gctggcggcg tgcctaatac atgcaagtcg  60
aacgaacttc cgttaattga ttatgacgta cttgtactga ttgagatttt aacacgaagt  120
gagtggcgaa cgggtgagta acacgtgggt aacctgccca gaagtagggg ataacacctg  180
gaaacagatg ctaataccgt ataacagaga aaaccgcatg gttttctttt aaaagatggc  240
tctgctatca cttctggatg gacccgcggc gtattagcta gttggtgagg caaaggctca  300
ccaaggcagt gatacgtagc cgacctgaga gggtaatcgg ccacattggg actgagacac  360
ggcccagact cctacgggag gcagcagtag ggaatcttcc acaatggacg caagtctgat  420
ggagcaacgc cgcgtgagtg aagaagggtt tcggctcgta aagctctgtt gttaaagaag  480
aacgtgggta agagtaactg tttacccagt gacggtattt aaccagaaag ccacggctaa  540
ctacgtgcca gcagccgcgg taatacgtag gtggcaagcg ttatccggat ttattgggcg  600
taaagcgagc gcaggcggtc ttttaagtct aatgtgaaag ccttcggctc aaccgaagaa  660
gtgcattgga aactgggaga cttgagtgca gaagaggaca gtggaactcc atgtgtagcg  720
gtgaaatgcg tagatatatg gaagaacacc agtggcgaag gcggctgtct ggtctgcaac  780
tgacgctgag gctcgaaagc atgggtagcg aacaggatta gataccctgg tagtccatgc  840
cgtaaacgat gattactaag tgttggaggg tttccgccct tcagtgctgc agctaacgca  900
ttaagtaatc cgcctgggga gtacgaccgc aaggttgaaa ctcaaaagaa ttgacggggg  960
cccgcacaag cggtggagca tgtggtttaa ttcgaagcta cgcgaagaac cttaccaggt  1020
cttgacatct tctgacagtc taagagatta gaggttccct tcggggacag aatgacaggt  1080
ggtgcatggt tgtcgtcagc tcgtgtcgtg agatgttggg ttaagtcccg caacgagcgc  1140
aacccttatt actagttgcc agcattaagt tgggcactct agtgagactg ccggtgacaa  1200
accggaggaa ggtggggacg acgtcaaatc atcatgcccc ttatgacctg ggctacacac  1260
gtgctacaat ggatggtaca acgagtcgcg agaccgcgag gttaagctaa tctcttaaaa  1320
ccattctcag ttcggactgt aggctgcaac tcgcctacac gaagtcggaa tcgctagtaa  1380
tcgcggatca gcatgccgcg gtgaatacgt tcccgggcct tgtacacacc gcccgtcaca  1440
ccatgagagt ttgtaac                                                 1457

SEQ ID NO: 165         moltype = DNA  length = 1415
FEATURE                Location/Qualifiers
source                 1..1415
                       mol_type = genomic DNA
                       organism = unidentified
                       note = DP101 ITS sequence
SEQUENCE: 165
tccgtaggtg aacctgcgga aggatcatta ctgtgattta gtactacact gcgtgagcgg  60
aacgaaaaca acaacaccta aaatgtggaa tatagcatat agtcgacaag agaaatctac  120
gaaaaacaaa caaaactttc aacaacggat ctcttggttc tcgcatcgat gaagagcgca  180
gcgaaatgcg atacctagtg tgaattgcag ccatcgtgaa tcatcgagtt cttgaacgca  240
cattgcgccc ctcggcattc cggggggcat gcctgtttga gcgtcgtttc catcttgcgc  300
gtgcgcagag ttgggggagc ggagcggacg acgtgtaaag agcgtcggag ctgcgactcg  360
cctgaaaggg agcgaagctg gccgagcgaa ctagactttt tttcagggac gcttggcggc  420
cgagagcgag tgttgcgaga caacaaaaag ctcgacctca aatcaggtag gaatacccgc  480
tgaacttaag catatcaata agcggaggaa aagaaaccaa cagggattgc ctcagtagcg  540
gcgagtgaag cggcaagagc tcagatttga aatcgtgctt tgcggcacga gttgtagatt  600
```

-continued

```
gcaggttgga gtctgtgtgg aaggcggtgt ccaagtccct tggaacaggg cgcccaggag  660
ggtgagagcc ccgtgggatg ccggcggaag cagtgaggcc cttctgacga gtcgagttgt  720
ttgggaatgc agctccaagc gggtggtaaa ttccatctaa ggctaaatac tggcgagaga  780
ccgatagcga acaagtactg tgaaggaaag atgaaaagca ctttgaaaag agagtgaaac  840
agcacgtgaa attgttgaaa gggaagggta ttgcgcccga catggggatt gcgcaccgct  900
gcctctcgtg ggcggcgctc tgggctttcc ctgggccagc atcggttctt gctgcaggag  960
aaggggttct ggaacgtggc tcttcggagt gttatagcca gggccagatg ctgcgtgcgg  1020
ggaccgagga ctgcggccgt gtaggtcacg gatgctggca gaacggcgca acaccgcccg  1080
tcttgaaaca tggaccaagg agtctaacgt ctatgcgagt gtttgggtgt gaaacccgta  1140
cgcgtaatga aagtgaacgt aggtcggacc ccctgccctc ggggagggga gcacgatcga  1200
ccgatcccga tgtttatcgg aaggatttga gtaggagcat agctgttggg acccgaaaga  1260
tggtgaacta tgcctgaata gggtgaagcc agaggaaact ctggtggagg ctcgtagcgg  1320
ttctgacgtg caaatcgatc gtcgaatttg ggtatagggg cgaaagacta atcgaaccat  1380
ctagtagctg gttcctgccg aagtttccct cagga                            1415
```